(12) United States Patent
Bernett et al.

(10) Patent No.: US 11,505,595 B2
(45) Date of Patent: Nov. 22, 2022

(54) TIM-3 TARGETED HETERODIMERIC FUSION PROTEINS CONTAINING IL-15/IL-15RA FC-FUSION PROTEINS AND TIM-3 ANTIGEN BINDING DOMAINS

(71) Applicant: Xencor, Inc., Monrovia, CA (US)

(72) Inventors: Matthew J. Bernett, Monrovia, CA (US); John Desjarlais, Pasadena, CA (US); Rumana Rashid, Temple City, CA (US); Rajat Varma, Monrovia, CA (US); Christine Bonzon, Los Angeles, CA (US)

(73) Assignee: Xencor, Inc., Monrovia, CA (US)

( * ) Notice: Subject to any disclaimer, the term of this patent is extended or adjusted under 35 U.S.C. 154(b) by 320 days.

(21) Appl. No.: 16/388,729

(22) Filed: Apr. 18, 2019

(65) Prior Publication Data

US 2019/0359684 A1 Nov. 28, 2019

Related U.S. Application Data

(60) Provisional application No. 62/659,626, filed on Apr. 18, 2018, provisional application No. 62/783,110, filed on Dec. 20, 2018.

(51) Int. Cl.
| | |
|---|---|
| *C07K 14/715* | (2006.01) |
| *C07K 14/54* | (2006.01) |
| *C07K 16/28* | (2006.01) |
| *C07K 19/00* | (2006.01) |
| *C12N 15/63* | (2006.01) |
| *A61K 38/00* | (2006.01) |

(52) U.S. Cl.
CPC ...... *C07K 14/7155* (2013.01); *C07K 14/5443* (2013.01); *C07K 16/2818* (2013.01); *C07K 19/00* (2013.01); *C12N 15/63* (2013.01); *A61K 38/00* (2013.01); *C07K 2317/30* (2013.01); *C07K 2317/524* (2013.01); *C07K 2317/526* (2013.01); *C07K 2317/53* (2013.01); *C07K 2317/56* (2013.01); *C07K 2317/66* (2013.01)

(58) Field of Classification Search
None
See application file for complete search history.

(56) References Cited

U.S. PATENT DOCUMENTS

| | | |
|---|---|---|
| 3,773,919 A | 11/1973 | Boswell et al. |
| 4,169,888 A | 10/1979 | Hanka et al. |
| 4,179,337 A | 12/1979 | Davis et al. |
| 4,256,746 A | 3/1981 | Miyashita et al. |
| 4,294,757 A | 10/1981 | Asai |
| 4,301,144 A | 11/1981 | Iwashita et al. |
| 4,307,016 A | 12/1981 | Asai et al. |
| 4,313,946 A | 2/1982 | Powell et al. |
| 4,315,929 A | 2/1982 | Freedman et al. |
| 4,322,348 A | 3/1982 | Asai et al. |
| 4,331,598 A | 5/1982 | Hasegawa et al. |
| 4,361,650 A | 5/1982 | Asai et al. |
| 4,362,663 A | 12/1982 | Kida et al. |
| 4,364,866 A | 12/1982 | Asai et al. |
| 4,364,935 A | 12/1982 | Kung et al. |
| 4,371,533 A | 2/1983 | Akimoto et al. |
| 4,424,219 A | 1/1984 | Hashimoto et al. |
| 4,450,254 A | 5/1984 | Isley et al. |
| 4,496,689 A | 1/1985 | Mitra |
| 4,640,835 A | 2/1987 | Shimizu et al. |
| 4,670,417 A | 6/1987 | Iwasaki et al. |
| 4,791,192 A | 12/1988 | Nakagawa et al. |
| 4,880,935 A | 11/1989 | Thorpe |
| 4,923,990 A | 5/1990 | Nakano et al. |
| 4,943,533 A | 7/1990 | Mendelsohn et al. |
| 4,970,198 A | 11/1990 | Lee et al. |
| 5,053,394 A | 10/1991 | Ellestad et al. |
| 5,070,092 A | 12/1991 | Kanda et al. |
| 5,084,468 A | 1/1992 | Saito et al. |
| 5,101,038 A | 3/1992 | Nakano et al. |
| 5,122,368 A | 6/1992 | Greenfield et al. |
| 5,187,186 A | 2/1993 | Kanda et al. |
| 5,208,020 A | 5/1993 | Chari et al. |
| 5,264,586 A | 11/1993 | Nicolaou et al. |
| 5,384,412 A | 1/1995 | Nicolaou et al. |
| 5,416,064 A | 5/1995 | Chari et al. |
| 5,475,092 A | 12/1995 | Chari et al. |
| 5,500,362 A | 3/1996 | Robinson et al. |
| 5,530,101 A | 6/1996 | Queen et al. |
| 5,541,087 A | 7/1996 | Lo et al. |
| 5,550,246 A | 8/1996 | Nicolaou et al. |
| 5,558,864 A | 9/1996 | Bendig et al. |

(Continued)

FOREIGN PATENT DOCUMENTS

| | | |
|---|---|---|
| EP | 0425235 B1 | 9/1996 |
| EP | 0927254 | 6/2005 |

(Continued)

OTHER PUBLICATIONS

Fabbi et al, Journal of Cytokine Biology, 2016, vol. 1, No. 2, pp. 1-7.*
Romee et al, Blood; Feb. 20, 2018; vol. 131; No. 23; pp. 2515-2527.*
U.S. Appl. No. 12/875,015, 2011-0054151, U.S. Pat. No. 9,493,578, Granted, filed Sep. 2, 2010, Mar. 3, 2011, Nov. 15, 2016.
U.S. Appl. No. 15/279,266, 2017-0058053, Abandoned, filed Sep. 28, 2016, Mar. 2, 2017.
U.S. Appl. No. 16/539,986, Pending, filed Aug. 13, 2019.
U.S. Appl. No. 13/648,951, 2013-0171095, Published, filed Oct. 10, 2012, Jul. 4, 2013.
U.S. Appl. No. 13/194,904, 2012-0028304, U.S. Pat. No. 8,637,641, Granted, filed Jul. 29, 2011, Feb. 2, 2012, Jan. 28, 2014.
U.S. Appl. No. 14/165,487, 2014-0249297, U.S. Pat. No. 9,605,061, Granted, filed Jan. 27, 2014, Sep. 4, 2014, Mar. 28, 2017.

(Continued)

*Primary Examiner* — Bridget E Bunner
*Assistant Examiner* — Fozia M Hamud
(74) *Attorney, Agent, or Firm* — Kelly A. Plummer; Christopher J. Betti; Morgan, Lewis & Bockius, LLP

(57) ABSTRACT

The present invention is directed to novel targeted heterodimeric fusion proteins comprising an IL-15/IL-15Rα Fc-fusion protein and a TIM-3 antibody fragment-Fc fusion protein.

12 Claims, 69 Drawing Sheets

Specification includes a Sequence Listing.

(56) References Cited

U.S. PATENT DOCUMENTS

| | | |
|---|---|---|
| 5,585,089 A | 12/1996 | Queen et al. |
| 5,585,097 A | 12/1996 | Bolt et al. |
| 5,585,499 A | 12/1996 | Chari et al. |
| 5,622,929 A | 4/1997 | Willner et al. |
| 5,635,483 A | 6/1997 | Pettit et al. |
| 5,641,780 A | 6/1997 | Amishiro et al. |
| 5,663,149 A | 9/1997 | Pettit et al. |
| 5,677,171 A | 10/1997 | Hudziak et al. |
| 5,693,761 A | 12/1997 | Queen et al. |
| 5,693,762 A | 12/1997 | Queen et al. |
| 5,703,080 A | 12/1997 | Nakakura et al. |
| 5,712,374 A | 1/1998 | Kuntsmann et al. |
| 5,714,586 A | 2/1998 | Kuntsmann et al. |
| 5,726,044 A | 3/1998 | Lo et al. |
| 5,731,168 A | 3/1998 | Carter et al. |
| 5,736,137 A | 4/1998 | Anderson et al. |
| 5,739,116 A | 4/1998 | Hamann et al. |
| 5,767,237 A | 6/1998 | Sakakibara et al. |
| 5,767,285 A | 6/1998 | Hamann et al. |
| 5,770,701 A | 6/1998 | McGahren et al. |
| 5,770,710 A | 6/1998 | McGahren et al. |
| 5,773,001 A | 6/1998 | Hamann et al. |
| 5,780,588 A | 7/1998 | Pettit et al. |
| 5,807,706 A | 9/1998 | Carter et al. |
| 5,821,333 A | 10/1998 | Carter et al. |
| 5,821,337 A | 10/1998 | Carter et al. |
| 5,824,805 A | 10/1998 | King et al. |
| 5,846,545 A | 12/1998 | Chari et al. |
| 5,859,205 A | 1/1999 | Adair et al. |
| 5,877,291 A | 3/1999 | Mezes et al. |
| 5,877,296 A | 3/1999 | Hamann et al. |
| 5,891,996 A | 4/1999 | Mateo de Acosta del Rio et al. |
| 5,892,020 A | 4/1999 | Mezes et al. |
| 5,945,311 A | 8/1999 | Lindhofer et al. |
| 5,968,509 A | 10/1999 | Gorman et al. |
| 6,054,297 A | 4/2000 | Carter et al. |
| 6,071,515 A | 6/2000 | Mezes et al. |
| 6,124,431 A | 9/2000 | Sakakibara et al. |
| 6,180,370 B1 | 1/2001 | Queen et al. |
| 6,214,345 B1 | 4/2001 | Firestone et al. |
| 6,235,883 B1 | 5/2001 | Jakobovits et al. |
| 6,329,507 B1 | 12/2001 | Mezes et al. |
| 6,407,213 B1 | 6/2002 | Carter et al. |
| 6,441,163 B1 | 8/2002 | Chari et al. |
| 6,455,677 B1 | 9/2002 | Park et al. |
| 6,506,883 B2 | 1/2003 | Meteo de Acosta del Rio et al. |
| 6,602,684 B1 | 8/2003 | Umana et al. |
| 6,632,927 B2 | 10/2003 | Adair et al. |
| 6,706,265 B1 | 3/2004 | Bolt et al. |
| 6,716,410 B1 | 4/2004 | Witztum |
| 6,723,538 B2 | 4/2004 | Mack et al. |
| 6,737,056 B1 | 5/2004 | Presta |
| 6,884,869 B2 | 4/2005 | Senter et al. |
| 6,989,452 B2 | 1/2006 | Ng et al. |
| 7,087,600 B2 | 8/2006 | Ng et al. |
| 7,112,324 B1 | 9/2006 | Dorken et al. |
| 7,129,261 B2 | 10/2006 | Ng et al. |
| 7,276,497 B2 | 10/2007 | Chari et al. |
| 7,276,585 B2 | 10/2007 | Lazar et al. |
| 7,303,749 B1 | 12/2007 | Chari |
| 7,355,008 B2 | 4/2008 | Stavenhagen et al. |
| 7,368,565 B2 | 5/2008 | Chari et al. |
| 7,498,302 B2 | 3/2009 | Ng et al. |
| 7,507,420 B2 | 3/2009 | Ng et al. |
| 7,517,903 B2 | 4/2009 | Chen et al. |
| 7,601,354 B2 | 10/2009 | Chari |
| 7,632,497 B2 | 12/2009 | Stavenhagen |
| 7,642,228 B2 | 1/2010 | Carter et al. |
| 7,691,962 B2 | 4/2010 | Boyd et al. |
| 7,695,936 B2 | 4/2010 | Carter et al. |
| 7,696,338 B2 | 4/2010 | Neville, Jr. et al. |
| 7,728,114 B2 | 6/2010 | Mach et al. |
| 7,834,152 B2 | 11/2010 | Strom et al. |
| 7,858,081 B2 | 12/2010 | Bernard et al. |
| 7,960,512 B2 | 6/2011 | Stavenhagen et al. |
| 8,003,774 B2 | 8/2011 | Stavenhagen et al. |
| 8,063,187 B2 | 11/2011 | Chu et al. |
| 8,114,967 B2 | 2/2012 | Bhatt et al. |
| 8,124,084 B2 | 2/2012 | LeFrancois et al. |
| 8,192,737 B2 | 6/2012 | Stavenhagen et al. |
| 8,216,574 B2 | 7/2012 | Stavenhagen |
| 8,216,805 B2 | 7/2012 | Carter et al. |
| 8,236,308 B2 | 8/2012 | Kischel et al. |
| 8,309,690 B2 | 11/2012 | Allan et al. |
| 8,367,805 B2 | 2/2013 | Chamberlain et al. |
| 8,409,568 B2 | 4/2013 | Gao et al. |
| 8,592,562 B2 | 11/2013 | Kannan et al. |
| 8,629,245 B2 | 1/2014 | Georgiou et al. |
| 8,637,641 B2 | 1/2014 | Dahiyat et al. |
| 8,679,493 B2 | 3/2014 | Georgiou et al. |
| 8,742,074 B2 | 6/2014 | Behrens et al. |
| 8,871,912 B2 | 10/2014 | Davis et al. |
| 8,940,288 B2 | 1/2015 | LeFrancois et al. |
| 8,940,289 B2 | 1/2015 | Wong et al. |
| 8,946,387 B2 | 2/2015 | Koenig et al. |
| 8,951,517 B2 | 2/2015 | Stavenhagen et al. |
| 9,028,815 B2 | 5/2015 | Stavenhagen et al. |
| 9,150,663 B2 | 10/2015 | Labrijn et al. |
| 9,308,258 B2 | 4/2016 | Kannan et al. |
| RE45,992 E | 5/2016 | Behrens et al. |
| 9,365,630 B2 | 6/2016 | LeFrancois et al. |
| 9,371,368 B2 | 6/2016 | LeFrancois et al. |
| 9,464,127 B2 | 10/2016 | Wong et al. |
| 9,493,533 B2 | 11/2016 | Bernard et al. |
| 9,505,848 B2 | 11/2016 | Davis et al. |
| 9,527,926 B2 | 12/2016 | Ho et al. |
| 9,562,109 B2 | 2/2017 | Von Kreudenstein et al. |
| 9,683,052 B2 | 6/2017 | Blein et al. |
| 9,683,053 B2 | 6/2017 | Blein et al. |
| 9,763,705 B2 | 9/2017 | Faulhaber |
| 9,763,765 B2 | 9/2017 | Horan et al. |
| 9,822,181 B2 | 11/2017 | Bonvini et al. |
| 9,856,327 B2 | 1/2018 | Bernett et al. |
| 9,931,377 B2 | 4/2018 | Pavlakis et al. |
| 9,932,387 B2 | 4/2018 | LeFrancois et al. |
| 9,969,790 B2 | 5/2018 | LeFrancois et al. |
| 10,011,858 B2 | 7/2018 | Igawa et al. |
| 10,138,303 B2 | 11/2018 | Ho et al. |
| 10,350,270 B2 | 7/2019 | McCauley |
| 10,550,185 B2 | 2/2020 | Bernett et al. |
| 2001/0035606 A1 | 11/2001 | Schoen |
| 2002/0076406 A1 | 6/2002 | Leung |
| 2002/0103345 A1 | 8/2002 | Zhu |
| 2002/0131968 A1 | 9/2002 | Waldmann et al. |
| 2003/0003097 A1 | 1/2003 | Reft et al. |
| 2003/0017979 A1 | 1/2003 | Mack et al. |
| 2003/0091561 A1 | 5/2003 | Van de Winkel |
| 2003/0157108 A1 | 8/2003 | Presta |
| 2003/0223999 A1 | 12/2003 | Lindhofer |
| 2004/0018191 A1 | 1/2004 | Wang |
| 2004/0071696 A1 | 4/2004 | Adams et al. |
| 2004/0162411 A1 | 8/2004 | Lanzavecchia |
| 2004/0170626 A1 | 9/2004 | Schuurman |
| 2004/0242851 A1 | 12/2004 | Zhu |
| 2005/0114037 A1 | 5/2005 | Desjarlais et al. |
| 2005/0136050 A1 | 6/2005 | Kufer et al. |
| 2005/0142133 A1 | 6/2005 | Lazar et al. |
| 2005/0176028 A1 | 8/2005 | Hofmeiser et al. |
| 2005/0191702 A1 | 9/2005 | Mack et al. |
| 2005/0238648 A1 | 10/2005 | Jacobs |
| 2005/0238649 A1 | 10/2005 | Doronina |
| 2006/0008883 A1 | 1/2006 | Lazar |
| 2006/0018897 A1 | 1/2006 | Lee et al. |
| 2006/0024298 A1 | 2/2006 | Lazar et al. |
| 2006/0024317 A1 | 2/2006 | Boyd |
| 2006/0073142 A1 | 4/2006 | Chan et al. |
| 2006/0074008 A1 | 4/2006 | Senter |
| 2006/0115481 A1 | 6/2006 | Lindhofer et al. |
| 2006/0121032 A1 | 6/2006 | Dahiyat et al. |
| 2006/0134105 A1 | 6/2006 | Lazar et al. |
| 2006/0235208 A1 | 10/2006 | Lazar |
| 2006/0257361 A1 | 11/2006 | Watanabe et al. |
| 2006/0263857 A1 | 11/2006 | LeFrancois et al. |
| 2007/0071675 A1 | 3/2007 | Wu et al. |

(56) References Cited

U.S. PATENT DOCUMENTS

| | | |
|---|---|---|
| 2007/0105199 A1 | 5/2007 | Yan et al. |
| 2007/0123479 A1 | 5/2007 | Kufer et al. |
| 2007/0148170 A1 | 6/2007 | Desjarlais |
| 2007/0287170 A1 | 12/2007 | Davis et al. |
| 2008/0044413 A1 | 2/2008 | Hammond et al. |
| 2008/0050370 A1 | 2/2008 | Glaser et al. |
| 2008/0138335 A1 | 6/2008 | Takahashi et al. |
| 2008/0213273 A1 | 9/2008 | Burge |
| 2008/0219974 A1 | 9/2008 | Bernett et al. |
| 2008/0242845 A1 | 10/2008 | Lazar et al. |
| 2009/0082213 A1 | 3/2009 | Horowitz et al. |
| 2009/0163699 A1 | 6/2009 | Desjarlais |
| 2009/0214539 A1 | 8/2009 | Grosmaire et al. |
| 2009/0238791 A1 | 9/2009 | Jacques et al. |
| 2009/0252683 A1 | 10/2009 | Kischel et al. |
| 2009/0252729 A1 | 10/2009 | Farrington et al. |
| 2009/0274692 A1 | 11/2009 | Tan et al. |
| 2009/0311253 A1 | 12/2009 | Ghayur et al. |
| 2009/0317869 A1 | 12/2009 | Alley et al. |
| 2010/0004431 A1 | 1/2010 | Bernett et al. |
| 2010/0015133 A1 | 1/2010 | Igawa et al. |
| 2010/0080814 A1 | 4/2010 | Desjarlais et al. |
| 2010/0150918 A1 | 6/2010 | Kufer et al. |
| 2010/0174053 A1 | 7/2010 | Johnson et al. |
| 2010/0178298 A1 | 7/2010 | Lindhofer |
| 2010/0183554 A1 | 7/2010 | Mach et al. |
| 2010/0226925 A1 | 9/2010 | Dillon et al. |
| 2010/0239567 A1 | 9/2010 | Esue |
| 2010/0239582 A1 | 9/2010 | Humphreys et al. |
| 2010/0256339 A1 | 10/2010 | Bossenmaier et al. |
| 2010/0256340 A1 | 10/2010 | Brinkmann et al. |
| 2010/0267934 A1 | 10/2010 | Van de Winkel et al. |
| 2010/0298542 A1 | 11/2010 | Igawa et al. |
| 2010/0322933 A1 | 12/2010 | Lindhofer et al. |
| 2010/0330089 A1 | 12/2010 | Damle et al. |
| 2010/0331527 A1 | 12/2010 | Davis et al. |
| 2011/0054151 A1 | 3/2011 | Lazar et al. |
| 2011/0076275 A1 | 3/2011 | Igawa et al. |
| 2011/0177500 A1 | 7/2011 | Winther et al. |
| 2011/0189178 A1 | 8/2011 | Desjarlais et al. |
| 2011/0189209 A1 | 8/2011 | Neville, Jr. et al. |
| 2011/0201032 A1 | 8/2011 | Zeng et al. |
| 2011/0217302 A1 | 9/2011 | Odegard et al. |
| 2011/0262439 A1 | 10/2011 | Kufer et al. |
| 2011/0275787 A1 | 11/2011 | Kufer et al. |
| 2011/0293619 A1 | 12/2011 | Kufer et al. |
| 2012/0028304 A1 | 2/2012 | Dahiyat et al. |
| 2012/0034228 A1 | 2/2012 | Kufer et al. |
| 2012/0121597 A1 | 5/2012 | Ho et al. |
| 2012/0149876 A1 | 6/2012 | Von Kreudenstein et al. |
| 2012/0156207 A1 | 6/2012 | Chu et al. |
| 2012/0177595 A1 | 7/2012 | Wong et al. |
| 2012/0251531 A1 | 10/2012 | Baehner et al. |
| 2012/0251541 A1 | 10/2012 | Baurin et al. |
| 2013/0039913 A1 | 2/2013 | Labrijn et al. |
| 2013/0089541 A1 | 4/2013 | D'Angelo et al. |
| 2013/0095097 A1 | 4/2013 | Blakenship et al. |
| 2013/0101586 A1 | 4/2013 | Riegler et al. |
| 2013/0115208 A1 | 5/2013 | Ho et al. |
| 2013/0129723 A1 | 5/2013 | Blakenship et al. |
| 2013/0131319 A1 | 5/2013 | Igawa et al. |
| 2013/0142793 A1 | 6/2013 | Ledbetter et al. |
| 2013/0171095 A1 | 7/2013 | Bernett et al. |
| 2013/0178605 A1 | 7/2013 | Blein et al. |
| 2013/0195849 A1 | 8/2013 | Kreudenstein et al. |
| 2013/0209355 A1 | 8/2013 | De Weers et al. |
| 2013/0267686 A1 | 10/2013 | Brinkmann |
| 2013/0336981 A1 | 12/2013 | de Kruif et al. |
| 2014/0024111 A1 | 1/2014 | Kannan et al. |
| 2014/0056879 A1 | 2/2014 | Lazar |
| 2014/0072581 A1 | 3/2014 | Dixit et al. |
| 2014/0086916 A1 | 3/2014 | Zha |
| 2014/0134128 A1 | 5/2014 | Wong et al. |
| 2014/0187753 A1 | 7/2014 | Blein et al. |
| 2014/0199294 A1 | 7/2014 | Mimoto et al. |
| 2014/0212435 A1 | 7/2014 | Moore et al. |
| 2014/0212436 A1 | 7/2014 | Moore et al. |
| 2014/0249297 A1 | 9/2014 | Lazar et al. |
| 2014/0288275 A1 | 9/2014 | Moore et al. |
| 2014/0294759 A1 | 10/2014 | Chu et al. |
| 2014/0294823 A1 | 10/2014 | Moore et al. |
| 2014/0294833 A1 | 10/2014 | Desjarlais et al. |
| 2014/0294835 A1 | 10/2014 | Moore et al. |
| 2014/0294836 A1 | 10/2014 | Chu et al. |
| 2014/0302064 A1 | 10/2014 | Moore |
| 2014/0322217 A1 | 10/2014 | Moore et al. |
| 2014/0335089 A1 | 11/2014 | Igawa et al. |
| 2014/0356381 A1 | 12/2014 | Moore et al. |
| 2014/0363426 A1 | 12/2014 | Moore et al. |
| 2014/0370013 A1 | 12/2014 | Desjarlais et al. |
| 2014/0370020 A1 | 12/2014 | Kuramochi et al. |
| 2014/0377269 A1 | 12/2014 | Mabry et al. |
| 2014/0377270 A1 | 12/2014 | Moore et al. |
| 2015/0071948 A1 | 3/2015 | Lazar et al. |
| 2015/0307629 A1 | 10/2015 | Bernett et al. |
| 2015/0351275 A1 | 12/2015 | Imbimbo et al. |
| 2016/0060360 A1 | 3/2016 | Moore et al. |
| 2016/0068584 A1 | 3/2016 | Bechard et al. |
| 2016/0068588 A1 | 3/2016 | Bernett et al. |
| 2016/0157951 A1 | 6/2016 | Schoenig et al. |
| 2016/0175459 A1 | 6/2016 | Gey et al. |
| 2016/0176969 A1 | 6/2016 | Bernett et al. |
| 2016/0184399 A1 | 6/2016 | Bechard et al. |
| 2016/0215063 A1 | 7/2016 | Bernett et al. |
| 2016/0229924 A1 | 8/2016 | Bernett et al. |
| 2016/0257749 A1* | 9/2016 | Lifke ................. A61K 47/6831 |
| 2016/0318986 A1 | 11/2016 | Morisseau et al. |
| 2016/0333067 A1 | 11/2016 | LeFrancois et al. |
| 2016/0347818 A1 | 12/2016 | LeFrancois et al. |
| 2016/0355608 A1 | 12/2016 | Bernett et al. |
| 2016/0367635 A1 | 12/2016 | Wong et al. |
| 2017/0020963 A1 | 1/2017 | Qu et al. |
| 2017/0056874 A1 | 3/2017 | Bechard et al. |
| 2017/0088597 A1 | 3/2017 | Wong et al. |
| 2017/0145078 A1 | 5/2017 | Davis et al. |
| 2017/0151310 A1 | 6/2017 | Felber et al. |
| 2017/0233497 A1 | 8/2017 | Labrijn et al. |
| 2018/0094077 A1 | 4/2018 | Blein et al. |
| 2018/0118805 A1 | 5/2018 | Bernett et al. |
| 2018/0118828 A1 | 5/2018 | Bernett et al. |
| 2018/0118836 A1 | 5/2018 | Bernett et al. |
| 2018/0127500 A1* | 5/2018 | Kehry ................. C07K 16/2809 |
| 2018/0127501 A1 | 5/2018 | Bernett et al. |
| 2018/0194860 A1 | 7/2018 | Von Kreudenstein et al. |
| 2018/0200366 A1 | 7/2018 | Wong et al. |
| 2018/0298079 A1 | 10/2018 | LeFrancois et al. |
| 2018/0312560 A1 | 11/2018 | Morisseau et al. |
| 2019/0016778 A1 | 1/2019 | Bernett et al. |
| 2019/0263877 A1 | 8/2019 | Yeung et al. |
| 2020/0247862 A1 | 8/2020 | Bernett et al. |
| 2021/0047407 A1 | 2/2021 | Christian et al. |

FOREIGN PATENT DOCUMENTS

| | | |
|---|---|---|
| EP | 1752471 | 2/2007 |
| EP | 1829895 | 5/2007 |
| EP | 3263581 | 1/2008 |
| EP | 2006381 | 12/2008 |
| EP | 2009101 A1 | 12/2008 |
| EP | 1801119 B1 | 6/2009 |
| EP | 2194066 | 6/2010 |
| EP | 2202245 A1 | 6/2010 |
| EP | 2522724 | 6/2011 |
| EP | 1718670 | 7/2011 |
| EP | 1934353 | 10/2011 |
| EP | 2155788 | 2/2014 |
| EP | 2388266 | 4/2014 |
| EP | 2724728 | 4/2014 |
| EP | 3093295 | 11/2016 |
| EP | 2769984 | 8/2017 |
| EP | 3235830 | 10/2017 |
| EP | 3252078 | 12/2017 |
| EP | 3030575 | 7/2018 |
| EP | 3265478 B1 | 9/2019 |

(56) References Cited

FOREIGN PATENT DOCUMENTS

| | | |
|---|---|---|
| EP | 3030262 B1 | 10/2019 |
| EP | 1899364 B1 | 2/2020 |
| WO | WO8705330 | 9/1987 |
| WO | WO9211018 | 7/1992 |
| WO | WO9321232 | 10/1993 |
| WO | WO9413804 | 5/1994 |
| WO | WO9520045 | 1/1995 |
| WO | WO9640210 | 6/1996 |
| WO | WO96027011 | 9/1996 |
| WO | WO1997041232 | 11/1997 |
| WO | WO98050431 | 11/1998 |
| WO | WO199937791 | 7/1999 |
| WO | WO99054440 | 10/1999 |
| WO | WO99066951 | 12/1999 |
| WO | WO200061739 A1 | 10/2000 |
| WO | WO2001010912 A1 | 2/2001 |
| WO | WO200124763 A2 | 4/2001 |
| WO | WO200129246 A1 | 4/2001 |
| WO | WO200162931 A1 | 8/2001 |
| WO | WO200188138 | 11/2001 |
| WO | WO2001083525 | 11/2001 |
| WO | WO2001090192 | 11/2001 |
| WO | WO200216368 | 2/2002 |
| WO | WO200230954 A1 | 4/2002 |
| WO | WO200231140 A1 | 4/2002 |
| WO | WO2002088172 A2 | 7/2002 |
| WO | WO2002062850 | 8/2002 |
| WO | WO2002083180 | 10/2002 |
| WO | WO2002098883 | 12/2002 |
| WO | WO2004010957 | 2/2004 |
| WO | WO2004043493 | 5/2004 |
| WO | WO2004103272 | 12/2004 |
| WO | WO2004106383 | 12/2004 |
| WO | WO2005014642 A2 | 2/2005 |
| WO | WO2005063816 | 7/2005 |
| WO | WO2005085282 | 9/2005 |
| WO | WO2005112919 A2 | 12/2005 |
| WO | WO2005118635 | 12/2005 |
| WO | WO2006020258 | 2/2006 |
| WO | WO2006034488 | 3/2006 |
| WO | WO2006036834 | 4/2006 |
| WO | WO2006063974 | 6/2006 |
| WO | WO2006072620 | 7/2006 |
| WO | WO2006110476 A2 | 10/2006 |
| WO | WO2006106905 | 12/2006 |
| WO | WO2007001677 | 1/2007 |
| WO | WO2007005612 | 1/2007 |
| WO | WO2007018431 A2 | 2/2007 |
| WO | WO2007033230 | 3/2007 |
| WO | WO2007042261 | 4/2007 |
| WO | WO2007046006 | 4/2007 |
| WO | WO2007047829 | 4/2007 |
| WO | WO2007059404 A2 | 5/2007 |
| WO | WO2007062037 | 5/2007 |
| WO | WO2007084342 | 7/2007 |
| WO | WO2007089149 A2 | 8/2007 |
| WO | WO2007093630 | 8/2007 |
| WO | WO2007098934 | 9/2007 |
| WO | WO2007110205 | 10/2007 |
| WO | WO2007113648 | 10/2007 |
| WO | WO2007128563 A1 | 11/2007 |
| WO | WO2007147901 | 12/2007 |
| WO | WO20070147901 | 12/2007 |
| WO | WO2008003103 | 1/2008 |
| WO | WO2008003115 | 1/2008 |
| WO | WO2008003116 | 1/2008 |
| WO | WO2008119096 | 10/2008 |
| WO | WO2008119566 | 10/2008 |
| WO | WO2008124858 | 10/2008 |
| WO | WO2008143794 | 11/2008 |
| WO | WO2008145142 | 12/2008 |
| WO | WO2008150494 | 12/2008 |
| WO | WO2009000006 | 12/2008 |
| WO | WO2009002562 | 12/2008 |
| WO | WO2009017394 A1 | 2/2009 |
| WO | WO2009017823 | 2/2009 |
| WO | WO2009030734 | 3/2009 |
| WO | WO2009032782 | 3/2009 |
| WO | WO2009036209 | 3/2009 |
| WO | WO2009086320 | 7/2009 |
| WO | WO2009089004 | 7/2009 |
| WO | WO2009106096 | 9/2009 |
| WO | WO2009106321 | 9/2009 |
| WO | WO2010017103 | 2/2010 |
| WO | WO2010028796 | 3/2010 |
| WO | WO2010033736 | 3/2010 |
| WO | WO2010034441 | 4/2010 |
| WO | WO2010037835 | 4/2010 |
| WO | WO2010042904 | 4/2010 |
| WO | WO2010062171 A2 | 6/2010 |
| WO | WO2010085682 | 7/2010 |
| WO | WO2010106180 | 9/2010 |
| WO | WO2010115551 | 10/2010 |
| WO | WO2010115552 | 10/2010 |
| WO | WO2010115553 | 10/2010 |
| WO | WO2010115589 | 10/2010 |
| WO | WO2010119119 | 10/2010 |
| WO | WO20100112193 | 10/2010 |
| WO | WO2010136172 | 12/2010 |
| WO | WO2010151792 | 12/2010 |
| WO | WO2010151808 | 12/2010 |
| WO | WO2011005621 | 1/2011 |
| WO | WO2011020047 A1 | 2/2011 |
| WO | WO2011028952 | 3/2011 |
| WO | WO2011036183 | 3/2011 |
| WO | WO2011066342 | 3/2011 |
| WO | WO2011051307 | 5/2011 |
| WO | WO2011063348 | 5/2011 |
| WO | WO2011066501 | 6/2011 |
| WO | WO2011121110 | 10/2011 |
| WO | WO2011131746 | 10/2011 |
| WO | WO2011133886 | 10/2011 |
| WO | WO2011143545 | 11/2011 |
| WO | WO2011131746 | 12/2011 |
| WO | WO2011159877 | 12/2011 |
| WO | WO2012016227 | 2/2012 |
| WO | WO2012018687 | 2/2012 |
| WO | WO2012032080 | 3/2012 |
| WO | WO2012040323 A2 | 3/2012 |
| WO | WO2012058768 | 5/2012 |
| WO | WO2012062596 | 5/2012 |
| WO | WO2012107417 | 8/2012 |
| WO | WO2012116453 | 9/2012 |
| WO | WO2012125495 | 9/2012 |
| WO | WO2012125850 | 9/2012 |
| WO | WO2012131555 | 10/2012 |
| WO | WO2012146394 | 11/2012 |
| WO | WO2012146628 | 11/2012 |
| WO | WO2012162067 | 11/2012 |
| WO | WO2012131555 | 12/2012 |
| WO | WO2012175222 | 12/2012 |
| WO | WO2013006544 | 1/2013 |
| WO | WO2013016714 | 1/2013 |
| WO | WO2013022855 | 2/2013 |
| WO | WO2013026833 | 2/2013 |
| WO | WO2013033008 | 3/2013 |
| WO | WO2013/055809 | 4/2013 |
| WO | WO2013047748 | 4/2013 |
| WO | WO2013055809 | 4/2013 |
| WO | WO2013063702 | 5/2013 |
| WO | WO2013096828 | 6/2013 |
| WO | WO2013107791 A1 | 7/2013 |
| WO | WO2013125667 | 8/2013 |
| WO | WO2013164694 | 11/2013 |
| WO | WO2013180201 | 12/2013 |
| WO | WO2014004586 | 1/2014 |
| WO | WO2014012085 | 1/2014 |
| WO | WO2014047231 | 3/2014 |
| WO | WO2014056783 | 4/2014 |
| WO | WO2014079000 | 5/2014 |
| WO | WO2014/110601 | 7/2014 |
| WO | WO2014110601 | 7/2014 |
| WO | WO2014113510 | 7/2014 |
| WO | WO2014145806 | 9/2014 |

(56) References Cited

FOREIGN PATENT DOCUMENTS

| WO | WO2014145907 | | 9/2014 |
|----|----|----|----|
| WO | WO2014164553 | | 10/2014 |
| WO | WO2014170032 | | 10/2014 |
| WO | WO2014207064 | | 12/2014 |
| WO | WO2014207173 | | 12/2014 |
| WO | WO2014209804 | | 12/2014 |
| WO | WO2015018528 | | 2/2015 |
| WO | WO2015018529 | | 2/2015 |
| WO | WO2015026892 | | 2/2015 |
| WO | WO2015063339 | | 5/2015 |
| WO | WO2015095392 | | 6/2015 |
| WO | WO2015095410 | | 6/2015 |
| WO | WO2015095423 | | 6/2015 |
| WO | WO2015103072 | | 7/2015 |
| WO | WO2015103928 | | 7/2015 |
| WO | WO2015131994 | | 9/2015 |
| WO | WO2015143079 | | 9/2015 |
| WO | WO2015149077 | | 10/2015 |
| WO | WO2015168379 | | 11/2015 |
| WO | WO2015184207 | | 12/2015 |
| WO | WO2015195163 | | 12/2015 |
| WO | WO2016004060 | | 1/2016 |
| WO | WO2016014984 | | 1/2016 |
| WO | WO2016028672 | | 2/2016 |
| WO | WO2016028896 | | 2/2016 |
| WO | WO2016079050 | | 5/2016 |
| WO | WO2016086186 | | 6/2016 |
| WO | WO2016086189 | | 6/2016 |
| WO | WO2016086189 | A2 | 6/2016 |
| WO | WO2016086196 | | 6/2016 |
| WO | WO2016086196 | A2 | 6/2016 |
| WO | WO2016095642 | | 6/2016 |
| WO | WO2016105450 | | 6/2016 |
| WO | WO2016106159 | | 6/2016 |
| WO | WO2016110584 | | 7/2016 |
| WO | WO2016115274 | | 7/2016 |
| WO | WO2016120789 | | 8/2016 |
| WO | WO2016141387 | | 9/2016 |
| WO | WO2016142314 | | 9/2016 |
| WO | WO2016182751 | | 11/2016 |
| WO | WO2017019846 | | 2/2017 |
| WO | WO2017112775 | | 6/2017 |
| WO | WO2017210443 | | 12/2017 |
| WO | WO2017210485 | | 12/2017 |
| WO | WO2017214092 | | 12/2017 |
| WO | WO2018007919 | A1 | 1/2018 |
| WO | WO2018041838 | | 3/2018 |
| WO | WO2018071918 | | 4/2018 |
| WO | WO2018071919 | | 4/2018 |
| WO | WO2018091661 | | 5/2018 |
| WO | WO2019006472 | | 1/2019 |
| WO | WO2019050521 | | 3/2019 |
| WO | WO2019204592 | | 10/2019 |
| WO | WO2019204665 | | 10/2019 |
| WO | WO2020077276 | | 4/2020 |

OTHER PUBLICATIONS

U.S. Appl. No. 15/444,087, 2017-0174757, To Be Aband, filed Feb. 27, 2017, Jun. 22, 2017.
U.S. Appl. No. 13/568,028, Abandoned, filed Aug. 6, 2012.
U.S. Appl. No. 14/853,622, 2016-0068588, Published, filed Sep. 14, 2015, Mar. 10, 2016.
U.S. Appl. No. 13/887,234, Abandoned, filed May 3, 2013.
U.S. Appl. No. 14/156,431, 2014-0212435, Abandoned, filed Jan. 15, 2014, Jul. 31, 2014.
U.S. Appl. No. 14/156,432, 2014-0212436, U.S. Pat. No. 9,738,722, Granted, filed Jan. 15, 2014, Jul. 31, 2014, Aug. 22, 2017.
U.S. Appl. No. 14/808,826, 2016-0060360, Abandoned, filed Jul. 24, 2015, Mar. 3, 2016.
U.S. Appl. No. 15/682,380, 2018-0201686, Abandoned, filed Aug. 21, 2017, Jul. 19, 2018.
U.S. Appl. No. 14/155,248, 2014-0322217, Allowed, filed Jan. 14, 2014, Oct. 30, 2014.
U.S. Appl. No. 14/155,334, 2014-0370013, Published, filed Jan. 14, 2014, Dec. 18, 2014.
U.S. Appl. No. 14/155,344, 2014-0294833, U.S. Pat. No. 9,701,759, Granted, filed Jan. 14, 2014, Oct. 2, 2014, Jul. 11, 2017.
U.S. Appl. No. 14/205,227, 2014-0294835, Abandoned, filed Mar. 11, 2014, Oct. 2, 2014.
U.S. Appl. No. 14/205,248, 2014-0288275, U.S. Pat. No. 9,650,446, Granted, filed Mar. 11, 2014, Sep. 25, 2014, May 16, 2017.
U.S. Appl. No. 15/589,908, 2018-0142040, Published, filed May 8, 2017, May 24, 2018.
U.S. Appl. No. 15/633,629, 2018-0215834, Allowed, filed Jun. 26, 2017, Aug. 2, 2018.
U.S. Appl. No. 14/214,418, 2014-0356381, U.S. Pat. No. 10,106,624, Granted, filed Mar. 14, 2014, Dec. 4, 2014, Oct. 23, 2018.
U.S. Appl. No. 16/137,389, Abandoned, filed Sep. 20, 2018.
U.S. Appl. No. 14/214,475, 2014-0294836, Allowed, filed Mar. 14, 2014, Oct. 2, 2014.
U.S. Appl. No. 14/217,166, 2014-0294759, Allowed, filed Mar. 17, 2014, Oct. 2, 2014.
U.S. Appl. No. 14/200,652, 2014-0302064, Published, filed Mar. 7, 2014, Oct. 9, 2014.
U.S. Appl. No. 14/207,489, 2014-0377270, U.S. Pat. No. 10,131,710, Granted, filed Mar. 12, 2014, Dec. 25, 2014, Nov. 20, 2018.
U.S. Appl. No. 16/162,172, 2019-0270810, Published, filed Oct. 16, 2018, Sep. 5, 2019.
U.S. Appl. No. 14/200,821, 2014-0294823, U.S. Pat. No. 9,605,084, Granted, filed Mar. 7, 2014, Oct. 2, 2014, Mar. 28, 2017.
U.S. Appl. No. 14/216,705, 2014-0363426, Published, filed Mar. 17, 2014, Dec. 11, 2014.
U.S. Appl. No. 15/444,026, 2018-0037668, U.S. Pat. No. 10,287,364, Granted, filed Feb. 27, 2017, Feb. 8, 2018, May 14, 2019.
U.S. Appl. No. 16/364,093, Pending, filed Mar. 25, 2019.
U.S. Appl. No. 14/673,695, 2015-0307629, Transferred, filed Mar. 30, 2015, Oct. 29, 2015.
U.S. Appl. No. 15/786,252, 2018-0094079, Published, filed Oct. 17, 2017, Apr. 5, 2018.
U.S. Appl. No. 14/952,705, 2016-0176969, Abandoned, filed Nov. 25, 2015, Jun. 23, 2016.
U.S. Appl. No. 14/952,714, 2016-0229924, Published, filed Nov. 25, 2015, Aug. 11, 2016.
U.S. Appl. No. 15/141,350, 2016-0355608, U.S. Pat. No. 10,259,887, Granted, filed Apr. 28, 2016, Dec. 8, 2016, Apr. 16, 2019.
U.S. Appl. No. 15/945,679, 2018-0282432, Published, filed Apr. 4, 2018, Oct. 4, 2018.
U.S. Appl. No. 15/945,681, 2018-0223000, Published, filed Apr. 4, 2018, Aug. 9, 2018.
U.S. Appl. No. 16/354,058, 2019-0202938, Published, filed Mar. 14, 2019, Jul. 4, 2019.
U.S. Appl. No. 14/952,786, 2016-0215063, Transferred, filed Nov. 25, 2015, Jul. 28, 2016.
U.S. Appl. No. 15/779,325, Pending, filed May 25, 2018.
U.S. Appl. No. 14/757,809, 2016-0355600, U.S. Pat. No. 10,428,155, Allowed, filed Dec. 22, 2015, Dec. 8, 2016, Oct. 1, 2019.
U.S. Appl. No. 16/530,946, Pending, filed Aug. 2, 2019.
U.S. Appl. No. 15/063,441, 2017-0037131, U.S. Pat. No. 10,227,411, Granted, filed Mar. 7, 2016, Feb. 9, 2017, Mar. 12, 2019.
U.S. Appl. No. 16/297,255, 2019-0194325, Published, filed Mar. 8, 2019, Jun. 27, 2019.
U.S. Appl. No. 15/372,360, 2017-0320947, U.S. Pat. No. 10,227,410, Granted, filed Dec. 7, 2016, Nov. 9, 2017, Mar. 12, 2019.
U.S. Appl. No. 16/489,539, Pending, filed Aug. 28, 2019.
U.S. Appl. No. 15/623,314, 2018-0118836, Published, filed Jun. 14, 2017, May 3, 2018.
U.S. Appl. No. 16/435,373, Pending, filed Jun. 7, 2019.
U.S. Appl. No. 16/435,375, Pending, filed Jun. 7, 2019.
U.S. Appl. No. 15/611,361, 2017-0349660, Published, filed Jun. 1, 2017, Dec. 7, 2017.
U.S. Appl. No. 15/611,683, 2017-0349657, Published, filed Jun. 1, 2017, Dec. 7, 2017.
U.S. Appl. No. 15/636,590, 2018-0118827, U.S. Pat. No. 10,316,088, Granted, filed Jun. 28, 2017, May 3, 2018, Jun. 11, 2019.
U.S. Appl. No. 16/393,900, 2019-0248898, Published, filed Apr. 24, 2019, Aug. 15, 2019.

(56) References Cited

OTHER PUBLICATIONS

U.S. Appl. No. 15/185,958, 2017-0081420, U.S. Pat. No. 9,850,320, Granted, filed Jun. 17, 2016, Mar. 23, 2017, Dec. 26, 2017.
U.S. Appl. No. 15/186,167, 2017-0081424, U.S. Pat. No. 9,856,327, Granted, filed Jun. 17, 2016, Mar. 23, 2017, Jan. 2, 2018.
U.S. Appl. No. 15/691,665, 2018-0127501, Published, filed Aug. 30, 2017, May 10, 2018.
U.S. Appl. No. 15/785,401, 2018-0118805, U.S. Pat. No. 10,501,543, Allowed, filed Oct. 16, 2017, May 3, 2018, Dec. 10, 2019.
U.S. Appl. No. 15/785,393, 2018-0118828, Allowed, filed Oct. 16, 2017, May 3, 2018.
U.S. Appl. No. 16/388,174, Pending, filed Apr. 18, 2019.
U.S. Appl. No. 16/388,811, Pending, filed Apr. 18, 2019.
U.S. Appl. No. 16/600,236, Pending, filed Oct. 11, 2019.
U.S. Appl. No. 16/025,963, 2019-0016778, Published, filed Jul. 2, 2018, Jan. 17, 2019.
U.S. Appl. No. 16/184,895, 2019-0263909, Published, filed Nov. 8, 2018, Aug. 29, 2019.
U.S. Appl. No. 16/184,929, 2019-0270816, Published, filed Nov. 8, 2018, Sep. 5, 2019.
U.S. Appl. No. 16/206,849, 2019-0241638, Published, filed Nov. 30, 2018, Aug. 8, 2019.
U.S. Appl. No. 16/375,777, Pending, filed Apr. 4, 2019.
U.S. Appl. No. 16/388,646, 2019-0352362, Published, filed Apr. 18, 2019, Nov. 21, 2019.
U.S. Appl. No. 16/592,656, Pending, filed Oct. 3, 2019.
Matthew J Bernett et al: Abstract 5565: Potency-reduced IL15/IL15R[alpha] heterodimeric Fc-fusions display enhanced in vivo activity through increased exposure 11, Cancer Research, vol. 78, No. 13(Suppl)., Apr. 18, 2018 (Apr. 18, 2018), pp. 1-2, XP055658295. abstract.
Kowalsky Stacy Jet al:"Superagonist IL-15-Armed Oncolytic Virus Elicits Potent Antitumor Immunity and Therapy That Are Enhanced with PD-1 Blockade", Molecular Therapy, Nature Publishing Group, GB, vol. 26, No. 10, Oct. 3, 2018 (Oct. 3, 2018), pp. 2476-2486, XP002794091, ISSN: 1525-0024, DOI: 10.1016/J.YMTHE.2018.07.013 abstract, figures 5 and 6.
Ha et al., Immunoglobulin Fc Heterodimer Platform Technology: From Design to Applications in Therapeutic Antibodies and Proteins., Front Immunol. 2016; 7: 394. Published online Oct. 6, 2016. doi: 10.3389/fimmu.2016.00394.
Rhode et al., Comparison of the Superagonist Complex, ALT-803, to IL15 as Cancer Immunotherapeutics in Animal Models., Cancer Immunol Res. Jan. 2016;4(1):49-60. doi: 10.1158/2326-6066.CIR-15-0093-T. Epub Oct. 28, 2015.
Steinbacher et al., An Fc-optimized NKG2D-immunoglobulin G Fusion Protein for Induction of Natural Killer Cell Reactivity Against Leukemia., Int J Cancer. Mar. 1, 2015;136(5):1073-84. doi: 10.1002/ijc.29083. Epub Jul. 28, 2014.
Prajapati et al., Functions of NKG2D in CD8 + T Cells: An Opportunity for Immunotherapy., Cell Mol Immunol. May 2018;15(5):470-479. doi: 10.1038/cmi.2017.161. Epub Feb. 5, 2018.
Wells, Additivity of mutational effects in proteins., Biochemistry 1990, 29, 37, 8509-8517.
Bork, Powers and Pitfalls in Sequence Analysis: The 70% Hurdle., Genome Res. 2000. 10:398-400.
Skolnick et al., From Genes to Protein Structure and Function: Novel Applications of Computational Approaches in the Genomic Era., Trends Biotechnol. Jan. 2000;18(1):34-9.
Doerks et al., Protein annotation: detective work for function prediction., Trends in Genetics, 1998 vol. 14, Issue 6, p. 248-250, Jun. 1, 1998.
Tokuriki et al., Stability effects of mutations and protein evolvability., Current Opinion in Structural Biology 2009, 19: 596-604.
Fabbi et al., Dual Roles of IL-15 in Cancer Biology, Journal of Cytokine Biology, 2016, vol. 1, No. 2, pp. 1-7.
Mathios et al., Therapeutic administration of IL-15 superagonist complex ALT-803 leads to long-term survival and durable antitumor immune response in a murine glioblastoma model., International Journal of Cancer, 2016; vol. 138, pp. 187-194.

Alter et al., Targeted IL-15-based Protein Fusion Complexes as Cancer Immunotherapy Approaches., J Immunological Sci. (2018); 2(1): 15-18.
Bailey et al., New interleukin-15 superagonist (IL-15SA) significantly enhances graft-versus-tumor activity., Oncotarget. Jul. 4, 2017; 8(27): 44366-44378.
Charych et al., NKTR-214, an Engineered Cytokine with Biased IL2 Receptor Binding, Increased Tumor Exposure, and Marked Efficacy in Mouse Tumor Models., Clin Cancer Res; 22(3) Feb. 1, 2016.
Chen et al., A targeted IL-15 fusion protein with potent antitumor activity., (2015) Cancer Biology & Therapy, 16:9, 1415-1421, DOI: 10.1080/15384047.2015.1071739.
Ghasemi et al., Selective targeting of IL-2 to NKG2D bearing cells for improved immunotherapy., Nature Communications vol. 7, Article No. 12878 (2016).
Jochems et al., The multi-functionality of N-809, a novel fusion protein encompassing anti-PD-L1 and the IL-15 superagonist fusion complex., OncoImmunology, 2019, vol. 8, No. 2, e1532764 (15 pages).
Klein et al., Cergutuzumab amunaleukin (CEA-IL2v), a CEAtargeted IL-2 variant-based immunocytokine for combination cancer immunotherapy: Overcoming limitations of aldesleukin and conventional IL-2-based immunocytokines.,(2017) OncoImmunology, 6:3, e1277306, DOI: 10.1080/2162402X.2016.1277306.
Olsen et al., Crystal Structure of the Interleukin-15 * Interleukin-15 Receptor αComplex., The Journal of Biological Chemistry vol. 282, No. 51, pp. 37191-37204, Dec. 21, 2007.
Vallera et al., IL15 Trispecific Killer Engagers (TriKE) Make Natural Killer Cells Specific to CD33p Targets While Also Inducing Persistence, In Vivo Expansion, and Enhanced Function., Clin Cancer Res; 22(14) Jul. 15, 2016.
Xu et al., Efficacy and Meehanism-of-Action of a Novel Superagonist Interleukin-15: Interleukin-15 Receptor α Su/Fc Fusion Complex in Syngeneic Murine Models of Multiple Myeloma., Cancer Res. May 15, 2013;73(10):3075-86.
Zhu et al., Novel Human Interleukin-15 Agonists., The Journal of Immunology; 2009; vol. 183, No. 6; pp. 1-28.
Bernard et al., Identification of an Interleukin-15α Receptor-binding Site on Human Interleukin-15*., The Journal of Biological Chemistry; 2004; vol. 279, No. 23, pp. 24313-24322.
Robinson et al., The potential and promise of IL-15 in immuno-oncogenic therapies, Immunology Letters, vol. 190, 2017, pp. 159-168.
Schmid et al., Design and characterisation of a novel interleukin-15 receptor alpha fusion protein and analysis of interleukin-15 complexation., PLoS One. Jul. 26, 2019;14(7):e0219313.
Genbank accession No. U31628, Dec. 19, 1995.
Muller, Dafne, Targeted cancer immunotherapy, Mimicking physiological trans-presentation of IL-15., Oncoimmunology. Oct. 1, 2012; 1(7): 1213-1214.
Garcin et al. High efficiency cell-specific targeting of cytokine activity. Nat Commun 5, 3016 (2014).
Kaspar et al., The antibody-mediated targeted delivery of interleukin-15 and GM-CSF to the tumor neovasculature inhibits tumor growth and metastasis., Cancer Res. May 15, 2007;67(10):4940-8.
Conlon et al., Redistribution, hyperproliferation, activation of natural killer cells and CD8 T cells, and cytokine production during first-in-human clinical trial of recombinant human interleukin-15 in patients with cancer., J Clin Oncol. Jan. 1, 2015;33(1):74-82.
List et al., Immunocytokines: a review of molecules in clinical development for cancer therapy., Clin Pharmacol. 2013; 5(Suppl 1): 29-45.
Gillies et al., Antibody-targeted interleukin 2 stimulates T-cell killing of autologous tumor cells., PNAS Feb. 15, 1992 89 (4) 1428-1432.
Albertini et al. Phase II trial of hu14.18-IL2 for patients with metastatic melanoma., Cancer Immunol Immunother. Dec. 2012;61(12):2261-71.
Ribas et al., Phase I/II open-label study of the biologic effects of the interleukin-2 immunocytokine EMD 273063 (hu14.18-IL2) in patients with metastatic malignant melanoma., J Transl Med. Jul. 29, 2009;7:68.

(56) References Cited

OTHER PUBLICATIONS

Hofmann et al., Generation, selection and preclinical characterization of an Fc-optimized FLT3 antibody for the treatment of myeloid leukemia., Leukemia. Jun. 2012;26(6):1228-37.
Kellner et al., Heterodimeric bispecific antibody-derivatives against CD19 and CD16 induce effective antibody-dependent cellular cytotoxicity against B-lymphoid tumor cells., Cancer Lett. Apr. 28, 2011;303(2):128-39.
Skera, Arne, 'Anticalins': a new class of engineered ligand-binding proteins with antibody-like properties., J Biotechnol. Jun. 2001;74(4):257-75.
Skera, Arne, Engineered protein scaffolds for molecular recognition., J Mol Recognit. Jul.-Aug. 2000;13(4):167-87.
Horton et al. Potent in vitro and in vivo activity of an Fc-engineered anti-CD19 monoclonal antibody against lymphoma and leukemia., Cancer Res, 2008, vol. 68, 8049-8057.
Kermer et al., An antibody fusion protein for cancer immunotherapy mimicking IL-15 trans-presentation at the tumor site., Mol Cancer Ther. Jun. 2012;11(6):1279-8.
Ortiz-Sánchez et al., Antibody-cytokine fusion proteins: applications in cancer therapy., Expert Opin Biol Ther. May 2008 ; 8(5): 609-632.
Zhu et al., Novel Human Interleukin-15 Agonists., J Immunol Sep. 15, 2009, 183 (6) 3598-3607.
Xia et al., In vivo effect of recombined IL-15/Fc fusion protein on EAU. Sichuan Da Xue Xue Bao Yi Xue Ban. Nov. 2008;39(6) 944-949.
Wu et al., IL-15Ra-IgG1-Fc Enhances IL-2 and IL-15 Anti-tumor Action through NK and CD8+ T Cells Proliferation and Activation., Journal of Molecular Cell Biology, vol. 2, Issue 4, Aug. 2010, pp. 217-222.
Ridgway et al., 'Knobs-into-holes' engineering of antibody CH3 domains for heavy chain heterodimerization., Protein Engineering, Design and Selection, vol. 9, Issue 7, Jul. 1996, pp. 617-621.
Carter P. Bispecific human IgG by design. J Immunol Methods. Feb. 1, 2001;248(1-2):7-15. doi: 10.1016/S0022-1759(00)00339-2. PMID: 11223065.
Atwell et al., Stable heterodimers from remodeling the domain interface of a homodimer using a phage display library 1 ..Journal of Molecular Biology, vol. 270, Issue 1,1997,pp. 26-35, ISSN 0022-2836, https://doi.org/10.1006/jmbi.1997.1116.
Merchant, et al., An efficient route to human bispecific IgG, Nature Biotechnology, 1998, vol. 16, pp. 677-681.
Klein, et al., Progress in overcoming the chain association issue in bispecific heterodimeric IgG antibodies, mAbs, Nov.-Dec. 2012, vol. 4, issue 6, pp. 653-663, doi: 10.4161/mabs.21379, Epub Aug. 27, 2012.
Deshpande et al., (2013), Kinetic analysis of cytokine-mediated receptor assembly using engineered FC heterodimers. Protein Science, 22: 1100-1108. https://doi.org/10.1002/pro.2285.
Dumont et al. Monomeric Fc Fusions. BioDrugs 20, 151-160 (2006). https://doi.org/10.2165/00063030-200620030-00002.
Belladonna et al., (2013) Bioengineering heterodimeric cytokines: turning promiscuous proteins into therapeutic agents, Biotechnology and Genetic Engineering Reviews, 29:2, 149-174, DOI: 10.1080/02648725.2013.801228.
Hinrichs, Christian S., Can interleukin-15 keep its therapeutic promise? Science Translational Medicine Mar. 7, 2018:vol. 10, Issue 431, eaar7532, DOI: 10.1126/scitranslmed.aar7532.
Rubinstein et al., Converting IL-15 to a superagonist by binding to soluble IL-15R{alpha}. Proc Natl Acad Sci U S A. Jun. 13, 2006;103(24):9166-71. doi: 10.1073/pnas.0600240103. Epub Jun. 6, 2006. PMID: 16757567; PMCID: PMC1482584.
Stoklasek et al., Combined IL-15/IL-15Ralpha immunotherapy maximizes IL-15 activity in vivo. J Immunol. Nov. 1, 2006;177(9):6072-80. doi: 10.4049/jimmunol.177.9.6072. PMID: 17056533; PMCID: PMC2847275.
Landolfi NF. A chimeric IL-2/Ig molecule possesses the functional activity of both proteins. J Immunol. Feb. 1, 1991;146(3):915-9. PMID: 1988502.
Zheng et al., Administration of noncytolytic IL-10/Fc in murine models of lipopolysaccharide-induced septic shock and allogeneic islet transplantation., J Immunol May 15, 1995, 154 (10) 5590-5600.
Low, et al., Oral and pulmonary delivery of FSH-Fc fusion proteins via neonatal Fc receptor-mediated transcytosis, Human Reproduction, vol. 20, Issue 7, Jul. 2005, pp. 1805-1813.
Kim et al., Targeting the IL-15 Receptor with an Antagonist IL-15 Mutant/Fcγ2a Protein Blocks Delayed-Type Hypersensitivity., J Immunol Jun. 15, 1998, 160 (12) 5742-5748.
Larrick et al., 2013, Inflammation, Advancing Age and Nutrition. D26 Chapter 28. Trophokines: Novel Therapy for Senescence-Related Fibrosis htto://dx rlo1.ora/10 1016/B978-0-12-397803-5.00028-9.
Mortier et al., Soluble interleukin-15 receptor alpha (IL-15R alpha)-sushi as a selective and potent agonist of IL-15 action through IL-15R beta/gamma. Hyperagonist IL-15 x IL-15R alpha fusion proteins. J Biol Chem. Jan. 20, 2006;281(3):1612-9. doi: 10.1074/jbc.M508624200. Epub Nov. 11, 2005. PMID: 16284400.
Wu J. IL-15 Agonists: The Cancer Cure Cytokine. J Mol Genet Med. Oct. 28, 2013;7:85. doi: 10.4172/1747-0862.1000085. PMID: 24587813; PMCID: PMC3938108.
C. Spiess et al., J. Biol. 288(37):26583- 93 (2013), Development of a D30 Human lgG4 Bispecific Antibody for Dual Targeting of Interleukin-4 (IL-4) and Interleukin-13 (IL-13) Cytokines.
Hopp et al. 1988. "A Short Polypeptide Marker Sequence Useful for Recombinant Protein Identification and Purification" Nat. Biotechnol. 6, 1204-1210.
Budagian et al., IL-15/IL-15 receptor biology: a guided tour through an expanding universe., Cytokine Growth Factor Rev. Aug. 2006;17(4):259-8.
Bodnar et al., A biophysical approach to IL-2 and IL-15 receptor function: Localization, conformation and interactions., Immunology Letters 116 (2008) 117-125.
Numerof et al., Cytokines as Potential Therapeutic Targets for Inflammatory Skin Diseases., Springer-Verlag, Berlin Heidelberg 2006.
Dumont, Francis J. (2005) lnterleukin-2 family cytokines: potential for therapeutic immmunoregulation, Expert Opinion on Therapeutic Patents, 15:5, 521-554.
Savio et al., IL-15: a relevant cytolcine for lymphoid homeostasis and autoimmune diseases., Biotecnologia Ap/icada 2006;23:87-93.
Lichtenegger et al., Targeting LAG-3 and PD-1 to Enhance T Cell Activation by Antigen-Presenting Cells., Front. Immunol. Feb. 27, 2018; 9: 385; pp. 1-12.
Guo et al., Immunobiology of the IL-15/IL-15Ra complex as an antitumor and antiviral agent., Cytokine Growth Factor Rev. Dec. 2017; 38: 10-21.
Ng et al., Heterodimeric IL15 Treatment Enhances Tumor Infiltration, Persistence, and Effector Functions of Adoptively Transferred Tumor-specific T Cells in the Absence of Lymphodepletion., Clin. Cancer Res. Jun. 2017; 23 (11): 2817-30.
Liang et al., Targeting IFNa to tumor by anti-PD-L1 creates feedforward antitumor responses to overcome checkpoint blockade resistance ., Nat. Commun. Nov. 2, 2018; 9 (1): 4586.
Chen et al., Therapeutic efficacy of an anti-PD-L1 antibody based immunocytokine in a metastatic mouse model of colorectal cancer., Biochem. Biophys. Res. Commun. Nov. 11, 2016; 480 (2): 160-5.
Kiefer et al., Immunocytokines and bispecific antibodies: two complementary strategies for the selective activation of immune cells at the tumor site., Immunol. Rev. Mar. 2016; 270 (1): 178-92; author manuscript; pp. 1-27.
Kim et al., IL-15 superagonist/IL-15RαSushi-Fc fusion complex (IL-15SA/IL-15RαSu-Fc; ALT-803) markedly enhances specific subpopulations of NK and memory CD8+ T cells, and mediates potent anti-tumor activity against murine breast and colon carcinomas., Oncotarget. Mar. 29, 2016; 7 (13): 16130-45.
Rogers et al., Molecular characterization of immunoglobulin D in mammals: immunoglobulin heavy constant delta genes in dogs, chimpanzees and four old world monkey species., Immunology. May 2006; 118 (1): 88-100.

(56) References Cited

OTHER PUBLICATIONS

Rowley J. et al., Inhibition of tumor growth by NK1. 1+ cells and CD8+ T cells activated by IL-15 through receptor β/common γ signaling in trans, The Journal of Immunology, 2008, V. 181, N. 12, p. 8237-8247, p. 8237.

Shen J. et al., Single variable domain-IgG fusion: a novel recombinant approach to Fc domain-containing bispecific antibodies, Journal of Biological Chemistry, 2006, V. 281, N. 16, p. 10706-10714, p. 10713.

Chen X. et al., Fusion protein linkers: property, design and functionality, Advanced drug delivery reviews, 2013, V. 65, N. 10, p. 1 357-1369, the whole text, p. 1365.

Maeda Y. et al., Engineering of functional chimeric protein G-VargulaLuciferase, Analytical biochemistry, 1997, V. 249, N. 2, p. 147-152, the whole text, p. 148, p. 151.

Gasser B. et al., Antibody production with yeasts and filamentous fungi: on the road to large scale? Biotechnology letters, 2007, V. 29, N. 2, p. 201-212, p. 208.

An Z., Therapeutic monoclonal antibodies: from bench to clinic, John Wiley and Sons, 2011, 896 p., p. 350.

Burns W. R. et al., A high molecular weight melanoma-associated antigenspecific chimeric antigen receptor redirects lymphocytes to target human melanomas, Cancer research, 2010, V. 70, N. 8, p. 3027-3033, p. 3028.

Colman P. M., Effects of amino acid sequence changes on antibodyantigen interactions, Research in Immunology, 1994, V. 145, N. 1, p. 33-36, c.33.

Safdari Y. et al., Antibody humanization methods-a review and update, Biotechnology and Genetic Engineering Reviews, 2013, V. 29, N. 2, p. 175-186, p. 178, 180.

Teplyakov A. et al., Antibody modeling assessment II. Structures and models, Proteins: Structure, Function, and Bioinformatics, 2014, V. 82, N. 8, p. 1563-1582, the whole text, p. 1582).

U.S. Appl. No. 12/631,508, filed Dec. 4, 2009, Chari et al.

(No Author Name) "A method for making multispecific antibodies having heteromultimeric and common components", Expert Opinion on Therapeutic Patents, Genentech, Inc. (1999) 9(6): 785-790, pp. 785-790.

"Polythene Glycol and Derivatives for Advanced PEGylation", Catalog 2005-2006, Nektar Therapeutics.

"Xencor Provides Data Updates on XmaB Bispecific Antibody Program and Announces Presentations at Upcoming American Society of Hematology 2014 Annual Meeting", Nov. 6, 2014, XP055255549, retrieved from the internet: http://files.shareholder.com/downloads/AMDA-2B2V8N/0x0x792404/77590b72-837a-4085-bc55-78fa500638dc/XNCR_News_2014_11_6_General_Releases.pdf.

Abbott Laboratories, Strategies and Current Approaches for Improving Drug-Like-Properties During Biologies Drug Candidate Selection, AAPS Webinar—Nov. 10, 2011.

Adams, et al., Avidity-Mediated Enhancement of In vivo Tumor Targeting by Single-Chain Fv Dimers, Clin Cancer Res, 2006, vol. 12(5), pp. 1599-1605, doi:10.1158/1078-0432.CCR-05-2217.

Alberola-lla et al., Stimulation Through the TCR/CD3 Complex Up-Regulates the CD2 Srface Expression on Human T Lymphocytes, Feb. 15, 1991.

Alibaud et al., A New Monoclonal Anti-CD3? Antibody Reactive on Paraffin Sections, Journal of Histochemistry & Cytochemistry, 2000, vol. 48, p. 1609.

An, et al., IgG2m4, an engineered antibody isotype with reduced Fc function, mAbs, 2009, vol. 1, Issue 6, pp. 572-579, www.landesbioscience.com/journals/mabs/article/10185.

Aplin et al., , Preparation, properties, and applications of carbohydrate conjugates of proteins and lipids, 1981, CRC Crit. Rev. Biochem., pp. 259-306.

Arnett, et al., Crystal structure of a human CD3-ε/σ dimer in complex with a UCHT1 single-chain antibody fragment, PNAS, 2004, vol. 101, No. 46, pp. 16268-16273.

Asano, et al., Cytotoxic enhancement of a bispecific diabody (Db) by format conversion to tandem single-chain variable fragment (taFv): The Case of the hEx3 Diabody, JBC Papers in Press, 2010, http://www.jbc.org/cgi/doi/10.1074/jbc.M110.172957.

Asano, et al., Highly Effective Recombinant Format of a Humanized IgG-like Bispecific Antibody for Cancer Immunotherapy with Retargeting of Lymphocytes to Tumor Cells, The Journal of Biological Chemistry, 2007, vol. 282, No. 38, pp. 27659-27665.

Atwell, et al., Stable Heterodimers from Remodeling the Domain Interface of a Homodimer using a Phage Display Library, J. Mol. Biol., 1997, vol. 270, pp. 26-35.

Baca et al., Antibody humanization using monovalent phage display, 1997, J. Biol. Chem. 272(16):10678-10684.

Baeuerle, et al., Response to Letter, "Correct TandAb protein," Molecular Immunology, 2007, vol. 44, p. 3084.

Baeuerle, et al., Review—Bispecific T-Cell Engaging Antibodies for Cancer Therapy, Cancer Res, 2009, vol. 69: (12), pp. 4941-4944.

Barbas, et al. In vitro evolution of a neutralizing human antibody to human immunodeficiency virus type 1 to enhance affinity and broaden strain cross-reactivity, 1994, Proc. Nat. Acad. Sci, USA 91:3809-3813.

Bargou et al., Tumor Regression in Cancer Patients by Very Low Doses of a T Cell-Engaging Antibody, Science, 2008, vol. 321, pp. 974-977.

Bernett et al., Multiple Bispecific Checkpoint Combinations Promote T cell activation., Nov. 11, 2016, retrieved from the internet: http://files.shareholder.com/downloads/AMDA-2B2V8N/0x0x916283/67AE1A8B-40E8-4316-9F79-384D06B2C395/XNCR_SITC_2016_PD1xCTLA4_Poster126_12Nov2016.pdf.

Bhatt, Sea Lane—DDD presentation, "Surrobodies™—A Novel Approach to Bispecifics . . . ," Aug. 8, 2012.

Bibollet-Ruche et al., The Quality of Chimpanzee T-Cell Activation and Simian Immunodeficiency Virus/Human Immunodeficiency Virus Susceptibility Achieved via Antibody-Mediated T-Cell Receptor/CD3 Stimulation Is a Function of the Anti-CD3 Antibody Isotype, Jul. 30, 2008.

Biochemica, Your apoptosis specialist, 1999, No. 2, pp. 34-37 (Roche Molecular Biochemicals).

Bird et al., Single-chain antigen-binding proteins, 1988, Science 242:423-426.

Bluemel, et al., Epitope distance to the target cell membrane and antigen size determine the potency of T cell-mediated lysis by BiTE antibodies specific for a large melanoma surface antigen, Cancer Immunol Immunother, 2010, vol. 59(8), pp. 1197-1209.

Borras, et al., Generic Approach for the Generation of Stable Humanized Single-chain Fv Fragments from Rabbit Monoclonal Antibodies, The Journal of Biological Chemistry, 2010, vol. 285, No. 12, pp. 9054-9066.

Bortoletto, Nicola et al., "Optimizing anti-CD3 affinity for effective T cell targeting against tumor cells.", Eur J Immunol. Nov. 2002;32(11):3102-7.

Boswell et al., Effects of Charge on Antibody Tissue Distribution and Pharmacokinetics, 2010, Bioconjugate Chem, 21 (21):2153-2163.

Brandl, et al., Bispecific antibody fragments with CD20 3 CD28 specificity allow effective autologous and allogeneic T-cell activation against malignant cells in peripheral blood and bone marrow cultures from patients with B-cell lineage leukemia and lymphoma, Experimental Hematology, 1999, vol. 27, pp. 1264-1270.

Brinkmann , et al., presentation slideshow—"Roche Penzberg & Roche date Glycart, Schlieren: Centers of Excellence for Recombinant Proteins".

Brinkmann, et al., A recombinant immunotoxin containing a disulfide-stabilized Fv fragment, Proc. Natl. Acad. Sci. USA, 1993, vol. 9 0, pp. 7538-7542.

Cao, et al., Oligomerization is required for the activity of recombinant soluble LOX-1., Febs J. Sep. 2009;276(17):4909-20. doi: 10.1111/j.1742-4658.2009.07190.x. Epub Jul. 31, 2009.

Carpenter, et al., Non-Fc Receptor-Binding Humanized Anti-CD3 Antibodies Induce Apoptosis of Activated Human T Cells, J. Immunol., 2000, vol. 165, No. 11, pp. 6205-6213.

Carter et al., Antibody-drug conjugates for cancer therapy, 2008, Cancer J. 14(3):154-169.

Carter et al., Humanization of an anti-p185HER2 antibody for human cancer therapy, 1992, Proc Natl Acad Sci USA 89:4285-9.

(56) References Cited

OTHER PUBLICATIONS

Castoldi, et al., Molecular characterization of novel trispecific ErbB-cMet-IGF1R antibodies and their antigen-binding properties, Protein Engineering, Design & Selection, 2012, vol. 25, No. 10, pp. 551-559.
Cemerski, et al., Suppression of mast cell degranulation through a dual-targeting tandem IgE-IgG Fc domain biologic engineered to bind with high affinity to FcyRIIb., Immunol Lett. Mar. 30, 2012;143(1):34-43. doi: 10.1016/j.imlet.2012.01.008. Epub Jan. 25, 2012.
Chames et al., Bispecific antibodies for cancer therapy—The light at the end of the tunnel?, mAbs, 2009, vol. 1, Issue 6, pp. 1-9.
Chang, et al., Monoclonal antibodies against oxidized low-density lipoprotein bind to apoptotic cells and inhibit their phagocytosis by elicited macrophages: evidence that oxidation-specific epitopes mediate macrophage recognition., Proc Natl Acad Sci USA. May 25, 1999;96(11):6353-8.
Chari et al., Immunoconjugates containing novel maytansinoids: promising anticancer drugs, 1992, Cancer Research 52: 127-131.
Chatal, 1989, Monoclonal Antibodies in Immunoscintigraphy, CRC Press (Book Abstract).
Chelius, et al., Structural and functional characterization of the trifunctional antibody catumaxomab, mAbs, 2010, vol. 2, Issue 3, pp. 309-319.
Chichili et al., A CD3xCD123 bispecific DART for redirecting host T cells to myelogenous leukemia: preclinical activity and safety in nonhuman primates., Sci Transl Med. May 27, 2015;7(289):289ra82. doi: 10.1126/scitranslmed.aaa5693.
Chichili et al., Co-targeting of PD-1 and CTLA-4 Inhibitory Pathways with Bispecific DART® and TRIDENT™ Molecules., Apr. 4, 2017, retrieved from the internet: http://files.shareholder.com/downloads/AMDA-278VRP/0x0x935572/8CC86417-40BA-41C0-935D-EF1B7DB0B5BB/AACR_2017_-_Co-targeting_PD-1_and_CTLA-4_Inhibitory_Pathways_with_DART_and_TRIDENT_Molecules.pdf.
Chothia et al., Canonical structures for the hypervariable regions of immunoglobulins, 1987, J. Mol. Biol. 196:901-917.
Chothia, et al., Structural Determinants in the Sequences of Immunoglobulin Variable Domain, J. Mol. Biol., 1998, vol. 278, pp. 457-479.
Chu et al., Immunotherapy with Long-Lived Anti-CD123 x Anti-CD3 Bispecific Antibodies Stimulates Potent T Cell Mediated Killing of Human AML Cell Lines and of CD123+ Cells In Monkeys: A Potential Therapy for Acute Myelogenous Leukemia, Blood 2014, 124:2316.
Chu et al., Immunotherapy with Long-Lived Anti-CD123 x Anti-CD3 Bispecific Antibodies Stimulates Potent T Cell-Mediated Killing of Human B Cell Lines and of Circulating and Lymphoid B Cells in Monkeys: A Potential Therapy for B Cell Lymphomas and Leukemias, Blood 2014, 124:3111.
Chu et al., Inhibition of B cell receptor-mediated activation of primary human B cells by coengagement of CD19 and FcgammaRIIb with Fc-engineered antibodies., Mol Immunol. Sep. 2008;45(15):3926-33. doi: 10.1016/j.molimm.2008.06.027. Epub Aug. 8, 2008.
Chu et al., Reduction of total IgE by targeted coengagement of IgE B-cell receptor and FcyRIIb with Fc-engineered antibody., J Allergy Clin Immunol. Apr. 2012;129(4):1102-15. doi: 10.1016/j.jaci.2011.11.029. Epub Jan. 16, 2012.
Conrad, et al., TCR and CD3 Antibody Cross-Reactivity in 44 Species, Cytometry Part A, 2007, vol. 71A, pp. 925-933.
Conrath, et al., Antigen Binding and Solubility Effects upon the Veneering of a Camel VHH in Framework-2 to Mimic a VH, J. Mol. Biol. , 2005, vol. 350, pp. 112-125.
Counterman et al., "Volumes of Individual Amino Acid Residues in Gas-Phase Peptide Ions.", J. Am. Chem. Soc., 1999, 121 (16), pp. 4031-4039.
Cuesta, et al., Multivalent antibodies: when design surpasses evolution, Trends in Biotechnology, 2010, vol. 28, No. 7, pp. 355-362, doi:10.1016/j.tibtech.2010.03.007.

D'Argouges, et al., Combination of rituximab with blinatumomab (MT103/MEDI-538), a T cell-engaging CD19-/CD3-bispecific antibody, for highly efficient lysis of human B lymphoma cells, Leukemia Research, 2009, vol. 33, pp. 465-473.
Davies et al., Expression of GnTIII in recombinant anti-CD20 CHO production cell line: expression of antibodies with altered glycoforms leads to an increase in ADCC through higher affinity for FCyRIII, 2001, Biotechnol Bioeng 74:288-294.
Davila, et al., Efficacy and Toxicity Management of 19-28z CAR T Cell Therapy in B Cell Acute Lymphoblastic Leukemia, Sci. Transl. Med., 2014, vol. 6, Issue 224, pp. 1-10, 224ra25.
Davis, et al., SEEDbodies: fusion proteins based on strand-exchange engineered domain (SEED) $C_H3$ heterodimers in an Fc analogue platform for asymmetric binders or immunofusions and bispecific antibodies, Protein Engineering, Design & Selection, 2010, vol. 23, No. 4 pp. 195-202.
De Groot et al., De-lmmunization of Therapeutic Proteins By T-Cell Epitope Modification, 2005, Dev. In Biologicals, 2005, 122:171-194.
De Pascalis et al., Grafting of "abbreviated" complementarity-determining regions containing specificity-determining residues essential for ligand contact to engineer a less immunogenic humanized monoclonal antibody, 2002, J. Immunol. 169:3076-3084.
Del Nagro et al., *A critical role for complement C3d and the B cell coreceptor* (CD19/CD21) *complex in the initiation of inflammatory arthritis.*, J. Immunol. Oct. 15, 2005;175(8):5379-89.
Demarest et al., Antibody therapeutics, antibody engineering, and the merits of protein stability, Current Opinin in Drug Discovery & Development, 2008 11(5): 675-587, Sep. 11, 2008.
Deyev, et al., Multivalency: the hallmark of antibodies used for optimization of tumor targeting by design, BioEssays, 2008, vol. 30, pp. 904-918.
DiGiammarino et al., Ligand association rates to the inner-variable-domain of a dual-variable-domain immunoglobulin are significantly impacted by linker design, mAbs3:5, 1-8; Sep.-Oct.; 3(5):487-94, Landes Bioscience, Sep. 1, 2011.
DiGiandomenico et al., *A multifunctional bispecific antibody protects against Pseudomonas aeruginosa.*, Sci Transl Med. Nov. 12, 2014;6(262):262ra155. doi: 10.1126/scitranslmed.3009655.
Dixon, et al., Activation of Human T Lymphocytes by Crosslinking of Anti-CD3 Monoclonal Antibodies, Journal of Leukocyte Biology, 1989, vol. 46, pp. 214-220.
Dong et al., A stable IgG-like bispecific antibody targeting the epidermal growth factor receptor and the type I insulin-like growth factor receptor demonstrates superior anti-tumor activity, mAbs 3:3, May-Jun. 2011: 273-288, May 1, 2011.
Doronina , Development of potent monoclonal antibody auristatin conjugates for cancer therapy, 2003, Nat Biotechnol 21(7):778-784.
Dreier, et al., Extremely Potent, Rapid and Costimulation-lndependent Cytotoxic T-cell Response Against Lymphoma Cells Catalyzed by a Single-Chain Bispecific Antibody, Int. J. Cancer, 2002, vol. 100, pp. 690-697.
Dreier, et al., T Cell Costimulus-lndependent and Very Efficacious Inhibition of Tumor Growth in Mice Bearing Subcutaneous or Leukemic Human B Cell Lymphoma Xenografts by a CD19-/CD3-Bispecific Single-Chain Antibody Construct, The Journal of Immunology, 2003, vol. 170, pp. 4397-4402.
Dubowchik et al., Receptor-mediated and enzyme-dependent targeting of cytotoxic anticancer drugs, 1999, Pharm. Therapeutics 83:67-123.
Ducry et al., Antibody-drug conjugates: linking cytotoxic payloads to monoclonal antibodies, 2010, Bioconjugate Chem. 21:5-13.
Dudgeon, et al., General strategy for the generation of human antibody variable domains with increased aggregation resistance, PNAS Early Edition, 2012, pp. 10879-10884, www.pnas.org/cgi/doi/10.1073/pnas.1202866109 & Supporting Information.
Duke, et al., Measurement of apoptosis and other forms of cell death, 2004, Curr protocols immunol. 3.17.1-3.17.16.
Duksin et al., Relationship of the structure and biological activity of the natural homologues of tunicamycin, 1982, J. Biol. Chem. 257:3105.
Duval, et al., A Bispecific Antibody Composed of a Nonneutralizing Antibody to the gp41 Immunodominant Region and an Anti-CD89

(56) References Cited

OTHER PUBLICATIONS

Antibody Directs Broad Human Immunodeficiency Virus Destruction by Neutrophils, Journal of Virology, 2008, pp. 4671-4674, doi:10.1128/JVI.02499-07.
Edge et al., Deglycosylation of glycoproteins by trifluoromethanesulfonic acid, 1981, Anal. Biochem. 118:131.
Elliott, et al., Antiparallel Conformation of Knob and Hole Aglycosylated HalfAntibody Homodimers Is Mediated by a CH2-CH3 Hydrophobic Interaction, Journal of Molecular Biology, 2014, vol. 426, Issue 9, pp. 1947-1957.
Feldmann et al., Novel Humanized and Highly Efficient Bispecific Antibodies Mediate Killing of Prostate Stem Cell Antigen-Expressing Tumor Cells by CD8+ and CD4+ T cells, Aug. 8, 2012, The Journal of Immunology, 189:3249-3259.
Feldmann et al., Retargeting of T Cells to Prostate Stem Cell Antigen Expressing Tumor Cells: Comparison of Different Antibody Formats, Dec. 28, 2010, The Prostate; 71:998-1011.
Fernandes, et al., T Cell Receptors are Structures Capable of Initiating Signaling in the Absence of Large Conformational Rearrangements, The Journal of Biological Chemistry, 2012, vol. 287, No. 16, pp. 13324-13335.
Fischer, Nicolas et al., "Bispecifc antibodies: molecules that enable novel therapeutic strategies", 2007, vol. 74, pp. 3-14.
Foreman, et al., ErbB3 Inhibitory Surrobodies Inhibit Tumor Cell Proliferation In Vitro and In Vivo, Mol Cancer Ther, 2012, vol. 11(7), pp. 1411-1420.
Foreman, et al., PEGS poster, "ErbB3 Inhibitory Surrobodies Inhibit Tumor Cell Proliferation In Vitro and In Vivo," 2012.
Fraker et al., Crystal structure of peptide cyclo-(D-VAL-L-PRO-L-VAL-D-PRO)$_3$, 1978, Biochem. Biophys. Res. Commun. 80(4):849-57.
Francois, et al., Construction of a Bispecific Antibody Reacting with the α- and ß-Chains of the Human IL-2 Receptor, The Journal of Immunology, May 15, 1993, vol. 150, No. 10, pp. 4610-4619.
F-star Modular Antibodies Fact Sheet, Apr. 2008, "Modular Antibody Technology" (w/ reference to Ruker WO 2006/072620 A1).
F-star Modular Antibodies Press Release, Mar. 28, 2008, "Antibody Engineering Company F-Star Buys Back Royalty Obligations. TVM Capital Joins Investor Syndicate.".
Fudenberg, et al., Serologic Demonstration of Dual Specificity of Rabbit Bivalent Hybrid Antibody, The Journal of Experimental Medicine, 1964, vol. 119(1), pp. 151-166.
Ganesan, et al., FcγRIIb on Liver Sinusoidal Endothelium Clears Small Immune Complexes, The Journal of Immunology, Nov. 15, 2012, vol. 189 No. 10, pp. 4981-4988.
GenBank AAA38124.1, immunoglobulin heavy-chain VJ region [Mus musculus] Protein/NCBI, Apr. 1993.
GenBank AAA39180.1, immunoglobulin light-chain VJ region [Mus musculus] Protein/NCBI, Apr. 1993.
Ghendler et al., One of the CD3ε Subunits within a T Cell Receptor Complex Lies in Close Proximity to the Cß FG Loop, J. Exp. Med., 1998, vol. 187, No. 9. pp. 1529-1536.
Ghetie et al., Multiple roles for the major histocompatibility complex Class I-related receptor FcRn, 2000, Annu Rev Immunol 18:739-766.
Gilliland, et al., Universal bispecific antibody for targeting tumor cells for destruction by cytotoxic T cells, Proc. Natl. Acad. Sci. USA, 1988, vol. 85, pp. 7719-7723.
Gorman et al., Reshaping a therapeutic CD4 antibody, Proc. Natl. Acad. Sci. 0508 r 7 USA 88:4181-4185, May 1991.
Grodzki & Bernstein, "Antibody Purification: Ion-Exchange Chromatography.", Methods Mol Biol 2010 ;588:27-32.
Gunasekaran et al., Enhancing Antibody Fc Heterodimer Formation through Electrostatic Steering Effects, Journal of Biological Chemistry, vol. 285, No. 25, pp. 19637-10946, Apr. 16, 2010 & Supplementary Tables.
Haagen, et al., The Efficacy of CD3 x CD19 Bispecific Monoclonal Antibody (BsAb) in a Clonogenic Assay: The Effect of Repeated Addition of BsAb, and Interleukin-2, Blood, 1995, vol. 85, No. 11, pp. 3208-3212.

Hakimuddin et al., A chemical method for the deglycosylation of proteins, 1987, Arch. Biochem. Biophys. 259:52.
Hamel, et al., The Role of the $V_L$- and $V_H$-Segments in the Preferential Reassociation of Immunoglobulin Subunits, Molecular Immunology, 1986, vol. 23, No. 5, pp. 503-510.
Hawkins et al., Selection of phage antibodies by binding affinity mimicking affinity maturation, 1992, J. Mol. Biol. 226:889-896.
Hayden-Ledbetter, et al., CD20-Directed Small Modular Immunopharmaceutical, TRU-015, Depletes Normal and Malignant B Cells, Clin Cancer Res, 2009, vol. 15(8), pp. 2739-2746.
He et al., Humanization and pharmacokinetics of a monoclonal antibody with specificity for both E- and P-selectin, 1998, J. Immunol. 160:1029-1035.
Hedvat et al., Dual Blockade of PD-1 and CTLA-4 with Bispecific Antibodies Promotes Human T cell Activation and Proliferation., Nov. 11, 2016, retrieved from the internet: http://files.shareholder.com/downloads/AMDA-2B2V8N/0x0x916284/D8084990-61EC-4DFE-8B76-60CF58B8C06F/CPI_bispecifics.pdf.
Hennecke et al., "Non-repetitive single-chain Fv linkers selected by selectively infective phage (SIP) technology.", Protein Eng. May 1998;11(5):405-10.
Hernandez-Caselles, et al., A study of CD33 (SIGLEC-3) antigen expression and function on activated human T and NK cells: two isoforms of CD33 are generated by alternative splicing, J. Leukoc. Biol., 2006, vol. 79, pp. 46-58.
Hexham, et al., Influence of relative binding affinity on efficacy in a panel of anti-CD3 scFv immunotoxins, Molecular Immunology, 2001, vol. 38, pp. 397-408.
Hinman et al., Preparation and characterization of monoclonal antibody conjugates of the calicheamicins: a novel and potent family of antitumor antibodies, 1993 Cancer Res. 53:3336-3342.
Hoffmann, et al., Serial killing of tumor cells by cytotoxic T cells redirected with a CD19-/CD3-bispecific single-chain antibody construct, Int. J. Cancer, 2005, vol. 115, pp. 98-104.
Holliger et al., "Diabodies": Small Bivalent and bispecific antibody fragments, 1993, Proc. Natl. Acad. Sci. U.S.A. 90:6444-6448.
Holliger et al., Engineering bispecific antibodies, 1993, Current Opinion Biotechnol. 4:446-449.
Houtenbos, et al., The novel bispecific diabody αCD40/αCD28 strengthens leukaemic dendritic cell-induced T-cell reactivity, British Journal of Haematology, 2008, vol. 142, pp. 273-283.
Hu et al., Minibody: A novel engineered anti-carcinoembryonic antigen antibody fragment (single-chain Fv-$C_H3$) which exhibits rapid, high-level targeting of xenografts, 1996, Cancer Res. 56:3055-3061.
Huston et al., Protein engineering antibody binding sites: recovery of specific activity in an anti-digoxin single-chain Fv analogue produced in *Escherichia coli*, 1988, Proc. Natl. Acad. Sci. U.S.A. 85:5879-5883.
Igawa et al., Reduced elimination of IgG antibodies by engineering the variable region, 2010, PEDS. 23(5): 385-392.
Igawa, $V_H/V_L$ interface engineering to promote selective expression and inhibit conformational isomerization of thrombopoietin receptor agonist single-chain diabody, Protein Engineering, Design & Selection, 2010, vol. 23, No. 8, pp. 667-677.
Ishigaki et al., Impact of Plasma Oxidized Low-Density Lipoprotein Removal on Atherosclerosis., Circulation 118: 75-83, 2008.
Jackson et al., In vitro antibody maturation, 1995, J. Immunol. 154(7):3310-9.
Jäger, et al., The Trifunctional Antibody Ertumaxomab Destroys Tumor Cells That Express Low Levels of Human Epidermal Growth Factor Receptor 2, Cancer Res, 2009, vol. 69(10), pp. 4270-4276.
Jefferis et al., Interaction sites on human IgG-Fc for FcγR: current models, 2002, Immunol Lett 82:57-65.
Jespers, et al., Crystal Structure of HEL4, a Soluble, Refoldable Human $V_H$ Single Domain with a Germ-line Scaffold, J. Mol. Biol., 2004, vol. 337, pp. 893-903.
Jimenez, et al., A recombinant, fully human, bispecific antibody neutralizes the biological activities mediated by both vascular endothelial growth factor receptors 2 and 3, Mol Cancer Ther, 2005, vol. 4(3), pp. 427-434.

(56) References Cited

OTHER PUBLICATIONS

Jin, et al., MetMAb, the One-Armed 5D5 Anti-c-Met Antibody, Inhibits Orthotopic Pancreatic Tumor Growth and Improves Survival, Cancer Res 2008, vol. 68, pp. 4360-4368.
Johnson et al., Anti-tumor activity of CC49-doxorubicin immunoconguates, 1995, Anticancer Res. 15:1387-93.
Johnson, et al., Effector Cell Recruitment with Novel Fv-based Dual-affinity Re-targeting Protein Leads to Potent Tumor Cytolysis and in Vivo B-cell Depletion, J. Mol. Biol., 2010, vol. 399, pp. 436-449.
Jones et al., Replacing the complementarity-determining regions in a human antibody with those from a mouse, 1986, Nature 321:522-525.
Jordan et al., Structural understanding of stabilization patterns in engineered bispecific Ig-like antibody molecules, Proteins 2009; 77:832-841, Jun. 19, 2009.
Jung, et al., Design of interchain disulfide bonds in the framework region of the Fv fragment of the monoclonal antibody B3, Proteins, 1994, vol. 19(1), pp. 35-47.
Jung, et al., Target Cell-restricted Triggering of the CD95 (APO-1/Fas) Death Receptor with Bispecific Antibody Fragments, Cancer Research, 2001, vol. 61, pp. 1846-1848.
Jungbluth et al., A monoclonal antibody recognizing human cancers with amplification/overexpression of the human epidermal growth factor receptor, 2003, Proc Natl Acad Sci USA. 100(2):639-44.
Kabat et al., 1991, Sequences of proteins of immunological interest, Department of Health and Human Services, Bethesda, vol. 1, $5^{th}$ Ed.
Kakutani et al., Accumulation of LOX-1 ligand in plasma and atherosclerotic lesions of Watanabe heritable hyperlipidemic rabbits: identification by a novel enzyme immunoassay.,Biochem Biophys Res Commun. Mar. 23, 2001;282(1):180-5.
Kanakaraj, et al., Simultaneous targeting of TNF and Ang2 with a novel bispecific antibody enhances efficacy in an in vivo model of arthritis, mAbs, 2012, vol. 4, Issue 5, pp. 600-613, http://dx.doi.org/10.4161/mabs.21227 & Supplemental Data.
Kettleborough et al., Humanization of a mouse monoclonal antibody by CDR-grafting: the importance of framework residues on loop conformation, 1991, Protein Eng. 4(7):773-83.
Keyna, et al., Surrogate Light Chain-Dependent Selection of Ig Heavy Chain V Regions, J. Immunol., 1995, vol. 155, pp. 5536-5542.
Kharmate et al., Inhibition of tumor promoting signals by activation of SSTR2 and opioid receptors in human breast cancer cells., Cancer Cell Int. Sep. 23, 2013;13(1):93. doi: 10.1186/1475-2867-13-93.
Kiewe, et al., Phase I Trial of the Trifunctional Anti-HER2 x Anti-CD3 Antibody Ertumaxomab in Metastatic Breast Cancer, Clin Cancer Res., 2006, vol. 12(10), pp. 3085-3091.
Kim et al., "Localization of the site of murine IgG1 molecule that is involved in binding the murine intestinal Fc receptor," Eur. J. Immunol., 24:2429-2434, 1994.
Kim et al., Mutational approaches to improve the biophysical properties of human single-domain antibodies., Biochim Biophys Acta. Nov. 2014;1844(11): 1983-2001. doi: 10.1016/j.bbapap.2014.07.008. Epub Jul. 24, 2014.
Kipriyanov, et al., Bispecific CD3 x CD19 Diabody for T Cell-Mediated Lysis of Malignant Human B Cells, Int. J. Cancer, 1998. Vol. 77, pp. 763-772.
Kipriyanov, et al., Bispecific Tandem Diabody for Tumor Therapy with Improved Antigen Binding and Pharmacokinetics, J. Mol. Biol., 1999, vol. 293, pp. 41-56.
Kipriyanov, et al., Effect of Domain Order on the Activity of Bacterially Produced Bispecific Single-chain Fv Antibodies, J. Mol. Biol., 2003, vol. 330, pp. 99-111.
Kipriyanov, et al., Two amino acid mutations in an anti-human CD3 single chain Fv antibody fragment that affect the yield on bacterial secretion but not the affinity, Protein Engineering, 1997, vol. 10, No. 4, pp. 445-453.

Klein et al., Progression of metastatic human prostate cancer to androgen independence in immunodeficient SDIC mice, 1997, Nature Medicine 3: 402-408.
Klinger, et al., Immunopharmacologic response of patients with B-lineage acute lymphoblastic leukemia to continuous infusion of T cell-engaging CD19/CD3-bispecific BiTE antibody blinatumomab, Blood, 2012, vol. 119, No. 26, pp. 6226-6233.
Koristka, et al., Retargeting of Human Regulatory T Cells by Single-Chain Bispecific Antibodies, The Journal of Immunology, 2012, vol. 188, pp. 1551-1558, www.jimmunol.org/cgi/doi/10.4049/jimmunol.1101760.
Kostelny, et al., Formation of a Bispecific Antibody by the Use of Leucine Zippers, The Journal of Immunology 1992, vol. 148, pp. 1547-1553.
Krah et al., "Single-domain antibodies for biomedical applications.", Immunopharmacol Immunotoxicol. 2016;38(1):21-8. doi: 10.3109/08923973.2015.1102934. Epub Nov. 9, 2015.
Krauss et al., Specificity grafting of human antibody frameworks selected from a phage display library: generation of a highly stable humanized anti-CD22 single-chain Fv fragment, 2003, Protein Engineering 16(10):753-759.
Krupka, et al., CD33 target validation and sustained depletion of AML blasts in long-term cultures by the bispecific T-cell-engaging antibody AMG 330, Blood, 2014, vol. 123, No. 3, pp. 356-365, Prepublished online Dec. 3, 2013; doi:10.1182/blood-2013-08-523548 & Data Supplement.
Kung, et al., Monoclonal Antibodies Defining Distinctive Human T Cell Surface Antigens, Science, 1979, vol. 206, pp. 347-349.
Kuppen, peter et al., The development and purification of a bispecific antibody for lymphokine-activated killer cell targeting against the rat colon carcinoma CC531., Cancer Immunol Immunother. Jun. 1993;36(6):403-8.
Laszlo et al., Cellular determinants for preclinical activity of a novel CD33/CD3 bispecific T-cell engager (BiTE) antibody, AMG 330, against human AML, blood 2014 123: 554-561, Dec. 5, 2013.
Lau et al., Conjugation of Doxorubicin to monoclonal anti-carcinoembryonic antigen antibody via novel thiol-directed cross-linking regents, 1995, Bioorg-Med-Chem. 3(10):1299-1304.
Lau et al., Novel doxorubicin-monoclonal anti-carcinoembryonic antigen antibody immunoconjugate activity in vitro, 1995, Bioorg-Med-Chem. 3(10):1305-12.
Lazar Declaration, Dec. 27, 2010, pp. 1-4.
Lewis, et al., Generation of bispecific IgG antibodies by structure-based design of an orthogonal Fab interface, Nature Biotechnology, 2014, doi:10.1038/nbt.2797 & Supplemental Information.
Li, et al., Construction and characterization of a humanized anti-human CD3 monoclonal antibody 12F6 with effective immunoregulation functions, Immunology, 2005, vol. 116, pp. 487-498.
Lindhofer, et al., Preferential Species-Restricted Heavy/Light Chain Pairing in Rat/Mouse Quadromas: Implications for a Single-Step Purification of Bispecific Antibodies, The Journal of Immunology, 1995, vol. 155, pp. 219-225.
Ling, et al., Interspecies Scaling of Therapeutic Monoclonal Antibodies: Initial Look, J Clin Pharmacol, 2009, vol. 49, pp. 1382-1402, doi: 10.1177/0091270009337134.
Link, et al., Production and Characterization of a Bispecific IgG Capable of Inducing T-Cell-Mediated Lysis of Malignant B Cells, Blood, 1993, vol. 81, No. 12, pp. 3343-3349.
Linke, et al., Catumaxomab, Clinical development and future directions, mAbs, 2010, vol. 2, Issue 2, pp. 129-136.
Little, et al., Letter to the Editor, "Flawed TandAb production," Molecular Immunology, 2007, vol. 44, p. 3083.
Liu et al., Asymmetrical Fc Engineering Greatly Enhances Antibodydependent Cellular Cytotoxicity (ADCC) Effector Function and Stability of the Modified Antibodies, J. Biol. Chem. 2014, 289: 3571-3590, Dec. 5, 2013.
Liu et al., Eradication of large colon tumor xenografts by targeted delivery of maytansinoids, 1996 Proc. Natl. Acad. Sci. USA 93:8618-8623.
Liu, et al., Crystallization of a Deglycosylated T Cell Receptor (TCR) Complexed with an Anti-TCR Fab Fragment, The Journal of Biological Chemistry, 1996, vol. 271, No. 52, pp. 33639-33646.

(56) References Cited

OTHER PUBLICATIONS

Lode et al., Targeted therapy with a novel enediyene antibiotic calicheamicins oˈ1 effectively suppress growth and dissemination of liver metastases in a syngeneic model of murine neuroblastoma, 1998, Cancer Res. 58:2928.

Löffler, et al., A recombinant bispecific single-chain antibody, CD19 x CD3, induces rapid, and high lymphoma-directed cytotoxicity by unstimulated T lymphocytes, Blood, 2000, vol. 95, No. 6, pp. 2098-2103.

Lu, et al., A Fully Human Recombinant IgG-like Bispecific Antibody to Both the Epidermal Growth Factor Receptor and the Insulin-like Growth Factor Receptor for Enhanced Antitumor Activity, The Journal of Biological Chemistry, 2005, vol. 280, No. 20, pp. 19665-19672.

Lu, et al., Di-diabody: a novel tetravalent bispecific antibody molecule by design, Journal of Immunological Methods, 2003, vol. 279, pp. 219-232.

Lu, et al., Fab-scFv fusion protein: an efficient approach to production of bispecific antibody fragments, Journal of Immunological Methods, 2002, vol. 267, pp. 213-226.

Lu, et al., The effect of variable domain orientation and arrangement on the antigen-binding activity of a recombinant human bispecific diabody, Biochemical and Biophysical Research Communications, 2004, vol. 318, pp. 507-513.

Lum, et al., The new face of bispecific antibodies: targeting cancer and much more, Experimental Hematology, 2006, vol. 34, pp. 1-6.

Lutterbuese, et al., AACR Poster, "Conversion of Cetuximab, Panitumumab, Trastuzumab and Omalizumab into T Cell-engaging BiTE Antibodies Creates Novel Drug Candidates of High Potency," 2008.

Lutterbuese, et al., T cell-engaging BiTE antibodies specific for EGFR potently eliminate KRAS- and BRAF-mutated colorectal cancer cells, PNAS Early Edition, 2010, www.pnas.org/cgi/doi/10.1073/pnas.1000976107 & Supporting Information.

Ma, et al., Expression and Characterization of a Divalent Chimeric AntiHuman CD3 Single Chain Antibody, Scand.J.Immunol, 1996, vol. 43, pp. 134-139.

Mabry, et al., A dual-targeting PDGFRβ/VEGF-A molecule assembled from stable antibody fragments demonstrates anti-angiogenic activity in vitro and in vivo, mAbs, 2010, vol. 2, Issue 1, pp. 20-34; www.landesbioscience.com/journals/mabs/article/10498 & Supplemental Information.

Mabry, et al., Engineering of stable bispecific antibodies targeting IL-17A and IL-23, Protein Engineering, Design & Selection, 2009, vol. 23, No. 3, pp. 115-127; doi:10.1093/protein/gzp073 & Supplementary Figures 1-8.

Mack, et al., A small bispecific antibody construct expressed as a functional single-chain molecule with high tumor cell cytotoxicity, Proc. Natl. Acad. Sci. USA, 1995, vol. 92, pp. 7021-7025.

Mack, et al., Biologic Properties of a Bispecific Single-Chain Antibody Directed Against 17-1A (EpCAM) and CD3—Tumor Cell-Dependent T Cell Stimulation and Cytotoxic Activity, The Journal of Immunology, 1997, vol. 158, pp. 3965-3970.

MacroGenics Factsheet, Dual Affinity Re-Targeting ("DART") Platform, 2010.

Mandler et al., Immunoconjugates of geldanamycin and anti-HER2 Monoclonal antibodies: antiproliferative activity on human breast carcinoma cell lines, 2000, J. Nat. Cancer Inst. 92(19):1573-1581.

Mandler et al., Modifications in synthesis strategy improve the yield and efficacy of geldanamycin-herceptin immunoconjugates, 2002, Bioconjugate Chem. 13:786-791).

Mandler et al., Synthesis and evaluation of antiproliferative activity of a geldanaymcin-herceptin™ immunojugates, 2000, Bioorganic & Med. Chem. Letters 10:1025-1028.

Mandy, et al., Effect of Reduction of Several Disulfide Bonds on the Properties and Recombination of Univalent Fragments of Rabbit Antibody, The Journal of Biological Chemistry, 1963, vol. 238, No. 1, pp. 206-213.

Mandy, et al., Recombination of Univalent Subunits Derived from Rabbit Antibody, The Journal of Biological Chemistry, 1961, vol. 236, No. 12, pp. 3221-3226.

Marks et al., By-passing immunization: building high affinity human antibodies by chain shuffling, 1992, Biotechnology 10:779-783.

Martin, et al., Generation of the Germline Peripheral B Cell Repertoire: VH81X-λ B Cells Are Unable to Complete All Developmental Programs, J. Immunol., 1998, vol. 160, pp. 3748-3758.

Martinez, et al., Characterization of a novel modification on IgG2 light chain: Evidence for the presence of O-linked mannosylation, J. Chromatogr. A, 2007, vol. 1156 pp. 183-187.

Marvin, Bispecific antibodies for dual-modality cancer therapy: killing two signaling cascades with one stone, Curr Opin Drug Discov Devel, 2006, vol. 9(2), pp. 184-193.

Marvin, et al., Recombinant approaches to IgG-like bispecific antibodies, Acta Pharmacologica Sinica, 2005, vol. 26 (6), pp. 649-658.

Mateo et al., Humanization of a mouse nonoclonal antibody that blocks the epidermal growth factor receptor: recovery of antagonistic activity, 1997, Immunotechnology, 3(1):71-81.

McPhee, Engineering human immunodeficiency virus 1 protease heterodimers as macromolecular inhibitors of viral maturation, Proc. Natl. Acad. Sci. USA, 1996, vol. 93, p. 11477-11481.

Meijer, et al., Isolation of Human Antibody Repertoires with Preservation of the Natural Heavy and Light Chain Pairing, J. Mol. Biol., 2006, vol. 358, pp. 764-772.

Mertens, Nico, "Tribodies: Fab-scFv fusion proteins as a platform to create multi-functional pharmaceuticals.", SpringerLink 2011, 135-149.

Metz, et al., Bispecific antibody derivatives with restricted binding functionalities that are activated by proteolytic processing, Protein Engineering, Design & Selection, 2012, vol. 25, No. 10, pp. 571-580.

Metz, et al., Bispecific digoxigenin-binding antibodies for targeted payload delivery, PNAS, 2011, vol. 108, No. 20, pp. 8194-8199.

Michaelson et al., Anti-tumor activity of stability-engineered IgG-like bispecific antibodies targeting TRAIL-R2 and LTbetaR, [mAbs 1:2, 128-141; Mar./Apr. 2009]; Mar. 11, 2009.

Michalk et al., Characterization of a novel single-chain bispecific antibody for retargeting of T cells to tumor cells via the TCR co-receptor CD8., PLoS One. Apr. 21, 2014;9(4):e95517. doi: 10.1371/journal.pone.0095517.

Miller et al., Stability engineering of scFvs for the development of bispecific and multivalent antibodies, PEDS, 2010, vol. 23, No. 7, pp. 549-557 & Supplementary Data.

Miller, biogen idee Stability Engineering and Production of IgG-like Bispecifc Antibodies, AAPS National Biotechnology Conference, Jun. 24 to Jun. 27, 2007.

Mimoto et al., Engineered antibody Fc variant with selectively enhanced FcγRIIb binding over both FcγRIIa(R131) and FcγRIIa(H131)., Protein Eng Des Sel. Oct. 2013;26(10):589-98. doi: 10.1093/protein/gzt022. Epub Jun. 5, 2013.

Mimoto, et al., Novel asymmetrically engineered antibody Fc variant with superior FcγR binding affinity and specificity compared with afucosylated Fc variant, mAbs, 2013, vol. 5, Issue 2, pp. 229-236.

Modjtahedi et al., Phase I trial and tumour localization of the anti-EGFR monoclonal antibody ICR62 in head and neck or lung cancer, 1996, Br J Cancer, 73(2):228-35.

Modjtahedi et al., Targeting of cells expressing wild-type EGFR and type-III mutant EGFR (EGFRVIII) by anti-EGFR MaB ICR62: a two-pronged attack for tumor therapy, 2003, Int J Cancer, 105(2):273-80.

Modjtahedi et al., Antitumor activity of combinations of antibodies directed against different epitopes on the extracellular domain of the human EGF receptor, 1993, J. Cell Biophys. 1993, 22(1-3):129-46.

Modjtahedi et al., The human EGF receptor as a target for cancer therapy: six new rat mAbs against the receptor on the breast carcinoma MDA-MB 468, 1993, Br J Cancer. 1993, 67(2):247-53.

Mølhøj, et al., CD19-/CD3-bispecific antibody of the BiTE class is far superior to tandem diabody with respect to redirected tumor cell lysis, Molecular Immunology 2007, vol. 44 , pp. 1935-1943.

(56) References Cited

OTHER PUBLICATIONS

Moore et al., Tuning T Cell Affinity Improves Efficacy and Safety of Anti-CD38 x Anti-CD3 Bispecific Antibodies in Monkeys—a Potential Therapy for Multiple Myeloma., 57th ASH Annual Meeting and Exposition (Dec. 5-8, 2015), American Society of Hematology, Orlando, Florida.
Moore, et al., A novel bispecific antibody format enables simultaneous bivalent and monovalent co-engagement of distinct target antigens., MAbs. Nov. 2011-Dec.; 3(6): 546-557; Published online Nov. 1, 2011. doi: 10.4161/mabs.3.6.18123.
Moore, et al., Application of dual affinity retargeting molecules to achieve optimal redirected T-cell killing of B-cell lymphoma, Blood, 2011, vol. 117, No. 17, pp. 4542-4551.
Moretti et al., BEAT® the bispecific challenge: a novel and efficient platform for the expression of bispecific IgGs. BMC Proceedings 2013 7(Suppl 6):O9.
Morrison, et al., News and Views: Two heads are better than one, Nature Biotechnology, 2007, vol. 25, No. 11, pp. 1233-1234.
Mosmann, 1983, Rapid colorimetric assay for cellular growth and survival: application to proliferation and cytotoxicity assays, J. Immunol. Methods 65:55-63.
Muda, et al., Therapeutic assessment of SEED: a new engineered antibody platform designed to generate mono and bispecific antibodies, Protein Engineering, Design & Selection, 2011, vol. 24, No. 5, pp. 447-454.
Muramatsu et al., Production and characterization of an active single-chain variable fragment antibody recognizing CD25., Cancer Lett. Jul. 28, 2005;225(2):225-36. Epub Jan. 23, 2005.
Murthy et al., Binding of an antagonistic monoclonal antibody to an intact and fragmented EGF-receptor polypeptide, 1987, Arch Biochem Biophys. 252(2):549-60.
Nagorsen, et al., Blinatumomab: A historical perspective, Pharmacology & Therapeutics, 2012, vol. 136, pp. 334-342, http://dx.doi.org/10.1016/j.pharmthera.2012.07.013.
Nelson, et al., Point of View: Antibody fragments—Hope and hype, mAbs, 2010, vol. 2, Issue 1, pp. 77-83.
Neville et al., Enhancement of immunotoxin efficacy by acid-cleavable cross-ling agents utilizing diphtheria toxin and toxin mutants, 1989, Biol. Chem. 264:14653-14661.
Nielsen, et al., Human T cells resistant to complement lysis by bivalent antibody can be efficiently lysed by dimers of monovalent antibody, Blood, 2002, vol. 100, No. 12, pp. 4067-4073.
Nisonoff, et al., Letters to the Editors: Recombination of a Mixture of Univalent Antibody Fragments of Different Specificity, Arch. Biochem. Biophys., 1961, pp. 460-462.
Nisonoff, et al., Quantitative Estimation of the Hybridization of Rabbit Antibodies, Nature, 1962, vol. 194, No. 4826, pp. 355-359.
North, et al., A New Clustering of Antibody CDR Loop Conformations, J. Mol. Biol., 2011, vol. 406, pp. 228-256, doi:10.1016/j.jmb.2010.10.030.
O'Connor et al., Humanization of an antibody against human protein C and calcium-dependence involving framework residues, 1998, Protein Eng 11:321-8.
Olafsen, et al., Covalent disulfide-linked anti-CEA diabody allows site-specific conjugation and radiolabeling for tumor targeting applications, Protein Engineering, Design & Selection, 2004, vol. 17, No. 1, pp. 21-27.
Ott et al., CTLA-4 and PD-1/PD-L1 blockade: new immunotherapeutic modalities with durable clinical benefit in melanoma patients., Clin Cancer Res. Oct. 1, 2013;19(19):5300-9. doi: 10.1158/1078-0432.CCR-13-0143.
Page et al., 1993, Intermantional. Journal of Oncology 3:473-476.
Panke, et al., Quantification of cell surface proteins with bispecific antibodies, Protein Engineering, Design & Selection, 2013, vol. 26, No. 10, pp. 645-654.
Pessano, et al., The T3/T cell receptor complex: antigenic distinction between the two 20-kd T3 (T3-δ and T3-ε) subunits, The EMBO Journal, 1985, vol. 4, No. 2, pp. 337-344.
Pettit et al., Antineoplastic agents 365. Dolastatin 10 SAR probes, 1998, Anti-Cancer Drug Design 13:243-277.

Pettit et al., Dolastatins 24. Synthesis of (-)-dolastatin 10.1 X-ray molecular structure of N,N-dimethylvalyl-valyl-dolaisoleuine tert-butyl ester, 1996, J. Chem. Soc. Perkin Trans. 1 5:859-863.
Pettit et al., Specific activities of dolastatin 10 and peptide derivatives against Cryptococcus neoformans, 1998, Antimicrob. Agents Chemother. 42(11):2961-2965.
Pettit et al., Structure-activity studies with chiral isomers and with segments of the antimitotic marine peptide dolastation 10, 1989, J. Am. Chem. Soc. 111:5463-5465.
Pettit, et al., The dolastatins; 18: Sterospecificsynthesis of dolaproinel, 1996, Synthesis 719-725.
Pichler et al., Differences of T-Cell Activation by the Anti-CD3 Antibodies Leu4 and BMA030, Mar. 30, 1987.
Potapov et al., Protein-Protein Recognition: Juxtaposition of Domain and Interface Cores in Immunoglobulins and Other Sandwich-like Proteins, J. Mol. Biol., 2004, vol. 342, pp. 665-679.
Presta et al., Humanization of an anti-vascular endothelial growth factor monoclonal antibody for the therapy of solid tumors and other disorders, 1997, Cancer Res.57(20):4593-9.
Queen et al., A humanized antibody that binds to the interleukin 2 receptor, 1989, Proc Natl Acad Sci, USA 86:10029-33.
Rader et al., A phage display approach for rapid antibody humanization: designed combinatorial V gene libraries, 1998, Proc. Natl. Acad. Sci. USA 95: 8910-8915.
Raghavan et al., Fc receptors and their interactios with immunoglobulins, 1996, Annu Rev Cell Dev Biol 12:181-220.
Rattel, et al., AACR Poster, "Validation of Cynomolgus Monkeys as Relevant Species for Safety Assessment of a Novel Human BiTE Antibody Platform for Cancer Therapy," 2010.
Reddy et al., Elimination of Fc receptor-dependent effector functions of a modified IgG4 monoclonal antibody to human CD4., J Immunol. Feb. 15, 2000;164(4):1925-33.
Reiter et al., Disulfide stabilization of antibody Fv: computer predictions and experimental evaluation, Protein Eng., 1995, vol. 8(12), pp. 1323-1331.
Reiter et al., Engineering interchain disulfide bonds into conserved framework regions of Fv fragments: improved biochemical characteristics of recombinant immunotoxins containing disulfide-stabilized Fv, Protein Eng., 1994, vol. 7(5), pp. 697-704.
Remington's Pharmaceutical Sciences 16th edition, Osol, A. Ed. (1980) (Book Abstract).
Repp, et al., Combined Fc-protein- and Fc-glyco-engineering of scFv-Fc fusion proteins synergistically enhances CD16a binding but does not further enhance NK-cell mediated ADCC, Journal of Immunological Methods, 2011, vol. 373, Issues 1-2, pp. 67-78.
Ridgway, et al., 'Knobs-into-holes' engineering of antibody CH3 domains for heavy chain heterodimerization, Protein Engineering,1996, vol. 9, No. 7, pp. 617-621.
Riechmann et al., Reshaping human antibodies for therapy, 1988, Nature 332:323-329.
Riethmüller, Symmetry breaking: bispecific antibodies, the beginnings, and 50 years on, Cancer Immunity, 2012, vol. 12, p. 12, pp. 1-7.
Rodeck et al., Interactions between growth factor receptors and corresponding monoclonal antibodies in human tumors, 1987, J Cell Biochem. 35(4):315-20.
Roguska et al., Humanization of murine monoclonal antibodies through variable domain resurfacing, 1994, Proc. Natl. Acad. Sci. USA 91:969-973.
Roosnek, et al., Triggering T Cells by Otherwise Inert Hybrid Anti-CD3/Antitumor Antibodies Requires Encounter with the Specific Target Cell, J . Exp. Med., 1989, vol. 170, pp. 297-302.
Roque et al., Antibodies and genetically engineered related molecules: production and purification, 2004, Biotechnol. Prog. 20:639-654.
Rose, et al., Mutation of Y407 in the CH3 domain dramatically alters glycosylation and structure of human IgG, mAbs, 2013, vol. 5, Issue 2, pp. 219-228.
Rose, et al., Quantitative Analysis of the Interaction Strength and Dynamics of Human IgG4 Half Molecules by Native Mass Spectrometry, Structure , 2011, vol. 19, pp. 1274-1282.

(56) References Cited

OTHER PUBLICATIONS

Rosok et al., A combinatorial library strategy for the rapid humanization of anticarcinoma BR 96 Fab, 1996, J. Biol. Chem. 271(37): 22611-22618.
Rossi, et al., A new class of bispecific antibodies to redirect T cells for cancer immunotherapy, mAbs 2014, vol. 6, Issue 2, pp. 381-391.
Roux, et al., Structural analysis of the nurse shark (new) antigen receptor (NAR): Molecular convergence of NAR and unusual mammalian immunoglobulins, Proc. Natl. Acad. Sci. USA, 1998, vol. 95, pp. 11804-11809.
Rudnick, et al., Affinity and Avidity in Antibody-Based Tumor Targeting, Cancer Biotherapy and Radiopharmaceuticals, 2009, vol. 24, No. 2, pp. 155-161, doi: 10.1089/cbr.2009.0627.
Röthlisberger, et al., Domain Interactions in the Fab Fragment: A Comparative Evaluation of the Single-chain Fv and Fab Format Engineered with Variable Domains of Different Stability, J. Mol. Biol., 2005, vol. 347, pp. 773-789.
Salmeron et al., A conformational epitope expressed upon association of CD3-epsilon with either CD3-delta or CD3-gamma is the main target for recognition by anti-CD3 monoclonal antibodies, Nov. 1, 1991.
Sancho et al., CD3-Surface Expression Is Required for CD4-p56ick-mediated Up-regulation of T Cell Antigen Receptor-CD3 Signaling in T Cells, Apr. 16, 1992.
Schaefer, et al., A Two-in-One Antibody against HER3 and EGFR Has Superior Inhibitory Activity Compared with Monospecific Antibodies, Cancer Cell, 2011, vol. 20, pp. 472-486 & Supplemental Information, pp. 1-21.
Schaefer, et al., Immunoglobulin domain crossover as a generic approach for the production of bispecific IgG antibodies, PNAS, 2011, vol. 108, No. 27, pp. 11187-11192.
Schlapschy, et al., Functional humanization of an anti-CD16 Fab fragment: obstacles of switching from murine λ human λ or κ light chains, Protein Engineering, Design & Selection, 2009, vol. 22, No. 3, pp. 175-188, doi:10.1093/protein/gzn066.
Schlereth, et al., Eradication of Tumors from a Human Colon Cancer Cell Line and from Ovarian Cancer Metastases in Immunodeficient Mice by a Single-Chain Ep-CAM-/CD3-Bispecific Antibody Construct, Cancer Res 2005, vol. 65(7), pp. 2882-2889.
Schlereth, et al., T-cell activation and B-cell depletion in chimpanzees treated with a bispecific anti-CD19/anti-CD3 single-chain antibody construct, Cancer Immunol Immunother, 2006, vol. 55, pp. 503-514, doi:10.1007/s00262-005-0001-1.
Schoonjans, et al., Fab Chains As an Efficient Heterodimerization Scaffold for the Production of Recombinant Bispecific and Trispecific Antibody Derivatives, The Journal of Immunology, 2000, vol. 165, pp. 7050-7057.
Schroder et al., The Peptides, vol. pp. 76-136, 1965, Academic Press.
Senter et al., Proceedings of the American Association for Cancer Research, 2004, vol. 45, Abstract No. 623.
Senter, Potent antibody drug conjugates for cancer therapy, 2009, Current Opin. Chem. Biol. 13:235.
Sforzini et al., Targeting of saporin to Hodgkin's lymphoma cells by anti-CD30 and anti-CD25 bispecific antibodies., Br J Haematol. Sep. 1998;102(4):1061-8.
Shalaby, et al., Development of Humanized Bispecific Antibodies Reactive with Cytotoxic Lymphocytes and Tumor Cells Overexpressing the HER2 Protooncogene, J.Exp.Med., 1992, vol. 175, pp. 217-225.
Shan, et al., Characterization of scFv-Ig Constructs Generated from the Anti-CD20 mAb 1F5 Using Linker Peptides of Varying Lengths, J Immunol, 1999, vol. 162, pp. 6589-6595.
Shearman, et al., Construction, Expression and Characterization of Humanized Antibodies Directed Against the Human α/β Cell Receptor, The Journal of Immunology, 1991, vol. 147, No. 12, pp. 4366-4373.
Shen, et al., Catumaxomab, a rat/murine hybrid trifunctional bispecific monoclonal antibody for the treatment of cancer, Curr Opin Mol Ther, 2008, vol. 10(3), pp. 273-284.

Shen, et al., Single Variable Domain-IgG Fusion: A Novel Recombinant Approach to Fc Domain-Containing Bispecific Antibodies, The Journal of Biological Chemistry, 2006, vol. 281, No. 16, pp. 10706-10714.
Shields et al., Lack of fucose on human IgG1 N-linked oligosaccharide improves binding to human FcγRIII and antibody-dependent cellular toxicity, 2002, J Biol Chem 277:26733-26740.
Shier et al., Identification of functional and structural amino-acid residues by parsimonious mutagenesis, 1995, Gene 169:147-155.
Shinkawa et al., The absence of fucose but not the presence of galactose or bisecting N-acetylglucosamine of human IgG1 complex-type oligosaccharides shows the critical role of enhancing antibody-dependent cellular cytotoxicity, 2003, J Biol Chem 278:3466-3473.
Skehan et al., Identification of functional and structural amino-acid residues by parsimonious mutagenesis, 1990, J. Natl. Cancer Inst. 82(13):1107-12.
Smith et al., Mouse model recapitulating human Fcγ receptor structural and functional diversity., Proc Natl Acad Sci USA. Apr. 17, 2012;109(16):6181-6. doi: 10.1073/pnas.1203954109. Epub Apr. 2, 2012.
Soumyarani et al., Oxidatively modified high density lipoprotein promotes inflammatory response in human monocytes-macrophages by enhanced production of ROS, TNF-α, MMP-9, and MMP-2., Mol Cell Biochem. Jul. 2012;366(1-2):277-85. doi: 10.1007/s11010-012-1306-y. Epub Apr. 17, 2012.
Spies et al., Alternative molecular formats and therapeutic applications for bispecific antibodies., Mol Immunol. Jan. 27, 2015. pii: S0161-5890(15)00005-X. doi: 10.1016/j.molimm.2015.01.003.
Spiess, et al., Bispecific antibodies with natural architecture produced by coculture of bacteria expressing two distinct half-antibodies, Nature Biotechnology, 2013, doi:10.1038/nbt.2621 & Supplemental Information.
Spranger et al., Mechanism of tumor rejection with doublets of CTLA-4, PD-1/PD-L1, or IDO blockade involves restored IL-2 production and proliferation of CD8(+) T cells directly within the tumor microenvironment., J Immunother Cancer. Feb. 18, 2014;2:3. doi: 10.1186/2051-1426-2-3. eCollection 2014.
Stamova, Unexpected recombinations in single chain bispecific anti-CD3-anti-CD33 antibodies can be avoided by a novel linker module, Oct. 29, 2011.
Stanfield, et al., Maturation of Shark Single-domain (IgNAR) Antibodies: Evidence for Induced-fit Binding, J. Mol. Biol., 2007, vol. 367, pp. 358-372.
Stewart, et al., Recombinant CD36 inhibits oxLDL-induced ICAM-1-dependent monocyte adhesion., Mol Immunol. Feb. 2006;43(3):255-67.
Strop, P. et al., Generating Bispecific Human IgG1 and IgG2 Antibodies from Any Antibody Pair, J. Mol. Biol., 2012, doi:10.1016/j.jmb.2012.04.020.
Szymkowski et al., Creating the next generation of protein therapeutics through rational drug design, Current opinion in drug discovery & development, Sep. 1, 2005, p. 590, XP055354917, England.
Tabrizi et al., Biodistribution mechanisms of therapeutic monoclonal antibodies in health and disease., Aaps J. Mar. 2010;12(1):33-43. doi: 10.1208/s12248-009-9157-5. Epub Nov. 19, 2009.
Tan et al., "Superhumanized" antibodies: reduction of immunogenic potential by complementarity-determining region grafting with human germline sequences: application to an anti-CD28, 2002, J. Immunol. 169:1119-1125.
Tan, Philip, Presentation at PepTalk, Jan. 25, 2013, "Bi-specific ADAPTIR Molecule Targeting CD86 and Delivering Monomeric IL10 to Inhibit Antigen Presenting Cells".
Tang et al., Selection of linkers for a catalytic single-chain antibody using phage display technology., Journal of Biological Chemistry, American Society for Biochemistry and Molecular Biology, US, vol. 271, No. 26, Jan. 1, 1996, p. 15682-9258.
Tarcsa et al., Chapter 10 Dual-Variable Domain Immunoglobulin (DVD-Ig™) Technology: A Versatile, Novel Format for the Next Generation of Dual-Targeting Biologies, Bispecific Antibodies 2011, pp. 171-185, 2011.

(56) References Cited

OTHER PUBLICATIONS

Teachey, et al., Cytokine release syndrome after blinatumomab treatment related to abnormal macrophage activation and ameliorated with cytokine-directed therapy, Blood, 2013, vol. 121, No. 26, pp. 5154-5157.
Tedgui, et al., Cytokines in atherosclerosis: pathogenic and regulatory pathways., Physiol Rev. Apr. 2006;86(2):515-81.
Terry M., "FDA Places Clinical Hold on AML Drug Co-Developed by Johnson & Johnson (JNJ) and Genmab A/S (Gen Co.)", Biospace 2016, Retrieved from the internet: https://www.biospace.com/article/fda-places-clinical-hold-on-aml-drug-co-developed-by-johnson-and-johnson-and-genmab-a-s-/.
Thompson, et al., An Anti-CD3 Single-chain Immunotoxin with a Truncated Diphtheria Toxin Avoids Inhibition by Pre-existing Antibodies in Human Blood, J.Biol.Chem., 1995, vol. 270, No. 47, pp. 28037-28041.
Thompson, et al., Improved binding of a bivalent single-chain immunotoxin results in increased efficacy for in vivo T-cell depletion, Protein Engineering, 2001, vol. 14, No. 12, pp. 1035-1041.
Thorne, et al., CD36 is a receptor for oxidized high density lipoprotein: implications for the development of atherosclerosis., FEBS Lett. Mar. 20, 2007;581(6):1227-32. Epub Feb. 28, 2007.
Thorpe et al., New coupling agents for the synthesis of immunotoxins containing a hindered disulfide bond with improved stability in Vivo, 1987, Cancer Res. 47:5924-5931.
Thotakura et al., Enzymatic deglycosylating of glycoproteins, 1987, Meth. Enzymol. 138:350.
Thurman et al., Detection of complement activation using monoclonal antibodies against C3d., J Clin Invest. May 2013;123(5):2218-30. doi: 10.1172/JCI65861. Epub Apr. 24, 2013.
Tomlinson et al., Methods for generating multivalent and bispecific antibody fragments, 2000, Methods Enzymol. 326:461-479.
Topp, et al., Targeted Therapy With the T-Cell-Engaging Antibody Blinatumomab of Chemotherapy-Refractory Minimal Residual Disease in B-Lineage Acute Lymphoblastic Leukemia Patients Results in High Response Rate and Prolonged Leukemia-Free Survival, J Clin Oncol vol. 29, No. 18, pp. 2493-2498, Jun. 2011.
Traunecker, et al., Bispecific single chain molecules (Janusins) target cytotoxic lymphocytes on HIV infected cells, The EMBO Journal, 1991, vol. 1, No. 12, pp. 3655-3659.
Tsurushita et al., Humanization of monoclonal antibodies, 2004, Molecular Biology of B Cells 533-545.
Umaña et al., Engineered glycoforms of an antineuro-blastoma IgG1 with optimized antibody-dependent cellular cytotoxic activity, 1999, Nat Biotechnol 17:176-180.
Valliere-Douglass, et al., O-Fucosylation of an antibody light chain: Characterization of a modification occurring on an IgG1 molecule, Glycobiology, 2009, vol. 19, No. 2, pp. 144-152, doi:10.1093/glycob/cwn116.
Van Boxel, et al., Some lessons from the systematic production and structural analysis of soluble αβ T-cell receptors, Journal of Immunological Methods, 2009, vol. 350, pp. 14-21.
Van Wauwe, et al., OKT3: A Monoclonal Anti-Human T Lymphoctye Antibody with Potent Mitogenic Properties, The Journal of Immunology, 1980, vol. 124, No. 6, pp. 2708-2713.
Verdier, et al., Determination of lymphocyte subsets and cytokine levels in Cynomolgus monkeys, Toxicology, 1995, vol. 105, pp. 81-90.
Verhoeyen et al., Reshaping human antibodies: grafting an antilysozyme activity, 1988, Science, 239:1534-1536.
Veri, et al., Therapeutic Control of B Cell Activation via Recruitment of Fcγ Receptor IIb (CD32B) Inhibitory Function With a Novel Bispecific Antibody Scaffold, Arthritis & Rheumatism, 2010, vol. 62, No. 7, pp. 1933-1943.
Vettermann, et al., Powered by pairing: The surrogate light chain amplifies immunoglobulin heavy chain signaling and pre-selects the antibody repertoire, Seminars in Immunology 18, 2006, pp. 44-55.
Von Kreudenstein, et al., Improving biophysical properties of a bispecific antibody scaffold to aid developability: Quality by molecular design, mAbs, 2013, vol. 5, Issue 5, pp. 1-9, http://dx.doi.org/10.4161/mabs.25632 & Supplemental Material.
Wang et al., Conserved amino acid networks involved in antibody variable domain interactions, Proteins, 2009, vol. 76, pp. 99-114.
Wang et al., Expression and characterization of recombinant soluble monkey CD3 molecules: mapping the FN18 polymorphic epitope, Molecular Immunology, 2004, vol. 40, pp. 1179-1188.
Wang, et al., A block in both early T lymphocyte and natural killer cell development in transgenic mice with high-copy numbers of the human CD3E gene, Proc. Natl. Acad. Sci. USA, 1994, vol. 91, pp. 9402-9406.
Ward, et al., Protein Engineering of Homodimeric Tyrosyl-tRNA Synthetase to Produce Active Heterodimers, The Journal of Biological Chemistry, 1986, vol. 261, No. 21, pp. 9576-9578.
Weatherill, et al., Towards a universal disulphide stabilised single chain Fv format: importance of interchain disulphide bond location and vL-vH orientation, Protein Engineering, Design & Selection, 2012, vol. 25, No. 7, pp. 321-329.
Weiner, et al., The Role of T Cell Activation Bispecific Antibody Therapy in Anti-CD3 X Antitumor, Journal of Immunology, 1994, vol. 152, pp. 2385-2392.
Wesolowski, et al., Single domain antibodies: promising experimental and therapeutic tools in infection and immunity, Med Microbiol Immunol, 2009, vol. 198, pp. 157-174.
Whitlow, et al., An improved linker for single-chain Fv with reduced aggregation and enhanced proteolytic stability, Protein Engineering, 1993, vol. 6, No. 8, pp. 989-995.
Wong, et al., The Mechanism of Anti-CD3 Monoclonal Antibodies, Transplantation, 1990, vol. 50, No. 4, pp. 683-689.
Woods, et al., LC-MS characterization and purity assessment of a prototype bispecific antibody, mAbs, 2013, vol. 5, Issue 5, pp. 711-722, http://dx.doi.org/10.4161/mabs.25488.
Woyke et al., In vitro activities and postantifungal effects of the potent dolastation 10 derivative auristatin PHE, 2001, Antimicrob. Agents and Chemother. 45(12):3580-3584.
Wu et al., Molectular construction and optimization of anti-human IL-11α/β dual variable domain immunoglobulin (DVD-Ig™) molecules, [mAbs 1:4, 339-347; Jul./Aug. 2009]; Landes Bioscience, Apr. 10, 2009.
Wu et al., Simultaneous targeting of multiple disease mediators by a dual-variable-domain immunoglobulin, (DVD-Ig™) molecules, Jul.-Aug. 2009; 339-347, Oct. 14, 2007.
Wu et al., Humanization of a murine monoclonal antibody by simultaneous optimization of framework and CDR residues, 1999, J. Mol. Biol. 294:151-162.
Wu, et al., Multimerization of a chimeric anti-CD20 single-chain Fv-Fc fusion protein is mediated through variable domain exchange, Protein Engineering, 2001, vol. 14, No. 12, pp. 1025-1033.
Wucherpfennig, et al., Structural Biology of the T-cell Receptor: Insights into Receptor Assembly, Ligand Recognition, and Initiation of Signaling, Cold Spring Harb Perspect Biol 2010;2:a005140.
Xie, et al., A new format of bispecific antibody: highly efficient heterodimerization, expression and tumor cell lysis, Journal of Immunological Methods, 2005, vol. 296, pp. 95-101, doi:10.1016/j.jim.2004.11.005.
Xu, et al., Combinatorial surrobody libraries, PNAS, 2008, vol. 105, No. 31, p. 10756-10761.
Xu, et al., Rapid optimization and prototyping for therapeutic antibody-like molecules, mAbs, 2013, vol. 5, Issue 2, pp. 237-254.
Xu, et al., Surrobodies with Functional Tails, J. Mol. Biol., 2010, vol. 397, pp. 352-360.
Yang et al., Differential in vitro activation of CD8-CD4+ and CD4-CD8+ T lymphocytes by combinations of anti-CD2 and anti-CD3 antibodies, Apr. 1, 1988.
Yelton et al., Affinity maturation of the BR96 anti-carcinoma antibody by codon-based mutagenesis, 1995, J. Immunol. 155:1994-2004.
Yeung, et al., Engineering human IgG1 affinity to human neonatal Fc receptor: impact of affinity improvement on pharmacokinetics in primates, J Immunol. Jun. 15, 2009;182(12):7663-71. doi: 10.4049/jimmunol.0804182.
Yoshino et al., Upgrading of flow cytometric analysis for absolute counts, cytokines and other antigenic molecules of cynomolgus

(56) References Cited

OTHER PUBLICATIONS monkeys (Macaca fascicularis) by using anti-human cross-reactive antibodies, Exp. Anim., 2000, vol. 49(2), pp. 97-100.
Yu et al., The biosynthetic gene cluster of the maytansinoids antitumor agent ansamitocin from actinosynnema pretiosum, 2002, PNAS 99:7968-7973.
Zalevsky et al. "Enhanced antibody half-life improves in vivo activity." Nature Biotechnology, vol. 28, No. 2, Feb. 1, 2010, pp. 157-159.
Zamyatnin AA., *Amino acid, peptide, and protein volume in solution.*, *Annu. Rev Biophys Bioeng.* 1984:13:145-65.
Zeidler, et al., The Fc-region of a new class of intact bispecific antibody mediates activation of accessory cells and NK cells and induces direct phagocytosis of tumour cells, Br J Cancer, 2000, vol. 83(2), pp. 261-266.
Zhu, et al., Identification of Heavy Chain Residues in a Humanized Anti-CD3 Antibody Important for Efficient Antigen Binding and T Cell Activation, The Journal of Immunology, 1995, vol. 155, pp. 1903-1910.
Zhu, et al., Remodeling domain interfaces to enhance heterodimer formation, Protein Science, 1997, vol. 6, pp. 781-788.
Zeibig et al., Effect of the oxLDL Binding Protein Fc-CD68 on Plaque Extension and Vulnerability in Atherosclerosis., Circulation Research 108: 695-703, 2011.
Zuo, et al., An efficient route to the production of an IgG-like bispecific antibody, Protein Engineering, 2000, vol. 13, No. 5, pp. 361-367.
Sun et al., Anti-CD20/CD3 T cell-dependent bispecific antibody for the treatment of B cell malignancies., Science Translational Medicine May 13, 2015: vol. 7, Issue 287, p. 287ra70 DOI: 10.1126/scitranslmed.aaa480.
Capizzi et al., Curative chemotherapy for acute myeloid leukemia: the development of high-dose ara-C from the laboratory to bedside., Invest New Drugs. 1996;14(3):249-56.
Giles et al., Intravenous corticosteroids to reduce gemtuzumab ozogamicin infusion reactions. Ann Pharmacother. Sep. 2003;37(9):1182-5.
Duong et al., Targeted treatment of acute myeloid leukemia in older adults: role of gemtuzumab ozogamicin., Clin Interv Aging. 2009;4:197-205. Epub May 14, 2009.
Sun et al. , Preclinical Characterization of Combinability and Potential Synergy of Anti-CD20/CD3 T-Cell Dependent Bispecific Antibody with Chemotherapy and PD-1/PD-L1 Blockade., Blood 2016 128:4168.
Gantke et al., Trispecific antibodies for CD16A-directed NK cell engagement and dual-targeting of tumor cells., Protein Eng Des Sel. Sep. 1, 2017;30(9):673-684. doi: 10.1093/protein/gzx043.
Zhang et al., The development of bispecific antibodies and their applications in tumor immune escape., Experimental Hematology & Oncology20176:12.
Krupka et al.,Blockade of the PD-1/PD-L1 axis augments lysis of AML cells by the CD33/CD3 BiTE antibody construct AMG 330: reversing a T-cell-induced immune escape mechanism., Leukemia. Feb. 2016;30(2):484-91. doi: 10.1038/leu.2015.214. Epub Aug. 4, 2015.
Osada et al., CEA/CD3-bispecific T cell-engaging (BiTE) antibody-mediated T lymphocyte cytotoxicity maximized by inhibition of both PD1 and PD-L1., Cancer Immunol Immunother. Jun. 2015;64(6):677-88. doi: 10.1007/s00262-015-1671-y. Epub Mar. 6, 2015.
Masarova et al., Immune Checkpoint Approaches in AML and MDS: A Next Frontier?, The Journal of Targeted Therapies in Cancer, Mar. 6, 2017 (Mar. 6, 2017), XP002784099.
Scott et al., Antibody therapy of cancer., Nat Rev Cancer. Mar. 22, 2012;12(4):278-87. doi: 10.1038/nrc3236.
Clynes et al., Redirected T Cell Cytotoxicity in Cancer Therapy., Annu Rev Med. Jan. 27, 2019;70:437-450. doi: 10.1146/annurev-med-062617-035821. Epub Oct. 31, 2018.
Merchant et al., Monovalent antibody design and mechanism of action of onartuzumab, a MET antagonist with anti-tumor activity as a therapeutic agent., Proc Natl Acad Sci USA. Aug. 6, 2013;110(32):E2987-96. doi: 10.1073/pnas.1302725110. Epub Jul. 23, 2013.
Fos et al., ICOS ligation recruits the p50alpha PI3K regulatory subunit to the immunological synapse., J Immunol. Aug. 1, 2008;181(3):1969-77.
Sanmamed et al., Agonists of Co-stimulation in Cancer Immunotherapy Directed Against CD137, OX40, GITR, CD27, CD28, and ICOS., Semin Oncol. Aug. 2015;42(4):640-55. doi: 10.1053/j.seminoncol. 2015.05.014. Epub Jun. 11, 2015.
Vieira et al., ICOS-mediated signaling regulates cytokine production by human T cells and provides a unique signal to selectively control the clonal expansion of Th2 helper cells., Eur J Immunol. May 2004;34(5):1282-90.
Madrenas et al., Conversion of CTLA-4 from inhibitor to activator of T cells with a bispecific tandem single-chain Fv ligand., J Immunol. May 15, 2004;172(10):5948-56.
Yokosuka et al., Spatiotemporal basis of CTLA-4 costimulatory molecule-mediated negative regulation of T cell activation., Immunity. Sep. 24, 2010;33(3):326-39. doi: 10.1016/j.immuni.2010.09. 006.
Carpenter et al., Activation of human B cells by the agonist CD40 antibody CP-870,893 and augmentation with simultaneous toll-like receptor 9 stimulation., J Transl Med. Nov. 11, 2009;7:93. doi: 10.1186/1479-5876-7-93.
Fan et al., Engagement of the ICOS pathway markedly enhances efficacy of CTLA-4 blockade in cancer immunotherapy., J Exp Med. Apr. 7, 2014;211(4):715-25. doi: 10.1084/jem.20130590. Epub Mar. 31, 2014.
Gilboa et al., Use of oligonucleotide aptamer ligands to modulate the function of immune receptors., Clin Cancer Res. Mar. 1, 2013;19(5):1054-62. doi: 10.1158/1078-0432.CCR-12-2067.
Uy et al., Preliminary Results of a Phase 1 Study of Flotetuzumab, a CD123x CD3 Bispecific Dart® Protein, in Patients with Relapsed/ Refractory Acute Myeloid Leukemia and Myelodysplastic Syndrome., Blood 2017 130:637.
Vey et al., Interim Results from a Phase 1 First-in-Human study of flotetuzumab, a CD123 x CD3 bispecific DART molecule, in AML/MDS., Annals of Oncology (2017) 28 (suppl_5): v355-v371. 10.1093/annonc/mdx373.
Ravandi et al., Complete Responses in Relapsed/Refractory Acute Myeloid Leukemia (AML) Patients on a Weekly Dosing Schedule of XmAb14045, a CD123 x CD3 T Cell-Engaging Bispecific Antibody: Initial Results of a Phase 1 Study., Blood 2018 132:763; doi: https://doi.org/10.1182/blood-2018-99-119786.
Bacac et al., A Novel Carcinoembryonic Antigen T-Cell Bispecific Antibody (CEA TCB) for the Treatment of Solid Tumors., Clin Cancer Res. Jul. 1, 2016;22(13):3286-97.
Chappel et al., "Identification of a Secondary Fcγ RI Binding Site within a Genetically Engineered Human IgG Actibody," J. Biol. Chem., 268(33):25124-25131 (Nov. 1993).
Chappel et al., "Identification of the Fcγ receptor class I binding site in human IgG through the use of recombinant lgG1/lgG2 hybrid and point-mutated antibodies," Pnas, USA, 88:9036-9040 (Oct. 1991).
Miranda-Carus et al., IL-15 and the initiation of cell contact-dependent synovial fibroblast-T lymphocyte cross-talk in rheumatoid arthritis: effect of methotrexate., 2004 J. Immunol. 13:1463-1476.
Koka et al., Cutting edge: murine dendritic cells require IL-15R alpha to prime NK cells., 2004 J. Immunol. 173:3594-3598.
Matsumoto et al., On-column refolding and characterization of soluble human interleukin-15 receptor alpha-chain produced in *Escherichia coli.*, Protein Purification and Expression, 2003 64-71.
Han et al., IL-15:IL-15 receptor alpha superagonist complex: high-level coexpression in recombinant mammalian cells, purification and characterization., Cytokine. Dec. 2011;56(3):804-10.
Stone et al., Design and characterization of a protein superagonist of IL-15 fused with IL-15Rα and a high-affinity T cell receptor., Biotechnol Prog. 2012; Nov.-Dec.;28(6):1588-97.
Kermer et al., An antibody fusion protein for cancer immunotherapy mimicking IL-15 trans-presentation at the tumor site., Mol Cancer Ther. Jun. 2012;11(6):1279-88.

(56) References Cited

OTHER PUBLICATIONS

Kermer et al., Combining Antibody-Directed Presentation of IL-15 and 4-1BBL in a Trifunctional Fusion Protein for Cancer Immunotherapy, Mol Cancer Ther. Jan. 2014;13(1):112-21.
C. Bergamaschi et al., "Intracellular Interaction of Interleukin-15 with Its Receptor during Production Leads to Mutual Stabilization and Increased Bioactivity", Journal of Biological Chemistry, vol. 283, No. 7, pp. 4189-4199, 2008.
Genbank accession No. NM_172174, Jan. 2011.
Genbank accession No. NP_002180, Sep. 2021.
S. Dubois et al., "IL-15Ra Recycles and Presents IL-15 In Trans to Neighbouring Cells", Immunity, vol. 17, 537-547, 2002.
Y Tagaya et al., "Generation of secretable and non-secretable interleukin-15 isoforms through alternate usage of signal peptides", Proc. Natl. Acad. Sci. USA, vol. 44, 14444-14449, 1997.
Genbank accession No. AF031167.1, Jan. 1998.
D Anderson et al, "Functional Characterization of the Human IL-15 Receptor α Chain and Close Linkage of IL15RA and IL2RA genes", J. Biol. Chem., vol. 270, No. 50, 29862-29869, 1995.
Assignment abstract of title for U.S. Appl. No. 12/666,052, Apr. 2011.
Mortier E et al., "Natural, Proteolytic Release of a Soluble Form of Human IL-15 Receptor α-Chain That Behaves as a Specific, High Affinity IL-15 Antagonist", J. Immunol 2004; 173: 1681-1688.
Wrangle et al., ALT-803, an IL-15 superagonist, in combination with nivolumab in patients with metastatic non-small cell lung cancer: a non-randomised, open-label, phase 1b trial., Lancet Oncol. May 2018;19(5):694-704. doi: 10.1016/S1470-2045(18)30148-7. Epub Apr. 5, 2018.
Sondel et al., Current and Potential Uses of Immunocytokines as Cancer Immunotherapy., Antibodies. 2012; 1: 149-71, Jul. 4, 2012.
Jin et al. The Design and Engineering of IgG-Like Bispecific Antibodies., Chapter9, Bispecific Antibodies, pp. 151-169, Jul. 2011.
Labrijn, et al., Efficient generation of stable bispecific IgG1 by controlled Fab-arm exchange, Proc Natl Acad Sci USA. Mar. 26, 2013;110(13):5145-50. doi: 10.1073/pnas.1220145110. Epub Mar. 11, 2013.
Milutinovic, et al., Abstract 4318: Development of a novel SurrobodyTM that simultaneously activates both death receptors DR4 and DR5 and induces cancer cell death with high potency., Cancer Res (2013) 73 (8 Supplement): 4318., Apr. 15, 2013.
Wawrzynczak et al., Methods for preparing immunotoxins: Effect of the linkage on activity and stability. In Immunoconjugates. Antibody Conjugates in Radio imaging and Therapy of Cancer. (C.-W. Vogel, editor). New York, Oxford University Press, pp. 28-55, (1987).
Wigginton et al., An immunoglobulin E-reactive chimeric human immunoglobulin G1 anti-idiotype inhibits basophil degranulation through cross-linking of FcεRI with FcγRIIb., Clin Exp Allergy. Feb. 2008;38(2):313-9. doi: 10.1111/j.1365-2222.2007.02896.x. Epub Dec. 7, 2007.
Schluns et al., Distinct cell types control lymphoid subset development by means of IL-15 and IL-15 receptor alpha expression., PNAS 101(5):5616-5621, Apr. 1, 2004.
Wei et al., The Sushi domain of soluble IL-15 receptor alpha is essential for binding IL-15 and inhibiting inflammatory and allogenic responses in vitro and in vivo., J Immunol. Jul. 1, 2001;167(1):277-82. doi:10.4049/jimmunol.167.1.277.
Yu et al. Simultaneous blockade of multiple immune system inhibitory checkpoints enhances antitumor activity mediated by interleukin-15 in a murine metastatic colon carcinoma model. Clin Cancer Res. 2010;16(24):6019-6028.
Vincent et al. Tumor targeting of the IL-15 superagonist RLI by an anti-GD2 antibody strongly enhances its antitumor potency. Int J Cancer. 2013;133(3):757-765.
Vincent et al. CS14-6. Development of two IL15 immunocytokines targeting either GD2- or CD20-tumoral bearing cells. Cytokine. 2011;56 (1):102.
Xu et al. The tumor immunosuppressive microenvironment impairs the therapy of anti-HER2/neu antibody. Protein Cell. 2012;3(6):441-449.
Bessard et al. High antitumor activity of RLI, an interleukin-15 (IL-15)-IL-15 receptor alpha fusion protein, in metastatic melanoma and colorectal cancer. Mol Cancer Ther. 2009;8(9):2736-2745.
Yu et al., "Simultaneous inhibition of two regulatory T-cell subsets enhanced Interleukin-15 efficacy in a prostate tumor model.", Proc Natl Acad Sci USA. 2012;109(16):6187-6192.
Perdreau et al. "Different dynamics of IL-15R activation following IL-15 cis- or trans-presentation." Eur Cytokine Netw. Dec. 2010;21(4):297-307.
Desbois et al. "IL-15 Trans-Signaling with the Superagonist RLI Promotes Effector/Memory CD8+ T Cell Responses and Enhances Antitumor Activity of PD-1 Antagonists.", J Immunol. Jul. 1, 2016;197(1):168-78. doi: 10.4049/jimmunol.1600019. Epub May 23, 2016.
Intlekofer et al., "At the Bench: Preclinical rationale for CTLA-4 and PD-1 blockade as cancer immunotherapy", Journal of Leukocyte Biology, vol. 94, Jul. 2013.
Melero et al.: "Evolving synergistic combinations of targeted immunotherapies to combat cancer", Nature Reviews, Cancer, vol. 15, 2015.
Waldmann: "The biology of interleukin-2 and interleukin-15: implications for cancer therapy and vaccine design", 2006, Nat Rev Immunol 6(8): 595-601.
Dubois et al., Preassociation of IL-15 with IL-15Ra-IgG1-Fc Enhances Its Activity on Proliferation of NK and CD8+/CD44high T Cells and Its Antitumor Action., J Immunol Feb. 15, 2008, 180 (4) 2099-2106; DOI: https://doi.org/10.4049/jimmunol.180.4.2099.

\* cited by examiner

Figure 2A

Human IL-15 precursor sequence SEQ ID NO:1

>sp|P40933
MRISKPHLRSISIQCYLCLLLNSHFLTEAGIHVFILGCFSAGLPKTEANWVNVISDLKKIEDLIQSMHIDATLYTES
DVHPSCKVTAMKCFLLELQVISLESGDASIHDTVENLIILANNSLSSNGNVTESGCKECEELEEKNIKEFLQSFVHI
VQMFINTS

Human IL-15 mature form sequence SEQ ID NO:2

>sp|P40933|49-162
NWVNVISDLKKIEDLIQSMHIDATLYTESDVHPSCKVTAMKCFLLELQVISLESGDASIHDTVENLIILANNSLSSN
GNVTESGCKECEELEEKNIKEFLQSFVHIVQMFINTS

Human IL-15Rα sequence SEQ ID NO:3

>sp|Q13261
MAPRRARGCRTLGLPALLLLLLLRPPATRGITCPPPMSVEHADIWVKSYSLYSRERYICNSGFKRKAGTSSLTECVL
NKATNVAHWTTPSLKCIRDPALVHQRPAPPSTVTTAGVTQPESLSPSGKEPAASSPSSNNTAATTAAIVPGSQLMP
SKSPSTGTTEISSHESSHGTPSQTTAKNWELTASASHQPPGVYPQGHSDTTVAISTSTVLLCGLSAVSLLACYLKSR
QTPPLASVEMEAMEALPVTWGTSSRDEDLENCSHHL

Human IL-15Rα, extracellular domain SEQ ID NO:5

>sp|Q13261|31-205
ITCPPPMSVEHADIWVKSYSLYSRERYICNSGFKRKAGTSSLTECVLNKATNVAHWTTPSLKCIRDPALVHQRPAPP
STVTTAGVTQPESLSPSGKEPAASSPSSNNTAATTAAIVPGSQLMPSKSPSTGTTEISSHESSHGTPSQTTAKNWE
LTASASHQPPGVYPQGHSDTT

Human IL-15Rα, sushi domain SEQ ID NO:4

>sp|Q13261|31-95
ITCPPPMSVEHADIWVKSYSLYSRERYICNSGFKRKAGTSSLTECVLNKATNVAHWTTPSLKCIR

Human IL-15Rß sequence (SEQ ID NO:6)

>sp|P14784
MAAPALSWRLPLLILLLPLATSWASAAVNGTSQFTCFYNSRANISCVWSQDGALQDTSCQVHAWPDRRRWNQTCELL
PVSQASWACNLILGAPDSQKLTTVDIVTLRVLCREGVRWRVMAIQDFKPFENLRLMAPISLQVVHVETHRCNISWEI
SQASHYFERHLEFEARTLSPGHTWEEAPLLTLKQKQEWICLETLTPDTQYEFQVRVKPLQGEFTTWSPWSQPLAFRT
KPAALGKDTIPWLGHLLVGLSGAFGFIILVYLLINCRNTGPWLKKVLKCNTPDPSKFFSQLSSEHGGDVQKWLSSPF
PSSSFSPGGLAPEISPLEVLERDKVTQLLLQQDKVPEPASLSSNHSLTSCFTNQGYFFFHLPDALEIEACQVYFTYD
PYSEEDPDEGVAGAPTGSSPQPLQPLSGEDDAYCTFPSRDDLLLFSPSLLGGPSPPSTAPGGSGAGEERMPPSLQER
VPRDWDPQPLGPPTPGVPDLVDFQPPPELVLREAGEEVPDAGPREGVSFPWSRPPGQGEFRALNARLPLNTDAYLSL
QELQGQDPTHLV

Human IL-15Rß, extracellular domain (SEQ ID NO:7)

>sp|P14784|27-240
AVNGTSQFTCFYNSRANISCVWSQDGALQDTSCQVHAWPDRRRWNQTCELLPVSQASWACNLILGAPDSQKLTTVDI
VTLRVLCREGVRWRVMAIQDFKPFENLRLMAPISLQVVHVETHRCNISWEISQASHYFERHLEFEARTLSPGHTWEE
APLLTLKQKQEWICLETLTPDTQYEFQVRVKPLQGEFTTWSPWSQPLAFRTKPAALGKDT

Figure 2B
Human common gamma chain sequence (SEQ ID NO:8)

>sp|P31785
MLKPSLPFTSLLFLQLPLLGVGLNTTILTPNGNEDTTADFFLTTMPTDSLSVSTLPLPEVQCFVFNVEYMNCTWNSS
SEPQPTNLTLHYWYKNSDNDKVQKCSHYLFSEEITSGCQLQKKEIHLYQTFVVQLQDPREPRRQATQMLKLQNLVIP
WAPENLTLHKLSESQLELNWNNRFLNHCLEHLVQYRTDWDHSWTEQSVDYRHKFSLPSVDGQKRYTFRVRSRFNPLC
GSAQHWSEWSHPIHWGSNTSKENPFLFALEAVVISVGSMGLIISLLCVYFWLERTMPRIPTLKNLEDLVTEYHGNFS
AWSGVSKGLAESLQPDYSERLCLVSEIPPKGGALGEGPGASPCNQHSPYWAPPCYTLKPET

Human common gamma chain, extracellular domain (SEQ ID NO:9)

>sp|P31785|23-262
LNTTILTPNGNEDTTADFFLTTMPTDSLSVSTLPLPEVQCFVFNVEYMNCTWNSSSEPQPTNLTLHYWYKNSDNDKV
QKCSHYLFSEEITSGCQLQKKEIHLYQTFVVQLQDPREPRRQATQMLKLQNLVIPWAPENLTLHKLSESQLELNWNN
RFLNHCLEHLVQYRTDWDHSWTEQSVDYRHKFSLPSVDGQKRYTFRVRSRFNPLCGSAQHWSEWSHPIHWGSNTSKE
NPFLFALEA

Figure 3

Human TIM-3 sequence (SEQ ID NO:10)

>sp|Q8TDQ0

MFSHLPFDCVLLLLLLLLTRSSEVEYRAEVGQNAYLPCFYTPAAPGNLVPVCWGKGACPVFECGNVVLRTDERDVNY
WTSRYWLNGDFRKGDVSLTIENVTLADSGIYCCRIQIPGIMNDEKFNLKLVIKPAKVTPAPTRQRDFTAAFPRMLTT
RGHGPAETQTLGSLPDINLTQISTLANELRDSRLANDLRDSGATIRIGIYIGAGICAGLALALIFGALIFKWYSHSK
EKIQNLSLISLANLPPSGLANAVAEGIRSEENIYTIEENVYEVEEPNEYYCYVSSRQQPSQPLGCRFAM

Human TIM-3 sequence, extracellular domain (SEQ ID NO:11)

>sp|Q8TDQ0|22-202

SEVEYRAEVGQNAYLPCFYTPAAPGNLVPVCWGKGACPVFECGNVVLRTDERDVNYWTSRYWLNGDFRKGDVSLTIE
NVTLADSGIYCCRIQIPGIMNDEKFNLKLVIKPAKVTPAPTRQRDFTAAFPRMLTTRGHGPAETQTLGSLPDINLTQ
ISTLANELRDSRLANDLRDSGATIRIG

Macaca fascicularis TIM-3 sequence (predicted) (SEQ ID NO:12)

>gi|355750365|gb|EHH54703.1

MFSHLPFDCVLLLLLLLLTRSSEVEYIAEVGQNAYLPCSYTPAPPGNLVPVCWGKGACPVFDCSNVVLRTDNRDVND
RTSGRYWLKGDFHKGDVSLTIENVTLADSGVYCCRIQIPGIMNDEKHNVKLVVIKPAKVTPAPTLQRDLTSAFPRML
TTGEHGPAETQTPGSLPDVNLTVSNFFCELQIFTLTNELRDSGATIRTAIYIAAGISAGLALALIFGALIFKWYSHS
KEKTQNLSLISLANIPPSGLANAVAEGIRSEENIYTIEEDVYEVEEPNEYYCYVSSGQQPSQPLGCRVAMP

Macaca fascicularis TIM-3 sequence, extracellular domain (predicted) (SEQ ID NO:13)

>gi|355750365|gb|EHH54703.1|22-203

SEVEYIAEVGQNAYLPCSYTPAPPGNLVPVCWGKGACPVFDCSNVVLRTDNRDVNDRTSGRYWLKGDFHKGDVSLTI
ENVTLADSGVYCCRIQIPGIMNDEKHNVKLVVIKPAKVTPAPTLQRDLTSAFPRMLTTGEHGPAETQTPGSLPDVNL
TVSNFFCELQIFTLTNELRDSGATIRTA

Figure 4A

| Monomer 1 | Monomer 2 |
|---|---|
| F405A | T394F |
| S364D | Y349K |
| S364E | L368K |
| S364E | Y349K |
| S364F | K370G |
| S364H | Y349K |
| S364H | Y349T |
| S364Y | K370G |
| T411K | K370E |
| V397S/F405A | T394F |
| K370R/T411K | K370E/T411E |
| L351E/S364D | Y349K/L351K |
| L351E/S364E | Y349K/L351K |
| L351E/T366D | L351K/T366K |
| P395T/V397S/F405A | T394F |
| S364D/K370G | S364Y/K370R |
| S364D/T394F | Y349K/F405A |
| S364E/F405A | Y349K/T394F |
| S364E/F405S | Y349K/T394Y |
| S364E/T411E | Y349K/D401K |
| S364H/D401K | Y349T/T411E |
| S364H/F405A | Y349T/T394F |
| S364H/T394F | Y349T/F405A |
| Y349C/S364E | Y349K/S354C |
| L351E/S364D/F405A | Y349K/L351K/T394F |
| L351K/S364H/D401K | Y349T/L351E/T411E |
| S364E/T411E/F405A | Y349K/T394F/D401K |
| S364H/D401K/F405A | Y349T/T394F/T411E |
| S364H/F405A/T411E | Y349T/T394F/D401K |

Figure 4B

| Monomer 1 | Monomer 2 |
| --- | --- |
| K370E/T411D | T411K |
| L368E/K409E | L368K |
| Y349T/T394F/S354C | S364H/F405A/Y349C |
| T411E | D401K |
| T411E | D401R/T411R |
| Q347E/K360E | Q347R |
| L368E | S364K |
| L368E/K370S | S364K |
| L368E/K370T | S364K |
| L368E/D401R | S364K |
| L368E/D401N | S364K |
| L368E | E357S/S364K |
| L368E | S364K/K409E |
| L368E | S364K/K409V |
| L368D | S364K |
| L368D/K370S | S364K |
| L368D/K370S | S364K/E357L |
| L368D/K370S | S364K/E357Q |
| T411E/K360E/Q362E | D401K |
| K370S | S364K |
| L368E/K370S | S364K/E357Q |
| K370S | S364K/E357Q |
| T411E/K360D | D401K |
| T411E/K360E | D401K |
| T411E/Q362E | D401K |
| T411E/N390D | D401K |
| T411E | D401K/Q347K |
| T411E | D401K/Q347R |
| T411E/K360D/Q362E | D401K |

Figure 4C

| Monomer 1 | Monomer 2 |
|---|---|
| T411E/K360E/N390D | D401K |
| T411E/Q362E/N390D | D401K |
| T411E/Q347R | D401K/K360D |
| T411E/Q347R | D401K/K360E |
| T411E/K360 | D401K/Q347K |
| T411E/K360D | D401K/Q347R |
| T411E/K360E | D401K/Q347K |
| T411E/K360E | D401K/Q347R |
| T411E/S364K | D401K/K370S |
| T411E/K370S | D401K/S364K |
| Q347E | E357Q |
| Q347E | E357Q/Q362K |
| K360D/Q362E | Q347R |
| K360D/Q362E | D401K |
| K360D/Q362E | Q347R/D401K |
| K360E/Q362E | Q347R |
| K360E/Q362E | D401K |
| K360E/Q362E | Q347R/D401K |
| Q362E/N390D | D401K |
| Q347E/K360D | D401N |
| K360D | Q347R/N390K |
| K360D | N390K/D401N |
| K360E | Y349H |
| K370S/Q347E | S364K |
| K370S/E357L | S364K |
| K370S/E357Q | S364K |
| K370S/Q347E/E357L | S364K |
| K370S/Q347E/E357Q | S364K |

Figure 4D

| Monomer 1 | Monomer 2 |
|---|---|
| L368D/K370S/Q347E | S364K |
| L368D/K370S/E357L | S364K |
| L368D/K370S/E357Q | S364K |
| L368D/K370S/Q347E/E357L | S364K |
| L368D/K370S/Q347E/E357Q | S364K |
| L368E/K370S/Q347E | S364K |
| L368E/K370S/E357L | S364K |
| L368E/K370S/E357Q | S364K |
| L368E/K370S/Q347E/E357L | S364K |
| L368E/K370S/Q347E/E357Q | S364K |
| L368D/K370T/Q347E | S364K |
| L368D/K370T/E357L | S364K |
| L368D/K370T/E357Q | S364K |
| L368D/K370T/Q347E/E357L | S364K |
| L368D/K370T/Q347E/E357Q | S364K |
| L368E/K370T/Q347E | S364K |
| L368E/K370T/E357L | S364K |
| L368E/K370T/E357Q | S364K |
| L368E/K370T/Q347E/E357L | S364K |
| L368E/K370T/Q347E/E357Q | S364K |
| T411E/Q362E | D401K/T411K |
| T411E/N390D | D401K/T411K |
| T411E/Q362E | D401R/T411R |
| T411E/N390D | D401R/T411R |
| Y407T | T366Y |
| F405A | T394W |
| T366Y/F405A | T394W/Y407T |
| Y407A | T366W |
| T366S/L368A/Y407V | T366W |
| T366S/L368A/Y407V/Y349C | T366W/S354C |

Figure 4E

| Monomer 1 | Monomer 2 |
| --- | --- |
| K392D/K409D | E356K/D399K |
| K370D/K392D/K409D | E356K/E357K/D399K |
| I199T/N203D/K247Q/R355Q/N384S/K392N/V397M/Q419E/K447_ | Q196K/I199T/P217R/P228R/N276K |
| I199T/N203D/K247Q/R355Q/N384S/K392N/V397M/Q419E/K447_ | Q196K/I199T/N276K |
| K247Q/R355Q/N384S/K392N/V397M/Q419E/K447_ | P217R/P228R/N276K |
| K247Q/R355Q/N384S/K392N/V397M/Q419E/K447_ | N276K |
| N384S/K392N/V397M/Q419E | N276K |
| D221E/P228E/L368E | D221R/P228R/K409R |
| C220E/P228E/L368E | C220R/E224R/P228R/K409R |
| F405L | K409R |
| T366I/K392M/T394W | F405A/Y407V |
| T366V/K409F | L351Y/Y407A |
| T366A/K392E/K409F/T411E | D399R/S400R/Y407A |
| L351K | L351E |
| I199T/N203D/K247Q/R355Q/Q419E/K447_ | Q196K/I199T/P217R/P228R/N276K |
| I199T/N203D/K247Q/R355Q/Q419E/K447_ | Q196K/I199T/N276K |
| K247Q/R355Q/Q419E/K447_ | P217R/P228R/N276K |
| K247Q/R355Q/Q419E/K447_ | N276K |
| I199T/N203D/K274Q/R355Q/N384S/K392N/V397M/Q419E/K447_ | |
| N208D/Q295E/N384D/Q418E/N421D | |
| N208D/Q295E/Q418E/N421D | |
| Q196K/I199T/P217R/P228R/N276K | |
| Q196K/I199T/N276K | |
| K274Q/R355Q/N384S/K392N/V397M/Q419E/K447_ | |
| Q295E/N384D/Q418E/N421D | |
| Q295E/Q418E/N421D | |
| P217R/P228R/N276K | |
| N276K | |
| E269Q/E272Q/E283Q/E357Q | |
| E269Q/E272Q/E283Q | |
| E269Q/E272Q | |
| E269Q/E283Q | |
| E272Q/E283Q | |
| E269Q | |

Figure 5

| Variant constant region | Substitutions |
|---|---|
| pI_ISO(-) | I199T/N203D/K274Q/R355Q/N384S/K392N/V397M/Q419E/K447_ |
| pI_ISO(-)-Fc only | K274Q/R355Q/N384S/K392N/V397M/Q419E/K447_ |
| pI_(-)_isosteric A | N208D/Q295E/N384D/Q418E/N421D |
| pI_(-)_isosteric A-Fc only | Q295E/N384D/Q418E/N421D |
| pI_(-)_isosteric_B | N208D/Q295E/Q418E/N421D |
| pI_(-)_isosteric_B-Fc only | Q295E/Q418E/N421D |
| pI_ISO(+RR) | Q196K/I199T/P217R/P228R/N276K |
| pI_ISO(+RR)-Fc only | P217R/P228R/N276K |
| pI_ISO(+) | Q196K/I199T/N276K |
| pI_ISO(+)-Fc only | N276K |
| pI_(+)_isosteric_A | E269Q/E272Q/E283Q/E357Q |
| pI_(+)_isosteric_B | E269Q/E272Q/E283Q |
| pI_(+)_isosteric_E269Q/E272Q | E269Q/E272Q |
| pI_(+)_isosteric_E269Q/E283Q | E269Q/E283Q |
| pI_(+)_isosteric_E272Q/E283Q | E272Q/E283Q |
| pI_(+)_isosteric_E269Q | E269Q |

Figure 6

Ablation Variants
G236R
S239G
S239K
S239Q
S239R
V266D
S267K
S267R
H268K
E269R
299R
299K
K322A
A327G
A327L
A327N
A327Q
L328E
P329K
A330L
A330S/P331S
I332K
I332R
V266D/A327Q
V266D/P329K
S267R/A327Q
S267R/P329K
G236R/L328R
E233P/L234V/L235A/G236_/S239K
E233P/L234V/L235A/G236_/S267K
E233P/L234V/L235A/G236_/S239K/A327G
E233P/L234V/L235A/G236_/S267K/A327G
E233P/L234V/L235A/G236_
S239K/S267K
267K/P329K

Figure 7A

| scIL-15/Rα-Fc monomer (-) | scFv-Fc monomer (+) |
|---|---|
| C220S | C220S |
| Heterodimer skew variants L368D/K370S | Heterodimer skew variants S364K/E357Q |
| Isosteric pI substitutions Q295E/N384D/Q418E/N421D | |
| FcKO E233P/L234V/L235A/G236_/S267K | FcKO E233P/L234V/L235A/G236_/S267K |
| ±M428L/N434S | ±M428L/N434S |

Figure 7B

| scFv-Fc monomer (-) | IL-15Rα(sushi)-Fc monomer (+) |
|---|---|
| C220S | C220S |
| Heterodimer skew variants L368D/K370S | Heterodimer skew variants S364K/E357Q |
| Isosteric pI substitutions Q295E/N384D/Q418E/N421D | |
| FcKO E233P/L234V/L235A/G236_/S267K | FcKO E233P/L234V/L235A/G236_/S267K |
| ±M428L/N434S | ±M428L/N434S |

Figure 7C

| scIL-15/Rα-Fc monomer (-) | Heavy Chain (+) |
|---|---|
| C220S | |
| Heterodimer skew variants L368D/K370S | Heterodimer skew variants S364K/E357Q |
| Isosteric pI substitutions Q295E/N384D/Q418E/N421D | |
| FcKO E233P/L234V/L235A/G236_/S267K | FcKO E233P/L234V/L235A/G236_/S267K |
| ±M428L/N434S | ±M428L/N434S |

Figure 7D

| Heavy Chain (-) | IL-15Rα(sushi)-Fc monomer (+) |
|---|---|
| | C220S |
| Heterodimer skew variants L368D/K370S | Heterodimer skew variants S364K/E357Q |
| Isosteric pI substitutions N208D/Q295E/N384D/Q418E/N421D | |
| FcKO E233P/L234V/L235A/G236_/S267K | FcKO E233P/L234V/L235A/G236_/S267K |
| ±M428L/N434S | ±M428L/N434S |

Figure 7E

| Heavy Chain-IL-15Rα(sushi) (−) | Heavy Chain (+) |
|---|---|
| Heterodimer skew variants L368D/K370S | Heterodimer skew variants S364K/E357Q |
| Isosteric pI substitutions N208D/Q295E/N384D/Q418E/N421D | Isosteric pI subsitutions Q196K/I199T/P217R/P228R/N276K |
| FcKO E233P/L234V/L235A/G236_/S267K | FcKO E233P/L234V/L235A/G236_/S267K |
| ±M428L/N434S | ±M428L/N434S |

Figure 7F

| Heavy Chain (−) | Heavy Chain-IL-15Rα(sushi) (+) |
|---|---|
| Heterodimer skew variants L368D/K370S | Heterodimer skew variants S364K/E357Q |
| Isosteric pI substitutions N208D/Q295E/N384D/Q418E/N421D | Isosteric pI subsitutions Q196K/I199T/P217R/P228R/N276K |
| FcKO E233P/L234V/L235A/G236_/S267K | FcKO E233P/L234V/L235A/G236_/S267K |
| ±M428L/N434S | ±M428L/N434S |

Figure 8

| Name | Sequence | SEQ ID NO: |
|---|---|---|
| (GGGGS)$_1$ or GGGGS | GGGGS | SEQ ID NO: 14 |
| (GGGGS)$_2$ | GGGGSGGGGS | SEQ ID NO: 15 |
| (GGGGS)$_3$ | GGGGSGGGGSGGGGS | SEQ ID NO: 16 |
| (GGGGS)$_4$ | GGGGSGGGGSGGGGSGGGGS | SEQ ID NO: 17 |
| (GGGGS)$_5$ | GGGGSGGGGSGGGGSGGGGSGGGGS | SEQ ID NO: 18 |
| (GGGGS)$_6$ | GGGGSGGGGSGGGGSGGGGSGGGGSGGGGS | SEQ ID NO: 19 |
| (GGGGS)$_7$ | GGGGSGGGGSGGGGSGGGGSGGGGSGGGGSGGGGS | SEQ ID NO: 20 |
| 30AA-linker | DPALVHQRPAPPGGGGSGGGGSGGGGSGGG | SEQ ID NO: 21 |
| (GKPGS)$_1$ or GKPGS | GKPGS | SEQ ID NO: 22 |
| (GKPGS)$_5$ | GKPGSGKPGSGKPGSGKPGSGKPGS | SEQ ID NO: 23 |
| (GKPGS)$_6$ | GKPGSGKPGSGKPGSGKPGSGKPGSGKPGS | SEQ ID NO: 24 |
| (GGGES)$_1$ or GGGES | GGGES | SEQ ID NO: 25 |

Additional useful domain linkers

| | |
|---|---|
| KTHTCPPCP ("half hinge") | SEQ ID NO:26 |
| EPKSSDKTHTCPPCP ("full hinge C220S variant") | SEQ ID NO:27 |
| GGGGSGGGGSKTHTCPPCP ("flex half hinge") | SEQ ID NO:28 |
| GKPGSGKPGSKTHTCPPCP ("charged half hinge1") | SEQ ID NO:29 |
| GKPGSKTHTCPPCP ("charged half hinge2") | SEQ ID NO:30 |

Figure 9A

Positive Charged scFv Linkers

| Name | Sequence | Length | Charge | SEQ ID NO: |
|---|---|---|---|---|
| Gly-Ser 15 | GGGGSGGGGSGGGGS | 15 | 0 | SEQ ID NO: 16 |
| Whitlow linker | GSTSGSGKPGSGEGSTKG | 18 | +1 | SEQ ID NO: 31 |
| 6paxA_1 (+A) | IRPRAIGGSKPRVA | 14 | +4 | SEQ ID NO: 32 |
| +B | GKGGSGKGGSGKGGS | 15 | +3 | SEQ ID NO: 33 |
| +C | GGKGSGGKGSGGKGS | 15 | +3 | SEQ ID NO: 34 |
| +D | GGGKSGGGKSGGGKS | 15 | +3 | SEQ ID NO: 35 |
| +E | GKGKSGKGKSGKGKS | 15 | +6 | SEQ ID NO: 36 |
| +F | GGGKSGGKGSGKGGS | 15 | +3 | SEQ ID NO: 37 |
| +G | GKPGSGKPGSGKPGS | 15 | +3 | SEQ ID NO: 38 |
| +H | GKPGSGKPGSGKPGSGKPGS | 20 | +4 | SEQ ID NO: 39 |
| +I | GKGKSGKGKSGKGKSGKGKS | 20 | +8 | SEQ ID NO: 40 |

Figure 9B

Negative Charged scFv Linkers

| Name | Sequence | Length | Charge | SEQ ID NO: |
|---|---|---|---|---|
| Gly-Ser 20 | GGGGSGGGGSGGGGSGGGGS | 20 | 0 | SEQ ID NO: 17 |
| 3hsc_2 (-A) | STAGDTHLGGEDFD | 14 | -4 | SEQ ID NO: 41 |
| -B | GEGGSGEGGSGEGGS | 15 | -3 | SEQ ID NO: 42 |
| -C | GGEGSGGEGSGGEGS | 15 | -3 | SEQ ID NO: 43 |
| -D | GGGESGGGESGGGES | 15 | -3 | SEQ ID NO: 44 |
| -E | GEGESGEGESGEGES | 15 | -6 | SEQ ID NO: 45 |
| -F | GGGESGGEGSGEGGS | 15 | -3 | SEQ ID NO: 46 |
| -G | GEGESGEGESGEGESGEGES | 20 | -8 | SEQ ID NO: 47 |

Figure 10

IL-15/Rα x anti-TIM-3 Backbone 1

>Chain 1 (SEQ ID NO:48)
/ASTKGPSVFPLAPSSKSTSGGTAALGCLVKDYFPEPVTVSWNSGALTSGVHTFPAVLQSSGLYSLSSVVTVPSSSLGTQTYICNVNHKPSNT
KVDKKVEPKSCDKTHTCPPCPAPPVAGPSVFLFPPKPKDTLMISRTPEVTCVVVDVKHEDPEVKFNWYVDGVEVHNAKTKPREEQYNSTYRVV
SVLTVLHQDWLNGKEYKCKVSNKALPAPIEKTISKAKGQPREPQVYTLPPSREQMTKNQVKLTCLVKGFYPSDIAVEWESNGQPENNYKTTPP
VLDSDGSFFLYSKLTVDKSRWQQGNVFSCSVMHEALHNHYTQKSLSLSPGK >Chain 2 (SEQ ID NO:49)
/EPKSSDKTHTCPPCPAPPVAGPSVFLFPPKPKDTLMISRTPEVTCVVVDVKHEDPEVKFNWYVDGVEVHNAKTKPREEEYNSTYRVVSVLTV
LHQDWLNGKEYKCKVSNKALPAPIEKTISKAKGQPREPQVYTLPPSREEMTKNQVSLTCDVSGFYPSDIAVEWESDGQPENNYKTTPPVLDSD
GSFFLYSKLTVDKSRWEQGDVFSCSVMHEALHNHYTQKSLSLSPGK

IL-15/Rα x anti-TIM-3 Backbone 2

>Chain 1 (SEQ ID NO:50)
/ASTKGPSVFPLAPSSKSTSGGTAALGCLVKDYFPEPVTVSWNSGALTSGVHTFPAVLQSSGLYSLSSVVTVPSSSLGTQTYICNVNHKPSDT
KVDKKVEPKSCDKTHTCPPCPAPPVAGPSVFLFPPKPKDTLMISRTPEVTCVVVDVKHEDPEVKFNWYVDGVEVHNAKTKPREEEYNSTYRVV
SVLTVLHQDWLNGKEYKCKVSNKALPAPIEKTISKAKGQPREPQVYTLPPSREEMTKNQVSLTCDVSGFYPSDIAVEWESDGQPENNYKTTPP
VLDSDGSFFLYSKLTVDKSRWEQGDVFSCSVMHEALHNHYTQKSLSLSPGK >Chain 2 (SEQ ID NO:51)
/EPKSSDKTHTCPPCPAPPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREQMTKNQVKLTCLVKGFYPSDIAVEWESNGQPENNYKTTPPVLDSD
GSFFLYSKLTVDKSRWQQGNVFSCSVMHEALHNHYTQKSLSLSPGK

IL-15/Rα x anti-TIM-3 Backbone 3

>Chain 1 (SEQ ID NO:52)
/ASTKGPSVFPLAPSSKSTSGGTAALGCLVKDYFPEPVTVSWNSGALTSGVHTFPAVLQSSGLYSLSSVVTVPSSSLGTQTYICNVNHKPSDT
KVDKKVEPKSCDKTHTCPPCPAPPVAGPSVFLFPPKPKDTLMISRTPEVTCVVVDVKHEDPEVKFNWYVDGVEVHNAKTKPREEEYNSTYRVV
SVLTVLHQDWLNGKEYKCKVSNKALPAPIEKTISKAKGQPREPQVYTLPPSREEMTKNQVSLTCDVSGFYPSDIAVEWESDGQPENNYKTTPP
VLDSDGSFFLYSKLTVDKSRWEQGDVFSCSVMHEALHNHYTQKSLSLSPGK >Chain 2 (SEQ ID NO:53)
/ASTKGPSVFPLAPSSKSTSGGTAALGCLVKDYFPEPVTVSWNSGALTSGVHTFPAVLQSSGLYSLSSVVTVPSSSLGTKTYTCNVNHKPSNT
KVDKKVERKSCDKTHTCPRCPAPPVAGPSVFLFPPKPKDTLMISRTPEVTCVVVDVKHEDPEVKFKWYVDGVEVHNAKTKPREEQYNSTYRVV
SVLTVLHQDWLNGKEYKCKVSNKALPAPIEKTISKAKGQPREPQVYTLPPSREQMTKNQVKLTCLVKGFYPSDIAVEWESNGQPENNYKTTPP
VLDSDGSFFLYSKLTVDKSRWQQGNVFSCSVMHEALHNHYTQKSLSLSPGK

Figure 11

Constant Light Chain – Kappa (SEQ ID NO:54)
/RTVAAPSVFIFPPSDEQLKSGTASVVCLLNNFYPREAKVQWKVDNALQSGNSQESVTEQDSKDSTYSLSSTLTLSKADYEKHKVYACEVTHQ
GLSSPVTKSFNRGEC

Constant Light Chain – Lambda (SEQ ID NO:55)
/GQPKAAPSVTLFPPSSEELQANKATLVCLISDFYPGAVTVAWKADSSPVKAGVETTTPSKQSNNKYAASSYLSLTP
EQWKSHRSYSCQVTHEGSTVEKTVAPTECS

Figure 12

>3H3[TIM-3]_H0L0 Variable Heavy (SEQ ID NO: 56-59)
QVQLKESGPGLVAPSQSLSITCTVSGFSLNGYGVNWVRQPPGKGLEWLGMIWGDGSTDYNSALKSRLSISKDNSKSQ
VFLKMNSLQTDDTARYYCARSYYTSDEDYWGQGTLVTVSA

>3H3[TIM-3]_H0L0 Variable Light (SEQ ID NO: 60-63)
DIVMSQSPSSLAVSAGEKVTMSCKSSQSLLNSRTRKNYLAWYQQKPGQSPKLLIYWASTRESGVPDRFTGSGSGTDF
TLTISSVLAEDLAVYYCKQSYSLRTFGGGTKLEIK

>3H3[TIM-3]_H1L2 Variable Heavy (SEQ ID NO: 64-67)
QVTLKESGPVLVKPTETLTLTCTVSGFSLNGYGVNWVRQPPGKGLEWLAMIWGDGSTDYNSALKSRLTISKDNSKSQ
VVLTMTNMDPVDTATYYCARSYYTSDEDYWGQGTLVTVSS

>3H3[TIM-3]_H1L2 Variable Light (SEQ ID NO: 68-71)
DIVLTQSPDSLAVSLGERATINCKSSQSLLNSRTRKNYLAWYQQKPGQSPKLLIYWASTRESGVPDRFTGSGSGTDF
TLTISSLQAEDVAVYYCKQSYSLRTFGGGTKVEIK

>3H3[TIM-3]_H1L2.1 Variable Heavy (SEQ ID NO: 72-75)
QVTLKESGPVLVKPTETLTLTCTVSGFSLNGYGVNWVRQPPGKGLEWLAMIWGDGSTDYNSALKSRLTISKDNSKSQ
VVLTMTNMDPVDTATYYCARSYYTSDEDYWGQGTLVTVSS

>3H3[TIM-3]_H1L2.1 Variable Light (SEQ ID NO: 76-79)
DIVMTQSPDSLAVSLGERATINCKSSQSLLNSRTRKNYLAWYQQKPGQSPKLLIYWASTRESGVPDRFTGSGSGTDF
TLTISSLQAEDVAVYYCKQSYSLRTFGGGTKVEIK

Figure 13A

>APE5137[TIM-3] Variable Heavy (SEQ ID NO: 80-83)
EVQLLESGGGLVQPGGSLRLSCAAASGFTFSSYDMSWVRQAPGKGLDWVSTISGGGTYTYYQDSVKGRFTISRDNSK
NTLYLQMNSLRAEDTAVYYCASMDYWGQGTTVTVSSA

>APE5137[TIM-3] Variable Light (SEQ ID NO: 84-87)
DIQMTQSPSSLSASVGDRVTITCRASQSIRRYLNWYHQKPGKAPKLLIYGASTLQSGVPSRFSGSGSGTDFTLTISS
LQPEDFAVYYCQQSHSAPLTFGGGTKVEIKR

>APE5121[TIM-3] Variable Heavy (SEQ ID NO: 88-91)
EVQVLESGGGLVQPGGSLRLYCVASGFTFSGSYAMSWVRQAPGKGLEWVSAISGSGGSTYYADSVKGRFTISRDNSK
NTLYLQMNSLRAEDTAVYYCAKKYYVGPADYWGQGTLVTVSSG

>APE5121[TIM-3] Variable Light (SEQ ID NO: 92-95)
DIVMTQSPDSLAVSLGERATINCKSSQSVLYSSNNKNYLAWYQHKPGQPPKLLIYWASTRESGVPDRFSGSGSGTDF
TLTISSLQAEDVAVYYCQQYYSSPLTFGGGTKIEVK

>ABTIM3-hum03[TIM-3] Variable Heavy ((SEQ ID NO: 96-99)
QVQLVQSGAEVKKPGASVKVSCKASGYTFTSYNMHWVRQAPGQGLEWIGDIYPGQGDTSYNQKFKGRATMTADKSTS
TVYMELSSLRSEDTAVYYCARVGGAFPMDYWGQGTLVTVSS

>ABTIM3-hum03[TIM-3] Variable Light (SEQ ID NO: 100-103)
DIVLTQSPDSLAVSLGERATINCRASESVEYYGTSLMQWYQQKPGQPPKLLIYAASNVESGVPDRFSGSGSGTDFTL
TISSLQAEDVAVYYCQQSRKDPSTFGGGTKVEIK

>ABTIM3-hum11[TIM-3] Variable Heavy (SEQ ID NO: 104-107)
QVQLVQSGAEVKKPGSSVKVSCKASGYTFTSYNMHWVRQAPGQGLEWMGDIYPGNGDTSYNQKFKGRVTITADKSTS
TVYMELSSLRSEDTAVYYCARVGGAFPMDYWGQGTTVTVSS

>ABTIM3-hum11[TIM-3] Variable Light (SEQ ID NO: 108-111)
AIQLTQSPSSLSASVGDRVTITCRASESVEYYGTSLMQWYQQKPGKAPKLLIYAASNVESGVPSRFSGSGSGTDFTL
TISSLQPEDFATYFCQQSRKDPSTFGGGTKVEIK

>ABTIM3-hum21[TIM-3] Variable Heavy (SEQ ID NO: 112-115))
QVQLVQSGAEVKKPGASVKVSCKASGYTFTSYNMHWVRQAPGQGLEWIGDIYPGQGDTSYNQKFKGRATMTADKSTS
TVYMELSSLRSEDTAVYYCARVGGAFPMDYWGQGTLVTVSS

>ABTIM3-hum21[TIM-3] Variable Light (SEQ ID NO: 116-119))
DIVLTQSPDSLAVSLGERATINCRASESVEYYGTSLMQWYQQKPGQPPKLLIYAASNVESGVPDRFSGSGSGTDFTL
TISSLQAEDVAVYYCQQSRKDPSTFGGGTKVEIK

>4177[TIM-3] Variable Heavy (SEQ ID NO: 120-123)
QVQLQESGPGLVKPSETLSLTCTVSGGSISSYYWSWIRQPPGKGLEWIGYIFHSGSTNYNPSLKSRVTISVDTSKNQ
FSLKLSSVTAADTAVYYCARDGEYFDMLTGFDYWGQGTLVTVSS

Figure 13B

>4177[TIM-3] Variable Light (SEQ ID NO: 124-127)
RCDIQMTQSPSSLSASVGDRVTITCRASQGISSWLAWYQQKPEKAPKSLIYAASSLQSGVPSRFSGSGSGTDFTLTI
SSLQPEDFATYYCQQYNSYPRTFGQGTKVEIK

>4545[TIM-3] Variable Heavy (SEQ ID NO: 128-131)
QVQLQESGPGLVKPSETLSLTCTVSGGSFSRGGYYWNWIRQPPGKGLEWIGYIYYSGSTNYNPSLKSRVTISLDTSK
NQFSLKLSSVTAADTAVYYCARDHYSSSWTFDYWGQGTLVTVSS

>4545[TIM-3] Variable Light (SEQ ID NO: 132-135)
EIVLTQSPATLSLSPGERATLSCRASQSVSSYLAWYQQKPGQAPRLLIYDASNRATGIPARFSGSGSGTDFTLTISS
LEPEDFAVYYCQQRSNWPPTFGQGTKLEIK

>8213[TIM-3] Variable Heavy (SEQ ID NO: 136-139)
QVQLVQSGAEVKKPGASVKVSCKASGYTFTSYWMHWVRQAPGQGLEWMGEINPSNGRTNYNEKFKTRVTITADTSTS
TAYMELSSLRSEDTAVYYCARGYYLYFDYWGQGTLVTVSS

>8213[TIM-3] Variable Light (SEQ ID NO: 140-143)
DIQMTQSPSSLSASVGDRVTITCHASQGIRINIGWYQQKPGKAPKLLIYHGTNLEDGVPSRFSGSGSGTDFTLTISS
LQPEDFATYYCVQYGQFPWTFGQGTKLEIK

>mAb15[TIM-3] Variable Heavy (SEQ ID NO: 144-147)
QVQLKESGPGLVAPSQSLSITCTVSGFSLTGYGVTWVRQPPGKGLEWLGMIWGDGNTDYNSGLKSRLNISKDNSKSQ
VFLKMNSLQTDDTARYYCARSYYYGPPDYWGQGTTLTVSS

>mAb15[TIM-3] Variable Light (SEQ ID NO: 148-151)
DIVMTQSPSSLAMSVGQKVTMSCKSSQSLLNSRSQKNYLAWYQRKPGQSPKLLLYFASTRESGVPDRFIGSGSGTDF
TLTISSVQAEDLADYFCHQHYNTPYTFGGGTKLEIK

>mAb58[TIM-3] Variable Heavy (SEQ ID NO: 152-155)
QIQLVQSGPELKKPGETVKISCKASGYTFTTYGMSWVKQAPGKGLKLMGWINTYSGAPTYADDFKGRFAFSLETSAS
AAYLQINNLKNEDTATYFCARKPPHYYVNSFDYWGQGTTLVTSS

>mAb58[TIM-3] Variable Light (SEQ ID NO: 156-159)
DIVMTQSPATLSVTPGDRVSLSCRASQSISDYLHWYQQKSHESPRLLIKYASQSISGIPSRFSGSGSGSDFTLSINS
VEPEDVGVYYCQNGHSFPYTFGGGTKLEIK

>TIM3-0433[TIM-3] Variable Heavy (SEQ ID NO: 160-163)
QITLKESGPTLVKPTQTLTLTCTFSGFSLSTSGMSVGWIRQPPGKGLEWLAHIWLNDDVFFNPALKSRLTITKDTSK
NQVVLTMTNMDPVDTATYYCVRANGYLYALDYWGQGTLVTVSS

>TIM3-0433[TIM-3] Variable Light (SEQ ID NO: 164-167)
ETTLTQSPAFMSATPGDKVNIACSASSSVSYTQWYQQKPGEAPKLWIYDAFKLAPGIPPRFSGSGYGTDFTLTINNI
ESEDAAYYFCHQWSSYPWTFGQGTKLEIK

Figure 13C

>TIM3-0434[TIM-3] Variable Heavy (SEQ ID NO: 168-171)
QITLKESGPTLVKPTQTLTLTCTFSGFSLSTSGMSVGWIRQPPGKGLEWLAHIWLNDDVFFNPALKSRLTITKDTSK
NQVVLTMTNMDPVDTATYYCVRANGYLYALDYWGQGTLVTVSS

>TIM3-0434[TIM-3] Variable Light (SEQ ID NO: 172-175)
DIQLTQSPSFLSASVGDRVTITCSASSSVSYTQWYQQKPGKAPKLWIYDAFKLAPGVPSRFSGSGSGTEFTLTISSL
QPEDFATYFCHQWSSYPWTFGQGTKLEIK

>TIM3-0438[TIM-3] Variable Heavy (SEQ ID NO: 176-179)
EVQLVESGGGLVQPGGSLRLSCAASGFNIKTTYMHWVRQAPGKGLEWVGRIDPADDNTKYAPKFQGKATISADTSKN
TAYLQMNSLRAEDTAVYYCVRDFGYVAWFAYWGQGTLVTVSS

>TIM3-0438[TIM-3] Variable Light (SEQ ID NO: 180-183)
DIVMTQSPLSLPVTPGEPASISCRASQSVDNYVAWYLQKPGQSPQLLIYYASNRYIGVPDRFSGSGSGTDFTLKISR
VEAEDVGVYYCQQHYSSPYTFGQGTKVEIK

>TIM3-0443[TIM-3] Variable Heavy (SEQ ID NO: 184-187)
EVQLVESGGGLVQPGGSLRLSCAASGFNIKTTYMHWVRQAPGKGLEWVGRIDPADDNTKYAPKFQGKATISADTSKN
TAYLQMNSLRAEDTAVYYCVRDFGYVAWFAYWGQGTLVTFSS

>TIM3-0443[TIM-3] Variable Light (SEQ ID NO: 188-191)
DIVMTQSPLSLPVTPGEPASISCRASQSVDNYVAWYLQKPGQSPQLLIYYASNRYIGVPDRFSGSGSGTDFTLKISR
VEAEDVGVYYCQQHYSSPYTFGQGTKVEIK

Figure 15

IL-15Rα(sushi-D96) (SEQ ID NO:192)
ITCPPPMSVEHADIWVKSYSLYSRERYICNSGFKRKAGTSSLTECVLNKATNVAHWTTPSLKCIRD

IL-15Rα(sushi-D96/P97) (SEQ ID NO:193)
ITCPPPMSVEHADIWVKSYSLYSRERYICNSGFKRKAGTSSLTECVLNKATNVAHWTTPSLKCIRDP

IL-15Rα(sushi-D96/P97/A98) (SEQ ID NO:194)
ITCPPPMSVEHADIWVKSYSLYSRERYICNSGFKRKAGTSSLTECVLNKATNVAHWTTPSLKCIRDPA

Figure 16

IL-15 (E87C)  (SEQ ID NO:195)
NWVNVISDLKKIEDLIQSMHIDATLYTESDVHPSCKVTAMKCFLLELQVISLESGDASIHDTVENLIILANNSLSSN
GNVTESGCKCCEELEEKNIKEFLQSFVHIVQMFINTS

IL-15 (V49C)  (SEQ ID NO:196)
NWVNVISDLKKIEDLIQSMHIDATLYTESDVHPSCKVTAMKCFLLELQCISLESGDASIHDTVENLIILANNSLSSN
GNVTESGCKECEELEEKNIKEFLQSFVHIVQMFINTS

IL-15 (L52C)  (SEQ ID NO: 197)
NWVNVISDLKKIEDLIQSMHIDATLYTESDVHPSCKVTAMKCFLLELQVISCESGDASIHDTVENLIILANNSLSSN
GNVTESGCKECEELEEKNIKEFLQSFVHIVQMFINTS

IL-15 (E89C)  (SEQ ID NO: 198)
NWVNVISDLKKIEDLIQSMHIDATLYTESDVHPSCKVTAMKCFLLELQVISLESGDASIHDTVENLIILANNSLSSN
GNVTESGCKECCELEEKNIKEFLQSFVHIVQMFINTS

IL-15 (Q48C)  (SEQ ID NO: 199)
NWVNVISDLKKIEDLIQSMHIDATLYTESDVHPSCKVTAMKCFLLELCVISLESGDASIHDTVENLIILANNSLSSN
GNVTESGCKECEELEEKNIKEFLQSFVHIVQMFINTS

IL-15 (E53C)  (SEQ ID NO: 200)
NWVNVISDLKKIEDLIQSMHIDATLYTESDVHPSCKVTAMKCFLLELQVISLCSGDASIHDTVENLIILANNSLSSN
GNVTESGCKECEELEEKNIKEFLQSFVHIVQMFINTS

IL-15 (C42S)  (SEQ ID NO: 201)
NWVNVISDLKKIEDLIQSMHIDATLYTESDVHPSCKVTAMKSFLLELQVISLESGDASIHDTVENLIILANNSLSSN
GNVTESGCKECEELEEKNIKEFLQSFVHIVQMFINTS

IL-15 (L45C)  (SEQ ID NO: 202)
NWVNVISDLKKIEDLIQSMHIDATLYTESDVHPSCKVTAMKCFLCELQVISLESGDASIHDTVENLIILANNSLSSN
GNVTESGCKECEELEEKNIKEFLQSFVHIVQMFINTS

Figure 17

IL-15Rα(sushi-D96/C97) (SEQ ID NO: 203)
ITCPPPMSVEHADIWVKSYSLYSRERYICNSGFKRKAGTSSLTECVLNKATNVAHWTTPSLKCIRDC

IL-15Rα(sushi-D96/P97/C98) (SEQ ID NO: 204)
ITCPPPMSVEHADIWVKSYSLYSRERYICNSGFKRKAGTSSLTECVLNKATNVAHWTTPSLKCIRDPC

IL-15Rα(sushi-D96/C97/A98) (SEQ ID NO: 205)
ITCPPPMSVEHADIWVKSYSLYSRERYICNSGFKRKAGTSSLTECVLNKATNVAHWTTPSLKCIRDCA

IL-15Rα(sushi-S40C) (SEQ ID NO: 206)
ITCPPPMSVEHADIWVKSYSLYSRERYICNSGFKRKAGTCSLTECVLNKATNVAHWTTPSLKCIR

IL-15Rα(sushi-K34C) (SEQ ID NO: 207)
ITCPPPMSVEHADIWVKSYSLYSRERYICNSGFCRKAGTSSLTECVLNKATNVAHWTTPSLKCIR

IL-15Rα(sushi-G38C) (SEQ ID NO: 208)
ITCPPPMSVEHADIWVKSYSLYSRERYICNSGFKRKACTSSLTECVLNKATNVAHWTTPSLKCIR

IL-15Rα(sushi-L42C) (SEQ ID NO: 209)
ITCPPPMSVEHADIWVKSYSLYSRERYICNSGFKRKAGTSSCTECVLNKATNVAHWTTPSLKCIR

IL-15Rα(sushi-A37C) (SEQ ID NO: 210)
ITCPPPMSVEHADIWVKSYSLYSRERYICNSGFKRKCGTSSLTECVLNKATNVAHWTTPSLKCIR

Figure 19A

N1D (SEQ ID NO: 211)
DWVNVISDLKKIEDLIQSMHIDATLYTESDVHPSCKVTAMKCFLLELQVISLESGDASIHDTVENLIILANNSLSSNGNVTESGCKECEELEE
KNIKEFLQSFVHIVQMFINTS

N4D (SEQ ID NO: 212)
NWVDVISDLKKIEDLIQSMHIDATLYTESDVHPSCKVTAMKCFLLELQVISLESGDASIHDTVENLIILANNSLSSNGNVTESGCKECEELEE
KNIKEFLQSFVHIVQMFINTS

D8N (SEQ ID NO: 213)
NWVNVISNLKKIEDLIQSMHIDATLYTESDVHPSCKVTAMKCFLLELQVISLESGDASIHDTVENLIILANNSLSSNGNVTESGCKECEELEE
KNIKEFLQSFVHIVQMFINTS

D30N (SEQ ID NO: 214)
NWVNVISDLKKIEDLIQSMHIDATLYTESNVHPSCKVTAMKCFLLELQVISLESGDASIHDTVENLIILANNSLSSNGNVTESGCKECEELEE
KNIKEFLQSFVHIVQMFINTS

D61N (SEQ ID NO: 215)
NWVNVISDLKKIEDLIQSMHIDATLYTESDVHPSCKVTAMKCFLLELQVISLESGDASIHNTVENLIILANNSLSSNGNVTESGCKECEELEE
KNIKEFLQSFVHIVQMFINTS

E64Q (SEQ ID NO: 216)
NWVNVISDLKKIEDLIQSMHIDATLYTESDVHPSCKVTAMKCFLLELQVISLESGDASIHDTVQNLIILANNSLSSNGNVTESGCKECEELEE
KNIKEFLQSFVHIVQMFINTS

N65D (SEQ ID NO: 217)
NWVNVISDLKKIEDLIQSMHIDATLYTESDVHPSCKVTAMKCFLLELQVISLESGDASIHDTVEDLIILANNSLSSNGNVTESGCKECEELEE
KNIKEFLQSFVHIVQMFINTS

Q108E (SEQ ID NO: 218)
NWVNVISDLKKIEDLIQSMHIDATLYTESDVHPSCKVTAMKCFLLELQVISLESGDASIHDTVENLIILANNSLSSNGNVTESGCKECEELEE
KNIKEFLQSFVHIVEMFINTS

N1D/D61N (SEQ ID NO: 219)
DWVNVISDLKKIEDLIQSMHIDATLYTESDVHPSCKVTAMKCFLLELQVISLESGDASIHNTVENLIILANNSLSSNGNVTESGCKECEELEE
KNIKEFLQSFVHIVQMFINTS

N1D/E64Q (SEQ ID NO: 220)
DWVNVISDLKKIEDLIQSMHIDATLYTESDVHPSCKVTAMKCFLLELQVISLESGDASIHDTVQNLIILANNSLSSNGNVTESGCKECEELEE
KNIKEFLQSFVHIVQMFINTS

N4D/D61N (SEQ ID NO: 221)
NWVDVISDLKKIEDLIQSMHIDATLYTESDVHPSCKVTAMKCFLLELQVISLESGDASIHNTVENLIILANNSLSSNGNVTESGCKECEELEE
KNIKEFLQSFVHIVQMFINTS

N4D/E64Q (SEQ ID NO: 222)
NWVDVISDLKKIEDLIQSMHIDATLYTESDVHPSCKVTAMKCFLLELQVISLESGDASIHDTVQNLIILANNSLSSNGNVTESGCKECEELEE
KNIKEFLQSFVHIVQMFINTS

D8N/D61N (SEQ ID NO: 223)
NWVNVISNLKKIEDLIQSMHIDATLYTESDVHPSCKVTAMKCFLLELQVISLESGDASIHNTVENLIILANNSLSSNGNVTESGCKECEELEE
KNIKEFLQSFVHIVQMFINTS

Figure 19B

D8N/E64Q (SEQ ID NO: 224)
NWVNVISNLKKIEDLIQSMHIDATLYTESDVHPSCKVTAMKCFLLELQVISLESGDASIHDTVQNLIILANNSLSSNGNVTESGCKECEELEE
KNIKEFLQSFVHIVQMFINTS

D61N/E64Q (SEQ ID NO: 225)
NWVNVISDLKKIEDLIQSMHIDATLYTESDVHPSCKVTAMKCFLLELQVISLESGDASIHNTVQNLIILANNSLSSNGNVTESGCKECEELEE
KNIKEFLQSFVHIVQMFINTS

E64Q/Q108E (SEQ ID NO: 226)
NWVNVISDLKKIEDLIQSMHIDATLYTESDVHPSCKVTAMKCFLLELQVISLESGDASIHDTVQNLIILANNSLSSNGNVTESGCKECEELEE
KNIKEFLQSFVHIVEMFINTS

N1D/N4D/D8N (SEQ ID NO: 227)
DWVDVISNLKKIEDLIQSMHIDATLYTESDVHPSCKVTAMKCFLLELQVISLESGDASIHDTVENLIILANNSLSSNGNVTESGCKECEELEE
KNIKEFLQSFVHIVQMFINTS

D61N/E64Q/N65D (SEQ ID NO: 228)
NWVNVISDLKKIEDLIQSMHIDATLYTESDVHPSCKVTAMKCFLLELQVISLESGDASIHNTVQDLIILANNSLSSNGNVTESGCKECEELEE
KNIKEFLQSFVHIVQMFINTS

N1D/D61N/E64Q/Q108E (SEQ ID NO: 229)
DWVNVISDLKKIEDLIQSMHIDATLYTESDVHPSCKVTAMKCFLLELQVISLESGDASIHNTVQNLIILANNSLSSNGNVTESGCKECEELEE
KNIKEFLQSFVHIVEMFINTS

N4D/D61N/E64Q/Q108E (SEQ ID NO: 230)
NWVDVISDLKKIEDLIQSMHIDATLYTESDVHPSCKVTAMKCFLLELQVISLESGDASIHNTVQNLIILANNSLSSNGNVTESGCKECEELEE
KNIKEFLQSFVHIVEMFINTS

N1D/N65D (SEQ ID NO: 231)
DWVNVISDLKKIEDLIQSMHIDATLYTESDVHPSCKVTAMKCFLLELQVISLESGDASIHDTVEDLIILANNSLSSNGNVTESGCKECEELEE
KNIKEFLQSFVHIVQMFINTS

N1D/Q108E (SEQ ID NO: 232)
DWVNVISDLKKIEDLIQSMHIDATLYTESDVHPSCKVTAMKCFLLELQVISLESGDASIHDTVENLIILANNSLSSNGNVTESGCKECEELEE
KNIKEFLQSFVHIVEMFINTS

N4D/N65D (SEQ ID NO: 233)
NWVDVISDLKKIEDLIQSMHIDATLYTESDVHPSCKVTAMKCFLLELQVISLESGDASIHDTVEDLIILANNSLSSNGNVTESGCKECEELEE
KNIKEFLQSFVHIVQMFINTS

D30N/N65D (SEQ ID NO: 234)
NWVNVISDLKKIEDLIQSMHIDATLYTESNVHPSCKVTAMKCFLLELQVISLESGDASIHDTVEDLIILANNSLSSNGNVTESGCKECEELEE
KNIKEFLQSFVHIVQMFINTS

D30N/Q108E (SEQ ID NO: 235)
NWVNVISDLKKIEDLIQSMHIDATLYTESNVHPSCKVTAMKCFLLELQVISLESGDASIHDTVENLIILANNSLSSNGNVTESGCKECEELEE
KNIKEFLQSFVHIVEMFINTS

N65D/Q108E (SEQ ID NO: 236)
NWVNVISDLKKIEDLIQSMHIDATLYTESDVHPSCKVTAMKCFLLELQVISLESGDASIHDTVEDLIILANNSLSSNGNVTESGCKECEELEE
KNIKEFLQSFVHIVEMFINTS

Figure 19C

E64Q/N65D (SEQ ID NO: 237)
NWVNVISDLKKIEDLIQSMHIDATLYTESDVHPSCKVTAMKCFLLELQVISLESGDASIHDTVQDLIILANNSLSSNGNVTESGCKECEELEE
KNIKEFLQSFVHIVQMFINTS

N1D/N4D/N65D (SEQ ID NO: 238)
DWVDVISDLKKIEDLIQSMHIDATLYTESDVHPSCKVTAMKCFLLELQVISLESGDASIHDTVEDLIILANNSLSSNGNVTESGCKECEELEE
KNIKEFLQSFVHIVQMFINTS

D30N/E64Q/N65D (SEQ ID NO: 239)
NWVNVISDLKKIEDLIQSMHIDATLYTESNVHPSCKVTAMKCFLLELQVISLESGDASIHDTVQDLIILANNSLSSNGNVTESGCKECEELEE
KNIKEFLQSFVHIVQMFINTS

N4D/D61N/N65D (SEQ ID NO: 240)
NWVDVISDLKKIEDLIQSMHIDATLYTESDVHPSCKVTAMKCFLLELQVISLESGDASIHNTVEDLIILANNSLSSNGNVTESGCKECEELEE
KNIKEFLQSFVHIVQMFINTS

Figure 20

| XENP | Variant | EC50 pM (NK cells) | Fold reduced (NK cells) | EC50 pM (CD8 T cells) | Fold reduced (CD8 T cells) |
|---|---|---|---|---|---|
| 20818 | WT | 200.6 | | 637.1 | |
| 21478 | single-chain | 848.5 | 4.2 | 4982.0 | 7.8 |
| 22815 | N1D | 281.3 | 1.4 | 1051.0 | 1.6 |
| 22816 | N4D | 321.9 | 1.6 | 1190.0 | 1.9 |
| 22817 | D8N | very weak | very weak | very weak | very weak |
| 22818 | D30N | 376.3 | 1.9 | 1366.0 | 2.1 |
| 22819 | D61N | 5934.0 | 29.6 | 161937.0 | >100 |
| 22820 | E64Q | 877.0 | 4.4 | 2858.0 | 4.5 |
| 22821 | N65D | 2883.0 | 14.4 | 6928.0 | 10.9 |
| 22822 | Q108E | 9777.0 | 48.7 | very weak | >100 |
| 22823 | N1D/D61N | 918.0 | 4.6 | 4225.0 | 6.6 |
| 22824 | N1D/E64Q | 1091.0 | 5.4 | 4228.0 | 6.6 |
| 22825 | N4D/D61N | 309.0 | 1.5 | 1070.0 | 1.7 |
| 22826 | N4D/E64Q | very weak | very weak | very weak | very weak |
| 22827 | D8N/D61N | ND | ND | ND | ND |
| 22828 | D8N/E64Q | 597.7 | 3.0 | 1658.0 | 2.6 |
| 22829 | D61N/E64Q | 458.2 | 2.3 | 2115.0 | 3.3 |
| 22830 | E64Q/Q108E | 436.6 | 2.2 | 1815.0 | 2.8 |
| 22831 | N1D/N4D/D8N | very weak | very weak | very weak | very weak |
| 22832 | D61N/E64Q/N65D | ND | ND | ND | ND |
| 22833 | N1D/D61N/E64Q/Q108E | ND | ND | ND | ND |
| 22834 | N4D/D61N/E64Q/Q108E | very weak | very weak | very weak | very weak | scIL-15/Rα x scFv scFv x ncIL-15/Rα scFv x dsIL-15/Rα scIL-15/Rα x Fab
Example: XENP27974

Fab x ncIL-15/Rα

Fab x dsIL-15/Rα mAb-scIL-15/Rα mAb-ncIL-15/Rα mAb-dsIL-15/Rα central-IL-15/Rα central-scIL-15/Rα

Figure 22

>XENP027974 human IL15Ra(sushi) (GGGGS)5-human IL15(N4D/N65D;single-Chain )-3H3[TIM-3] H1 L2.1 Fab IgG1 Fc(216) IgG1 pI(-) Isosteric A C220S/PVA /S267K/L368D/K370S-IgG1 PVA /S267K/S364K/E357Q

*Chain 1 human_IL15Ra(sushi)_(GGGGS)5-human_IL15(N4D/N65D;single-Chain )_Fc(216)_IgG1_pI(-)_Isosteric_A_C220S/PVA_/S267K/L368D/K370S scIL-15/Ra-Fc Chain* (SEQ ID NO: 241)
ITCPPPMSVEHADIWVKSYSLYSRERYICNSGFKRKAGTSSLTECVLNKATNVAHWTTPSLKCIR/<u>GGGGSGGGGSG GGGSGGGGSGGGGS</u>/NWVDVISDLKKIEDLIQSMHIDATLYTESDVHPSCKVTAMKCFLLELQVISLESGDASIHDT VEDLIILANNSLSSNGNVTESGCKECEELEEKNIKEFLQSFVHIVQMFINTS/EPKSSDKTHTCPPCPAPPVAGPSV FLFPPKPKDTLMISRTPEVTCVVVDVKHEDPEVKFNWYVDGVEVHNAKTKPREEEYNSTYRVVSVLTVLHQDWLNGK EYKCKVSNKALPAPIEKTISKAKGQPREPQVYTLPPSREEMTKNQVSLTCDVSGFYPSDIAVEWESDGQPENNYKTT PPVLDSDGSFFLYSKLTVDKSRWEQGDVFSCSVMHEALHNHYTQKSLSLSPGK

*Chain 2 3H3[TIM-3]_H1_L2.1_Fab_IgG1_PVA_/S267K/S364K/E357Q Fab-Fc Heavy Chain* (SEQ ID NO: 242)
QVTLKESGPVLVKPTETLTLTCTVSGFSLNGYGVNWVRQPPGKGLEWLAMIWGDGSTDYNSALKSRLTISKDNSKSQ VVLTMTNMDPVDTATYYCARSYYTSDEDYWGQGTLVTVSS/ASTKGPSVFPLAPSSKSTSGGTAALGCLVKDYFPEP VTVSWNSGALTSGVHTFPAVLQSSGLYSLSSVVTVPSSSLGTQTYICNVNHKPSNTKVDKKVEPKSCDKTHTCPPCP APPVAGPSVFLFPPKPKDTLMISRTPEVTCVVVDVKHEDPEVKFNWYVDGVEVHNAKTKPREEQYNSTYRVVSVLTV LHQDWLNGKEYKCKVSNKALPAPIEKTISKAKGQPREPQVYTLPPSREQMTKNQVKLTCLVKGFYPSDIAVEWESNG QPENNYKTTPPVLDSDGSFFLYSKLTVDKSRWQQGNVFSCSVMHEALHNHYTQKSLSLSPGK

*Chain 3 3H3[TIM-3]_H1_L2.1_Fab Light Chain* (SEQ ID NO: 243)
DIVMTQSPDSLAVSLGERATINCKSSQSLLNSRTRKNYLAWYQQKPGQSPKLLIYWASTRESGVPDRFTGSGSGTDF TLTISSLQAEDVAVYYCKQSYSLRTFGGGTKVEIK/RTVAAPSVFIFPPSDEQLKSGTASVVCLLNNFYPREAKVQW KVDNALQSGNSQESVTEQDSKDSTYSLSSTLTLSKADYEKHKVYACEVTHQGLSSPVTKSFNRGEC

Figure 23

*XENP016432 Nivolumab_H0L0_IgG1_PVA_/S267K Heavy Chain* (SEQ ID NO: 244)

QVQLVESGGGVVQPGRSLRLDCKASGITFSNSGMHWVRQAPGKGLEWVAVIWYDGSKRYYADSVKGRFTISRDNSKN
TLFLQMNSLRAEDTAVYYCATNDDYWGQGTLVTVSS/ASTKGPSVFPLAPSSKSTSGGTAALGCLVKDYFPEPVTVS
WNSGALTSGVHTFPAVLQSSGLYSLSSVVTVPSSSLGTQTYICNVNHKPSNTKVDKKVEPKSCDKTHTCPPCPAPPV
AGPSVFLFPPKPKDTLMISRTPEVTCVVVDVKHEDPEVKFNWYVDGVEVHNAKTKPREEQYNSTYRVVSVLTVLHQD
WLNGKEYKCKVSNKALPAPIEKTISKAKGQPREPQVYTLPPSREEMTKNQVSLTCLVKGFYPSDIAVEWESNGQPEN
NYKTTPPVLDSDGSFFLYSKLTVDKSRWQQGNVFSCSVMHEALHNHYTQKSLSLSPGK

*XENP016432 Nivolumab_H0L0_IgG1_PVA_/S267K Light Chain* (SEQ ID NO: 245)

EIVLTQSPATLSLSPGERATLSCRASQSVSSYLAWYQQKPGQAPRLLIYDASNRATGIPARFSGSGSGTDFTLTISS
LEPEDFAVYYCQQSSNWPRTFGQGTKVEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC

Figure 29

>XENP027979 human_IL15Ra(sushi)_(GGGGS)5-human_IL15(N4D/N65D;single-Chain
)-3H3[TIM-3]_H1_L2.1_Fab_IgG1_Fc(216)_IgG1_pI(-
)_Isosteric_A_C220S/PVA_/S267K/L368D/K370S/M428L/N434S-
IgG1_PVA_/S267K/S364K/E357Q/M428L/N434S Chain 1 human_IL15Ra(sushi)_(GGGGS)5-human_IL15(N4D/N65D;single-Chain
)_Fc(216)_IgG1_pI(-)_Isosteric_A_C220S/PVA_/S267K/L368D/K370S/M428L/N434S scIL-15/Ra-Fc Chain
(SEQ ID NO: 246)
ITCPPPMSVEHADIWVKSYSLYSRERYICNSGFKRKAGTSSLTECVLNKATNVAHWTTPSLKCIR/GGGGSGGGGSGGG
GSGGGGSGGGGS/NWVDVISDLKKIEDLIQSMHIDATLYTESDVHPSCKVTAMKCFLLELQVISLESGDASIHDTVEDLII
LANNSLSSNGNVTESGCKECEELEEKNIKEFLQSFVHIVQMFINTS/EPKSSDKTHTCPPCPAPPVAGPSVFLFPPKPKDTL
MISRTPEVTCVVVDVKHEDPEVKFNWYVDGVEVHNAKTKPREEEYNSTYRVVSVLTVLHQDWLNGKEYKCKVSNKAL
PAPIEKTISKAKGQPREPQVYTLPPSREEMTKNQVSLTCDVSGFYPSDIAVEWESDGQPENNYKTTPPVLDSDGSFFLYS
KLTVDKSRWEQGDVFSCSVLHEALHSHYTQKSLSLSPGK Chain 2 3H3[TIM-3]_H1_L2.1_Fab_IgG1_PVA_/S267K/S364K/E357Q/M428L/N434S Fab-Fc Heavy Chain
(SEQ ID NO: 247)
QVTLKESGPVLVKPTETLTLTCTVSGFSLNGYGVNWVRQPPGKGLEWLAMIWGDGSTDYNSALKSRLTISKDNSKSQV
VLTMTNMDPVDTATYYCARSYYTSDEDYWGQGTLVTVSS/ASTKGPSVFPLAPSSKSTSGGTAALGCLVKDYFPEPVTV
SWNSGALTSGVHTFPAVLQSSGLYSLSSVVTVPSSSLGTQTYICNVNHKPSNTKVDKKVEPKSCDKTHTCPPCPAPPVAG
PSVFLFPPKPKDTLMISRTPEVTCVVVDVKHEDPEVKFNWYVDGVEVHNAKTKPREEQYNSTYRVVSVLTVLHQDWLN
GKEYKCKVSNKALPAPIEKTISKAKGQPREPQVYTLPPSREQMTKNQVKLTCLVKGFYPSDIAVEWESNGQPENNYKTT
PPVLDSDGSFFLYSKLTVDKSRWQQGNVFSCSVLHEALHSHYTQKSLSLSPGK Chain 3 3H3[TIM-3]_H1_L2.1_Fab Light Chain (SEQ ID NO: 248)
DIVMTQSPDSLAVSLGERATINCKSSQSLLNSRTRKNYLAWYQQKPGQSPKLLIYWASTRESGVPDRFTGSGSGTDFTL
TISSLQAEDVAVYYCKQSYSLRTFGGGTKVEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC Figure 30
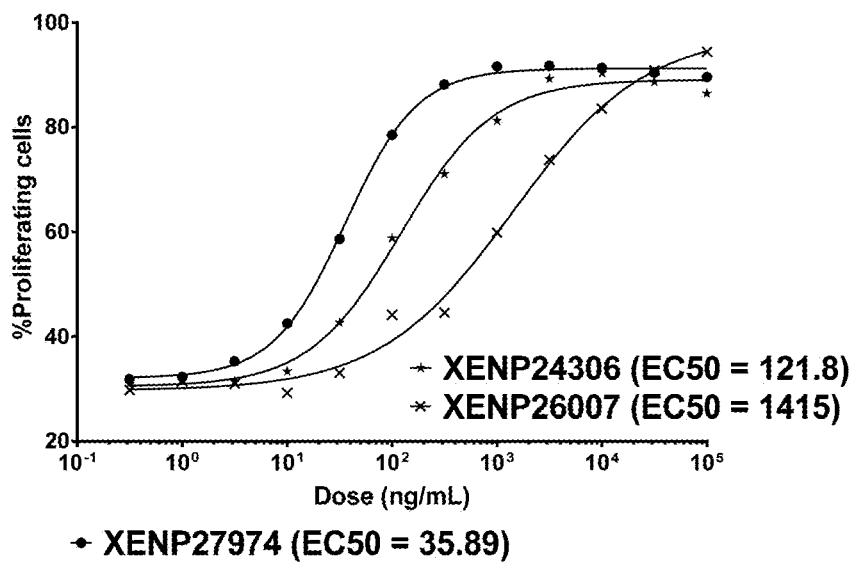
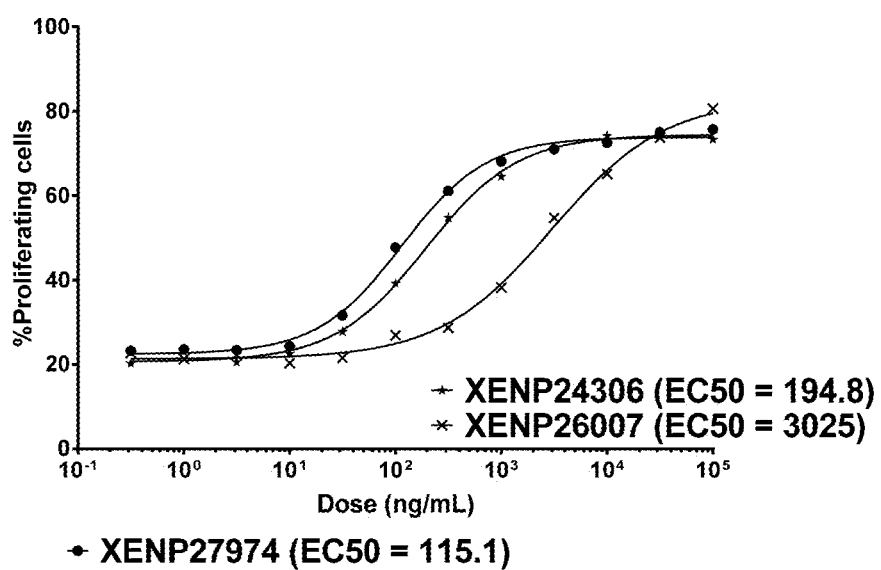

Figure 31
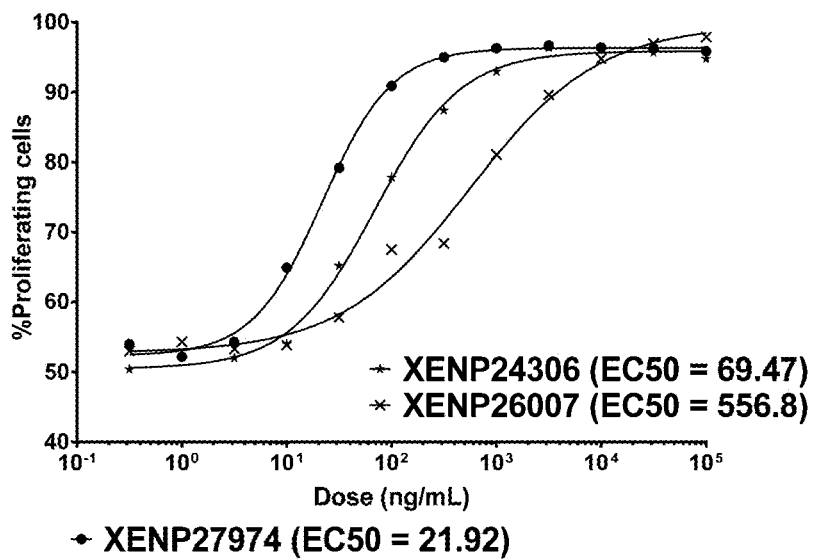
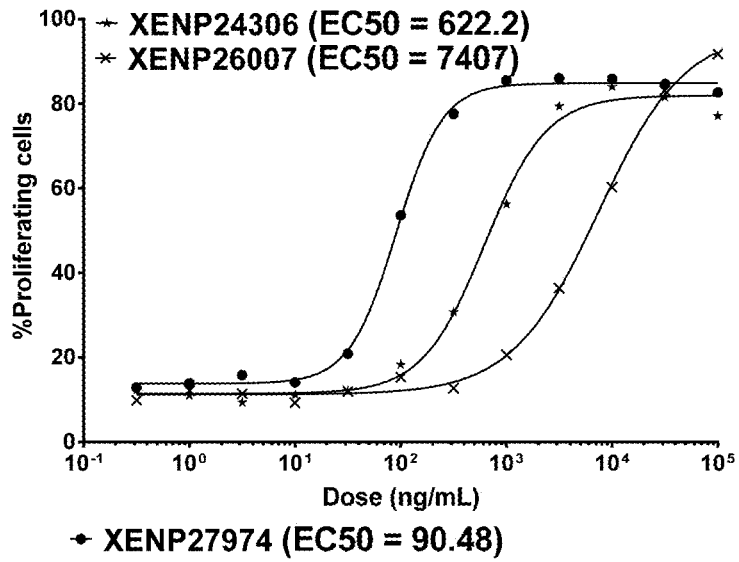

Figure 32
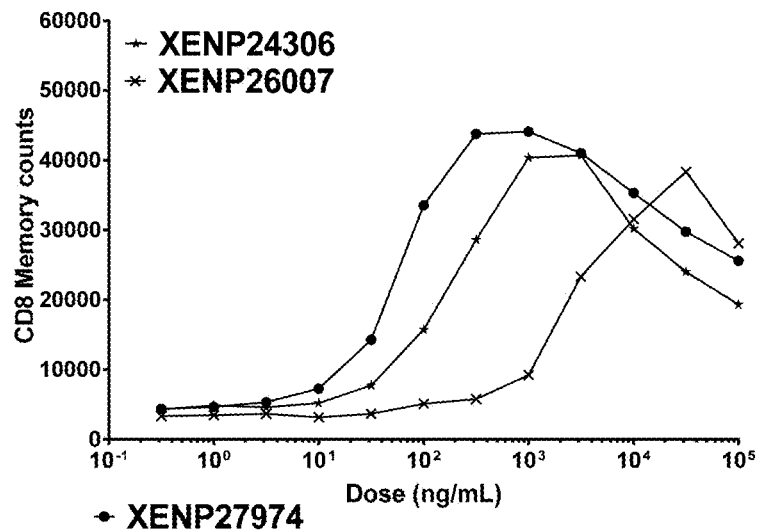
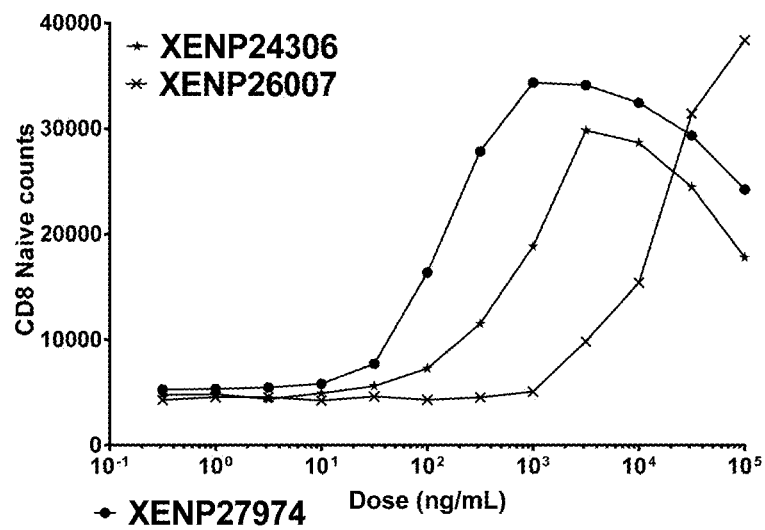

Figure 33
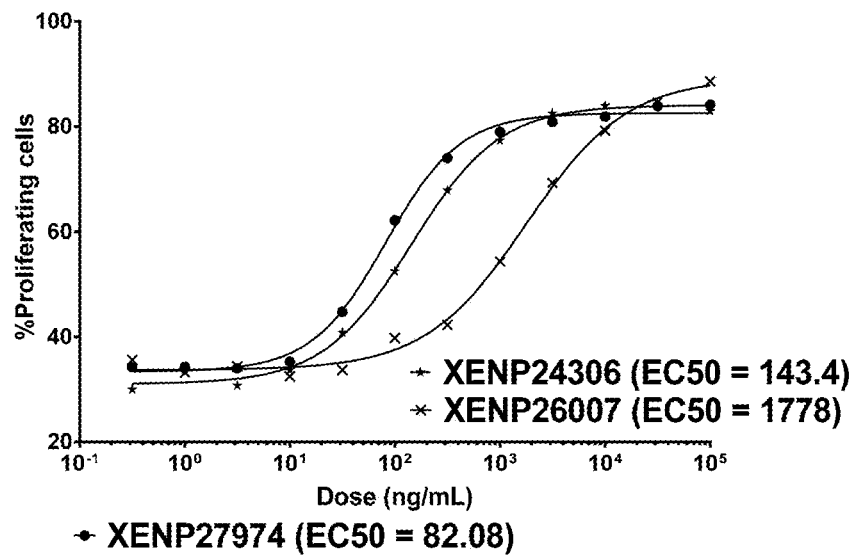
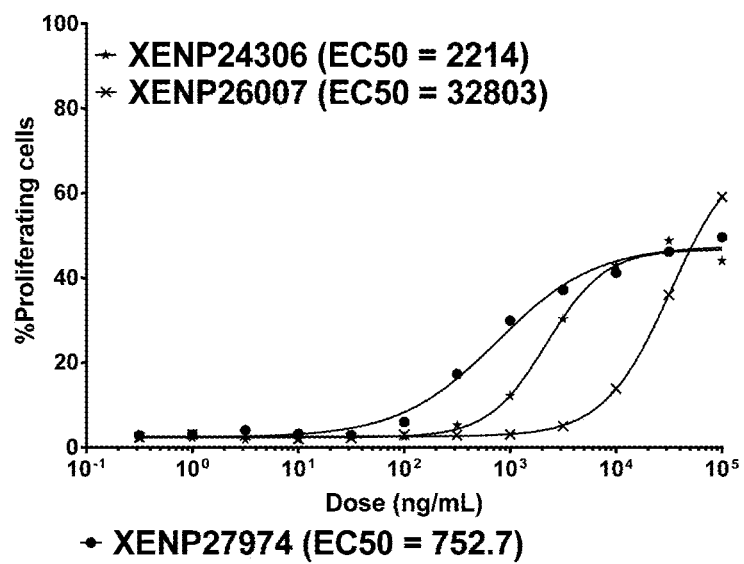

Figure 39

>XENP22853 human_IL15_(GGGGS)1-human_IL15Ra(Sushi)_(GGGGS)1_Fc(216)_IgG1_pI(-)_Isosteric_A_C220S/PVA_/S267K/L368D/K370S/M428L/N434S-Fc(216)_IgG1_C220S/PVA_/S267K/S364K/E357Q/M428L/N434S XENP22853 Chain 1 - human_IL15_(GGGGS)1-Fc(216)_IgG1_pI(-)_Isosteric_A_C220S/PVA_/S267K/L368D/K370S/M428L/N434S (SEQ ID NO: 249)

NWVNVISDLKKIEDLIQSMHIDATLYTESDVHPSCKVTAMKCFLLELQVISLESGDASIHDTVENLIILANNSLSSNGNVTE
SGCKECEELEEKNIKEFLQSFVHIVQMFINTS/GGGGS/EPKSSDKTHTCPPCPAPPVAGPSVFLFPPKPKDTLMISRTPEV
TCVVVDVKHEDPEVKFNWYVDGVEVHNAKTKPREEEYNSTYRVVSVLTVLHQDWLNGKEYKCKVSNKALPAPIEKTIS
KAKGQPREPQVYTLPPSREEMTKNQVSLTCDVSGFYPSDIAVEWESDGQPENNYKTTPPVLDSDGSFFLYSKLTVDKSR
WEQGDVFSCSVLHEALHSHYTQKSLSLSPGK

XENP22853 Chain 2 - human_IL15Ra(Sushi)_(GGGGS)1-Fc(216)_IgG1_C220S/PVA_/S267K/S364K/E357Q/M428L/N434S (SEQ ID NO: 250)

ITCPPPMSVEHADIWVKSYSLYSRERYICNSGFKRKAGTSSLTECVLNKATNVAHWTTPSLKCIR/GGGGS/EPKSSDKTH
TCPPCPAPPVAGPSVFLFPPKPKDTLMISRTPEVTCVVVDVKHEDPEVKFNWYVDGVEVHNAKTKPREEQYNSTYRVV
SVLTVLHQDWLNGKEYKCKVSNKALPAPIEKTISKAKGQPREPQVYTLPPSREQMTKNQVKLTCLVKGFYPSDIAVEWE
SNGQPENNYKTTPPVLDSDGSFFLYSKLTVDKSRWQQGNVFSCSVLHEALHSHYTQKSLSLSPGK

Figure 40

>XENP24113 human_IL15_N4D/N65D_(GGGGS)1-human_IL15Ra(Sushi)_(GGGGS)1_Fc(216)_IgG1_pI(-
)_Isosteric_A_C220S/PVA_/S267K/L368D/K370S/M428L/N434S-
Fc(216)_IgG1_C220S/PVA_/S267K/S364K/E357Q/M428L/N434S XENP24113 Chain 1 - human_IL15_N4D/N65D_(GGGGS)1-Fc(216)_IgG1_pI(-
)_Isosteric_A_C220S/PVA_/S267K/L368D/K370S/M428L/N434S (SEQ ID NO: 251)

NWVDVISDLKKIEDLIQSMHIDATLYTESDVHPSCKVTAMKCFLLELQVISLESGDASIHDTVEDLIILANNSLSSNGNVTE
SGCKECEELEEKNIKEFLQSFVHIVQMFINTS/GGGGS/EPKSSDKTHTCPPCPAPPVAGPSVFLFPPKPKDTLMISRTPEV
TCVVVDVKHEDPEVKFNWYVDGVEVHNAKTKPREEEYNSTYRVVSVLTVLHQDWLNGKEYKCKVSNKALPAPIEKTIS
KAKGQPREPQVYTLPPSREEMTKNQVSLTCDVSGFYPSDIAVEWESDGQPENNYKTTPPVLDSDGSFFLYSKLTVDKSR
WEQGDVFSCSVLHEALHSHYTQKSLSLSPGK

XENP24113 Chain 2 - human_IL15Ra(Sushi)_(GGGGS)1-
Fc(216)_IgG1_C220S/PVA_/S267K/S364K/E357Q/M428L/N434S (SEQ ID NO: 252)

ITCPPPMSVEHADIWVKSYSLYSRERYICNSGFKRKAGTSSLTECVLNKATNVAHWTTPSLKCIR/GGGGS/EPKSSDKTH
TCPPCPAPPVAGPSVFLFPPKPKDTLMISRTPEVTCVVVDVKHEDPEVKFNWYVDGVEVHNAKTKPREEQYNSTYRVV
SVLTVLHQDWLNGKEYKCKVSNKALPAPIEKTISKAKGQPREPQVYTLPPSREQMTKNQVKLTCLVKGFYPSDIAVEWE
SNGQPENNYKTTPPVLDSDGSFFLYSKLTVDKSRWQQGNVFSCSVLHEALHSHYTQKSLSLSPGK

Figure 41

>XENP24294 human_IL15Ra(sushi)_(GGGGS)5-human_IL15_N4D/N65D_(single-Chain)-empty-Fc_Fc(216)_IgG1_pI(-)_Isosteric_A_C220S/PVA_/S267K/L368D/K370S/M428L/N434S-Fc(216)_IgG1_C220S/PVA_/S267K/S364K/E357Q/M428L/N434S XENP24294 Chain 1 - human_IL15Ra(sushi)_(GGGGS)5-human_IL15_N4D/N65D_(single-Chain)-Fc(216)_IgG1_pI(-)_Isosteric_A_C220S/PVA_/S267K/L368D/K370S/M428L/N434S (SEQ ID NO: 253)

ITCPPPMSVEHADIWVKSYSLYSRERYICNSGFKRKAGTSSLTECVLNKATNVAHWTTPSLKCIR/GGGGSGGGGSGGGGSGGGGSGGGGS/NWVDVISDLKKIEDLIQSMHIDATLYTESDVHPSCKVTAMKCFLLELQVISLESGDASIHDTVEDLIILANNSLSSNGNVTESGCKECEELEEKNIKEFLQSFVHIVQMFINTS/EPKSSDKTHTCPPCPAPPVAGPSVFLFPPKPKDTLMISRTPEVTCVVVDVKHEDPEVKFNWYVDGVEVHNAKTKPREEEYNSTYRVVSVLTVLHQDWLNGKEYKCKVSNKALPAPIEKTISKAKGQPREPQVYTLPPSREEMTKNQVSLTCDVSGFYPSDIAVEWESDGQPENNYKTTPPVLDSDGSFFLYSKLTVDKSRWEQGDVFSCSVLHEALHSHYTQKSLSLSPGK

XENP24294 Chain 2 - empty-Fc(216)_IgG1_C220S/PVA_/S267K/S364K/E357Q/M428L/N434S (SEQ ID NO: 254)

EPKSSDKTHTCPPCPAPPVAGPSVFLFPPKPKDTLMISRTPEVTCVVVDVKHEDPEVKFNWYVDGVEVHNAKTKPREEQYNSTYRVVSVLTVLHQDWLNGKEYKCKVSNKALPAPIEKTISKAKGQPREPQVYTLPPSREQMTKNQVKLTCLVKGFYPSDIAVEWESNGQPENNYKTTPPVLDSDGSFFLYSKLTVDKSRWQQGNVFSCSVLHEALHSHYTQKSLSLSPGK

Figure 42

>XENP24306 human_IL15_D30N/E64Q/N65D_(GGGGS)1-
human_IL15Ra(Sushi)_(GGGGS)1_Fc(216)_IgG1_pI(-
)_Isosteric_A_C220S/PVA_/S267K/L368D/K370S/M428L/N434S-
Fc(216)_IgG1_C220S/PVA_/S267K/S364K/E357Q/M428L/N434S XENP24306 Chain 1 - human_IL15_D30N/E64Q/N65D_(GGGGS)1-Fc(216)_IgG1_pI(-
)_Isosteric_A_C220S/PVA_/S267K/L368D/K370S/M428L/N434S (SEQ ID NO: 255)

NWVNVISDLKKIEDLIQSMHIDATLYTESNVHPSCKVTAMKCFLLELQVISLESGDASIHDTVQDLIILANNSLSSNGNVTE
SGCKECEELEEKNIKEFLQSFVHIVQMFINTS/GGGGS/EPKSSDKTHTCPPCPAPPVAGPSVFLFPPKPKDTLMISRTPEV
TCVVVDVKHEDPEVKFNWYVDGVEVHNAKTKPREEEYNSTYRVVSVLTVLHQDWLNGKEYKCKVSNKALPAPIEKTIS
KAKGQPREPQVYTLPPSREEMTKNQVSLTCDVSGFYPSDIAVEWESDGQPENNYKTTPPVLDSDGSFFLYSKLTVDKSR
WEQGDVFSCSVLHEALHSHYTQKSLSLSPGK

XENP24306 Chain 2 - human_IL15Ra(Sushi)_(GGGGS)1-
Fc(216)_IgG1_C220S/PVA_/S267K/S364K/E357Q/M428L/N434S (SEQ ID NO: 256)

ITCPPPMSVEHADIWVKSYSLYSRERYICNSGFKRKAGTSSLTECVLNKATNVAHWTTPSLKCIR/GGGGS/EPKSSDKTH
TCPPCPAPPVAGPSVFLFPPKPKDTLMISRTPEVTCVVVDVKHEDPEVKFNWYVDGVEVHNAKTKPREEQYNSTYRVV
SVLTVLHQDWLNGKEYKCKVSNKALPAPIEKTISKAKGQPREPQVYTLPPSREQMTKNQVKLTCLVKGFYPSDIAVEWE
SNGQPENNYKTTPPVLDSDGSFFLYSKLTVDKSRWQQGNVFSCSVLHEALHSHYTQKSLSLSPGK

Figure 44A

>XENP21993_human_IL15Ra(sushi)_(GGGGS)5-human_IL15(single-chain)-empty-Fc_Fc(216)_IgG1_pI(-)_Isosteric_A_C220S/PVA_/S267K/L368D/K370S-Fc(216)_IgG1_C220S/PVA_/S267K/S364K/E357Q Chain 1 - human_IL15Ra(sushi)_(GGGGS)5-human_IL15(single-chain)_Fc(216)_IgG1_pI(-)_Isosteric_A_C220S/PVA_/S267K/L368D/K370S (SEQ ID NO: 257)
ITCPPPMSVEHADIWVKSYSLYSRERYICNSGFKRKAGTSSLTECVLNKATNVAHWTTPSLKCIR/GGGGSGGGGSGGG
GSGGGGSGGGGS/NWVNVISDLKKIEDLIQSMHIDATLYTESDVHPSCKVTAMKCFLLELQVISLESGDASIHDTVENLII
LANNSLSSNGNVTESGCKECEELEEKNIKEFLQSFVHIVQMFINTS/EPKSSDKTHTCPPCPAPPVAGPSVFLFPPKPKDTL
MISRTPEVTCVVVDVKHEDPEVKFNWYVDGVEVHNAKTKPREEEYNSTYRVVSVLTVLHQDWLNGKEYKCKVSNKAL
PAPIEKTISKAKGQPREPQVYTLPPSREEMTKNQVSLTCDVSGFYPSDIAVEWESDGQPENNYKTTPPVLDSDGSFFLYS
KLTVDKSRWEQGDVFSCSVMHEALHNHYTQKSLSLSPGK Chain 2 - empty_Fc(216)_IgG1_C220S/PVA_/S267K/S364K/E357Q (SEQ ID NO: 258)
EPKSSDKTHTCPPCPAPPVAGPSVFLFPPKPKDTLMISRTPEVTCVVVDVKHEDPEVKFNWYVDGVEVHNAKTKPREE
QYNSTYRVVSVLTVLHQDWLNGKEYKCKVSNKALPAPIEKTISKAKGQPREPQVYTLPPSREQMTKNQVKLTCLVKGFY
PSDIAVEWESNGQPENNYKTTPPVLDSDGSFFLYSKLTVDKSRWQQGNVFSCSVMHEALHNHYTQKSLSLSPGK >XENP24050_human_IL15Ra(sushi)_(GGGGS)5-human_IL15_N4D/N65D_(single-chain)-empty-Fc_Fc(216)_IgG1_pI(-)_Isosteric_A_C220S/PVA_/S267K/L368D/K370S-Fc(216)_IgG1_C220S/PVA_/S267K/S364K/E357Q Chain 1 - human_IL15Ra(sushi)_(GGGGS)5-human_IL15_N4D/N65D_(single-chain)_Fc(216)_IgG1_pI(-)_Isosteric_A_C220S/PVA_/S267K/L368D/K370S (SEQ ID NO: 259)
ITCPPPMSVEHADIWVKSYSLYSRERYICNSGFKRKAGTSSLTECVLNKATNVAHWTTPSLKCIR/GGGGSGGGGSGGG
GSGGGGSGGGGS/NWVDVISDLKKIEDLIQSMHIDATLYTESDVHPSCKVTAMKCFLLELQVISLESGDASIHDTVEDLII
LANNSLSSNGNVTESGCKECEELEEKNIKEFLQSFVHIVQMFINTS/EPKSSDKTHTCPPCPAPPVAGPSVFLFPPKPKDTL
MISRTPEVTCVVVDVKHEDPEVKFNWYVDGVEVHNAKTKPREEEYNSTYRVVSVLTVLHQDWLNGKEYKCKVSNKAL
PAPIEKTISKAKGQPREPQVYTLPPSREEMTKNQVSLTCDVSGFYPSDIAVEWESDGQPENNYKTTPPVLDSDGSFFLYS
KLTVDKSRWEQGDVFSCSVMHEALHNHYTQKSLSLSPGK Chain 2 - empty_Fc(216)_IgG1_C220S/PVA_/S267K/S364K/E357Q (SEQ ID NO: 260)
EPKSSDKTHTCPPCPAPPVAGPSVFLFPPKPKDTLMISRTPEVTCVVVDVKHEDPEVKFNWYVDGVEVHNAKTKPREE
QYNSTYRVVSVLTVLHQDWLNGKEYKCKVSNKALPAPIEKTISKAKGQPREPQVYTLPPSREQMTKNQVKLTCLVKGFY
PSDIAVEWESNGQPENNYKTTPPVLDSDGSFFLYSKLTVDKSRWQQGNVFSCSVMHEALHNHYTQKSLSLSPGK

Figure 44B

>XENP29281 human_IL15Ra(sushi)_(GGGGS)5-human_IL15_D30N_(single-chain)-empty-Fc_Fc(216)_IgG1_pI(-)_Isosteric_A_C220S/PVA_/S267K/L368D/K370S-Fc(216)_IgG1_C220S/PVA_/S267K/S364K/E357Q Chain 1 - human_IL15Ra(sushi)_(GGGGS)5-human_IL15_D30N_(single-chain)_Fc(216)_IgG1_pI(-)_Isosteric_A_C220S/PVA_/S267K/L368D/K370S (SEQ ID NO: 261)
ITCPPPMSVEHADIWVKSYSLYSRERYICNSGFKRKAGTSSLTECVLNKATNVAHWTTPSLKCIR/GGGGSGGGGSGGGGSGGGGSGGGGS/NWVNVISDLKKIEDLIQSMHIDATLYTESNVHPSCKVTAMKCFLLELQVISLESGDASIHDTVENLII LANNSLSSNGNVTESGCKECEELEEKNIKEFLQSFVHIVQMFINTS/EPKSSDKTHTCPPCPAPPVAGPSVFLFPPKPKDTL MISRTPEVTCVVVDVKHEDPEVKFNWYVDGVEVHNAKTKPREEEYNSTYRVVSVLTVLHQDWLNGKEYKCKVSNKAL PAPIEKTISKAKGQPREPQVYTLPPSREEMTKNQVSLTCDVSGFYPSDIAVEWESDGQPENNYKTTPPVLDSDGSFFLYS KLTVDKSRWEQGDVFSCSVMHEALHNHYTQKSLSLSPGK Chain 2 - empty_Fc(216)_IgG1_C220S/PVA_/S267K/S364K/E357Q (SEQ ID NO: 262)
EPKSSDKTHTCPPCPAPPVAGPSVFLFPPKPKDTLMISRTPEVTCVVVDVKHEDPEVKFNWYVDGVEVHNAKTKPREE QYNSTYRVVSVLTVLHQDWLNGKEYKCKVSNKALPAPIEKTISKAKGQPREPQVYTLPPSREQMTKNQVKLTCLVKGFY PSDIAVEWESNGQPENNYKTTPPVLDSDGSFFLYSKLTVDKSRWQQGNVFSCSVMHEALHNHYTQKSLSLSPGK >XENP29285 human_IL15Ra(sushi)_(GGGGS)5-human_IL15_D30N/N65D_(single-chain)-empty-Fc_Fc(216)_IgG1_pI(-)_Isosteric_A_C220S/PVA_/S267K/L368D/K370S-Fc(216)_IgG1_C220S/PVA_/S267K/S364K/E357Q Chain 1 - human_IL15Ra(sushi)_(GGGGS)5-human_IL15_D30N/N65D_(single-chain)_Fc(216)_IgG1_pI(-)_Isosteric_A_C220S/PVA_/S267K/L368D/K370S (SEQ ID NO: 263)
ITCPPPMSVEHADIWVKSYSLYSRERYICNSGFKRKAGTSSLTECVLNKATNVAHWTTPSLKCIR/GGGGSGGGGSGGGGSGGGGSGGGGS/NWVNVISDLKKIEDLIQSMHIDATLYTESNVHPSCKVTAMKCFLLELQVISLESGDASIHDTVEDLII LANNSLSSNGNVTESGCKECEELEEKNIKEFLQSFVHIVQMFINTS/EPKSSDKTHTCPPCPAPPVAGPSVFLFPPKPKDTL MISRTPEVTCVVVDVKHEDPEVKFNWYVDGVEVHNAKTKPREEEYNSTYRVVSVLTVLHQDWLNGKEYKCKVSNKAL PAPIEKTISKAKGQPREPQVYTLPPSREEMTKNQVSLTCDVSGFYPSDIAVEWESDGQPENNYKTTPPVLDSDGSFFLYS KLTVDKSRWEQGDVFSCSVMHEALHNHYTQKSLSLSPGK Chain 2 - empty_Fc(216)_IgG1_C220S/PVA_/S267K/S364K/E357Q (SEQ ID NO: 264)
EPKSSDKTHTCPPCPAPPVAGPSVFLFPPKPKDTLMISRTPEVTCVVVDVKHEDPEVKFNWYVDGVEVHNAKTKPREE QYNSTYRVVSVLTVLHQDWLNGKEYKCKVSNKALPAPIEKTISKAKGQPREPQVYTLPPSREQMTKNQVKLTCLVKGFY PSDIAVEWESNGQPENNYKTTPPVLDSDGSFFLYSKLTVDKSRWQQGNVFSCSVMHEALHNHYTQKSLSLSPGK

Figure 44C

>XENP29286_human_IL15Ra(sushi)_(GGGGS)5-human_IL15_D30N/E64Q/N65D_(single-chain)-empty-Fc_Fc(216)_IgG1_pI(-)_Isosteric_A_C220S/PVA_/S267K/L368D/K370S-Fc(216)_IgG1_C220S/PVA_/S267K/S364K/E357Q Chain 1 - human_IL15Ra(sushi)_(GGGGS)5-human_IL15_D30N/E64Q/N65D_(single-chain)_Fc(216)_IgG1_pI(-)_Isosteric_A_C220S/PVA_/S267K/L368D/K370S (SEQ ID NO: 265)
ITCPPPMSVEHADIWVKSYSLYSRERYICNSGFKRKAGTSSLTECVLNKATNVAHWTTPSLKCIR/GGGGSGGGGSGGG
GSGGGGSGGGGS/NWVNVISDLKKIEDLIQSMHIDATLYTESNVHPSCKVTAMKCFLLELQVISLESGDASIHDTVQDLII
LANNSLSSNGNVTESGCKECEELEEKNIKEFLQSFVHIVQMFINTS/EPKSSDKTHTCPPCPAPPVAGPSVFLFPPKPKDTL
MISRTPEVTCVVVDVKHEDPEVKFNWYVDGVEVHNAKTKPREEEYNSTYRVVSVLTVLHQDWLNGKEYKCKVSNKAL
PAPIEKTISKAKGQPREPQVYTLPPSREEMTKNQVSLTCDVSGFYPSDIAVEWESDGQPENNYKTTPPVLDSDGSFFLYS
KLTVDKSRWEQGDVFSCSVMHEALHNHYTQKSLSLSPGK Chain 2 - empty_Fc(216)_IgG1_C220S/PVA_/S267K/S364K/E357Q (SEQ ID NO: 266)
EPKSSDKTHTCPPCPAPPVAGPSVFLFPPKPKDTLMISRTPEVTCVVVDVKHEDPEVKFNWYVDGVEVHNAKTKPREE
QYNSTYRVVSVLTVLHQDWLNGKEYKCKVSNKALPAPIEKTISKAKGQPREPQVYTLPPSREQMTKNQVKLTCLVKGFY
PSDIAVEWESNGQPENNYKTTPPVLDSDGSFFLYSKLTVDKSRWQQGNVFSCSVMHEALHNHYTQKSLSLSPGK

Figure 46

> XENC1000 human_IL15Ra(sushi)_(GGGGS)5-human_IL15(D30N/N65D;single-Chain
)-3H3[TIM-3]_H1_L2.1_Fab_IgG1_Fc(216)_IgG1_pI(-)_Isosteric_A_C220S/PVA_/S267K/L368D/K370S-
IgG1_PVA_/S267K/S364K/E357Q Chain 1 human_IL15Ra(sushi)_(GGGGS)5-human_IL15(D30N/N65D;single-Chain
)_Fc(216)_IgG1_pI(-)_Isosteric_A_C220S/PVA_/S267K/L368D/K370S scIL-15/Ra-Fc Chain (SEQ ID NO: 267)
ITCPPPMSVEHADIWVKSYSLYSRERYICNSGFKRKAGTSSLTECVLNKATNVAHWTTPSLKCIR/GGGGSGGGGSGGG
GSGGGGSGGGGS/NWVNVISDLKKIEDLIQSMHIDATLYTESNVHPSCKVTAMKCFLLELQVISLESGDASIHDTVEDLII
LANNSLSSNGNVTESGCKECEELEEKNIKEFLQSFVHIVQMFINTS/EPKSSDKTHTCPPCPAPPVAGPSVFLFPPKPDTL
MISRTPEVTCVVVDVKHEDPEVKFNWYVDGVEVHNAKTKPREEEYNSTYRVVSVLTVLHQDWLNGKEYKCKVSNKAL
PAPIEKTISKAKGQPREPQVYTLPPSREEMTKNQVSLTCDVSGFYPSDIAVEWESDGQPENNYKTTPPVLDSDGSFFLYS
KLTVDKSRWEQGDVFSCSVMHEALHNHYTQKSLSLSPGK Chain 2 3H3[TIM-3]_H1_L2.1_Fab_IgG1_PVA_/S267K/S364K/E357Q Fab-Fc Heavy Chain (SEQ ID NO: 268)
QVTLKESGPVLVKPTETLTLTCTVSGFSLNGYGVNWVRQPPGKGLEWLAMIWGDGSTDYNSALKSRLTISKDNSKSQV
VLTMTNMDPVDTATYYCARSYYTSDEDYWGQGTLVTVSS/ASTKGPSVFPLAPSSKSTSGGTAALGCLVKDYFPEPVTV
SWNSGALTSGVHTFPAVLQSSGLYSLSSVVTVPSSSLGTQTYICNVNHKPSNTKVDKKVEPKSCDKTHTCPPCPAPPVAG
PSVFLFPPKPDTLMISRTPEVTCVVVDVKHEDPEVKFNWYVDGVEVHNAKTKPREEQYNSTYRVVSVLTVLHQDWLN
GKEYKCKVSNKALPAPIEKTISKAKGQPREPQVYTLPPSREQMTKNQVKLTCLVKGFYPSDIAVEWESNGQPENNYKTT
PPVLDSDGSFFLYSKLTVDKSRWQQGNVFSCSVMHEALHNHYTQKSLSLSPGK Chain 3 3H3[TIM-3]_H1_L2.1_Fab Light Chain (SEQ ID NO: 269)
DIVMTQSPDSLAVSLGERATINCKSSQSLLNSRTRKNYLAWYQQKPGQSPKLLIYWASTRESGVPDRFTGSGSGTDFTL
TISSLQAEDVAVYYCKQSYSLRTFGGGTKVEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC

Figure 47

> XENC1001 human_IL15Ra(sushi)_(GGGGS)5-human_IL15(D30N/E64Q/N65D;single-Chain
)-3H3[TIM-3]_H1_L2.1_Fab_IgG1_Fc(216)_IgG1_pI(-)_Isosteric_A_C220S/PVA_/S267K/L368D/K370S-
IgG1_PVA_/S267K/S364K/E357Q Chain 1 human_IL15Ra(sushi)_(GGGGS)5-human_IL15(D30N/E64Q/N65D;single-Chain
)_Fc(216)_IgG1_pI(-)_Isosteric_A_C220S/PVA_/S267K/L368D/K370S scIL-15/Ra-Fc Chain (SEQ ID NO: 270)
ITCPPPMSVEHADIWVKSYSLYSRERYICNSGFKRKAGTSSLTECVLNKATNVAHWTTPSLKCIR/GGGGSGGGGSGGG
GSGGGGSGGGGS/NWVNVISDLKKIEDLIQSMHIDATLYTESNVHPSCKVTAMKCFLLELQVISLESGDASIHDTVQDLII
LANNSLSSNGNVTESGCKECEELEEKNIKEFLQSFVHIVQMFINTS/EPKSSDKTHTCPPCPAPPVAGPSVFLFPPKPKDTL
MISRTPEVTCVVVDVKHEDPEVKFNWYVDGVEVHNAKTKPREEEYNSTYRVVSVLTVLHQDWLNGKEYKCKVSNKAL
PAPIEKTISKAKGQPREPQVYTLPPSREEMTKNQVSLTCDVSGFYPSDIAVEWESDGQPENNYKTTPPVLDSDGSFFLYS
KLTVDKSRWEQGDVFSCSVMHEALHNHYTQKSLSLSPGK Chain 2 3H3[TIM-3]_H1_L2.1_Fab_IgG1_PVA_/S267K/S364K/E357Q Fab-Fc Heavy Chain (SEQ ID NO: 271)
QVTLKESGPVLVKPTETLTLTCTVSGFSLNGYGVNWVRQPPGKGLEWLAMIWGDGSTDYNSALKSRLTISKDNSKSQV
VLTMTNMDPVDTATYYCARSYYTSDEDYWGQGTLVTVSS/ASTKGPSVFPLAPSSKSTSGGTAALGCLVKDYFPEPVTV
SWNSGALTSGVHTFPAVLQSSGLYSLSSVVTVPSSSLGTQTYICNVNHKPSNTKVDKKVEPKSCDKTHTCPPCPAPPVAG
PSVFLFPPKPKDTLMISRTPEVTCVVVDVKHEDPEVKFNWYVDGVEVHNAKTKPREEQYNSTYRVVSVLTVLHQDWLN
GKEYKCKVSNKALPAPIEKTISKAKGQPREPQVYTLPPSREQMTKNQVKLTCLVKGFYPSDIAVEWESNGQPENNYKTT
PPVLDSDGSFFLYSKLTVDKSRWQQGNVFSCSVMHEALHNHYTQKSLSLSPGK Chain 3 3H3[TIM-3]_H1_L2.1_Fab Light Chain (SEQ ID NO: 272)
DIVMTQSPDSLAVSLGERATINCKSSQSLLNSRTRKNYLAWYQQKPGQSPKLLIYWASTRESGVPDRFTGSGSGTDFTL
TISSLQAEDVAVYYCKQSYSLRTFGGGTKVEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC

Figure 48A

> XENC1002 human_IL15Ra(sushi)_(GGGGS)5-human_IL15(D30N/N65D;single-Chain
)-3H3[TIM-3]_H1_L2.1_Fab_IgG1_Fc(216)_IgG1_pI(-
)_Isosteric_A_C220S/PVA_/S267K/L368D/K370S/M428L/N434S-
IgG1_PVA_/S267K/S364K/E357Q/M428L/N434S

*Chain 1 human_IL15Ra(sushi)_(GGGGS)5-human_IL15(D30N/N65D;single-Chain* (SEQ ID NO: 273)
*)_Fc(216)_IgG1_pI(-)_Isosteric_A_C220S/PVA_/S267K/L368D/K370S/M428L/N434S scIL-15/Ra-Fc Chain*
ITCPPPMSVEHADIWVKSYSLYSRERYICNSGFKRKAGTSSLTECVLNKATNVAHWTTPSLKCIR/GGGGSGGGGSGGG
GSGGGGSGGGGS/NWVNVISDLKKIEDLIQSMHIDATLYTESNVHPSCKVTAMKCFLLELQVISLESGDASIHDTVEDLII
LANNSLSSNGNVTESGCKECEELEEKNIKEFLQSFVHIVQMFINTS/EPKSSDKTHTCPPCPAPPVAGPSVFLFPPKPKDTL
MISRTPEVTCVVVDVKHEDPEVKFNWYVDGVEVHNAKTKPREEEYNSTYRVVSVLTVLHQDWLNGKEYKCKVSNKAL
PAPIEKTISKAKGQPREPQVYTLPPSREEMTKNQVSLTCDVSGFYPSDIAVEWESDGQPENNYKTTPPVLDSDGSFFLYS
KLTVDKSRWEQGDVFSCSVLHEALHSHYTQKSLSLSPGK

*Chain 2 3H3[TIM-3]_H1_L2.1_Fab_IgG1_PVA_/S267K/S364K/E357Q/M428L/N434S Fab-Fc Heavy Chain*

(SEQ ID NO: 274)
QVTLKESGPVLVKPTETLTLTCTVSGFSLNGYGVNWVRQPPGKGLEWLAMIWGDGSTDYNSALKSRLTISKDNSKSQV
VLTMTNMDPVDTATYYCARSYYTSDEDYWGQGTLVTVSS/ASTKGPSVFPLAPSSKSTSGGTAALGCLVKDYFPEPVTV
SWNSGALTSGVHTFPAVLQSSGLYSLSSVVTVPSSSLGTQTYICNVNHKPSNTKVDKKVEPKSCDKTHTCPPCPAPPVAG
PSVFLFPPKPKDTLMISRTPEVTCVVVDVKHEDPEVKFNWYVDGVEVHNAKTKPREEQYNSTYRVVSVLTVLHQDWLN
GKEYKCKVSNKALPAPIEKTISKAKGQPREPQVYTLPPSREQMTKNQVKLTCLVKGFYPSDIAVEWESNGQPENNYKTT
PPVLDSDGSFFLYSKLTVDKSRWQQGNVFSCSVLHEALHSHYTQKSLSLSPGK

*Chain 3 3H3[TIM-3]_H1_L2.1_Fab Light Chain* (SEQ ID NO: 275)
DIVMTQSPDSLAVSLGERATINCKSSQSLLNSRTRKNYLAWYQQKPGQSPKLLIYWASTRESGVPDRFTGSGSGTDFTL
TISSLQAEDVAVYYCKQSYSLRTFGGGTKVEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC

Figure 48B

> XENC1003 human_IL15Ra(sushi)_(GGGGS)5-human_IL15(D30N/E64Q/N65D;single-Chain
)-3H3[TIM-3]_H1_L2.1_Fab_IgG1_Fc(216)_IgG1_pI(-
)_Isosteric_A_C220S/PVA_/S267K/L368D/K370S/M428L/N434S-
IgG1_PVA_/S267K/S364K/E357Q/M428L/N434S

*Chain 1 human_IL15Ra(sushi)_(GGGGS)5-human_IL15(D30N/E64Q/N65D;single-Chain
)_Fc(216)_IgG1_pI(-)_Isosteric_A_C220S/PVA_/S267K/L368D/K370S/M428L/N434S scIL-15/Ra-Fc Chain*
(SEQ ID NO: 276)
ITCPPPMSVEHADIWVKSYSLYSRERYICNSGFKRKAGTSSLTECVLNKATNVAHWTTPSLKCIR/GGGGSGGGGSGGG
GSGGGGSGGGGS/NWVNVISDLKKIEDLIQSMHIDATLYTESNVHPSCKVTAMKCFLLELQVISLESGDASIHDTVQDLII
LANNSLSSNGNVTESGCKECEELEEKNIKEFLQSFVHIVQMFINTS/EPKSSDKTHTCPPCPAPPVAGPSVFLFPPKPKDTL
MISRTPEVTCVVVDVKHEDPEVKFNWYVDGVEVHNAKTKPREEEYNSTYRVVSVLTVLHQDWLNGKEYKCKVSNKAL
PAPIEKTISKAKGQPREPQVYTLPPSREEMTKNQVSLTCDVSGFYPSDIAVEWESDGQPENNYKTTPPVLDSDGSFFLYS
KLTVDKSRWEQGDVFSCSVLHEALHSHYTQKSLSLSPGK

*Chain 2 3H3[TIM-3]_H1_L2.1_Fab_IgG1_PVA_/S267K/S364K/E357Q/M428L/N434S Fab-Fc Heavy Chain*

(SEQ ID NO: 277)
QVTLKESGPVLVKPTETLTLTCTVSGFSLNGYGVNWVRQPPGKGLEWLAMIWGDGSTDYNSALKSRLTISKDNSKSQV
VLTMTNMDPVDTATYYCARSYYTSDEDYWGQGTLVTVSS/ASTKGPSVFPLAPSSKSTSGGTAALGCLVKDYFPEPVTV
SWNSGALTSGVHTFPAVLQSSGLYSLSSVVTVPSSSLGTQTYICNVNHKPSNTKVDKKVEPKSCDKTHTCPPCPAPPVAG
PSVFLFPPKPKDTLMISRTPEVTCVVVDVKHEDPEVKFNWYVDGVEVHNAKTKPREEQYNSTYRVVSVLTVLHQDWLN
GKEYKCKVSNKALPAPIEKTISKAKGQPREPQVYTLPPSREQMTKNQVKLTCLVKGFYPSDIAVEWESNGQPENNYKTT
PPVLDSDGSFFLYSKLTVDKSRWQQGNVFSCSVLHEALHSHYTQKSLSLSPGK

*Chain 3 3H3[TIM-3]_H1_L2.1_Fab Light Chain* (SEQ ID NO: 278)
DIVMTQSPDSLAVSLGERATINCKSSQSLLNSRTRKNYLAWYQQKPGQSPKLLIYWASTRESGVPDRFTGSGSGTDFTL
TISSLQAEDVAVYYCKQSYSLRTFGGGTKVEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC

Figure 49A

>XENP26007 human_IL15Ra(sushi)_(GGGGS)5-human_IL15(N4D/N65D;single-Chain)-
Numax_IgG1_Fc(216)_IgG1_pI(-)_Isosteric_A_C220S/PVA_/S267K/L368D/K370S-
IgG1_PVA_/S267K/S364K/E357Q Chain 1 - human_IL15Ra(sushi)_(GGGGS)5-human_IL15(N4D/N65D;single-Chain)_Fc(216)_IgG1_pI(-
)_Isosteric_A_C220S/PVA_/S267K/L368D/K370S scIL-15/Rα-Fc Chain (SEQ ID NO: 279)

*ITCPPPMSVEHADIWVKSYSLYSRERYICNSGFKRKAGTSSLTECVLNKATNVAHWTTPSLKCIR*/<ins>GGGGSGGGGSGGG
GSGGGGSGGGGS</ins>/NWVDVISDLKKIEDLIQSMHIDATLYTESDVHPSCKVTAMKCFLLELQVISLESGDASIHDTVEDLI
LANNSLSSNGNVTESGCKECEELEEKNIKEFLQSFVHIVQMFINTS/EPKSSDKTHTCPPCPAPPVAGPSVFLFPPKPKDTL
MISRTPEVTCVVVDVKHEDPEVKFNWYVDGVEVHNAKTKPREEEYNSTYRVVSVLTVLHQDWLNGKEYKCKVSNKAL
PAPIEKTISKAKGQPREPQVYTLPPSREEMTKNQVSLTCDVSGFYPSDIAVEWESDGQPENNYKTTPPVLDSDGSFFLYS
KLTVDKSRWEQGDVFSCSVMHEALHNHYTQKSLSLSPGK Chain 2 - Numax_IgG1_PVA_/S267K/S364K/E357Q Heavy Chain (SEQ ID NO: 280)
QVTLRESGPALVKPTQTLTLTCTFSGFSLS<ins>TAGMSVG</ins>WIRQPPGKALEWLA<ins>DIWWDDKKHYNPSLKDR</ins>LTISKDTSKN
QVVLKVTNMDPADTATYYCARD<ins>MIFNFYFDV</ins>WGQGTTVTVSS/ASTKGPSVFPLAPSSKSTSGGTAALGCLVKDYFPE
PVTVSWNSGALTSGVHTFPAVLQSSGLYSLSSVVTVPSSSLGTQTYICNVNHKPSNTKVDKKVEPKSCDKTHTCPPCPAP
PVAGPSVFLFPPKPKDTLMISRTPEVTCVVVDVKHEDPEVKFNWYVDGVEVHNAKTKPREEQYNSTYRVVSVLTVLHQ
DWLNGKEYKCKVSNKALPAPIEKTISKAKGQPREPQVYTLPPSREQMTKNQVKLTCLVKGFYPSDIAVEWESNGQPEN
NYKTTPPVLDSDGSFFLYSKLTVDKSRWQQGNVFSCSVMHEALHNHYTQKSLSLSPGK Chain 3 - Numax Light Chain (SEQ ID NO: 281)
DIQMTQSPSTLSASVGDRVTITC<ins>SASSRVGYMH</ins>WYQQKPGKAPKLLIY<ins>DTSKLAS</ins>GVPSRFSGSGSGTEFTLTISSLQPD
DFATYYC<ins>FQGSGYPFT</ins>FGGGTKVEIK/RTVAAPSVFIFPPSDEQLKSGTASVVCLLNNFYPREAKVQWKVDNALQSGNS
QESVTEQDSKDSTYSLSSTLTLSKADYEKHKVYACEVTHQGLSSPVTKSFNRGEC

Figure 49B

>XENP29481 human_IL15Ra(sushi)_(GGGGS)5-human_IL15(D30N/N65D;single-chain)-
Numax_IgG1_Fc(216)_IgG1_pI(-)_Isosteric_A_C220S/PVA_/S267K/L368D/K370S-
IgG1_PVA_/S267K/S364K/E357Q Chain 1 - human_IL15Ra(sushi)_(GGGGS)5-human_IL15(D30N/N65D;single-chain)_Fc(216)_IgG1_pI(-
)_Isosteric_A_C220S/PVA_/S267K/L368D/K370S (SEQ ID NO: 282)
ITCPPPMSVEHADIWVKSYSLYSRERYICNSGFKRKAGTSSLTECVLNKATNVAHWTTPSLKCIR/GGGGSGGGGSGGG
GSGGGGSGGGGS/NWVNVISDLKKIEDLIQSMHIDATLYTESNVHPSCKVTAMKCFLLELQVISLESGDASIHDTVEDLII
LANNSLSSNGNVTESGCKECEELEEKNIKEFLQSFVHIVQMFINTS/EPKSSDKTHTCPPCPAPPVAGPSVFLFPPKPKDTL
MISRTPEVTCVVVDVKHEDPEVKFNWYVDGVEVHNAKTKPREEEYNSTYRVVSVLTVLHQDWLNGKEYKCKVSNKAL
PAPIEKTISKAKGQPREPQVYTLPPSREEMTKNQVSLTCDVSGFYPSDIAVEWESDGQPENNYKTTPPVLDSDGSFFLYS
KLTVDKSRWEQGDVFSCSVMHEALHNHYTQKSLSLSPGK Chain 2 - Numax_IgG1_PVA_/S267K/S364K/E357Q (SEQ ID NO: 283)
QVTLRESGPALVKPTQTLTLTCTFSGFSLSTAGMSVGWIRQPPGKALEWLADIWWDDKKHYNPSLKDRLTISKDTSKN
QVVLKVTNMDPADTATYYCARDMIFNFYFDVWGQGTTVTVSS/ASTKGPSVFPLAPSSKSTSGGTAALGCLVKDYFPE
PVTVSWNSGALTSGVHTFPAVLQSSGLYSLSSVVTVPSSSLGTQTYICNVNHKPSNTKVDKKVEPKSCDKTHTCPPCPAP
PVAGPSVFLFPPKPKDTLMISRTPEVTCVVVDVKHEDPEVKFNWYVDGVEVHNAKTKPREEQYNSTYRVVSVLTVLHQ
DWLNGKEYKCKVSNKALPAPIEKTISKAKGQPREPQVYTLPPSREQMTKNQVKLTCLVKGFYPSDIAVEWESNGQPEN
NYKTTPPVLDSDGSFFLYSKLTVDKSRWQQGNVFSCSVMHEALHNHYTQKSLSLSPGK Chain 3 - Numax LC (SEQ ID NO: 284)
DIQMTQSPSTLSASVGDRVTITCSASSRVGYMHWYQQKPGKAPKLLIYDTSKLASGVPSRFSGSGSGTEFTLTISSLQPD
DFATYYCFQGSGYPFTFGGGTKVEIK/RTVAAPSVFIFPPSDEQLKSGTASVVCLLNNFYPREAKVQWKVDNALQSGNS
QESVTEQDSKDSTYSLSSTLTLSKADYEKHKVYACEVTHQGLSSPVTKSFNRGEC

Figure 49C

>XENP30432 human_IL15Ra(sushi)_(GGGGS)5-human_IL15(D30N/E64Q/N65D;single-chain)-
Numax_IgG1_Fc(216)_IgG1_pI(-)_Isosteric_A_C220S/PVA_/S267K/L368D/K370S-
IgG1_PVA_/S267K/S364K/E357Q Chain 1 - human_IL15Ra(sushi)_(GGGGS)5-human_IL15(D30N/E64Q/N65D;single-
chain)_Fc(216)_IgG1_pI(-)_Isosteric_A_C220S/PVA_/S267K/L368D/K370S (SEQ ID NO: 285)

ITCPPPMSVEHADIWVKSYSLYSRERYICNSGFKRKAGTSSLTECVLNKATNVAHWTTPSLKCIR/GGGGSGGGGSGGG
GSGGGGSGGGGS/NWVNVISDLKKIEDLIQSMHIDATLYTESNVHPSCKVTAMKCFLLELQVISLESGDASIHDTVQDLII
LANNSLSSNGNVTESGCKECEELEEKNIKEFLQSFVHIVQMFINTS/EPKSSDKTHTCPPCPAPPVAGPSVFLFPPKPKDTL
MISRTPEVTCVVVDVKHEDPEVKFNWYVDGVEVHNAKTKPREEEYNSTYRVVSVLTVLHQDWLNGKEYKCKVSNKAL
PAPIEKTISKAKGQPREPQVYTLPPSREEMTKNQVSLTCDVSGFYPSDIAVEWESDGQPENNYKTTPPVLDSDGSFFLYS
KLTVDKSRWEQGDVFSCSVMHEALHNHYTQKSLSLSPGK

Chain 2 - Numax_VH_IgG1_IgG1_PVA_/S267K/S364K/E357Q (SEQ ID NO: 286)

QVTLRESGPALVKPTQTLTLTCTFSGFSLSTAGMSVGWIRQPPGKALEWLADIWWDDKKHYNPSLKDRLTISKDTSKN
QVVLKVTNMDPADTATYYCARDMIFNFYFDVWGQGTTVTVSS/ASTKGPSVFPLAPSSKSTSGGTAALGCLVKDYFPE
PVTVSWNSGALTSGVHTFPAVLQSSGLYSLSSVVTVPSSSLGTQTYICNVNHKPSNTKVDKKVEPKSCDKTHTCPPCPAP
PVAGPSVFLFPPKPKDTLMISRTPEVTCVVVDVKHEDPEVKFNWYVDGVEVHNAKTKPREEQYNSTYRVVSVLTVLHQ
DWLNGKEYKCKVSNKALPAPIEKTISKAKGQPREPQVYTLPPSREQMTKNQVKLTCLVKGFYPSDIAVEWESNGQPEN
NYKTTPPVLDSDGSFFLYSKLTVDKSRWQQGNVFSCSVMHEALHNHYTQKSLSLSPGK

Chain 3 - Numax LC (SEQ ID NO: 287)

DIQMTQSPSTLSASVGDRVTITCSASSRVGYMHWYQQKPGKAPKLLIYDTSKLASGVPSRFSGSGSGTEFTLTISSLQPD
DFATYYCFQGSGYPFTFGGGTKVEIK/RTVAAPSVFIFPPSDEQLKSGTASVVCLLNNFYPREAKVQWKVDNALQSGNS
QESVTEQDSKDSTYSLSSTLTLSKADYEKHKVYACEVTHQGLSSPVTKSFNRGEC

TIM-3 TARGETED HETERODIMERIC FUSION PROTEINS CONTAINING IL-15/IL-15RA FC-FUSION PROTEINS AND TIM-3 ANTIGEN BINDING DOMAINS

CROSS-REFERENCE TO RELATED APPLICATIONS

This application claims priority to U.S. Provisional Patent Application Nos. 62/659,626, filed Apr. 18, 2018 and 62/783,110, filed Dec. 20, 2018, which are expressly incorporated herein by reference in their entirety, with particular reference to the figures, legends, and claims therein.

The instant application contains a Sequence Listing which has been submitted electronically in ASCII format and is hereby incorporated by reference in its entirety. Said ASCII copy, created on May 30, 2019, is named 067461-5223-US_SL.txt and is 325,104 bytes in size.

BACKGROUND OF THE INVENTION

Two very promising approaches in cancer immunotherapy include cytokine-based treatments and blockade of immune checkpoint proteins such as PD-1.

Cytokines such as IL-2 and IL-15 function in aiding the proliferation and differentiation of B cells, T cells, and NK cells. Both cytokines exert their cell signaling function through binding to a trimeric complex consisting of two shared receptors, the common gamma chain (γc; CD132) and IL-2 receptor beta-chain (IL-2Rβ; CD122), as well as an alpha chain receptor unique to each cytokine: IL-2 receptor alpha (IL-2Rα; CD25) or IL-15 receptor alpha (IL-15Rα; CD215). Both cytokines are considered as potentially valuable therapeutics in oncology, and IL-2 has been approved for use in patients with metastatic renal-cell carcinoma and malignant melanoma. Currently, there are no approved uses of recombinant IL-15, although several clinical trials are ongoing. However, as potential drugs, both cytokines suffer from a very fast clearance, with half-lives measured in minutes. IL-2 immunotherapy has been associated with systemic toxicity when administered in high doses to overcome fast clearance. Such systemic toxicity has also been reported with IL-15 immunotherapy in recent clinical trials (Guo et al., J Immunol, 2015, 195(5):2353-64).

Immune checkpoint proteins such as PD-1 are up-regulated following T cell activation to preclude autoimmunity by exhausting activated T cells upon binding to immune checkpoint ligands such as PD-L1. However, immune checkpoint proteins are also up-regulated in tumor-infiltrating lymphocytes (TILs), and immune checkpoint ligands are overexpressed on tumor cells, contributing to immune escape by tumor cells. De-repression of TILs by blockade of immune checkpoint interactions by drugs such as Opdivo® (nivolumab) and Keytruda® (pembrolizumab) have proven highly effective in treatment of cancer. Despite the promise of checkpoint blockade therapies such as nivolumab and pembrolizumab, many patients still fail to achieve sufficient response to checkpoint blockade alone.

Therefore, there remains an unmet need in oncology treatment for therapeutic strategies with cytokines that do not require high doses and are targeted to tumors to avoid systemic toxicity. Further, there is a need to identify additional therapeutic modalities to stack with checkpoint blockade that could increase patient response rate.

The present invention addresses these needs and caveats by providing TIM-3-targeted IL-15 heterodimeric fusion proteins with enhanced half-life and more selective targeted of TILs to improve safety profile, and which synergistically combine with checkpoint blockade antibodies (FIG. 1).

BRIEF SUMMARY OF THE INVENTION

In one aspect, the present invention provides a targeted IL-15/IL-15Rα heterodimeric protein comprising: (a) a first monomer comprising, from N- to C-terminal: i) an IL-15 sushi domain; ii) a first domain linker; iii) a variant IL-15 domain; iv) a second domain linker; v) a first variant Fc domain comprising CH2-CH3; and (b) a second monomer comprising, from N- to C-terminal: i) a scFv domain; ii) a third domain linker; iii) a second variant Fc domain comprising CH2-CH3; wherein the scFv domain comprises a first variable heavy domain, an scFv linker and a first variable light domain, wherein the scFv domain binds human TIM-3.

In other aspects of the present invention, provided herein is a targeted IL-15/IL-15Rα heterodimeric protein comprising: (a) a first monomer comprising, from N- to C-terminal: i) an IL-15 sushi domain; ii) a first domain linker; iii) a first variant Fc domain comprising CH2-CH3; (b) a second monomer comprising, from N- to C-terminal: i) a scFv domain; ii) a third domain linker; iii) a second variant Fc domain comprising CH2-CH3; wherein the scFv domain comprises a first variable heavy domain, an scFv linker and a first variable light domain; and (c) a third monomer comprising a variant IL-15 domain; wherein the scFv domain binds human TIM-3.

In one aspect, provided are "scIL-15/Rα×Fab" format heterodimeric proteins. Such "scIL-15/Rα×Fab" format heterodimeric proteins include: a) a first monomer comprising, from N- to C-terminal: i) an IL-15Rα(sushi) domain; ii) a first domain linker; iii) an IL-15 variant; iv) a second domain linker; v) a first variant Fc domain comprising CH2-CH3; b) a second monomer comprising, from N- to C-terminal, VH-CH1-hinge-CH2-CH3, wherein CH2-CH3 is a second variant Fc domain; and c) a third monomer comprising a VL-CL. The VH and VL are a variable heavy domain and a variable light domain, respectively, that form a human TIM-3 antigen binding domain. In some embodiments, the second domain linker is an antibody hinge.

In certain embodiments of the "scIL-15/Rα×Fab" format heterodimeric protein, the first variant Fc domain the second variant Fc domain comprises one of the following skew variant sets: S267K/L368D/K370S:S267K/S364K/E357Q; S364K/E357Q:L368D/K370S; L368D/K370S:S364K; L368E/K370S:S364K; T411E/K360E/Q362E:D401K; L368D/K370S:S364K/E357L and K370S:S364K/E357Q according to EU numbering. In an exemplary embodiment, the skew variant set is S364K/E357Q:L368D/K370S.

In an exemplary embodiment of the "scIL-15/Rα×Fab" format heterodimeric protein, the "scIL-15/Rα×Fab" format heterodimeric protein includes: a) a first monomer comprising, from N- to C-terminal: i) an IL-15Rα(sushi) domain; ii) a first domain linker; iii) an IL-15 variant; iv) a hinge; v) a first variant Fc domain comprising CH2-CH3; b) a second monomer comprising, from N- to C-terminal, VH-CH1-hinge-CH2-CH3, wherein the CH2-CH3 is a second variant Fc domain; and c) a third monomer comprising a VL-CL. The VH and VL are a variable heavy domain and a variable light domain, respectively, that form a human TIM-3 antigen binding domain. In such embodiments, the first variant Fc domain comprises skew variants L368D/K370S and the second variant Fc domain comprises skew variants S364K/E357Q the first and second variant Fc domains each comprise FcKO variants E233P/L234V/L235A/G236del/

S267K, the first variant Fc domain comprises pI variants Q295E/N384D/Q418E/N421D, wherein numbering is according to EU numbering. In some embodiments, the hinge of the first monomer comprises amino acid substitution C220S, wherein numbering is according to EU numbering. In an exemplary embodiment, the first and second variant Fc domains each further comprise half-life extension variants M428:/N434S.

In some embodiments of the "scIL-15/RαxFab" format heterodimeric protein, the IL-15 variant of the heterodimeric protein provided herein comprises an amino acid substitution(s) selected from the group consisting of N1D, N4D, D8N, D30N, D61N, E64Q, N65D, Q108E, N4D/N65D, D30N/N65D, and D30N/E64Q/N65D. In an exemplary embodiment, the IL-15 variant comprises amino acid substitutions N4D/N65D, D30N/N65D, or D30N/E64Q/N65D In an exemplary embodiment, the "scIL-15/RαxFab" format heterodimeric protein is XENP27974, XENP27979, XENC1000, XENC1001, XENC1002, or XENC1003.

In certain embodiment, the VH and VL of the scIL-15/Rα×Fab" format heterodimeric proteins provided herein are the variable heavy domain and variable domain of any of the TIM-3 antigen binding domains in FIGS. 12 and 13. In an exemplary embodiment, the TIM-3 antigen binding domain is 3H3_H1_L2.1.

In one aspect, provided herein is a heterodimeric protein having the "scIL-15/Rα X scFv" format. In one embodiment, the heterodimeric protein includes: a) a first monomer comprising, from N- to C-terminal: i) an IL-15Rα(sushi) domain; ii) a first domain linker; iii) an IL-15 variant; iv) a second domain linker; and v) a first variant Fc domain comprising CH2-CH3; and b) a second monomer comprising, from N- to C-terminal: i) a scFv domain; ii) a third domain linker; and iii) a second variant Fc domain comprising CH2-CH3. In some embodiments, the scFv domain comprises a variable heavy domain (VH), an scFv linker and a variable light domain (VL), and the scFv domain binds human TIM-3. In some embodiments of the "scIL-15/Rα× scFv" format heterodimeric protein, the second domain linker and the third domain linker are each an antibody hinge.

In certain embodiments, the first variant Fc domain the second variant Fc domain comprises one of the following skew variant sets: S267K/L368D/K370S:S267K/S364K/E357Q; S364K/E357Q:L368D/K370S; L368D/K370S:S364K; L368E/K370S:S364K; T411E/K360E/Q362E:D401K; L368D/K370S:S364K/E357L and K370S:S364K/E357Q, according to EU numbering. In an exemplary embodiment, the skew variant set is S364K/E357Q:L368D/K370S.

In some embodiments of the "scIL-15/RαxscFv" format, the heterodimeric protein includes: a) a first monomer comprising, from N- to C-terminal: i) an IL-15Rα(sushi) domain; ii) a first domain linker; iii) an IL-15 variant; iv) a hinge; and v) a first variant Fc domain comprising CH2-CH3; and b) a second monomer comprising, from N- to C-terminal: i) a scFv domain; ii) a hinge; and iii) a second variant Fc domain comprising CH2-CH3. In some embodiments, the scFv domain comprises a variable heavy domain (VH), an scFv linker and a variable light domain (VL), and the scFv domain binds human TIM-3. In such embodiments, the first variant Fc domain comprises skew variants L368D/K370S and the second variant Fc domain comprises skew variants S364K/E357Q, the first and second variant Fc domains each comprise FcKO variants E233P/L234V/L235A/G236del/S267K, the first variant Fc domain comprises pI variants Q295E/N384D/Q418E/N421D, and the numbering is according to EU numbering. In certain embodiments, the first and second hinges each comprise amino acid substitution C220S, wherein numbering is according to EU numbering. In one embodiment, the first and second variant Fc domains each further comprise half-life extension variants M428:/N434S.

In another aspect, provided herein are "scFv×ncIL-15/Rα" format heterodimeric proteins. Such heterodimeric proteins include: a) a first monomer comprising, from N- to C-terminal: i) a scFv domain; ii) a first domain linker; and iii) a first variant Fc domain comprising CH2-CH3; b) a second monomer comprising, from N- to C-terminal: i) an IL-15Rα(sushi) domain; ii) a second domain linker; and iii) a second variant Fc domain comprising CH2-CH3; and c) a third monomer comprising an IL-15 variant. The scFv domain comprises a variable heavy domain (VH), an scFv linker and a variable light domain (VL), and the scFv domain binds human TIM-3. In one embodiment, the first domain linker and the second domain linker are each an antibody hinge.

In some embodiments of the "scFv×ncIL-15/Rα" format heterodimeric protein, the first variant Fc domain the second variant Fc domain comprises one of the following skew variant sets: S267K/L368D/K370S:S267K/S364K/E357Q; S364K/E357Q:L368D/K370S; L368D/K370S:S364K; L368E/K370S:S364K; T411E/K360E/Q362E:D401K; L368D/K370S:S364K/E357L and K370S:S364K/E357Q, according to EU numbering. In an exemplary embodiment, the skew variant set is S364K/E357Q:L368D/K370S.

In an exemplary embodiment, the "scFv×ncIL-15/Rα" format heterodimeric protein includes: a) a first monomer comprising, from N- to C-terminal: i) a scFv domain; ii) a hinge; and iii) a first variant Fc domain comprising CH2-CH3; b) a second monomer comprising, from N- to C-terminal: i) an IL-15Rα(sushi) domain; ii) a hinge; and iii) a second variant Fc domain comprising CH2-CH3; and c) a third monomer comprising an IL-15 variant. Further, the scFv domain comprises a variable heavy domain (VH), an scFv linker and a variable light domain (VL), and the scFv domain binds human TIM-3. In such embodiments, the first variant Fc domain comprises skew variants L368D/K370S and the second variant Fc domain comprises skew variants S364K/E357Q, the first and second variant Fc domains each comprise FcKO variants E233P/L234V/L235A/G236del/S267K, the first variant Fc domain comprises pI variants Q295E/N384D/Q418E/N421D, and wherein numbering is according to EU numbering. In certain embodiments, the first and second hinges each comprise amino acid substitution C220S, wherein numbering is according to EU numbering. In one embodiment, the first and second variant Fc domains each further comprise half-life extension variants M428:/N434S.

In another aspect, provided herein are "scFv×dsIL-15/Rα" format heterodimeric proteins. The "scFv×dsIL-15/Rα" format heterodimeric protein includes: a) a first monomer comprising, from N- to C-terminal: i) a variant IL-15Rα (sushi) domain comprising an amino acid substituted for a cysteine residue; ii) a first domain linker; and iii) a first variant Fc domain comprising CH2-CH3; b) a second monomer comprising, from N- to C-terminal: i) a scFv domain; ii) a second domain linker; iii) a second variant Fc domain comprising CH2-CH3; an c) a third monomer comprising an IL-15 variant comprising an amino acid substituted for a cysteine residue. The scFv domain comprises a variable heavy domain (VH), an scFv linker and a variable light domain (VL), wherein the cysteine residue of the variant IL-15Rα(sushi) domain and the cysteine residue of the IL-15 variant form a disulfide bond and the scFv domain binds human TIM-3. In certain embodiments, the first domain linker and the second domain linker are each an antibody hinge.

In some embodiments of the "scFv×dsIL-15/Rα" format heterodimeric protein, the first variant Fc domain the second variant Fc domain comprises one of the following skew variant sets: S267K/L368D/K370S:S267K/S364K/E357Q; S364K/E357Q:L368D/K370S; L368D/K370S:S364K; L368E/K370S:S364K; T411E/K360E/Q362E:D401K; L368D/K370S:S364K/E357L and K370S:S364K/E357Q, according to EU numbering. In an exemplary embodiment, the skew variant set is S364K/E357Q:L368D/K370S.

In an exemplary embodiment, the "scFv×dsIL-15/Rα" format heterodimeric protein includes: a) a first monomer comprising, from N- to C-terminal: i) a variant IL-15Rα (sushi) domain comprising an amino acid substituted for a cysteine residue; ii) a hinge; and iii) a first variant Fc domain comprising CH2-CH3; b) a second monomer comprising, from N- to C-terminal: i) a scFv domain; ii) a hinge; iii) a second variant Fc domain comprising CH2-CH3; an c) a third monomer comprising an IL-15 variant comprising an amino acid substituted for a cysteine residue. The scFv domain comprises a variable heavy domain (VH), an scFv linker and a variable light domain (VL), wherein the cysteine residue of the variant IL-15Rα(sushi) domain and the cysteine residue of the IL-15 variant form a disulfide bond and the scFv domain binds human TIM-3. In such embodiments, the first variant Fc domain comprises skew variants L368D/K370S and the second variant Fc domain comprises skew variants S364K/E357Q, the first and second variant Fc domains each comprise FcKO variants E233P/L234V/L235A/G236del/S267K, the first variant Fc domain comprises pI variants Q295E/N384D/Q418E/N421D, wherein numbering is according to EU numbering. In certain embodiments, the hinges of the first and second monomers each comprise amino acid substitution C220S, wherein numbering is according to EU numbering. In some embodiments, the first and second variant Fc domains each comprise half-life extension variants M428:/N434S.

In one aspect, provided herein are "Fab×ncIL-15/Rα" format heterodimeric proteins. Such heterodimeric proteins include: a) a first monomer comprising, from N- to C-terminal, VH-CH1-hinge-CH2-CH3, wherein the CH2-CH3 is a first variant Fc domain; b) a second monomer comprising, from N- to C-terminal: i) an IL-15Rα(sushi) domain; ii) a first domain linker; iii) a first variant Fc domain comprising CH2-CH3; c) a third monomer comprising a light chain comprising VL-CL; and d) a fourth monomer comprising an IL-15 variant. The VH and VL are a variable heavy domain and a variable light domain, respectively, that form a human TIM-3 antigen binding domain. In some embodiments, the first domain linker is an antibody hinge.

In some embodiments of the "Fab×ncIL-15/Rα" format heterodimeric protein, the first variant Fc domain the second variant Fc domain comprises one of the following skew variant sets: S267K/L368D/K370S:S267K/S364K/E357Q; S364K/E357Q:L368D/K370S; L368D/K370S:S364K; L368E/K370S:S364K; T411E/K360E/Q362E:D401K; L368D/K370S:S364K/E357L and K370S:S364K/E357Q, according to EU numbering. In an exemplary embodiment, the skew variant set is S364K/E357Q:L368D/K370S.

In exemplary embodiments, the "Fab×ncIL-15/Rα" format heterodimeric protein includes: a) a first monomer comprising, from N- to C-terminal, VH-CH1-hinge-CH2-CH3, wherein the CH2-CH3 is a first variant Fc domain; b) a second monomer comprising, from N- to C-terminal: i) an IL-15Rα(sushi) domain; ii) a hinge; iii) a first variant Fc domain comprising CH2-CH3; c) a third monomer comprising a light chain comprising VL-CL; and d) a fourth monomer comprising an IL-15 variant. The VH and VL are a variable heavy domain and a variable light domain, respectively, that form a human TIM-3 antigen binding domain. In such embodiments, the first variant Fc domain comprises skew variants L368D/K370S and the second variant Fc domain comprises skew variants S364K/E357Q, the first and second variant Fc domains each comprise FcKO variants E233P/L234V/L235A/G236del/S267K, and the hinge-first variant Fc domain of the first monomer comprises pI variants N208D/Q295E/N384D/Q418E/N421D, wherein numbering is according to EU numbering. In some embodiments, the hinge of the second monomer comprises amino acid substitution C220S, wherein numbering is according to EU numbering. In certain embodiments, the first and second variant Fc domains each further comprise half-life extension variants M428:/N434S.

In another aspect, provided herein are "Fab×dsIL-15/Rα" format heterodimeric proteins. Such "Fab×dsIL-15/Rα" format heterodimeric proteins include: a) a first monomer comprising, from N- to C-terminal, VH-CH1-hinge-CH2-CH3, wherein CH2-CH3 is a first variant Fc domain; b) a second monomer comprising, from N- to C-terminal: i) a variant IL-15Rα(sushi) domain comprising an amino acid substituted for a cysteine residue; ii) a first domain linker; and iii) a first variant Fc domain comprising CH2-CH3; c) a third monomer comprising, from N- to C-terminal, VL-CL; and d) a fourth monomer comprising an IL-15 variant comprising an amino acid substituted for a cysteine residue. Further, the cysteine residue of the variant IL-15Rα(sushi) domain and the cysteine residue of the IL-15 variant form a disulfide bond, and the VH and VL are a variable heavy domain and a variable light domain, respectively, that form a human TIM-3 antigen binding domain. In some embodiments, the first domain linker is an antibody hinge.

In some embodiments of the "Fab×dsIL-15/Rα" format heterodimeric protein, the first variant Fc domain the second variant Fc domain comprises one of the following skew variant sets: S267K/L368D/K370S:S267K/S364K/E357Q; S364K/E357Q:L368D/K370S; L368D/K370S:S364K; L368E/K370S:S364K; T411E/K360E/Q362E:D401K; L368D/K370S:S364K/E357L and K370S:S364K/E357Q, according to EU numbering. In an exemplary embodiment, the skew variant set is S364K/E357Q:L368D/K370S.

In an exemplary embodiment, the "Fab×dsIL-15/Rα" format heterodimeric protein includes: a) a first monomer comprising, from N- to C-terminal, VH-CH1-hinge-CH2-CH3, wherein CH2-CH3 is a first variant Fc domain; b) a second monomer comprising, from N- to C-terminal: i) a variant IL-15Rα(sushi) domain comprising an amino acid substituted for a cysteine residue; ii) a hinge; and iii) a first variant Fc domain comprising CH2-CH3; c) a third monomer comprising, from N- to C-terminal, VL-CL; and d) a fourth monomer comprising an IL-15 variant comprising an amino acid substituted for a cysteine residue. Further, the cysteine residue of the variant IL-15Rα(sushi) domain and the cysteine residue of the IL-15 variant form a disulfide bond, and the VH and VL are a variable heavy domain and a variable light domain, respectively, that form a human-TIM-3 antigen binding domain. In such embodiments, the first variant Fc domain comprises skew variants L368D/K370S and the second variant Fc domain comprises skew variants S364K/E357Q, the first and second variant Fc domains each comprise FcKO variants E233P/L234V/L235A/G236del/S267K, and the hinge-first variant Fc domain of the first monomer comprises pI variants N208D/Q295E/N384D/Q418E/N421D, wherein numbering is according to EU numbering. In certain embodiments, the hinge of the second monomer comprises amino acid substitution C220S, wherein numbering is according to EU numbering. In some embodiments, the first and second variant Fc domains each further comprise half-life extension variants M428:/N434S.

In one aspect, provided herein are "mAb-scIL-15/Rα" format heterodimeric proteins. The "mAb-scIL-15/Rα" format heterodimeric proteins include: a) a first monomer comprising, from N- to C-terminal, VH-CH1-hinge-CH2-CH3, wherein the CH2-CH3 is a first variant Fc domain; b) a second monomer comprising, from N- to C-terminal, VH-CH1-hinge-CH2-CH3-domain linker-IL-15Rα(sushi) domain-domain linker-IL-15 variant, wherein the CH2-CH3 is a second variant Fc domain; and c) a third monomer and fourth monomer that each comprises, from N- to C-terminal, VL-CL. Further, the VH of the first monomer and the VL of the third monomer form a first human TIM-3 binding domain, and the VH of the second monomer and the VL of the fourth monomer form a second human TIM-3 binding domain.

In some embodiments of the "mAb-scIL-15/Rα" format heterodimeric protein, the first variant Fc domain the second variant Fc domain comprises one of the following skew variant sets: S267K/L368D/K370S:S267K/S364K/E357Q; S364K/E357Q:L368D/K370S; L368D/K370S:S364K; L368E/K370S:S364K; T411E/K360E/Q362E:D401K; L368D/K370S:S364K/E357L and K370S:S364K/E357Q, according to EU numbering. In an exemplary embodiment, the skew variant set is S364K/E357Q:L368D/K370S.

In some embodiments of the "mAb-scIL-15/Rα" format heterodimeric protein, the first variant Fc domain comprises skew variants L368D/K370S and the second variant Fc domain comprises skew variants S364K/E357Q, and the first and second variant Fc domains each comprise FcKO variants E233P/L234V/L235A/G236del/S267K, wherein numbering is according to EU numbering. In certain embodiments, a) the hinge-first variant Fc domain of the first monomer further comprises pI substitutions N208D/Q295E/N384D/Q418D/N421D and the hinge-second variant Fc domain of the second monomer further comprises pI variants Q196K/I199T/P271R/P228R/N276K; b) the hinge-first variant Fc domain of the first monomer further comprises pI substitutions N208D/Q295E/N384D/Q418D/N421D; or c) the hinge-second variant Fc domain of the second monomer further comprises pI variants Q196K/I199T/P271R/P228R/N276K, wherein numbering is according to EU numbering.

In some embodiments of the "mAb-scIL-15/Rα" format heterodimeric protein, the first variant Fc domain comprises skew variants S364K/E357Q and the second variant Fc domain comprises skew variants L368D/K370S, and the first and second variant Fc domains each comprise FcKO variants E233P/L234V/L235A/G236del/S267K, wherein numbering is according to EU numbering. In such embodiments, a) the hinge-first variant Fc domain of the first monomer further comprises pI substitutions Q196K/I199T/P271R/P228R/N276K and the hinge-second variant Fc domain of the second monomer further comprises pI variants N208D/Q295E/N384D/Q418D/N421D; b) the hinge-first variant Fc domain of the first monomer further comprises pI substitutions Q196K/I199T/P271R/P228R/N276K; or c) the hinge-second variant Fc domain of the second monomer further comprises pI variants N208D/Q295E/N384D/Q418D/N421D, wherein numbering is according to EU numbering.

In some embodiments of the "mAb-scIL-15/Rα" format heterodimeric protein, the first and second variant Fc domains each further comprise half-life extension variants M428:/N434S.

In another aspect, provided herein are "mAb-ncIL-15/Rα" format heterodimeric proteins. Such heterodimeric protein include: a) a first monomer comprising, from N- to C-terminal, VH-CH1-hinge-CH2-CH3, wherein the CH2-CH3 is a first variant Fc domain; b) a second monomer comprising, from N- to C-terminal, VH-CH1-hinge-CH2-CH3-domain linker-IL-15Rα(sushi) domain, wherein the CH2-CH3 is a second variant Fc domain; c) a third monomer comprising an IL-15 variant; and d) a fourth and fifth monomer that each comprises, from N- to C-terminal, VL-CL. The VH of the first monomer and the VL of the fourth monomer form a first human TIM-3 binding domain, and the VH of the second monomer and the VL of the fifth monomer form a second human TIM-3 binding domain.

In some embodiments of the "mAb-ncIL-15/Rα" format heterodimeric protein, the first variant Fc domain the second variant Fc domain comprises one of the following skew variant sets: S267K/L368D/K370S:S267K/S364K/E357Q; S364K/E357Q:L368D/K370S; L368D/K370S:S364K; L368E/K370S:S364K; T411E/K360E/Q362E:D401K; L368D/K370S:S364K/E357L and K370S:S364K/E357Q, according to EU numbering. In an exemplary embodiment, the skew variant set is S364K/E357Q:L368D/K370S.

In an exemplary embodiment of the "mAb-ncIL-15/Rα" format heterodimeric protein, the first variant Fc domain comprises skew variants L368D/K370S and the second variant Fc domain comprises skew variants S364K/E357Q, and the first and second variant Fc domains each comprise FcKO variants E233P/L234V/L235A/G236del/S267K, wherein numbering is according to EU numbering. In some embodiments, a) the hinge-first variant Fc domain of the first monomer further comprises pI substitutions N208D/Q295E/N384D/Q418D/N421D and the hinge-second variant Fc domain of the second monomer further comprises pI variants Q196K/I199T/P271R/P228R/N276K; b) the hinge-first variant Fc domain of the first monomer further comprises pI substitutions N208D/Q295E/N384D/Q418D/N421D; or c) the hinge-second variant Fc domain of the second monomer further comprises pI variants Q196K/I199T/P271R/P228R/N276K, wherein numbering is according to EU numbering.

In another exemplary embodiment of the "mAb-ncIL-15/Rα" format heterodimeric protein, the first variant Fc domain comprises skew variants S364K/E357Q and the second variant Fc domain comprises skew variants L368D/K370S, and the first and second variant Fc domains each comprise FcKO variants E233P/L234V/L235A/G236del/S267K, wherein numbering is according to EU numbering. In certain embodiments, a) the hinge-first variant Fc domain of the first monomer further comprises pI substitutions Q196K/I199T/P271R/P228R/N276K and the hinge-second variant Fc domain of the second monomer further comprises pI variants N208D/Q295E/N384D/Q418D/N421D; b) the hinge-first variant Fc domain of the first monomer further comprises pI substitutions Q196K/I199T/P271R/P228R/N276K; or c) the hinge-second variant Fc domain of the second monomer comprises pI variants N208D/Q295E/N384D/Q418D/N421D, wherein numbering is according to EU numbering.

In certain embodiments, the first and second variant Fc domains each further comprise half-life extension variants M428:/N434S.

In another aspect, provided herein are "mAb-dsIL-15/Rα" heterodimeric proteins. Such "mAb-dsIL-15/Rα" heterodimeric proteins include: a) a first monomer comprising, from N- to C-terminal, VH-CH1-hinge-CH2-CH3, wherein the CH2-CH3 is a first variant Fc domain; b) a second monomer comprising, from N- to C-terminal, VH-CH1-hinge-CH2-CH3-domain linker-variant IL-15Rα(sushi) domain, wherein the variant IL-15Rα(sushi) domain an amino acid substituted for a cysteine residue and wherein the CH2-CH3 is a second variant Fc domain; c) a third monomer comprising an IL-15 variant comprising an amino acid substituted for a cysteine residue; and d) a fourth and fifth monomer that each comprises, from N- to C-terminal, VL-CL. The cysteine residue of the variant IL-15Rα(sushi) domain and the cysteine residue of the IL-15 variant form a disulfide bond, the VH of the first monomer and the VL of the fourth monomer form a first human TIM-3 binding domain, and the VH of the second monomer and the VL of the fifth monomer form a second human TIM-3 binding domain.

In some embodiments, the first variant Fc domain the second variant Fc domain comprises one of the following skew variant sets: S267K/L368D/K370S:S267K/S364K/E357Q; S364K/E357Q:L368D/K370S; L368D/K370S:S364K; L368E/K370S:S364K; T411E/K360E/Q362E:D401K; L368D/K370S:S364K/E357L and K370S:S364K/E357Q according to EU numbering. In an exemplary embodiment, the skew variant set is S364K/E357Q:L368D/K370S.

In an exemplary embodiment of the "mAb-dsIL-15/Rα" heterodimeric proteins, the first variant Fc domain comprises skew variants L368D/K370S and the second variant Fc domain comprises skew variants S364K/E357Q and the first and second variant Fc domains each comprise FcKO variants E233P/L234V/L235A/G236del/S267K, wherein numbering is according to EU numbering. In some embodiments, a) the hinge-first variant Fc domain of the first monomer further comprises pI substitutions N208D/Q295E/N384D/Q418D/N421D and the hinge-second variant Fc domain of the second monomer further comprises pI variants Q196K/I199T/P271R/P228R/N276K; b) the hinge-first variant Fc domain of the first monomer further comprises pI substitutions N208D/Q295E/N384D/Q418D/N421D; or c) the hinge-second variant Fc domain of the second monomer further comprises pI variants Q196K/I199T/P271R/P228R/N276K, wherein numbering is according to EU numbering.

In another exemplary embodiment of the "mAb-dsIL-15/Rα" heterodimeric proteins, the first variant Fc domain comprises skew variants S364K/E357Q and the second variant Fc domain comprises skew variants L368D/K370S, and the first and second variant Fc domains each comprise FcKO variants E233P/L234V/L235A/G236del/S267K, wherein numbering is according to EU numbering. In certain embodiments, a) the hinge-first variant Fc domain of the first monomer further comprises pI substitutions Q196K/I199T/P271R/P228R/N276K and the hinge-second variant Fc domain of the second monomer further comprises pI variants N208D/Q295E/N384D/Q418D/N421D; b) the hinge-first variant Fc domain of the first monomer further comprises pI substitutions Q196K/I199T/P271R/P228R/N276K; or c) the hinge-second variant Fc domain of the second monomer further comprises pI variants N208D/Q295E/N384D/Q418D/N421D, wherein numbering is according to EU numbering. In certain embodiments, the first and second variant Fc domains each further comprise half-life extension variants M428:/N434S.

In one aspect, provided herein are "central-IL-15/Rα" format heterodimeric proteins. Such "central-IL-15/Rα" format heterodimeric proteins include: a) a first monomer comprising, from N- to C-terminal, a VH-CH1-domain linker-IL-15 variant-hinge-CH2-CH3, wherein the CH2-CH3 is a first variant Fc domain; b) a second monomer comprising, from N- to C-terminal, a VH-CH1-domain linker-IL-15Rα(sushi) domain-hinge-CH2-CH3, wherein the CH2-CH3 is a second variant Fc domain; and c) a third and fourth monomer that each comprises, from N- to C-terminal, VL-CL. The VH of the first monomer and the VL of the third monomer form a first human TIM-3 binding domain, and the VH of the second monomer and the VL of the fourth monomer form a second human TIM-3 binding domain.

In some embodiments of the "central-IL-15/Rα" format heterodimeric protein, the first variant Fc domain the second variant Fc domain comprises one of the following skew variant sets: S267K/L368D/K370S:S267K/S364K/E357Q; S364K/E357Q:L368D/K370S; L368D/K370S:S364K; L368E/K370S:S364K; T411E/K360E/Q362E:D401K; L368D/K370S:S364K/E357L and K370S:S364K/E357Q according to EU numbering. In an exemplary embodiment, the skew variant set is S364K/E357Q:L368D/K370S.

In an exemplary embodiment, the first variant Fc domain comprises skew variants L368D/K370S and the second variant Fc domain comprise the skew variant pair S364K/E357Q the first and second variant Fc domains each comprise FcKO variants E233P/L234V/L235A/G236del/S267K, and the first variant Fc domain comprises pI substitutions Q295E/N384D/Q418D/N421D, wherein numbering is according to EU numbering.

In an exemplary embodiment of the "central-IL-15/Rα" format heterodimeric protein, the first variant Fc domain comprises skew variants S364K/E357Q and the second variant Fc domain comprise the skew variant pair L368D/K370S, the first and second variant Fc domains each comprise FcKO variants E233P/L234V/L235A/G236del/S267K, and the second variant Fc domain of the second monomer comprises pI substitutions Q295E/N384D/Q418D/N421D, wherein numbering is according to EU numbering. In some embodiments of the "central-IL-15/Rα" format heterodimeric protein, the hinge of the first and second monomers each comprise amino acid substitution C220S, wherein numbering is according to EU numbering. In certain embodiments, the first and second variant Fc domains each further comprise half-life extension variants M428:/N434S.

In another aspect, provided herein are "central-scIL-15/Rα" format heterodimeric proteins. Such "central-scIL-15/Rα" format heterodimeric proteins include: a) a first monomer comprising, from N- to C-terminal, VH-CH1-domain linker-IL-15Rα(sushi) domain-domain linker-IL-15 variant-hinge-CH2-CH3, wherein the CH2-CH3 is a first variant Fc domain; b) a second monomer comprising, from N- to C-terminal, a VH-CH1-hinge-CH2-CH3, wherein the CH2-CH3 is a second variant Fc domain; and c) a third and fourth monomer that each comprises, from N- to C-terminal, VL-CL. The VH of the first monomer and the VL of the third monomer form a first human TIM-3 binding domain, and the VH of the second monomer and the VL of the fourth monomer form a second human TIM-3 binding domain.

In some embodiments of the "central-scIL-15/Rα" format heterodimeric protein, the first variant Fc domain the second variant Fc domain comprises one of the following skew variant sets: S267K/L368D/K370S:S267K/S364K/E357Q; S364K/E357Q:L368D/K370S; L368D/K370S:S364K; L368E/K370S:S364K; T411E/K360E/Q362E:D401K; L368D/K370S:S364K/E357L and K370S:S364K/E357Q, according to EU numbering. In an exemplary embodiment, the skew variant set is S364K/E357Q:L368D/K370S.

In an exemplary embodiment, the first variant Fc domain comprises skew variants L368D/K370S and the second variant Fc domain comprises skew variants S364K/E357Q, the first and second variant Fc domains each comprise FcKO variants E233P/L234V/L235A/G236del/S267K, and the first variant Fc domain comprises pI variants Q295E/N384D/Q418E/N421D, wherein numbering is according to EU numbering. In some embodiments, the hinge of the first monomer comprises amino acid substitution C220S, wherein numbering is according to EU numbering. In certain embodiments, the first and second variant Fc domains each further comprise half-life extension variants M428:/N434S.

In certain embodiment, the VH and VL of any of the heterodimeric proteins provided herein are the variable heavy domain and variable domain of any of the TIM-3 antigen binding domains in FIGS. 12 and 13. In an exemplary embodiment, the TIM-3 antigen binding domain is 3H3_H1_L2.1.

In some embodiments, the IL-15 variant of the heterodimeric protein provided herein comprises an amino acid substitution(s) selected from the group consisting of N1D, N4D, D8N, D30N, D61N, E64Q, N65D, Q108E, N4D/N65D, D30N/N65D, and D30N/E64Q/N65D. In an exemplary embodiment, the IL-15 variant comprises amino acid substitutions N4D/N65D, D30N/N65D, or D30N/E64Q/N65D In one aspect, provided herein is a pharmaceutical composition that includes any of the heterodimeric proteins disclosed herein and a pharmaceutically acceptable carrier.

In another aspect, provided herein is a method of treating a patient in need thereof comprising administering to the patient any one of the heterodimeric proteins or pharmaceutical compositions disclosed herein. In some embodiments, the method further comprising administering an antibody, where the antibody is an anti-PD-1 antibody, an anti-PD-L1 antibody, an anti-CTLA-4 antibody, an anti-TIM-3 antibody or an-anti-TIGIT antibody.

In another aspect, provided herein are nucleic acid compositions that include one or more nucleic acids encoding any of the heterodimeric proteins disclosed herein, expression vectors that include the nucleic acids, host cells that include the nucleic acids or expression vectors. Also provided herein are methods of making subject heterodimeric proteins by culturing host cells under suitable conditions and recovering the heterodimeric proteins.

BRIEF DESCRIPTION OF THE DRAWINGS

FIGS. 2A-2B depict the sequences for IL-15 and its receptors.

FIG. 3 depicts the sequences for TIM-3, including both human and cyno (predicted), to facilitate the development of antigen binding domains that bind to both for ease of clinical development.

FIGS. 4A-4E depict useful pairs of Fc heterodimerization variant sets (including skew and pI variants). There are variants for which there are no corresponding "monomer 2" variants; these are pI variants which can be used alone on either monomer.

FIG. 5 depicts a list of isosteric variant antibody constant regions and their respective substitutions. pI_(−) indicates lower pI variants, while pI_(+) indicates higher pI variants. These can be optionally and independently combined with other heterodimerization variants of the inventions (and other variant types as well, as outlined herein.)

FIG. 6 depicts useful ablation variants that ablate FcγR binding (sometimes referred to as "knock outs" or "KO" variants). Generally, ablation variants are found on both monomers, although in some cases they may be on only one monomer.

FIGS. 7A-7F show particularly useful embodiments of "non-cytokine"/"non-Fv" components of the TIM-3-targeting IL-15/Rα-Fc fusion proteins of the invention.

FIG. 8 depicts a number of exemplary variable length linkers for use in IL-15/Rα-Fc fusion proteins. In some embodiments, these linkers find use linking the C-terminus of IL-15 and/or IL-15Rα(sushi) to the N-terminus of the Fc region. In some embodiments, these linkers find use fusing IL-15 to the IL-15Rα(sushi).

FIGS. 9A and 9B depict a number of charged scFv linkers that find use in increasing or decreasing the pI of heterodimeric antibodies that utilize one or more scFv as a component. The (+H) positive linker finds particular use herein. A single prior art scFv linker with single charge is referenced as "Whitlow", from Whitlow et al., Protein Engineering 6(8):989-995 (1993). It should be noted that this linker was used for reducing aggregation and enhancing proteolytic stability in scFvs.

FIG. 10 shows the sequences of several useful TIM-3-targeting IL-15/Rα-Fc fusion format backbones based on human IgG1, without the cytokine sequences (e.g., the Il-15 and/or IL-15Rα(sushi)) or VH, and further excluding light chain backbones which are depicted in FIG. 11. Backbone 1 is based on human IgG1 (356E/358M allotype), and includes the S364K/E357Q:L368D/K370S skew variants, C220S and the Q295E/N384D/Q418E/N421D pI variants on the chain with L368D/K370S skew variants and the E233P/L234V/L235A/G236del/S267K ablation variants on both chains. Backbone 2 is based on human IgG1 (356E/358M allotype), and includes the S364K/E357Q:L368D/K370S skew variants, the N208D/Q295E/N384D/Q418E/N421D pI variants on the chain with L368D/K370S skew variants, C220S in the chain with S364K/E357Q variants, and the E233P/L234V/L235A/G236del/S267K ablation variants on both chains. Backbone 3 is based on human IgG1 (356E/358M allotype), and includes the S364K/E357Q:L368D/K370S skew variants, the N208D/Q295E/N384D/Q418E/N421D pI variants on the chains with L368D/K370S skew variants, the Q196K/I199T/P217R/P228R/N276K pI variants on the chains with S364K/E357Q variants, and the E233P/L234V/L235A/G236del/S267K ablation variants on both chains. Such backbone sequences can be included, for example, in the "scIL-15/Rα X Fab" format heterodimeric proteins described herein.). In some embodiments, the "scIL-15/RαxFab" format heterodimeric protein includes: a) a first monomer that includes, from N- to C-terminus, an IL-15Rα(sushi) domain-(domain linker)-IL-15 variant-(hinge)-CH2-CH3, where hinge-CH2-CH3 has the amino acid sequence of "Chain 2" of any of the backbone sequences in FIG. 10 (SEQ ID NO: 49, 51 and 53); b) a second monomer that includes, from N- to C-terminus, a VH-CH1-hinge-CH2-CH3, where VH is a variable heavy domain and CH1-hinge-CH2-CH3 has the amino acid sequence of Chain 1 of any one of the backbone sequences in FIG. 10 (SEQ ID NO: 48, 50 and 52), and c) a light chain that includes from, N- to C-terminus, VL-VC, where VL is a variable light domain and VC has the sequence of "Constant Light Chain—Kappa" or "Constant Light Chain—Lambda" in FIG. 11 (SEQ ID NO: 54-55). In an exemplary embodiment, the IL-15 variant includes amino acid substitutions N4D/N65D, D30N/N65D, or D30N/E64Q/N65D. In exemplary embodiments, the VH and VL are the variable heavy domain and variable light domain, respectively, of any of the TIM-3 ABDs provided in FIGS. 12 and 13A-C.

Figure 1:
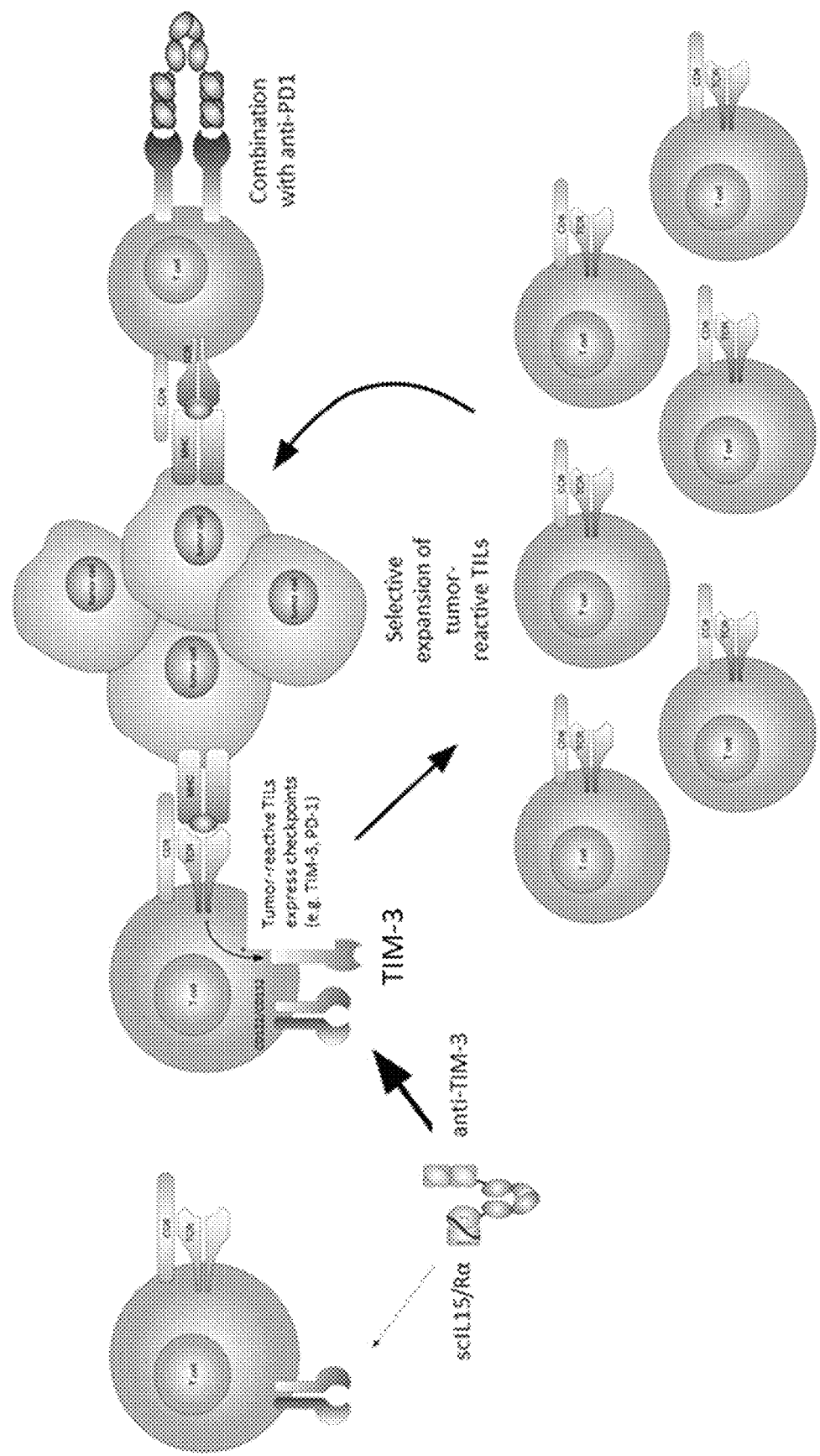
FIG. 1 depicts selectivity of TIM-3-targeted IL-15/Rα-Fc fusion proteins for tumor-reactive tumor-infiltrating lymphocytes expressing PD-1, and its combination with PD-1 blockade antibody.

In certain embodiments, these sequences can be of the 356D/358L allotype. In other embodiments, these sequences can include either the N297A or N297S substitutions. In some other embodiments, these sequences can include the M428L/N434S Xtend mutations. In yet other embodiments, these sequences can instead be based on human IgG4, and include a S228P (EU numbering, this is S241P in Kabat) variant on both chains that ablates Fab arm exchange as is known in the art. In yet further embodiments, these sequences can instead be based on human IgG2. Further, these sequences may instead utilize the other skew variants, pI variants, and ablation variants depicted in the Figures.

As will be appreciated by those in the art and outlined below, these sequences can be used with any IL-15 and IL-15Rα(sushi) pairs outlined herein, including but not limited to scIL-15/Rα, ncIL-15/Rα, and dsIL-15/Rα, as schematically depicted in FIG. 21. Further as will be appreciated by those in the art and outlined below, any IL-15 and/or IL-15Rα(sushi) variants can be incorporated in these backbones. Furthermore as will be appreciated by those in the art and outlined below, these sequences can be used with any VH and VL pairs outlined herein, including either a scFv or a Fab.

Included within each of these backbones are sequences that are 90, 95, 98 and 99% identical (as defined herein) to the recited sequences, and/or contain from 1, 2, 3, 4, 5, 6, 7, 8, 9 or 10 additional amino acid substitutions (as compared to the "parent" of the Figure, which, as will be appreciated by those in the art, already contain a number of amino acid modifications as compared to the parental human IgG1 (or IgG2 or IgG4, depending on the backbone). That is, the recited backbones may contain additional amino acid modifications (generally amino acid substitutions) in addition to the skew, pI and ablation variants contained within the backbones of this figure.

FIG. 11 depicts the "non-Fv" backbone of light chains (i.e. constant light chain) which find use in TIM-3-targeting IL-15/Rα-Fc fusion proteins of the invention.

FIG. 12 depicts the variable region sequences for a select number of anti-TIM-3 antibody binding domains. The CDRs are underlined. As noted herein and is true for every sequence herein containing CDRs, the exact identification of the CDR locations may be slightly different depending on the numbering used as is shown in Table 2, and thus included herein are not only the CDRs that are underlined but also CDRs included within the VH and VL domains using other numbering systems. Furthermore, as for all the sequences in the Figures, these VH and VL sequences can be used either in a scFv format or in a Fab format.

FIGS. 13A-13C depict the variable regions of additional TIM-3 ABDs which may find use in the TIM-3-targeting IL-15/Rα-Fc fusion proteins of the invention. The CDRs are underlined. As noted herein and is true for every sequence herein containing CDRs, the exact identification of the CDR locations may be slightly different depending on the numbering used as is shown in Table 2, and thus included herein are not only the CDRs that are underlined but also CDRs included within the VH and VL domains using other numbering systems. Furthermore, as for all the sequences in the Figures, these VH and VL sequences can be used either in a scFv format or in a Fab format.

Figure 14:
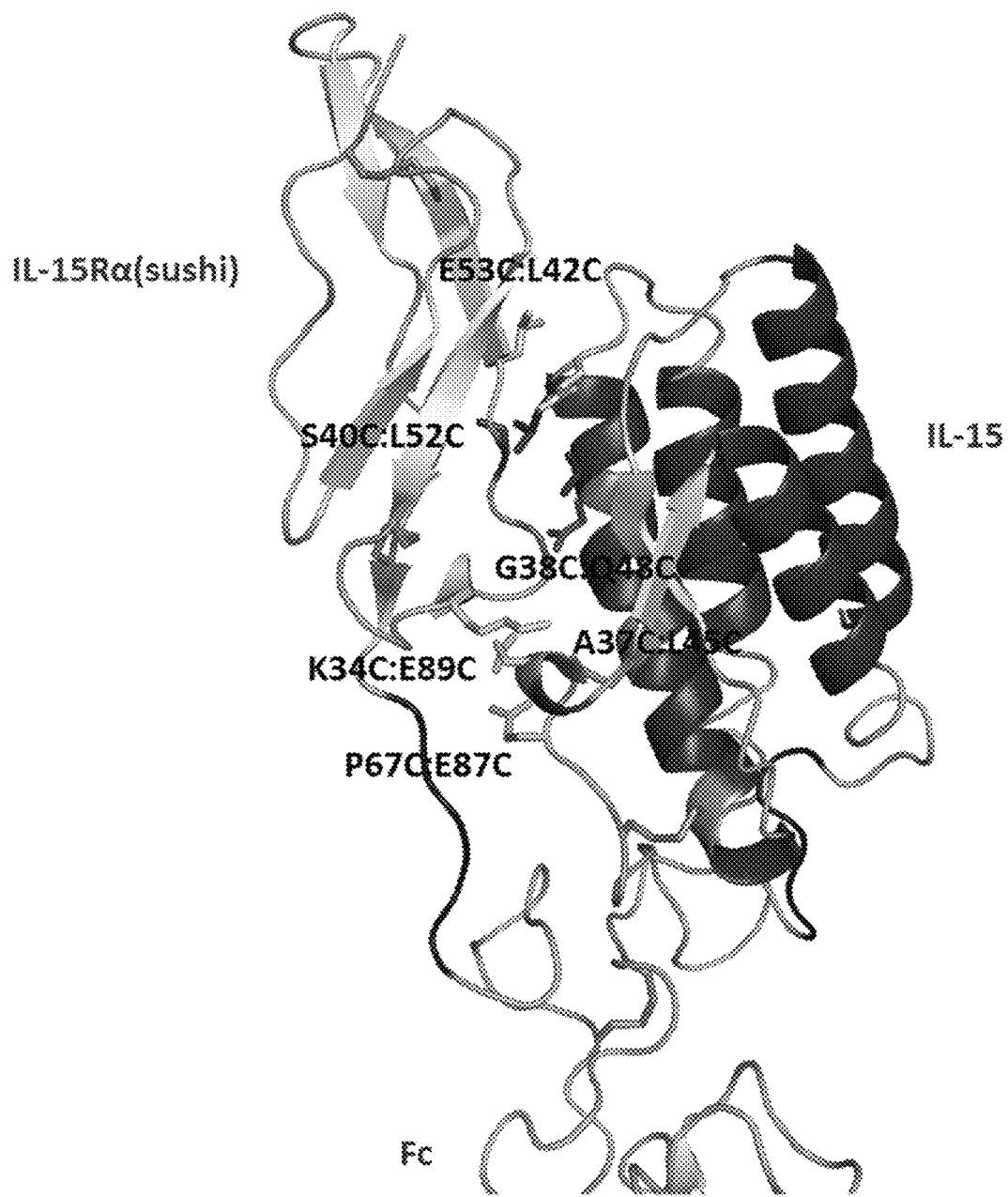

FIG. 14 depicts a structural model of the IL-15/Rα heterodimer showing locations of engineered disulfide bond pairs.

FIG. 15 depicts sequences for illustrative IL-15Rα(sushi) variants engineered with additional residues at the C-terminus to serve as a scaffold for engineering cysteine residues.

FIG. 16 depicts sequences for illustrative IL-15 variants engineered with cysteines in order to form covalent disulfide bonds with IL-15Rα(sushi) variants engineered with cysteines.

FIG. 17 depicts sequences for illustrative IL-15Rα(sushi) variants engineered with cysteines in order to form covalent disulfide bonds with IL-15 variants engineered with cysteines.

Figure 18:
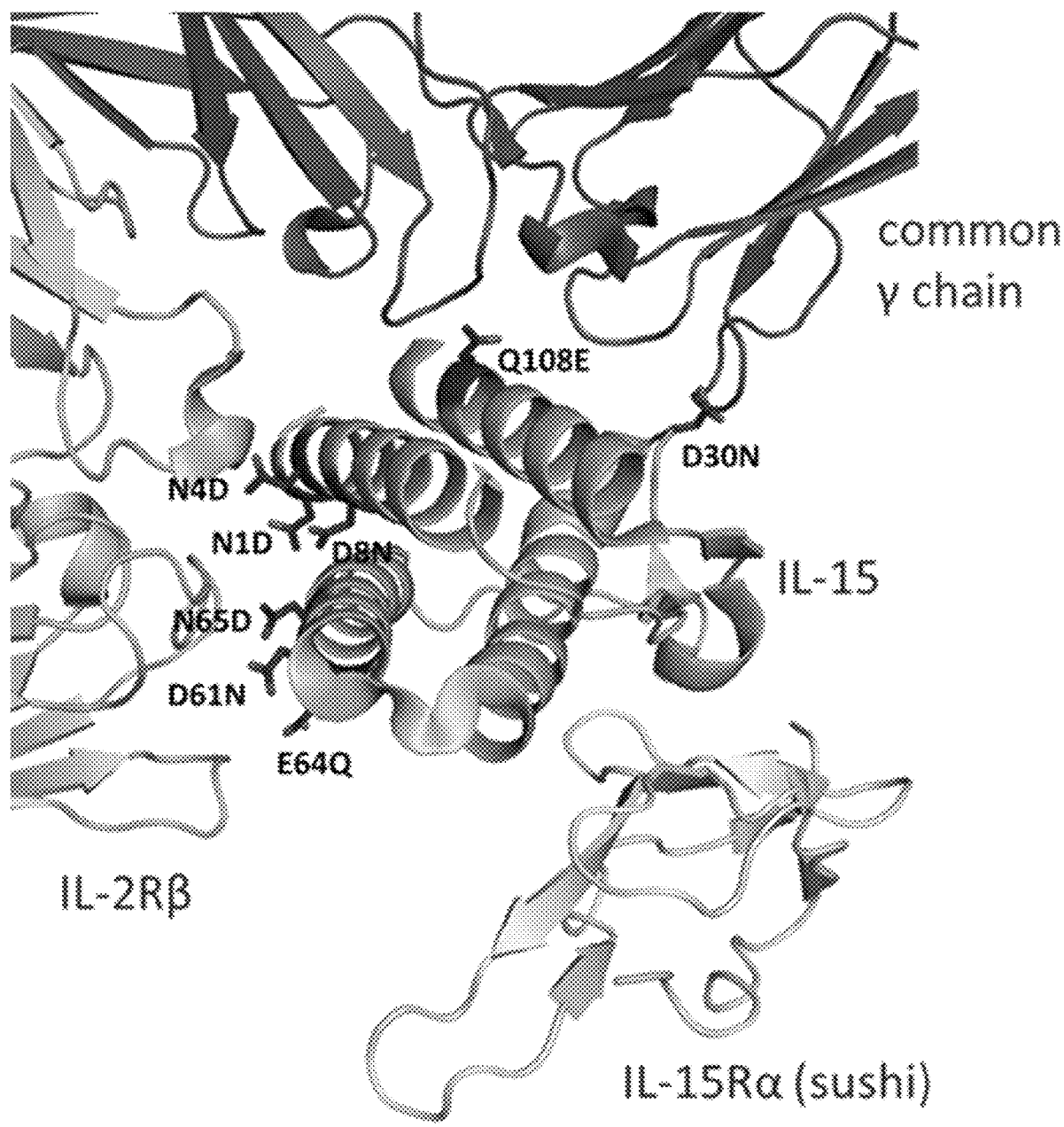

FIG. 18 depicts the structure of IL-15 complexed with IL-15Rα, IL-2Rβ, and common gamma chain. Locations of substitutions designed to reduce potency are shown.

FIG. 19A-19C depicts sequences for illustrative IL-15 variants engineered for reduced potency. Included within each of these variant IL-15 sequences are sequences that are 90, 95, 98 and 99% identical (as defined herein) to the recited sequences, and/or contain from 1, 2, 3, 4, 5, 6, 7, 8, 9 or 10 additional amino acid substitutions. In a non-limiting example, the recited sequences may contain additional amino acid modifications such as those contributing to formation of covalent disulfide bonds as shown in FIG. 16 and FIG. 17.

FIG. 20 depicts EC50 for induction of NK and CD8$^+$ T cells proliferation by variant IL-15/Rα-Fc fusion proteins, and fold reduction in EC50 relative to XENP20818, the wild type. These fusion proteins do not contain a TIM-3 ABD.

FIGS. 21A-21K depict several formats for the TIM-3-targeting IL-15/Rα-Fc fusion proteins of the present invention. The "scIL-15/RαxscFv" format (FIG. 21A) comprises IL-15Rα(sushi) fused to IL-15 by a variable length linker (termed "scIL-15/Rα") which is then fused to the N-terminus of a heterodimeric Fc-region, with an scFv fused to the other side of the heterodimeric Fc. The "scFvxncIL-15/Rα" format (FIG. 21B) comprises an scFv fused to the N-terminus of a heterodimeric Fc-region, with IL-15Rα(sushi) fused to the other side of the heterodimeric Fc, while IL-15 is transfected separately so that a non-covalent IL-15/Rα complex is formed. The "scFvxdsIL-15/Rα" format (FIG. 21C) is the same as the "scFvxncIL-15/Rα" format, but wherein IL-15Rα(sushi) and IL-15 are covalently linked as a result of engineered cysteines. The "scIL-15/RαxFab" format (FIG. 21D) comprises IL-15Rα(sushi) fused to IL-15 by a variable length linker (termed "scIL-15/Rα") which is then fused to the N-terminus of a heterodimeric Fc-region, with a variable heavy chain (VH) fused to the other side of the heterodimeric Fc, while a corresponding light chain is transfected separately so as to form a Fab with the VH. The "ncIL-15/RαxFab" format (FIG. 21E) comprises a VH fused to the N-terminus of a heterodimeric Fc-region, with IL-15Rα(sushi) fused to the other side of the heterodimeric Fc, while a corresponding light chain is transfected separately so as to form a Fab with the VH, and while IL-15 is transfected separately so that a non-covalent IL-15/Rα complex is formed. The "dsIL-15/RαxFab" format (FIG. 21F) is the same as the "ncIL-15/RαxFab" format, but wherein IL-15Rα(sushi) and IL-15 are covalently linked as a result of engineered cysteines. The "mAb-scIL-15/Rα" format (FIG. 21G) comprises VH fused to the N-terminus of a first and a second heterodimeric Fc, with IL-15 is fused to IL-15Rα(sushi) which is then further fused to the C-terminus of one of the heterodimeric Fc-region, while corresponding light chains are transfected separately so as to form a Fabs with the VHs. The "mAb-ncIL-15/Rα" format (FIG. 21H) comprises VH fused to the N-terminus of a first and a second heterodimeric Fc, with IL-15Rα(sushi) fused to the C-terminus of one of the heterodimeric Fc-region, while corresponding light chains are transfected separately so as to form a Fabs with the VHs, and while and while IL-15 is transfected separately so that a non-covalent IL-15/Rα complex is formed. The "mAb-dsIL-15/Rα" format (FIG. 21I) is the same as the "mAb-ncIL-15/Rα" format, but wherein IL-15Rα(sushi) and IL-15 are covalently linked as a result of engineered cysteines. The "central-IL-15/Rα" format (FIG. 21J) comprises a VH recombinantly fused to the N-terminus of IL-15 which is then further fused to one side of a heterodimeric Fc and a VH recombinantly fused to the N-terminus of IL-15Rα(sushi) which is then further fused to the other side of the heterodimeric Fc, while corresponding light chains are transfected separately so as to form a Fabs with the VHs. The "central-scIL-15/Rα" format (FIG. 21K) comprises a VH fused to the N-terminus of IL-15Rα(sushi) which is fused to IL-15 which is then further fused to one side of a heterodimeric Fc and a VH fused to the other side of the heterodimeric Fc, while corresponding light chains are transfected separately so as to form a Fabs with the VHs.

FIG. 22 depicts sequences of XENP27974, an illustrative TIM-3-targeting IL-15/Rα-Fc fusion protein of the "scIL-15/RαxFab" format. The CDRs are in bold. As noted herein and is true for every sequence herein containing CDRs, the exact identification of the CDR locations may be slightly different depending on the numbering used as is shown in Table 2, and thus included herein are not only the CDRs that are underlined but also CDRs included within the $V_H$ and $V_L$ domains using other numbering systems. IL-15 and IL-15Rα(sushi) are underlined, linkers are double underlined (although as will be appreciated by those in the art, the linkers can be replaced by other linkers, some of which are depicted in the Figures, and slashes (/) indicate the border(s) between IL-15, IL-15Rα, linkers, variable regions, and constant/Fc regions.

FIG. 23 depicts the sequences for XENP16432, a bivalent anti-PD-1 mAb with an ablation variant (E233P/L234V/L235A/G236del/S267K, "IgG1_PVA_/S267k"). The CDRs are underlined. As noted herein and is true for every sequence herein containing CDRs, the exact identification of the CDR locations may be slightly different depending on the numbering used as is shown in Table 2, and thus included herein are not only the CDRs that are underlined but also CDRs included within the $V_H$ and $V_L$ domains using other numbering systems.

Figure 24A:
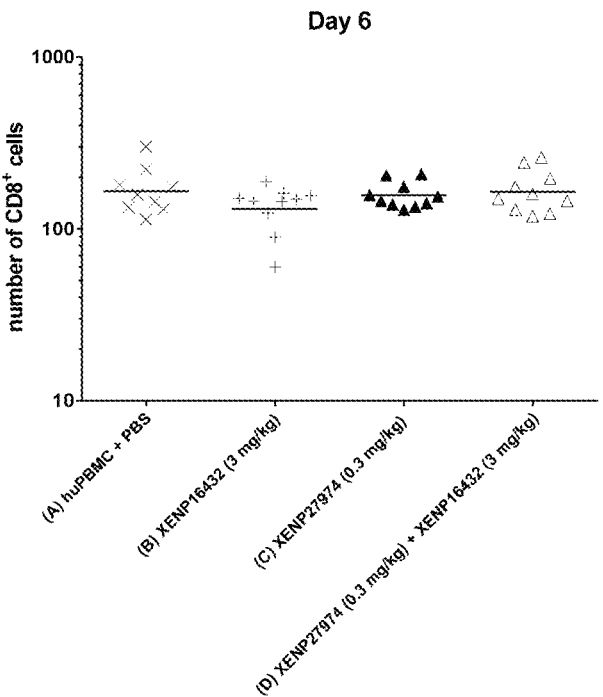
Figure 24B:
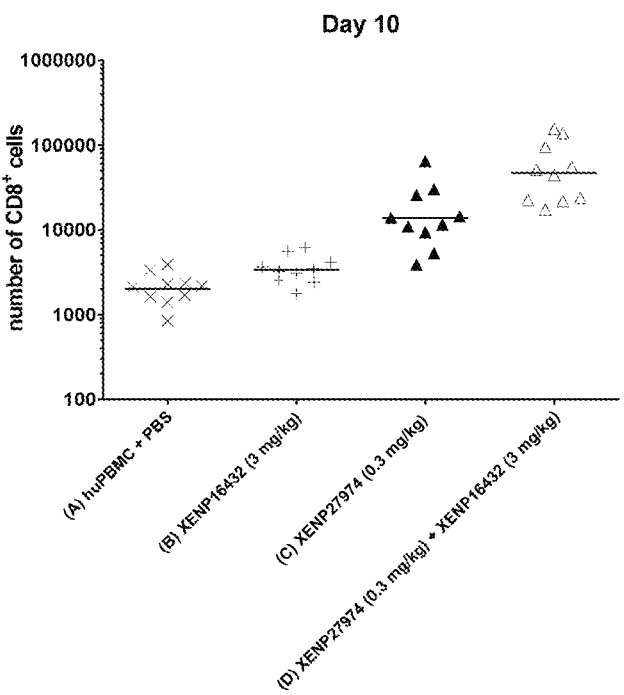

FIGS. 24A-24B depict CD8+ T cell counts in whole blood of PBMC-engrafted NSG mice on Days A) 6 and B) 10 after first dose of the indicated test articles.

Figure 25A:
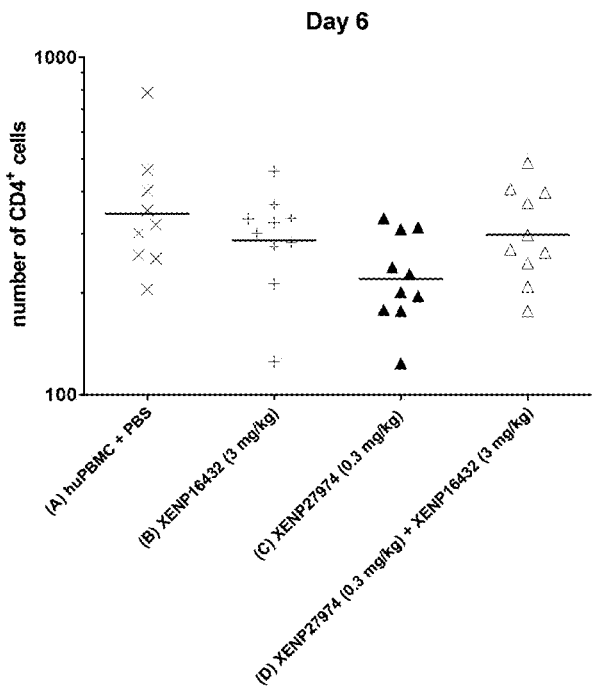
Figure 25B:
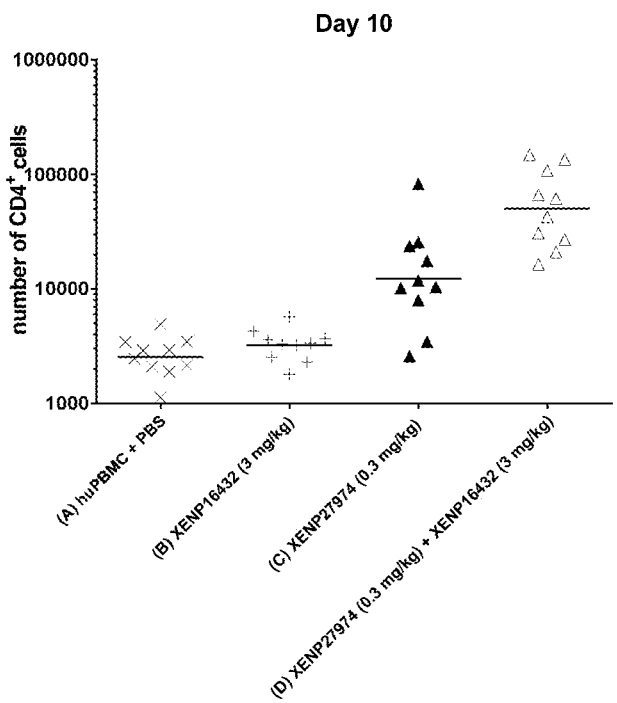

FIGS. 25A-25B depict CD4+ T cell counts in whole blood of PBMC-engrafted NSG mice on Days A) 6 and B) 10 after first dose of the indicated test articles.

Figure 26A:
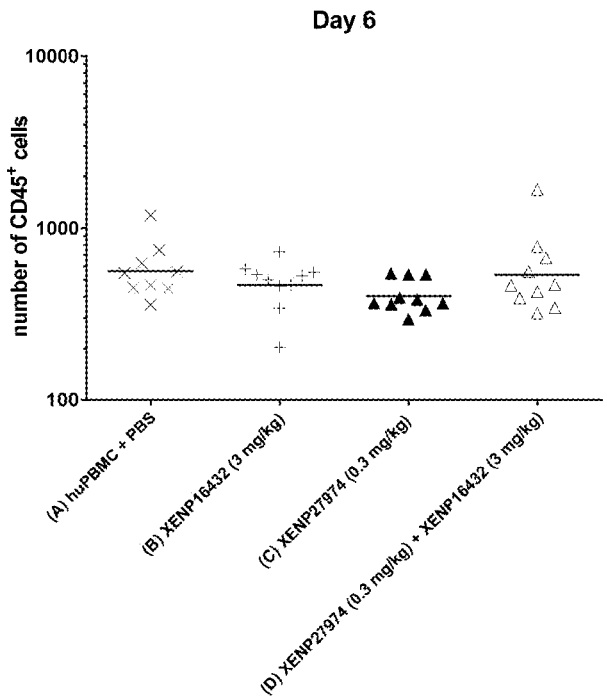
Figure 26B:
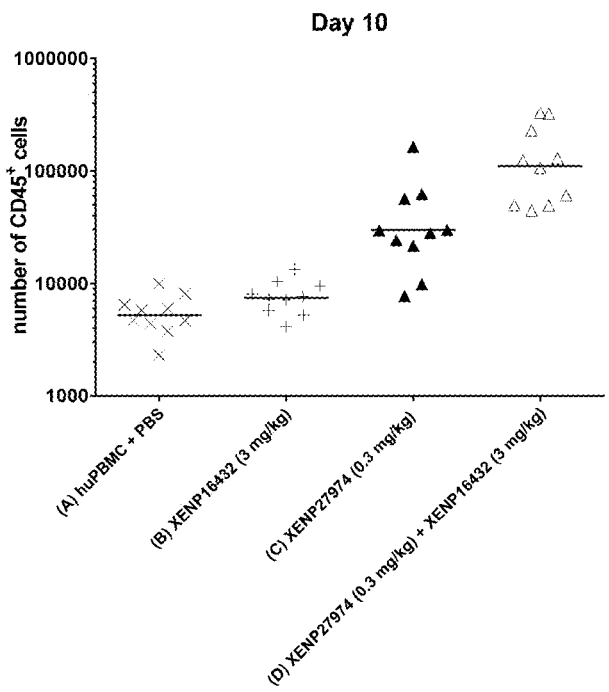

FIGS. 26A-26B depict CD45+ T cell counts in whole blood of PBMC-engrafted NSG mice on Days A) 6 and B) 10 after first dose of the indicated test articles.

Figure 27A:
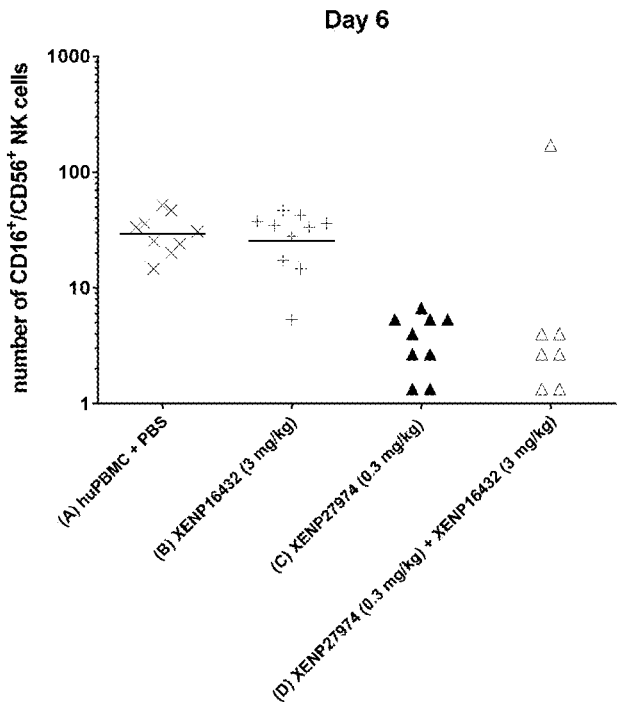
Figure 27B:
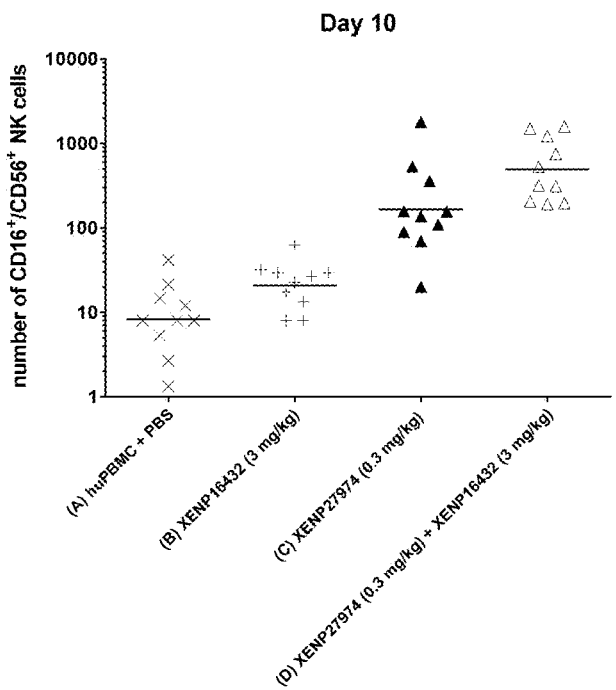

FIGS. 27A-27B depict CD16+CD56+ NK cell counts in whole blood of PBMC-engrafted NSG mice on Days A) 6 and B) 10 after first dose of the indicated test articles.

Figure 28:
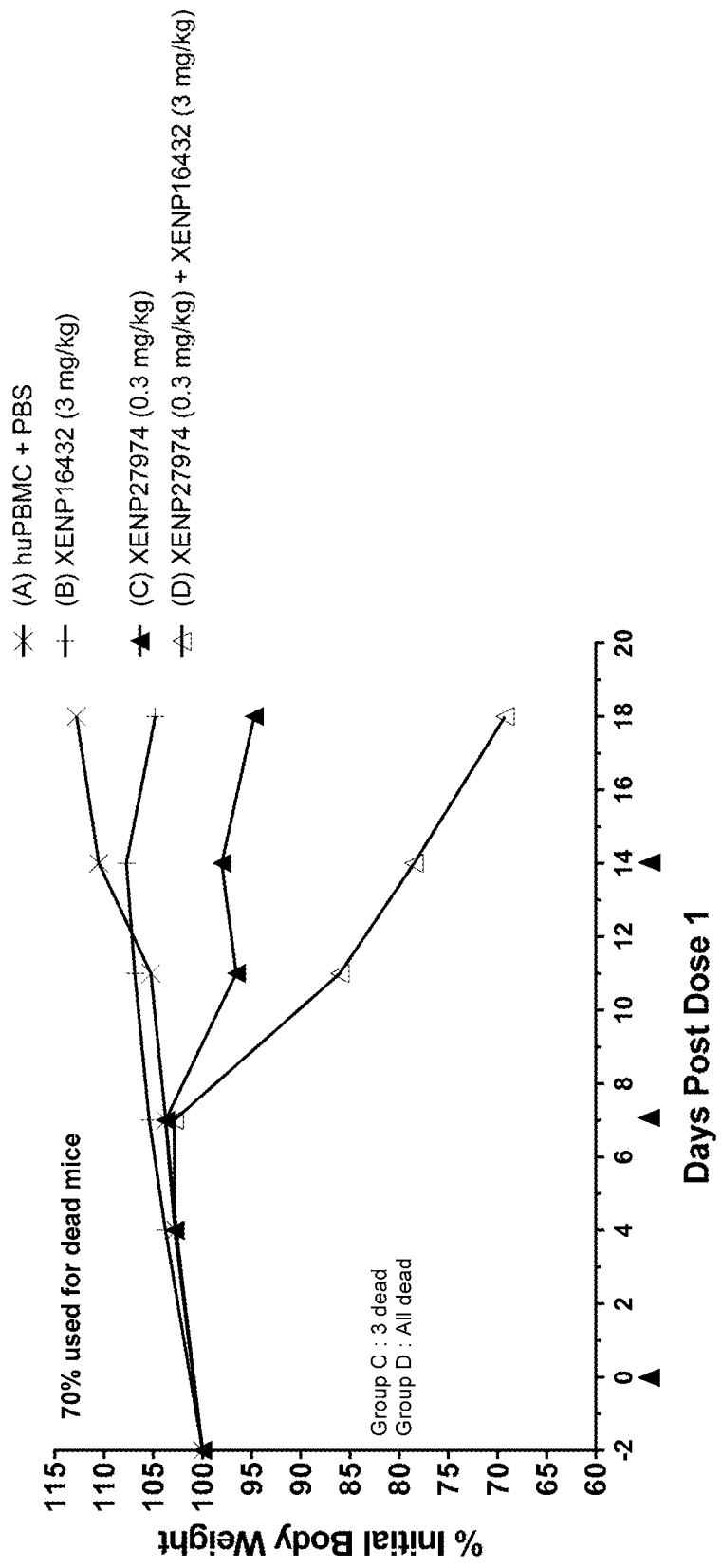

FIG. 28 depicts the change in body weight (as percentage of initial body weight) of PBMC-engrafted NSG mice after dosing with the indicated test articles.

FIG. 29 depicts the sequence of XENP27979 that include M428L/N434S variants in both Fc domains.

FIG. 30 depicts induction of A) CD8+ T cells and B) CD4+ T cells proliferation by TIM-3-targeted IL-15/Rα-Fc fusions (and controls) as indicated by percentage proliferating cells (determined based on CFSE dilution). The data show that the TIM-3-targeted IL-15/Rα-Fc fusion is more potent in inducing proliferation of both CD8+ and CD4+ T cells in comparison to untargeted IL-15(D30N/E64Q/N65D)/Rα-Fc fusion (as well as control RSV-targeted IL-15/Rα-Fc fusion).

FIG. 31 depicts induction of A) CD8 memory T cell and B) CD8 naive T cell proliferation by TIM-3-targeted IL-15/Rα-Fc fusions (and controls) as indicated by percentage proliferating cells (determined based on CFSE dilution). The data show that the TIM-3-targeted IL-15/Rα-Fc fusion is much more potent in inducing proliferation of CD8 memory T cells in comparison to untargeted IL-15(D30N/E64Q/N65D)/Rα-Fc fusion (as well as control RSV-targeted IL-15/Rα-Fc fusion). Notably, the TIM-3-targeted IL-15/Rα-Fc fusion is also more potent in inducing proliferation of CD8 memory T cells in comparison to CD8 naive T cells.

FIG. 32 depicts induction of A) CD8 memory T cell and B) CD8 naive T cell proliferation by TIM-3-targeted IL-15/Rα-Fc fusions (and controls) as indicated by cell counts.

FIG. 33 depicts induction of A) CD4 memory T cell and B) CD4 naive T cell proliferation by TIM-3-targeted IL-15/Rα-Fc fusions (and controls) as indicated by percentage proliferating cells (determined based on CFSE dilution). The data show that the TIM-3-targeted IL-15/Rα-Fc fusion is much more potent in inducing proliferation of CD4 memory T cells in comparison to untargeted IL-15(D30N/E64Q/N65D)/Rα-Fc fusion (as well as control RSV-targeted IL-15/Rα-Fc fusion). Notably, the TIM-3-targeted IL-15/Rα-Fc fusion is also more potent in inducing proliferation of CD4 memory T cells in comparison to CD4 naive T cells.

Figure 34:
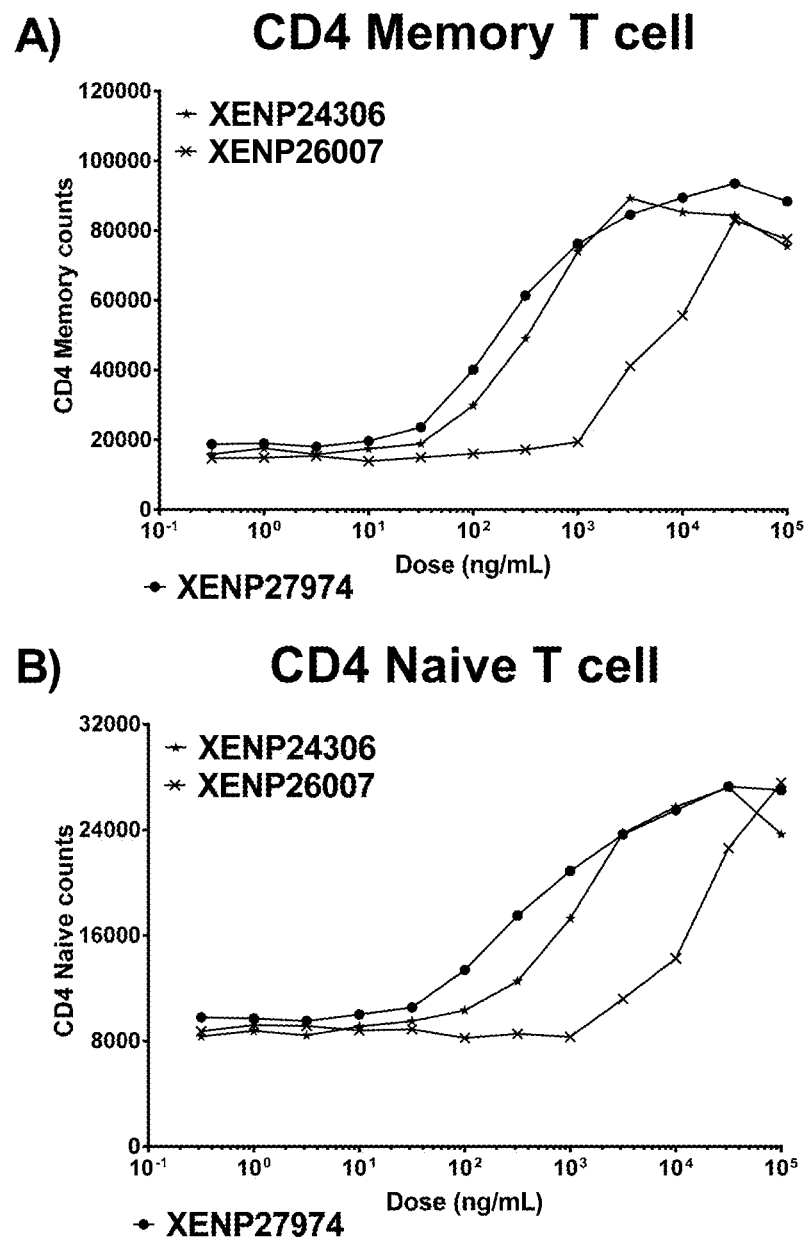

FIG. 34 depicts induction of A) CD4 memory T cell and B) CD4 naive T cell proliferation by TIM-3-targeted IL-15/Rα-Fc fusions (and controls) as indicated by cell counts.

Figure 35:
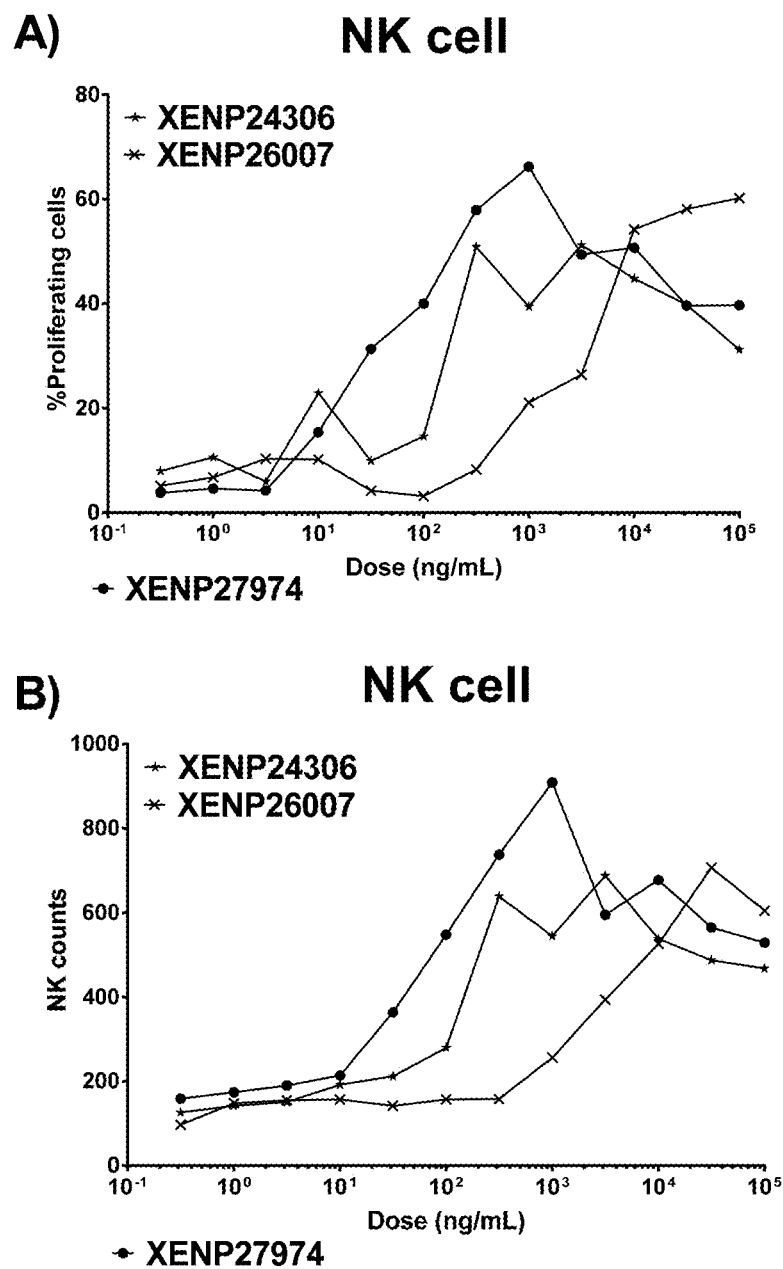

FIG. 35 depicts induction of NK cells proliferation by TIM-3-targeted IL-15/Rα-Fc fusions (and controls) as indicated A) percentage proliferating cells (determined based on CFSE dilution) and B) by cell counts. The data show that TIM-3-targeted IL-15/Rα-Fc fusions are much more potent in inducing proliferation of NK cells in comparison to untargeted IL-15(D30N/E64Q/N65D)/Rα-Fc fusion (as well as control RSV-targeted IL-15/Rα-Fc fusion).

Figure 36:
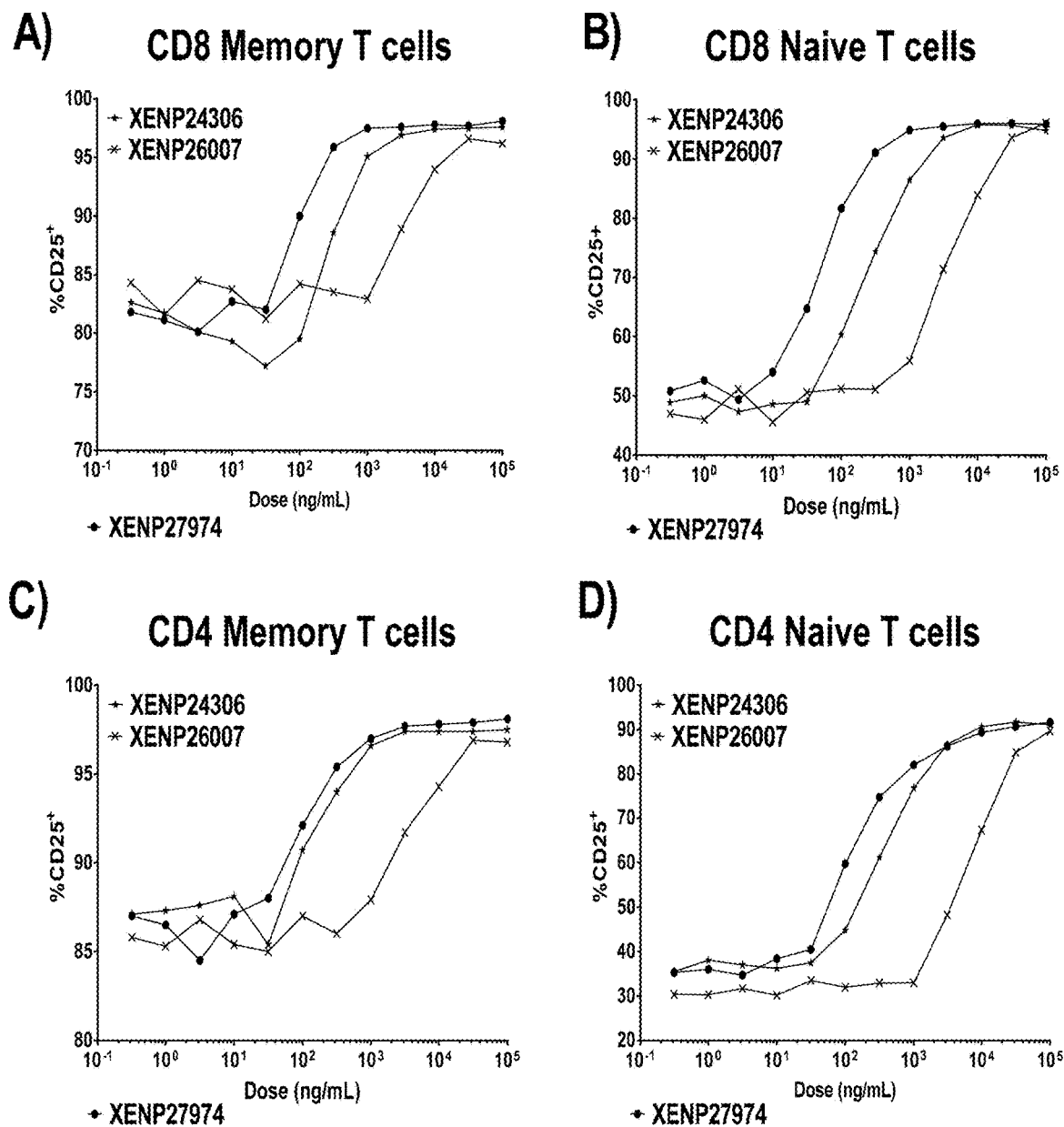

FIG. 36 depicts activation of CD8+ T cells as indicated by A) percentage CD8 memory T cells expressing CD25, B) percentage CD8 naive T cells expressing CD25, C) percentage CD4 memory T cells expressing CD25, and D) percentage CD4 naive T cells expressing CD25 following incubation with TIM-3-targeted IL-15/Rα-Fc fusions (and controls). The data show that TIM-3-targeted IL-15/Rα-Fc fusions appear to upregulate CD25 in CD8 memory and naive T cells more potently in comparison to untargeted IL-15(D30N/E64Q/N65D)/Rα-Fc fusion (as well as control RSV-targeted IL-15/Rα-Fc fusion).

Figure 37:
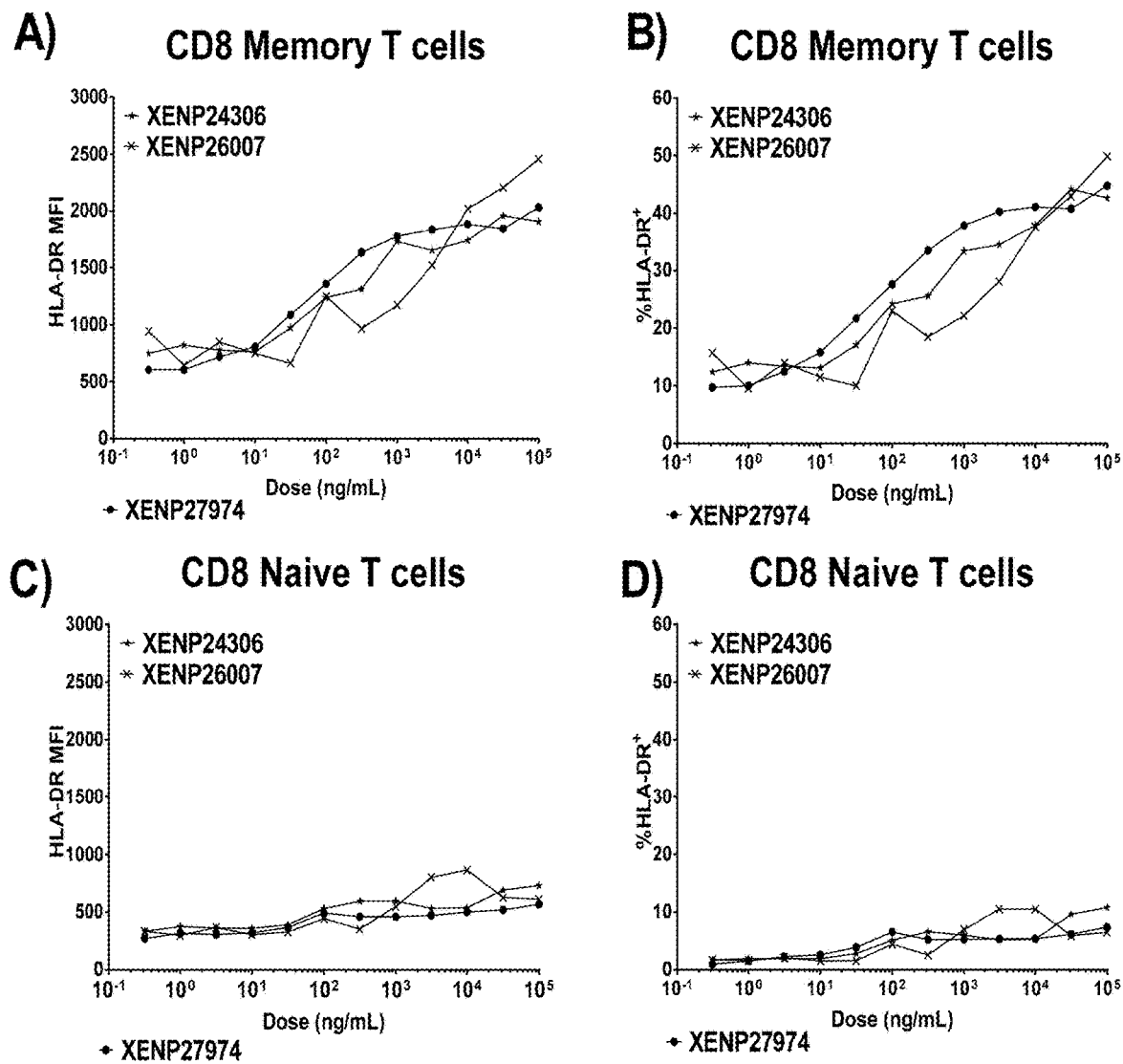

FIG. 37 depicts activation of CD8+ T cells as indicated by A) HLA-DR MFI on CD8 memory T cells, B) percentage CD8 memory T cells expressing HLA-DR, C) HLA-DR MFI on CD8 naive T cells, and D) percentage CD8 naive T cells expressing HLA-DR following incubation with TIM-3-targeted IL-15/Rα-Fc fusions (and controls).

Figure 38:
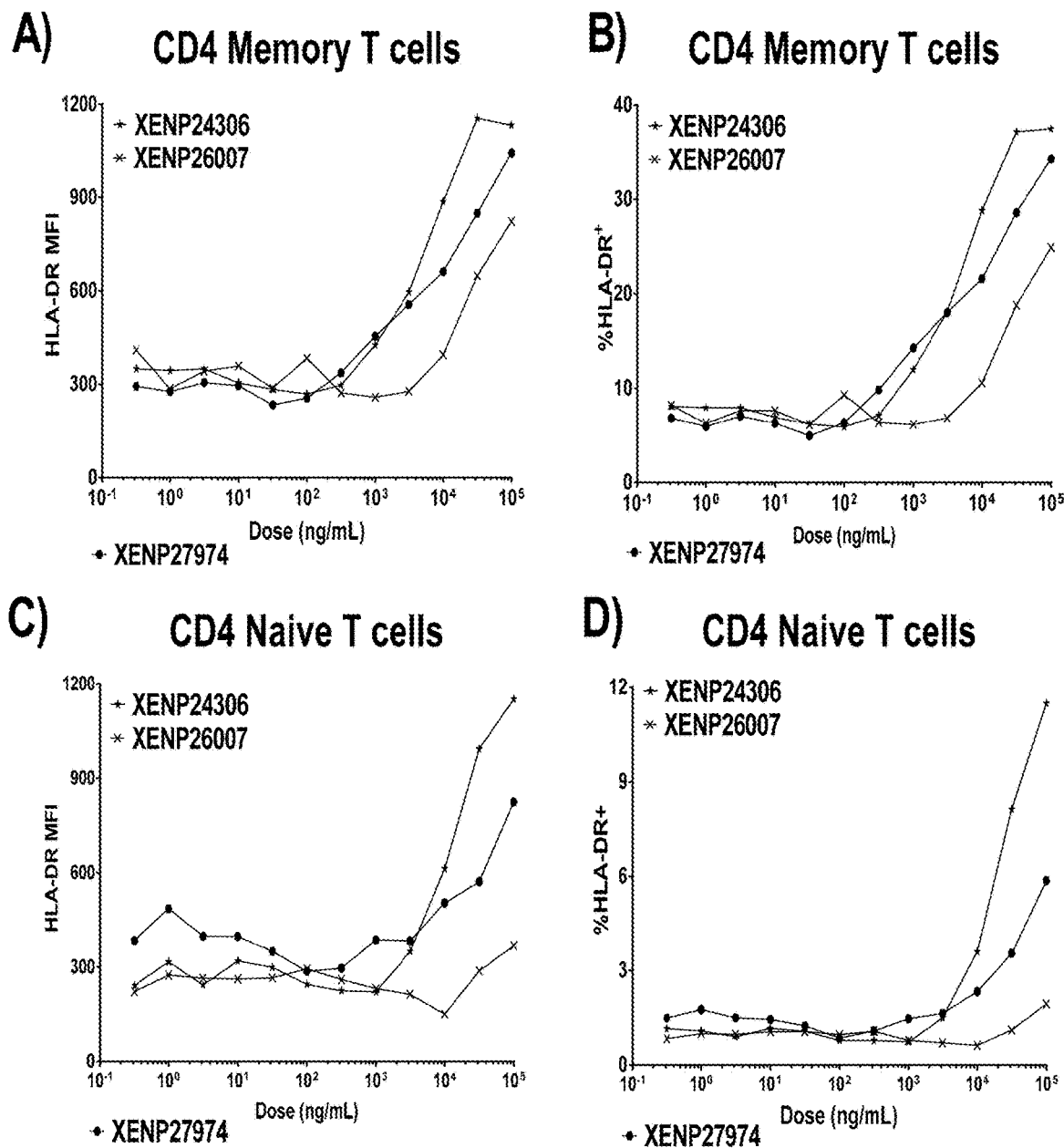

FIG. 38 depicts activation of CD4+ T cells as indicated by A) HLA-DR MFI on CD4 memory T cells, B) percentage CD4 memory T cells expressing HLA-DR, C) HLA-DR MFI on CD4 naive T cells, and D) percentage CD4 naive T cells expressing HLA-DR following incubation with TIM-3-targeted IL-15/Rα-Fc fusions (and controls).

FIG. 39 depicts the sequences of XENP22853, an IL-15/Rα-heteroFc fusion comprising a wild-type IL-15 and Xtend Fc (M428L/N434S) variant. IL-15 and IL-15Rα(sushi) are underlined, linkers are double underlined (although as will be appreciated by those in the art, the linkers can be replaced by other linkers, some of which are depicted in the Figures, and slashes (/) indicate the border(s) between IL-15, IL-15Rα, linkers, and constant/Fc regions.

FIG. 40 depicts the sequences of XENP24113, an IL-15/Rα-heteroFc fusion comprising a IL-15(N4D/N65D) variant and Xtend Fc (M428L/N434S) variant. IL-15 and IL-15Rα (sushi) are underlined, linkers are double underlined (although as will be appreciated by those in the art, the linkers can be replaced by other linkers, some of which are depicted in the Figures, and slashes (/) indicate the border(s) between IL-15, IL-15Rα, linkers, and constant/Fc regions.

FIG. 41 depicts the sequences of XENP24294, an scIL-15/Rα-Fc fusion comprising a IL-15(N4D/N65D) variant and Xtend Fc (M428L/N434S) substitution. IL-15 and IL-15Rα(sushi) are underlined, linkers are double underlined (although as will be appreciated by those in the art, the linkers can be replaced by other linkers, some of which are depicted in the Figures, and slashes (/) indicate the border(s) between IL-15, IL-15Rα, linkers, and constant/Fc regions.

FIG. 42 depicts the sequences of XENP24306, an IL-15/Rα-heteroFc fusion comprising a IL-15(D30N/E64Q/N65D) variant and Xtend Fc (M428L/N434S) substitution. IL-15 and IL-15Rα(sushi) are underlined, linkers are double underlined (although as will be appreciated by those in the art, the linkers can be replaced by other linkers, some of which are depicted in the Figures, and slashes (/) indicate the border(s) between IL-15, IL-15Rα, linkers, and constant/Fc regions.

Figure 43:
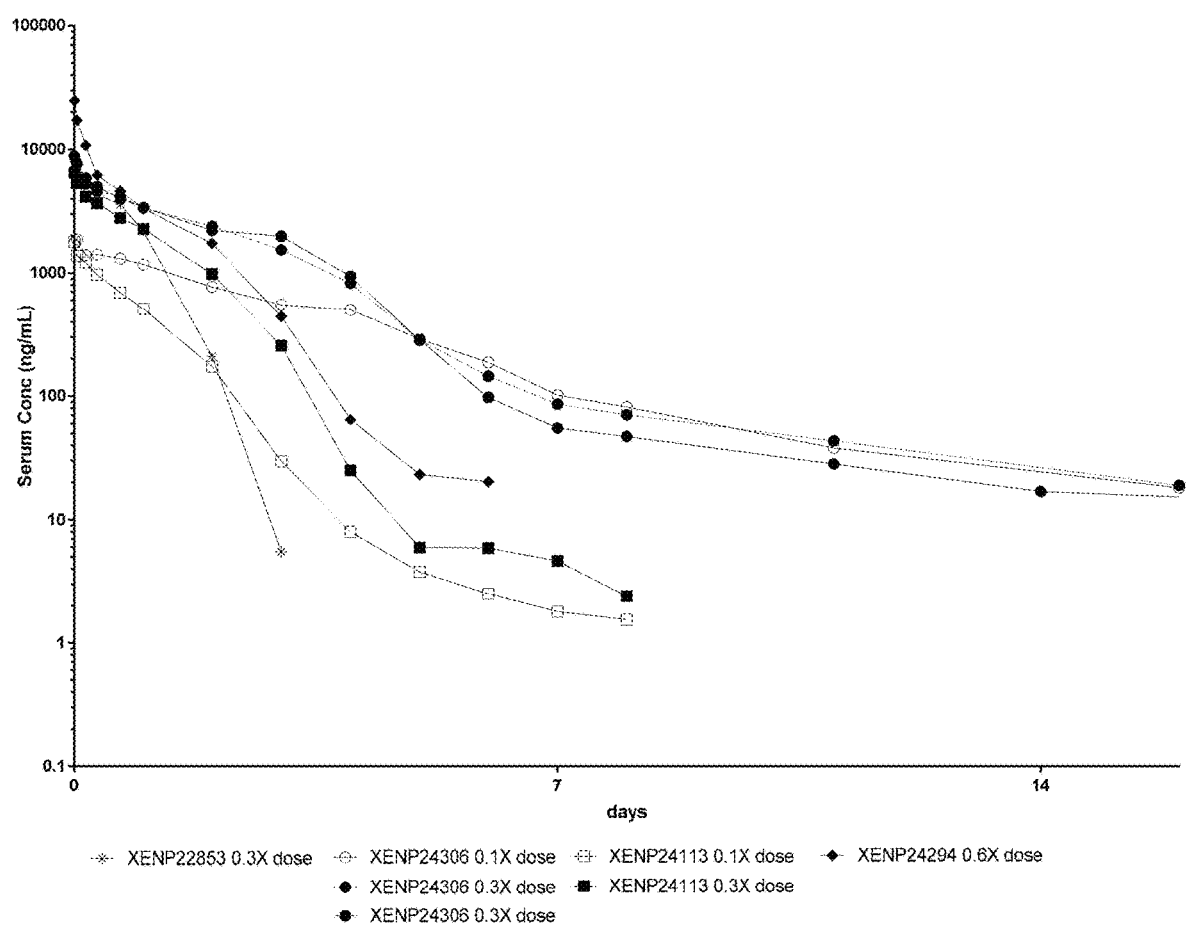
Figure 45A:
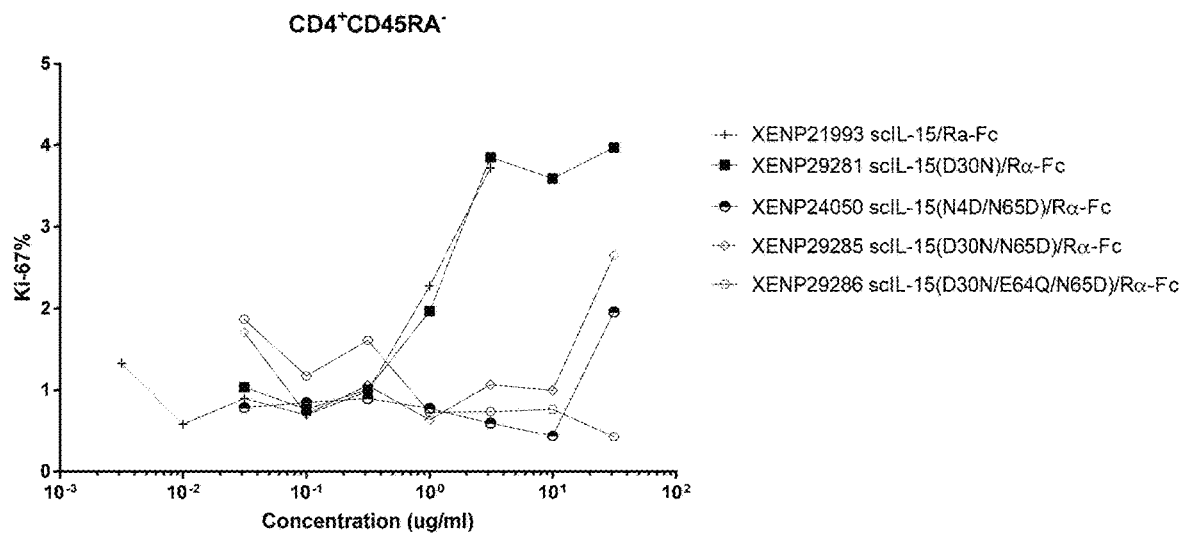
Figure 45B:
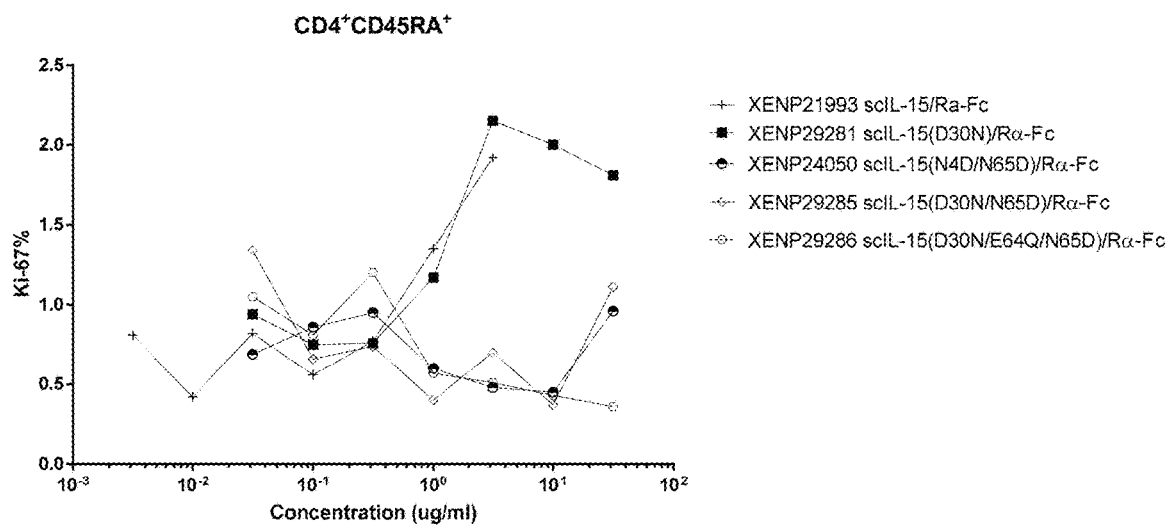
Figure 45C:
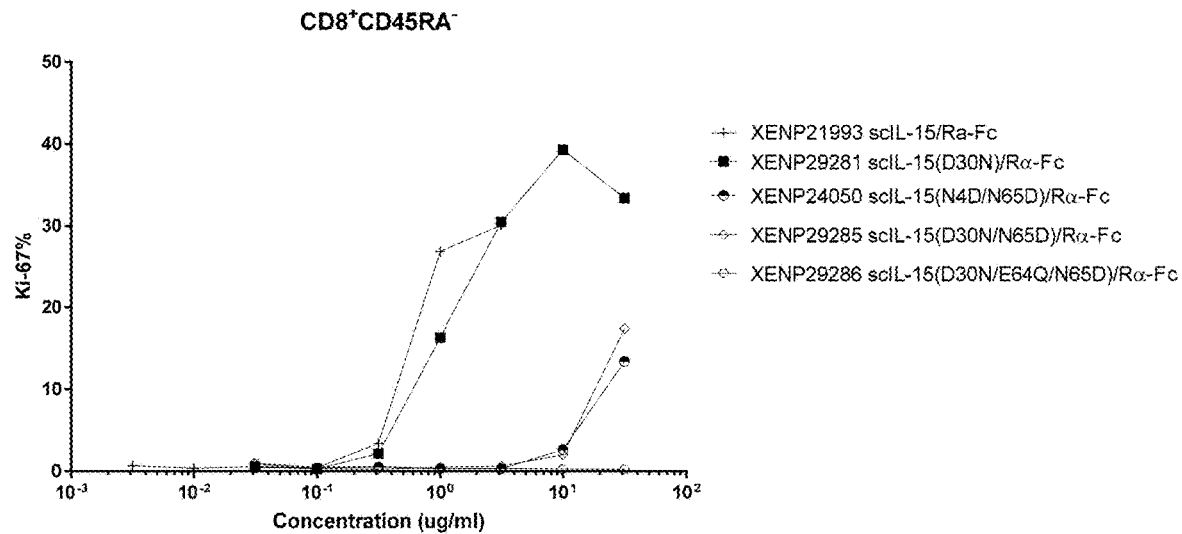
Figure 45D:
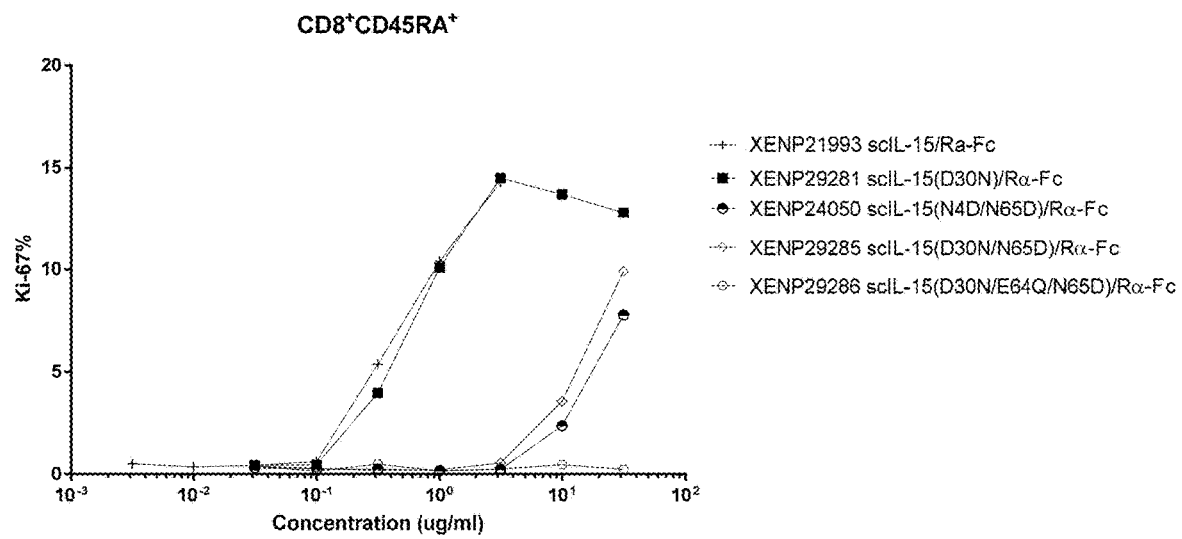
Figure 45E:
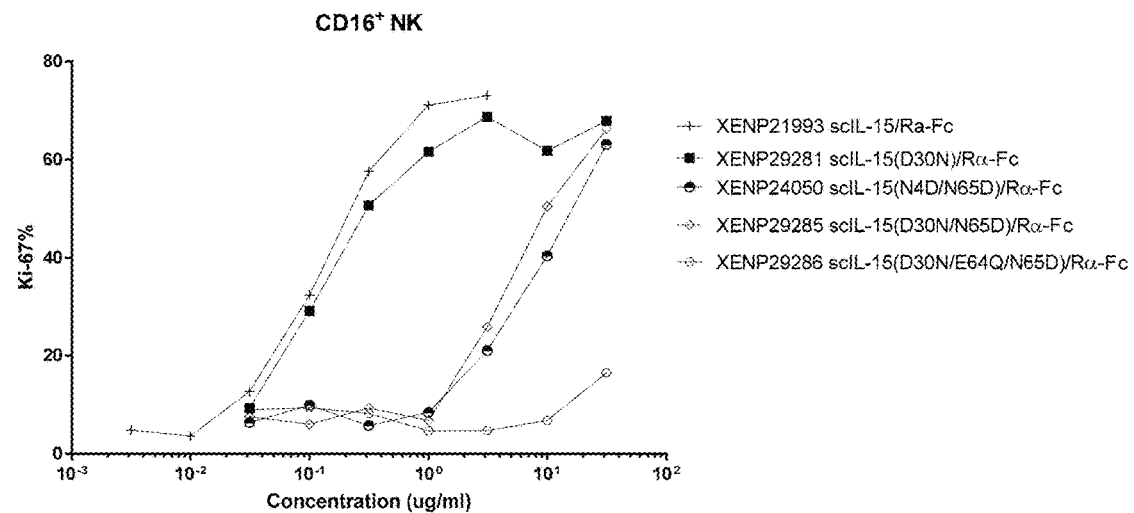
Figure 45F:
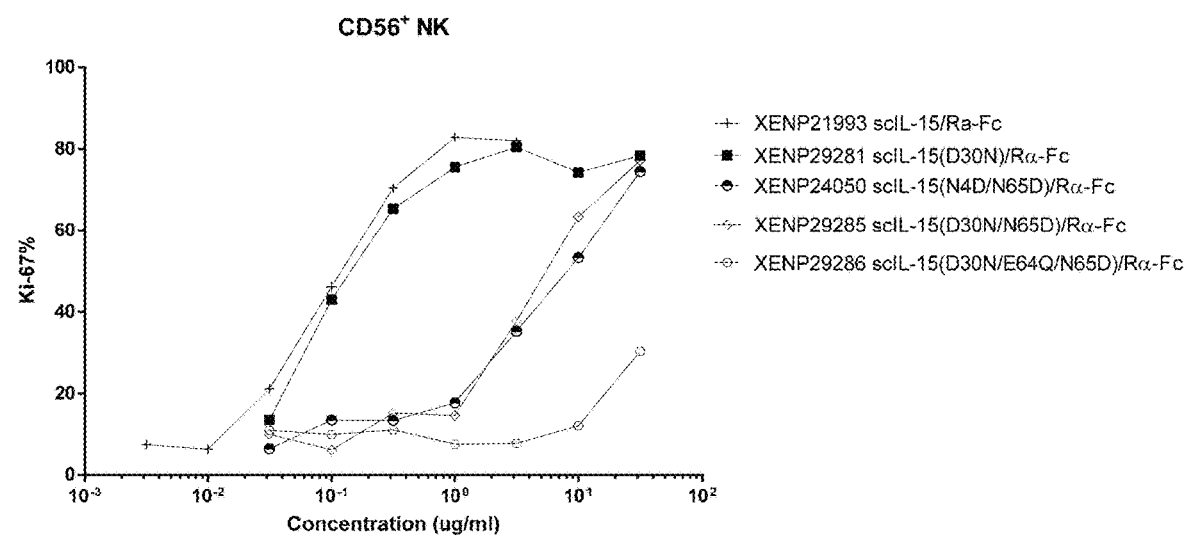
Figure 45G:
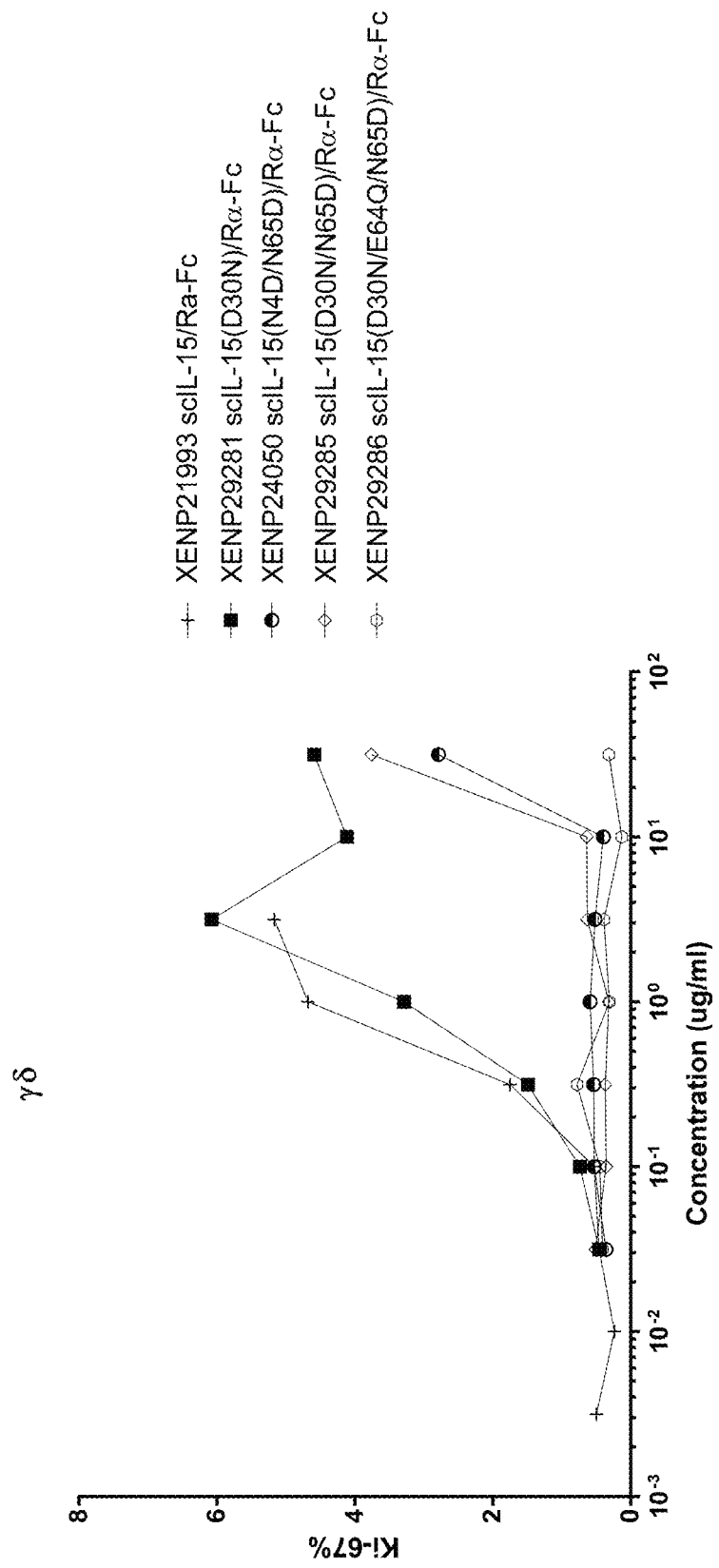

FIG. 43 depicts the serum concentration of the indicated test articles over time in cynomolgus monkeys following a first dose at the indicated relative concentrations.

FIG. 44A-FIG. 44C depict sequences of illustrative scIL-15/Rα-Fc fusions comprising additional IL-15 potency variants. IL-15 and IL-15Rα(sushi) are underlined, linkers are double underlined (although as will be appreciated by those in the art, the linkers can be replaced by other linkers, some of which are depicted in Figures some of which are depicted in FIGS. 9 and 10), and slashes (/) indicate the border(s) between IL-15, IL-15Rα, linkers, variable regions, and constant/Fc regions.

FIG. 45 depicts percentage of A) CD4+CD45RA−, B) CD4+CD45RA+, C) CD8+CD45RA−, D) CD8+CD45RA+, E) CD16+NK cells, F) CD56+NK cells, and G) γδ cells expression Ki67 following incubation of PBMCs with the indicated test articles for 3 days.

FIG. 46 depicts sequences of illustrative TIM-3-targeted IL-15/Rα-Fc fusions comprising IL-15(D30N/N65D) variant. The CDRs are in bold. As noted herein and is true for every sequence herein containing CDRs, the exact identification of the CDR locations may be slightly different depending on the numbering used as is shown in Table 2, and thus included herein are not only the CDRs that are underlined but also CDRs included within the VH and VL domains using other numbering systems. IL-15 and IL-15Rα(sushi) are underlined, linkers are double underlined (although as will be appreciated by those in the art, the linkers can be replaced by other linkers, some of which are depicted in FIGS. 9 and 10), and slashes (/) indicate the border(s) between IL-15, IL-15Rα, linkers, variable regions, and constant/Fc regions.

FIG. 47 depicts sequences of illustrative TIM-3-targeted IL-15/Rα-Fc fusions comprising IL-15(D30N/E64Q/N65D) variant. The CDRs are in bold. As noted herein and is true for every sequence herein containing CDRs, the exact identification of the CDR locations may be slightly different depending on the numbering used as is shown in Table 2, and thus included herein are not only the CDRs that are underlined but also CDRs included within the VH and VL domains using other numbering systems. IL-15 and IL-15Rα(sushi) are underlined, linkers are double underlined (although as will be appreciated by those in the art, the linkers can be replaced by other linkers, some of which are depicted in FIGS. 9 and 10), and slashes (/) indicate the border(s) between IL-15, IL-15Rα, linkers, variable regions, and constant/Fc regions.

FIG. 48A and FIG. 48B depict sequences of illustrative TIM-3-targeted IL-15/Rα-Fc fusions comprising Xtend (M428L/N434S) substitutions for enhancing serum half-life. The CDRs are in bold. As noted herein and is true for every sequence herein containing CDRs, the exact identification of the CDR locations may be slightly different depending on the numbering used as is shown in Table 2, and thus included herein are not only the CDRs that are underlined but also CDRs included within the $V_H$ and $V_L$ domains using other numbering systems. IL-15 and IL-15Rα(sushi) are underlined, linkers are double underlined (although as will be appreciated by those in the art, the linkers can be replaced by other linkers, some of which are depicted in FIGS. 9 and 10), and slashes (/) indicate the border(s) between IL-15, IL-15Rα, linkers, variable regions, and constant/Fc regions. It should be noted that any of the sequences depicted herein may include or exclude the M428L/N434S substitutions.

FIG. 49A-49C depicts the sequences of XENP26007, XENP29481, and XENP30432, control RSV-targeted IL-15/Rα-Fc fusions. The CDRs are underlined. As noted herein and is true for every sequence herein containing CDRs, the exact identification of the CDR locations may be slightly different depending on the numbering used as is shown in Table 2, and thus included herein are not only the CDRs that are underlined but also CDRs included within the VH and VL domains using other numbering systems. IL-15 and IL-15Rα(sushi) are italicized, linkers are double underlined (although as will be appreciated by those in the art, the linkers can be replaced by other linkers, some of which are depicted in Figures some of which are depicted in FIGS. 9 and 10), and slashes (/) indicate the border(s) between IL-15, IL-15Rα, linkers, variable regions, and constant/Fc regions.

DETAILED DESCRIPTION OF THE INVENTION

I. Definitions

In order that the application may be more completely understood, several definitions are set forth below. Such definitions are meant to encompass grammatical equivalents.

By "ablation" herein is meant a decrease or removal of activity. Thus for example, "ablating FcγR binding" means the Fc region amino acid variant has less than 50% starting binding as compared to an Fc region not containing the specific variant, with less than 70-80-90-95-98% loss of activity being preferred, and in general, with the activity being below the level of detectable binding in a Biacore assay. Of particular use in the ablation of FcγR binding are those shown in FIG. 6. However, unless otherwise noted, the Fc monomers of the invention retain binding to the FcRn receptor.

By "ADCC" or "antibody dependent cell-mediated cytotoxicity" as used herein is meant the cell-mediated reaction wherein nonspecific cytotoxic cells that express FcγRs recognize bound antibody on a target cell and subsequently cause lysis of the target cell. ADCC is correlated with binding to FcγRIIIa; increased binding to FcγRIIIa leads to an increase in ADCC activity. As is discussed herein, many embodiments of the invention ablate ADCC activity entirely.

By "ADCP" or antibody dependent cell-mediated phagocytosis as used herein is meant the cell-mediated reaction wherein nonspecific cytotoxic cells that express FcγRs recognize bound antibody on a target cell and subsequently cause phagocytosis of the target cell.

By "antigen binding domain" or "ABD" herein is meant a set of six Complementary Determining Regions (CDRs) that, when present as part of a polypeptide sequence, specifically binds a target antigen as discussed herein. Thus, a "TIM-3 antigen binding domain" binds a human TIM-3 antigen as outlined herein. As is known in the art, these CDRs are generally present as a first set of variable heavy CDRs (vhCDRs or $V_H$CDR5) and a second set of variable light CDRs (vlCDRs or $V_L$CDR5), each comprising three CDRs: vhCDR1, vhCDR2, vhCDR3 for the heavy chain and vlCDR1, vlCDR2 and vlCDR3 for the light. The CDRs are present in the variable heavy and variable light domains, respectively, and together form an Fv region. Thus, in some cases, the six CDRs of the antigen binding domain are contributed by a variable heavy and variable light chain. In a "Fab" format, the set of 6 CDRs are contributed by two different polypeptide sequences, the variable heavy domain (VH or vh or $V_H$; containing the vhCDR1, vhCDR2 and vhCDR3) and the variable light domain (VL or vl or $V_L$; containing the vlCDR1, vlCDR2 and vlCDR3), with the C-terminus of the VH domain being attached to the N-terminus of the CH1 domain of the heavy chain and the C-terminus of the VL domain being attached to the N-terminus of the constant light domain (and thus forming the light chain). In a scFv format, the VH and VL domains are covalently attached, generally through the use of a linker as outlined herein, into a single polypeptide sequence, which can be either (starting from the N-terminus) VH-linker-VL or VL-linker-vh, with the former being generally preferred (including optional domain linkers on each side, depending on the format used (e.g., from FIG. 1 of U.S. 62/353,511).

By "modification" herein is meant an amino acid substitution, insertion, and/or deletion in a polypeptide sequence or an alteration to a moiety chemically linked to a protein. For example, a modification may be an altered carbohydrate or PEG structure attached to a protein. By "amino acid modification" herein is meant an amino acid substitution, insertion, and/or deletion in a polypeptide sequence. For clarity, unless otherwise noted, the amino acid modification is always to an amino acid coded for by DNA, e.g., the 20 amino acids that have codons in DNA and RNA.

By "amino acid substitution" or "substitution" herein is meant the replacement of an amino acid at a particular position in a parent polypeptide sequence with a different amino acid. In particular, in some embodiments, the substitution is to an amino acid that is not naturally occurring at the particular position, either not naturally occurring within the organism or in any organism. For example, the substitution E272Y refers to a variant polypeptide, in this case an Fc variant, in which the glutamic acid at position 272 is replaced with tyrosine. For clarity, a protein which has been engineered to change the nucleic acid coding sequence but not change the starting amino acid (for example exchanging CGG (encoding arginine) to CGA (still encoding arginine) to increase host organism expression levels) is not an "amino acid substitution"; that is, despite the creation of a new gene encoding the same protein, if the protein has the same amino acid at the particular position that it started with, it is not an amino acid substitution.

By "amino acid insertion" or "insertion" as used herein is meant the addition of an amino acid sequence at a particular position in a parent polypeptide sequence. For example, −233E or 233E designates an insertion of glutamic acid after position 233 and before position 234. Additionally, −233ADE or A233ADE designates an insertion of AlaAspGlu after position 233 and before position 234.

By "amino acid deletion" or "deletion" as used herein is meant the removal of an amino acid sequence at a particular position in a parent polypeptide sequence. For example, E233- or E233#, E233( ) or E233del designates a deletion of glutamic acid at position 233. Additionally, EDA233- or EDA233# designates a deletion of the sequence GluAspAla that begins at position 233.

By "variant protein" or "protein variant", or "variant" as used herein is meant a protein that differs from that of a parent protein by virtue of at least one amino acid modification. Protein variant may refer to the protein itself, a composition comprising the protein, or the amino sequence that encodes it. Preferably, the protein variant has at least one amino acid modification compared to the parent protein, e.g., from about one to about seventy amino acid modifications, and preferably from about one to about five amino acid modifications compared to the parent. As described below, in some embodiments the parent polypeptide, for example an Fc parent polypeptide, is a human wild type sequence, such as the Fc region from IgG1, IgG2, IgG3 or IgG4. The protein variant sequence herein will preferably possess at least about 80% identity with a parent protein sequence, and most preferably at least about 90% identity, more preferably at least about 95-98-99% identity. Variant protein can refer to the variant protein itself, compositions comprising the protein variant, or the DNA sequence that encodes it.

Accordingly, by "Fc variant" or "variant Fc" as used herein is meant a protein comprising an amino acid modification in an Fc domain. The Fc variants of the present invention are defined according to the amino acid modifications that compose them. Thus, for example, N434S or 434S is an Fc variant with the substitution serine at position 434 relative to the parent Fc polypeptide, wherein the numbering is according to the EU index. Likewise, M428L/N434S defines an Fc variant with the substitutions M428L and N434S relative to the parent Fc polypeptide. The identity of the WT amino acid may be unspecified, in which case the aforementioned variant is referred to as 428L/434S. It is noted that the order in which substitutions are provided is arbitrary, that is to say that, for example, 428L/434S is the same Fc variant as M428L/N434S, and so on. For all positions discussed in the present invention that relate to antibodies, unless otherwise noted, amino acid position numbering is according to the EU index. The EU index or EU index as in Kabat or EU numbering scheme refers to the numbering of the EU antibody (Edelman et al., 1969, Proc Natl Acad Sci USA 63:78-85, hereby entirely incorporated by reference). The modification can be an addition, deletion, or substitution. Substitutions can include naturally occurring amino acids and, in some cases, synthetic amino acids. Examples include U.S. Pat. No. 6,586,207; WO 98/48032;

WO 03/073238; US2004-0214988A1; WO 05/35727A2; WO 05/74524A2; J. W. Chin et al., (2002), Journal of the American Chemical Society 124:9026-9027; J. W. Chin, & P. G. Schultz, (2002), ChemBioChem 11:1135-1137; J. W. Chin, et al., (2002), PICAS United States of America 99:11020-11024; and, L. Wang, & P. G. Schultz, (2002), Chem. 1-10, all entirely incorporated by reference.

As used herein, "protein" herein is meant at least two covalently attached amino acids, which includes proteins, polypeptides, oligopeptides and peptides.

By "residue" as used herein is meant a position in a protein and its associated amino acid identity. For example, Asparagine 297 (also referred to as Asn297 or N297) is a residue at position 297 in the human antibody IgG1.

By "Fab" or "Fab region" as used herein is meant the polypeptide that comprises the VH, CH1, VL, and CL immunoglobulin domains. Fab may refer to this region in isolation, or this region in the context of a full length antibody, antibody fragment or Fab fusion protein.

By "Fv" or "Fv fragment" or "Fv region" as used herein is meant a polypeptide that comprises the VL and VH domains of a single antibody. As will be appreciated by those in the art, these generally are made up of two chains, or can be combined (generally with a linker as discussed herein) to form an scFv.

By "single chain Fv" or "scFv" herein is meant a variable heavy domain covalently attached to a variable light domain, generally using a scFv linker as discussed herein, to form a scFv or scFv domain. A scFv domain can be in either orientation from N- to C-terminus (VH-linker-VL or VL-linker-VH).

By "IgG subclass modification" or "isotype modification" as used herein is meant an amino acid modification that converts one amino acid of one IgG isotype to the corresponding amino acid in a different, aligned IgG isotype. For example, because IgG1 comprises a tyrosine and IgG2 a phenylalanine at EU position 296, a F296Y substitution in IgG2 is considered an IgG subclass modification.

By "non-naturally occurring modification" as used herein is meant an amino acid modification that is not isotypic. For example, because none of the IgGs comprise a serine at position 434, the substitution 434S in IgG1, IgG2, IgG3, or IgG4 (or hybrids thereof) is considered a non-naturally occurring modification.

By "amino acid" and "amino acid identity" as used herein is meant one of the 20 naturally occurring amino acids that are coded for by DNA and RNA.

By "effector function" as used herein is meant a biochemical event that results from the interaction of an antibody Fc region with an Fc receptor or ligand. Effector functions include but are not limited to ADCC, ADCP, and CDC.

By "Fc gamma receptor", "FcγR" or "FcgammaR" as used herein is meant any member of the family of proteins that bind the IgG antibody Fc region and is encoded by an FcγR gene. In humans this family includes but is not limited to FcγRI (CD64), including isoforms FcγRIa, FcγRIb, and FcγRIc; FcγRII (CD32), including isoforms FcγRIIa (including allotypes H131 and R131), FcγRIIb (including FcγRIIb-1 and FcγRIIb-2), and FcγRIIc; and FcγRIII (CD16), including isoforms FcγRIIIa (including allotypes V158 and F158) and FcγRIIIb (including allotypes FcγRIIb-NA1 and FcγRIIb-NA2) (Jefferis et al., 2002, Immunol Lett 82:57-65, entirely incorporated by reference), as well as any undiscovered human FcγRs or FcγR isoforms or allotypes.

By "FcRn" or "neonatal Fc Receptor" as used herein is meant a protein that binds the IgG antibody Fc region and is encoded at least in part by an FcRn gene. As is known in the art, the functional FcRn protein comprises two polypeptides, often referred to as the heavy chain and light chain. The light chain is beta-2-microglobulin and the heavy chain is encoded by the FcRn gene. Unless otherwise noted herein, FcRn or an FcRn protein refers to the complex of FcRn heavy chain with beta-2-microglobulin. A variety of FcRn variants can be used to increase binding to the FcRn receptor, and in some cases, to increase serum half-life. In general, unless otherwise noted, the Fc monomers of the invention retain binding to the FcRn receptor (and, as noted below, can include amino acid variants to increase binding to the FcRn receptor).

By "parent polypeptide" as used herein is meant a starting polypeptide that is subsequently modified to generate a variant. The parent polypeptide may be a naturally occurring polypeptide, or a variant or engineered version of a naturally occurring polypeptide. Parent polypeptide may refer to the polypeptide itself, compositions that comprise the parent polypeptide, or the amino acid sequence that encodes it.

By "Fc" or "Fc region" or "Fc domain" as used herein is meant the polypeptide comprising the constant region of an antibody excluding the first constant region immunoglobulin domain (e.g., CH1) and in some cases, part of the hinge. For IgG, the Fc domain comprises immunoglobulin domains CH2 and CH3 (Cγ2 and Cγ3) and the lower hinge region between CH1 (Cγ1) and CH2 (Cγ2). Thus, in some cases, the Fc domain includes, from N- to C-terminal, CH2-CH3 and hinge-CH2-CH3. In some embodiments, the Fc domain is that from IgG1, IgG2, IgG3 or IgG4, with IgG1 hinge-CH2-CH3 and IgG4 hinge-CH2-CH3 finding particular use in many embodiments. Additionally, in certain embodiments, wherein the Fc domain is a human IgG1 Fc domain, the hinge includes a C220S amino acid substitution. Furthermore, in some embodiments where the Fc domain is a human IgG4 Fc domain, the hinge includes a S228P amino acid substitution. Although the boundaries of the Fc region may vary, the human IgG heavy chain Fc region is usually defined to include residues C226 or P230 to its carboxyl-terminus, wherein the numbering is according to the EU index as in Kabat. Accordingly, "CH" domains in the context of IgG are as follows: "CH1" refers to positions 118-215 according to the EU index as in Kabat. "Hinge" refers to positions 216-230 according to the EU index as in Kabat. "CH2" refers to positions 231-340 according to the EU index as in Kabat, and "CH3" refers to positions 341-447 according to the EU index as in Kabat. Thus, the "Fc domain" includes the —CH2-CH3 domain, and optionally a hinge domain (hinge-CH2-CH3).

As will be appreciated by those in the art, the exact numbering and placement of the heavy constant region domains can be different among different numbering systems. A useful comparison of heavy constant region numbering according to EU and Kabat is as below, see Edelman et al., 1969, Proc Natl Acad Sci USA 63:78-85 and Kabat et al., 1991, Sequences of Proteins of Immunological Interest, 5th Ed., United States Public Health Service, National Institutes of Health, Bethesda, entirely incorporated by reference.

TABLE 1

|  | EU Numbering | Kabat Numbering |
| --- | --- | --- |
| CH1 | 118-215 | 114-223 |
| Hinge | 216-230 | 226-243 |
| CH2 | 231-340 | 244-360 |
| CH3 | 341-447 | 361-478 |

In the embodiments herein, when a scFv or IL-15 complex is attached to an Fc domain, it is the C-terminus of the scFv, IL-15 or IL-15Rα construct that is attached to the Fc domain via a domain linker; for example, a hinge domain as depicted in FIG. 8. In some embodiments, as is more fully described below, amino acid modifications are made to the Fc region, for example to alter binding to one or more FcγR receptors or to the FcRn receptor, and to enable heterodimer formation and purification, as outlined herein.

By "heavy constant region" herein is meant the CH1-hinge-CH2-CH3 portion of an antibody.

By "Fc fusion protein" or "immunoadhesin" herein is meant a protein comprising an Fc region, generally linked (optionally through a linker moiety, as described herein) to a different protein, such as to IL-15 and/or IL-15R, as described herein. In some instances, two Fc fusion proteins can form a homodimeric Fc fusion protein or a heterodimeric fusion protein with the latter being preferred. In some cases, one monomer of the heterodimeric fusion protein comprises an Fc domain alone (e.g., an empty Fc domain) and the other monomer is a Fc fusion, comprising a variant Fc domain and a protein domain, such as a receptor, ligand or other binding partner.

By "position" as used herein is meant a location in the sequence of a protein. Positions may be numbered sequentially, or according to an established format, for example the EU index for antibody numbering.

By "strandedness" in the context of the monomers of the heterodimeric antibodies of the invention herein is meant that, similar to the two strands of DNA that "match", heterodimerization variants are incorporated into each monomer so as to preserve the ability to "match" to form heterodimers. For example, if some pI variants are engineered into monomer A (e.g., making the pI higher) then steric variants that are "charge pairs" that can be utilized as well do not interfere with the pI variants, e.g., the charge variants that make a pI higher are put on the same "strand" or "monomer" to preserve both functionalities. Similarly, for "skew" variants that come in pairs of a set as more fully outlined below, the skilled artisan will consider pI in deciding into which strand or monomer that incorporates one set of the pair will go, such that pI separation is maximized using the pI of the skews as well.

By "target cell" as used herein is meant a cell that expresses the target antigen, in this case, TIM-3.

By "variable region" as used herein is meant the region of an immunoglobulin that comprises one or more Ig domains substantially encoded by any of the Vκ, Vλ, and/or VH genes that make up the kappa, lambda, and heavy chain immunoglobulin genetic loci respectively.

By "wild type or WT" herein is meant an amino acid sequence or a nucleotide sequence that is found in nature, including allelic variations. A WT protein has an amino acid sequence or a nucleotide sequence that has not been intentionally modified.

The TIM-3 targeted heterodimeric proteins of the present invention are generally isolated or recombinant. "Isolated," when used to describe the various polypeptides disclosed herein, means a polypeptide that has been identified and separated and/or recovered from a cell or cell culture from which it was expressed. Ordinarily, an isolated polypeptide will be prepared by at least one purification step. An "isolated protein," refers to a protein which is substantially free of other proteins having different binding specificities. "Recombinant" means the proteins are generated using recombinant nucleic acid techniques in exogeneous host cells.

"Percent (%) amino acid sequence identity" with respect to a protein sequence is defined as the percentage of amino acid residues in a candidate sequence that are identical with the amino acid residues in the specific (parental) sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. One particular program is the ALIGN-2 program outlined at paragraphs [0279] to [0280] of US Pub. No. 20160244525, hereby incorporated by reference.

The degree of identity between an amino acid sequence of the present invention ("invention sequence") and the parental amino acid sequence is calculated as the number of exact matches in an alignment of the two sequences, divided by the length of the "invention sequence," or the length of the parental sequence, whichever is the shortest. The result is expressed in percent identity.

In some embodiments, two or more amino acid sequences are at least 50%, 60%, 70%, 80%, or 90% identical. In some embodiments, two or more amino acid sequences are at least 95%, 97%, 98%, 99%, or even 100% identical.

"Specific binding" or "specifically binds to" or is "specific for" a particular antigen or an epitope (in this case, human TIM-3) means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target.

Specific binding for a particular antigen or an epitope can be exhibited, for example, by an antibody having a KD for an antigen or epitope of at least about $10^{-4}$ M, at least about $10^{-5}$ M, at least about $10^{-6}$ M, at least about $10^{-7}$ M, at least about $10^{-8}$M, at least about $10^{-9}$ M, alternatively at least about $10^{-10}$ M, at least about $10^{-11}$ M, at least about $10^{-12}$M, or greater, where KD refers to a dissociation rate of a particular antibody-antigen interaction. Typically, an antibody that specifically binds an antigen will have a KD that is 20-, 50-, 100-, 500-, 1000-, 5,000-, 10,000- or more times greater for a control molecule relative to the antigen or epitope.

Also, specific binding for a particular antigen or an epitope can be exhibited, for example, by an antibody having a KA or Ka for an antigen or epitope of at least 20-, 50-, 100-, 500-, 1000-, 5,000-, 10,000- or more times greater for the epitope relative to a control, where KA or Ka refers to an association rate of a particular antibody-antigen interaction. Binding affinity is generally measured using a Biacore assay.

II. Introduction

The invention provides heterodimeric fusion proteins that contain an IL-15 complex on one side and an anti-human TIM-3 antigen binding domain on the other. Thus, the heterodimeric fusion proteins of the invention can bind to the checkpoint TIM-3 antigen and can complex with the common gamma chain (γc; CD132) and/or the IL-2 receptor β-chain (IL-2Rβ; CD122). In general, the heterodimeric fusion proteins of the invention have three functional components: an IL-15/IL-15Rα(sushi) component, generally referred to herein as an "IL-15 complex", an anti-TIM-3 ABD component which serves as a "targeting" moiety by bringing the fusion protein to a cell expressing TIM-3, and an Fc component, each of which can take different forms and each of which can be combined with the other components in any configuration.

In general, as is more fully described herein, the fusion proteins of the invention are heterodimeric proteins that are based on the association of antibody Fc domains. That is, by using two different variant Fc domains that have been engineered to favor the formation of heterodimers over homodimers, the heterodimeric proteins are formed. In this case, one of the variant Fc domains is fused to an IL-15/RA complex and the other has a TIM-3 ABD as more fully outlined herein. By including optional pI variants, the heterodimers can be more easily purified away from the homodimers. Additionally, the inclusion of ablation variants eliminates the effector functions of the Fc domains.

A. IL-15/IL-15Rα(Sushi) Domains

As shown in the figures, the IL-15 complex can take several forms. As stated above, the IL-15 protein on its own is less stable than when complexed with the IL-15Rα protein. As is known in the art, the IL-15Rα protein contains a "sushi domain", which is the shortest region of the receptor that retains IL-15 binding activity. Thus, while heterodimeric fusion proteins comprising the entire IL-15Rα protein can be made, preferred embodiments herein include complexes that just use the sushi domain, the sequence of which is shown in the figures.

Accordingly, the IL-15 complex generally comprises the IL-15 protein and the sushi domain of IL IL-15Rα (unless otherwise noted that the full length sequence is used, "IL-15Rα", "IL-15Rα(sushi)", "IL-15RA" and "sushi" are used interchangeably throughout).

Importantly, the IL-15 component is generally engineered to reduce its potency. In many embodiments, the wild-type IL-15 is too potent and can cause undesirable toxicity. Accordingly, the IL-15 component of the IL-15 complex can have one or more amino acid substitutions that result in decreased activity. Various amino acid substitutions were made (see FIG. 19) and tested (see FIG. 20). Of particular interest in some embodiments are a double variant, N4D/N65D or D30N/N65D, or a triple variant, D30N/E64Q/N65D.

The targeted IL-15/IL-15Rα heterodimeric fusion proteins of the present invention include an IL-15/IL-15 receptor alpha (IL-15Rα)-Fc fusion monomer; reference is made to US2018/0118828, filed 16 Oct. 2017, U.S. Ser. No. 62/408,655, filed on Oct. 14, 2016, U.S. Ser. No. 62/416,087, filed on Oct. Nov. 1, 2016, U.S. Ser. No. 62/443,465, filed on Jan. 6, 2017, U.S. Ser. No. 62/477,926, filed on Mar. 28, 2017, and U.S. Ser. No. 62/659,571, filed on Apr. 18, 2018, hereby incorporated by reference in their entirety and in particular for the sequences outlined therein. In some cases, the IL-15 and IL-15 receptor alpha (IL-15Rα) protein domains are in different orientations. Exemplary embodiments of IL-15/IL-15Rα-Fc fusion monomers are provided in XENP21480 (chain 1; FIG. 64A), XENP22022 (chain 1, FIG. 64D), XENP22112, (chains 1 and 3; FIG. 64E), XENP22641 (chains 2 and 4; FIG. 64F), XENP22642, (chains 1 and 4; FIG. 64H) and XENP22644 (chains 1 and 4; FIG. 64I) as described, for example, in US2018/0118828.

1. IL-15 Variants

In some embodiments, the human IL-15 protein has the amino acid sequence set forth in NCBI Ref. Seq. No. NP_000576.1 as shown in FIG. 2. In some cases, the coding sequence of human IL-15 is set forth in NCBI Ref. Seq. No. NM_000585. An exemplary IL-15 protein of the Fc fusion heterodimeric protein outlined herein can have the amino acid sequence of SEQ ID NO:2 or amino acids 49-162 of SEQ ID NO:1. In some embodiments, the IL-15 protein has at least 90%, e.g., 90%, 91%, 92%, 93%, 94%, 95%, 96%, 97%, 98%, 99%, or more sequence identity to SEQ ID NO:2. In some embodiments, the IL-15 protein has the amino acid sequence set forth in SEQ ID NO:2 except with the amino acid substitution N72D. In other embodiments, the IL-15 protein has the amino acid sequence of SEQ ID NO:2 except with one or more amino acid substitutions selected from the group consisting of C42S, L45C, Q48C, V49C, L52C, E53C, E87C, and E89C. In some aspects, the IL-15 protein has one or more amino acid substitutions selected from the group consisting of N1D, N4D, D8N, D30N, D61N, E64Q, N65D, and Q108E. In other embodiments, the amino acid substitutions are N4D/N65D or D30N/N65D. In some embodiments, the amino acid substitution is Q108E. In certain embodiments, the amino acid substitution is N65D. In other embodiments, the amino acid substitutions are D30N/E64Q/N65D. In certain embodiments, the amino acid substitution is N65D. In some instances, the amino acid substitutions are N1D/N65D. In some instances, the amino acid substitutions are D30N/N65D. Optionally, the IL-15 protein also has an N72D substitution. The IL-15 protein of the Fc fusion protein can have 1, 2, 3, 4, 5, 6, 7, 8 or 9 amino acid substitutions. In some embodiments, the IL-15 protein of the Fc fusion protein comprises a D30N substitution. In some embodiments, the IL-15 protein of the Fc fusion protein comprises a N65D substitution. In some embodiments, the IL-15 protein of the Fc fusion contains one or more amino acid substitutions at the IL-15:CD132 interface. In certain embodiments, the Fc fusion protein described herein induces proliferation of NK cells and CD8+ T cells.

In some embodiments, the human IL-15 receptor alpha (IL-15Rα) protein has the amino acid sequence set forth in NCBI Ref. Seq. No. NP_002180.1 or SEQ ID NO:3. In some cases, the coding sequence of human IL-15Rα is set forth in NCBI Ref. Seq. No. NM_002189.3. An exemplary the IL-15Rα protein of the Fc fusion heterodimeric protein outlined herein can comprise or consist of the sushi domain of SEQ ID NO:3 (e.g., amino acids 31-95 of SEQ ID NO:3), or in other words, the amino acid sequence of SEQ ID NO:4. In some embodiments, the IL-15Rα protein has the amino acid sequence of SEQ ID NO:4 and an amino acid insertion selected from the group consisting of D96, P97, A98, D96/P97, D96/C97, D96/P97/A98, D96/P97/C98, and D96/C97/A98, wherein the amino acid position is relative to full-length human IL-15Rα protein or SEQ ID NO:3. For instance, amino acid(s) such as D (e.g., Asp), P (e.g., Pro), A (e.g., Ala), DP (e.g., Asp-Pro), DC (e.g., Asp-Cys), DPA (e.g., Asp-Pro-Ala), DPC (e.g., Asp-Pro-Cys), or DCA (e.g., Asp-Cys-Ala) can be added to the C-terminus of the IL-15Rα protein of SEQ ID NO:4. In some embodiments, the IL-15Rα protein has the amino acid sequence of SEQ ID NO:4 and one or more amino acid substitutions selected from the group consisting of K34C, A37C, G38C, 540C, and L42C, wherein the amino acid position is relative to SEQ ID NO:4. The IL-15Rα protein can have 1, 2, 3, 4, 5, 6, 7, 8 or more amino acid mutations (e.g., substitutions, insertions and/or deletions).

2. IL-15/RA Complexes

As outlined herein, the IL-15 variants and the sushi domain can be complexed in at least three different ways.

Figure 21A:
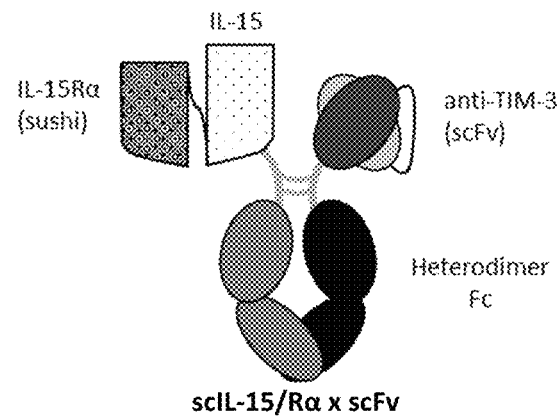
Figure 21B:
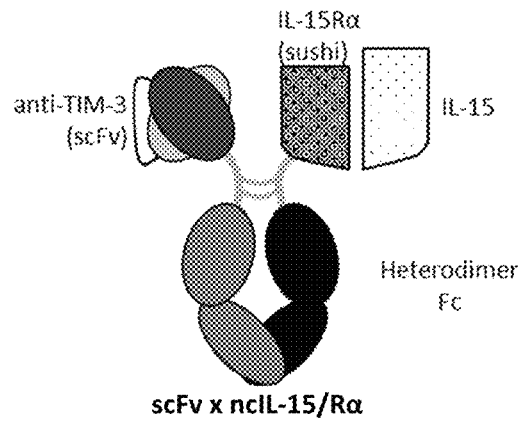

In some embodiments, as shown in FIG. 21B, for example, the IL-15 protein and the IL-15Rα(sushi) are not covalently attached, but rather are self-assembled through regular ligand-ligand interactions. As is more fully described herein, it can be either the IL-15 domain or the sushi domain that is covalently linked to the Fc domain (generally using an optional domain linker). Again, of particular use in this embodiment are a double variant, N4D/N65D or D30N/N65D, or a triple variant, D30N/E64Q/N65D, used with a wild type sushi domain.

Figure 21C:
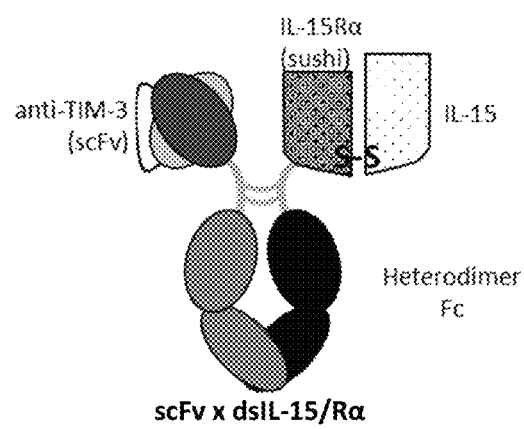
Figure 21D:
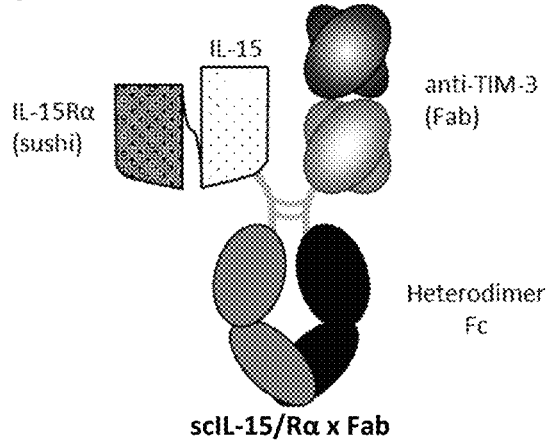

In alternative embodiments, the variant IL-15 can be complexed to the sushi domain using a domain linker, such that they are covalently attached as generally shown in FIG. 21D; this figure depicts the sushi domain as the N-terminal domain, although this can be reversed. Again, of particular use in this embodiment are a double variant, N4D/N65D or D30N/N65D, or a triple variant, D30N/E64Q/N65D, used with a wild type sushi domain.

Alternatively, each of the IL-15 and sushi domains can be engineered to contain a cysteine amino acid, that forms a disulfide bond to form the complex as is generally shown in FIG. 21C, again, with either the IL-15 domain or the sushi domain being covalently attached (using an optional domain linker) to the Fc domain. Again, of particular use in this embodiment are a double variant, N4D/N65D or D30N/N65D (additionally including an amino acid substitution to cysteine), or a triple variant, D30N/E64Q/N65D (additionally including an amino acid substitution to cysteine), used with a sushi domain also comprising an amino acid substitution to provide a cysteine.

Additional particular embodiments are outlined below.

B. Anti-TIM-3 Components

In some embodiments, the heterodimeric fusion proteins provided herein include some antibody components.

Traditional antibody structural units typically comprise a tetramer. Each tetramer is typically composed of two identical pairs of polypeptide chains, each pair having one "light" (typically having a molecular weight of about 25 kDa) and one "heavy" chain (typically having a molecular weight of about 50-70 kDa). Human light chains are classified as kappa and lambda light chains. The present invention is directed to antibodies or antibody fragments (antibody monomers) that generally are based on the IgG class, which has several subclasses, including, but not limited to IgG1, IgG2, IgG3, and IgG4. In general, IgG1, IgG2 and IgG4 are used more frequently than IgG3. It should be noted that IgG1 has different allotypes with polymorphisms at 356 (D or E) and 358 (L or M). The sequences depicted herein use the 356D/358M allotype, however the other allotype is included herein. That is, any sequence inclusive of an IgG1 Fc domain included herein can have 356E/358L replacing the 356D/358M allotype.

In addition, many of the monomer sequences herein have at least one the cysteines at position 220 replaced by a serine, to reduce disulfide formation. Specifically included within the sequences herein are one or both of these cysteines replaced (C220S).

Thus, "isotype" as used herein is meant any of the subclasses of immunoglobulins defined by the chemical and antigenic characteristics of their constant regions.

The amino-terminal portion of each chain includes a variable region of about 100 to 110 or more amino acids primarily responsible for antigen recognition, generally referred to in the art and herein as the "Fv domain" or "Fv region". In the variable region, three loops are gathered for each of the V domains of the heavy chain and light chain to form an antigen-binding site. Each of the loops is referred to as a complementarity-determining region (hereinafter referred to as a "CDR"), in which the variation in the amino acid sequence is most significant. "Variable" refers to the fact that certain segments of the variable region differ extensively in sequence among antibodies. Variability within the variable region is not evenly distributed. Instead, the V regions consist of relatively invariant stretches called framework regions (FRs) of 15-30 amino acids separated by shorter regions of extreme variability called "hypervariable regions" that are each 9-15 amino acids long or longer.

Each VH and VL is composed of three hypervariable regions ("complementary determining regions," "CDRs") and four FRs, arranged from amino-terminus to carboxy-terminus in the following order: FR1-CDR1-FR2-CDR2-FR3-CDR3-FR4.

The hypervariable region generally encompasses amino acid residues from about amino acid residues 24-34 (LCDR1; "L" denotes light chain), 50-56 (LCDR2) and 89-97 (LCDR3) in the light chain variable region and around about 31-35B (HCDR1; "H" denotes heavy chain), 50-65 (HCDR2), and 95-102 (HCDR3) in the heavy chain variable region; Kabat et al., SEQUENCES OF PROTEINS OF IMMUNOLOGICAL INTEREST, 5th Ed. Public Health Service, National Institutes of Health, Bethesda, Md. (1991) and/or those residues forming a hypervariable loop (e.g. residues 26-32 (LCDR1), 50-52 (LCDR2) and 91-96 (LCDR3) in the light chain variable region and 26-32 (HCDR1), 53-55 (HCDR2) and 96-101 (HCDR3) in the heavy chain variable region; Chothia and Lesk (1987) J. Mol. Biol. 196:901-917. Specific CDRs of the invention are described below.

As will be appreciated by those in the art, the exact numbering and placement of the CDRs can be different among different numbering systems. However, it should be understood that the disclosure of a variable heavy and/or variable light sequence includes the disclosure of the associated (inherent) CDRs. Accordingly, the disclosure of each variable heavy region is a disclosure of the vhCDRs (e.g. vhCDR1, vhCDR2 and vhCDR3) and the disclosure of each variable light region is a disclosure of the vlCDRs (e.g. vlCDR1, vlCDR2 and vlCDR3).

A useful comparison of CDR numbering is as below, see Lafranc et al., Dev. Comp. Immunol. 27(1):55-77 (2003):

TABLE 2

| | Kabat + Chothia | IMGT | Kabat | AbM | Chothia | Contact | Xencor |
|---|---|---|---|---|---|---|---|
| vhCDR1 | 26-35 | 27-38 | 31-35 | 26-35 | 26-32 | 30-35 | 27-35 |
| vhCDR2 | 50-65 | 56-65 | 50-65 | 50-58 | 52-56 | 47-58 | 54-61 |
| vhCDR3 | 95-102 | 105-117 | 95-102 | 95-102 | 95-102 | 93-101 | 103-116 |
| vlCDR1 | 24-34 | 27-38 | 24-34 | 24-34 | 24-34 | 30-36 | 27-38 |
| vlCDR2 | 50-56 | 56-65 | 50-56 | 50-56 | 50-56 | 46-55 | 56-62 |
| vlCDR3 | 89-97 | 105-117 | 89-97 | 89-97 | 89-97 | 89-96 | 97-105 |

Throughout the present specification, the Kabat numbering system is generally used when referring to a residue in the variable domain (approximately, residues 1-107 of the light chain variable region and residues 1-113 of the heavy chain variable region) and the EU numbering system for Fc regions (e.g, Kabat et al., supra (1991)).

The present invention provides a large number of different CDR sets. In this case, a "full CDR set" comprises the three variable light and three variable heavy CDRs, e.g. a vlCDR1, vlCDR2, vlCDR3, vhCDR1, vhCDR2 and vhCDR3. These can be part of a larger variable light or variable heavy domain, respectfully. In addition, as more fully outlined herein, the variable heavy and variable light domains can be on separate polypeptide chains, when a heavy and light chain is used (for example when Fabs are used), or on a single polypeptide chain in the case of scFv sequences.

The CDRs contribute to the formation of the antigen-binding, or more specifically, epitope binding site of antibodies. "Epitope" refers to a determinant that interacts with a specific antigen binding site in the variable region of an antibody molecule known as a paratope. Epitopes are groupings of molecules such as amino acids or sugar side chains and usually have specific structural characteristics, as well as specific charge characteristics. A single antigen may have more than one epitope.

The epitope may comprise amino acid residues directly involved in the binding (also called immunodominant component of the epitope) and other amino acid residues, which are not directly involved in the binding, such as amino acid residues which are effectively blocked by the specifically antigen binding peptide; in other words, the amino acid residue is within the footprint of the specifically antigen binding peptide.

Epitopes may be either conformational or linear. A conformational epitope is produced by spatially juxtaposed amino acids from different segments of the linear polypeptide chain. A linear epitope is one produced by adjacent amino acid residues in a polypeptide chain. Conformational and nonconformational epitopes may be distinguished in that the binding to the former but not the latter is lost in the presence of denaturing solvents.

An epitope typically includes at least 3, and more usually, at least 5 or 8-10 amino acids in a unique spatial conformation. Antibodies that recognize the same epitope can be verified in a simple immunoassay showing the ability of one antibody to block the binding of another antibody to a target antigen, for example "binning." As outlined below, the invention not only includes the enumerated antigen binding domains and antibodies herein, but those that compete for binding with the epitopes bound by the enumerated antigen binding domains.

The carboxy-terminal portion of each chain defines a constant region primarily responsible for effector function. Kabat et al. collected numerous primary sequences of the variable regions of heavy chains and light chains. Based on the degree of conservation of the sequences, they classified individual primary sequences into the CDR and the framework and made a list thereof (see SEQUENCES OF IMMUNOLOGICAL INTEREST, 5th edition, NIH publication, No. 91-3242, E. A. Kabat et al., entirely incorporated by reference).

In the IgG subclass of immunoglobulins, there are several immunoglobulin domains in the heavy chain. By "immunoglobulin (Ig) domain" herein is meant a region of an immunoglobulin having a distinct tertiary structure. Of interest in the present invention are the heavy chain domains, including, the constant heavy (CH) domains and the hinge domains. In the context of IgG antibodies, the IgG isotypes each have three CH regions. Accordingly, "CH" domains in the context of IgG are as follows: "CH1" refers to positions 118-220 according to the EU index as in Kabat. "CH2" refers to positions 237-340 according to the EU index as in Kabat, and "CH3" refers to positions 341-447 according to the EU index as in Kabat. As shown herein and described below, the pI variants can be in one or more of the CH regions, as well as the hinge region, discussed below.

Another type of Ig domain of the heavy chain is the hinge region. By "hinge" or "hinge region" or "antibody hinge region" or "immunoglobulin hinge region" herein is meant the flexible polypeptide comprising the amino acids between the first and second constant domains of an antibody. Structurally, the IgG CH1 domain ends at EU position 220, and the IgG CH2 domain begins at residue EU position 237. Thus for IgG the antibody hinge is herein defined to include positions 221 (D221 in IgG1) to 236 (G236 in IgG1), wherein the numbering is according to the EU index as in Kabat. In some embodiments, for example in the context of an Fc region, the lower hinge is included, with the "lower hinge" generally referring to positions 226 or 230. As noted herein, pI variants can be made in the hinge region as well.

The light chain generally comprises two domains, the variable light domain (containing the light chain CDRs and together with the variable heavy domains forming the Fv region), and a constant light chain region (often referred to as CL or Cκ).

Another region of interest for additional substitutions, outlined herein, is the Fc region.

Thus, the present heterodimeric fusion proteins provided herein include one or more antibody domains. As described herein and known in the art, the heterodimeric antibodies provided herein comprise different domains within the heavy and light chains, which can be overlapping as well. These domains include, but are not limited to, the Fc domain, the CH1 domain, the CH2 domain, the CH3 domain, the hinge domain, the heavy constant domain (CH1-hinge-Fc domain or CH1-hinge-CH2-CH3), the variable heavy domain, the variable light domain, the light constant domain, Fab domains and scFv domains.

As generally outlined herein, the heterodimeric proteins of the invention include one or more Fvs that bind human TIM-3. "Hepatitis A virus cellular receptor 2," "HAVCR2," "T-cell immunoglobulin and mucin-domain containing-3," "TIM-3," "TIM3," "CD366" (e.g., Genebank Accession Numbers NM_032782 and NP_116171 (human)) refers to an immune checkpoint that belongs to TIM family cell surface receptor proteins. Together with PD-1 and LAG-3, TIM-3 mediates the CD8+ T cell exhaustion. TIM-3 expression is upregulated in tumor-infiltrating lymphocytes in lung, gastric, head and neck cancer, schwannoma, melanoma and follicular B-cell non-Hodgkin lymphoma and may interact with the PD-1 pathway in the dysfunction al CD8+ and Tregs in cancer. Exemplary sequences for TIM-3 are depicted in FIG. 3.

This Fv, or anti-TIM-3 component (the anti-TIM-3 antigen binding domain or TIM-3 ABD) of the subject heterodimer fusion proteins is generally a set of 6 CDRs and/or a variable heavy domain and a variable light domain that form an Fv domain that can bind human TIM-3. As described herein, there are a number of different formats that can be used, generally either by using a scFv or a Fab as outlined herein.

In certain embodiments, the ABDs of the invention comprise a heavy chain variable region with frameworks from a particular germline heavy chain immunoglobulin gene and/or a light chain variable region from a particular germline light chain immunoglobulin gene. For example, such ABDs may comprise or consist of a human ABD comprising heavy or light chain variable regions that are "the product of" or "derived from" a particular germline sequence. An ABD that is "the product of" or "derived from" a human germline immunoglobulin sequence can be identified as such by comparing the amino acid sequence of the ABD to the amino acid sequences of human germline immunoglobulins and selecting the human germline immunoglobulin sequence that is closest in sequence (i.e., greatest % identity) to the sequence of the ABD. An ABD that is "the product of" or "derived from" a particular human germline immunoglobulin sequence may contain amino acid differences as compared to the germline sequence, due to, for example, CDRs, naturally-occurring somatic mutations or intentional introduction of site-directed mutation. However, a humanized ABD typically is at least 90% identical in amino acids sequence to an amino acid sequence encoded by a human germline immunoglobulin gene and contains amino acid residues that identify the ABD as being derived from human sequences when compared to the germline immunoglobulin amino acid sequences of other species (e.g., murine germline sequences). In certain cases, a humanized ABD may be at least 95, 96, 97, 98 or 99%, or even at least 96%, 97%, 98%, or 99% identical in amino acid sequence to the amino acid sequence encoded by the germline immunoglobulin gene. Typically, a humanized ABD derived from a particular human germline sequence will display no more than 10-20 amino acid differences from the amino acid sequence encoded by the human germline immunoglobulin gene (prior to the introduction of any skew, pI and ablation variants herein; that is, the number of variants is generally low, prior to the introduction of the variants of the invention). In certain cases, the humanized ABD may display no more than 5, or even no more than 4, 3, 2, or 1 amino acid difference from the amino acid sequence encoded by the germline immunoglobulin gene (again, prior to the introduction of any skew, pI and ablation variants herein; that is, the number of variants is generally low, prior to the introduction of the variants of the invention). In one embodiment, the parent ABD has been affinity matured, as is known in the art. Structure-based methods may be employed for humanization and affinity maturation, for example as described in U.S. Ser. No. 11/004,590. Selection based methods may be employed to humanize and/or affinity mature antibody variable regions, including but not limited to methods described in Wu et al., 1999, J. Mol. Biol. 294:151-162; Baca et al., 1997, J. Biol. Chem. 272(16):10678-10684; Rosok et al., 1996, J. Biol. Chem. 271(37): 22611-22618; Rader et al., 1998, Proc. Natl. Acad. Sci. USA 95: 8910-8915; Krauss et al., 2003, Protein Engineering 16(10):753-759, all entirely incorporated by reference. Other humanization methods may involve the grafting of only parts of the CDRs, including but not limited to methods described in U.S. Ser. No. 09/810,510; Tan et al., 2002, J. Immunol. 169:1119-1125; De Pascalis et al., 2002, J. Immunol. 169:3076-3084, all entirely incorporated by reference.

As shown herein, the anti-TIM-3 ABD can be in the form of either a Fab or an scFv.

In some embodiments, for example as depicted in FIGS. 21B and C, the anti-TIM-3 ABD is a scFv, wherein the VH and VL domains are joined using an scFv linker, which can be optionally a charged scFv linker. As will be appreciated by those in the art, the scFv can be assembled from N- to C-terminus, as N-VH-scFv linker-VL-C or as N-VL-scFv linker-VH-C, with the C terminus of the scFv domain generally being linked to the hinge-CH2-CH3 Fc domain, wherein the hinge in this case serving as a domain linker. Suitable Fvs (including CDR sets and variable heavy/variable light domains) can be used in scFv formats or Fab formats are shown in the Figures as well as disclosed in WO2017/218707, the contents are hereby incorporated in its entirety for all purposes, and in particular for the TIM-3 ABDs in FIG. 13, the data in FIG. 21 and FIG. 22 and SEQ ID NO:s 20765-20884, SEQ ID NO:s 37587-37698 and SEQ ID NO:s 36347-36706 sequences in the sequence listing.

As will further be appreciated by those in the art, all or part of the hinge (which can also be a wild type hinge from IgG1, IgG2 or IgG4 or a variant thereof, such as the IgG4 S241P or S228P hinge variant with the substitution proline at position 228 relative to the parent IgG4 hinge polypeptide (wherein the numbering S228P is according to the EU index and the S241P is the Kabat numbering)) can be used as the domain linker between the scFv and the CH2-CH3 domain, or a different domain linker such as depicted in the Figures can be used.

Alternatively, the TIM-3 ABD can be in the form of a Fab fragment. In this embodiment, the ABD is made up of a variable heavy domain, contributed by a heavy chain, and a variable light domain, contributed by a light chain. Suitable Fvs (including CDR sets and variable heavy/variable light domains) can be used in scFv formats or Fab formats are shown in the Figures as well as disclosed in WO2017/218707, the contents are hereby incorporated in its entirety for all purposes, and in particular for the TIM-3 ABDs in FIG. 13, the data in FIG. 21 and FIG. 22 and SEQ ID NO:s 20765-20884, SEQ ID NO:s 37587-37698 and SEQ ID NO:s 36347-36706 sequences in the sequence listing.

As will be appreciated by those in the art, suitable TIM-3 binding domains can comprise a set of 6 CDRs as depicted in the sequence listing and figures (e.g., FIGS. 12 and 13), either as they are underlined/bolded or, in the case where a different numbering scheme is used as described herein and as shown in Table 2, as the CDRs that are identified using other alignments within the variable heavy (VH) domain and variable light domain (VL) sequences of those depicted in the figures (e.g., FIGS. 12 and 13A-C) and the sequence listing. Suitable TIM-3 ABDs that find use in the subject targeted IL-15/IL-15Rα heterodimeric fusion proteins can also include the entire VH and VL sequences as depicted in these sequences and figures, used as scFvs or as Fabs.

In one embodiment, the TIM-3 antigen binding domain includes the 6 CDRs (i.e., vhCDR1-3 and vlCDR1-3) of any of the TIM-3 binding domains described in FIGS. 12 and 13A-C or the sequence listing.

In addition to the parental CDR sets disclosed in the figures and sequence listing that form an ABD to TIM-3, provided herein are variant TIM-3 ABDS having CDRs that include at least one modification of the TIM-3 ABD CDRs disclosed herein (e.g., FIGS. 12 and 13A-C). In one embodiment, the heterodimeric fusion protein includes a TIM-3 ABD that includes a set of 6 CDRs with 1, 2, 3, 4, 5, 6, 7, 8, 9, 10 amino acid modifications as compared to the 6 CDRs of a TIM-3 ABD as depicted in FIGS. 112 and 3A-C or the sequence listing. In certain embodiments, the TIM-3 ABD is capable of binding TIM-3 antigen, as measured by at least one of a Biacore, surface plasmon resonance (SPR) and/or BLI (biolayer interferometry, e.g., Octet assay) assay, with the latter finding particular use in many embodiments.

In one embodiment, the TIM-3 ABD of the subject targeted IL-15/IL-15Rα heterodimeric fusion protein includes 6 CDRs that are at least 90, 95, 97, 98 or 99% identical to the 6 CDRs of a TIM-3 ABD as depicted in FIGS. 12 and 13A-C or the sequence listing. In certain embodiments, the TIM-3 ABD is capable of binding to the TIM-3, as measured by at least one of a Biacore, surface plasmon resonance (SPR) and/or BLI (biolayer interferometry, e.g., Octet assay) assay, with the latter finding particular use in many embodiments.

In one embodiment of the subject targeted IL-15/IL-15Rα heterodimeric fusion protein, the TIM-3 antigen binding domain includes the 6 CDRs (i.e., vhCDR1-3 and vlCDR1-3) of one of the following TIM-3 ABDs: 3H3[TIM-3]_H0_L0, 3H3[TIM-3]_H1_L2, 3H3[TIM-3]_H1_L2.1, APE137[TIM-3], APE5121[TIM-3], ABTIM3-hum03[TIM-3], ABTIM3-hum11[TIM-3], ABTIM3-hum21[TIM-3], 4177[TIM-3], 4545[Tim-3], 8213[TIM-3], mAb15[TIM-3], mAb58[TIM-3], TIM3-0433[TIM-3], TIM3-0434[TIM-3], TIM3-0438[TIM3], and TIM3-0443[TIM3] (see, e.g., FIGS. 12 and 13A-C). In an exemplary embodiments, the TIM-3ABD is 3H3[TIM-3]_H1_L2.1.

In one embodiment, the TIM-3 antigen binding domain is a variant TIM-3 antigen binding domain that includes 6 CDRs (i.e., vhCDR1-3 and vlCDR1-3), where the 6 CDRs include 1, 2, 3, 4, 5, 6, 7, 8, 9, or 10 modifications as compared to the 6 CDRs of one of the following TIM-3 ABDs: 3H3[TIM-3]_H0_L0, 3H3[TIM-3]_H1_L2, 3H3[TIM-3]_H1_L2.1, APE137[TIM-3], APE5121[TIM-3], ABTIM3-hum03[TIM-3], ABTIM3-hum11[TIM-3], ABTIM3-hum21[TIM-3], 4177[TIM-3], 4545[Tim-3], 8213[TIM-3], mAb15[TIM-3], mAb58[TIM-3], TIM3-0433[TIM-3], TIM3-0434[TIM-3], TIM3-0438[TIM3], and TIM3-0443[TIM3] (see, e.g., FIGS. 12 and 13A-C). In an exemplary embodiments, the TIM-3ABD is 3H3[TIM-3]_H1_L2.1.

In one embodiment, the TIM-3 antigen binding domain of the IL-15/IL-15Rα heterodimeric fusion protein is a variant TIM-3 antigen binding domain that includes 6 CDRs (i.e., vhCDR1-3 and vlCDR1-3), where the 6 CDRs are at least 90, 95, 97, 98 or 99% identical as compared to the 6 CDRs of one of the following TIM-3 ABDs: 3H3[TIM-3]_H0_L0, 3H3[TIM-3]_H1_L2, 3H3[TIM-3]_H1_L2.1, APE137[TIM-3], APE5121[TIM-3], ABTIM3-hum03[TIM-3], ABTIM3-hum11[TIM-3], ABTIM3-hum21[TIM-3], 4177[TIM-3], 4545[Tim-3], 8213[TIM-3], mAb15[TIM-3], mAb58[TIM-3], TIM3-0433[TIM-3], TIM3-0434[TIM-3], TIM3-0438[TIM3], and TIM3-0443[TIM3] (see, e.g., FIGS. 12 and 13A-C). In an exemplary embodiments, the TIM-3ABD is 3H3[TIM-3]_H1_L2.1.

In some embodiments, the TIM-3 ABD of the IL-15/IL-15Rα heterodimeric fusion protein includes the variable heavy domain (VH) and variable light domain (VL) of any of the LAG-ABDs disclosed herein, including, but not limited to those disclosed in FIGS. 12 and 13A-C. In addition to the parental TIM-3 variable heavy and variable light domains disclosed herein, provided herein are subject targeted IL-15/IL-15Rα heterodimeric fusion proteins having one or more TIM-3 ABDs that include a variable heavy domain and/or a variable light domain that are variants of a TIM-3 ABD VH and VL domain disclosed herein. In one embodiment, the variant VH domain and/or VL domain has from 1, 2, 3, 4, 5, 6, 7, 8, 9 or 10 amino acid changes from a VH and/or VL domain of a TIM-3 ABD depicted in FIGS. 12, 13A-C or the sequence listing. In certain embodiments, the TIM-3 ABD is capable of binding to TIM-3, as measured at least one of a Biacore, surface plasmon resonance (SPR) and/or BLI (biolayer interferometry, e.g., Octet assay) assay, with the latter finding particular use in many embodiments.

In one embodiment, the variant VH and/or VL domain of the IL-15/IL-15Rα heterodimeric fusion protein is at least 90, 95, 97, 98 or 99% identical to the VH and/or VL of a TIM-3 ABD as depicted in FIGS. 12 and 13A-C and the sequence listing. In certain embodiments, the TIM-3 ABD is capable of binding to TIM-3, as measured by at least one of a Biacore, surface plasmon resonance (SPR) and/or BLI (biolayer interferometry, e.g., Octet assay) assay, with the latter finding particular use in many embodiments.

In some embodiments, the TIM-3 ABD includes the VH and VL of a one of the following TIM-3 ABDs: 3H3[TIM-3]_H0_L0, 3H3[TIM-3]_H1_L2, 3H3[TIM-3]_H1_L2.1, APE137[TIM-3], APE5121[TIM-3], ABTIM3-hum03[TIM-3], ABTIM3-hum11[TIM-3], ABTIM3-hum21[TIM-3], 4177[TIM-3], 4545[Tim-3], 8213[TIM-3], mAb15[TIM-3], mAb58[TIM-3], TIM3-0433[TIM-3], TIM3-0434[TIM-3], TIM3-0438[TIM3], and TIM3-0443[TIM3] (see, e.g., FIGS. 12 and 13A-C). In an exemplary embodiments, the TIM-3ABD is 3H3[TIM-3]_H1_L2.1.

In some embodiments, the TIM-3 ABD includes a VH and VL, where the VH and/or VL includes 1, 2, 3, 4, 5, 6, 7, 8, 9 or 10 amino acid modifications as compared to a VH and/or VL of one of the following TIM-3 ABDs: 3H3[TIM-3]_H0_L0, 3H3[TIM-3]_H1_L2, 3H3[TIM-3]_H1_L2.1, APE137[TIM-3], APE5121[TIM-3], ABTIM3-hum03[TIM-3], ABTIM3-hum11[TIM-3], ABTIM3-hum21[TIM-3], 4177[TIM-3], 4545[Tim-3], 8213[TIM-3], mAb15[TIM-3], mAb58[TIM-3], TIM3-0433[TIM-3], TIM3-0434[TIM-3], TIM3-0438[TIM3], and TIM3-0443[TIM3] (see, e.g., FIGS. 12 and 13A-C). In an exemplary embodiments, the TIM-3ABD is 3H3[TIM-3]_H1_L2.1.

In certain embodiments, the TIM-3 ABD includes a VH and VL, where the VH and VL are at least 90, 95, 97, 98 or 99% identical as compared to a VH and VL of one of the following TIM-3 ABDs: 3H3[TIM-3]_H0_L0, 3H3[TIM-3]_H1_L2, 3H3[TIM-3]_H1_L2.1, APE137[TIM-3], APE5121[TIM-3], ABTIM3-hum03[TIM-3], ABTIM3-hum11[TIM-3], ABTIM3-hum21[TIM-3], 4177[TIM-3], 4545[Tim-3], 8213[TIM-3], mAb15[TIM-3], mAb58[TIM-3], TIM3-0433[TIM-3], TIM3-0434[TIM-3], TIM3-0438[TIM3], and TIM3-0443[TIM3] (see, e.g., FIGS. 12 and 13A-C). In an exemplary embodiments, the TIM-3ABD is 3H3[TIM-3]_H1_L2.1.

C. Fc Domains

The Fc domain component of the invention is as described herein, which generally contains skew variants and/or optional pI variants and/or ablation variants are outlined herein. See for example the disclosure of WO2017/218707 under the heading "IV Heterodimeric Antibodies", including sections IV.A, IV.B, IV.C, IV.D, IV.E, IV.F, IV.G, IV.H and IV.I, all of which are expressly incorporated by reference in their entirety. Of particular use in the heterodimeric proteins of the present invention are Fc domains containing "skew variants", "pI variants", "ablation variants" and FcRn variants as outlined therein. Particularly useful combinations of such variants are depicted, for example, FIGS. 7A-F.

The Fc domains can be derived from IgG Fc domains, e.g., IgG1, IgG2, IgG3 or IgG4 Fc domains. In an exemplary embodiment, the subject heterodimeric fusion protein provided herein includes an IgG1 Fc domain. The following describes Fc domains that are useful for IL-15/IL-15Rα Fc fusion monomers and anti-TIM-3 antibody fragments of the targeted IL-15/IL-15Rα heterodimeric fusion proteins.

Thus, the "Fc domain" includes the —CH2-CH3 domain, and optionally a hinge domain, and can be from human IgG1, IgG2, IgG3 or IgG4, with Fc domains derived from IgG1. In some of the embodiments herein, when a protein fragment, e.g., IL-15 or IL-15Rα is attached to an Fc domain, it is the C-terminus of the IL-15 or IL-15Rα construct that is attached to all or part of the hinge of the Fc domain. In other embodiments, when a protein fragment, e.g., IL-15 or IL-15Rα, is attached to an Fc domain, it is the C-terminus of the IL-15 or IL-15Rα construct that is attached to the CH1 domain of the Fc domain.

In some of the constructs and sequences outlined herein of an Fc domain protein, the C-terminus of the IL-15 or IL-15Rα protein fragment is attached to the N-terminus of a domain linker, the C-terminus of which is attached to the N-terminus of a constant Fc domain (N-IL-15 or IL-15Rα protein fragment-linker-Fc domain-C) although that can be switched (N-Fc domain-linker-IL-15 or IL-15Rα protein fragment-C). In other constructs and sequence outlined herein, C-terminus of a first protein fragment is attached to the N-terminus of a second protein fragment, optionally via a domain linker, the C-terminus of the second protein fragment is attached to the N-terminus of a constant Fc domain, optionally via a domain linker. In yet other constructs and sequences outlined herein, a constant Fc domain that is not attached to a first protein fragment or a second protein fragment is provided. A heterodimeric fusion protein can contain two or more of the exemplary monomeric Fc domain proteins described herein. Any domain linker can be used to attach a IL-15 or IL-15Rα protein fragment to an Fc domain of the heterodimeric fusion protein provided herein. In some embodiments, the linker is any one of the linkers in FIG. 8.

In some embodiments, the linker is a "domain linker", used to link any two domains (e.g., IL-15 or IL-15Rαprotein fragment to Fc domain or scFv to Fc domain) as outlined herein together, some of which are depicted in FIGS. 7C and 8. While any suitable linker can be used, many embodiments utilize a glycine-serine polymer, including for example (GS)n, (GSGGS)n (SEQ ID NO: 288), (GGGGS)n (SEQ ID NO: 289), and (GGGS)n (SEQ ID NO: 290), where n is an integer of at least one (and generally from 1 to 2 to 3 to 4 to 5) as well as any peptide sequence that allows for recombinant attachment of the two domains with sufficient length and flexibility to allow each domain to retain its biological function. In some cases, and with attention being paid to "strandedness", as outlined below, charged domain linkers.

In one embodiment, the heterodimeric fusion proteins contain at least two constant domains which can be engineered to produce heterodimers, such as pI engineering. Other Fc domains that can be used include fragments that contain one or more of the CH1, CH2, CH3, and hinge domains of the invention that have been pI engineered. In particular, the formats depicted in FIG. 21 are heterodimeric fusion proteins, meaning that the protein has two associated Fc sequences self-assembled into a heterodimeric Fc domain and at least one fusion protein (e.g., 1, 2 or more fusion proteins) as more fully described below. In some cases, a first fusion protein is linked to a first Fc and a second fusion protein is linked to a second Fc. In other cases, a first fusion protein is linked to a first Fc, and the first fusion protein is non-covalently attached to a second fusion protein that is not linked to an Fc. In some cases, the heterodimeric fusion protein contains a first fusion protein linked to a second fusion protein which is linked a first Fc sequence, and a second Fc sequence that is not linked to either the first or second fusion proteins.

Accordingly, in some embodiments the present invention provides heterodimeric fusion proteins that rely on the use of two different heavy chain variant Fc sequences, that will self-assemble to form a heterodimeric Fc domain fusion polypeptide.

The present invention is directed to novel constructs to provide heterodimeric fusion proteins that allow binding to one or more binding partners, ligands or receptors. The heterodimeric fusion constructs are based on the self-assembling nature of the two Fc domains of the heavy chains of antibodies, e.g., two "monomers" that assemble into a "dimer". Heterodimeric Fc fusions are made by altering the amino acid sequence of each monomer as more fully discussed below. Thus, the present invention is generally directed to the creation of heterodimeric fusion proteins which can co-engage binding partner(s) or ligand(s) or receptor(s) in several ways, relying on amino acid variants in the constant regions that are different on each chain to promote heterodimeric formation and/or allow for ease of purification of heterodimers over the homodimers. Specific variants that are included in the Fc domains of specific embodiments of the subject heterodimeric fusion protein are described in greater detail below.

1. Heterodimerization Variants

The present invention provides heterodimeric proteins, including heterodimeric fusion proteins in a variety of formats. Such heterodimeric proteins include two different Fc domains (one on each of the first and second monomers) that include modifications that facilitate the heterodimerization of the first and second monomers and/or allow for ease of purification of heterodimers over homodimers, collectively referred to herein as "heterodimerization variants." As discussed below, heterodimerization variants can include skew variants (e.g., the "knobs and holes" and "charge pairs" variants described below) as well as "pI variants" that facilitates the separation of homodimers away from heterodimers. As is generally described in U.S. Pat. No. 9,605,084, hereby incorporated by reference in its entirety and specifically as below for the discussion of heterodimerization variants, useful mechanisms for heterodimerization include "knobs and holes" ("KIH") as described in U.S. Pat. No. 9,605,084, "electrostatic steering" or "charge pairs" as described in U.S. Pat. No. 9,605,084, pI variants as described in U.S. Pat. No. 9,605,084, and general additional Fc variants as outlined in U.S. Pat. No. 9,605,084 and below.

a. Skew Variants

In some embodiments, the subject heterodimeric protein includes skew variants, which are one or more amino acid modifications in a first Fc domain (A) and/or a second Fc domain (B) that favor the formation of Fc heterodimers (Fc dimers that include the first and the second Fc domain; A-B) over Fc homodimers (Fc dimers that include two of the first Fc domain or two of the second Fc domain; A-A or B-B). Suitable skew variants are included in the FIG. 29 of US Publ. App. No. 2016/0355608, hereby incorporated by reference in its entirety and specifically for its disclosure of skew variants, as well as in FIG. 4.

One mechanism for skew variants is generally referred to in the art as "knobs and holes," referring to amino acid engineering that creates steric influences to favor heterodimeric formation and disfavor homodimeric formation, as described in U.S. Ser. No. 61/596,846, Ridgway et al., Protein Engineering 9(7):617 (1996); Atwell et al., J. Mol. Biol. 1997 270:26; U.S. Pat. No. 8,216,805, all of which are hereby incorporated by reference in their entirety and specifically for the disclosure of "knobs and holes" mutations. This is sometime referred to herein as "steric variants." The figures identify a number of "monomer A-monomer B" pairs that rely on "knobs and holes". In addition, as described in Merchant et al., Nature Biotech. 16:677 (1998), these "knobs and holes" mutations can be combined with disulfide bonds to further favor formation of Fc heterodimers.

An additional mechanism for skew variants that finds use in the generation of heterodimers is sometimes referred to as "electrostatic steering" as described in Gunasekaran et al., J. Biol. Chem. 285(25):19637 (2010), hereby incorporated by reference in its entirety. This is sometimes referred to herein as "charge pairs." In this embodiment, electrostatics are used to skew the formation towards heterodimerization. As those in the art will appreciate, these may also have an effect on pI, and thus on purification, and thus could in some cases also be considered pI variants. However, as these were generated to force heterodimerization and were not used as purification tools, they are classified as "skew variants." These include, but are not limited to, D221E/P228E/L368E paired with D221R/P228R/K409R (e.g., these are "monomer" corresponding sets) and C220E/P228E/368E paired with C220R/E224R/P228R/K409R.

In some embodiments, the skew variants advantageously and simultaneously favor heterodimerization based on both the "knobs and holes" mechanism as well as the "electrostatic steering" mechanisms described above. In some embodiments, the heterodimeric protein includes one or more sets of such heterodimerization skew variants. These variants come in "pairs" of "sets." That is, one set of the pair is incorporated into the first monomer and the other set of the pair is incorporated into the second monomer. Exemplary "skew variants' in this category include S364K/E357Q: L368D/K370S; L368D/K370S:S364K; L368E/K370S: S364K; T411T/E360E/Q362E:D401K; L368D/K370S: S364K/E357L; K370S:S364K/E357Q; or a T366S/L368A/ Y407V: T366W (optionally including a bridging disulfide, T366S/L368A/Y407V/Y349C: T366W/S354C) "skew" variant amino acid substitution sets. In terms of nomenclature, the pair "S364K/E357Q:L368D/K370S" means that one of the monomers includes an Fc domain that includes the amino acid substitutions S364K and E357Q and the other monomer includes an Fc domain that includes the amino acid substitutions L368D and K370S; as above, the "strandedness" of these pairs depends on the starting pI. It should be noted that these sets do not necessarily behave as "knobs in holes" variants, with a one-to-one correspondence between a residue on one monomer and a residue on the other. That is, these pairs of sets may instead form an interface between the two monomers that encourages heterodimer formation and discourages homodimer formation, allowing the percentage of heterodimers that spontaneously form under biological conditions to be over 90%, rather than the expected 50% (25% homodimer A/A:50% heterodimer A/B:25% homodimer B/B).

In exemplary embodiments, the heterodimeric fusion protein includes a S364K/E357Q:L368D/K370S; L368D/ K370S:S364K; L368E/K370S:S364K; T411T/E360E/ Q362E:D401K; L368D/K370S:S364K/E357L; K370S: S364K/E357Q; or a T366S/L368A/Y407V: T366W (optionally including a bridging disulfide, T366S/L368A/ Y407V/Y349C: T366W/S354C) "skew" variant amino acid substitution set. In an exemplary embodiment, the heterodimeric fusion protein includes a "S364K/E357Q: L368D/ K370S" amino acid substitution set.

In some embodiments, the skew variants provided herein are independently incorporated with other modifications, including, but not limited to, other skew variants (see, e.g., in FIG. 37 of US Publ. App. No. 2012/0149876, herein incorporated by reference, particularly for its disclosure of skew variants), pI variants, isotpypic variants, FcRn variants, ablation variants, etc. into one or both of the first and second Fc domains of the heterodimeric fusion protein. Further, individual modifications can also independently and optionally be included or excluded from the subject heterodimeric fusion proteins.

b. pI (Isoelectric Point) Variants for Heterodimers

In some embodiments, the heterodimeric fusion protein includes purification variants that advantageously allow for the separation of heterodimeric fusion proteins from homodimeric proteins ("pI variants").

In general, as will be appreciated by those in the art, there are two general categories of pI variants: those that increase the pI of the protein (basic changes) and those that decrease the pI of the protein (acidic changes). As described herein, all combinations of these variants can be done: one monomer may be wild type, or a variant that does not display a significantly different pI from wild-type, and the other can be either more basic or more acidic. Alternatively, each monomer is changed, one to more basic and one to more acidic.

There are several basic mechanisms that can lead to ease of purifying heterodimeric proteins. One such mechanism relies on the use of pI variants which include one or more modifications that affect the isoelectric point of one or both of the monomers of the fusion protein, such that each monomer, and subsequently each dimeric species, has a different pI, thus allowing the isoelectric purification of A-A, A-B and B-B dimeric proteins. Alternatively, some formats also allow separation on the basis of size. As is further outlined above, it is also possible to "skew" the formation of heterodimers over homodimers using skew variants. Thus, a combination of heterodimerization skew variants and pI variants find particular use in the subject heterodimeric fusion proteins provided herein.

Additionally, as more fully outlined below, depending on the format of the heterodimeric fusion protein, pI variants can be either contained within the constant region and/or Fc domains of a monomer, and/or domain linkers can be used. In some embodiments, the heterodimeric fusion protein includes additional modifications for alternative functionalities can also create pI changes, such as Fc, FcRn and KO variants.

In the embodiments that utilizes pI as a separation mechanism to allow the purification of heterodimeric fusion proteins, amino acid modifications can be introduced into one or both of the monomers of the heterodimeric fusion protein. That is, the pI of one of the monomers (referred to herein for simplicity as "monomer A") can be engineered away from monomer B, or both monomer A and B can be changed, with the pI of monomer A increasing and the pI of monomer B decreasing. As discussed, the pI changes of either or both monomers can be done by removing or adding a charged residue (e.g., a neutral amino acid is replaced by a positively or negatively charged amino acid residue, e.g., glutamine to glutamic acid), changing a charged residue from positive or negative to the opposite charge (e.g. aspartic acid to lysine) or changing a charged residue to a neutral residue (e.g., loss of a charge; lysine to serine.). A number of these variants are shown in the figures, including, FIGS. 4 and 5.

Creating a sufficient change in pI in at least one of the monomers such that heterodimers can be separated from homodimers can be done by using a "wild type" heavy chain constant region and a variant region that has been engineered to either increase or decrease its pI (wt A: B+ or wt A: B−), or by increasing one region and decreasing the other region (A+: B− or A−: B+).

Thus, in general, a component of some embodiments of the present subject fusion proteins are amino acid variants in the Fc domains or constant domain regions that are directed to altering the isoelectric point (pI) of at least one, if not both, of the monomers of a dimeric protein by incorporating amino acid substitutions ("pI variants" or "pI substitutions") into one or both of the monomers. The separation of the heterodimers from the two homodimers can be accomplished if the pIs of the two monomers differ by as little as 0.1 pH unit, with 0.2, 0.3, 0.4 and 0.5 or greater all finding use in the present invention.

As will be appreciated by those in the art, the number of pI variants to be included on each or both monomer(s) of a heterodimeric fusion protein to achieve good separation will depend in part on the starting pI of the components. That is, to determine which monomer to engineer or in which "direction" (e.g., more positive or more negative), the sequences of the Fc domains and any IL-15, IL-15Rα or linker included in each monomer are calculated and a decision is made from there based on the pIs of the monomers. As is known in the art, different Fc domains, linkers IL-15, and IL-15Rα will have different starting pIs. In general, as outlined herein, the pIs are engineered to result in a total pI difference of each monomer of at least about 0.1 logs, with 0.2 to 0.5 being preferred as outlined herein.

In general, as will be appreciated by those in the art, there are two general categories of amino acid modifications that affect pI: those that increase the pI of the protein (basic changes) and those that decrease the pI of the protein (acidic changes). As described herein, all combinations of these variants can be used: one monomer may include a wild type Fc domain, or a variant Fc domain that does not display a significantly different pI from wild-type, and the other monomer includes a Fc domain that is either more basic or more acidic. Alternatively, each monomer may be changed, one to more basic and one to more acidic.

In the case where pI variants are used to achieve heterodimerization, a more modular approach to designing and purifying heterodimeric fusion proteins is provided. Thus, in some embodiments, heterodimerization variants (including skew and pI variants) must be engineered. In addition, in some embodiments, the possibility of immunogenicity resulting from the pI variants is significantly reduced by importing pI variants from different IgG isotypes such that pI is changed without introducing significant immunogenicity (see isotypic variants below). Thus, an additional problem to be solved is the elucidation of low pI constant domains with high human sequence content, e.g. the minimization or avoidance of non-human residues at any particular position. Alternatively or in addition to isotypic substitutions, the possibility of immunogenicity resulting from the pI variants is significantly reduced by utilizing isosteric substitutions (e.g., Asn to Asp; and Gln to Glu).

A side benefit that can occur with this pI engineering is also the extension of serum half-life and increased FcRn binding. That is, as described in US Publ. App. No. US 2012/0028304 (incorporated by reference in its entirety and specifically for the disclosure of pI variants that provide additional function), lowering the pI of antibody constant domains (including those found in Fc fusions) can lead to longer serum retention in vivo. These pI variants for increased serum half-life also facilitate pI changes for purification.

In addition, it should be noted that the pI variants of the heterodimerization variants give an additional benefit for the analytics and quality control process of Fc fusion proteins, as the ability to either eliminate, minimize and distinguish when homodimers are present is significant. Similarly, the ability to reliably test the reproducibility of the heterodimeric fusion protein production is important.

Exemplary combinations of pI variants are shown in FIGS. 4 and 5, and FIG. 30 of US Publ. App. No. 2016/0355608, all of which are herein incorporated by reference in its entirety and specifically for the disclosure of pI variants. As outlined herein and shown in the figures, these changes are shown relative to IgG1, but all isotypes can be altered this way, as well as isotype hybrids. In the case where the heavy chain constant domain is from IgG2-4, R133E and R133Q can also be used.

In some embodiments, modifications are made in the hinge of the Fc domain, including positions 208, 216, 217, 218, 219, 220, 221, 222, 223, 224, 225, 226, 227, 228, 229, and 230 based on EU numbering. Thus, pI mutations and particularly substitutions can be made in one or more of positions 216-230, with 1, 2, 3, 4 or 5 mutations finding use. Again, all possible combinations are contemplated, alone or with other pI variants in other domains.

Specific substitutions that find use in lowering the pI of hinge domains include, but are not limited to, a deletion at position 221, a non-native valine or threonine at position 222, a deletion at position 223, a non-native glutamic acid at position 224, a deletion at position 225, a deletion at position 235 and a deletion or a non-native alanine at position 236. In some cases, only pI substitutions are done in the hinge domain, and in others, these substitution(s) are added to other pI variants in other domains in any combination.

In some embodiments, mutations can be made in the CH2 region, including positions 233, 234, 235, 236, 274, 296, 300, 309, 320, 322, 326, 327, 334 and 339, based on EU numbering. It should be noted that changes in 233-236 can be made to increase effector function (along with 327A) in the IgG2 backbone. Again, all possible combinations of these 14 positions can be made; e.g., a heterodimeric fusion protein may include a variant Fc domain with 1, 2, 3, 4, 5, 6, 7, 8, 9 or 10 CH2 pI substitutions.

Specific substitutions that find use in lowering the pI of CH2 domains include, but are not limited to, a non-native glutamine or glutamic acid at position 274, a non-native phenylalanine at position 296, a non-native phenylalanine at position 300, a non-native valine at position 309, a non-native glutamic acid at position 320, a non-native glutamic acid at position 322, a non-native glutamic acid at position 326, a non-native glycine at position 327, a non-native glutamic acid at position 334, a non-native threonine at position 339, and all possible combinations within CH2 and with other domains.

In this embodiment, the modifications can be independently and optionally selected from position 355, 359, 362, 384, 389, 392, 397, 418, 419, 444 and 447 (EU numbering) of the CH3 region. Specific substitutions that find use in lowering the pI of CH3 domains include, but are not limited to, a non-native glutamine or glutamic acid at position 355, a non-native serine at position 384, a non-native asparagine or glutamic acid at position 392, a non-native methionine at position 397, a non-native glutamic acid at position 419, a non-native glutamic acid at position 359, a non-native glutamic acid at position 362, a non-native glutamic acid at position 389, a non-native glutamic acid at position 418, a non-native glutamic acid at position 444, and a deletion or non-native aspartic acid at position 447. Exemplary embodiments of pI variants are provided in FIG. 5.

In one embodiment, the heterodimeric fusion protein includes a monomer with a variant Fc domain having pI variant modifications 295E/384D/418E/421D (Q295E/N384D/Q418E/N421D when relative to human IgG1). In one embodiment, the heterodimeric fusion protein includes a monomer with a variant Fc domain having pI variant modifications 208D/295E/384D/418E/421D (N208D/Q295E/N384D/Q418E/N421D when relative to human IgG1). In some embodiments, the heterodimeric fusion protein includes a monomer with a variant Fc domain having pI variant modifications 295E/384D/418E/421D (Q295E/

N384D/Q418E/N421D when relative to human IgG1). In one embodiment, the heterodimeric fusion protein includes a monomer with a variant Fc domain having pI variant modifications 196K/199T/217R/228R/276K (Q196K/I199T/P217R/P228R/N276K) when relative to human IgG1).

In one embodiment, the heterodimeric fusion protein includes a monomer with a variant Fc domain having pI variant modifications 217R/228R/276K (P217R/P228R/N276K when relative to human IgG1). Additional exemplary pI variant modification that can be incorporated into the Fc domain of a subject are depicted in FIG. 5.

2. Additional Fc Variants for Additional Functionality

In addition to pI amino acid variants, there are a number of useful Fc amino acid modification that can be made for a variety of reasons, including, but not limited to, altering binding to one or more FcγR receptors, altered binding to FcRn receptors, etc.

Accordingly, the proteins of the invention can include amino acid modifications, including the heterodimerization variants outlined herein, which includes the pI variants and steric variants. Each set of variants can be independently and optionally included or excluded from any particular heterodimeric protein.

a. FcγR Variants

Accordingly, there are a number of useful Fc substitutions that can be made to alter binding to one or more of the FcγR receptors. Substitutions that result in increased binding as well as decreased binding can be useful. For example, it is known that increased binding to FcγRIIIa results in increased ADCC (antibody dependent cell-mediated cytotoxicity; the cell-mediated reaction wherein nonspecific cytotoxic cells that express FcγRs recognize bound antibody on a target cell and subsequently cause lysis of the target cell). Similarly, decreased binding to FcγRIIb (an inhibitory receptor) can be beneficial as well in some circumstances. Amino acid substitutions that find use in the present invention include those listed in U.S. Ser. No. 11/124,620 (particularly FIG. 41), Ser. Nos. 11/174,287, 11/396,495, 11/538,406, all of which are expressly incorporated herein by reference in their entirety and specifically for the variants disclosed therein. Particular variants that find use include, but are not limited to, 236A, 239D, 239E, 332E, 332D, 239D/332E, 267D, 267E, 328F, 267E/328F, 236A/332E, 239D/332E/330Y, 239D, 332E/330L, 243A, 243L, 264A, 264V and 299T.

In addition, amino acid substitutions that increase affinity for FcγRIIc can also be included in the Fc domain variants outlined herein. The substitutions described in, for example, U.S. Ser. Nos. 11/124,620 and 14/578,305 are useful.

In addition, there are additional Fc substitutions that find use in increased binding to the FcRn receptor and increased serum half-life, as specifically disclosed in U.S. Ser. No. 12/341,769, hereby incorporated by reference in its entirety, including, but not limited to, 434S, 434A, 428L, 308F, 259I, 428L/434S, 259I/308F, 436I/428L, 436I or V/434S, 436V/428L and 259I/308F/428L.

b. Ablation Variants

Similarly, another category of functional variants are "FcγR ablation variants" or "Fc knock out (FcKO or KO)" variants. In these embodiments, for some therapeutic applications, it is desirable to reduce or remove the normal binding of the Fc domain to one or more of all of the Fcγ receptors (e.g., FcγR1, FcγRIIa, FcγRIIb, FcγRIIIa, etc.) to avoid additional mechanisms of action. That is, for example, in many embodiments, particularly in the use of bispecific immunomodulatory antibodies desirable to ablate FcγRIIIa binding to eliminate or significantly reduce ADCC activity such that one of the Fc domains comprises one or more Fcγ receptor ablation variants. These ablation variants are depicted in FIG. 31 of U.S. Ser. No. 15/141,350, all of which are herein incorporated by reference in its entirety, and each can be independently and optionally included or excluded, with preferred aspects utilizing ablation variants selected from the group consisting of G236R/L328R, E233P/L234V/L235A/G236del/S239K, E233P/L234V/L235A/G236del/S267K, E233P/L234V/L235A/G236del/S239K/A327G, E233P/L234V/L235A/G236del/S267K/A327G and E233P/L234V/L235A/G236del, according to the EU index. It should be noted that the ablation variants referenced herein ablate FcγR binding but generally not FcRn binding.

Exemplary ablation variants are provided in FIG. 5.

c. Combination of Heterodimeric and Fc Variants

As will be appreciated by those in the art, all of the recited heterodimerization variants (including skew and/or pI variants) can be optionally and independently combined in any way, as long as they retain their "strandedness" or "monomer partition". In addition, all of these variants can be combined into any of the heterodimerization formats.

In the case of pI variants, while embodiments finding particular use are shown in the Figures, other combinations can be generated, following the basic rule of altering the pI difference between two monomers to facilitate purification.

In addition, any of the heterodimerization variants, skew and pI, are also independently and optionally combined with Fc ablation variants, Fc variants, FcRn variants, as generally outlined herein.

In addition, a monomeric Fc domain can comprise a set of amino acid substitutions that includes C220S/S267K/L368D/K370S or C220S/S267K/S364K/E357Q.

In addition, the heterodimeric fusion proteins can comprise skew variants (e.g., a set of amino acid substitutions as shown in FIGS. 1A-1C of U.S. Ser. No. 15/141,350, all of which are herein incorporated by reference in its entirety), with particularly useful skew variants being selected from the group consisting of S364K/E357Q:L368D/K370S; L368D/K370S:S364K; L368E/K370S:S364K; T411E/K360E/Q362E:D401K; L368D/K370S:S364K/E357L, K370S:S364K/E357Q, T366S/L368A/Y407V: T366W and T366S/L368A/Y407V/Y349C: T366W/S354C, optionally ablation variants, optionally charged domain linkers and the heavy chain comprises pI variants.

In some embodiments, the Fc domain comprising an amino acid substitution selected from the group consisting of: 236R, 239D, 239E, 243L, M252Y, V259I, 267D, 267E, 298A, V308F, 328F, 328R, 330L, 332D, 332E, M428L, N434A, N434S, 236R/328R, 239D/332E, M428L, 236R/328F, V259I/V308F, 267E/328F, M428L/N434S, Y436I/M428L, Y436V/M428L, Y436I/N434S, Y436V/N434S, 239D/332E/330L, M252Y/S254T/T256E, V259I/V308F/M428L, E233P/L234V/L235A/G236del/S267K, G236R/L328R and PVA/S267K. In some cases, the Fc domain comprises the amino acid substitution 239D/332E. In other cases, the Fc domain comprises the amino acid substitution G236R/L328R or PVA/S267K.

In one embodiment, a particular combination of skew and pI variants that finds use in the present invention is T366S/L368A/Y407V: T366W (optionally including a bridging disulfide, T366S/L368A/Y407V/Y349C: T366W/S354C) with one monomer comprises Q295E/N384D/Q418E/N481D and the other a positively charged domain linker. As will be appreciated in the art, the "knobs in holes" variants do not change pI, and thus can be used on either monomer.

Useful combination of variants that can be used in particular formats of the invention are included in FIGS. 7A-7F.

III. Targeted IL-15/IL-15Rα Fc Fusion×TIM-3 ABD Heterodimeric Proteins

Provided herein are heterodimeric fusion proteins that can bind to the checkpoint inhibitor TIM-3 antigen and can complex with the common gamma chain (γc; CD132) and/or the Il-2 receptor β-chain (IL-2Rβ; CD122). The heterodimeric fusion proteins can contain an IL-15/IL-15Rα-Fc fusion protein and an antibody fusion protein. The IL-15/IL-15Rα-Fc fusion protein can include as IL-15 protein (generally including amino acid substitutions) covalently attached to an IL-15Rα, and an Fc domain. Optionally, the IL-15 protein and IL-15Rα protein are noncovalently attached.

IV. Useful Formats of the Invention

As shown in FIG. 21, there are a number of useful formats of the targeted IL-15/IL-15Rα-Fc heterodimeric fusion proteins of the invention. In general, the heterodimeric fusion proteins of the invention have three functional components: an IL-15/IL-15Rα(sushi) component, an anti-TIM-3 component, and an Fc component, each of which can take different forms as outlined herein and each of which can be combined with the other components in any configuration.

The first and the second variant Fc domains can have a set of amino acid substitutions selected from the group consisting of a) S267K/L368D/K370S:S267K/S364K/E357Q; b) S364K/E357Q:L368D/K370S; c) L368D/K370S:S364K; d) L368E/K370S:S364K; e) T411E/K360E/Q362E:D401K; f) L368D/K370S:S364K/E357L and g) K370S:S364K/E357Q, according to EU numbering. In an exemplary embodiment, the skew variants are S364K/E357Q:L368D/K370S.

In some embodiments, the first and/or the second Fc domains have an additional set of pI amino acid substitutions selected from the following pI variants: Q295E/N384D/Q418E/N421D, N208/Q295E/N384D/Q418E/N421D or Q196K/I199T/P217R/P228R/N276K, according to EU numbering.

Optionally, the first and/or the second Fc domains have an additional set of ablation ("FcKO") variants selected from the following FcKO variants: G236R/L328R, E233P/L234V/L235A/G236del/S239K, E233P/L234V/L235A/G236del/S267K, E233P/L234V/L235A/G236del/S239K/A327G, E233P/L234V/L235A/G236del/S267K/A327G and E233P/L234V/L235A/G236del, according to EU numbering.

Optionally, the first and/or second Fc domains have 428L/434S variants for half-life extension.

In embodiments wherein a hinge or partial hinge is used to link an Fc domain to a scFv, IL-15 or IL-15Rα domain, the hinge may optional include a C220S substitution to prevent the hinge from forming undesirable disulfide bonds with any light chains.

Exemplary formats of the subject heterodimeric fusion proteins are provided below.

A. scIL-15/RαxscFv

One embodiment is shown in FIG. 21A, and comprises two monomers. The first monomer comprises, from N- to C-terminus, the IL-15Rα(sushi) domain-(domain linker)-IL-15 variant-(domain linker)-CH2-CH3 (with the second domain linker frequently being a hinge domain), and the second monomer comprises VH-scFv linker-VL-hinge-CH2-CH3 or VL-scFv linker-VH-hinge-CH2-CH3, although in either orientation a domain linker can be substituted for the hinge. This is generally referred to as "scIL-15/RαxscFv", with the "sc" standing for "single chain" referring to the attachment of the IL-15 variant and IL-15Rα(sushi) domain using a covalent linker. Preferred combinations of variants for this embodiment are found in FIGS. 21A and B.

In one embodiment, the targeted IL-15/IL-15Rα heterodimeric protein is an "scIL-15/RαxscFv" format heterodimeric protein that includes: a) a first monomer that includes, from N- to C-terminus, an IL-15Rα(sushi) domain-(domain linker)-IL-15 variant-(domain linker)-CH2-CH3, where CH2-CH3 is a first Fc domain; and b) a second monomer that includes, from N- to C-terminus, an anti-TIM-3 scFv-(domain linker)-CH2-CH3, where CH2-CH3 is a second Fc domain. Any useful domain linker can be used to attach the various components of the heterodimeric protein including, but not limited to those in FIGS. 8 and 9A-C. In an exemplary embodiment, the domain linkers that attach the IL-15 variant to the first Fc domain and the anti-TIM-3 scFv to the second Fc domain are each antibody hinge domains.

In some embodiments, the anti-TIM-3 scFv includes a variable heavy domain (VH) covalently attached to a variable light domain (VL) by an scFv linker (e.g., FIGS. 9A-C). In one embodiment, the anti-TIM-3 scFv is from N- to C-terminus VH-scFv linker-VL. In another embodiment, the anti-TIM-3 scFv is from N- to C-terminus VL-scFv linker-VH. The C-terminus of the anti-TIM-3 scFv is attached to the N terminus of the first Fc domain by a domain linker (e.g., an antibody hinge domain).

In the scIL-15/RαxscFv format, one preferred embodiment utilizes an anti-TIM-3 ABD having any of the variable heavy and light domain pairs as shown in FIGS. 12 and 13A-C.

In the scIL-15/RαxscFv format, one preferred embodiment utilizes an anti-TIM-3 ABD having the variable heavy and light domain pair of 3H3[TIM-3]_H1_L2.1 as shown in FIG. 12. In one embodiment, the "scIL-15/RαxscFv" format heterodimeric protein includes: a) a first monomer that includes, from N- to C-terminus, an IL-15Rα(sushi) domain-(domain linker)-IL-15 variant-(hinge)-CH2-CH3, where CH2-CH3 is a first Fc domain; and b) a second monomer that includes, from N- to C-terminus, an anti-TIM-3 scFv-(hinge)-CH2-CH3, where CH2-CH3 is a second Fc domain, and where the anti-TIM-3 scFv includes the variable heavy domain and variable light domain of 3H3[TIM-3]_H1_L2.1.

In the scIL-15/RαxscFv format, one preferred embodiment utilizes an IL-15 variant that includes amino acid substitutions N4D/N65D, D30N/N65D, or D30N/E64Q/N65D. In one embodiment, the "scIL-15/RαxscFv" format heterodimeric protein includes: a) a first monomer that includes, from N- to C-terminus, an IL-15Rα(sushi) domain-(domain linker)-IL-15 variant-(hinge)-CH2-CH3, where CH2-CH3 is a first Fc domain; and b) a second monomer that includes, from N- to C-terminus, anti-TIM-3 scFv-(hinge)-CH2-CH3, where CH2-CH3 is a second Fc domain, and where the IL-15 variant includes amino acid substitutions N4D/N65D, D30N/N65D, or D30N/E64Q/N65D. In an exemplary embodiment, the TIM-3 scFv includes the VH and VL of any of the TIM-3 ABDs in FIGS. 12 and 13A-C and the IL-15 variant includes amino acid substitutions N4D/N65D. In another exemplary embodiment, the TIM-3 scFv includes the VH and VL of any of the TIM-3 ABDs in FIGS. 12 and 13A-C and the IL-15 variant includes amino acid substitutions D30N/N65D. In yet another exemplary embodiment, the TIM-3 scFv includes the VH and VL of any of the TIM-3 ABDs in FIGS. 12 and 13A-C and the IL-15 variant includes amino acid substitutions D30N/E64Q/N65D.

In the scIL-15/RαxscFv format, one preferred embodiment utilizes an anti-TIM-3 ABD having the variable heavy and light domain pair of 3H3[TIM-3]_H1_L2.1 as shown in FIG. 12, with either the IL-15 N4D/N65D variant or the IL-15 D30N/N65D variant or the IL-15 D30N/E64Q/N65D variant. In one embodiment, the "scIL-15/RαxscFv" format heterodimeric protein includes: a) a first monomer that includes, from N- to C-terminus, an IL-15Rα(sushi) domain-(domain linker)-IL-15 variant-(hinge)-CH2-CH3, where CH2-CH3 is a first Fc domain; and b) a second monomer that includes, from N- to C-terminus, anti-TIM-3 scFv-(hinge)-CH2-CH3, where CH2-CH3 is a second Fc domain, where the anti-TIM-3 scFv includes the variable heavy domain and variable light domain of 3H3[TIM-3]_H1_L2.1, and where the IL-15 variant includes amino acid substitutions N4D/N65D, D30N/N65D, or D30N/E64Q/N65D.

In the scIL-15/RαxscFv format, one preferred embodiment utilizes the skew variant pair S364K/E357Q:L368D/K370S. In one embodiment, the targeted IL-15/IL-15Rα heterodimeric protein is an "scIL-15/RαxscFv" format heterodimeric protein that includes: a) a first monomer that includes, from N- to C-terminus, an IL-15Rα(sushi) domain-(domain linker)-IL-15 variant-(domain linker)-CH2-CH3, where CH2-CH3 is a first variant Fc domain; and b) a second monomer that includes, from N- to C-terminus, anti-TIM-3 scFv-(domain linker)-CH2-CH3, where CH2-CH3 is a second variant Fc domain, and where the first and second variant Fc domains include the skew variant pair S364K/E357Q: L368D/K370S. In an exemplary embodiment, the first variant Fc domain includes skew variants L368D/K370S, and the second variant Fc domain includes skew variants L368D/K370S.

In one embodiment, the targeted IL-15/IL-15Rα heterodimeric protein is an "scIL-15/RαxscFv" format heterodimeric protein that includes: a) a first monomer that includes, from N- to C-terminus, an IL-15Rα(sushi) domain-(domain linker)-IL-15 variant-(domain linker)-CH2-CH3, where CH2-CH3 is a first variant Fc domain; and b) a second monomer that includes, from N- to C-terminus, anti-TIM-3 scFv-(domain linker)-CH2-CH3, where CH2-CH3 is a second variant Fc domain, where the IL-15 variant includes amino acid substitutions N4D/N65D, D30N/N65D, or D30N/E64Q/N65D, and where the first and second variant Fc domains include the skew variant pair S364K/E357Q: L368D/K370S. In an exemplary embodiment, the first variant Fc domain includes skew variants L368D/K370S, and the second variant Fc domain includes skew variants L368D/K370S. In an exemplary embodiment, the TIM-3 scFv includes the VH and VL of any of the TIM-3 ABDs in FIGS. 12 and 13A-C and the IL-15 variant includes amino acid substitutions N4D/N65D. In another exemplary embodiment, the TIM-3 scFv includes the VH and VL of any of the TIM-3 ABDs in FIGS. 12 and 13A-C and the IL-15 variant includes amino acid substitutions D30N/N65D. In yet another exemplary embodiment, the TIM-3 scFv includes the VH and VL of any of the TIM-3 ABDs in FIGS. 12 and 13A-C and the IL-15 variant includes amino acid substitutions D30N/E64Q/N65D.

In the scIL-15/RαxscFv format, one preferred embodiment utilizes an anti-TIM-3 ABD having the variable heavy and light domain pair of 3H3[TIM-3]_H1_L2.1 as shown in FIG. 12 and the skew variant pair S364K/E357Q:L368D/K370S. In one embodiment, the "scIL-15/RαxscFv" format heterodimeric protein includes: a) a first monomer that includes, from N- to C-terminus, an IL-15Rα(sushi) domain-(domain linker)-IL-15 variant-(hinge)-CH2-CH3, where CH2-CH3 is a first variant Fc domain; and b) a second monomer that includes, from N- to C-terminus, anti-TIM-3 scFv-(hinge)-CH2-CH3, where CH2-CH3 is a second variant Fc domain, where the anti-TIM-3 scFv includes the variable heavy domain and variable light domain of 3H3 [TIM-3]_H1_L2.1, and where the first and second variant Fc domains include the skew variant pair S364K/E357Q: L368D/K370S. In an exemplary embodiment, the first variant Fc domain includes skew variants L368D/K370S, and the second variant Fc domain includes skew variants L368D/K370S.

In the scIL-15/RαxscFv format, one preferred embodiment utilizes an anti-TIM-3 ABD having the variable heavy and light domain pair of 3H3[TIM-3]_H1_L2.1 as shown in FIG. 12 and the skew variant pair S364K/E357Q:L368D/K370S with either the IL-15 N4D/N65D variant or the IL-15 D30N/N65D variant or the IL-15 D30N/E64Q/N65D variant. In one embodiment, the "scIL-15/RαxscFv" format heterodimeric protein includes: a) a first monomer that includes, from N- to C-terminus, an IL-15Rα(sushi) domain-(domain linker)-IL-15 variant-(hinge)-CH2-CH3, where CH2-CH3 is a first variant Fc domain; and b) a second monomer that includes, from N- to C-terminus, anti-TIM-3 scFv-(hinge)-CH2-CH3, where CH2-CH3 is a second variant Fc domain, where the anti-TIM-3 scFv includes the variable heavy domain and variable light domain of 3H3 [TIM-3]_H1_L2.1, where the IL-15 variant includes amino acid substitutions N4D/N65D, D30N/N65D, or D30N/E64Q/N65D, and where the first and second variant Fc domains include the skew variant pair S364K/E357Q: L368D/K370S. In an exemplary embodiment, the first variant Fc domain includes skew variants L368D/K370S, and the second variant Fc domain includes skew variants L368D/K370S. In a particular embodiment, the IL-15 variant includes amino acid substitutions N4D/N65D and the scFv includes the variable heavy and light domain pair of 3H3[TIM-3]_H1_L2.1. In one embodiment, the IL-15 variant includes amino acid substitutions D30N/N65D and the scFv includes the variable heavy and light domain pair of 3H3[TIM-3]_H1_L2.1. In yet another embodiment, the IL-15 variant is the IL-15 D30N/E64Q/N65D variant and the scFv includes the variable heavy and light domain pair of 3H3[TIM-3]_H1_L2.1.

In the scIL-15/RαxscFv format, one preferred embodiment utilizes the skew variant set S364K/E357Q:L368D/K370S, the pI variants Q295E/N384D/Q418E/N421D, the ablation variants E233P/L234V/L235A/G236_/S267K on both first and second monomers, and optionally the 428L/434S variants on both first and second monomers.

In one embodiment, the "scIL-15/RαxscFv" format heterodimeric protein includes: a) a first monomer that includes, from N- to C-terminus, an IL-15Rα(sushi) domain-(domain linker)-IL-15 variant-(domain linker)-CH2-CH3, where CH2-CH3 is a first variant Fc domain; and b) a second monomer that includes, from N- to C-terminus, anti-TIM-3 scFv-(hinge)-CH2-CH3, where CH2-CH3 is a second variant Fc domain; where the first variant Fc domain includes skew variants L368D/K370S and the second variant Fc domain includes skew variants S364K/E357Q, where the first and second variant Fc domains each include FcKO variants E233P/L234V/L235A/G236del/S267K, where the first variant Fc domain includes pI variants Q295E/N384D/Q418E/N421D, and where numbering is according to EU numbering. In some embodiments, the hinge of the first and second monomers also each include amino acid substitution C220S. In certain embodiments, the first and second variant Fc domains each further include half-life extension variants M428L/N434S. In an exemplary embodiment, the IL-15 variant includes amino acid substitutions N4D/N65D, D30N/N65D, or D30N/E64Q/N65D. In an exemplary embodiment, the TIM-3 scFv includes the VH and VL of any of the TIM-3 ABDs in FIGS. 12 and 13A-C and the IL-15 variant includes amino acid substitutions N4D/N65D. In another exemplary embodiment, the TIM-3 scFv includes the VH and VL of any of the TIM-3 ABDs in FIGS. 12 and 13A-C and the IL-15 variant includes amino acid substitutions D30N/N65D. In yet another exemplary embodiment, the TIM-3 scFv includes the VH and VL of any of the TIM-3 ABDs in FIGS. 12 and 13A-C and the IL-15 variant includes amino acid substitutions D30N/E64Q/N65D.

In the scIL-15/RαxscFv format, one preferred embodiment utilizes an anti-TIM-3 ABD having the variable heavy and light domain pair 3H3[TIM-3]_H1_L2.1 as shown in FIG. 12 with the FIG. 21A format, the skew variant set S364K/E357Q:L368D/K370S, the pI variants Q295E/N384D/Q418E/N421D, the ablation variants E233P/L234V/L235A/G236_/S267K on both first and second monomers, and optionally the 428L/434S variants on both first and second monomers.

In one embodiment, the "scIL-15/RαxscFv" format heterodimeric protein includes: a) a first monomer that includes, from N- to C-terminus, an IL-15Rα(sushi) domain-(domain linker)-IL-15 variant-(domain linker)-CH2-CH3, where CH2-CH3 is a first variant Fc domain; and b) a second monomer that includes, from N- to C-terminus, anti-TIM-3 scFv-(hinge)-CH2-CH3, where CH2-CH3 is a second variant Fc domain; where the anti-TIM-3 scFv includes the variable heavy domain and variable light domain of 3H3[TIM-3]_H1_L2.1, where the first variant Fc domain includes skew variants L368D/K370S and the second variant Fc domain includes skew variants S364K/E357Q where the first and second variant Fc domains each include FcKO variants E233P/L234V/L235A/G236del/S267K, where the first variant Fc domain includes pI variants Q295E/N384D/Q418E/N421D, and where numbering is according to EU numbering. In some embodiments, the hinge of the first and second monomers also each include amino acid substitution C220S. In certain embodiments, the first and second variant Fc domains each further include half-life extension variants M428L/N434S. In a particular embodiment, the IL-15 variant includes amino acid substitutions N4D/N65D and the scFv includes the variable heavy and light domain pair of 3H3[TIM-3]_H1_L2.1. In one embodiment, the IL-15 variant includes amino acid substitutions D30N/N65D and the scFv includes the variable heavy and light domain pair of 3H3[TIM-3]_H1_L2.1. In yet another embodiment, the IL-15 variant is the IL-15 D30N/E64Q/N65D variant and the scFv includes the variable heavy and light domain pair of 3H3[TIM-3]_H1_L2.1.

B. scFvxncIL-15/Rα

This embodiment is shown in FIG. 21B, and comprises three monomers. The first monomer comprises, from N- to C-terminus, the IL-15Rα(sushi) domain-domain linker-CH2-CH3, and the second monomer comprises VH-scFv linker-VL-hinge-CH2-CH3 or VL-scFv linker-vh-hinge-CH2-CH3, although in either orientation a domain linker can be substituted for the hinge. The third monomer is the variant IL-15 domain. This is generally referred to as "ncIL-15/RαxscFv" or "scFvxncIL-15/Rα" with the "nc" standing for "non-covalent" referring to the self-assembling non-covalent attachment of the IL-15 variant and IL-15Rα (sushi) domain.

In one embodiment, the targeted IL-15/IL-15Rα heterodimeric protein is an "scFvxncIL-15/Rα" format heterodimeric protein that includes: a) a first monomer that includes, from N- to C-terminus, an anti-TIM-3 scFv-(domain linker)-CH2-CH3, where CH2-CH3 is a first Fc domain; b) a second monomer that includes, from N- to C-terminus, an IL-15Rα (sushi) domain-(domain linker)-CH2-CH3, where CH2-CH3 is a second Fc domain; and c) an IL-15 variant, where the IL-15 variant and the IL-15Rα(sushi) domain form an IL-15 complex. Any useful domain linker can be used to attach the various components of the heterodimeric protein including, but not limited to those in FIGS. 8 and 9A-C. In an exemplary embodiment, the domain linkers that attach the anti-TIM-3 scFv to the first Fc domain and the IL-15Rα (sushi) domain to the second Fc domain are each antibody hinge domains.

In some embodiments, the anti-TIM-3 scFv includes a variable heavy domain (VH) covalently attached to a variable light domain (VL) by an scFv linker (e.g., FIGS. 9A-C). In one embodiment, the anti-TIM-3 scFv is, from N- to C-terminus, VH-scFv linker-VL. In another embodiment, the anti-TIM-3 scFv is, from N- to C-terminus, VL-scFv linker-VH. The C-terminus of the anti-TIM-3 scFv is attached to the N terminus of the first Fc domain by a domain linker (e.g., an antibody hinge domain).

In the ncIL-15/RαxscFv format, one preferred embodiment utilizes an anti-TIM-3 ABD having any of the variable heavy and light domain pairs as shown in FIG. 12.

In the ncIL-15/RαxscFv format, one preferred embodiment utilizes an anti-TIM-3 ABD having the variable heavy and light domain pair of 3H3[TIM-3]_H1_L2.1 as shown in FIG. 12.

In one embodiment, the targeted IL-15/IL-15Rα heterodimeric protein is an "scFvxncIL-15/Rα" format heterodimeric protein that includes: a) a first monomer that includes, from N- to C-terminus, an anti-TIM-3 scFv-(domain linker)-CH2-CH3, where CH2-CH3 is a first Fc domain; b) a second monomer that includes, from N- to C-terminus, an IL-15Rα (sushi) domain-(domain linker)-CH2-CH3, where CH2-CH3 is a second Fc domain; and c) an IL-15 variant, where the IL-15 variant and the IL-15Rα(sushi) domain form an IL-15 complex, and where the anti-TIM-3 scFv includes the variable heavy domain and variable light domain of 3H3 [TIM-3]_H1_L2.1.

In the ncIL-15/RαxscFv format, one preferred embodiment utilizes an IL-15 variant that includes amino acid substitutions N4D/N65D, D30N/N65D, or D30N/E64Q/N65D. In one embodiment, the targeted IL-15/IL-15Rα heterodimeric protein is an "scFvxncIL-15/Rα" format heterodimeric protein that includes: a) a first monomer that includes, from N- to C-terminus, an anti-TIM-3 scFv-(domain linker)-CH2-CH3, where CH2-CH3 is a first Fc domain; b) a second monomer that includes, from N- to C-terminus, an IL-15Rα(sushi) domain-(domain linker)-CH2-CH3, where CH2-CH3 is a second Fc domain; and c) an IL-15 variant, where the IL-15 variant and the IL-15Rα (sushi) domain form an IL-15 complex, and where the IL-15 variant includes amino acid substitutions N4D/N65D, D30N/N65D, or D30N/E64Q/N65D. In an exemplary embodiment, the TIM-3 scFv includes the VH and VL of any of the TIM-3 ABDs in FIGS. 12 and 13A-C and the IL-15 variant includes amino acid substitutions N4D/N65D. In another exemplary embodiment, the TIM-3 scFv includes the VH and VL of any of the TIM-3 ABDs in FIGS. 12 and 13A-C and the IL-15 variant includes amino acid substitutions D30N/N65D. In yet another exemplary embodiment, the TIM-3 scFv includes the VH and VL of any of the TIM-3 ABDs in FIGS. 12 and 13A-C and the IL-15 variant includes amino acid substitutions D30N/E64Q/N65D.

In the ncIL-15/RαxscFv format, one preferred embodiment utilizes an anti-TIM-3 ABD having the variable heavy and light domain pair of 3H3[TIM-3]_H1_L2.1 as shown in FIG. 12, with either the IL-15 N4D/N65D variant or the IL-15 D30N/N65D variant or the IL-15 D30N/E64Q/N65D variant. In one embodiment, the targeted IL-15/IL-15Rα heterodimeric protein is an "scFvxncIL-15/Rα" format heterodimeric protein that includes: a) a first monomer that includes, from N- to C-terminus, an anti-TIM-3 scFv-(domain linker)-CH2-CH3, where CH2-CH3 is a first Fc domain; b) a second monomer that includes, from N- to C-terminus, an IL-15Rα(sushi) domain-(domain linker)-CH2-CH3, where CH2-CH3 is a second Fc domain; and c) an IL-15 variant, where the IL-15 variant and the IL-15Rα(sushi) domain form an IL-15 complex, where the anti-TIM-3 scFv includes the variable heavy domain and variable light domain of 3H3[TIM-3]_H1_L2.1, and where the IL-15 variant includes amino acid substitutions N4D/N65D, D30N/N65D, or D30N/E64Q/N65D. In a particular embodiment, the IL-15 variant includes amino acid substitutions N4D/N65D and the scFv includes the variable heavy and light domain pair of 3H3[TIM-3]_H1_L2.1. In one embodiment, the IL-15 variant includes amino acid substitutions D30N/N65D and the scFv includes the variable heavy and light domain pair of 3H3[TIM-3]_H1_L2.1. In yet another embodiment, the IL-15 variant includes amino acid substitutions D30N/E64Q/N65D and the scFv includes the variable heavy and light domain pair of 3H3[TIM-3]_H1_L2.1.

In the ncIL-15/RαxscFv format, one preferred embodiment utilizes the skew variant pair S364K/E357Q:L368D/K370S. In one embodiment, the targeted IL-15/IL-15Rα heterodimeric protein is an "scFvxncIL-15/Rα" format heterodimeric protein that includes: a) a first monomer that includes, from N- to C-terminus, an anti-TIM-3 scFv-(domain linker)-CH2-CH3, where CH2-CH3 is a first variant Fc domain; b) a second monomer that includes, from N- to C-terminus, an IL-15Rα(sushi) domain-(domain linker)-CH2-CH3, where CH2-CH3 is a second variant Fc domain; and c) an IL-15 variant, where the IL-15 variant and the IL-15Rα(sushi) domain form an IL-15 complex, and where the first and second variant Fc domains include the skew variant pair S364K/E357Q:L368D/K370S. In an exemplary embodiment, the first variant Fc domain includes skew variants L368D/K370S, and the second variant Fc domain includes skew variants S364K/E357Q.

In one embodiment, the targeted IL-15/IL-15Rα heterodimeric protein is an "scFvxncIL-15/Rα" format heterodimeric protein that includes: a) a first monomer that includes, from N- to C-terminus, an anti-TIM-3 scFv-(domain linker)-CH2-CH3, where CH2-CH3 is a first variant Fc domain; b) a second monomer that includes, from N- to C-terminus, an IL-15Rα(sushi) domain-(domain linker)-CH2-CH3, where CH2-CH3 is a second variant Fc domain; and c) an IL-15 variant, where the IL-15 variant and the IL-15Rα(sushi) domain form an IL-15 complex, where the IL-15 variant includes amino acid substitutions N4D/N65D, D30N/N65D, or D30N/E64Q/N65D, and where the first and second variant Fc domains include the skew variant pair S364K/E357Q:L368D/K370S. In an exemplary embodiment, the first variant Fc domain includes skew variants L368D/K370S, and the second variant Fc domain includes skew variants S364K/E357Q. In an exemplary embodiment, the TIM-3 scFv includes the VH and VL of any of the TIM-3 ABDs in FIGS. 12 and 13A-C and the IL-15 variant includes amino acid substitutions N4D/N65D. In another exemplary embodiment, the TIM-3 scFv includes the VH and VL of any of the TIM-3 ABDs in FIGS. 12 and 13A-C and the IL-15 variant includes amino acid substitutions D30N/N65D. In yet another exemplary embodiment, the TIM-3 scFv includes the VH and VL of any of the TIM-3 ABDs in FIGS. 12 and 13A-C and the IL-15 variant includes amino acid substitutions D30N/E64Q/N65D.

In the ncIL-15/RαxscFv format, one preferred embodiment utilizes an anti-TIM-3 ABD having the variable heavy and light domain pair of 3H3[TIM-3]_H1_L2.1 as shown in FIG. 12 and the skew variant pair S364K/E357Q:L368D/K370S. In one embodiment, the targeted IL-15/IL-15Rα heterodimeric protein is an "scFvxncIL-15/Rα" format heterodimeric protein that includes: a) a first monomer that includes, from N- to C-terminus, an anti-TIM-3 scFv-(domain linker)-CH2-CH3, where CH2-CH3 is a first variant Fc domain; b) a second monomer that includes, from N- to C-terminus, an IL-15Rα(sushi) domain-(domain linker)-CH2-CH3, where CH2-CH3 is a second variant Fc domain; and c) an IL-15 variant, where the IL-15 variant and the IL-15Rα(sushi) domain form an IL-15 complex, where the anti-TIM-3 scFv includes the variable heavy domain and variable light domain of 3H3[TIM-3]_H1_L2.1, and where the first and second variant Fc domains include the skew variant pair S364K/E357Q:L368D/K370S.

In the ncIL-15/RαxscFv format, one preferred embodiment utilizes an anti-TIM-3 ABD having the variable heavy and light domain pair of 3H3[TIM-3]_H1_L2.1 as shown in FIG. 12 and the skew variant pair S364K/E357Q:L368D/K370S with either the IL-15 N4D/N65D variant or the IL-15 D30N/N65D variant or the IL-15 D30N/E64Q/N65D variant. In an exemplary embodiment, the first variant Fc domain includes skew variants L368D/K370S, and the second variant Fc domain includes skew variants L368D/K370S. In one embodiment, the targeted IL-15/IL-15Rα heterodimeric protein is an "scFvxncIL-15/Rα" format heterodimeric protein that includes: a) a first monomer that includes, from N- to C-terminus, an anti-TIM-3 scFv-(domain linker)-CH2-CH3, where CH2-CH3 is a first variant Fc domain; b) a second monomer that includes, from N- to C-terminus, an IL-15Rα(sushi) domain-(domain linker)-CH2-CH3, where CH2-CH3 is a second variant Fc domain; and c) an IL-15 variant, where the IL-15 variant and the IL-15Rα(sushi) domain form an IL-15 complex, where the anti-TIM-3 scFv includes the variable heavy domain and variable light domain of 3H3[TIM-3]_H1_L2.1, where the IL-15 variant includes amino acid substitutions N4D/N65D, D30N/N65D, or D30N/E64Q/N65D, and where the first and second variant Fc domains include the skew variant pair S364K/E357Q:L368D/K370S. In a particular embodiment, the IL-15 variant includes amino acid substitutions N4D/N65D and the scFv includes the variable heavy and light domain pair of 3H3[TIM-3]_H1_L2.1. In one embodiment, the IL-15 variant includes amino acid substitutions D30N/N65D and the scFv includes the variable heavy and light domain pair of 3H3[TIM-3]_H1_L2.1. In yet another embodiment, the IL-15 variant includes amino acid substitutions D30N/E64Q/N65D and the scFv includes the variable heavy and light domain pair of 3H3[TIM-3]_H1_L2.1.

In the ncIL-15/RαxscFv format, one preferred embodiment utilizes the skew variant set S364K/E357Q:L368D/K370S, the pI variants Q295E/N384D/Q418E/N421D, the ablation variants E233P/L234V/L235A/G236_/S267K on both first and second monomers, and optionally the 428L/434S variants on both first and second monomers.

In one embodiment, the targeted IL-15/IL-15Rα heterodimeric protein is an "scFv×ncIL-15/Rα" format heterodimeric protein that includes: a) a first monomer that includes, from N- to C-terminus, an anti-TIM-3 scFv-(domain linker)-CH2-CH3, where CH2-CH3 is a first variant Fc domain; b) a second monomer that includes, from N- to C-terminus, an IL-15Rα(sushi) domain-(domain linker)-CH2-CH3, where CH2-CH3 is a second variant Fc domain; and c) an IL-15 variant, where the IL-15 variant and the IL-15Rα(sushi) domain form an IL-15 complex, where the first variant Fc domain includes skew variants L368D/K370S and the second variant Fc domain includes skew variants S364K/E357Q, where the first and second variant Fc domains each include FcKO variants E233P/L234V/L235A/G236del/S267K, where the first variant Fc domain includes pI variants Q295E/N384D/Q418E/N421D, and where numbering is according to EU numbering. In some embodiments, the hinge of the first and second monomers also each include amino acid substitution C220S. In certain embodiments, the first and second variant Fc domains each further include half-life extension variants M428L/N434S. In an exemplary embodiment, the IL-15 variant includes amino acid substitutions N4D/N65D, D30N/N65D, or D30N/E64Q/N65D. In an exemplary embodiment, the TIM-3 scFv includes the VH and VL of any of the TIM-3 ABDs in FIGS. 12 and 13A-C and the IL-15 variant includes amino acid substitutions N4D/N65D. In another exemplary embodiment, the TIM-3 scFv includes the VH and VL of any of the TIM-3 ABDs in FIGS. 12 and 13A-C and the IL-15 variant includes amino acid substitutions D30N/N65D. In yet another exemplary embodiment, the TIM-3 scFv includes the VH and VL of any of the TIM-3 ABDs in FIGS. 12 and 13A-C and the IL-15 variant includes amino acid substitutions D30N/E64Q/N65D.

In the ncIL-15/Rα×scFv format, one preferred embodiment utilizes an anti-TIM-3 ABD the variable heavy and light domain pair of 3H3[TIM-3]_H1_L2.1 as shown in FIG. 12 with the FIG. 21B format, the skew variant set S364K/E357Q:L368D/K370S, the pI variants Q295E/N384D/Q418E/N421D, the ablation variants E233P/L234V/L235A/G236_/S267K on both first and second monomers, and optionally the 428L/434S variants on both first and second monomers.

In one embodiment, the targeted IL-15/IL-15Rα heterodimeric protein is an "scFv×ncIL-15/Rα" format heterodimeric protein that includes: a) a first monomer that includes, from N- to C-terminus, an anti-TIM-3 scFv-(domain linker)-CH2-CH3, where CH2-CH3 is a first variant Fc domain; b) a second monomer that includes, from N- to C-terminus, an IL-15Rα(sushi) domain-(domain linker)-CH2-CH3, where CH2-CH3 is a second variant Fc domain; and c) an IL-15 variant, where the IL-15 variant and the IL-15Rα(sushi) domain form an IL-15 complex, where the anti-TIM-3 scFv includes the variable heavy domain and variable light domain of 3H3[TIM-3]_H1_L2.1, where the first variant Fc domain includes skew variants L368D/K370S and the second variant Fc domain includes skew variants S364K/E357Q, where the first and second variant Fc domains each include FcKO variants E233P/L234V/L235A/G236del/S267K, where the first variant Fc domain includes pI variants Q295E/N384D/Q418E/N421D, and where numbering is according to EU numbering. In some embodiments, the hinge of the first and second monomers also each include amino acid substitution C220S. In certain embodiments, the first and second variant Fc domains each further include half-life extension variants M428L/N434S. In a particular embodiment, the IL-15 variant includes amino acid substitutions N4D/N65D and the scFv includes the variable heavy and light domain pair of 3H3[TIM-3]_H1_L2.1. In one embodiment, the IL-15 variant includes amino acid substitutions D30N/N65D and the scFv includes the variable heavy and light domain pair of 3H3[TIM-3]_H1_L2.1. In another embodiment, the IL-15 variant includes amino acid substitutions D30N/E64Q/N65D and the scFv includes the variable heavy and light domain pair of 3H3[TIM-3]_H1_L2.1.

C. scFv×dsIL-15/Rα

This embodiment is shown in FIG. 21C, and comprises three monomers. The first monomer comprises, from N- to C-terminus, the IL-15Rα(sushi) domain-domain linker-CH2-CH3, wherein the IL-15Rα(sushi) domain has an engineered cysteine residue and the second monomer comprises VH-scFv linker-VL-hinge-CH2-CH3 or VL-scFv linker-vh-hinge-CH2-CH3, although in either orientation a domain linker can be substituted for the hinge. The third monomer is the variant IL-15 domain, also engineered to have a cysteine variant amino acid, thus allowing a disulfide bridge to form between the IL-15Rα(sushi) domain and the variant IL-15 domain. This is generally referred to as "scFv×dsIL-15/Rα" or "dsIL-15/Rα×scFv", with the "ds" standing for "disulfide".

In one embodiment, the targeted IL-15/IL-15Rα heterodimeric protein is an "scFv×dsIL-15/Rα" format heterodimeric protein that includes: a) a first monomer that includes, from N- to C-terminus, an anti-TIM-3 scFv-(domain linker)-CH2-CH3, where CH2-CH3 is a first Fc domain; b) a second monomer that includes, from N- to C-terminus, an IL-15Rα (sushi) domain-(domain linker)-CH2-CH3, where CH2-CH3 is a second Fc domain and the IL-15Rα(sushi) domain includes an amino acid substitution for a cysteine residue; and c) an IL-15 variant that includes an amino acid substitution for a cysteine residue, and where the cysteine residue on the IL-15 variant and the cysteine residue on the IL-15Rα (sushi) domain form a disulfide bond. Any useful domain linker can be used to attach the various components of the heterodimeric protein including, but not limited to those in FIGS. 8 and 9A-C. In an exemplary embodiment, the domain linkers that attach the anti-TIM-3 scFv to the first Fc domain and the IL-15Rα(sushi) domain to the second Fc domain and are each antibody hinge domains.

Any useful domain linker can be used to attach the various components of the heterodimeric protein including, but not limited to those in FIGS. 8 and 9A-C. In an exemplary embodiment, the domain linkers that attach the anti-TIM-3 scFv to the first Fc domain and the IL-15Rα(sushi) domain to the second Fc domain and are each antibody hinge domains (e.g., an antibody hinge domain).

In some embodiments, the anti-TIM-3 scFv includes a variable heavy domain (VH) covalently attached to a variable light domain (VL) by an scFv linker (e.g., FIGS. 9A-C). In one embodiment, the anti-TIM-3 scFv is from N- to C-terminus VH-scFv linker-VL. In another embodiment, the anti-TIM-3 scFv is from N- to C-terminus VL-scFv linker-VH. The C-terminus of the anti-TIM-3 scFv is attached to the N terminus of the first Fc domain by a domain linker (e.g., an antibody hinge domain).

In the dsIL-15/Rα×scFv format, one preferred embodiment utilizes an anti-TIM-3 ABD having any of the variable heavy and light domain pairs as shown in FIGS. 12 and 13A-C.

In the dsIL-15/RαxscFv format, one preferred embodiment utilizes an anti-TIM-3 ABD having the variable heavy and light domain pair of 3H3[TIM-3]_H1_L2.1 as shown in FIG. 12.

In one embodiment, the targeted IL-15/IL-15Rα heterodimeric protein is an "scFvxdsIL-15/Rα" format heterodimeric protein that includes: a) a first monomer that includes, from N- to C-terminus, an anti-TIM-3 scFv-(domain linker)-CH2-CH3, where CH2-CH3 is a first Fc domain; b) a second monomer that includes, from N- to C-terminus, an IL-15Rα (sushi) domain-(domain linker)-CH2-CH3, where CH2-CH3 is a second Fc domain and the IL-15Rα(sushi) domain includes an amino acid substitution for a cysteine residue; and c) an IL-15 variant that includes an amino acid substitution for a cysteine residue, where the cysteine residue on the IL-15 variant and the cysteine residue on the IL-15Rα (sushi) domain form a disulfide bond, and where the anti-TIM-3 scFv includes the variable heavy domain and variable light domain of 3H3[TIM-3]_H1_L2.1.

In the dsIL-15/RαxscFv format, one preferred embodiment utilizes the IL-15 N4D/N65D variant or the IL-15 D30N/N65D variant or the IL-15 D30N/E64Q/N65D variant, as well as appropriate cysteine substitutions. In one embodiment, the targeted IL-15/IL-15Rα heterodimeric protein is an "scFvxdsIL-15/Rα" format heterodimeric protein that includes: a) a first monomer that includes, from N- to C-terminus, an anti-TIM-3 scFv-(domain linker)-CH2-CH3, where CH2-CH3 is a first Fc domain; b) a second monomer that includes, from N- to C-terminus, an IL-15Rα (sushi) domain-(domain linker)-CH2-CH3, where CH2-CH3 is a second Fc domain and the IL-15Rα(sushi) domain includes an amino acid substitution for a cysteine residue; and c) an IL-15 variant that includes an amino acid substitution for a cysteine residue, where the cysteine residue on the IL-15 variant and the cysteine residue on the IL-15Rα (sushi) domain form a disulfide bond, and where the IL-15 variant includes amino acid substitutions N4D/N65D, D30N/N65D, or D30N/E64Q/N65D. In an exemplary embodiment, the TIM-3 scFv includes the VH and VL of any of the TIM-3 ABDs in FIGS. 12 and 13A-C and the IL-15 variant includes amino acid substitutions N4D/N65D. In another exemplary embodiment, the TIM-3 scFv includes the VH and VL of any of the TIM-3 ABDs in FIGS. 12 and 13A-C and the IL-15 variant includes amino acid substitutions D30N/N65D. In yet another exemplary embodiment, the TIM-3 scFv includes the VH and VL of any of the TIM-3 ABDs in FIGS. 12 and 13A-C and the IL-15 variant includes amino acid substitutions D30N/E64Q/N65D.

In the dsIL-15/RαxscFv format, one preferred embodiment utilizes an anti-TIM-3 ABD having the variable heavy and light domain pair of 3H3[TIM-3]_H1_L2.1 as shown in FIG. 12, with either the IL-15 N4D/N65D variant or the IL-15 D30N/N65D variant or the IL-15 D30N/E64Q/N65D variant, as well as appropriate cysteine substitutions. In one embodiment, the targeted IL-15/IL-15Rα heterodimeric protein is an "scFvxdsIL-15/Rα" format heterodimeric protein that includes: a) a first monomer that includes, from N- to C-terminus, an anti-TIM-3 scFv-(domain linker)-CH2-CH3, where CH2-CH3 is a first Fc domain; b) a second monomer that includes, from N- to C-terminus, an IL-15Rα (sushi) domain-(domain linker)-CH2-CH3, where CH2-CH3 is a second Fc domain and the IL-15Rα(sushi) domain includes an amino acid substitution for a cysteine residue; and c) an IL-15 variant that includes an amino acid substitution for a cysteine residue, where the cysteine residue on the IL-15 variant and the cysteine residue on the IL-15Rα (sushi) domain form a disulfide bond, where the anti-TIM-3 scFv includes the variable heavy domain and variable light domain of 3H3[TIM-3]_H1_L2.1, and where the IL-15 variant includes amino acid substitutions N4D/N65D, D30N/N65D, or D30N/E64Q/N65D. In a particular embodiment, the IL-15 variant includes amino acid substitutions N4D/N65D and the scFv includes the variable heavy and light domain pair of 3H3[TIM-3]_H1_L2.1. In one embodiment, the IL-15 variant includes amino acid substitutions D30N/N65D and the scFv includes the variable heavy and light domain pair of 3H3[TIM-3]_H1_L2.1. In another embodiment, the IL-15 variant includes amino acid substitutions D30N/E64Q/N65D and the scFv includes the variable heavy and light domain pair of 3H3[TIM-3]_H1_L2.1.

In the dsIL-15/RαxscFv format, one preferred embodiment utilizes the skew variant pair S364K/E357Q:L368D/K370S. In one embodiment, the targeted IL-15/IL-15Rα heterodimeric protein is an "scFvxdsIL-15/Rα" format heterodimeric protein that includes: a) a first monomer that includes, from N- to C-terminus, an anti-TIM-3 scFv-(domain linker)-CH2-CH3, where CH2-CH3 is a first variant Fc domain; b) a second monomer that includes, from N- to C-terminus, an IL-15Rα(sushi) domain-(domain linker)-CH2-CH3, where CH2-CH3 is a second variant Fc domain and the IL-15Rα(sushi) domain includes an amino acid substitution for a cysteine residue; and c) an IL-15 variant that includes an amino acid substitution for a cysteine residue, where the cysteine residue on the IL-15 variant and the cysteine residue on the IL-15Rα(sushi) domain form a disulfide bond, and where the first and second variant Fc domains include the skew variant pair S364K/E357Q:L368D/K370S. In an exemplary embodiment, the first variant Fc domain includes skew variants L368D/K370S, and the second variant Fc domain includes skew variants S364K/E357Q.

In one embodiment, the targeted IL-15/IL-15Rα heterodimeric protein is an "scFvxdsIL-15/Rα" format heterodimeric protein that includes: a) a first monomer that includes, from N- to C-terminus, an anti-TIM-3 scFv-(domain linker)-CH2-CH3, where CH2-CH3 is a first variant Fc domain; b) a second monomer that includes, from N- to C-terminus, an IL-15Rα(sushi) domain-(domain linker)-CH2-CH3, where CH2-CH3 is a second variant Fc domain and the IL-15Rα (sushi) domain includes an amino acid substitution for a cysteine residue; and c) an IL-15 variant that includes an amino acid substitution for a cysteine residue, where the cysteine residue on the IL-15 variant and the cysteine residue on the IL-15Rα(sushi) domain form a disulfide bond, where the IL-15 variant includes amino acid substitutions N4D/N65D, D30N/N65D, or D30N/E64Q/N65D, and where the first and second variant Fc domains include the skew variant pair S364K/E357Q:L368D/K370S. In an exemplary embodiment, the first variant Fc domain includes skew variants L368D/K370S, and the second variant Fc domain includes skew variants S364K/E357Q. In an exemplary embodiment, the TIM-3 scFv includes the VH and VL of any of the TIM-3 ABDs in FIGS. 12 and 13A-C and the IL-15 variant includes amino acid substitutions N4D/N65D. In another exemplary embodiment, the TIM-3 scFv includes the VH and VL of any of the TIM-3 ABDs in FIGS. 12 and 13A-C and the IL-15 variant includes amino acid substitutions D30N/N65D. In yet another exemplary embodiment, the TIM-3 scFv includes the VH and VL of any of the TIM-3 ABDs in FIGS. 12 and 13A-C and the IL-15 variant includes amino acid substitutions D30N/E64Q/N65D.

In the dsIL-15/RαxscFv format, one preferred embodiment utilizes an anti-TIM-3 ABD having the variable heavy and light domain pair of 3H3[TIM-3]_H1_L2.1 as shown in FIG. 12 and the skew variant pair S364K/E357Q:L368D/K370S. In one embodiment, the targeted IL-15/IL-15Rα heterodimeric protein is an "scFv×dsIL-15/Rα" format heterodimeric protein that includes: a) a first monomer that includes, from N- to C-terminus, an anti-TIM-3 scFv-(domain linker)-CH2-CH3, where CH2-CH3 is a first variant Fc domain; b) a second monomer that includes, from N- to C-terminus, an IL-15Rα(sushi) domain-(domain linker)-CH2-CH3, where CH2-CH3 is a second variant Fc domain and the IL-15Rα(sushi) domain includes an amino acid substitution for a cysteine residue; and c) an IL-15 variant that includes an amino acid substitution for a cysteine residue, where the cysteine residue on the IL-15 variant and the cysteine residue on the IL-15Rα(sushi) domain form a disulfide bond, where the anti-TIM-3 scFv includes the variable heavy domain and variable light domain of 3H3[TIM-3]_H1_L2.1, and where the first and second variant Fc domains include the skew variant pair S364K/E357Q:L368D/K370S.

In the dsIL-15/Rα×scFv format, one preferred embodiment utilizes an anti-TIM-3 ABD having the variable heavy and light domain pair of 3H3[TIM-3]_H1_L2.1 as shown in FIG. 12 and the skew variant pair S364K/E357Q:L368D/K370S with either the IL-15 N4D/N65D variant or the IL-15 D30N/N65D variant or the IL-15 D30N/E64Q/N65D variant with the appropriate cysteine substitutions.

In one embodiment, the targeted IL-15/IL-15Rα heterodimeric protein is an "scFv×dsIL-15/Rα" format heterodimeric protein that includes: a) a first monomer that includes, from N- to C-terminus, an anti-TIM-3 scFv-(domain linker)-CH2-CH3, where CH2-CH3 is a first variant Fc domain; b) a second monomer that includes, from N- to C-terminus, an IL-15Rα(sushi) domain-(domain linker)-CH2-CH3, where CH2-CH3 is a second variant Fc domain and the IL-15Rα(sushi) domain includes an amino acid substitution for a cysteine residue; and c) an IL-15 variant that includes an amino acid substitution for a cysteine residue, where the cysteine residue on the IL-15 variant and the cysteine residue on the IL-15Rα(sushi) domain form a disulfide bond, where the anti-TIM-3 scFv includes the variable heavy domain and variable light domain of 3H3[TIM-3]_H1_L2.1, where the IL-15 variant includes amino acid substitutions N4D/N65D, D30N/N65D, or D30N/E64Q/N65D, and where the first and second variant Fc domains include the skew variant pair S364K/E357Q: L368D/K370S. In an exemplary embodiment, the first variant Fc domain includes skew variants L368D/K370S, and the second variant Fc domain includes skew variants S364K/E357Q. In a particular embodiment, the IL-15 variant includes amino acid substitutions N4D/N65D and the scFv includes the variable heavy and light domain pair of 3H3[TIM-3]_H1_L2.1. In one embodiment, the IL-15 variant includes amino acid substitutions D30N/N65D and the scFv includes the variable heavy and light domain pair of 3H3[TIM-3]_H1_L2.1. In another embodiment, the IL-15 variant includes amino acid substitutions D30N/E64Q/N65D and the scFv includes the variable heavy and light domain pair of 3H3[TIM-3]_H1_L2.1.

In the dsIL-15/Rα×scFv format, one preferred embodiment utilizes the skew variant set S364K/E357Q:L368D/K370S, the pI variants Q295E/N384D/Q418E/N421D, the ablation variants E233P/L234V/L235A/G236_/S267K on both first and second monomers, and optionally the 428L/434S variants on both first and second monomers.

In one embodiment, the targeted IL-15/IL-15Rα heterodimeric protein is an "scFv×dsIL-15/Rα" format heterodimeric protein that includes: a) a first monomer that includes, from N- to C-terminus, an anti-TIM-3 scFv-(hinge)-CH2-CH3, where CH2-CH3 is a first variant Fc domain; b) a second monomer that includes, from N- to C-terminus, an IL-15Rα(sushi) domain-(domain linker)-CH2-CH3, where CH2-CH3 is a second variant Fc domain and the IL-15Rα(sushi) domain includes an amino acid substitution for a cysteine residue; and c) an IL-15 variant that includes an amino acid substitution for a cysteine residue, where the cysteine residue on the IL-15 variant and the cysteine residue on the IL-15Rα(sushi) domain form a disulfide bond, where the first variant Fc domain includes skew variants L368D/K370S and the second variant Fc domain includes skew variants S364K/E357Q, where the first and second variant Fc domains each include FcKO variants E233P/L234V/L235A/G236del/S267K, where the first variant Fc domain includes pI variants Q295E/N384D/Q418E/N421D, and where numbering is according to EU numbering. In some embodiments, the hinge of the first monomer and second monomer also each include amino acid substitution C220S. In certain embodiments, the first and second variant Fc domains each further include half-life extension variants M428L/N434S. In an exemplary embodiment, the IL-15 variant includes amino acid substitutions N4D/N65D, D30N/N65D, or D30N/E64Q/N65D. In an exemplary embodiment, the TIM-3 scFv includes the VH and VL of any of the TIM-3 ABDs in FIGS. 12 and 13A-C and the IL-15 variant includes amino acid substitutions N4D/N65D. In another exemplary embodiment, the TIM-3 scFv includes the VH and VL of any of the TIM-3 ABDs in FIGS. 12 and 13A-C and the IL-15 variant includes amino acid substitutions D30N/N65D. In yet another exemplary embodiment, the TIM-3 scFv includes the VH and VL of any of the TIM-3 ABDs in FIGS. 12 and 13A-C and the IL-15 variant includes amino acid substitutions D30N/E64Q/N65D.

In the dsIL-15/Rα×scFv format, one preferred embodiment utilizes an anti-TIM-3 ABD the variable heavy and light domain pair of 3H3[TIM-3]_H1_L2.1 as shown in FIG. 12 with the FIG. 21C format, the skew variant set S364K/E357Q:L368D/K370S, the pI variants Q295E/N384D/Q418E/N421D, the ablation variants E233P/L234V/L235A/G236_/S267K on both first and second monomers, and optionally the 428L/434S variants on both first and second monomers.

In one embodiment, the targeted IL-15/IL-15Rα heterodimeric protein is an "scFv×dsIL-15/Rα" format heterodimeric protein that includes: a) a first monomer that includes, from N- to C-terminus, an anti-TIM-3 scFv-(hinge)-CH2-CH3, where CH2-CH3 is a first variant Fc domain; b) a second monomer that includes, from N- to C-terminus, an IL-15Rα(sushi) domain-(domain linker)-CH2-CH3, where CH2-CH3 is a second variant Fc domain and the IL-15Rα(sushi) domain includes an amino acid substitution for a cysteine residue; and c) an IL-15 variant that includes an amino acid substitution for a cysteine residue, where the cysteine residue on the IL-15 variant and the cysteine residue on the IL-15Rα(sushi) domain form a disulfide bond, where the anti-TIM-3 scFv includes the variable heavy domain and variable light domain of 3H3[TIM-3]_H1_L2.1, where the first variant Fc domain includes skew variants L368D/K370S and the second variant Fc domain includes skew variants S364K/E357Q, where the first and second variant Fc domains each include FcKO variants E233P/L234V/L235A/G236del/S267K, where the first variant Fc domain includes pI variants Q295E/N384D/Q418E/N421D, and where numbering is according to EU numbering. In some embodiments, the hinge of the first monomer and second monomer also each include amino acid substitution C220S. In certain embodiments, the first and second variant Fc domains each further include half-life extension variants M428L/N434S. In a particular embodiment, the IL-15 variant includes amino acid substitutions N4D/N65D and the scFv includes the variable heavy and light domain pair of 3H3[TIM-3]_H1_L2.1. In one embodiment, the IL-15 variant includes amino acid substitutions D30N/N65D and the scFv includes the variable heavy and light domain pair of 3H3[TIM-3]_H1_L2.1. In yet another embodiment, the IL-15 variant includes amino acid substitutions D30N/E64Q/N65D and the scFv includes the variable heavy and light domain pair of 3H3[TIM-3]_H1_L2.1.

D. scIL-15/RαxFab

This embodiment is shown in FIG. 21D, and comprises three monomers. The first monomer comprises, from N- to C-terminus, the IL-15Rα(sushi) domain-(domain linker)-variant IL-15-domain linker-CH2-CH3 and the second monomer comprises a heavy chain, VH-CH1-hinge-CH2-CH3. The third monomer is a light chain, VL-CL. This is generally referred to as "scIL-15/RαxFab", with the "sc" standing for "single chain". The scIL-15/RαxFab format (see FIG. 21D) comprises IL-15Rα(sushi) fused to a variant IL-15 by a variable length linker (termed "scIL-15/Rα") which is then fused to the N-terminus of a heterodimeric Fc-region (inclusive of the hinge). The second monomer is a heavy chain, VH-CH1-hinge-CH2-CH3, while a corresponding light chain (the third monomer) is transfected separately so as to form a Fab with the VH.

In one embodiment, the targeted IL-15/IL-15Rα heterodimeric protein is an "scIL-15/RαxFab" format heterodimeric protein that includes: a) a first monomer that includes, from N- to C-terminus, an IL-15Rα(sushi) domain-(domain linker)-IL-15 variant-(domain linker)-CH2-CH3, where CH2-CH3 is a first Fc domain; b) a second monomer that includes, from N- to C-terminus, a VH-CH1-hinge-CH2-CH3, where VH is a variable heavy domain and CH2-CH3 is a second Fc domain, and c) a light chain that includes from, N- to C-terminus, VL-VC, where VL is a variable light domain, where VH and VL form a TIM-3 binding domain. Any useful domain linker can be used to attach the various components of the heterodimeric protein including, but not limited to those in FIGS. 8 and 9A-C. In an exemplary embodiment, the domain linkers that attach the IL-15 variant to the first Fc domain is an antibody hinge domain (e.g., an antibody hinge domain).

In the scIL-15/RαxFab format, one preferred embodiment utilizes an anti-TIM-3 ABD having any of the variable heavy and light domain pairs as shown in FIGS. 12 and 13A-C.

In the scIL-15/RαxFab format, one preferred embodiment utilizes an anti-TIM-3 ABD having the variable heavy and light domain pair of 3H3[TIM-3]_H1_L2.1 as shown in FIG. 12.

In one embodiment, 2A11_H1.144_L2.142 the targeted IL-15/IL-15Rα heterodimeric protein is an "scIL-15/Rαx Fab" format heterodimeric protein that includes: a) a first monomer that includes, from N- to C-terminus, an IL-15Rα (sushi) domain-(domain linker)-IL-15 variant-(domain linker)-CH2-CH3, where CH2-CH3 is a first Fc domain; b) a second monomer that includes, from N- to C-terminus, a VH-CH1-hinge-CH2-CH3, where VH is a variable heavy domain and CH2-CH3 is a second Fc domain, and c) a light chain that includes from, N- to C-terminus, VL-VC, where VL is a variable light domain, and where VH and VL are the variable heavy domain and variable light domain of 3H3 [TIM-3]_H1_L2.1, respectively.

In the scIL-15/RαxFab format, one preferred embodiment utilizes an IL-15 variant that includes amino acid substitutions N4D/N65D, D30N/N65D, or D30N/E64Q/N65D. In one embodiment, the targeted IL-15/IL-15Rα heterodimeric protein is an "scIL-15/RαxFab" format heterodimeric protein that includes: a) a first monomer that includes, from N- to C-terminus, an IL-15Rα(sushi) domain-(domain linker)-IL-15 variant-(domain linker)-CH2-CH3, where CH2-CH3 is a first Fc domain; b) a second monomer that includes, from N- to C-terminus, a VH-CH1-hinge-CH2-CH3, where VH is a variable heavy domain and CH2-CH3 is a second Fc domain, and c) a light chain that includes from, N- to C-terminus, VL-VC, where VL is a variable light domain, where VH and VL form a TIM-3 binding domain, and where the IL-15 variant includes amino acid substitutions N4D/N65D, D30N/N65D, or D30N/E64Q/N65D. In an exemplary embodiment, the VH and VL are the VH and VL of any of the TIM-3 ABDs in FIGS. 12 and 13A-C and the IL-15 variant includes amino acid substitutions N4D/N65D. In another exemplary embodiment, the VH and VL are the VH and VL of any of the TIM-3 ABDs in FIGS. 12 and 13A-C and the IL-15 variant includes amino acid substitutions D30N/N65D. In yet another exemplary embodiment, the VH and VL are the VH and VL of any of the TIM-3 ABDs in FIGS. 12 and 13A-C and the IL-15 variant includes amino acid substitutions D30N/E64Q/N65D.

In the scIL-15/RαxFab format, one preferred embodiment utilizes an anti-TIM-3 ABD having the variable heavy and light domain pair of 3H3[TIM-3]_H1_L2.1 as shown in FIG. 12, with either the IL-15 N4D/N65D variant or the IL-15 D30N/N65D variant or the IL-15 D30N/E64Q/N65D variant. In one embodiment, the targeted IL-15/IL-15Rα heterodimeric protein is an "scIL-15/RαxFab" format heterodimeric protein that includes: a) a first monomer that includes, from N- to C-terminus, an IL-15Rα(sushi) domain-(domain linker)-IL-15 variant-(domain linker)-CH2-CH3, where CH2-CH3 is a first Fc domain; b) a second monomer that includes, from N- to C-terminus, a VH-CH1-hinge-CH2-CH3, where VH is a variable heavy domain and CH2-CH3 is a second Fc domain, and c) a light chain that includes from, N- to C-terminus, VL-VC, where VL is a variable light domain, where VH and VL are the variable heavy domain and variable light domain of 3H3[TIM-3]_ H1_L2.1, and where the IL-15 variant includes amino acid substitutions N4D/N65D, D30N/N65D, or D30N/E64Q/N65D. In a particular embodiment, the IL-15 variant includes amino acid substitutions N4D/N65D and VH and VL are the variable heavy domain and variable light domain of 3H3[TIM-3]_H1_L2.1. In one embodiment, the IL-15 variant includes amino acid substitutions D30N/N65D and VH and VL are the variable heavy domain and variable light domain of 3H3[TIM-3]_H1_L2.1. In yet another embodiment, the IL-15 variant includes amino acid substitutions D30N/E64Q/N65D and VH and VL are the variable heavy domain and variable light domain of 3H3[TIM-3]_H1_L2.1.

In the scIL-15/RαxFab format, one preferred embodiment utilizes the skew variant pair S364K/E357Q:L368D/K370S. In one embodiment, the targeted IL-15/IL-15Rα heterodimeric protein is an "scIL-15/RαxFab" format heterodimeric protein that includes: a) a first monomer that includes, from N- to C-terminus, an IL-15Rα(sushi) domain-(domain linker)-IL-15 variant-(domain linker)-CH2-CH3, where CH2-CH3 is a first variant Fc domain; b) a second monomer that includes, from N- to C-terminus, a VH-CH1-hinge-CH2-CH3, where VH is a variable heavy domain and CH2-CH3 is a second variant Fc domain, and c)

a light chain that includes from, N- to C-terminus, VL-VC, where VL is a variable light domain, where VH and VL form a TIM-3 binding domain, and where the first and second variant Fc domains include the skew variant pair S364K/E357Q:L368D/K370S. In an exemplary embodiment, the first variant Fc domain includes skew variants L368D/K370S, and the second variant Fc domain includes skew variants S364K/E357Q. In an exemplary embodiment, the VH and VL are the VH and VL of any of the TIM-3 ABDs in FIGS. 12 and 13A-C and the IL-15 variant includes amino acid substitutions N4D/N65D. In another exemplary embodiment, the VH and VL are the VH and VL of any of the TIM-3 ABDs in FIGS. 12 and 13A-C and the IL-15 variant includes amino acid substitutions D30N/N65D. In yet another exemplary embodiment, the VH and VL are the VH and VL of any of the TIM-3 ABDs in FIGS. 12 and 13A-C and the IL-15 variant includes amino acid substitutions D30N/E64Q/N65D.

In one embodiment, the targeted IL-15/IL-15Rα heterodimeric protein is an "scIL-15/RαxFab" format heterodimeric protein that includes: a) a first monomer that includes, from N- to C-terminus, an IL-15Rα(sushi) domain-(domain linker)-IL-15 variant-(domain linker)-CH2-CH3, where CH2-CH3 is a first variant Fc domain; b) a second monomer that includes, from N- to C-terminus, a VH-CH1-hinge-CH2-CH3, where VH is a variable heavy domain and CH2-CH3 is a second variant Fc domain, and c) a light chain that includes from, N- to C-terminus, VL-VC, where VL is a variable light domain, where VH and VL form a TIM-3 binding domain, where the IL-15 variant includes amino acid substitutions N4D/N65D, D30N/N65D, or D30N/E64Q/N65D, and where the first and second variant Fc domains include the skew variant pair S364K/E357Q:L368D/K370S. In an exemplary embodiment, the first variant Fc domain includes skew variants L368D/K370S, and the second variant Fc domain includes skew variants S364K/E357Q.

In the scIL-15/RαxFab format, one preferred embodiment utilizes an anti-TIM-3 ABD having the variable heavy and light domain pair of 3H3[TIM-3]_H1_L2.1 as shown in FIG. 12 and the skew variant pair S364K/E357Q:L368D/K370S. In one embodiment, the targeted IL-15/IL-15Rα heterodimeric protein is an "scIL-15/RαxFab" format heterodimeric protein that includes: a) a first monomer that includes, from N- to C-terminus, an IL-15Rα(sushi) domain-(domain linker)-IL-15 variant-(domain linker)-CH2-CH3, where CH2-CH3 is a first variant Fc domain; b) a second monomer that includes, from N- to C-terminus, a VH-CH1-hinge-CH2-CH3, where VH is a variable heavy domain and CH2-CH3 is a second variant Fc domain, and c) a light chain that includes from, N- to C-terminus, VL-VC, where VL is a variable light domain, where VH and VL are the variable heavy domain and variable light domain of 3H3[TIM-3]_H1_L2.1, respectively, and where the first and second variant Fc domains include the skew variant pair S364K/E357Q: L368D/K370S.

In the scIL-15/RαxFab format, one preferred embodiment utilizes an anti-TIM-3 ABD having the variable heavy and light domain pair of 3H3[TIM-3]_H1_L2.1 as shown in FIG. 12 and the skew variant pair S364K/E357Q:L368D/K370S with either the IL-15 N4D/N65D variant or the IL-15 D30N/N65D variant or the IL-15 D30N/E64Q/N65D variant. In one embodiment, the targeted IL-15/IL-15Rα heterodimeric protein is an "scIL-15/RαxFab" format heterodimeric protein that includes: a) a first monomer that includes, from N- to C-terminus, an IL-15Rα(sushi) domain-(domain linker)-IL-15 variant-(domain linker)-CH2-CH3, where CH2-CH3 is a first variant Fc domain; b) a second monomer that includes, from N- to C-terminus, a VH-CH1-hinge-CH2-CH3, where VH is a variable heavy domain and CH2-CH3 is a second variant Fc domain, and c) a light chain that includes from, N- to C-terminus, VL-VC, where VL is a variable light domain, where VH and VL are the variable heavy domain and variable light domain of 3H3[TIM-3]_H1_L2.1, where the IL-15 variant includes amino acid substitutions N4D/N65D, D30N/N65D, or D30N/E64Q/N65D, and where the first and second variant Fc domains include the skew variant pair S364K/E357Q:L368D/K370S. In an exemplary embodiment, the first variant Fc domain includes skew variants L368D/K370S, and the second variant Fc domain includes skew variants S364K/E357Q. In a particular embodiment, the IL-15 variant includes amino acid substitutions N4D/N65D and VH and VL are the variable heavy domain and variable light domain of 3H3[TIM-3]_H1_L2.1. In one embodiment, the IL-15 variant includes amino acid substitutions D30N/N65D and VH and VL are the variable heavy domain and variable light domain of 3H3[TIM-3]_H1_L2.1. In another embodiment, the IL-15 variant includes amino acid substitutions D30N/E64Q/N65D and VH and VL are the variable heavy domain and variable light domain of 3H3[TIM-3]_H1_L2.1.

In the scIL-15/RαxFab format, one preferred embodiment utilizes the skew variant set S364K/E357Q:L368D/K370S, the pI variants Q295E/N384D/Q418E/N421D, the ablation variants E233P/L234V/L235A/G236_/S267K on both first and second monomers, and optionally the 428L/434S variants on both first and second monomers.

In one embodiment, the targeted IL-15/IL-15Rα heterodimeric protein is an "scIL-15/RαxFab" format heterodimeric protein that includes: a) a first monomer that includes, from N- to C-terminus, an IL-15Rα(sushi) domain-(domain linker)-IL-15 variant-(domain linker)-CH2-CH3, where CH2-CH3 is a first variant Fc domain; b) a second monomer that includes, from N- to C-terminus, a VH-CH1-hinge-CH2-CH3, where VH is a variable heavy domain and CH2-CH3 is a second variant Fc domain, and c) a light chain that includes from, N- to C-terminus, VL-VC, where VL is a variable light domain, where VH and VL form a TIM-3 binding domain, where the first variant Fc domain includes skew variants L368D/K370S and the second variant Fc domain includes skew variants S364K/E357Q, where the first and second variant Fc domains each include FcKO variants E233P/L234V/L235A/G236del/S267K, where the first variant Fc domain includes pI variants Q295E/N384D/Q418E/N421D, and where numbering is according to EU numbering. In some embodiments, the hinge of the first monomer also includes amino acid substitution C220S. In certain embodiments, the first and second variant Fc domains each further include half-life extension variants M428L/N434S. In an exemplary embodiment, the IL-15 variant includes amino acid substitutions N4D/N65D, D30N/N65D, or D30N/E64Q/N65D. In an exemplary embodiment, the VH and VL are the VH and VL of any of the TIM-3 ABDs in FIGS. 12 and 13A-C and the IL-15 variant includes amino acid substitutions N4D/N65D. In another exemplary embodiment, the VH and VL are the VH and VL of any of the TIM-3 ABDs in FIGS. 12 and 13A-C and the IL-15 variant includes amino acid substitutions D30N/N65D. In yet another exemplary embodiment, the VH and VL are the VH and VL of any of the TIM-3 ABDs in FIGS. 12 and 13A-C and the IL-15 variant includes amino acid substitutions D30N/E64Q/N65D.

In the scIL-15/RαxFab format, one preferred embodiment utilizes an anti-TIM-3 ABD the variable heavy and light domain pair of 3H3[TIM-3]_H1_L2.1 as shown in FIG. 12 with the FIG. 21D format, the skew variant set S364K/E357Q:L368D/K370S, the pI variants Q295E/ N384D/Q418E/N421D, the ablation variants E233P/L234V/ L235A/G236_/S267K on both first and second monomers, and optionally the 428L/434S variants on both first and second monomers.

In one embodiment, the targeted IL-15/IL-15Rα heterodimeric protein is an "scIL-15/Rα×Fab" format heterodimeric protein that includes: a) a first monomer that includes, from N- to C-terminus, an IL-15Rα(sushi) domain-(domain linker)-IL-15 variant-(domain linker)-CH2-CH3, where CH2-CH3 is a first variant Fc domain; b) a second monomer that includes, from N- to C-terminus, a VH-CH1-hinge-CH2-CH3, where VH is a variable heavy domain and CH2-CH3 is a second variant Fc domain, and c) a light chain that includes from, N- to C-terminus, VL-VC, where VL is a variable light domain, where VH and VL are the variable heavy domain and variable light domain of 3H3[TIM-3]_ H1_L2.1, where the first variant Fc domain includes skew variants L368D/K370S and the second variant Fc domain includes skew variants S364K/E357Q, where the first and second variant Fc domains each include FcKO variants E233P/L234V/L235A/G236del/S267K, where the first variant Fc domain includes pI variants Q295E/N384D/Q418E/ N421D, and where numbering is according to EU numbering. In some embodiments, the hinge of the first monomer also includes amino acid substitution C220S. In certain embodiments, the first and second variant Fc domains each further include half-life extension variants M428L/N434S. In a particular embodiment, the IL-15 variant includes amino acid substitutions N4D/N65D and the scFv includes the variable heavy and light domain pair of 3H3[TIM-3]_ H1_L2.1. In one embodiment, the IL-15 variant includes amino acid substitutions D30N/N65D and the scFv includes the variable heavy and light domain pair of 3H3[TIM-3]_ H1_L2.1. In yet another embodiment, the IL-15 variant includes amino acid substitutions D30N/E64Q/N65D and the scFv includes the variable heavy and light domain pair of 3H3[TIM-3]_H1_L2.1.

E. Fab×ncIL-15/Rα

Figure 21E:
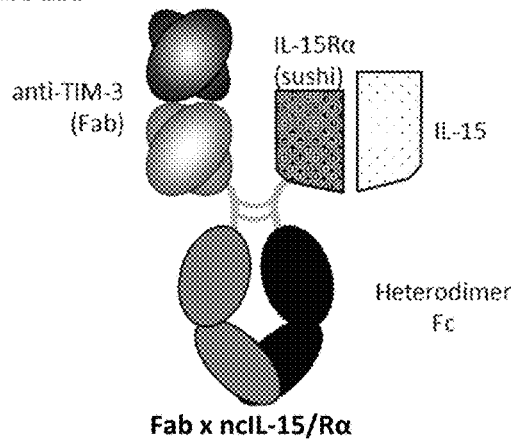

This embodiment is shown in FIG. 21E, and comprises four monomers. The first monomer comprises, from N- to C-terminus, the IL-15Rα(sushi)domain-(domain linker)-CH2-CH3, and the second monomer comprises a heavy chain, VH-CH1-hinge-CH2-CH3. The third monomer is the light chain that includes, from N- to C-terminus, a variable light domain (VL) and a light constant domain (CL). The fourth monomer is a variant IL-15 domain. This is generally referred to as "Fab×ncIL-15/Rα", with the "nc" standing for "non-covalent" referring to the self-assembling non-covalent attachment of the IL-15 variant and IL-15Rα(sushi) domain.

In one embodiment, the targeted IL-15/IL-15Rα heterodimeric protein is an "Fab×ncIL-15/Rα" format heterodimeric protein that includes: a) a first monomer that includes, from N- to C-terminus, a VH-CH1-hinge-CH2-CH3, where VH is a variable heavy domain and CH2-CH3 is a first Fc domain; b) a second monomer that includes, from N- to C-terminus, an IL-15Rα(sushi) domain-(domain linker)-CH2-CH3, where CH2-CH3 is a second Fc domain; c) a third monomer that includes from, N- to C-terminus, VL-VC, where VL is a variable light domain, and d) a fourth monomer comprising an IL-15 variant, where the VH and the VL form a TIM-3 binding domain, and where the IL-15 and IL-15Rα(sushi) domain form an IL-15 complex. Any useful domain linker can be used to attach the various components of the heterodimeric protein including, but not limited to those in FIGS. 8 and 9A-C. In an exemplary embodiment, the domain linkers that attach the IL-15Rα(sushi) domain to the second Fc domain is an antibody hinge domain (e.g., an antibody hinge domain).

In the Fab×ncIL-15/Rα format, one preferred embodiment utilizes an anti-TIM-3 ABD having any of the variable heavy and light domain pairs as shown in FIG. 12.

In the Fab×ncIL-15/Rα format, one preferred embodiment utilizes an anti-TIM-3 ABD having the variable heavy and light domain pair of 3H3[TIM-3]_H1_L2.1 as shown in FIG. 12.

In one embodiment, the targeted IL-15/IL-15Rα heterodimeric protein is a "Fab×ncIL-15/Rα" format heterodimeric protein that includes: a) a first monomer that includes, from N- to C-terminus, a VH-CH1-hinge-CH2-CH3, where VH is a variable heavy domain and CH2-CH3 is a first Fc domain; b) a second monomer that includes, from N- to C-terminus, an IL-15Rα(sushi) domain-(domain linker)-CH2-CH3, where CH2-CH3 is a second Fc domain; c) a third monomer that includes from, N- to C-terminus, VL-VC, where VL is a variable light domain, and d) a fourth monomer comprising an IL-15 variant, where the VH and the VL are the variable heavy domain and variable light domain of 3H3 [TIM-3]_H1_L2.1, respectively, and where the IL-15 and IL-15Rα(sushi) domain form an IL-15 complex.

In the Fab×ncIL-15/Rα format, one preferred embodiment utilizes an IL-15 variant that includes amino acid substitutions N4D/N65D, D30N/N65D, or D30N/E64Q/ N65D. In one embodiment, the targeted IL-15/IL-15Rα heterodimeric protein is a "Fab×ncIL-15/Rα" format heterodimeric protein that includes: a) a first monomer that includes, from N- to C-terminus, a VH-CH1-hinge-CH2-CH3, where VH is a variable heavy domain and CH2-CH3 is a first Fc domain; b) a second monomer that includes, from N- to C-terminus, an IL-15Rα(sushi) domain-(domain linker)-CH2-CH3, where CH2-CH3 is a second Fc domain; c) a third monomer that includes from, N- to C-terminus, VL-VC, where VL is a variable light domain, and d) a fourth monomer comprising an IL-15 variant, where the VH and the VL form a TIM-3 binding domain, where the IL-15 and IL-15Rα(sushi) domain form an IL-15 complex, and where the IL-15 variant includes amino acid substitutions N4D/ N65D, D30N/N65D, or D30N/E64Q/N65D. In an exemplary embodiment, the VH and VL are the VH and VL of any of the TIM-3 ABDs in FIGS. 12 and 13A-C and the IL-15 variant includes amino acid substitutions N4D/N65D. In another exemplary embodiment, the VH and VL are the VH and VL of any of the TIM-3 ABDs in FIGS. 12 and 13A-C and the IL-15 variant includes amino acid substitutions D30N/N65D. In yet another exemplary embodiment, the VH and VL are the VH and VL of any of the TIM-3 ABDs in FIGS. 12 and 13A-C and the IL-15 variant includes amino acid substitutions D30N/E64Q/N65D.

In the Fab×ncIL-15/Rα format, one preferred embodiment utilizes an anti-TIM-3 ABD having the variable heavy and light domain pair of 3H3[TIM-3]_H1_L2.1 as shown in FIG. 12, with either the IL-15 N4D/N65D variant or the IL-15 D30N/N65D variant or the IL-15 D30N/E64Q/N65D variant. In one embodiment, the targeted IL-15/IL-15Rα heterodimeric protein is a "Fab×ncIL-15/Rα" format heterodimeric protein that includes: a) a first monomer that includes, from N- to C-terminus, a VH-CH1-hinge-CH2-CH3, where VH is a variable heavy domain and CH2-CH3 is a first Fc domain; b) a second monomer that includes, from N- to C-terminus, an IL-15Rα(sushi) domain-(domain linker)-CH2-CH3, where CH2-CH3 is a second Fc domain;

c) a third monomer that includes from, N- to C-terminus, VL-VC, where VL is a variable light domain, and d) a fourth monomer comprising an IL-15 variant, where the VH and the VL form a TIM-3 binding domain, where the IL-15 and IL-15Rα(sushi) domain form an IL-15 complex, where VH and VL are the variable heavy domain and variable light domain of 3H3[TIM-3]_H1_L2.1, and where the IL-15 variant includes amino acid substitutions N4D/N65D, D30N/N65D, or D30N/E64Q/N65D. In a particular embodiment, the IL-15 variant includes amino acid substitutions N4D/N65D and VH and VL are the variable heavy domain and variable light domain of 3H3[TIM-3]_H1_L2.1. In one embodiment, the IL-15 variant includes amino acid substitutions D30N/N65D and VH and VL are the variable heavy domain and variable light domain of 3H3[TIM-3]_H1_L2.1. In yet another embodiment, the IL-15 variant includes amino acid substitutions D30N/E64Q/N65D and VH and VL are the variable heavy domain and variable light domain of 3H3[TIM-3]_H1_L2.1.

In the FabxncIL-15/Rα format, one preferred embodiment utilizes the skew variant pair S364K/E357Q:L368D/K370S. In one embodiment, the targeted IL-15/IL-15Rα heterodimeric protein is an "FabxncIL-15/Rα" format heterodimeric protein that includes: a) a first monomer that includes, from N- to C-terminus, a VH-CH1-hinge-CH2-CH3, where VH is a variable heavy domain and CH2-CH3 is a first variant Fc domain; b) a second monomer that includes, from N- to C-terminus, an IL-15Rα(sushi) domain-(domain linker)-CH2-CH3, where CH2-CH3 is a second variant Fc domain; c) a third monomer that includes from, N- to C-terminus, VL-VC, where VL is a variable light domain, and d) a fourth monomer comprising an IL-15 variant, where the VH and the VL form a TIM-3 binding domain, where the IL-15 and IL-15Rα(sushi) domain form an IL-15 complex, and where the first and second variant Fc domains include the skew variant pair S364K/E357Q:L368D/K370S. In an exemplary embodiment, the first variant Fc domain includes skew variants L368D/K370S, and the second variant Fc domain includes skew variants S364K/E357Q.

In one embodiment, the targeted IL-15/IL-15Rα heterodimeric protein is an "FabxncIL-15/Rα" format heterodimeric protein that includes: a) a first monomer that includes, from N- to C-terminus, a VH-CH1-hinge-CH2-CH3, where VH is a variable heavy domain and CH2-CH3 is a first variant Fc domain; b) a second monomer that includes, from N- to C-terminus, an IL-15Rα(sushi) domain-(domain linker)-CH2-CH3, where CH2-CH3 is a second variant Fc domain; c) a third monomer that includes from, N- to C-terminus, VL-VC, where VL is a variable light domain, and d) a fourth monomer comprising an IL-15 variant, where the VH and the VL form a TIM-3 binding domain, where the IL-15 and IL-15Rα(sushi) domain form an IL-15 complex, where the IL-15 variant includes amino acid substitutions N4D/N65D, D30N/N65D, or D30N/E64Q/N65D, and where the first and second variant Fc domains include the skew variant pair S364K/E357Q:L368D/K370S. In an exemplary embodiment, the first variant Fc domain includes skew variants L368D/K370S, and the second variant Fc domain includes skew variants S364K/E357Q. In an exemplary embodiment, the VH and VL are the VH and VL of any of the TIM-3 ABDs in FIGS. 12 and 13A-C and the IL-15 variant includes amino acid substitutions N4D/N65D. In another exemplary embodiment, the VH and VL are the VH and VL of any of the TIM-3 ABDs in FIGS. 12 and 13A-C and the IL-15 variant includes amino acid substitutions D30N/N65D. In yet another exemplary embodiment, the VH and VL are the VH and VL of any of the TIM-3 ABDs in FIGS. 12 and 13A-C and the IL-15 variant includes amino acid substitutions D30N/E64Q/N65D.

In the FabxncIL-15/Rα format, one preferred embodiment utilizes an anti-TIM-3 ABD having the variable heavy and light domain pair of 3H3[TIM-3]_H1_L2.1 as shown in FIG. 12 and the skew variant pair S364K/E357Q:L368D/K370S. In one embodiment, the targeted IL-15/IL-15Rα heterodimeric protein is a "FabxncIL-15/Rα" format heterodimeric protein that includes: a) a first monomer that includes, from N- to C-terminus, a VH-CH1-hinge-CH2-CH3, where VH is a variable heavy domain and CH2-CH3 is a first variant Fc domain; b) a second monomer that includes, from N- to C-terminus, an IL-15Rα(sushi) domain-(domain linker)-CH2-CH3, where CH2-CH3 is a second variant Fc domain; c) a third monomer that includes from, N- to C-terminus, VL-VC, where VL is a variable light domain, and d) a fourth monomer comprising an IL-15 variant, where the VH and the VL are the variable heavy domain and variable light domain of 3H3[TIM-3]_H1_L2.1, respectively, where the IL-15 and IL-15Rα(sushi) domain form an IL-15 complex and where the first and second variant Fc domains include the skew variant pair S364K/E357Q:L368D/K370S.

In the FabxncIL-15/Rα format, one preferred embodiment utilizes an anti-TIM-3 ABD having the variable heavy and light domain pair of 3H3[TIM-3]_H1_L2.1 as shown in FIG. 12 and the skew variant pair S364K/E357Q:L368D/K370S with either the IL-15 N4D/N65D variant or the IL-15 D30N/N65D variant or the IL-15 D30N/E64Q/N65D variant.

In one embodiment, the targeted IL-15/IL-15Rα heterodimeric protein is a "FabxncIL-15/Rα" format heterodimeric protein that includes: a) a first monomer that includes, from N- to C-terminus, a VH-CH1-hinge-CH2-CH3, where VH is a variable heavy domain and CH2-CH3 is a first variant Fc domain; b) a second monomer that includes, from N- to C-terminus, an IL-15Rα(sushi) domain-(domain linker)-CH2-CH3, where CH2-CH3 is a second variant Fc domain; c) a third monomer that includes from, N- to C-terminus, VL-VC, where VL is a variable light domain, and d) a fourth monomer comprising an IL-15 variant, where the VH and the VL form a TIM-3 binding domain, where the IL-15 and IL-15Rα(sushi) domain form an IL-15 complex, where VH and VL are the variable heavy domain and variable light domain of 3H3[TIM-3]_H1_L2.1, where the IL-15 variant includes amino acid substitutions N4D/N65D, D30N/N65D, or D30N/E64Q/N65D, and where the first and second variant Fc domains include the skew variant pair S364K/E357Q:L368D/K370S. In an exemplary embodiment, the first variant Fc domain includes skew variants L368D/K370S, and the second variant Fc domain includes skew variants S364K/E357Q. In a particular embodiment, the IL-15 variant includes amino acid substitutions N4D/N65D and VH and VL are the variable heavy domain and variable light domain of 3H3[TIM-3]_H1_L2.1. In one embodiment, the IL-15 variant includes amino acid substitutions D30N/N65D and VH and VL are the variable heavy domain and variable light domain of 3H3[TIM-3]_H1_L2.1. In another embodiment, the IL-15 variant includes amino acid substitutions D30N/E64Q/N65D and VH and VL are the variable heavy domain and variable light domain of 3H3[TIM-3]_H1_L2.1.

In the FabxncIL-15/Rα format, one preferred embodiment utilizes the skew variant set S364K/E357Q:L368D/K370S, the pI variants Q295E/N384D/Q418E/N421D, the ablation variants E233P/L234V/L235A/G236_/S267K on both first and second monomers, and optionally the 428L/434S variants on both first and second monomers.

In one embodiment, the targeted IL-15/IL-15Rα heterodimeric protein is a "Fab×ncIL-15/Rα" format heterodimeric protein that includes: a) a first monomer that includes, from N- to C-terminus, a VH-CH1-hinge-CH2-CH3, where VH is a variable heavy domain and CH2-CH3 is a first variant Fc domain; b) a second monomer that includes, from N- to C-terminus, an IL-15Rα(sushi) domain-(domain linker)-CH2-CH3, where CH2-CH3 is a second variant Fc domain; c) a third monomer that includes from, N- to C-terminus, VL-VC, where VL is a variable light domain, and d) a fourth monomer comprising an IL-15 variant, where the VH and the VL form a TIM-3 binding domain, where the IL-15 and IL-15Rα(sushi) domain form an IL-15 complex, where the first variant Fc domain includes skew variants L368D/K370S and the second variant Fc domain includes skew variants S364K/E357Q, where the first and second variant Fc domains each include FcKO variants E233P/L234V/L235A/G236del/S267K, where the hinge-first variant Fc domain of the first monomer includes pI variants N208D/Q295E/N384D/Q418E/N421D, and where numbering is according to EU numbering. In some embodiments, the hinge of the second monomer also includes amino acid substitution C220S. In certain embodiments, the first and second variant Fc domains each further include half-life extension variants M428L/N434S. In an exemplary embodiment, the IL-15 variant includes amino acid substitutions N4D/N65D, D30N/N65D, or D30N/E64Q/N65D. In an exemplary embodiment, the VH and VL are the VH and VL of any of the TIM-3 ABDs in FIGS. 12 and 13A-C and the IL-15 variant includes amino acid substitutions N4D/N65D. In another exemplary embodiment, the VH and VL are the VH and VL of any of the TIM-3 ABDs in FIGS. 12 and 13A-C and the IL-15 variant includes amino acid substitutions D30N/N65D. In yet another exemplary embodiment, the VH and VL are the VH and VL of any of the TIM-3 ABDs in FIGS. 12 and 13A-C and the IL-15 variant includes amino acid substitutions D30N/E64Q/N65D.

In the Fab×ncIL-15/Rα format, one preferred embodiment utilizes an anti-TIM-3 ABD the variable heavy and light domain pair of 3H3[TIM-3]_H1_L2.1 as shown in FIG. 12 with the FIG. 21E format, the skew variant set S364K/E357Q:L368D/K370S, the pI variants Q295E/N384D/Q418E/N421D, the ablation variants E233P/L234V/L235A/G236_/S267K on both first and second monomers, and optionally the 428L/434S variants on both first and second monomers.

In one embodiment, the targeted IL-15/IL-15Rα heterodimeric protein is a "Fab×ncIL-15/Rα" format heterodimeric protein that includes: a) a first monomer that includes, from N- to C-terminus, a VH-CH1-hinge-CH2-CH3, where VH is a variable heavy domain and CH2-CH3 is a first variant Fc domain; b) a second monomer that includes, from N- to C-terminus, an IL-15Rα(sushi) domain-(domain linker)-CH2-CH3, where CH2-CH3 is a second variant Fc domain; c) a third monomer that includes from, N- to C-terminus, VL-VC, where VL is a variable light domain, and d) a fourth monomer comprising an IL-15 variant, where the VH and the VL form a TIM-3 binding domain, where the IL-15 and IL-15Rα(sushi) domain form an IL-15 complex, where VH and VL are the variable heavy domain and variable light domain of 3H3[TIM-3]_H1_L2.1, where the first variant Fc domain includes skew variants L368D/K370S and the second variant Fc domain includes skew variants S364K/E357Q, where the first and second variant Fc domains each include FcKO variants E233P/L234V/L235A/G236del/S267K, where the hinge-first variant Fc domain of the first monomer includes pI variants N208D/Q295E/N384D/Q418E/N421D, and where numbering is according to EU numbering. In some embodiments, the hinge of the second monomer also includes amino acid substitution C220S. In certain embodiments, the first and second variant Fc domains each further include half-life extension variants M428L/N434S. In a particular embodiment, the IL-15 variant includes amino acid substitutions N4D/N65D and VH and VL are the variable heavy domain and variable light domain of 3H3[TIM-3]_H1_L2.1. In one embodiment, the IL-15 variant includes amino acid substitutions D30N/N65D and VH and VL are the variable heavy domain and variable light domain of 3H3[TIM-3]_H1_L2.1. In another embodiment, the IL-15 variant includes amino acid substitutions D30N/E64Q/N65D and VH and VL are the variable heavy domain and variable light domain of 3H3[TIM-3]_H1_L2.1.

F. Fab×dsIL-15/Rα

Figure 21F:
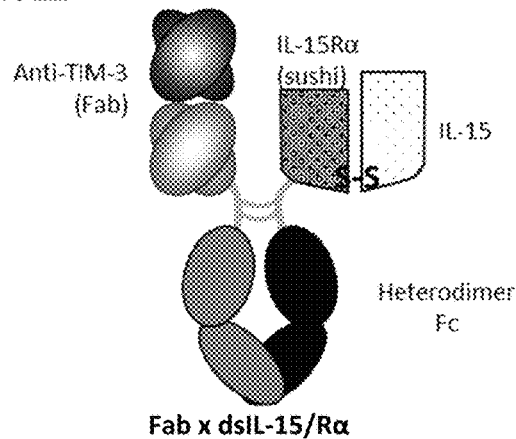

This embodiment is shown in FIG. 21F, and comprises four monomers. The first monomer comprises, from N- to C-terminus, the IL-15Rα(sushi)domain-domain linker-CH2-CH3, wherein the IL-15Rα(sushi)domain has been engineered to contain a cysteine residue, and the second monomer comprises a heavy chain, VH-CH1-hinge-CH2-CH3. The third monomer is a light chain that includes, from N- to C-terminus, a variable light domain (VL) and a constant light domain (CL). The fourth monomer is the variant IL-15 domain, also engineered to have a cysteine residue, such that a disulfide bridge is formed under native cellular conditions. This is generally referred to as "Fab×dsIL-15/Rα", with the "ds" standing for "disulfide".

In one embodiment, the targeted IL-15/IL-15Rα heterodimeric protein is an "Fab×dsIL-15/Rα" format heterodimeric protein that includes: a) a first monomer that includes, from N- to C-terminus, a VH-hinge-CH2-CH3, where VH is a variable heavy domain and CH2-CH3 is a first Fc domain; b) a second monomer that includes, from N- to C-terminus, an IL-15Rα(sushi) domain-(domain linker)-CH2-CH3, where CH2-CH3 is a second Fc domain and the IL-15Rα (sushi) domain includes an amino acid substitution for a cysteine residue; c) a third monomer that includes, from N- to C-terminus, a VL-CL, where VL is a variable light domain; and d) an IL-15 variant that includes an amino acid substitution for a cysteine residue, where the VH and VL form a TIM-3 binding domain, and where the cysteine residue on the IL-15 variant and the cysteine residue on the IL-15Rα(sushi) domain form a disulfide bond. Any useful domain linker can be used to attach the various components of the heterodimeric protein including, but not limited to those in FIGS. 8 and 9A-C. In an exemplary embodiment, the domain linkers that attach the IL-15Rα(sushi) domain to the second Fc domain is an antibody hinge domain (e.g., an antibody hinge domain).

In the Fab×dsIL-15/Rα format, one preferred embodiment utilizes an anti-TIM-3 ABD having any of the variable heavy and light domain pairs as shown in FIG. 12.

In the Fab×dsIL-15/Rα format, one preferred embodiment utilizes an anti-TIM-3 ABD having the variable heavy and light domain pair of 3H3[TIM-3]_H1_L2.1 as shown in FIG. 12.

In one embodiment, the targeted IL-15/IL-15Rα heterodimeric protein is an "Fab×dsIL-15/Rα" format heterodimeric protein that includes: a) a first monomer that includes, from N- to C-terminus, a VH-hinge-CH2-CH3, where VH is a variable heavy domain and CH2-CH3 is a first Fc domain; b) a second monomer that includes, from N- to C-terminus, an IL-15Rα(sushi) domain-(domain linker)-CH2-CH3, where CH2-CH3 is a second Fc domain and the IL-15Rα (sushi) domain includes an amino acid substitution for a cysteine residue; c) a third monomer that includes, from N- to C-terminus, a VL-CL, where VL is a variable light domain; and d) an IL-15 variant that includes an amino acid substitution for a cysteine residue, where the VH and VL are the variable heavy domain and variable light domain of 3H3[TIM-3]_H1_L2.1, respectively, and where the cysteine residue on the IL-15 variant and the cysteine residue on the IL-15Rα(sushi) domain form a disulfide bond.

In the Fab×dsIL-15/Rα format, one preferred embodiment utilizes an IL-15 variant that includes amino acid substitutions N4D/N65D, D30N/N65D, or D30N/E64Q/N65D, with the appropriate cysteine amino acid substitutions. In one embodiment, the targeted IL-15/IL-15Rα heterodimeric protein is an "Fab×dsIL-15/Rα" format heterodimeric protein that includes: a) a first monomer that includes, from N- to C-terminus, a VH-hinge-CH2-CH3, where VH is a variable heavy domain and CH2-CH3 is a first Fc domain; b) a second monomer that includes, from N- to C-terminus, an IL-15Rα(sushi) domain-(domain linker)-CH2-CH3, where CH2-CH3 is a second Fc domain and the IL-15Rα(sushi) domain includes an amino acid substitution for a cysteine residue; c) a third monomer that includes, from N- to C-terminus, a VL-CL, where VL is a variable light domain; and d) an IL-15 variant that includes an amino acid substitution for a cysteine residue, where the VH and VL form a TIM-3 binding domain, where the cysteine residue on the IL-15 variant and the cysteine residue on the IL-15Rα(sushi) domain form a disulfide bond, and where the IL-15 variant includes amino acid substitutions N4D/N65D, D30N/N65D, or D30N/E64Q/N65D. In an exemplary embodiment, the VH and VL are the VH and VL of any of the TIM-3 ABDs in FIGS. 12 and 13A-C and the IL-15 variant includes amino acid substitutions N4D/N65D. In another exemplary embodiment, the VH and VL are the VH and VL of any of the TIM-3 ABDs in FIGS. 12 and 13A-C and the IL-15 variant includes amino acid substitutions D30N/N65D. In yet another exemplary embodiment, the VH and VL are the VH and VL of any of the TIM-3 ABDs in FIGS. 12 and 13A-C and the IL-15 variant includes amino acid substitutions D30N/E64Q/N65D.

In the Fab×dsIL-15/Rα format, one preferred embodiment utilizes an anti-TIM-3 ABD having the variable heavy and light domain pair of 3H3[TIM-3]_H1_L2.1 as shown in FIG. 12, with either the IL-15 N4D/N65D variant or the IL-15 D30N/N65D variant or the IL-15 D30N/E64Q/N65D variant, with the appropriate cysteine amino acid substitutions. In one embodiment, the targeted IL-15/IL-15Rα heterodimeric protein is an "Fab×dsIL-15/Rα" format heterodimeric protein that includes: a) a first monomer that includes, from N- to C-terminus, a VH-hinge-CH2-CH3, where VH is a variable heavy domain and CH2-CH3 is a first Fc domain; b) a second monomer that includes, from N- to C-terminus, an IL-15Rα(sushi) domain-(domain linker)-CH2-CH3, where CH2-CH3 is a second Fc domain and the IL-15Rα (sushi) domain includes an amino acid substitution for a cysteine residue; c) a third monomer that includes, from N- to C-terminus, a VL-CL, where VL is a variable light domain; and d) an IL-15 variant that includes an amino acid substitution for a cysteine residue, where the VH and VL form a TIM-3 binding domain, where the cysteine residue on the IL-15 variant and the cysteine residue on the IL-15Rα (sushi) domain form a disulfide bond, where VH and VL are the variable heavy domain and variable light domain of 3H3[TIM-3]_H1_L2.1, and where the IL-15 variant includes amino acid substitutions N4D/N65D, D30N/N65D, or D30N/E64Q/N65D. In a particular embodiment, the IL-15 variant includes amino acid substitutions N4D/N65D and VH and VL are the variable heavy domain and variable light domain of 3H3[TIM-3]_H1_L2.1. In one embodiment, the IL-15 variant includes amino acid substitutions D30N/N65D and VH and VL are the variable heavy domain and variable light domain of 3H3[TIM-3]_H1_L2.1. In another embodiment, the IL-15 variant includes amino acid substitutions D30N/E64Q/N65D and VH and VL are the variable heavy domain and variable light domain of 3H3[TIM-3]_H1_L2.1.

In the Fab×dsIL-15/Rα format, one preferred embodiment utilizes the skew variant pair S364K/E357Q:L368D/K370S. In one embodiment, the targeted IL-15/IL-15Rα heterodimeric protein is an "Fab×dsIL-15/Rα" format heterodimeric protein that includes: a) a first monomer that includes, from N- to C-terminus, a VH-hinge-CH2-CH3, where VH is a variable heavy domain and CH2-CH3 is a first variant Fc domain; b) a second monomer that includes, from N- to C-terminus, an IL-15Rα(sushi) domain-(domain linker)-CH2-CH3, where CH2-CH3 is a second variant Fc domain and the IL-15Rα(sushi) domain includes an amino acid substitution for a cysteine residue; c) a third monomer that includes, from N- to C-terminus, a VL-CL, where VL is a variable light domain; and d) an IL-15 variant that includes an amino acid substitution for a cysteine residue, where the VH and VL form a TIM-3 binding domain, where the cysteine residue on the IL-15 variant and the cysteine residue on the IL-15Rα(sushi) domain form a disulfide bond, and where the first and second variant Fc domains include the skew variant pair S364K/E357Q:L368D/K370S. In an exemplary embodiment, the first variant Fc domain includes skew variants L368D/K370S, and the second variant Fc domain includes skew variants S364K/E357Q.

In one embodiment, the targeted IL-15/IL-15Rα heterodimeric protein is an "Fab×dsIL-15/Rα" format heterodimeric protein that includes: a) a first monomer that includes, from N- to C-terminus, a VH-hinge-CH2-CH3, where VH is a variable heavy domain and CH2-CH3 is a first variant Fc domain; b) a second monomer that includes, from N- to C-terminus, an IL-15Rα(sushi) domain-(domain linker)-CH2-CH3, where CH2-CH3 is a second variant Fc domain and the IL-15Rα(sushi) domain includes an amino acid substitution for a cysteine residue; c) a third monomer that includes, from N- to C-terminus, a VL-CL, where VL is a variable light domain; and d) an IL-15 variant that includes an amino acid substitution for a cysteine residue, where the VH and VL form a TIM-3 binding domain, where the cysteine residue on the IL-15 variant and the cysteine residue on the IL-15Rα(sushi) domain form a disulfide bond, where the IL-15 variant includes amino acid substitutions N4D/N65D, D30N/N65D, or D30N/E64Q/N65D, and where the first and second variant Fc domains include the skew variant pair S364K/E357Q:L368D/K370S. In an exemplary embodiment, the first variant Fc domain includes skew variants L368D/K370S, and the second variant Fc domain includes skew variants S364K/E357Q. In an exemplary embodiment, the VH and VL are the VH and VL of any of the TIM-3 ABDs in FIGS. 12 and 13A-C and the IL-15 variant includes amino acid substitutions N4D/N65D. In another exemplary embodiment, the VH and VL are the VH and VL of any of the TIM-3 ABDs in FIGS. 12 and 13A-C and the IL-15 variant includes amino acid substitutions D30N/N65D. In yet another exemplary embodiment, the VH and VL are the VH and VL of any of the TIM-3 ABDs in FIGS. 12 and 13A-C and the IL-15 variant includes amino acid substitutions D30N/E64Q/N65D.

In the FabxdsIL-15/Rα format, one preferred embodiment utilizes an anti-TIM-3 ABD having the variable heavy and light domain pair of 3H3[TIM-3]_H1_L2.1 as shown in FIG. 12 and the skew variant pair S364K/E357Q:L368D/K370S. In one embodiment, the targeted IL-15/IL-15Rα heterodimeric protein is an "FabxdsIL-15/Rα" format heterodimeric protein that includes: a) a first monomer that includes, from N- to C-terminus, a VH-hinge-CH2-CH3, where VH is a variable heavy domain and CH2-CH3 is a first variant Fc domain; b) a second monomer that includes, from N- to C-terminus, an IL-15Rα(sushi) domain-(domain linker)-CH2-CH3, where CH2-CH3 is a variant second Fc domain and the IL-15Rα(sushi) domain includes an amino acid substitution for a cysteine residue; c) a third monomer that includes, from N- to C-terminus, a VL-CL, where VL is a variable light domain; and d) an IL-15 variant that includes an amino acid substitution for a cysteine residue, where the VH and VL are the variable heavy domain and variable light domain of 3H3[TIM-3]_H1_L2.1, respectively, where the cysteine residue on the IL-15 variant and the cysteine residue on the IL-15Rα(sushi) domain form a disulfide bond, and where the first and second variant Fc domains include the skew variant pair S364K/E357Q: L368D/K370S.

In the FabxdsIL-15/Rα format, one preferred embodiment utilizes an anti-TIM-3 ABD having the variable heavy and light domain pair of 3H3[TIM-3]_H1_L2.1 as shown in FIG. 12 and the skew variant pair S364K/E357Q:L368D/K370S with either the IL-15 N4D/N65D variant or the IL-15 D30N/N65D variant or the IL-15 D30N/E64Q/N65D variant with appropriate cysteine substitutions. In one embodiment, the targeted IL-15/IL-15Rα heterodimeric protein is an "FabxdsIL-15/Rα" format heterodimeric protein that includes: a) a first monomer that includes, from N- to C-terminus, a VH-hinge-CH2-CH3, where VH is a variable heavy domain and CH2-CH3 is a first variant Fc domain; b) a second monomer that includes, from N- to C-terminus, an IL-15Rα(sushi) domain-(domain linker)-CH2-CH3, where CH2-CH3 is a second variant Fc domain and the IL-15Rα(sushi) domain includes an amino acid substitution for a cysteine residue; c) a third monomer that includes, from N- to C-terminus, a VL-CL, where VL is a variable light domain; and d) an IL-15 variant that includes an amino acid substitution for a cysteine residue, where the VH and VL form a TIM-3 binding domain, where the cysteine residue on the IL-15 variant and the cysteine residue on the IL-15Rα(sushi) domain form a disulfide bond, where VH and VL are the variable heavy domain and variable light domain of 3H3[TIM-3]_H1_L2.1, where the IL-15 variant includes amino acid substitutions N4D/N65D, D30N/N65D, or D30N/E64Q/N65D, and where the first and second variant Fc domains include the skew variant pair S364K/E357Q: L368D/K370S. In a particular embodiment, the IL-15 variant includes amino acid substitutions N4D/N65D and VH and VL are the variable heavy domain and variable light domain of 3H3[TIM-3]_H1_L2.1. In one embodiment, the IL-15 variant includes amino acid substitutions D30N/N65D and VH and VL are the variable heavy domain and variable light domain of 3H3[TIM-3]_H1_L2.1. In another embodiment, the IL-15 variant includes amino acid substitutions D30N/E64Q/N65D and VH and VL are the variable heavy domain and variable light domain of 3H3[TIM-3]_H1_L2.1.

In the FabxdsIL-15/Rα format, one preferred embodiment utilizes the skew variant set S364K/E357Q:L368D/K370S, the pI variants Q295E/N384D/Q418E/N421D, the ablation variants E233P/L234V/L235A/G236_/S267K on both first and second monomers, and optionally the 428L/434S variants on both first and second monomers.

In one embodiment, the targeted IL-15/IL-15Rα heterodimeric protein is an "FabxdsIL-15/Rα" format heterodimeric protein that includes: a) a first monomer that includes, from N- to C-terminus, a VH-hinge-CH2-CH3, where VH is a variable heavy domain and CH2-CH3 is a first variant Fc domain; b) a second monomer that includes, from N- to C-terminus, an IL-15Rα(sushi) domain-(domain linker)-CH2-CH3, where CH2-CH3 is a second variant Fc domain and the IL-15Rα(sushi) domain includes an amino acid substitution for a cysteine residue; c) a third monomer that includes, from N- to C-terminus, a VL-CL, where VL is a variable light domain; and d) an IL-15 variant that includes an amino acid substitution for a cysteine residue, where the VH and VL form a TIM-3 binding domain, where the cysteine residue on the IL-15 variant and the cysteine residue on the IL-15Rα(sushi) domain form a disulfide bond, where the first variant Fc domain includes skew variants L368D/K370S and the second variant Fc domain includes skew variants S364K/E357Q, where the first and second variant Fc domains each include FcKO variants E233P/L234V/L235A/G236del/S267K, where the hinge-first variant Fc domain of the first monomer includes pI variants N208D/Q295E/N384D/Q418E/N421D, and where numbering is according to EU numbering. In some embodiments, the hinge of the second monomer also includes amino acid substitution C220S. In certain embodiments, the first and second variant Fc domains each further include half-life extension variants M428L/N434S. In an exemplary embodiment, the IL-15 variant includes amino acid substitutions N4D/N65D, D30N/N65D, or D30N/E64Q/N65D. In an exemplary embodiment, the VH and VL are the VH and VL of any of the TIM-3 ABDs in FIGS. 12 and 13A-C and the IL-15 variant includes amino acid substitutions N4D/N65D. In another exemplary embodiment, the VH and VL are the VH and VL of any of the TIM-3 ABDs in FIGS. 12 and 13A-C and the IL-15 variant includes amino acid substitutions D30N/N65D. In yet another exemplary embodiment, the VH and VL are the VH and VL of any of the TIM-3 ABDs in FIGS. 12 and 13A-C and the IL-15 variant includes amino acid substitutions D30N/E64Q/N65D.

In the FabxdsIL-15/Rα format, one preferred embodiment utilizes an anti-TIM-3 ABD having the variable heavy and light domain pair of 3H3[TIM-3]_H1_L2.1 as shown in FIG. 12 with the FIG. 21F format, the skew variant set S364K/E357Q: L368D/K370S, the pI variants Q295E/N384D/Q418E/N421D, the ablation variants E233P/L234V/L235A/G236_/S267K on both first and second monomers, and optionally the 428L/434S variants on both first and second monomers.

In one embodiment, the targeted IL-15/IL-15Rα heterodimeric protein is an "FabxdsIL-15/Rα" format heterodimeric protein that includes: a) a first monomer that includes, from N- to C-terminus, a VH-hinge-CH2-CH3, where VH is a variable heavy domain and CH2-CH3 is a first variant Fc domain; b) a second monomer that includes, from N- to C-terminus, an IL-15Rα(sushi) domain-(domain linker)-CH2-CH3, where CH2-CH3 is a second variant Fc domain and the IL-15Rα(sushi) domain includes an amino acid substitution for a cysteine residue; c) a third monomer that includes, from N- to C-terminus, a VL-CL, where VL is a variable light domain; and d) an IL-15 variant that includes an amino acid substitution for a cysteine residue, where the VH and VL form a TIM-3 binding domain, where the cysteine residue on the IL-15 variant and the cysteine residue on the IL-15Rα(sushi) domain form a disulfide bond, where VH and VL are the variable heavy domain and variable light domain of 3H3[TIM-3]_H1_L2.1, where the first variant Fc domain includes skew variants L368D/K370S and the second variant Fc domain includes skew variants S364K/E357Q where the first and second variant Fc domains each include FcKO variants E233P/L234V/L235A/G236del/S267K, where the hinge-first variant Fc domain of the first monomer includes pI variants N208D/Q295E/N384D/Q418E/N421D, and where numbering is according to EU numbering. In some embodiments, the hinge of the second monomer also includes amino acid substitution C220S. In a particular embodiment, the IL-15 variant includes amino acid substitutions N4D/N65D and VH and VL are the variable heavy domain and variable light domain of 3H3[TIM-3]_H1_L2.1. In one embodiment, the IL-15 variant includes amino acid substitutions D30N/N65D and VH and VL are the variable heavy domain and variable light domain of 3H3[TIM-3]_H1_L2.1. In another embodiment, the IL-15 variant includes amino acid substitutions D30N/E64Q/N65D and VH and VL are the variable heavy domain and variable light domain of 3H3[TIM-3]_H1_L2.1.

G. mAb-scIL-15/Rα

Figure 21G:
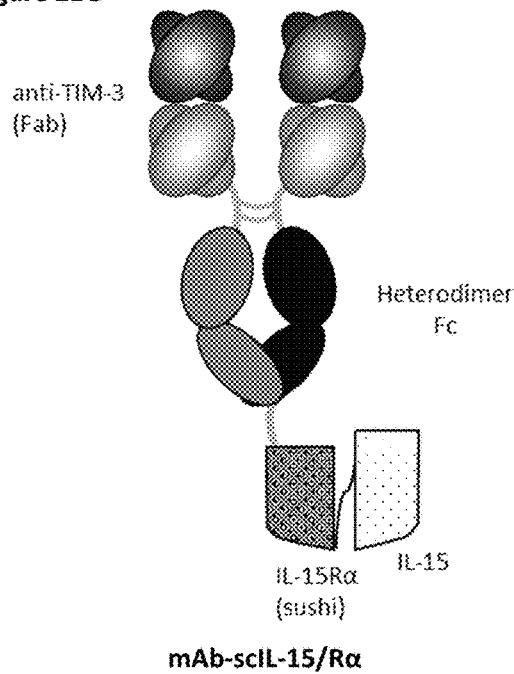

This embodiment is shown in FIG. 21G, and comprises three monomers (although the fusion protein is a tetramer). The first monomer comprises a heavy chain, VH-CH1-hinge-CH2-CH3. The second monomer comprises a heavy chain with a scIL-15 complex, VH-CH1-hinge-CH2-CH3-domain linker-IL-15Rα(sushi)domain-domain linker-IL-15 variant. The third (and fourth) monomer are light chains, VL-CL. This is generally referred to as "mAb-scIL-15/Rα", with the "sc" standing for "single chain". This binds the TIM-3 molecule bivalently.

In one embodiment, the targeted IL-15/IL-15Rα heterodimeric protein is an "mAb-scIL-15/Rα" format heterodimeric protein that includes: a) a first monomer that includes, from N- to C-terminus, a VH-hinge-CH2-CH3, where CH2-CH3 is a first Fc domain; b) a second monomer that includes, from N- to C-terminus, a VH-hinge-CH2-CH3-(domain linker)-IL-15Rα(sushi) domain-(domain linker)-IL-15 variant, where CH2-CH3 is a second Fc domain; and c) a third and fourth monomer that each include, from N- to C-terminus, a VL-CL, where VL is a variable light domain, where the VH of the first monomer and the VL of the third monomer form a first TIM-3 binding domain, where the VH of the second monomer and the VL of the fourth monomer form a second TIM-3 binding domain, and where the IL-15 variant and the IL-15Rα(sushi) domain form an IL-15 complex. Any useful domain linker can be used to attach the various components of the heterodimeric protein including, but not limited to those in FIGS. 8 and 9A-C.

In the mAb-scIL-15/Rα format, one preferred embodiment utilizes an anti-TIM-3 ABD having any of the variable heavy and light domain pairs as shown in FIG. 12.

In the mAb-scIL-15/Rα format, one preferred embodiment utilizes an anti-TIM-3 ABD having the variable heavy and light domain pair of 3H3[TIM-3]_H1_L2.1 as shown in FIG. 12.

In one embodiment, the targeted IL-15/IL-15Rα heterodimeric protein is an "mAb-scIL-15/Rα" format heterodimeric protein that includes: a) a first monomer that includes, from N- to C-terminus, a VH-hinge-CH2-CH3, where CH2-CH3 is a first Fc domain; b) a second monomer that includes, from N- to C-terminus, a VH-hinge-CH2-CH3-(domain linker)-IL-15Rα(sushi) domain-(domain linker)-IL-15 variant, where CH2-CH3 is a second Fc domain; and c) a third and fourth monomer that each include, from N- to C-terminus, a VL-CL, where VL is a variable light domain, where the VH of the first monomer and the VL of the third monomer are the variable heavy domain and variable light domain of 3H3[TIM-3]_H1_L2.1, respectively, where the VH of the second monomer and the VL of the fourth monomer are the variable heavy domain and variable light domain of 3H3[TIM-3]_H1_L2.1, respectively, and where the IL-15 variant and the IL-15Rα(sushi) domain form an IL-15 complex.

In the mAb-scIL-15/Rα format, one preferred embodiment utilizes an IL-15 variant that includes amino acid substitutions N4D/N65D, D30N/N65D, or D30N/E64Q/N65D. In one embodiment, the targeted IL-15/IL-15Rα heterodimeric protein is an "mAb-scIL-15/Rα" format heterodimeric protein that includes: a) a first monomer that includes, from N- to C-terminus, a VH-hinge-CH2-CH3, where CH2-CH3 is a first Fc domain; b) a second monomer that includes, from N- to C-terminus, a VH-hinge-CH2-CH3-(domain linker)-IL-15Rα(sushi) domain-(domain linker)-IL-15 variant, where CH2-CH3 is a second Fc domain; and c) a third and fourth monomer that each include, from N- to C-terminus, a VL-CL, where VL is a variable light domain, where the VH of the first monomer and the VL of the third monomer form a first TIM-3 binding domain, where the VH of the second monomer and the VL of the fourth monomer form a second TIM-3 binding domain, where the IL-15 variant and the IL-15Rα(sushi) domain form an IL-15 complex, and where the IL-15 variant includes amino acid substitutions N4D/N65D, D30N/N65D, or D30N/E64Q/N65D. In an exemplary embodiment, the VH and VL are the VH and VL of any of the TIM-3 ABDs in FIGS. 12 and 13A-C and the IL-15 variant includes amino acid substitutions N4D/N65D. In another exemplary embodiment, the VH and VL are the VH and VL of any of the TIM-3 ABDs in FIGS. 12 and 13A-C and the IL-15 variant includes amino acid substitutions D30N/N65D. In yet another exemplary embodiment, the VH and VL are the VH and VL of any of the TIM-3 ABDs in FIGS. 12 and 13A-C and the IL-15 variant includes amino acid substitutions D30N/E64Q/N65D.

In the mAb-scIL-15/Rα format, one preferred embodiment utilizes an anti-TIM-3 ABD having the variable heavy and light domain pair of 3H3[TIM-3]_H1_L2.1 as shown in FIG. 12, with either the IL-15 N4D/N65D variant or the IL-15 D30N/N65D variant or the IL-15 D30N/E64Q/N65D variant. In one embodiment, the targeted IL-15/IL-15Rα heterodimeric protein is an "mAb-scIL-15/Rα" format heterodimeric protein that includes: a) a first monomer that includes, from N- to C-terminus, a VH-hinge-CH2-CH3, where CH2-CH3 is a first Fc domain; b) a second monomer that includes, from N- to C-terminus, a VH-hinge-CH2-CH3-(domain linker)-IL-15Rα(sushi) domain-(domain linker)-IL-15 variant, where CH2-CH3 is a second Fc domain; and c) a third and fourth monomer that each include, from N- to C-terminus, a VL-CL, where VL is a variable light domain, where the VH of the first monomer and the VL of the third monomer form a first TIM-3 binding domain, where the VH of the second monomer and the VL of the fourth monomer form a second TIM-3 binding domain, where the IL-15 variant and the IL-15Rα(sushi) domain form an IL-15 complex, where VH and VL are the variable heavy domain and variable light domain of 3H3[TIM-3]_H1_L2.1, and where the IL-15 variant includes amino acid substitutions N4D/N65D, D30N/N65D, or D30N/E64Q/N65D. In a particular embodiment, the IL-15 variant includes amino acid substitutions N4D/N65D and VH and VL are the variable heavy domain and variable light domain of 3H3[TIM-3]_H1_L2.1. In one embodiment, the IL-15 variant includes amino acid substitutions D30N/N65D and VH and VL are the variable heavy domain and variable light domain of 3H3[TIM-3]_H1_L2.1. In another embodiment, the IL-15 variant includes amino acid substitutions D30N/E64Q/N65D and VH and VL are the variable heavy domain and variable light domain of 3H3[TIM-3]_H1_L2.1.

In the mAb-scIL-15/Rα format, one preferred embodiment utilizes the skew variant pair S364K/E357Q:L368D/K370S. In one embodiment, the targeted IL-15/IL-15Rα heterodimeric protein is an "mAb-scIL-15/Rα," format heterodimeric protein that includes: a) a first monomer that includes, from N- to C-terminus, a VH-hinge-CH2-CH3, where CH2-CH3 is a first variant Fc domain; b) a second monomer that includes, from N- to C-terminus, a VH-hinge-CH2-CH3-(domain linker)-IL-15Rα(sushi) domain-(domain linker)-IL-15 variant, where CH2-CH3 is a second variant Fc domain; and c) a third and fourth monomer that each include, from N- to C-terminus, a VL-CL, where VL is a variable light domain, where the VH of the first monomer and the VL of the third monomer form a first TIM-3 binding domain, where the VH of the second monomer and the VL of the fourth monomer form a second TIM-3 binding domain, where the IL-15 variant and the IL-15Rα(sushi) domain form an IL-15 complex, and where the first and second variant Fc domains include the skew variant pair S364K/E357Q:L368D/K370S. In an exemplary embodiment, the first variant Fc domain includes skew variants L368D and K370S, and the second variant Fc domain includes skew variants S364K and E357Q. In an exemplary embodiment, the first variant Fc domain includes skew variants S364K and E357Q, the second variant Fc domain includes skew variants E357Q L368D and K370S.

In one embodiment, the targeted IL-15/IL-15Rα heterodimeric protein is an "mAb-scIL-15/Rα," format heterodimeric protein that includes: a) a first monomer that includes, from N- to C-terminus, a VH-hinge-CH2-CH3, where CH2-CH3 is a first variant Fc domain; b) a second monomer that includes, from N- to C-terminus, a VH-hinge-CH2-CH3-(domain linker)-IL-15Rα(sushi) domain-(domain linker)-IL-15 variant, where CH2-CH3 is a second variant Fc domain; and c) a third and fourth monomer that each include, from N- to C-terminus, a VL-CL, where VL is a variable light domain, where the VH of the first monomer and the VL of the third monomer form a first TIM-3 binding domain, where the VH of the second monomer and the VL of the fourth monomer form a second TIM-3 binding domain, where the IL-15 variant and the IL-15Rα(sushi) domain form an IL-15 complex, where the IL-15 variant includes amino acid substitutions N4D/N65D, D30N/N65D, or D30N/E64Q/N65D, and where the first and second variant Fc domains include the skew variant pair S364K/E357Q:L368D/K370S. In an exemplary embodiment, the first variant Fc domain includes skew variants L368D and K370S, and the second variant Fc domain includes skew variants S364K and E357Q. In an exemplary embodiment, the first variant Fc domain includes skew variants S364K and E357Q and the second variant Fc domain includes skew variants L368D and K370S. In an exemplary embodiment, the VH and VL are the VH and VL of any of the TIM-3 ABDs in FIGS. 12 and 13A-C and the IL-15 variant includes amino acid substitutions N4D/N65D. In another exemplary embodiment, the VH and VL are the VH and VL of any of the TIM-3 ABDs in FIGS. 12 and 13A-C and the IL-15 variant includes amino acid substitutions D30N/N65D. In yet another exemplary embodiment, the VH and VL are the VH and VL of any of the TIM-3 ABDs in FIGS. 12 and 13A-C and the IL-15 variant includes amino acid substitutions D30N/E64Q/N65D.

In the mAb-scIL-15/Rα format, one preferred embodiment utilizes an anti-TIM-3 ABD having the variable heavy and light domain pair of 3H3[TIM-3]_H1_L2.1 as shown in FIG. 12 and the skew variant pair S364K/E357Q:L368D/K370S. In one embodiment, the targeted IL-15/IL-15Rα heterodimeric protein is an "mAb-scIL-15/Rα" format heterodimeric protein that includes: a) a first monomer that includes, from N- to C-terminus, a VH-hinge-CH2-CH3, where CH2-CH3 is a first variant Fc domain; b) a second monomer that includes, from N- to C-terminus, a VH-hinge-CH2-CH3-(domain linker)-IL-15Rα(sushi) domain-(domain linker)-IL-15 variant, where CH2-CH3 is a second variant Fc domain; and c) a third and fourth monomer that each include, from N- to C-terminus, a VL-CL, where VL is a variable light domain, where the VH of the first monomer and the VL of the third monomer are the variable heavy domain and variable light domain of 3H3[TIM-3]_H1_L2.1, respectively, where the VH of the second monomer and the VL of the fourth monomer are the variable heavy domain and variable light domain of 3H3[TIM-3]_H1_L2.1, respectively, where the IL-15 variant and the IL-15Rα(sushi) domain form an IL-15 complex, where the IL-15 variant and the IL-15Rα(sushi) domain form an IL-15 complex, and where the first and second variant Fc domains include the skew variant pair S364K/E357Q: L368D/K370S. In an exemplary embodiment, the first variant Fc domain includes skew variants L368D and K370S, and the second variant Fc domain includes skew variants S364K and E357Q. In an exemplary embodiment, the first variant Fc domain includes skew variants S364K and E357Q, and the second variant Fc domain includes skew variants L368D and K370S.

In the mAb-scIL-15/Rα format, one preferred embodiment utilizes an anti-TIM-3 ABD having the variable heavy and light domain pair of 3H3[TIM-3]_H1_L2.1 as shown in FIG. 12 and the skew variant pair S364K/E357Q:L368D/K370S with either the IL-15 N4D/N65D variant or the IL-15 D30N/N65D variant or the IL-15 D30N/E64Q/N65D variant. In one embodiment, the targeted IL-15/IL-15Rα heterodimeric protein is an "mAb-scIL-15/Rα" format heterodimeric protein that includes: a) a first monomer that includes, from N- to C-terminus, a VH-hinge-CH2-CH3, where CH2-CH3 is a first variant Fc domain; b) a second monomer that includes, from N- to C-terminus, a VH-hinge-CH2-CH3-(domain linker)-IL-15Rα(sushi) domain-(domain linker)-IL-15 variant, where CH2-CH3 is a second variant Fc domain; and c) a third and fourth monomer that each include, from N- to C-terminus, a VL-CL, where VL is a variable light domain, where the VH of the first monomer and the VL of the third monomer form a first TIM-3 binding domain, where the VH of the second monomer and the VL of the fourth monomer form a second TIM-3 binding domain, where the IL-15 variant and the IL-15Rα(sushi) domain form an IL-15 complex, where VH and VL are the variable heavy domain and variable light domain of 3H3 [TIM-3]_H1_L2.1, where the IL-15 variant includes amino acid substitutions N4D/N65D, D30N/N65D, or D30N/E64Q/N65D, and where the first and second variant Fc domains include the skew variant pair S364K/E357Q: L368D/K370S. In an exemplary embodiment, the first variant Fc domain includes skew variants L368D and K370S, and the second variant Fc domain includes skew variants S364K and E357Q. In a particular embodiment, the IL-15 variant includes amino acid substitutions N4D/N65D and VH and VL are the variable heavy domain and variable light domain of 3H3[TIM-3]_H1_L2.1. In one embodiment, the IL-15 variant includes amino acid substitutions D30N/N65D and VH and VL are the variable heavy domain and variable light domain of 3H3[TIM-3]_H1_L2.1. In another embodiment, the IL-15 variant includes amino acid substitutions D30N/E64Q/N65D and VH and VL are the variable heavy domain and variable light domain of 3H3[TIM-3]_H1_L2.1. In an exemplary embodiment, the first variant Fc domain includes skew variants L368D and K370S, and the second variant Fc domain includes skew variants S364K and E357Q. In an exemplary embodiment, the first variant Fc domain includes skew variants S364K and E357Q, and the second variant Fc domain includes skew variants L368D and K370S.

In the mAb-scIL-15/Rα format, one preferred embodiment utilizes the skew variant set S364K/E357Q:L368D/K370S, the pI variants N208D/Q295E/N384D/Q418D/N421D and/or Q196K/I199T/P271R/P228R/N276K, the ablation variants E233P/L234V/L235A/G236_/S267K on both first and second monomers, and optionally the 428L/434S variants on both first and second monomers.

In one embodiment, the targeted IL-15/IL-15Rα heterodimeric protein is an "mAb-scIL-15/Rα" format heterodimeric protein that includes: a) a first monomer that includes, from N- to C-terminus, a VH-hinge-CH2-CH3, where CH2-CH3 is a first variant Fc domain; b) a second monomer that includes, from N- to C-terminus, a VH-hinge-CH2-CH3-(domain linker)-IL-15Rα(sushi) domain-(domain linker)-IL-15 variant, where CH2-CH3 is a second variant Fc domain; and c) a third and fourth monomer that each include, from N- to C-terminus, a VL-CL, where VL is a variable light domain, where the VH of the first monomer and the VL of the third monomer form a first TIM-3 binding domain, where the VH of the second monomer and the VL of the fourth monomer form a second TIM-3 binding domain, where the IL-15 variant and the IL-15Rα(sushi) domain form an IL-15 complex, where the first variant Fc domain includes skew variants L368D/K370S and the second variant Fc domain include the skew variant pair S364K/E357Q, where the first and second variant Fc domains each include FcKO variants E233P/L234V/L235A/G236del/S267K, where the hinge-first variant Fc domain of the first monomer includes pI substitutions N208D/Q295E/N384D/Q418D/N421D and the hinge-second variant Fc domain of the second monomer includes pI variants Q196K/I199T/P271R/P228R/N276K, and where numbering is according to EU numbering. In one embodiment, the targeted IL-15/IL-15Rα heterodimeric protein is an "mAb-scIL-15/Rα" format heterodimeric protein that includes: a) a first monomer that includes, from N- to C-terminus, a VH-hinge-CH2-CH3, where CH2-CH3 is a first variant Fc domain; b) a second monomer that includes, from N- to C-terminus, a VH-hinge-CH2-CH3-(domain linker)-IL-15Rα(sushi) domain-(domain linker)-IL-15 variant, where CH2-CH3 is a second variant Fc domain; and c) a third and fourth monomer that each include, from N- to C-terminus, a VL-CL, where VL is a variable light domain, where the VH of the first monomer and the VL of the third monomer form a first TIM-3 binding domain, where the VH of the second monomer and the VL of the fourth monomer form a second TIM-3 binding domain, where the IL-15 variant and the IL-15Rα (sushi) domain form an IL-15 complex, where the first variant Fc domain includes skew variants L368D/K370S and the second variant Fc domain include the skew variant pair S364K/E357Q, where the first and second variant Fc domains each include FcKO variants E233P/L234V/L235A/G236del/S267K, where the hinge-first variant Fc domain of the first monomer includes pI substitutions N208D/Q295E/N384D/Q418D/N421D, and where numbering is according to EU numbering. In one embodiment, the targeted IL-15/IL-15Rα heterodimeric protein is an "mAb-scIL-15/Rα" format heterodimeric protein that includes: a) a first monomer that includes, from N- to C-terminus, a VH-hinge-CH2-CH3, where CH2-CH3 is a first variant Fc domain; b) a second monomer that includes, from N- to C-terminus, a VH-hinge-CH2-CH3-(domain linker)-IL-15Rα(sushi) domain-(domain linker)-IL-15 variant, where CH2-CH3 is a second variant Fc domain; and c) a third and fourth monomer that each include, from N- to C-terminus, a VL-CL, where VL is a variable light domain, where the VH of the first monomer and the VL of the third monomer form a first TIM-3 binding domain, where the VH of the second monomer and the VL of the fourth monomer form a second TIM-3 binding domain, where the IL-15 variant and the IL-15Rα (sushi) domain form an IL-15 complex, where the first variant Fc domain includes skew variants S364K/E357Q and the second variant Fc domain include the skew variant pair L368D/K370S, where the first and second variant Fc domains each include FcKO variants E233P/L234V/L235A/G236del/S267K, where the hinge-first variant Fc domain of the first monomer includes pI substitutions Q196K/I199T/P271R/P228R/N276K and the hinge-second variant Fc domain of the second monomer includes pI variants N208D/Q295E/N384D/Q418D/N421D, and where numbering is according to EU numbering. In one embodiment, the targeted IL-15/IL-15Rα heterodimeric protein is an "mAb-scIL-15/Rα" format heterodimeric protein that includes: a) a first monomer that includes, from N- to C-terminus, a VH-hinge-CH2-CH3, where CH2-CH3 is a first variant Fc domain; b) a second monomer that includes, from N- to C-terminus, a VH-hinge-CH2-CH3-(domain linker)-IL-15Rα(sushi) domain-(domain linker)-IL-15 variant, where CH2-CH3 is a second variant Fc domain; and c) a third and fourth monomer that each include, from N- to C-terminus, a VL-CL, where VL is a variable light domain, where the VH of the first monomer and the VL of the third monomer form a first TIM-3 binding domain, where the VH of the second monomer and the VL of the fourth monomer form a second TIM-3 binding domain, where the IL-15 variant and the IL-15Rα(sushi) domain form an IL-15 complex, where the first variant Fc domain includes skew variants S364K/

E357Q and the second variant Fc domain include the skew variant pair L368D/K370S, where the first and second variant Fc domains each include FcKO variants E233P/L234V/L235A/G236del/S267K, where the hinge-first variant Fc domain of the first monomer includes pI substitutions Q196K/I199T/P271R/P228R/N276K, and where numbering is according to EU numbering. In one embodiment, the targeted IL-15/IL-15Rα heterodimeric protein is an "mAb-scIL-15/Rα" format heterodimeric protein that includes: a) a first monomer that includes, from N- to C-terminus, a VH-hinge-CH2-CH3, where CH2-CH3 is a first variant Fc domain; b) a second monomer that includes, from N- to C-terminus, a VH-hinge-CH2-CH3-(domain linker)-IL-15Rα(sushi) domain-(domain linker)-IL-15 variant, where CH2-CH3 is a second variant Fc domain; and c) a third and fourth monomer that each include, from N- to C-terminus, a VL-CL, where VL is a variable light domain, where the VH of the first monomer and the VL of the third monomer form a first TIM-3 binding domain, where the VH of the second monomer and the VL of the fourth monomer form a second TIM-3 binding domain, where the IL-15 variant and the IL-15Rα(sushi) domain form an IL-15 complex, where the first variant Fc domain includes skew variants S364K/E357Q and the second variant Fc domain include the skew variant pair L368D/K370S, where the first and second variant Fc domains each include FcKO variants E233P/L234V/L235A/G236del/S267K, where the hinge-first variant Fc domain of the hinge-second variant Fc domain of the second monomer includes pI variants N208D/Q295E/N384D/Q418D/N421D, and where numbering is according to EU numbering. In certain embodiments, the first and second variant Fc domains each further include half-life extension variants M428L/N434S. In an exemplary embodiment, the IL-15 variant includes amino acid substitutions N4D/N65D, D30N/N65D, or D30N/E64Q/N65D. In an exemplary embodiment, the VH and VL are the VH and VL of any of the TIM-3 ABDs in FIGS. 12 and 13A-C and the IL-15 variant includes amino acid substitutions N4D/N65D. In another exemplary embodiment, the VH and VL are the VH and VL of any of the TIM-3 ABDs in FIGS. 12 and 13A-C and the IL-15 variant includes amino acid substitutions D30N/N65D. In yet another exemplary embodiment, the VH and VL are the VH and VL of any of the TIM-3 ABDs in FIGS. 12 and 13A-C and the IL-15 variant includes amino acid substitutions D30N/E64Q/N65D.

In the mAb-scIL-15/Rα format, one preferred embodiment utilizes an anti-TIM-3 ABD the variable heavy and light domain pair of 3H3[TIM-3]_H1_L2.1 as shown in FIG. 12 with the FIG. 21G format, the skew variant set S364K/E357Q:L368D/K370S, the pI variants N208D/Q295E/N384D/Q418D/N421D and/or Q196K/I199T/P271R/P228R/N276K, the ablation variants E233P/L234V/L235A/G236_/S267K on both first and second monomers, and optionally the 428L/434S variants on both first and second monomers.

In one embodiment, the targeted IL-15/IL-15Rα heterodimeric protein is an "mAb-scIL-15/Rα" format heterodimeric protein that includes: a) a first monomer that includes, from N- to C-terminus, a VH-hinge-CH2-CH3, where CH2-CH3 is a first variant Fc domain; b) a second monomer that includes, from N- to C-terminus, a VH-hinge-CH2-CH3-(domain linker)-IL-15Rα(sushi) domain-(domain linker)-IL-15 variant, where CH2-CH3 is a second variant Fc domain; and c) a third and fourth monomer that each include, from N- to C-terminus, a VL-CL, where VL is a variable light domain, where the VH of the first monomer and the VL of the third monomer form a first TIM-3 binding domain, where the VH of the second monomer and the VL of the fourth monomer form a second TIM-3 binding domain, where the IL-15 variant and the IL-15Rα(sushi) domain form an IL-15 complex, where VH and VL are the variable heavy domain and variable light domain of 3H3[TIM-3]_H1_L2.1, where the first variant Fc domain includes skew variants L368D/K370S and the second variant Fc domain include the skew variant pair S364K/E357Q, where the first and second variant Fc domains each include FcKO variants E233P/L234V/L235A/G236del/S267K, where the hinge-first variant Fc domain of the first monomer includes pI substitutions N208D/Q295E/N384D/Q418D/N421D and the hinge-second variant Fc domain of the second monomer includes pI variants Q196K/I199T/P271R/P228R/N276K, and where numbering is according to EU numbering. In one embodiment, the targeted IL-15/IL-15Rα heterodimeric protein is an "mAb-scIL-15/Rα" format heterodimeric protein that includes: a) a first monomer that includes, from N- to C-terminus, a VH-hinge-CH2-CH3, where CH2-CH3 is a first variant Fc domain; b) a second monomer that includes, from N- to C-terminus, a VH-hinge-CH2-CH3-(domain linker)-IL-15Rα(sushi) domain-(domain linker)-IL-15 variant, where CH2-CH3 is a second variant Fc domain; and c) a third and fourth monomer that each include, from N- to C-terminus, a VL-CL, where VL is a variable light domain, where the VH of the first monomer and the VL of the third monomer form a first TIM-3 binding domain, where the VH of the second monomer and the VL of the fourth monomer form a second TIM-3 binding domain, where the IL-15 variant and the IL-15Rα(sushi) domain form an IL-15 complex, where VH and VL are the variable heavy domain and variable light domain of 3H3[TIM-3]_H1_L2.1, where the first variant Fc domain includes skew variants L368D/K370S and the second variant Fc domain include the skew variant pair S364K/E357Q, where the first and second variant Fc domains each include FcKO variants E233P/L234V/L235A/G236del/S267K, where the hinge-first variant Fc domain of the first monomer includes pI substitutions N208D/Q295E/N384D/Q418D/N421D, and where numbering is according to EU numbering. In one embodiment, the targeted IL-15/IL-15Rα heterodimeric protein is an "mAb-scIL-15/Rα" format heterodimeric protein that includes: a) a first monomer that includes, from N- to C-terminus, a VH-hinge-CH2-CH3, where CH2-CH3 is a first variant Fc domain; b) a second monomer that includes, from N- to C-terminus, a VH-hinge-CH2-CH3-(domain linker)-IL-15Rα(sushi) domain-(domain linker)-IL-15 variant, where CH2-CH3 is a second variant Fc domain; and c) a third and fourth monomer that each include, from N- to C-terminus, a VL-CL, where VL is a variable light domain, where the VH of the first monomer and the VL of the third monomer form a first TIM-3 binding domain, where the VH of the second monomer and the VL of the fourth monomer form a second TIM-3 binding domain, where the IL-15 variant and the IL-15Rα(sushi) domain form an IL-15 complex, where VH and VL are the variable heavy domain and variable light domain of 3H3[TIM-3]_H1_L2.1, where the first variant Fc domain includes skew variants L368D/K370S and the second variant Fc domain include the skew variant pair S364K/E357Q, where the first and second variant Fc domains each include FcKO variants E233P/L234V/L235A/G236del/S267K, where the hinge-second variant Fc domain of the second monomer includes pI variants Q196K/I199T/P271R/P228R/N276K, and where numbering is according to EU numbering. In one embodiment, the targeted IL-15/IL-15Rα heterodimeric protein is an "mAb-scIL-15/Rα" format heterodimeric protein that includes: a) a first monomer that includes, from N- to C-terminus, a VH-hinge-CH2-CH3, where CH2-CH3 is a first variant Fc domain; b) a second monomer that includes, from N- to C-terminus, a VH-hinge-CH2-CH3-(domain linker)-IL-15Rα(sushi) domain-(domain linker)-IL-15 variant, where CH2-CH3 is a second variant Fc domain; and c) a third and fourth monomer that each include, from N- to C-terminus, a VL-CL, where VL is a variable light domain, where the VH of the first monomer and the VL of the third monomer form a first TIM-3 binding domain, where the VH of the second monomer and the VL of the fourth monomer form a second TIM-3 binding domain, where the IL-15 variant and the IL-15Rα(sushi) domain form an IL-15 complex, where VH and VL are the variable heavy domain and variable light domain of 3H3 [TIM-3]_H1_L2.1, where the first variant Fc domain includes skew variants S364K/E357Q and the second variant Fc domain include the skew variant pair L368D/K370S, where the first and second variant Fc domains each include FcKO variants E233P/L234V/L235A/G236del/S267K, where the hinge-first variant Fc domain of the first monomer includes pI substitutions Q196K/I199T/P271R/P228R/N276K and the hinge-second variant Fc domain of the second monomer includes pI variants N208D/Q295E/N384D/Q418D/N421D, and where numbering is according to EU numbering. In one embodiment, the targeted IL-15/IL-15Rα heterodimeric protein is an "mAb-scIL-15/Rα" format heterodimeric protein that includes: a) a first monomer that includes, from N- to C-terminus, a VH-hinge-CH2-CH3, where CH2-CH3 is a first variant Fc domain; b) a second monomer that includes, from N- to C-terminus, a VH-hinge-CH2-CH3-(domain linker)-IL-15Rα(sushi) domain-(domain linker)-IL-15 variant, where CH2-CH3 is a second variant Fc domain; and c) a third and fourth monomer that each include, from N- to C-terminus, a VL-CL, where VL is a variable light domain, where the VH of the first monomer and the VL of the third monomer form a first TIM-3 binding domain, where the VH of the second monomer and the VL of the fourth monomer form a second TIM-3 binding domain, where the IL-15 variant and the IL-15Rα(sushi) domain form an IL-15 complex, where VH and VL are the variable heavy domain and variable light domain of 3H3 [TIM-3]_H1_L2.1, where the first variant Fc domain includes skew variants S364K/E357Q and the second variant Fc domain include the skew variant pair L368D/K370S, where the first and second variant Fc domains each include FcKO variants E233P/L234V/L235A/G236del/S267K, where the hinge-first variant Fc domain of the hinge-second variant Fc domain of the second monomer includes pI variants N208D/Q295E/N384D/Q418D/N421D, and where numbering is according to EU numbering. In certain embodiments, the first and second variant Fc domains each further include half-life extension variants M428L/N434S. In a particular embodiment, the IL-15 variant includes amino acid substitutions N4D/N65D and VH and VL are the variable heavy domain and variable light domain of 3H3 [TIM-3]_H1_L2.1. In one embodiment, the IL-15 variant includes amino acid substitutions D30N/N65D and VH and VL are the variable heavy domain and variable light domain of 3H3[TIM-3]_H1_L2.1. In another embodiment, the IL-15 variant includes amino acid substitutions D30N/E64Q/N65D and VH and VL are the variable heavy domain and variable light domain of 3H3[TIM-3]_H1_L2.1.

H. mAb-ncIL-15/Rα

Figure 21H:
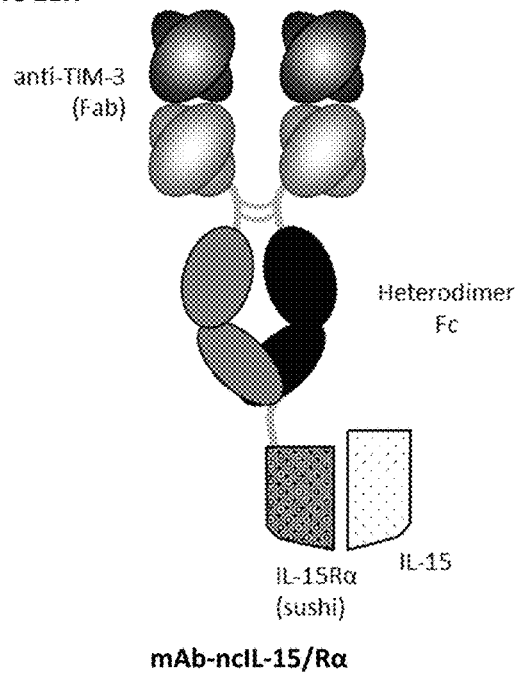

This embodiment is shown in FIG. 21H, and comprises four monomers (although the heterodimeric fusion protein is a pentamer). The first monomer comprises a heavy chain, VH-CH1-hinge-CH2-CH3. The second monomer comprises a heavy chain with an IL-15Rα(sushi) domain: e.g., VH-CH1-hinge-CH2-CH3-domain linker-IL-15Rα(sushi) domain. The third monomer is a variant IL-15 domain. The fourth (and fifth) monomer are light chains, VL-CL. This is generally referred to as "mAb-ncIL-15/Rα", with the "nc" standing for "non-covalent". This also binds the TIM-3 bivalently.

In one embodiment, the targeted IL-15/IL-15Rα heterodimeric protein is an "mAb-ncIL-15/Rα" format heterodimeric protein that includes: a) a first monomer that includes, from N- to C-terminus, a VH-hinge-CH2-CH3, where CH2-CH3 is a first Fc domain; b) a second monomer that includes, from N- to C-terminus, a VH-hinge-CH2-CH3-(domain linker)-IL-15Rα(sushi) domain-(domain linker), where CH2-CH3 is a second Fc domain; c) a third monomer that includes an IL-15 variant; and d) a fourth and fifth monomer that each include, from N- to C-terminus, a VL-CL, where VL is a variable light domain, where the VH of the first monomer and the VL of the fourth monomer form a first TIM-3 binding domain, where the VH of the second monomer and the VL of the fifth monomer form a second TIM-3 binding domain, and where the IL-15 variant and the IL-15Rα(sushi) domain form an IL-15 complex. Any useful domain linker can be used to attach the various components of the heterodimeric protein including, but not limited to those in FIGS. 8 and 9A-C.

In the mAb-ncIL-15/Rα format, one preferred embodiment utilizes an anti-TIM-3 ABD having any of the variable heavy and light domain pairs as shown in FIG. 12.

In the mAb-ncIL-15/Rα format, one preferred embodiment utilizes an anti-TIM-3 ABD having the variable heavy and light domain pair of 3H3[TIM-3]_H1_L2.1 as shown in FIG. 12.

In one embodiment, the targeted IL-15/IL-15Rα heterodimeric protein is an "mAb-ncIL-15/Rα" format heterodimeric protein that includes: a) a first monomer that includes, from N- to C-terminus, a VH-hinge-CH2-CH3, where CH2-CH3 is a first Fc domain; b) a second monomer that includes, from N- to C-terminus, a VH-hinge-CH2-CH3-(domain linker)-IL-15Rα(sushi) domain-(domain linker), where CH2-CH3 is a second Fc domain; c) a third monomer that includes an IL-15 variant; and d) a fourth and fifth monomer that each include, from N- to C-terminus, a VL-CL, where VL is a variable light domain, where the VH of the first monomer and the VL of the fourth monomer are the variable heavy domain and variable light domain of 3H3[TIM-3]_H1_L2.1, respectively, where the VH of the second monomer and the VL of the fifth monomer are the variable heavy domain and variable light domain of 3H3[TIM-3]_H1_L2.1, respectively, and where the IL-15 variant and the IL-15Rα (sushi) domain form an IL-15 complex.

In the mAb-ncIL-15/Rα format, one preferred embodiment utilizes an IL-15 variant that includes amino acid substitutions N4D/N65D, D30N/N65D, or D30N/E64Q/N65D. In one embodiment, the targeted IL-15/IL-15Rα heterodimeric protein is an "mAb-ncIL-15/Rα" format heterodimeric protein that includes: a) a first monomer that includes, from N- to C-terminus, a VH-hinge-CH2-CH3, where CH2-CH3 is a first Fc domain; b) a second monomer that includes, from N- to C-terminus, a VH-hinge-CH2-CH3-(domain linker)-IL-15Rα(sushi) domain-(domain linker), where CH2-CH3 is a second Fc domain; c) a third monomer that includes an IL-15 variant; and d) a fourth and fifth monomer that each include, from N- to C-terminus, a VL-CL, where VL is a variable light domain, where the VH of the first monomer and the VL of the fourth monomer form a first TIM-3 binding domain, where the VH of the second monomer and the VL of the fifth monomer form a second TIM-3 binding domain, where the IL-15 variant and the IL-15Rα(sushi) domain form an IL-15 complex, where the IL-15 variant and the IL-15Rα(sushi) domain form an IL-15 complex, and where the IL-15 variant includes amino acid substitutions N4D/N65D, D30N/N65D, or D30N/E64Q/N65D. In an exemplary embodiment, the VH and VL are the VH and VL of any of the TIM-3 ABDs in FIGS. 12 and 13A-C and the IL-15 variant includes amino acid substitutions N4D/N65D. In another exemplary embodiment, the VH and VL are the VH and VL of any of the TIM-3 ABDs in FIGS. 12 and 13A-C and the IL-15 variant includes amino acid substitutions D30N/N65D. In yet another exemplary embodiment, the VH and VL are the VH and VL of any of the TIM-3 ABDs in FIGS. 12 and 13A-C and the IL-15 variant includes amino acid substitutions D30N/E64Q/N65D.

In the mAb-ncIL-15/Rα format, one preferred embodiment utilizes an anti-TIM-3 ABD having the variable heavy and light domain pair of 3H3[TIM-3]_H1_L2.1 as shown in FIG. 12, with either the IL-15 N4D/N65D variant or the IL-15 D30N/N65D variant or the IL-15 D30N/E64Q/N65D variant. In one embodiment, the targeted IL-15/IL-15Rα heterodimeric protein is an "mAb-ncIL-15/Rα" format heterodimeric protein that includes: a) a first monomer that includes, from N- to C-terminus, a VH-hinge-CH2-CH3, where CH2-CH3 is a first Fc domain; b) a second monomer that includes, from N- to C-terminus, a VH-hinge-CH2-CH3-(domain linker)-IL-15Rα(sushi) domain-(domain linker), where CH2-CH3 is a second Fc domain; c) a third monomer that includes an IL-15 variant; and d) a fourth and fifth monomer that each include, from N- to C-terminus, a VL-CL, where VL is a variable light domain, where the VH of the first monomer and the VL of the fourth monomer form a first TIM-3 binding domain, where the VH of the second monomer and the VL of the fifth monomer form a second TIM-3 binding domain, where the IL-15 variant and the IL-15Rα(sushi) domain form an IL-15 complex, where VH and VL are the variable heavy domain and variable light domain of 3H3[TIM-3]_H1_L2.1, and where the IL-15 variant includes amino acid substitutions N4D/N65D, D30N/N65D, or D30N/E64Q/N65D. In a particular embodiment, the IL-15 variant includes amino acid substitutions N4D/N65D and VH and VL are the variable heavy domain and variable light domain of 3H3[TIM-3]_H1_L2.1. In one embodiment, the IL-15 variant includes amino acid substitutions D30N/N65D and VH and VL are the variable heavy domain and variable light domain of 3H3[TIM-3]_H1_L2.1. In another embodiment, the IL-15 variant includes amino acid substitutions D30N/E64Q/N65D and VH and VL are the variable heavy domain and variable light domain of 3H3[TIM-3]_H1_L2.1.

In the mAb-ncIL-15/Rα format, one preferred embodiment utilizes the skew variant pair S364K/E357Q:L368D/K370S. In one embodiment, the targeted IL-15/IL-15Rα heterodimeric protein is an "mAb-ncIL-15/Rα" format heterodimeric protein that includes: a) a first monomer that includes, from N- to C-terminus, a VH-hinge-CH2-CH3, where CH2-CH3 is a first variant Fc domain; b) a second monomer that includes, from N- to C-terminus, a VH-hinge-CH2-CH3-(domain linker)-IL-15Rα(sushi) domain-(domain linker), where CH2-CH3 is a second variant Fc domain; c) a third monomer that includes an IL-15 variant; and d) a fourth and fifth monomer that each include, from N- to C-terminus, a VL-CL, where VL is a variable light domain, where the VH of the first monomer and the VL of the fourth monomer form a first TIM-3 binding domain, where the VH of the second monomer and the VL of the fifth monomer form a second TIM-3 binding domain, where the IL-15 variant and the IL-15Rα(sushi) domain form an IL-15 complex, and where the first and second variant Fc domains include the skew variant pair S364K/E357Q:L368D/K370S. In an exemplary embodiment, the first variant Fc domain includes skew variants L368D/K370S, and the second variant Fc domain includes skew variants S364K/E357Q. In another exemplary embodiment, the first variant Fc domain includes skew variants S364K/E357Q, and the second variant Fc domain includes skew variants L368D/K370S.

In one embodiment, the targeted IL-15/IL-15Rα heterodimeric protein is an "mAb-ncIL-15/Rα" format heterodimeric protein that includes: a) a first monomer that includes, from N- to C-terminus, a VH-hinge-CH2-CH3, where CH2-CH3 is a first variant Fc domain; b) a second monomer that includes, from N- to C-terminus, a VH-hinge-CH2-CH3-(domain linker)-IL-15Rα(sushi) domain-(domain linker), where CH2-CH3 is a second variant Fc domain; c) a third monomer that includes an IL-15 variant; and d) a fourth and fifth monomer that each include, from N- to C-terminus, a VL-CL, where VL is a variable light domain, where the VH of the first monomer and the VL of the fourth monomer form a first TIM-3 binding domain, where the VH of the second monomer and the VL of the fifth monomer form a second TIM-3 binding domain, where the IL-15 variant and the IL-15Rα(sushi) domain form an IL-15 complex, where the IL-15 variant includes amino acid substitutions N4D/N65D, D30N/N65D, or D30N/E64Q/N65D, and where the first and second variant Fc domains include the skew variant pair S364K/E357Q:L368D/K370S. In an exemplary embodiment, the first variant Fc domain includes skew variants L368D/K370S, and the second variant Fc domain includes skew variants S364K/E357Q. In another exemplary embodiment, the first variant Fc domain includes skew variants S364K/E357Q, and the second variant Fc domain includes skew variants L368D/K370S. In an exemplary embodiment, the VH and VL are the VH and VL of any of the TIM-3 ABDs in FIGS. 12 and 13A-C and the IL-15 variant includes amino acid substitutions N4D/N65D. In another exemplary embodiment, the VH and VL are the VH and VL of any of the TIM-3 ABDs in FIGS. 12 and 13A-C and the IL-15 variant includes amino acid substitutions D30N/N65D. In yet another exemplary embodiment, the VH and VL are the VH and VL of any of the TIM-3 ABDs in FIGS. 12 and 13A-C and the IL-15 variant includes amino acid substitutions D30N/E64Q/N65D.

In the mAb-ncIL-15/Rα format, one preferred embodiment utilizes an anti-TIM-3 ABD having the variable heavy and light domain pair of 3H3[TIM-3]_H1_L2.1 as shown in FIG. 12 and the skew variant pair S364K/E357Q:L368D/K370S. In one embodiment, the targeted IL-15/IL-15Rα heterodimeric protein is an "mAb-ncIL-15/Rα" format heterodimeric protein that includes: a) a first monomer that includes, from N- to C-terminus, a VH-hinge-CH2-CH3, where CH2-CH3 is a first variant Fc domain; b) a second monomer that includes, from N- to C-terminus, a VH-hinge-CH2-CH3-(domain linker)-IL-15Rα(sushi) domain-(domain linker), where CH2-CH3 is a second variant Fc domain; c) a third monomer that includes an IL-15 variant; and d) a fourth and fifth monomer that each include, from N- to C-terminus, a VL-CL, where VL is a variable light domain, where the VH of the first monomer and the VL of the fourth monomer are the variable heavy domain and variable light domain of 3H3[TIM-3]_H1_L2.1, respectively, where the VH of the second monomer and the VL of the fifth monomer are the variable heavy domain and variable light domain of 3H3[TIM-3]_H1_L2.1, respectively, where the IL-15 variant and the IL-15Rα(sushi) domain form an IL-15 complex, and where the first and second variant Fc domains include the skew variant pair S364K/E357Q:L368D/K370S.

In the mAb-ncIL-15/Rα format, one preferred embodiment utilizes an anti-TIM-3 ABD having the variable heavy and light domain pair of 3H3[TIM-3]_H1_L2.1 as shown in FIG. 12 and the skew variant pair S364K/E357Q:L368D/K370S with either the IL-15 N4D/N65D variant or the IL-15 D30N/N65D variant or the IL-15 D30N/E64Q/N65D variant. In one embodiment, the targeted IL-15/IL-15Rα heterodimeric protein is an "mAb-ncIL-15/Rα" format heterodimeric protein that includes: a) a first monomer that includes, from N- to C-terminus, a VH-hinge-CH2-CH3, where CH2-CH3 is a first variant Fc domain; b) a second monomer that includes, from N- to C-terminus, a VH-hinge-CH2-CH3-(domain linker)-IL-15Rα(sushi) domain-(domain linker), where CH2-CH3 is a second variant Fc domain; c) a third monomer that includes an IL-15 variant; and d) a fourth and fifth monomer that each include, from N- to C-terminus, a VL-CL, where VL is a variable light domain, where the VH of the first monomer and the VL of the fourth monomer form a first TIM-3 binding domain, where the VH of the second monomer and the VL of the fifth monomer form a second TIM-3 binding domain, where the IL-15 variant and the IL-15Rα(sushi) domain form an IL-15 complex, where the IL-15 variant and the IL-15Rα(sushi) domain form an IL-15 complex, where VH and VL are the variable heavy domain and variable light domain of 3H3 [TIM-3]_H1_L2.1, where the IL-15 variant includes amino acid substitutions N4D/N65D, D30N/N65D, or D30N/E64Q/N65D, and where the first and second variant Fc domains include the skew variant pair S364K/E357Q:L368D/K370S. In an exemplary embodiment, the first variant Fc domain includes skew variants L368D/K370S, and the second variant Fc domain includes skew variants S364K/E357Q. In an exemplary embodiment, the first variant Fc domain includes skew variants S364K/E357Q, and the second variant Fc domain includes skew variants L368D/K370S. In a particular embodiment, the IL-15 variant includes amino acid substitutions N4D/N65D and VH and VL are the variable heavy domain and variable light domain of 3H3[TIM-3]_H1_L2.1. In one embodiment, the IL-15 variant includes amino acid substitutions D30N/N65D and VH and VL are the variable heavy domain and variable light domain of 3H3[TIM-3]_H1_L2.1. In another embodiment, the IL-15 variant includes amino acid substitutions D30N/E64Q/N65D and VH and VL are the variable heavy domain and variable light domain of 3H3[TIM-3]_H1_L2.1.

In the mAb-ncIL-15/Rα format, one preferred embodiment utilizes the skew variant set S364K/E357Q:L368D/K370S, the pI variants N208D/Q295E/N384D/Q418D/N421D and/or Q196K/I199T/P271R/P228R/N276K, the ablation variants E233P/L234V/L235A/G236_/S267K on both first and second monomers, and optionally the 428L/434S variants on both first and second monomers.

In one embodiment, the targeted IL-15/IL-15Rα heterodimeric protein is an "mAb-ncIL-15/Rα" format heterodimeric protein that includes: a) a first monomer that includes, from N- to C-terminus, a VH-hinge-CH2-CH3, where CH2-CH3 is a first variant Fc domain; b) a second monomer that includes, from N- to C-terminus, a VH-hinge-CH2-CH3-(domain linker)-IL-15Rα(sushi) domain-(domain linker), where CH2-CH3 is a second variant Fc domain; c) a third monomer that includes an IL-15 variant; and d) a fourth and fifth monomer that each include, from N- to C-terminus, a VL-CL, where VL is a variable light domain, where the VH of the first monomer and the VL of the fourth monomer form a first TIM-3 binding domain, where the VH of the second monomer and the VL of the fifth monomer form a second TIM-3 binding domain, where the IL-15 variant and the IL-15Rα(sushi) domain form an IL-15 complex, where the IL-15 variant and the IL-15Rα(sushi) domain form an IL-15 complex, where the first variant Fc domain includes skew variants L368D/K370S and the second variant Fc domain include the skew variant pair S364K/E357Q, where the first and second variant Fc domains each include FcKO variants E233P/L234V/L235A/G236del/S267K, where the hinge-first variant Fc domain of the first monomer includes pI substitutions N208D/Q295E/N384D/Q418D/N421D and the hinge-second variant Fc domain of the second monomer includes pI variants Q196K/I199T/P271R/P228R/N276K, and where numbering is according to EU numbering. In one embodiment, the targeted IL-15/IL-15Rα heterodimeric protein is an "mAb-ncIL-15/Rα" format heterodimeric protein that includes: a) a first monomer that includes, from N- to C-terminus, a VH-hinge-CH2-CH3, where CH2-CH3 is a first variant Fc domain; b) a second monomer that includes, from N- to C-terminus, a VH-hinge-CH2-CH3-(domain linker)-IL-15Rα(sushi) domain-(domain linker), where CH2-CH3 is a second variant Fc domain; c) a third monomer that includes an IL-15 variant; and d) a fourth and fifth monomer that each include, from N- to C-terminus, a VL-CL, where VL is a variable light domain, where the VH of the first monomer and the VL of the fourth monomer form a first TIM-3 binding domain, where the VH of the second monomer and the VL of the fifth monomer form a second TIM-3 binding domain, where the IL-15 variant and the IL-15Rα(sushi) domain form an IL-15 complex, where the IL-15 variant and the IL-15Rα(sushi) domain form an IL-15 complex, where the first variant Fc domain includes skew variants L368D/K370S and the second variant Fc domain include the skew variant pair S364K/E357Q, where the first and second variant Fc domains each include FcKO variants E233P/L234V/L235A/G236del/S267K, where the hinge-first variant Fc domain of the first monomer includes pI substitutions N208D/Q295E/N384D/Q418D/N421D, and where numbering is according to EU numbering. In one embodiment, the targeted IL-15/IL-15Rα heterodimeric protein is an "mAb-ncIL-15/Rα" format heterodimeric protein that includes: a) a first monomer that includes, from N- to C-terminus, a VH-hinge-CH2-CH3, where CH2-CH3 is a first variant Fc domain; b) a second monomer that includes, from N- to C-terminus, a VH-hinge-CH2-CH3-(domain linker)-IL-15Rα(sushi) domain-(domain linker), where CH2-CH3 is a second variant Fc domain; c) a third monomer that includes an IL-15 variant; and d) a fourth and fifth monomer that each include, from N- to C-terminus, a VL-CL, where VL is a variable light domain, where the VH of the first monomer and the VL of the fourth monomer form a first TIM-3 binding domain, where the VH of the second monomer and the VL of the fifth monomer form a second TIM-3 binding domain, where the IL-15 variant and the IL-15Rα(sushi) domain form an IL-15 complex, where the IL-15 variant and the IL-15Rα(sushi) domain form an IL-15 complex, where the first variant Fc domain includes skew variants L368D/K370S and the second variant Fc domain include the skew variant pair S364K/E357Q, where the first and second variant Fc domains each include FcKO variants E233P/L234V/L235A/G236del/S267K, where the hinge-second variant Fc domain of the second monomer includes pI variants Q196K/I199T/P271R/P228R/N276K, and where numbering is according to EU numbering. In one embodiment, the targeted IL-15/IL-15Rα heterodimeric protein is an "mAb-ncIL-15/Rα" format heterodimeric protein that includes: a) a first monomer that includes, from N- to C-terminus, a VH-hinge-CH2-CH3, where CH2-CH3 is a first variant Fc domain; b) a second monomer that includes, from N- to C-terminus, a VH-hinge-CH2-CH3-(domain linker)-IL-15Rα(sushi) domain-(domain linker), where CH2-CH3 is a second variant Fc domain; c) a third monomer that includes an IL-15 variant; and d) a fourth and fifth monomer that each include, from N- to C-terminus, a VL-CL, where VL is a variable light domain, where the VH of the first monomer and the VL of the fourth monomer form a first TIM-3 binding domain, where the VH of the second monomer and the VL of the fifth monomer form a second TIM-3 binding domain, where the IL-15 variant and the IL-15Rα(sushi) domain form an IL-15 complex, where the IL-15 variant and the IL-15Rα(sushi) domain form an IL-15 complex, where the first variant Fc domain includes skew variants S364K/E357Q and the second variant Fc domain include the skew variant pair L368D/K370S, where the first and second variant Fc domains each include FcKO variants E233P/L234V/L235A/G236del/S267K, where the hinge-first variant Fc domain of the first monomer includes pI substitutions Q196K/I199T/P271R/P228R/N276K and the hinge-second variant Fc domain of the second monomer includes pI variants N208D/Q295E/N384D/Q418D/N421D, and where numbering is according to EU numbering. In one embodiment, the targeted IL-15/IL-15Rα heterodimeric protein is an "mAb-ncIL-15/Rα" format heterodimeric protein that includes: a) a first monomer that includes, from N- to C-terminus, a VH-hinge-CH2-CH3, where CH2-CH3 is a first variant Fc domain; b) a second monomer that includes, from N- to C-terminus, a VH-hinge-CH2-CH3-(domain linker)-IL-15Rα(sushi) domain-(domain linker), where CH2-CH3 is a second variant Fc domain; c) a third monomer that includes an IL-15 variant; and d) a fourth and fifth monomer that each include, from N- to C-terminus, a VL-CL, where VL is a variable light domain, where the VH of the first monomer and the VL of the fourth monomer form a first TIM-3 binding domain, where the VH of the second monomer and the VL of the fifth monomer form a second TIM-3 binding domain, where the IL-15 variant and the IL-15Rα(sushi) domain form an IL-15 complex, where the IL-15 variant and the IL-15Rα(sushi) domain form an IL-15 complex, where the first variant Fc domain includes skew variants S364K/E357Q and the second variant Fc domain include the skew variant pair L368D/K370S, where the first and second variant Fc domains each include FcKO variants E233P/L234V/L235A/G236del/S267K, where the hinge-first variant Fc domain of the first monomer includes pI substitutions Q196K/I199T/P271R/P228R/N276K, and where numbering is according to EU numbering. In one embodiment, the targeted IL-15/IL-15Rα heterodimeric protein is an "mAb-ncIL-15/Rα" format heterodimeric protein that includes: a) a first monomer that includes, from N- to C-terminus, a VH-hinge-CH2-CH3, where CH2-CH3 is a first variant Fc domain; b) a second monomer that includes, from N- to C-terminus, a VH-hinge-CH2-CH3-(domain linker)-IL-15Rα(sushi) domain-(domain linker), where CH2-CH3 is a second variant Fc domain; c) a third monomer that includes an IL-15 variant; and d) a fourth and fifth monomer that each include, from N- to C-terminus, a VL-CL, where VL is a variable light domain, where the VH of the first monomer and the VL of the fourth monomer form a first TIM-3 binding domain, where the VH of the second monomer and the VL of the fifth monomer form a second TIM-3 binding domain, where the IL-15 variant and the IL-15Rα(sushi) domain form an IL-15 complex, where the IL-15 variant and the IL-15Rα(sushi) domain form an IL-15 complex, where the first variant Fc domain includes skew variants S364K/E357Q and the second variant Fc domain include the skew variant pair L368D/K370S, where the first and second variant Fc domains each include FcKO variants E233P/L234V/L235A/G236del/S267K, where the hinge-second variant Fc domain of the second monomer includes pI variants N208D/Q295E/N384D/Q418D/N421D, and where numbering is according to EU numbering. In certain embodiments, the first and second variant Fc domains each further include half-life extension variants M428L/N434S. In an exemplary embodiment, the IL-15 variant includes amino acid substitutions N4D/N65D, D30N/N65D, or D30N/E64Q/N65D. In an exemplary embodiment, the VH and VL are the VH and VL of any of the TIM-3 ABDs in FIGS. 12 and 13A-C and the IL-15 variant includes amino acid substitutions N4D/N65D. In another exemplary embodiment, the VH and VL are the VH and VL of any of the TIM-3 ABDs in FIGS. 12 and 13A-C and the IL-15 variant includes amino acid substitutions D30N/N65D. In yet another exemplary embodiment, the VH and VL are the VH and VL of any of the TIM-3 ABDs in FIGS. 12 and 13A-C and the IL-15 variant includes amino acid substitutions D30N/E64Q/N65D.

In the mAb-ncIL-15/Rα format, one preferred embodiment utilizes an anti-TIM-3 ABD variable heavy and light domain pair of 3H3[TIM-3]_H1_L2.1 as shown in FIG. 12 with the FIG. 21H format, the skew variant set S364K/E357Q:L368D/K370S, the pI variants N208D/Q295E/N384D/Q418D/N421D and/or Q196K/I199T/P271R/P228R/N276K, the ablation variants E233P/L234V/L235A/G236_/S267K on both first and second monomers, and optionally the 428L/434S variants on both first and second monomers. In an exemplary embodiment, the IL-15 variant includes amino acid substitutions N4D/N65D, D30N/N65D, or D30N/E64Q/N65D.

In one embodiment, the targeted IL-15/IL-15Rα heterodimeric protein is an "mAb-ncIL-15/Rα" format heterodimeric protein that includes: a) a first monomer that includes, from N- to C-terminus, a VH-hinge-CH2-CH3, where CH2-CH3 is a first variant Fc domain; b) a second monomer that includes, from N- to C-terminus, a VH-hinge-CH2-CH3-(domain linker)-IL-15Rα(sushi) domain-(domain linker), where CH2-CH3 is a second variant Fc domain; c) a third monomer that includes an IL-15 variant; and d) a fourth and fifth monomer that each include, from N- to C-terminus, a VL-CL, where VL is a variable light domain, where the VH of the first monomer and the VL of the fourth monomer form a first TIM-3 binding domain, where the VH of the second monomer and the VL of the fifth monomer form a second TIM-3 binding domain, where the IL-15 variant and the IL-15Rα(sushi) domain form an IL-15 complex, where the IL-15 variant and the IL-15Rα(sushi) domain form an IL-15 complex, where VH and VL are the variable heavy domain and variable light domain of 3H3[TIM-3]_H1_L2.1, where the first variant Fc domain includes skew variants L368D/K370S and the second variant Fc domain include the skew variant pair S364K/E357Q where the first and second variant Fc domains each include FcKO variants E233P/L234V/L235A/G236del/S267K, where the hinge-first variant Fc domain of the first monomer includes pI substitutions N208D/Q295E/N384D/Q418D/N421D and the hinge-second variant Fc domain of the second monomer includes pI variants Q196K/I199T/P271R/P228R/N276K, and where numbering is according to EU numbering. In one embodiment, the targeted IL-15/IL-15Rα heterodimeric protein is an "mAb-ncIL-15/Rα" format heterodimeric protein that includes: a) a first monomer that includes, from N- to C-terminus, a VH-hinge-CH2-CH3, where CH2-CH3 is a first variant Fc domain; b) a second monomer that includes, from N- to C-terminus, a VH-hinge-CH2-CH3-(domain linker)-IL-15Rα(sushi) domain-(domain linker), where CH2-CH3 is a second variant Fc domain; c) a third monomer that includes an IL-15 variant; and d) a fourth and fifth monomer that each include, from N- to C-terminus, a VL-CL, where VL is a variable light domain, where the VH of the first monomer and the VL of the fourth monomer form a first TIM-3 binding domain, where the VH of the second monomer and the VL of the fifth monomer form a second TIM-3 binding domain, where the IL-15 variant and the IL-15Rα(sushi) domain form an IL-15 complex, where the IL-15 variant and the IL-15Rα(sushi) domain form an IL-15 complex, where VH and VL are the variable heavy domain and variable light domain of 3H3[TIM-3]_H1_L2.1, where the first variant Fc domain includes skew variants L368D/K370S and the second variant Fc domain include the skew variant pair S364K/E357Q, where the first and second variant Fc domains each include FcKO variants E233P/L234V/L235A/G236del/S267K, where the hinge-first variant Fc domain of the first monomer includes pI substitutions N208D/Q295E/N384D/Q418D/N421D, and where numbering is according to EU numbering. In one embodiment, the targeted IL-15/IL-15Rα heterodimeric protein is an "mAb-ncIL-15/Rα" format heterodimeric protein that includes: a) a first monomer that includes, from N- to C-terminus, a VH-hinge-CH2-CH3, where CH2-CH3 is a first variant Fc domain; b) a second monomer that includes, from N- to C-terminus, a VH-hinge-CH2-CH3-(domain linker)-IL-15Rα(sushi) domain-(domain linker), where CH2-CH3 is a second variant Fc domain; c) a third monomer that includes an IL-15 variant; and d) a fourth and fifth monomer that each include, from N- to C-terminus, a VL-CL, where VL is a variable light domain, where the VH of the first monomer and the VL of the fourth monomer form a first TIM-3 binding domain, where the VH of the second monomer and the VL of the fifth monomer form a second TIM-3 binding domain, where the IL-15 variant and the IL-15Rα(sushi) domain form an IL-15 complex, where the IL-15 variant and the IL-15Rα(sushi) domain form an IL-15 complex, where VH and VL are the variable heavy domain and variable light domain of 3H3[TIM-3]_H1_L2.1, where the first variant Fc domain includes skew variants L368D/K370S and the second variant Fc domain include the skew variant pair S364K/E357Q, where the first and second variant Fc domains each include FcKO variants E233P/L234V/L235A/G236del/S267K, where the hinge-second variant Fc domain of the second monomer includes pI variants Q196K/I199T/P271R/P228R/N276K, and where numbering is according to EU numbering. In one embodiment, the targeted IL-15/IL-15Rα heterodimeric protein is an "mAb-ncIL-15/Rα" format heterodimeric protein that includes: a) a first monomer that includes, from N- to C-terminus, a VH-hinge-CH2-CH3, where CH2-CH3 is a first variant Fc domain; b) a second monomer that includes, from N- to C-terminus, a VH-hinge-CH2-CH3-(domain linker)-IL-15Rα(sushi) domain-(domain linker), where CH2-CH3 is a second variant Fc domain; c) a third monomer that includes an IL-15 variant; and d) a fourth and fifth monomer that each include, from N- to C-terminus, a VL-CL, where VL is a variable light domain, where the VH of the first monomer and the VL of the fourth monomer form a first TIM-3 binding domain, where the VH of the second monomer and the VL of the fifth monomer form a second TIM-3 binding domain, where the IL-15 variant and the IL-15Rα(sushi) domain form an IL-15 complex, where the IL-15 variant and the IL-15Rα(sushi) domain form an IL-15 complex, where VH and VL are the variable heavy domain and variable light domain of 3H3[TIM-3]_H1_L2.1, where the first variant Fc domain includes skew variants S364K/E357Q and the second variant Fc domain include the skew variant pair L368D/K370S, where the first and second variant Fc domains each include FcKO variants E233P/L234V/L235A/G236del/S267K, where the hinge-first variant Fc domain of the first monomer includes pI substitutions Q196K/I199T/P271R/P228R/N276K and the hinge-second variant Fc domain of the second monomer includes pI variants N208D/Q295E/N384D/Q418D/N421D, and where numbering is according to EU numbering. In one embodiment, the targeted IL-15/IL-15Rα heterodimeric protein is an "mAb-ncIL-15/Rα" format heterodimeric protein that includes: a) a first monomer that includes, from N- to C-terminus, a VH-hinge-CH2-CH3, where CH2-CH3 is a first variant Fc domain; b) a second monomer that includes, from N- to C-terminus, a VH-hinge-CH2-CH3-(domain linker)-IL-15Rα(sushi) domain-(domain linker), where CH2-CH3 is a second variant Fc domain; c) a third monomer that includes an IL-15 variant; and d) a fourth and fifth monomer that each include, from N- to C-terminus, a VL-CL, where VL is a variable light domain, where the VH of the first monomer and the VL of the fourth monomer form a first TIM-3 binding domain, where the VH of the second monomer and the VL of the fifth monomer form a second TIM-3 binding domain, where the IL-15 variant and the IL-15Rα(sushi) domain form an IL-15 complex, where the IL-15 variant and the IL-15Rα(sushi) domain form an IL-15 complex, where VH and VL are the variable heavy domain and variable light domain of 3H3 [TIM-3]_H1_L2.1, where the first variant Fc domain includes skew variants S364K/E357Q and the second variant Fc domain include the skew variant pair L368D/K370S, where the first and second variant Fc domains each include FcKO variants E233P/L234V/L235A/G236del/S267K, where the hinge-first variant Fc domain of the first monomer includes pI substitutions Q196K/I199T/P271R/P228R/

N276K, and where numbering is according to EU numbering. In one embodiment, the targeted IL-15/IL-15Rα heterodimeric protein is an "mAb-ncIL-15/Rα" format heterodimeric protein that includes: a) a first monomer that includes, from N- to C-terminus, a VH-hinge-CH2-CH3, where CH2-CH3 is a first variant Fc domain; b) a second monomer that includes, from N- to C-terminus, a VH-hinge-CH2-CH3-(domain linker)-IL-15Rα(sushi) domain-(domain linker), where CH2-CH3 is a second variant Fc domain; c) a third monomer that includes an IL-15 variant; and d) a fourth and fifth monomer that each include, from N- to C-terminus, a VL-CL, where VL is a variable light domain, where the VH of the first monomer and the VL of the fourth monomer form a first TIM-3 binding domain, where the VH of the second monomer and the VL of the fifth monomer form a second TIM-3 binding domain, where the IL-15 variant and the IL-15Rα(sushi) domain form an IL-15 complex, where the IL-15 variant and the IL-15Rα(sushi) domain form an IL-15 complex, where VH and VL are the variable heavy domain and variable light domain of 3H3 [TIM-3]_H1_L2.1, where the first variant Fc domain includes skew variants S364K/E357Q and the second variant Fc domain include the skew variant pair L368D/K370S, where the first and second variant Fc domains each include FcKO variants E233P/L234V/L235A/G236del/S267K, where the hinge-second variant Fc domain of the second monomer includes pI variants N208D/Q295E/N384D/Q418D/N421D, and where numbering is according to EU numbering. In certain embodiments, the first and second variant Fc domains each further include half-life extension variants M428L/N434S. In a particular embodiment, the IL-15 variant includes amino acid substitutions N4D/N65D and VH and VL are the variable heavy domain and variable light domain of 3H3[TIM-3]_H1_L2.1. In one embodiment, the IL-15 variant includes amino acid substitutions D30N/N65D and VH and VL are the variable heavy domain and variable light domain of 3H3[TIM-3]_H1_L2.1. In another embodiment, the IL-15 variant includes amino acid substitutions D30N/E64Q/N65D and VH and VL are the variable heavy domain and variable light domain of 3H3[TIM-3]_H1_L2.1.

I. mAb-dsIL-15/Rα

Figure 21I:
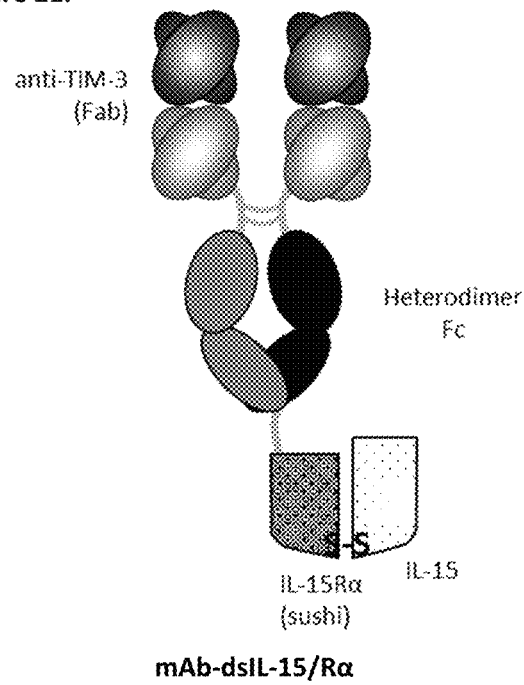

This embodiment is shown in FIG. 21I, and comprises four monomers (although the heterodimeric fusion protein is a pentamer). The first monomer comprises a heavy chain, VH-CH1-hinge-CH2-CH3. The second monomer comprises a heavy chain with an IL-15Rα(sushi) domain: e.g., VH-CH1-hinge-CH2-CH3-domain linker-IL-15Rα(sushi) domain, where the IL-15Rα(sushi) domain has been engineered to contain a cysteine residue. The third monomer is a variant IL-15 domain, which has been engineered to contain a cysteine residue, such that the IL-15 complex is formed under physiological conditions. The fourth (and fifth) monomer are light chains, VL-CL. This is generally referred to as "mAb-dsIL-15/Rα", with the "ds" standing for "disulfide", and it binds TIM-3 bivalently.

In one embodiment, the targeted IL-15/IL-15Rα heterodimeric protein is an "mAb-dsIL-15/Rα" format heterodimeric protein that includes: a) a first monomer that includes, from N- to C-terminus, a VH-hinge-CH2-CH3, where CH2-CH3 is a first Fc domain; b) a second monomer that includes, from N- to C-terminus, a VH-hinge-CH2-CH3-(domain linker)-IL-15Rα(sushi) domain-(domain linker), where the IL-15Rα(sushi) domain includes an amino acid substitution for a cysteine residue and CH2-CH3 is a second Fc domain; c) a third monomer that includes an IL-15 variant that includes an amino acid substitution for a cysteine residue; and d) a fourth and fifth monomer that each include, from N- to C-terminus, a VL-CL, where VL is a variable light domain, where the VH of the first monomer and the VL of the fourth monomer form a first TIM-3 binding domain, where the VH of the second monomer and the VL of the fifth monomer form a second TIM-3 binding domain, and where the cysteine residue on the IL-15 variant and the cysteine residue on the IL-15Rα(sushi) domain form a disulfide bond. Any useful domain linker can be used to attach the various components of the heterodimeric protein including, but not limited to those in FIGS. 8 and 9A-C.

In the mAb-dsIL-15/Rα format, one preferred embodiment utilizes an anti-TIM-3 ABD having any of the variable heavy and light domain pairs as shown in FIG. 12.

In the mAb-dsIL-15/Rα format, one preferred embodiment utilizes an anti-TIM-3 ABD having the variable heavy and light domain pair of 3H3[TIM-3]_H1_L2.1 as shown in FIG. 12.

In one embodiment, the targeted IL-15/IL-15Rα heterodimeric protein is an "mAb-dsIL-15/Rα" format heterodimeric protein that includes: a) a first monomer that includes, from N- to C-terminus, a VH-hinge-CH2-CH3, where CH2-CH3 is a first Fc domain; b) a second monomer that includes, from N- to C-terminus, a VH-hinge-CH2-CH3-(domain linker)-IL-15Rα(sushi) domain-(domain linker), where the IL-15Rα(sushi) domain includes an amino acid substitution for a cysteine residue and CH2-CH3 is a second Fc domain; c) a third monomer that includes an IL-15 variant that includes an amino acid substitution for a cysteine residue; and d) a fourth and fifth monomer that each include, from N- to C-terminus, a VL-CL, where VL is a variable light domain, where the VH of the first monomer and the VL of the fourth monomer are the variable heavy domain and variable light domain 3H3[TIM-3]_H1_L2.1, respectively, where the VH of the second monomer and the VL of the fifth monomer are the variable heavy domain and variable light domain of 3H3[TIM-3]_H1_L2.1, respectively, and where the cysteine residue on the IL-15 variant and the cysteine residue on the IL-15Rα(sushi) domain form a disulfide bond.

In the mAb-dsIL-15/Rα format, one preferred embodiment utilizes an IL-15 variant that includes amino acid substitutions N4D/N65D, D30N/N65D, or D30N/E64Q/N65D, with the appropriate cysteine amino acid substitutions. In one embodiment, the targeted IL-15/IL-15Rα heterodimeric protein is an "mAb-dsIL-15/Rα" format heterodimeric protein that includes: a) a first monomer that includes, from N- to C-terminus, a VH-hinge-CH2-CH3, where CH2-CH3 is a first Fc domain; b) a second monomer that includes, from N- to C-terminus, a VH-hinge-CH2-CH3-(domain linker)-IL-15Rα(sushi) domain-(domain linker), where the IL-15Rα(sushi) domain includes an amino acid substitution for a cysteine residue and CH2-CH3 is a second Fc domain; c) a third monomer that includes an IL-15 variant that includes an amino acid substitution for a cysteine residue; and d) a fourth and fifth monomer that each include, from N- to C-terminus, a VL-CL, where VL is a variable light domain, where the VH of the first monomer and the VL of the fourth monomer form a first TIM-3 binding domain, where the VH of the second monomer and the VL of the fifth monomer form a second TIM-3 binding domain, where the cysteine residue on the IL-15 variant and the cysteine residue on the IL-15Rα(sushi) domain form a disulfide bond, and where the IL-15 variant includes amino acid substitutions N4D/N65D, D30N/N65D, or D30N/E64Q/N65D. In an exemplary embodiment, the VH and VL are the VH and VL of any of the TIM-3 ABDs in FIGS. 12 and 13A-C and the IL-15 variant includes amino acid substitutions N4D/N65D. In another exemplary embodiment, the VH and VL are the VH and VL of any of the TIM-3 ABDs in FIGS. 12 and 13A-C and the IL-15 variant includes amino acid substitutions D30N/N65D. In yet another exemplary embodiment, the VH and VL are the VH and VL of any of the TIM-3 ABDs in FIGS. 12 and 13A-C and the IL-15 variant includes amino acid substitutions D30N/E64Q/N65D.

In the mAb-dsIL-15/Rα format, one preferred embodiment utilizes an anti-TIM-3 ABD having the variable heavy and light domain pair of 3H3[TIM-3]_H1_L2.1 as shown in FIG. 12, with either the IL-15 N4D/N65D variant or the IL-15 D30N/N65D variant or the IL-15 D30N/E64Q/N65D variant, with the appropriate cysteine amino acid substitutions. In one embodiment, the targeted IL-15/IL-15Rα heterodimeric protein is an "mAb-dsIL-15/Rα" format heterodimeric protein that includes: a) a first monomer that includes, from N- to C-terminus, a VH-hinge-CH2-CH3, where CH2-CH3 is a first Fc domain; b) a second monomer that includes, from N- to C-terminus, a VH-hinge-CH2-CH3-(domain linker)-IL-15Rα(sushi) domain-(domain linker), where the IL-15Rα(sushi) domain includes an amino acid substitution for a cysteine residue and CH2-CH3 is a second Fc domain; c) a third monomer that includes an IL-15 variant that includes an amino acid substitution for a cysteine residue; and d) a fourth and fifth monomer that each include, from N- to C-terminus, a VL-CL, where VL is a variable light domain, where the VH of the first monomer and the VL of the fourth monomer form a first TIM-3 binding domain, where the VH of the second monomer and the VL of the fifth monomer form a second TIM-3 binding domain, where the cysteine residue on the IL-15 variant and the cysteine residue on the IL-15Rα(sushi) domain form a disulfide bond, where VH and VL are the variable heavy domain and variable light domain of 3H3[TIM-3]_H1_L2.1, and where the IL-15 variant includes amino acid substitutions N4D/N65D, D30N/N65D, or D30N/E64Q/N65D. In a particular embodiment, the IL-15 variant includes amino acid substitutions N4D/N65D and VH and VL are the variable heavy domain and variable light domain of 3H3[TIM-3]_H1_L2.1. In one embodiment, the IL-15 variant includes amino acid substitutions D30N/N65D and VH and VL are the variable heavy domain and variable light domain of 3H3[TIM-3]_H1_L2.1. In another embodiment, the IL-15 variant includes amino acid substitutions D30N/E64Q/N65D and VH and VL are the variable heavy domain and variable light domain of 3H3[TIM-3]_H1_L2.1.

In the mAb-dsIL-15/Rα format, one preferred embodiment utilizes the skew variant pair S364K/E357Q:L368D/K370S. In one embodiment, the targeted IL-15/IL-15Rα heterodimeric protein is an "mAb-dsIL-15/Rα" format heterodimeric protein that includes: a) a first monomer that includes, from N- to C-terminus, a VH-hinge-CH2-CH3, where CH2-CH3 is a first variant Fc domain; b) a second monomer that includes, from N- to C-terminus, a VH-hinge-CH2-CH3-(domain linker)-IL-15Rα(sushi) domain-(domain linker), where the IL-15Rα(sushi) domain includes an amino acid substitution for a cysteine residue and CH2-CH3 is a second variant Fc domain; c) a third monomer that includes an IL-15 variant that includes an amino acid substitution for a cysteine residue; and d) a fourth and fifth monomer that each include, from N- to C-terminus, a VL-CL, where VL is a variable light domain, where the VH of the first monomer and the VL of the fourth monomer form a first TIM-3 binding domain, where the VH of the second monomer and the VL of the fifth monomer form a second TIM-3 binding domain, where the cysteine residue on the IL-15 variant and the cysteine residue on the IL-15Rα(sushi) domain form a disulfide bond, and where the first and second variant Fc domains include the skew variant pair S364K/E357Q: L368D/K370S. In an exemplary embodiment, the first variant Fc domain includes skew variants L368D/K370S, and the second variant Fc domain includes skew variants S364K/E357Q. In another exemplary embodiment, the first variant Fc domain includes skew variants S364K/E357Q, and the second variant Fc domain includes skew variants L368D/K370S.

In one embodiment, the targeted IL-15/IL-15Rα heterodimeric protein is an "mAb-dsIL-15/Rα" format heterodimeric protein that includes: a) a first monomer that includes, from N- to C-terminus, a VH-hinge-CH2-CH3, where CH2-CH3 is a first variant Fc domain; b) a second monomer that includes, from N- to C-terminus, a VH-hinge-CH2-CH3-(domain linker)-IL-15Rα(sushi) domain-(domain linker), where the IL-15Rα(sushi) domain includes an amino acid substitution for a cysteine residue and CH2-CH3 is a second variant Fc domain; c) a third monomer that includes an IL-15 variant that includes an amino acid substitution for a cysteine residue; and d) a fourth and fifth monomer that each include, from N- to C-terminus, a VL-CL, where VL is a variable light domain, where the VH of the first monomer and the VL of the fourth monomer form a first TIM-3 binding domain, where the VH of the second monomer and the VL of the fifth monomer form a second TIM-3 binding domain, where the cysteine residue on the IL-15 variant and the cysteine residue on the IL-15Rα(sushi) domain form a disulfide bond, where the IL-15 variant includes amino acid substitutions N4D/N65D, D30N/N65D, or D30N/E64Q/N65D, and where the first and second variant Fc domains include the skew variant pair S364K/E357Q:L368D/K370S. In an exemplary embodiment, the first variant Fc domain includes skew variants L368D/K370S, and the second variant Fc domain includes skew variants S364K/E357Q. In another exemplary embodiment, the first variant Fc domain includes skew variants S364K/E357Q, and the second variant Fc domain includes skew variants L368D/K370S. In an exemplary embodiment, the VH and VL are the VH and VL of any of the TIM-3 ABDs in FIGS. 12 and 13A-C and the IL-15 variant includes amino acid substitutions N4D/N65D. In another exemplary embodiment, the VH and VL are the VH and VL of any of the TIM-3 ABDs in FIGS. 12 and 13A-C and the IL-15 variant includes amino acid substitutions D30N/N65D. In yet another exemplary embodiment, the VH and VL are the VH and VL of any of the TIM-3 ABDs in FIGS. 12 and 13A-C and the IL-15 variant includes amino acid substitutions D30N/E64Q/N65D.

In the mAb-dsIL-15/Rα format, one preferred embodiment utilizes an anti-TIM-3 ABD having the variable heavy and light domain pair of 3H3[TIM-3]_H1_L2.1 as shown in FIG. 12 and the skew variant pair S364K/E357Q:L368D/K370S. In one embodiment, the targeted IL-15/IL-15Rα heterodimeric protein is an "mAb-dsIL-15/Rα" format heterodimeric protein that includes: a) a first monomer that includes, from N- to C-terminus, a VH-hinge-CH2-CH3, where CH2-CH3 is a first variant Fc domain; b) a second monomer that includes, from N- to C-terminus, a VH-hinge-CH2-CH3-(domain linker)-IL-15Rα(sushi) domain-(domain linker), where the IL-15Rα(sushi) domain includes an amino acid substitution for a cysteine residue and CH2-CH3 is a second variant Fc domain; c) a third monomer that includes an IL-15 variant that includes an amino acid substitution for a cysteine residue; and d) a fourth and fifth monomer that each include, from N- to C-terminus, a VL-CL, where VL is a variable light domain, where the VH of the first monomer and the VL of the fourth monomer are the variable heavy domain and variable light domain of 3H3[TIM-3]_H1_L2.1, respectively, where the VH of the second monomer and the VL of the fifth monomer are the variable heavy domain and variable light domain of 3H3 [TIM-3]_H1_L2.1, respectively, where the cysteine residue on the IL-15 variant and the cysteine residue on the IL-15Rα (sushi) domain form a disulfide bond, and where the first and second variant Fc domains include the skew variant pair S364K/E357Q:L368D/K370S.

In the mAb-dsIL-15/Rα format, one preferred embodiment utilizes an anti-TIM-3 ABD having the variable heavy and light domain pair of 3H3[TIM-3]_H1_L2.1 as shown in FIG. 12 and the skew variant pair S364K/E357Q:L368D/K370S with either the IL-15 N4D/N65D variant or the IL-15 D30N/N65D variant or the IL-15 D30N/E64Q/N65D variant with appropriate cysteine substitutions. In one embodiment, the targeted IL-15/IL-15Rα heterodimeric protein is an "mAb-dsIL-15/Rα" format heterodimeric protein that includes: a) a first monomer that includes, from N- to C-terminus, a VH-hinge-CH2-CH3, where CH2-CH3 is a first Fc domain; b) a second monomer that includes, from N- to C-terminus, a VH-hinge-CH2-CH3-(domain linker)-IL-15Rα(sushi) domain-(domain linker), where the IL-15Rα (sushi) domain includes an amino acid substitution for a cysteine residue and CH2-CH3 is a second Fc domain; c) a third monomer that includes an IL-15 variant that includes an amino acid substitution for a cysteine residue; and d) a fourth and fifth monomer that each include, from N- to C-terminus, a VL-CL, where VL is a variable light domain, where the VH of the first monomer and the VL of the fourth monomer form a first TIM-3 binding domain, where the VH of the second monomer and the VL of the fifth monomer form a second TIM-3 binding domain where the cysteine residue on the IL-15 variant and the cysteine residue on the IL-15Rα(sushi) domain form a disulfide bond, where VH and VL are the variable heavy domain and variable light domain of 3H3[TIM-3]_H1_L2.1, where the IL-15 variant includes amino acid substitutions N4D/N65D, D30N/N65D, or D30N/E64Q/N65D, and where the first and second variant Fc domains include the skew variant pair S364K/E357Q: L368D/K370S. In an exemplary embodiment, the first variant Fc domain includes skew variants L368D/K370S, and the second variant Fc domain includes skew variants S364K/E357Q. In an exemplary embodiment, the first variant Fc domain includes skew variants S364K/E357Q, and the second variant Fc domain includes skew variants L368D/K370S. In a particular embodiment, the IL-15 variant includes amino acid substitutions N4D/N65D and VH and VL are the variable heavy domain and variable light domain of 3H3[TIM-3]_H1_L2.1. In one embodiment, the IL-15 variant includes amino acid substitutions D30N/N65D and VH and VL are the variable heavy domain and variable light domain of 3H3[TIM-3]_H1_L2.1. In another embodiment, the IL-15 variant includes amino acid substitutions D30N/E64Q/N65D and VH and VL are the variable heavy domain and variable light domain of 3H3[TIM-3]_H1_L2.1.

In the mAb-dsIL-15/Rα format, one preferred embodiment utilizes the skew variant set S364K/E357Q:L368D/K370S, the pI variants N208D/Q295E/N384D/Q418D/N421D and/or Q196K/I199T/P271R/P228R/N276K, the ablation variants E233P/L234V/L235A/G236_/S267K on both first and second monomers, and optionally the 428L/434S variants on both first and second monomers.

In one embodiment, the targeted IL-15/IL-15Rα heterodimeric protein is an "mAb-dsIL-15/Rα" format heterodimeric protein that includes: a) a first monomer that includes, from N- to C-terminus, a VH-hinge-CH2-CH3, where CH2-CH3 is a first Fc domain; b) a second monomer that includes, from N- to C-terminus, a VH-hinge-CH2-CH3-(domain linker)-IL-15Rα(sushi) domain-(domain linker), where the IL-15Rα(sushi) domain includes an amino acid substitution for a cysteine residue and CH2-CH3 is a second Fc domain; c) a third monomer that includes an IL-15 variant that includes an amino acid substitution for a cysteine residue; and d) a fourth and fifth monomer that each include, from N- to C-terminus, a VL-CL, where VL is a variable light domain, where the VH of the first monomer and the VL of the fourth monomer form a first TIM-3 binding domain, where the VH of the second monomer and the VL of the fifth monomer form a second TIM-3 binding domain, where the cysteine residue on the IL-15 variant and the cysteine residue on the IL-15Rα(sushi) domain form a disulfide bond, where the first variant Fc domain includes skew variants L368D/K370S and the second variant Fc domain include the skew variant pair S364K/E357Q, where the first and second variant Fc domains each include FcKO variants E233P/L234V/L235A/G236del/S267K, where the hinge-first variant Fc domain of the first monomer includes pI substitutions N208D/Q295E/N384D/Q418D/N421D and the hinge-second variant Fc domain of the second monomer includes pI variants Q196K/I199T/P271R/P228R/N276K, and where numbering is according to EU numbering. In one embodiment, the targeted IL-15/IL-15Rα heterodimeric protein is an "mAb-dsIL-15/Rα" format heterodimeric protein that includes: a) a first monomer that includes, from N- to C-terminus, a VH-hinge-CH2-CH3, where CH2-CH3 is a first Fc domain; b) a second monomer that includes, from N- to C-terminus, a VH-hinge-CH2-CH3-(domain linker)-IL-15Rα(sushi) domain-(domain linker), where the IL-15Rα (sushi) domain includes an amino acid substitution for a cysteine residue and CH2-CH3 is a second Fc domain; c) a third monomer that includes an IL-15 variant that includes an amino acid substitution for a cysteine residue; and d) a fourth and fifth monomer that each include, from N- to C-terminus, a VL-CL, where VL is a variable light domain, where the VH of the first monomer and the VL of the fourth monomer form a first TIM-3 binding domain, where the VH of the second monomer and the VL of the fifth monomer form a second TIM-3 binding domain, where the cysteine residue on the IL-15 variant and the cysteine residue on the IL-15Rα(sushi) domain form a disulfide bond, where the first variant Fc domain includes skew variants L368D/K370S and the second variant Fc domain include the skew variant pair S364K/E357Q, where the first and second variant Fc domains each include FcKO variants E233P/L234V/L235A/G236del/S267K, where the hinge-first variant Fc domain of the first monomer includes pI substitutions N208D/Q295E/N384D/Q418D/N421D, and where numbering is according to EU numbering. In one embodiment, the targeted IL-15/IL-15Rα heterodimeric protein is an "mAb-dsIL-15/Rα" format heterodimeric protein that includes: a) a first monomer that includes, from N- to C-terminus, a VH-hinge-CH2-CH3, where CH2-CH3 is a first Fc domain; b) a second monomer that includes, from N- to C-terminus, a VH-hinge-CH2-CH3-(domain linker)-IL-15Rα(sushi) domain-(domain linker), where the IL-15Rα(sushi) domain includes an amino acid substitution for a cysteine residue and CH2-CH3 is a second Fc domain; c) a third monomer that includes an IL-15 variant that includes an amino acid substitution for a cysteine residue; and d) a fourth and fifth monomer that each include, from N- to C-terminus, a VL-CL, where VL is a variable light domain, where the VH of the first monomer and the VL of the fourth monomer form a first TIM-3 binding domain, where the VH of the second monomer and the VL of the fifth monomer form a second TIM-3 binding domain, where the cysteine residue on the IL-15 variant and the cysteine residue on the IL-15Rα(sushi) domain form a disulfide bond, where the first variant Fc domain includes skew variants L368D/K370S and the second variant Fc domain include the skew variant pair S364K/E357Q, where the first and second variant Fc domains each include FcKO variants E233P/L234V/L235A/G236del/S267K, where the hinge-second variant Fc domain of the second monomer includes pI variants Q196K/I199T/P271R/P228R/N276K, and where numbering is according to EU numbering. In one embodiment, the targeted IL-15/IL-15Rα heterodimeric protein is an "mAb-dsIL-15/Rα" format heterodimeric protein that includes: a) a first monomer that includes, from N- to C-terminus, a VH-hinge-CH2-CH3, where CH2-CH3 is a first Fc domain; b) a second monomer that includes, from N- to C-terminus, a VH-hinge-CH2-CH3-(domain linker)-IL-15Rα(sushi) domain-(domain linker), where the IL-15Rα(sushi) domain includes an amino acid substitution for a cysteine residue and CH2-CH3 is a second Fc domain; c) a third monomer that includes an IL-15 variant that includes an amino acid substitution for a cysteine residue; and d) a fourth and fifth monomer that each include, from N- to C-terminus, a VL-CL, where VL is a variable light domain, where the VH of the first monomer and the VL of the fourth monomer form a first TIM-3 binding domain, where the VH of the second monomer and the VL of the fifth monomer form a second TIM-3 binding domain, where the cysteine residue on the IL-15 variant and the cysteine residue on the IL-15Rα(sushi) domain form a disulfide bond, where the first variant Fc domain includes skew variants S364K/E357Q and the second variant Fc domain include the skew variant pair L368D/K370S, where the first and second variant Fc domains each include FcKO variants E233P/L234V/L235A/G236del/S267K, where the hinge-first variant Fc domain of the first monomer includes pI substitutions Q196K/I199T/P271R/P228R/N276K and the hinge-second variant Fc domain of the second monomer includes pI variants N208D/Q295E/N384D/Q418D/N421D, and where numbering is according to EU numbering. In one embodiment, the targeted IL-15/IL-15Rα heterodimeric protein is an "mAb-dsIL-15/Rα" format heterodimeric protein that includes: a) a first monomer that includes, from N- to C-terminus, a VH-hinge-CH2-CH3, where CH2-CH3 is a first Fc domain; b) a second monomer that includes, from N- to C-terminus, a VH-hinge-CH2-CH3-(domain linker)-IL-15Rα(sushi) domain-(domain linker), where the IL-15Rα(sushi) domain includes an amino acid substitution for a cysteine residue and CH2-CH3 is a second Fc domain; c) a third monomer that includes an IL-15 variant that includes an amino acid substitution for a cysteine residue; and d) a fourth and fifth monomer that each include, from N- to C-terminus, a VL-CL, where VL is a variable light domain, where the VH of the first monomer and the VL of the fourth monomer form a first TIM-3 binding domain, where the VH of the second monomer and the VL of the fifth monomer form a second TIM-3 binding domain, where the cysteine residue on the IL-15 variant and the cysteine residue on the IL-15Rα(sushi) domain form a disulfide bond, where the first variant Fc domain includes skew variants S364K/E357Q and the second variant Fc domain include the skew variant pair L368D/K370S, where the first and second variant Fc domains each include FcKO variants E233P/L234V/L235A/G236del/S267K, where the hinge-first variant Fc domain of the first monomer includes pI substitutions Q196K/I199T/P271R/P228R/N276K, and where numbering is according to EU numbering. In one embodiment, the targeted IL-15/IL-15Rα heterodimeric protein is an "mAb-dsIL-15/Rα" format heterodimeric protein that includes: a) a first monomer that includes, from N- to C-terminus, a VH-hinge-CH2-CH3, where CH2-CH3 is a first Fc domain; b) a second monomer that includes, from N- to C-terminus, a VH-hinge-CH2-CH3-(domain linker)-IL-15Rα(sushi) domain-(domain linker), where the IL-15Rα(sushi) domain includes an amino acid substitution for a cysteine residue and CH2-CH3 is a second Fc domain; c) a third monomer that includes an IL-15 variant that includes an amino acid substitution for a cysteine residue; and d) a fourth and fifth monomer that each include, from N- to C-terminus, a VL-CL, where VL is a variable light domain, where the VH of the first monomer and the VL of the fourth monomer form a first TIM-3 binding domain, where the VH of the second monomer and the VL of the fifth monomer form a second TIM-3 binding domain, where the cysteine residue on the IL-15 variant and the cysteine residue on the IL-15Rα(sushi) domain form a disulfide bond, where the first variant Fc domain includes skew variants S364K/E357Q and the second variant Fc domain include the skew variant pair L368D/K370S, where the first and second variant Fc domains each include FcKO variants E233P/L234V/L235A/G236del/S267K, where the hinge-second variant Fc domain of the second monomer includes pI variants N208D/Q295E/N384D/Q418D/N421D, and where numbering is according to EU numbering. In certain embodiments, the first and second variant Fc domains each further include half-life extension variants M428L/N434S. In an exemplary embodiment, the IL-15 variant includes amino acid substitutions N4D/N65D, D30N/N65D, or D30N/E64Q/N65D. In an exemplary embodiment, the IL-15 variant includes amino acid substitutions N4D/N65D, D30N/N65D, or D30N/E64Q/N65D. In an exemplary embodiment, the VH and VL are the VH and VL of any of the TIM-3 ABDs in FIGS. 12 and 13A-C and the IL-15 variant includes amino acid substitutions N4D/N65D. In another exemplary embodiment, the VH and VL are the VH and VL of any of the TIM-3 ABDs in FIGS. 12 and 13A-C and the IL-15 variant includes amino acid substitutions D30N/N65D. In yet another exemplary embodiment, the VH and VL are the VH and VL of any of the TIM-3 ABDs in FIGS. 12 and 13A-C and the IL-15 variant includes amino acid substitutions D30N/E64Q/N65D.

In the mAb-dsIL-15/Rα format, one preferred embodiment utilizes an anti-TIM-3 ABD variable heavy and light domain pair of 3H3[TIM-3]_H1_L2.1 as shown in FIG. 12 with the FIG. 21I format, the skew variant set S364K/E357Q:L368D/K370S, the pI variants N208D/Q295E/N384D/Q418D/N421D and/or Q196K/I199T/P271R/P228R/N276K, the ablation variants E233P/L234V/L235A/G236_/S267K on both first and second monomers, and optionally the 428L/434S variants on both first and second monomers.

In one embodiment, the targeted IL-15/IL-15Rα heterodimeric protein is an "mAb-dsIL-15/Rα" format heterodimeric protein that includes: a) a first monomer that includes, from N- to C-terminus, a VH-hinge-CH2-CH3, where CH2-CH3 is a first Fc domain; b) a second monomer that includes, from N- to C-terminus, a VH-hinge-CH2-CH3-(domain linker)-IL-15Rα(sushi) domain-(domain linker), where the IL-15Rα(sushi) domain includes an amino acid substitution for a cysteine residue and CH2-CH3 is a second Fc domain; c) a third monomer that includes an IL-15 variant that includes an amino acid substitution for a cysteine residue;

and d) a fourth and fifth monomer that each include, from N- to C-terminus, a VL-CL, where VL is a variable light domain, where the VH of the first monomer and the VL of the fourth monomer form a first TIM-3 binding domain, where the VH of the second monomer and the VL of the fifth monomer form a second TIM-3 binding domain, where the cysteine residue on the IL-15 variant and the cysteine residue on the IL-15Rα(sushi) domain form a disulfide bond, where VH and VL are the variable heavy domain and variable light domain of 3H3[TIM-3]_H1_L2.1, where the first variant Fc domain includes skew variants L368D/K370S and the second variant Fc domain include the skew variant pair S364K/E357Q, where the first and second variant Fc domains each include FcKO variants E233P/L234V/L235A/G236del/S267K, where the hinge-first variant Fc domain of the first monomer includes pI substitutions N208D/Q295E/N384D/Q418D/N421D and the hinge-second variant Fc domain of the second monomer includes pI variants Q196K/I199T/P271R/P228R/N276K, and where numbering is according to EU numbering. In one embodiment, the targeted IL-15/IL-15Rα heterodimeric protein is an "mAb-dsIL-15/Rα" format heterodimeric protein that includes: a) a first monomer that includes, from N- to C-terminus, a VH-hinge-CH2-CH3, where CH2-CH3 is a first Fc domain; b) a second monomer that includes, from N- to C-terminus, a VH-hinge-CH2-CH3-(domain linker)-IL-15Rα(sushi) domain-(domain linker), where the IL-15Rα (sushi) domain includes an amino acid substitution for a cysteine residue and CH2-CH3 is a second Fc domain; c) a third monomer that includes an IL-15 variant that includes an amino acid substitution for a cysteine residue; and d) a fourth and fifth monomer that each include, from N- to C-terminus, a VL-CL, where VL is a variable light domain, where the VH of the first monomer and the VL of the fourth monomer form a first TIM-3 binding domain, where the VH of the second monomer and the VL of the fifth monomer form a second TIM-3 binding domain, where the cysteine residue on the IL-15 variant and the cysteine residue on the IL-15Rα(sushi) domain form a disulfide bond, where VH and VL are the variable heavy domain and variable light domain of 3H3[TIM-3]_H1_L2.1, where the first variant Fc domain includes skew variants L368D/K370S and the second variant Fc domain include the skew variant pair S364K/E357Q, where the first and second variant Fc domains each include FcKO variants E233P/L234V/L235A/G236del/S267K, where the hinge-first variant Fc domain of the first monomer includes pI substitutions N208D/Q295E/N384D/Q418D/N421D, and where numbering is according to EU numbering. In one embodiment, the targeted IL-15/IL-15Rα heterodimeric protein is an "mAb-dsIL-15/Rα" format heterodimeric protein that includes: a) a first monomer that includes, from N- to C-terminus, a VH-hinge-CH2-CH3, where CH2-CH3 is a first Fc domain; b) a second monomer that includes, from N- to C-terminus, a VH-hinge-CH2-CH3-(domain linker)-IL-15Rα(sushi) domain-(domain linker), where the IL-15Rα (sushi) domain includes an amino acid substitution for a cysteine residue and CH2-CH3 is a second Fc domain; c) a third monomer that includes an IL-15 variant that includes an amino acid substitution for a cysteine residue; and d) a fourth and fifth monomer that each include, from N- to C-terminus, a VL-CL, where VL is a variable light domain, where the VH of the first monomer and the VL of the fourth monomer form a first TIM-3 binding domain, where the VH of the second monomer and the VL of the fifth monomer form a second TIM-3 binding domain, where the cysteine residue on the IL-15 variant and the cysteine residue on the IL-15Rα(sushi) domain form a disulfide bond, where VH and VL are the variable heavy domain and variable light domain of 3H3[TIM-3]_H1_L2.1, where the first variant Fc domain includes skew variants S364K/E357Q and the second variant Fc domain include the skew variant pair L368D/K370S, where the first and second variant Fc domains each include FcKO variants E233P/L234V/L235A/G236del/S267K, where the hinge-first variant Fc domain of the first monomer includes pI substitutions Q196K/I199T/P271R/P228R/N276K and the hinge-second variant Fc domain of the second monomer includes pI variants N208D/Q295E/N384D/Q418D/N421D, and where numbering is according to EU numbering. In one embodiment, the targeted IL-15/IL-15Rα heterodimeric protein is an "mAb-dsIL-15/Rα" format heterodimeric protein that includes: a) a first monomer that includes, from N- to C-terminus, a VH-hinge-CH2-CH3, where CH2-CH3 is a first Fc domain; b) a second monomer that includes, from N- to C-terminus, a VH-hinge-CH2-CH3-(domain linker)-IL-15Rα(sushi) domain-(domain linker), where the IL-15Rα(sushi) domain includes an amino acid substitution for a cysteine residue and CH2-CH3 is a second Fc domain; c) a third monomer that includes an IL-15 variant that includes an amino acid substitution for a cysteine residue; and d) a fourth and fifth monomer that each include, from N- to C-terminus, a VL-CL, where VL is a variable light domain, where the VH of the first monomer and the VL of the fourth monomer form a first TIM-3 binding domain, where the VH of the second monomer and the VL of the fifth monomer form a second TIM-3 binding domain, where the cysteine residue on the IL-15 variant and the cysteine residue on the IL-15Rα(sushi) domain form a disulfide bond, where VH and VL are the variable heavy domain and variable light domain of 3H3[TIM-3]_H1_L2.1, where the first variant Fc domain includes skew variants S364K/E357Q and the second variant Fc domain include the skew variant pair L368D/K370S, where the first and second variant Fc domains each include FcKO variants E233P/L234V/L235A/G236del/S267K, where the hinge-first variant Fc domain of the first monomer includes pI substitutions Q196K/I199T/P271R/P228R/N276K, and where numbering is according to EU numbering. In one embodiment, the targeted IL-15/IL-15Rα heterodimeric protein is an "mAb-dsIL-15/Rα" format heterodimeric protein that includes: a) a first monomer that includes, from N- to C-terminus, a VH-hinge-CH2-CH3, where CH2-CH3 is a first Fc domain; b) a second monomer that includes, from N- to C-terminus, a VH-hinge-CH2-CH3-(domain linker)-IL-15Rα(sushi) domain-(domain linker), where the IL-15Rα(sushi) domain includes an amino acid substitution for a cysteine residue and CH2-CH3 is a second Fc domain; c) a third monomer that includes an IL-15 variant that includes an amino acid substitution for a cysteine residue; and d) a fourth and fifth monomer that each include, from N- to C-terminus, a VL-CL, where VL is a variable light domain, where the VH of the first monomer and the VL of the fourth monomer form a first TIM-3 binding domain, where the VH of the second monomer and the VL of the fifth monomer form a second TIM-3 binding domain, where the cysteine residue on the IL-15 variant and the cysteine residue on the IL-15Rα(sushi) domain form a disulfide bond, where VH and VL are the variable heavy domain and variable light domain of 3H3 [TIM-3]_H1_L2.1, where the first variant Fc domain includes skew variants S364K/E357Q and the second variant Fc domain include the skew variant pair L368D/K370S, where the first and second variant Fc domains each include FcKO variants E233P/L234V/L235A/G236del/S267K, where the hinge-second variant Fc domain of the second monomer includes pI variants N208D/Q295E/N384D/Q418D/N421D, and where numbering is according to EU numbering. In certain embodiments, the first and second variant Fc domains each further include half-life extension variants M428L/N434S. In a particular embodiment, the IL-15 variant includes amino acid substitutions N4D/N65D and VH and VL are the variable heavy domain and variable light domain of 3H3[TIM-3]_H1_L2.1. In one embodiment, the IL-15 variant includes amino acid substitutions D30N/N65D and VH and VL are the variable heavy domain and variable light domain of 3H3[TIM-3]_H1_L2.1. In another embodiment, the IL-15 variant includes amino acid substitutions D30N/E64Q/N65D and VH and VL are the variable heavy domain and variable light domain of 3H3[TIM-3]_H1_L2.1.

J. Central-IL-15/Rα

Figure 21J:
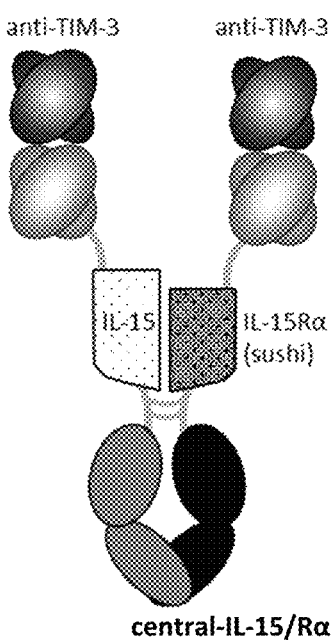

This embodiment is shown in FIG. 21J, and comprises four monomers forming a tetramer. The first monomer comprises a VH-CH1-[optional domain linker]-IL-15 variant-[optional domain linker]-CH2-CH3, with the second optional domain linker sometimes being the hinge domain. The second monomer comprises a VH-CH1-[optional domain linker]-IL-15Rα(sushi) domain-[optional domain linker]-CH2-CH3, with the second optional domain linker sometimes being the hinge domain. The third (and fourth) monomers are light chains, VL-CL. This is generally referred to as "central-IL-15/Rα".

In one embodiment, the targeted IL-15/IL-15Rα heterodimeric protein is an "central-IL-15/Rα" format heterodimeric protein that includes: a) a first monomer that includes, from N- to C-terminus, a VH-(domain linker)-IL-15 variant-(domain linker)-CH2-CH3, where CH2-CH3 is a first Fc domain; b) a second monomer that includes, from N- to C-terminus, a VH-(domain linker)-IL-15Rα(sushi) domain-(domain linker)-CH2-CH3, where CH2-CH3 is a second Fc domain; and d) a third and fourth monomer that each include from N- to C-terminus, a VL-CL, where the VH of the first monomer and the VL of the third monomer form a first TIM-3 binding domain, where the VH of the second monomer and the VL of the fourth monomer form a second TIM-3 binding domain, and where the IL-15 variant and the IL-15Rα(sushi) domain form an IL-15 complex. Any useful domain linker can be used to attach the various components of the heterodimeric protein including, but not limited to those in FIGS. 8 and 9A-C. In an exemplary embodiment, the domain linkers that attach the IL-15 variant to the first Fc domain and the IL-15Rα(sushi) domain to the second Fc domain are each antibody hinge domains.

In the central-IL-15/Rα format, one preferred embodiment utilizes an anti-TIM-3 ABD having any of the variable heavy and light domain pairs as shown in FIG. 12.

In the central-IL-15/Rα format, one preferred embodiment utilizes an anti-TIM-3 ABD having the variable heavy and light domain pair of 3H3[TIM-3]_H1_L2.1 as shown in FIG. 12.

In one embodiment, the targeted IL-15/IL-15Rα heterodimeric protein is an "central-IL-15/Rα" format heterodimeric protein that includes: a) a first monomer that includes, from N- to C-terminus, a VH-(domain linker)-IL-15 variant-(domain linker)-CH2-CH3, where CH2-CH3 is a first Fc domain; b) a second monomer that includes, from N- to C-terminus, a VH-(domain linker)-IL-15Rα(sushi) domain-(domain linker)-CH2-CH3, where CH2-CH3 is a second Fc domain; and d) a third and fourth monomer that each include from N- to C-terminus, a VL-CL, where the VH of the first monomer and the VL of the third monomer are the variable heavy domain and variable light domain of 3H3[TIM-3]_H1_L2.1, respectively, where the VH of the second monomer and the VL of the fourth monomer are the variable heavy domain and variable light domain of 3H3[TIM-3]_H1_L2.1, respectively, and where the IL-15 variant and the IL-15Rα(sushi) domain form an IL-15 complex.

In the "central-IL-15/Rα" format, one preferred embodiment utilizes an IL-15 variant that includes amino acid substitutions N4D/N65D, D30N/N65D, or D30N/E64Q/N65D. In one embodiment, the targeted IL-15/IL-15Rα heterodimeric protein is an "central-IL-15/Rα" format heterodimeric protein that includes: a) a first monomer that includes, from N- to C-terminus, a VH-(domain linker)-IL-15 variant-(domain linker)-CH2-CH3, where CH2-CH3 is a first Fc domain; b) a second monomer that includes, from N- to C-terminus, a VH-(domain linker)-IL-15Rα(sushi) domain-(domain linker)-CH2-CH3, where CH2-CH3 is a second Fc domain; and d) a third and fourth monomer that each include from N- to C-terminus, a VL-CL, where the VH of the first monomer and the VL of the third monomer form a first TIM-3 binding domain, where the VH of the second monomer and the VL of the fourth monomer form a second TIM-3 binding domain, where the IL-15 variant and the IL-15Rα(sushi) domain form an IL-15 complex, and where the IL-15 variant includes amino acid substitutions N4D/N65D, D30N/N65D, or D30N/E64Q/N65D. In an exemplary embodiment, the VH and VL are the VH and VL of any of the TIM-3 ABDs in FIGS. 12 and 13A-C and the IL-15 variant includes amino acid substitutions N4D/N65D. In another exemplary embodiment, the VH and VL are the VH and VL of any of the TIM-3 ABDs in FIGS. 12 and 13A-C and the IL-15 variant includes amino acid substitutions D30N/N65D. In yet another exemplary embodiment, the VH and VL are the VH and VL of any of the TIM-3 ABDs in FIGS. 12 and 13A-C and the IL-15 variant includes amino acid substitutions D30N/E64Q/N65D.

In the central-IL-15/Rα format, one preferred embodiment utilizes an anti-TIM-3 ABD having the variable heavy and light domain pair of 3H3[TIM-3]_H1_L2.1 as shown in FIG. 12, with either the IL-15 N4D/N65D variant or the IL-15 D30N/N65D variant or the IL-15 D30N/E64Q/N65D variant. In one embodiment, the targeted IL-15/IL-15Rα heterodimeric protein is an "central-IL-15/Rα" format heterodimeric protein that includes: a) a first monomer that includes, from N- to C-terminus, a VH-(domain linker)-IL-15 variant-(domain linker)-CH2-CH3, where CH2-CH3 is a first Fc domain; b) a second monomer that includes, from N- to C-terminus, a VH-(domain linker)-IL-15Rα(sushi) domain-(domain linker)-CH2-CH3, where CH2-CH3 is a second Fc domain; and d) a third and fourth monomer that each include from N- to C-terminus, a VL-CL, where the VH of the first monomer and the VL of the third monomer form a first TIM-3 binding domain, where the VH of the second monomer and the VL of the fourth monomer form a second TIM-3 binding domain, where the IL-15 variant and the IL-15Rα(sushi) domain form an IL-15 complex, where VH and VL are the variable heavy domain and variable light domain of 3H3[TIM-3]_H1_L2.1, and where the IL-15 variant includes amino acid substitutions N4D/N65D, D30N/N65D, or D30N/E64Q/N65D. In certain embodiments, the first and second variant Fc domains each further include half-life extension variants M428L/N434S. In a particular embodiment, the IL-15 variant includes amino acid substitutions N4D/N65D and VH and VL are the variable heavy domain and variable light domain of 3H3[TIM-3]_H1_L2.1. In one embodiment, the IL-15 variant includes amino acid substitutions D30N/N65D and VH and VL are the variable heavy domain and variable light domain of 3H3[TIM-3]_H1_L2.1. In another embodiment, the IL-15 variant includes amino acid substitutions D30N/E64Q/N65D and VH and VL are the variable heavy domain and variable light domain of 3H3[TIM-3]_H1_L2.1.

In the central-IL-15/Rα format, one preferred embodiment utilizes the skew variant pair S364K/E357Q:L368D/K370S. In one embodiment, the targeted IL-15/IL-15Rα heterodimeric protein is an "central-IL-15/Rα" format heterodimeric protein that includes: a) a first monomer that includes, from N- to C-terminus, a VH-(domain linker)-IL-15 variant-(domain linker)-CH2-CH3, where CH2-CH3 is a first Fc domain; b) a second monomer that includes, from N- to C-terminus, a VH-(domain linker)-IL-15Rα(sushi) domain-(domain linker)-CH2-CH3, where CH2-CH3 is a second Fc domain; and d) a third and fourth monomer that each include from N- to C-terminus, a VL-CL, where the VH of the first monomer and the VL of the third monomer form a first TIM-3 binding domain, where the VH of the second monomer and the VL of the fourth monomer form a second TIM-3 binding domain, where the IL-15 variant and the IL-15Rα(sushi) domain form an IL-15 complex, and where the first and second variant Fc domains include the skew variant pair S364K/E357Q: L368D/K370S. In an exemplary embodiment, the first variant Fc domain includes skew variants S364K and E357Q, and the second variant Fc domain includes skew variants L368D and K370S. In another exemplary embodiment, the first variant Fc domain includes skew variants L368D and K370S, and the second variant Fc domain includes skew variants S364K and E357Q.

In one embodiment, the targeted IL-15/IL-15Rα heterodimeric protein is an "central-IL-15/Rα" format heterodimeric protein that includes: a) a first monomer that includes, from N- to C-terminus, a VH-(domain linker)-IL-15 variant-(domain linker)-CH2-CH3, where CH2-CH3 is a first Fc domain; b) a second monomer that includes, from N- to C-terminus, a VH-(domain linker)-IL-15Rα(sushi) domain-(domain linker)-CH2-CH3, where CH2-CH3 is a second Fc domain; and d) a third and fourth monomer that each include from N- to C-terminus, a VL-CL, where the VH of the first monomer and the VL of the third monomer form a first TIM-3 binding domain, where the VH of the second monomer and the VL of the fourth monomer form a second TIM-3 binding domain, where the IL-15 variant and the IL-15Rα (sushi) domain form an IL-15 complex, where the IL-15 variant includes amino acid substitutions N4D/N65D, D30N/N65D, or D30N/E64Q/N65D, and where the first and second variant Fc domains include the skew variant pair S364K/E357Q:L368D/K370S. In an exemplary embodiment, the first variant Fc domain includes skew variants S364K and E357Q, and the second variant Fc domain includes skew variants L368D and K370S. In another exemplary embodiment, the first variant Fc domain includes skew variants L368D and K370S, and the second variant Fc domain includes skew variants S364K and E357Q. In an exemplary embodiment, the VH and VL are the VH and VL of any of the TIM-3 ABDs in FIGS. 12 and 13A-C and the IL-15 variant includes amino acid substitutions N4D/N65D. In another exemplary embodiment, the VH and VL are the VH and VL of any of the TIM-3 ABDs in FIGS. 12 and 13A-C and the IL-15 variant includes amino acid substitutions D30N/N65D. In yet another exemplary embodiment, the VH and VL are the VH and VL of any of the TIM-3 ABDs in FIGS. 12 and 13A-C and the IL-15 variant includes amino acid substitutions D30N/E64Q/N65D.

In the central-IL-15/Rα format, one preferred embodiment utilizes an anti-TIM-3 ABD having the variable heavy and light domain pair of 3H3[TIM-3]_H1_L2.1 as shown in FIG. 12 and the skew variant pair S364K/E357Q:L368D/K370S. In one embodiment, the targeted IL-15/IL-15Rα heterodimeric protein is an "central-IL-15/Rα" format heterodimeric protein that includes: a) a first monomer that includes, from N- to C-terminus, a VH-(domain linker)-IL-15 variant-(domain linker)-CH2-CH3, where CH2-CH3 is a first variant Fc domain; b) a second monomer that includes, from N- to C-terminus, a VH-(domain linker)-IL-15Rα (sushi) domain-(domain linker)-CH2-CH3, where CH2-CH3 is a second variant Fc domain; and d) a third and fourth monomer that each include from N- to C-terminus, a VL-CL, where the VH of the first monomer and the VL of the third monomer are the variable heavy domain and variable light domain of 3H3[TIM-3]_H1_L2.1, respectively, where the VH of the second monomer and the VL of the fourth monomer are the variable heavy domain and variable light domain of 3H3[TIM-3]_H1_L2.1, respectively, where the IL-15 variant and the IL-15Rα(sushi) domain form an IL-15 complex, and where the first and second variant Fc domains include the skew variant pair S364K/E357Q: L368D/K370S.

In the central-IL-15/Rα format, one preferred embodiment utilizes an anti-TIM-3 ABD having the variable heavy and light domain pair of 3H3[TIM-3]_H1_L2.1 as shown in FIG. 12 and the skew variant pair S364K/E357Q:L368D/K370S with either the IL-15 N4D/N65D variant or the IL-15 D30N/E64Q/N65D variant with appropriate cysteine substitutions. In one embodiment, the targeted IL-15/IL-15Rα heterodimeric protein is an "central-IL-15/Rα" format heterodimeric protein that includes: a) a first monomer that includes, from N- to C-terminus, a VH-(domain linker)-IL-15 variant-(domain linker)-CH2-CH3, where CH2-CH3 is a first variant Fc domain; b) a second monomer that includes, from N- to C-terminus, a VH-(domain linker)-IL-15Rα (sushi) domain-(domain linker)-CH2-CH3, where CH2-CH3 is a second variant Fc domain; and d) a third and fourth monomer that each include from N- to C-terminus, a VL-CL, where the VH of the first monomer and the VL of the third monomer form a first TIM-3 binding domain, where the VH of the second monomer and the VL of the fourth monomer form a second TIM-3 binding domain, where the IL-15 variant and the IL-15Rα(sushi) domain form an IL-15 complex, where VH and VL are the variable heavy domain and variable light domain of 3H3[TIM-3]_H1_L2.1, where the IL-15 variant includes amino acid substitutions N4D/N65D, D30N/N65D, or D30N/E64Q/N65D, and where the first and second variant Fc domains include the skew variant pair S364K/E357Q:L368D/K370S. In an exemplary embodiment, the first variant Fc domain includes skew variants S364K and E357Q, and the second variant Fc domain includes skew variants L368D and K370S. In another exemplary embodiment, the first variant Fc domain includes skew variants L368D and K370S, and the second variant Fc domain includes skew variants S364K and E357Q. In certain embodiments, the first and second variant Fc domains each further include half-life extension variants M428L/N434S. In a particular embodiment, the IL-15 variant includes amino acid substitutions N4D/N65D and VH and VL are the variable heavy domain and variable light domain of 3H3[TIM-3]_H1_L2.1. In one embodiment, the IL-15 variant includes amino acid substitutions D30N/N65D and VH and VL are the variable heavy domain and variable light domain of 3H3[TIM-3]_H1_L2.1. In another embodiment, the IL-15 variant includes amino acid substitutions D30N/E64Q/N65D and VH and VL are the variable heavy domain and variable light domain of 3H3[TIM-3]_H1_L2.1.

In the central-IL-15/Rα format, one preferred embodiment utilizes the skew variant set S364K/E357Q:L368D/K370S, the pI variants Q295E/N384D/Q418E/N421D, the ablation variants E233P/L234V/L235A/G236_/S267K on both first and second monomers, and optionally the 428L/434S variants on both first and second monomers.

In one embodiment, the targeted IL-15/IL-15Rα heterodimeric protein is an "central-IL-15/Rα" format heterodimeric protein that includes: a) a first monomer that includes, from N- to C-terminus, a VH-(domain linker)-IL-15 variant-(hinge)-CH2-CH3, where CH2-CH3 is a first variant Fc domain; b) a second monomer that includes, from N- to C-terminus, a VH-(domain linker)-IL-15Rα(sushi) domain-(hinge)-CH2-CH3, where CH2-CH3 is a second variant Fc domain; and d) a third and fourth monomer that each include from N- to C-terminus, a VL-CL, where the VH of the first monomer and the VL of the third monomer form a first TIM-3 binding domain, where the VH of the second monomer and the VL of the fourth monomer form a second TIM-3 binding domain, where the IL-15 variant and the IL-15Rα (sushi) domain form an IL-15 complex, where the first variant Fc domain includes skew variants L368D/K370S and the second variant Fc domain include the skew variant pair S364K/E357Q, where the first and second variant Fc domains each include FcKO variants E233P/L234V/L235A/G236del/S267K, where the first variant Fc domain includes pI substitutions Q295E/N384D/Q418D/N421D, and where numbering is according to EU numbering. In one embodiment, the targeted IL-15/IL-15Rα heterodimeric protein is an "central-IL-15/Rα" format heterodimeric protein that includes: a) a first monomer that includes, from N- to C-terminus, a VH-(domain linker)-IL-15 variant-(hinge)-CH2-CH3, where CH2-CH3 is a first variant Fc domain; b) a second monomer that includes, from N- to C-terminus, a VH-(domain linker)-IL-15Rα(sushi) domain-(hinge)-CH2-CH3, where CH2-CH3 is a second variant Fc domain; and d) a third and fourth monomer that each include from N- to C-terminus, a VL-CL, where the VH of the first monomer and the VL of the third monomer form a first TIM-3 binding domain, where the VH of the second monomer and the VL of the fourth monomer form a second TIM-3 binding domain, where the IL-15 variant and the IL-15Rα(sushi) domain form an IL-15 complex, where the first variant Fc domain includes skew variants S364K/E357Q and the second variant Fc domain include the skew variant pair L368D/K370S, where the first and second variant Fc domains each include FcKO variants E233P/L234V/L235A/G236del/S267K, where the second variant Fc domain of the second monomer includes pI substitutions Q295E/N384D/Q418D/N421D, and where numbering is according to EU numbering. In certain embodiments, the first and second variant Fc domains each further include half-life extension variants M428L/N434S. In an exemplary embodiment, the IL-15 variant includes amino acid substitutions N4D/N65D, D30N/N65D, or D30N/E64Q/N65D. In an exemplary embodiment, the IL-15 variant includes amino acid substitutions N4D/N65D, D30N/N65D, or D30N/E64Q/N65D. In an exemplary embodiment, the VH and VL are the VH and VL of any of the TIM-3 ABDs in FIGS. 12 and 13A-C and the IL-15 variant includes amino acid substitutions N4D/N65D. In another exemplary embodiment, the VH and VL are the VH and VL of any of the TIM-3 ABDs in FIGS. 12 and 13A-C and the IL-15 variant includes amino acid substitutions D30N/N65D. In yet another exemplary embodiment, the VH and VL are the VH and VL of any of the TIM-3 ABDs in FIGS. 12 and 13A-C and the IL-15 variant includes amino acid substitutions D30N/E64Q/N65D.

Figure 21K:
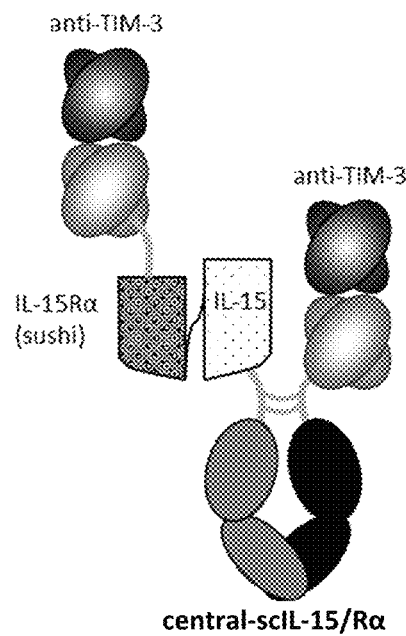

In the central-IL-15/Rα format, one preferred embodiment utilizes an anti-TIM-3 ABD having the variable heavy and light domain pair of 3H3[TIM-3]_H1_L2.1 as shown in FIG. 12 with the FIG. 21K, the skew variant set S364K/E357Q:L368D/K370S, the pI variants Q295E/N384D/Q418E/N421D, the ablation variants E233P/L234V/L235A/G236_/S267K on both first and second monomers, and optionally the 428L/434S variants on both first and second monomers. In one embodiment, the targeted IL-15/IL-15Rα heterodimeric protein is an "central-IL-15/Rα" format heterodimeric protein that includes: a) a first monomer that includes, from N- to C-terminus, a VH-(domain linker)-IL-15 variant-(hinge)-CH2-CH3, where CH2-CH3 is a first variant Fc domain; b) a second monomer that includes, from N- to C-terminus, a VH-(domain linker)-IL-15Rα(sushi) domain-(hinge)-CH2-CH3, where CH2-CH3 is a second variant Fc domain; and d) a third and fourth monomer that each include from N- to C-terminus, a VL-CL, where the VH of the first monomer and the VL of the third monomer form a first TIM-3 binding domain, where the VH of the second monomer and the VL of the fourth monomer form a second TIM-3 binding domain, where the IL-15 variant and the IL-15Rα(sushi) domain form an IL-15 complex, where VH and VL are the variable heavy and variable light domain of 3H3[TIM-3]_H1_L2.1, where the first variant Fc domain includes skew variants L368D/K370S and the second variant Fc domain include the skew variant pair S364K/E357Q, where the first and second variant Fc domains each include FcKO variants E233P/L234V/L235A/G236del/S267K, where the first variant Fc domain includes pI substitutions Q295E/N384D/Q418D/N421D, and where numbering is according to EU numbering. In one embodiment, the targeted IL-15/IL-15Rα heterodimeric protein is an "central-IL-15/Rα" format heterodimeric protein that includes: a) a first monomer that includes, from N- to C-terminus, a VH-(domain linker)-IL-15 variant-(hinge)-CH2-CH3, where CH2-CH3 is a first variant Fc domain; b) a second monomer that includes, from N- to C-terminus, a VH-(domain linker)-IL-15Rα(sushi) domain-(hinge)-CH2-CH3, where CH2-CH3 is a second variant Fc domain; and d) a third and fourth monomer that each include from N- to C-terminus, a VL-CL, where the VH of the first monomer and the VL of the third monomer form a first TIM-3 binding domain, where the VH of the second monomer and the VL of the fourth monomer form a second TIM-3 binding domain, where the IL-15 variant and the IL-15Rα(sushi) domain form an IL-15 complex, where VH and VL are the variable heavy domain and variable light domain of 3H3 [TIM-3]_H1_L2.1, where the first variant Fc domain includes skew variants S364K/E357Q and the second variant Fc domain include the skew variant pair L368D/K370S, where the first and second variant Fc domains each include FcKO variants E233P/L234V/L235A/G236del/S267K, where the second variant Fc domain of the second monomer includes pI substitutions Q295E/N384D/Q418D/N421D, and where numbering is according to EU numbering. In certain embodiments, the first and second variant Fc domains each further include half-life extension variants M428L/N434S. In certain embodiments, the first and second variant Fc domains each further include half-life extension variants M428L/N434S. In a particular embodiment, the IL-15 variant includes amino acid substitutions N4D/N65D and VH and VL are the variable heavy domain and variable light domain of 3H3[TIM-3]_H1_L2.1. In one embodiment, the IL-15 variant includes amino acid substitutions D30N/N65D and VH and VL are the variable heavy domain and variable light domain of 3H3[TIM-3]_H1_L2.1. In another embodiment, the IL-15 variant includes amino acid substitutions D30N/E64Q/N65D and VH and VL are the variable heavy domain and variable light domain of 3H3[TIM-3]_H1_L2.1.

K. Central-scIL-15/Rα

This embodiment is shown in FIG. 21K, and comprises four monomers forming a tetramer. The first monomer comprises a VH-CH1-[optional domain linker]-IL-15Rα(sushi) domain-domain linker-IL-15 variant-[optional domain linker]-CH2-CH3, with the second optional domain linker sometimes being the hinge domain. The second monomer comprises a VH-CH1-hinge-CH2-CH3. The third (and fourth) monomers are light chains, VL-CL. This is generally referred to as "central-scIL-15/Rα", with the "sc" standing for "single chain".

In one embodiment, the targeted IL-15/IL-15Rα heterodimeric protein is an "central-scIL-15/Rα" format heterodimeric protein that includes: a) a first monomer that includes, from N- to C-terminus, a VH-(domain linker)-IL-15Rα(sushi) domain-(domain linker)-IL-15 variant-(domain linker)-CH2-CH3, where CH2-CH3 is a first Fc domain; b) a second monomer that includes, from N- to C-terminus, a VH-hinge-CH2-CH3, where CH2-CH3 is a second Fc domain; and d) a third and fourth monomer that each include from N- to C-terminus, a VL-CL, where the VH of the first monomer and the VL of the third monomer form a first TIM-3 binding domain, where the VH of the second monomer and the VL of the fourth monomer form a second TIM-3 binding domain, and where the IL-15 variant and the IL-15Rα(sushi) domain form an IL-15 complex. Any useful domain linker can be used to attach the various components of the heterodimeric protein including, but not limited to those in FIGS. 8 and 9A-C. In an exemplary embodiment, the domain linker that attaches the IL-15 variant to the first Fc domain is an antibody hinge domain.

In the central-scIL-15/Rα format, one preferred embodiment utilizes an anti-TIM-3 ABD having any of the variable heavy and light domain pairs as shown in FIG. 12.

In the central-scIL-15/Rα format, one preferred embodiment utilizes an anti-TIM-3 ABD having the variable heavy and light domain pair of 3H3[TIM-3]_H1_L2.1 as shown in as shown in FIG. 12.

In one embodiment, the targeted IL-15/IL-15Rα heterodimeric protein is an "central-scIL-15/Rα" format heterodimeric protein that includes: a) a first monomer that includes, from N- to C-terminus, a VH-(domain linker)-IL-15Rα(sushi) domain-(domain linker)-IL-15 variant-(domain linker)-CH2-CH3, where CH2-CH3 is a first Fc domain; b) a second monomer that includes, from N- to C-terminus, a VH-hinge-CH2-CH3, where CH2-CH3 is a second Fc domain; and d) a third and fourth monomer that each include from N- to C-terminus, a VL-CL, where the VH of the first monomer and the VL of the third monomer are the variable heavy domain and variable light domain of 7G8_H3.30_L1.34, respectively, where the VH of the second monomer and the VL of the fourth monomer are the variable heavy domain and variable light domain of 3H3 [TIM-3]_H1_L2.1, respectively, and where the IL-15 variant and the IL-15Rα(sushi) domain form an IL-15 complex.

In the central-scIL-15/Rα format, one preferred embodiment utilizes an IL-15 variant that includes amino acid substitutions N4D/N65D, D30N/N65D, or D30N/E64Q/N65D. In one embodiment, the targeted IL-15/IL-15Rα heterodimeric protein is an "central-scIL-15/Rα" format heterodimeric protein that includes: a) a first monomer that includes, from N- to C-terminus, a VH-(domain linker)-IL-15Rα(sushi) domain-(domain linker)-IL-15 variant-(domain linker)-CH2-CH3, where CH2-CH3 is a first Fc domain; b) a second monomer that includes, from N- to C-terminus, a VH-hinge-CH2-CH3, where CH2-CH3 is a second Fc domain; and d) a third and fourth monomer that each include from N- to C-terminus, a VL-CL, where the VH of the first monomer and the VL of the third monomer form a first TIM-3 binding domain, where the VH of the second monomer and the VL of the fourth monomer form a second TIM-3 binding domain, where the IL-15 variant and the IL-15Rα(sushi) domain form an IL-15 complex, and where the IL-15 variant includes amino acid substitutions N4D/N65D, D30N/N65D, or D30N/E64Q/N65D. In an exemplary embodiment, the VH and VL are the VH and VL of any of the TIM-3 ABDs in FIGS. 12 and 13A-C and the IL-15 variant includes amino acid substitutions N4D/N65D. In another exemplary embodiment, the VH and VL are the VH and VL of any of the TIM-3 ABDs in FIGS. 12 and 13A-C and the IL-15 variant includes amino acid substitutions D30N/N65D. In yet another exemplary embodiment, the VH and VL are the VH and VL of any of the TIM-3 ABDs in FIGS. 12 and 13A-C and the IL-15 variant includes amino acid substitutions D30N/E64Q/N65D.

In the central-scIL-15/Rα format, one preferred embodiment utilizes an anti-TIM-3 ABD having the variable heavy and light domain pair of 3H3[TIM-3]_H1_L2.1 as shown in FIG. 12, with either the IL-15 N4D/N65D variant or the IL-15 D30N/N65D variant or the IL-15 D30N/E64Q/N65D variant. In one embodiment, the targeted IL-15/IL-15Rα heterodimeric protein is an "central-scIL-15/Rα" format heterodimeric protein that includes: a) a first monomer that includes, from N- to C-terminus, a VH-(domain linker)-IL-15Rα(sushi) domain-(domain linker)-IL-15 variant-(domain linker)-CH2-CH3, where CH2-CH3 is a first Fc domain; b) a second monomer that includes, from N- to C-terminus, a VH-hinge-CH2-CH3, where CH2-CH3 is a second Fc domain; and d) a third and fourth monomer that each include from N- to C-terminus, a VL-CL, where the VH of the first monomer and the VL of the third monomer form a first TIM-3 binding domain, where the VH of the second monomer and the VL of the fourth monomer form a second TIM-3 binding domain, where the IL-15 variant and the IL-15Rα (sushi) domain form an IL-15 complex, where VH and VL are the variable heavy domain and variable light domain of 3H3[TIM-3]_H1_L2.1, and where the IL-15 variant includes amino acid substitutions N4D/N65D, D30N/N65D, or D30N/E64Q/N65D. In a particular embodiment, the IL-15 variant includes amino acid substitutions N4D/N65D and VH and VL are the variable heavy domain and variable light domain of 3H3[TIM-3]_H1_L2.1. In one embodiment, the IL-15 variant includes amino acid substitutions D30N/N65D and VH and VL are the variable heavy domain and variable light domain of 3H3[TIM-3]_H1_L2.1. In another embodiment, the IL-15 variant includes amino acid substitutions D30N/E64Q/N65D and VH and VL are the variable heavy domain and variable light domain of 3H3[TIM-3]_H1_L2.1.

In the central-scIL-15/Rα format, one preferred embodiment utilizes the skew variant pair S364K/E357Q:L368D/K370S. In one embodiment, the targeted IL-15/IL-15Rα heterodimeric protein is an "central-scIL-15/Rα" format heterodimeric protein that includes: a) a first monomer that includes, from N- to C-terminus, a VH-(domain linker)-IL-15Rα(sushi) domain-(domain linker)-IL-15 variant-(domain linker)-CH2-CH3, where CH2-CH3 is a first variant Fc domain; b) a second monomer that includes, from N- to C-terminus, a VH-hinge-CH2-CH3, where CH2-CH3 is a second variant Fc domain; and d) a third and fourth monomer that each include from N- to C-terminus, a VL-CL, where the VH of the first monomer and the VL of the third monomer form a first TIM-3 binding domain, where the VH of the second monomer and the VL of the fourth monomer form a second TIM-3 binding domain, where the IL-15 variant and the IL-15Rα(sushi) domain form an IL-15 complex, and where the first and second variant Fc domains include the skew variant pair S364K/E357Q: L368D/K370S. In an exemplary embodiment, the first variant Fc domain includes skew variants L368D and K370S, and the second variant Fc domain includes skew variants S364K and E357Q.

In one embodiment, the targeted IL-15/IL-15Rα heterodimeric protein is an "central-scIL-15/Rα" format heterodimeric protein that includes: a) a first monomer that includes, from N- to C-terminus, a VH-(domain linker)-IL-15Rα (sushi) domain-(domain linker)-IL-15 variant-(domain linker)-CH2-CH3, where CH2-CH3 is a first variant Fc domain; b) a second monomer that includes, from N- to C-terminus, a VH-hinge-CH2-CH3, where CH2-CH3 is a second variant Fc domain; and d) a third and fourth monomer that each include from N- to C-terminus, a VL-CL, where the VH of the first monomer and the VL of the third monomer form a first TIM-3 binding domain, where the VH of the second monomer and the VL of the fourth monomer form a second TIM-3 binding domain, where the IL-15 variant and the IL-15Rα(sushi) domain form an IL-15 complex, where the IL-15 variant includes amino acid substitutions N4D/N65D, D30N/N65D, or D30N/E64Q/N65D, and where the first and second variant Fc domains include the skew variant pair S364K/E357Q:L368D/K370S. In an exemplary embodiment, the first variant Fc domain includes skew variants L368D and K370S, and the second variant Fc domain includes skew variants S364K and E357Q. In an exemplary embodiment, the VH and VL are the VH and VL of any of the TIM-3 ABDs in FIGS. 12 and 13A-C and the IL-15 variant includes amino acid substitutions N4D/N65D. In another exemplary embodiment, the VH and VL are the VH and VL of any of the TIM-3 ABDs in FIGS. 12 and 13A-C and the IL-15 variant includes amino acid substitutions D30N/N65D. In yet another exemplary embodiment, the VH and VL are the VH and VL of any of the TIM-3 ABDs in FIGS. 12 and 13A-C and the IL-15 variant includes amino acid substitutions D30N/E64Q/N65D.

In the central-scIL-15/Rα format, one preferred embodiment utilizes an anti-TIM-3 ABD having the variable heavy and light domain pair of 3H3[TIM-3]_H1_L2.1 as shown in FIG. 12 and the skew variant pair S364K/E357Q:L368D/K370S. In one embodiment, the targeted IL-15/IL-15Rα heterodimeric protein is an "central-scIL-15/Rα" format heterodimeric protein that includes: a) a first monomer that includes, from N- to C-terminus, a VH-(domain linker)-IL-15Rα(sushi) domain-(domain linker)-IL-15 variant-(domain linker)-CH2-CH3, where CH2-CH3 is a first variant Fc domain; b) a second monomer that includes, from N- to C-terminus, a VH-hinge-CH2-CH3, where CH2-CH3 is a second variant Fc domain; and d) a third and fourth monomer that each include from N- to C-terminus, a VL-CL, where the VH of the first monomer and the VL of the third monomer are the variable heavy domain and variable light domain 3H3[TIM-3]_H1_L2.1, respectively, where the VH of the second monomer and the VL of the fourth monomer are the variable heavy domain and variable light domain of 3H3[TIM-3]_H1_L2.1, respectively, where the IL-15 variant and the IL-15Rα(sushi) domain form an IL-15 complex, and where the first and second variant Fc domains include the skew variant pair S364K/E357Q:L368D/K370S. In an exemplary embodiment, the first variant Fc domain includes skew variants L368D and K370S, and the second variant Fc domain includes skew variants S364K and E357Q.

In the central-scIL-15/Rα format, one preferred embodiment utilizes an anti-TIM-3 ABD having the variable heavy and light domain pair of 3H3[TIM-3]_H1_L2.1 as shown in FIG. 12 and the skew variant pair S364K/E357Q:L368D/K370S with either the IL-15 N4D/N65D variant or the IL-15 D30N/N65D variant or the IL-15 D30N/E64Q/N65D variant. In one embodiment, the targeted IL-15/IL-15Rα heterodimeric protein is an "central-scIL-15/Rα" format heterodimeric protein that includes: a) a first monomer that includes, from N- to C-terminus, a VH-(domain linker)-IL-15Rα(sushi) domain-(domain linker)-IL-15 variant-(domain linker)-CH2-CH3, where CH2-CH3 is a first variant Fc domain; b) a second monomer that includes, from N- to C-terminus, a VH-hinge-CH2-CH3, where CH2-CH3 is a second variant Fc domain; and d) a third and fourth monomer that each include from N- to C-terminus, a VL-CL, where the VH of the first monomer and the VL of the third monomer form a first TIM-3 binding domain, where the VH of the second monomer and the VL of the fourth monomer form a second TIM-3 binding domain, where the IL-15 variant and the IL-15Rα(sushi) domain form an IL-15 complex, where VH and VL are the variable heavy domain and variable light domain of 3H3[TIM-3]_H1_L2.1, where the IL-15 variant includes amino acid substitutions N4D/N65D, D30N/N65D, or D30N/E64Q/N65D, and where the first and second variant Fc domains include the skew variant pair L368D/K370S:S364K/E357Q. In an exemplary embodiment, the first variant Fc domain includes skew variants L368D/K370S, and the second variant Fc domain includes skew variants S364K/E357Q. In a particular embodiment, the IL-15 variant includes amino acid substitutions N4D/N65D and VH and VL are the variable heavy domain and variable light domain of 3H3[TIM-3]_H1_L2.1. In one embodiment, the IL-15 variant includes amino acid substitutions D30N/N65D and VH and VL are the variable heavy domain and variable light domain of 3H3[TIM-3]_H1_L2.1. In another embodiment, the IL-15 variant includes amino acid substitutions D30N/E64Q/N65D and VH and VL are the variable heavy domain and variable light domain of 3H3[TIM-3]_H1_L2.1.

In the central-scIL-15/Rα format, one preferred embodiment utilizes the skew variant set S364K/E357Q:L368D/K370S, the pI variants Q295E/N384D/Q418E/N421D, the ablation variants E233P/L234V/L235A/G236_/S267K on both first and second monomers, and optionally the 428L/434S variants on both first and second monomers.

In one embodiment, the targeted IL-15/IL-15Rα heterodimeric protein is an "central-scIL-15/Rα" format heterodimeric protein that includes: a) a first monomer that includes, from N- to C-terminus, a VH-(domain linker)-IL-15Rα(sushi) domain-(domain linker)-IL-15 variant-(hinge)-CH2-CH3, where CH2-CH3 is a first variant Fc domain; b) a second monomer that includes, from N- to C-terminus, a VH-hinge-CH2-CH3, where CH2-CH3 is a second variant Fc domain; and d) a third and fourth monomer that each include from N- to C-terminus, a VL-CL, where the VH of the first monomer and the VL of the third monomer form a first TIM-3 binding domain, where the VH of the second monomer and the VL of the fourth monomer form a second TIM-3 binding domain, where the IL-15 variant and the IL-15Rα(sushi) domain form an IL-15 complex, where the first variant Fc domain includes skew variants L368D/K370S and the second variant Fc domain includes skew variants S364K/E357Q, where the first and second variant Fc domains each include FcKO variants E233P/L234V/L235A/G236del/S267K, where the first variant Fc domain includes pI variants Q295E/N384D/Q418E/N421D, and where numbering is according to EU numbering. In an exemplary embodiment, the IL-15 variant includes amino acid substitutions N4D/N65D, D30N/N65D, or D30N/E64Q/N65D. In an exemplary embodiment, the IL-15 variant includes amino acid substitutions N4D/N65D, D30N/N65D, or D30N/E64Q/N65D. In an exemplary embodiment, the VH and VL are the VH and VL of any of the TIM-3 ABDs in FIGS. 12 and 13A-C and the IL-15 variant includes amino acid substitutions N4D/N65D. In another exemplary embodiment, the VH and VL are the VH and VL of any of the TIM-3 ABDs in FIGS. 12 and 13A-C and the IL-15 variant includes amino acid substitutions D30N/N65D. In yet another exemplary embodiment, the VH and VL are the VH and VL of any of the TIM-3 ABDs in FIGS. 12 and 13A-C and the IL-15 variant includes amino acid substitutions D30N/E64Q/N65D.

In the central-scIL-15/Rα format, one preferred embodiment utilizes an anti-TIM-3 ABD having the variable heavy and light domain pair of 3H3[TIM-3]_H1_L2.1 as shown in FIG. 12 with the FIG. 21K format, the skew variant set S364K/E357Q: L368D/K370S, the pI variants Q295E/N384D/Q418E/N421D, the ablation variants E233P/L234V/L235A/G236_/S267K on both first and second monomers, and optionally the 428L/434S variants on both first and second monomers.

In one embodiment, the targeted IL-15/IL-15Rα heterodimeric protein is an "central-scIL-15/Rα" format heterodimeric protein that includes: a) a first monomer that includes, from N- to C-terminus, a VH-(domain linker)-IL-15Rα(sushi) domain-(domain linker)-IL-15 variant-(hinge)-CH2-CH3, where CH2-CH3 is a first variant Fc domain; b) a second monomer that includes, from N- to C-terminus, a VH-hinge-CH2-CH3, where CH2-CH3 is a second variant Fc domain; and d) a third and fourth monomer that each include from N- to C-terminus, a VL-CL, where the VH of the first monomer and the VL of the third monomer form a first TIM-3 binding domain, where the VH of the second monomer and the VL of the fourth monomer form a second TIM-3 binding domain, where the IL-15 variant and the IL-15Rα(sushi) domain form an IL-15 complex, where VH and VL are the variable heavy domain and variable light domain of 3H3[TIM-3]_H1_L2.1, where the first variant Fc domain includes skew variants L368D/K370S and the second variant Fc domain includes skew variants S364K/E357Q where the first and second variant Fc domains each include FcKO variants E233P/L234V/L235A/G236del/S267K, where the first variant Fc domain includes pI variants Q295E/N384D/Q418E/N421D, and where numbering is according to EU numbering. In certain embodiments, the hinge of the first monomer further includes variant C220S. In certain embodiments, the first and second variant Fc domains each further include half-life extension variants M428L/N434S. In a particular embodiment, the IL-15 variant includes amino acid substitutions N4D/N65D and VH and VL are the variable heavy domain and variable light domain of 3H3[TIM-3]_H1_L2.1. In one embodiment, the IL-15 variant includes amino acid substitutions D30N/N65D and VH and VL are the variable heavy domain and variable light domain of 3H3[TIM-3]_H1_L2.1. In another embodiment, the IL-15 variant includes amino acid substitutions D30N/E64Q/N65D and VH and VL are the variable heavy domain and variable light domain of 3H3[TIM-3]_H1_L2.1.

V. Particularly Useful Embodiments of the Invention

The present invention provides a targeted IL-15/IL-15Rα-Fc heterodimeric protein comprising at least two monomers, one of which contains an anti-TIM-3 ABD and the other that contains an IL-15/RA complex, joined using heterodimeric Fc domains.

In some embodiments, the first and the second variant Fc domains have a set of amino acid substitutions selected from the group consisting of S267K/L368D/K370S:S267K/S364K/E357Q; S364K/E357Q:L368D/K370S; L368D/K370S:S364K; L368E/K370S: S364K; T411E/K360E/Q362E:D401K; L368D/K370S:S364K/E357L and K370S: S364K/E357Q, according to EU numbering.

In some instances, the first and/or the second variant Fc domains have an additional set of amino acid substitutions comprising Q295E/N384D/Q418E/N421D, according to EU numbering. In some cases, the first and/or the second Fc domains have an additional set of amino acid substitutions consisting of G236R/L328R, E233P/L234V/L235A/G236del/S239K, E233P/L234V/L235A/G236del/S267K, E233P/L234V/L235A/G236del/S239K/A327G, E233P/L234V/L235A/G236del/S267K/A327G and E233P/L234V/L235A/G236del, according to EU numbering.

In some embodiments, the IL-15 protein has a polypeptide sequence selected from the group consisting of SEQ ID NO:1 (full-length human IL-15) and SEQ ID NO:2 (truncated human IL-15), and the IL-15Rα protein has a polypeptide sequence selected from the group consisting of SEQ ID NO:3 (full-length human IL-15Rα) and SEQ ID NO:4 (sushi domain of human IL-15Rα).

In embodiments the IL-15 protein and the IL-15Rα protein can have a set of amino acid substitutions selected from the group consisting of E87C: D96/P97/C98; E87C: D96/C97/A98; V49C: S40C; L52C: S40C; E89C: K34C; Q48C: G38C; E53C: L42C; C42S: A37C; and L45C: A37C, respectively.

In some embodiments, the IL-15 protein is a variant protein that has a sequence selected from FIG. 19 and FIG. 20 to reduce potency. In some embodiments, the IL-15 protein is a variant protein having one or more amino acid substitutions at the IL-15:CD132 interface.

In some embodiments, the TIM-3 antigen binding domain comprises an anti-TIM-3 scFv or an anti-TIM-3 Fab. In an exemplary embodiment, the TIM-3 ABD includes the VH and VL of any of the TIM-3 ABDs depicted in FIGS. 12 and 13A-C.

In an exemplary embodiment, the targeted IL-15/IL-15Rα heterodimeric protein is an "scIL-15/RαxFab" format heterodimeric protein that includes: a) a first monomer that includes, from N- to C-terminus, an IL-15Rα(sushi) domain-(domain linker)-IL-15 variant-(domain linker)-CH2-CH3, where CH2-CH3 is a first variant Fc domain; b) a second monomer that includes, from N- to C-terminus, a VH-CH1-hinge-CH2-CH3, where VH is a variable heavy domain and CH2-CH3 is a second variant Fc domain, and c) a light chain that includes from, N- to C-terminus, VL-VC, where VL is a variable light domain, where VH and VL form a TIM-3 binding domain, where the IL-15 variant is an IL-15 N4D/N65D variant, where the first variant Fc domain includes skew variants L368D/K370S and the second variant Fc domain includes skew variants S364K/E357Q, where the first and second variant Fc domains each include FcKO variants E233P/L234V/L235A/G236del/S267K, where the first variant Fc domain includes pI variants Q295E/N384D/Q418E/N421D, and where numbering is according to EU numbering. In certain embodiments, the first and second variant Fc domains each further include half-life extension variants M428L/N434S. In certain embodiments, the hinge of the first monomer includes also includes amino acid substitution C220S and the first and second variant Fc domains each further include half-life extension variants M428L/N434S. In some embodiments, the VH and VL are the variable heavy domain and variable light domain of any of the TIM-3 ABDs in FIG. 12 or 13A-C. In some embodiments, the VH and VL are the variable heavy domain and variable light domain of 3H3[TIM-3]_H1_L2.1 (FIG. 12).

In an exemplary embodiment, the targeted IL-15/IL-15Rα heterodimeric protein is an "scIL-15/RαxFab" format heterodimeric protein that includes: a) a first monomer that includes, from N- to C-terminus, an IL-15Rα(sushi) domain-(domain linker)-IL-15 variant-(domain linker)-CH2-CH3, where CH2-CH3 is a first variant Fc domain; b) a second monomer that includes, from N- to C-terminus, a VH-CH1-hinge-CH2-CH3, where VH is a variable heavy domain and CH2-CH3 is a second variant Fc domain, and c) a light chain that includes from, N- to C-terminus, VL-VC, where VL is a variable light domain, where VH and VL form a TIM-3 binding domain, where the IL-15 variant is an IL-15 D30N/N65D variant, where the first variant Fc domain includes skew variants L368D/K370S and the second variant Fc domain includes skew variants S364K/E357Q, where the first and second variant Fc domains each include FcKO variants E233P/L234V/L235A/G236del/S267K, where the first variant Fc domain includes pI variants Q295E/N384D/Q418E/N421D, and where numbering is according to EU numbering. In some embodiments, the hinge of the first monomer also includes amino acid substitution C220S. In certain embodiments, the first and second variant Fc domains each further include half-life extension variants M428L/N434S. In certain embodiments, the hinge of the first monomer includes also includes amino acid substitution C220S and the first and second variant Fc domains each further include half-life extension variants M428L/N434S.

In some embodiments, the VH and VL are the variable heavy domain and variable light domain of any of the TIM-3 ABDs in FIG. 12 or 13A-C. In some embodiments, the VH and VL are the variable heavy domain and variable light domain of 3H3[TIM-3]_H1_L2.1 (FIG. 12).

In an exemplary embodiment, the targeted IL-15/IL-15Rα heterodimeric protein is an "scIL-15/RαxFab" format heterodimeric protein that includes: a) a first monomer that includes, from N- to C-terminus, an IL-15Rα(sushi) domain-(domain linker)-IL-15 variant-(domain linker)-CH2-CH3, where CH2-CH3 is a first variant Fc domain; b) a second monomer that includes, from N- to C-terminus, a VH-CH1-hinge-CH2-CH3, where VH is a variable heavy domain and CH2-CH3 is a second variant Fc domain, and c) a light chain that includes from, N- to C-terminus, VL-VC, where VL is a variable light domain, where VH and VL form a TIM-3 binding domain, where the IL-15 variant is an IL-15 D30N/E64Q/N65D variant, where the first variant Fc domain includes skew variants L368D/K370S and the second variant Fc domain includes skew variants S364K/E357Q, where the first and second variant Fc domains each include FcKO variants E233P/L234V/L235A/G236del/S267K, where the first variant Fc domain includes pI variants Q295E/N384D/Q418E/N421D, and where numbering is according to EU numbering. In some embodiments, the hinge of the first monomer also includes amino acid substitution C220S. In certain embodiments, the first and second variant Fc domains each further include half-life extension variants M428L/N434S. In certain embodiments, the hinge of the first monomer includes also includes amino acid substitution C220S and the first and second variant Fc domains each further include half-life extension variants M428L/N434S. In some embodiments, the VH and VL are the variable heavy domain and variable light domain of any of the TIM-3 ABDs in FIG. 12 or 13A-C. In some embodiments, the VH and VL are the variable heavy domain and variable light domain of 3H3[TIM-3]_H1_L2.1 (FIG. 12).

Useful "backbone" sequences that can be included in the "scIL-15/RαxFab" format heterodimeric protein are depicted in FIG. 10. In some embodiments, the "scIL-15/RαxFab" format heterodimeric protein that includes: a) a first monomer that includes, from N- to C-terminus, an IL-15Rα(sushi) domain-(domain linker)-IL-15 variant-(hinge)-CH2-CH3, where hinge-CH2-CH3 has the amino acid sequence of Chain 2 of "Backbone 1" in FIG. 10 (SEQ ID NO: 49); b) a second monomer that includes, from N- to C-terminus, a VH-CH1-hinge-CH2-CH3, where VH is a variable heavy domain and CH1-hinge-CH2-CH3 has the amino acid sequence of Chain 1 of "Backbone 1" in FIG. 10 (SEQ ID NO: 48), and c) a light chain that includes from, N- to C-terminus, VL-VC, where VL is a variable light domain and VC has the sequence of "Constant Light Chain—Kappa" in FIG. 11 (SEQ ID NO: 54). In certain embodiments, the "scIL-15/RαxFab" format heterodimeric protein that includes: a) a first monomer that includes, from N- to C-terminus, an IL-15Rα(sushi) domain-(domain linker)-IL-15 variant-(hinge)-CH2-CH3, where hinge-CH2-CH3 has the amino acid sequence of Chain 2 of "Backbone 2" in FIG. 10 (SEQ ID NO: 51); b) a second monomer that includes, from N- to C-terminus, a VH-CH1-hinge-CH2-CH3, where VH is a variable heavy domain and CH1-hinge-CH2-CH3 has the amino acid sequence of Chain 1 of "Backbone 2" in FIG. 10 (SEQ ID NO: 50), and c) a light chain that includes from, N- to C-terminus, VL-VC, where VL is a variable light domain and VC has the sequence of "Constant Light Chain—Kappa" in FIG. 11 (SEQ ID NO: 54). In some embodiments, the "scIL-15/RαxFab" format heterodimeric protein that includes: a) a first monomer that includes, from N- to C-terminus, an IL-15Rα(sushi) domain-(domain linker)-IL-15 variant-(hinge)-CH2-CH3, where hinge-CH2-CH3 has the amino acid sequence of Chain 2 of "Backbone 3" in FIG. 10 (SEQ ID NO: 53); b) a second monomer that includes, from N- to C-terminus, a VH-CH1-hinge-CH2-CH3, where VH is a variable heavy domain and CH1-hinge-CH2-CH3 has the amino acid sequence of Chain 1 of "Backbone 3" in FIG. 10 (SEQ ID NO: 52), and c) a light chain that includes from, N- to C-terminus, VL-VC, where VL is a variable light domain and VC has the sequence of "Constant Light Chain—Kappa" in FIG. 11 (SEQ ID NO: 54). In an exemplary embodiment, the IL-15 variant includes amino acid substitutions N4D/N65D, D30N/N65D, or D30N/E64Q/N65D. In an exemplary embodiment, the IL-15 variant includes amino acid substitutions N4D/N65D, D30N/N65D, or D30N/E64Q/N65D. In an exemplary embodiment, the VH and VL are the VH and VL of any of the TIM-3 ABDs in FIGS. 12 and 13A-C and the IL-15 variant includes amino acid substitutions N4D/N65D. In another exemplary embodiment, the VH and VL are the VH and VL of any of the TIM-3 ABDs in FIGS. 12 and 13A-C and the IL-15 variant includes amino acid substitutions D30N/N65D. In yet another exemplary embodiment, the VH and VL are the VH and VL of any of the TIM-3 ABDs in FIGS. 12 and 13A-C and the IL-15 variant includes amino acid substitutions D30N/E64Q/N65D.

Particularly preferred TIM-3 targeted IL-15/IL-15Rα-Fc heterodimeric fusion proteins include XENP27974, XENP27979, XENC1000, XENC1001, XENC1002, and XENC1003 "scIL-15/Rα×Fab" format heterodimeric protein. Exemplary embodiments of the TIM-3 targeted IL-15/IL-15Rα-Fc heterodimeric fusion proteins are shown in as described in FIG. 22 and FIG. 29, FIG. 46, FIG. 47 and FIGS. 48A and B. respectively.

VI. Nucleic Acids of the Invention

The invention further provides nucleic acid compositions encoding the targeted IL-15/IL-15Rα-Fc heterodimeric fusion proteins of the invention (or, in the case of a monomer Fc domain protein, nucleic acids encoding those as well).

As will be appreciated by those in the art, the nucleic acid compositions will depend on the format of the targeted IL-15/IL-15Rα-Fc heterodimeric fusion protein. Thus, for example, when the format requires three amino acid sequences, three nucleic acid sequences can be incorporated into one or more expression vectors for expression. Similarly, some formats only two nucleic acids are needed; again, they can be put into one or two expression vectors, or four or 5. As noted herein, some constructs have two copies of a light chain, for example.

As is known in the art, the nucleic acids encoding the components of the invention can be incorporated into expression vectors as is known in the art, and depending on the host cells used to produce the targeted IL-15/IL-15Rα-Fc heterodimeric fusion proteins of the invention. Generally the nucleic acids are operably linked to any number of regulatory elements (promoters, origin of replication, selectable markers, ribosomal binding sites, inducers, etc.). The expression vectors can be extra-chromosomal or integrating vectors.

The nucleic acids and/or expression vectors of the invention are then transformed into any number of different types of host cells as is well known in the art, including mammalian, bacterial, yeast, insect and/or fungal cells, with mammalian cells (e.g., CHO cells), finding use in many embodiments.

In some embodiments, nucleic acids encoding each monomer, as applicable depending on the format, are each contained within a single expression vector, generally under different or the same promoter controls. In embodiments of particular use in the present invention, each of these two or three nucleic acids are contained on a different expression vector.

The targeted IL-15/IL-15Rα-Fc heterodimeric fusion protein of the invention are made by culturing host cells comprising the expression vector(s) as is well known in the art. Once produced, traditional fusion protein or antibody purification steps are done, including an ion exchange chromatography step. As discussed herein, having the pIs of the two monomers differ by at least 0.5 can allow separation by ion exchange chromatography or isoelectric focusing, or other methods sensitive to isoelectric point. That is, the inclusion of pI substitutions that alter the isoelectric point (pI) of each monomer so that such that each monomer has a different pI and the heterodimer also has a distinct pI, thus facilitating isoelectric purification of the heterodimer (e.g., anionic exchange columns, cationic exchange columns). These substitutions also aid in the determination and monitoring of any contaminating homodimers post-purification (e.g., IEF gels, cIEF, and analytical IEX columns).

VII. Biological and Biochemical Functionality of TIM-3 Antibody×IL-15/IL-15Rα Heterodimeric Immunomodulatory Fusion Proteins Generally the targeted IL-15/IL-15Rα-Fc heterodimeric fusion proteins of the invention are administered to patients with cancer, and efficacy is assessed, in a number of ways as described herein. Thus, while standard assays of efficacy can be run, such as cancer load, size of tumor, evaluation of presence or extent of metastasis, etc., immuno-oncology treatments can be assessed on the basis of immune status evaluations as well. This can be done in a number of ways, including both in vitro and in vivo assays. For example, evaluation of changes in immune status along with "old fashioned" measurements such as tumor burden, size, invasiveness, LN involvement, metastasis, etc. can be done. Thus, any or all of the following can be evaluated: the inhibitory effects of the heterodimeric proteins on CD4$^+$ T cell activation or proliferation, CD8$^+$ T (CTL) cell activation or proliferation, CD8+ T cell-mediated cytotoxic activity and/or CTL mediated cell depletion, NK cell activity and NK mediated cell depletion, the potentiating effects of the heterodimeric protein on Treg cell differentiation and proliferation and Treg- or myeloid derived suppressor cell (MDSC)-mediated immunosuppression or immune tolerance, and/or the effects of heterodimeric protein on proinflammatory cytokine production by immune cells, e.g., IL-2, IFN-γ or TNF-α production by T or other immune cells.

In some embodiments, assessment of treatment is done by evaluating immune cell proliferation, using for example, CFSE dilution method, Ki67 intracellular staining of immune effector cells, and $^3$H-thymidine incorporation method.

In some embodiments, assessment of treatment is done by evaluating the increase in gene expression or increased protein levels of activation-associated markers, including one or more of: CD25, CD69, CD137, ICOS, PD1, GITR, OX40, and cell degranulation measured by surface expression of CD107A.

In general, gene expression assays are done as is known in the art.

In general, protein expression measurements are also similarly done as is known in the art.

In some embodiments, assessment of treatment is done by assessing cytotoxic activity measured by target cell viability detection via estimating numerous cell parameters such as enzyme activity (including protease activity), cell membrane permeability, cell adherence, ATP production, co-enzyme production, and nucleotide uptake activity. Specific examples of these assays include, but are not limited to, Trypan Blue or PI staining, $^{51}$Cr or $^{35}$S release method, LDH activity, MTT and/or WST assays, Calcein-AM assay, Luminescent based assay, and others.

In some embodiments, assessment of treatment is done by assessing T cell activity measured by cytokine production, measure either intracellularly in culture supernatant using cytokines including, but not limited to, IFNγ, TNFα, GM-CSF, IL2, IL6, IL4, IL5, IL10, IL13 using well known techniques.

Accordingly, assessment of treatment can be done using assays that evaluate one or more of the following: (i) increases in immune response, (ii) increases in activation of αβ and/or γδ T cells, (iii) increases in cytotoxic T cell activity, (iv) increases in NK and/or NKT cell activity, (v) alleviation of αβ and/or γδT-cell suppression, (vi) increases in pro-inflammatory cytokine secretion, (vii) increases in IL-2 secretion; (viii) increases in interferon-γ production, (ix) increases in Th1 response, (x) decreases in Th2 response, (xi) decreases or eliminates cell number and/or activity of at least one of regulatory T cells (Tregs).

A. Assays to Measure Efficacy

In some embodiments, T cell activation is assessed using a Mixed Lymphocyte Reaction (MLR) assay as is known in the art. An increase in activity indicates immunostimulatory activity. Appropriate increases in activity are outlined below.

In one embodiment, the signaling pathway assay measures increases or decreases in immune response as measured for an example by phosphorylation or de-phosphorylation of different factors, or by measuring other post translational modifications. An increase in activity indicates immunostimulatory activity. Appropriate increases in activity are outlined below.

In one embodiment, the signaling pathway assay measures increases or decreases in activation of αβ and/or γδ T cells as measured for an example by cytokine secretion or by proliferation or by changes in expression of activation markers like for an example CD137, CD107a, PD1, etc. An increase in activity indicates immunostimulatory activity. Appropriate increases in activity are outlined below.

In one embodiment, the signaling pathway assay measures increases or decreases in cytotoxic T cell activity as measured for an example by direct killing of target cells like for an example cancer cells or by cytokine secretion or by proliferation or by changes in expression of activation markers like for an example CD137, CD107a, PD1, etc. An increase in activity indicates immunostimulatory activity. Appropriate increases in activity are outlined below.

In one embodiment, the signaling pathway assay measures increases or decreases in NK and/or NKT cell activity as measured for an example by direct killing of target cells like for an example cancer cells or by cytokine secretion or by changes in expression of activation markers like for an example CD107a, etc. An increase in activity indicates immunostimulatory activity. Appropriate increases in activity are outlined below.

In one embodiment, the signaling pathway assay measures increases or decreases in αβ and/or γδ T-cell suppression, as measured for an example by cytokine secretion or by proliferation or by changes in expression of activation markers like for an example CD137, CD107a, PD1, etc. An increase in activity indicates immunostimulatory activity. Appropriate increases in activity are outlined below.

In one embodiment, the signaling pathway assay measures increases or decreases in pro-inflammatory cytokine secretion as measured for example by ELISA or by Luminex or by Multiplex bead based methods or by intracellular staining and FACS analysis or by Alispot etc. An increase in activity indicates immunostimulatory activity. Appropriate increases in activity are outlined below.

In one embodiment, the signaling pathway assay measures increases or decreases in IL-2 secretion as measured for example by ELISA or by Luminex or by Multiplex bead based methods or by intracellular staining and FACS analysis or by Alispot etc. An increase in activity indicates immunostimulatory activity. Appropriate increases in activity are outlined below.

In one embodiment, the signaling pathway assay measures increases or decreases in interferon-γ production as measured for example by ELISA or by Luminex or by Multiplex bead based methods or by intracellular staining and FACS analysis or by Alispot etc. An increase in activity indicates immunostimulatory activity. Appropriate increases in activity are outlined below.

In one embodiment, the signaling pathway assay measures increases or decreases in Th1 response as measured for an example by cytokine secretion or by changes in expression of activation markers. An increase in activity indicates immunostimulatory activity. Appropriate increases in activity are outlined below.

In one embodiment, the signaling pathway assay measures increases or decreases in Th2 response as measured for an example by cytokine secretion or by changes in expression of activation markers. An increase in activity indicates immunostimulatory activity. Appropriate increases in activity are outlined below.

In one embodiment, the signaling pathway assay measures increases or decreases cell number and/or activity of at least one of regulatory T cells (Tregs), as measured for example by flow cytometry or by IHC. A decrease in response indicates immunostimulatory activity. Appropriate decreases are the same as for increases, outlined below.

In one embodiment, the signaling pathway assay measures increases or decreases in M2 macrophages cell numbers, as measured for example by flow cytometry or by IHC. A decrease in response indicates immunostimulatory activity. Appropriate decreases are the same as for increases, outlined below.

In one embodiment, the signaling pathway assay measures increases or decreases in M2 macrophage pro-tumorigenic activity, as measured for an example by cytokine secretion or by changes in expression of activation markers. A decrease in response indicates immunostimulatory activity. Appropriate decreases are the same as for increases, outlined below.

In one embodiment, the signaling pathway assay measures increases or decreases in N2 neutrophils increase, as measured for example by flow cytometry or by IHC. A decrease in response indicates immunostimulatory activity. Appropriate decreases are the same as for increases, outlined below.

In one embodiment, the signaling pathway assay measures increases or decreases in N2 neutrophils pro-tumorigenic activity, as measured for an example by cytokine secretion or by changes in expression of activation markers. A decrease in response indicates immunostimulatory activity. Appropriate decreases are the same as for increases, outlined below.

In one embodiment, the signaling pathway assay measures increases or decreases in inhibition of T cell activation, as measured for an example by cytokine secretion or by proliferation or by changes in expression of activation markers like for an example CD137, CD107a, PD1, etc. An increase in activity indicates immunostimulatory activity. Appropriate increases in activity are outlined below.

In one embodiment, the signaling pathway assay measures increases or decreases in inhibition of CTL activation as measured for an example by direct killing of target cells like for an example cancer cells or by cytokine secretion or by proliferation or by changes in expression of activation markers like for an example CD137, CD107a, PD1, etc. An increase in activity indicates immunostimulatory activity. Appropriate increases in activity are outlined below.

In one embodiment, the signaling pathway assay measures increases or decreases in αβ and/or γδ T cell exhaustion as measured for an example by changes in expression of activation markers. A decrease in response indicates immunostimulatory activity. Appropriate decreases are the same as for increases, outlined below.

In one embodiment, the signaling pathway assay measures increases or decreases αβ and/or γδ T cell response as measured for an example by cytokine secretion or by proliferation or by changes in expression of activation markers like for an example CD137, CD107a, PD1, etc. An increase in activity indicates immunostimulatory activity. Appropriate increases in activity are outlined below.

In one embodiment, the signaling pathway assay measures increases or decreases in stimulation of antigen-specific memory responses as measured for an example by cytokine secretion or by proliferation or by changes in expression of activation markers like for an example CD45RA, CCR7 etc. An increase in activity indicates immunostimulatory activity. Appropriate increases in activity are outlined below.

In one embodiment, the signaling pathway assay measures increases or decreases in apoptosis or lysis of cancer cells as measured for an example by cytotoxicity assays such as for an example MTT, Cr release, Calcine AM, or by flow cytometry based assays like for an example CFSE dilution or propidium iodide staining etc. An increase in activity indicates immunostimulatory activity. Appropriate increases in activity are outlined below.

In one embodiment, the signaling pathway assay measures increases or decreases in stimulation of cytotoxic or cytostatic effect on cancer cells. as measured for an example by cytotoxicity assays such as for an example MTT, Cr release, Calcine AM, or by flow cytometry based assays like for an example CFSE dilution or propidium iodide staining etc. An increase in activity indicates immunostimulatory activity. Appropriate increases in activity are outlined below.

In one embodiment, the signaling pathway assay measures increases or decreases direct killing of cancer cells as measured for an example by cytotoxicity assays such as for an example MTT, Cr release, Calcine AM, or by flow cytometry based assays like for an example CFSE dilution or propidium iodide staining etc. An increase in activity indicates immunostimulatory activity. Appropriate increases in activity are outlined below.

In one embodiment, the signaling pathway assay measures increases or decreases Th17 activity as measured for an example by cytokine secretion or by proliferation or by changes in expression of activation markers. An increase in activity indicates immunostimulatory activity. Appropriate increases in activity are outlined below.

In one embodiment, the signaling pathway assay measures increases or decreases in induction of complement dependent cytotoxicity and/or antibody dependent cell-mediated cytotoxicity, as measured for an example by cytotoxicity assays such as for an example MTT, Cr release, Calcine AM, or by flow cytometry based assays like for an example CFSE dilution or propidium iodide staining etc. An increase in activity indicates immunostimulatory activity. Appropriate increases in activity are outlined below.

In one embodiment, T cell activation is measured for an example by direct killing of target cells like for an example cancer cells or by cytokine secretion or by proliferation or by changes in expression of activation markers like for an example CD137, CD107a, PD1, etc. For T-cells, increases in proliferation, cell surface markers of activation (e.g., CD25, CD69, CD137, PD1), cytotoxicity (ability to kill target cells), and cytokine production (e.g., IL-2, IL-4, IL-6, IFN-γ, TNF-a, IL-10, IL-17A) would be indicative of immune modulation that would be consistent with enhanced killing of cancer cells.

In one embodiment, NK cell activation is measured for example by direct killing of target cells like for an example cancer cells or by cytokine secretion or by changes in expression of activation markers like for an example CD107a, etc. For NK cells, increases in proliferation, cytotoxicity (ability to kill target cells and increases CD107a, granzyme, and perforin expression), cytokine production (e.g., IFNγ and TNF), and cell surface receptor expression (e.g., CD25) would be indicative of immune modulation that would be consistent with enhanced killing of cancer cells.

In one embodiment, γδ T cell activation is measured for example by cytokine secretion or by proliferation or by changes in expression of activation markers.

In one embodiment, Th1 cell activation is measured for example by cytokine secretion or by changes in expression of activation markers.

Appropriate increases in activity or response (or decreases, as appropriate as outlined above), are increases of 10%, 20%, 30%, 40%, 50%, 60%, 70%, 80%, 90%, 95% or 98 to 99% percent over the signal in either a reference sample or in control samples, for example test samples that do not contain a heterodimeric protein of the invention. Similarly, increases of at least one-, two-, three-, four- or five-fold as compared to reference or control samples show efficacy.

VIII. Treatments

Once made, the compositions of the invention find use in a number of oncology applications, by treating cancer, generally by promoting T cell activation (e.g., T cells are no longer suppressed) with the binding of the heterodimeric fusion proteins of the invention.

Accordingly, the targeted IL-15/IL-15Rα-Fc heterodimeric compositions of the invention find use in the treatment of these cancers.

A. Targeted IL-15/IL-15Rα-Fc Heterodimeric Protein Compositions for In Vivo Administration Formulations of the antibodies used in accordance with the present invention are prepared for storage by mixing an antibody having the desired degree of purity with optional pharmaceutically acceptable carriers, excipients or stabilizers (as generally outlined in Remington's Pharmaceutical Sciences 16th edition, Osol, A. Ed. [1980]), in the form of lyophilized formulations or aqueous solutions. Acceptable carriers, buffers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

B. Combination Therapies

In some embodiments, the heterodimeric proteins of the invention can be used in combination therapies with antibodies that bind to different checkpoint proteins, e.g., not TIM-3 antibodies. In this way, the targeted IL-15/IL-15Rα-Fc binding domains of the additional antibody do not compete for binding with the targeted IL-15/IL-15Rα-Fc heterodimeric protein. In this way, a sort of "triple combination" therapy is achieved, as three receptors are engaged (two from the targeted IL-15/IL-15Rα-Fc heterodimeric protein and one from the additional antibody). As discussed herein, the heterodimeric protein can have different valencies and specifities as outlined herein.

Surprisingly, as shown herein, these combinations can result in synergistic effects when co-administered. In this context, "co-administration" means that the two moieties can be administered simultaneously or sequentially. That is, in some cases, the drugs may be administered simultaneously, although generally this is through the use of two separate IV infusions; that is, the drugs are generally not combined into a single dosage unit. Alternatively, co-administration includes the sequential administration of the two separate drugs, either in a single day or separate days (including separate days over time).

1. Anti-PD-1 Antibodies for Use in Co-Administration Therapies

As is known in the art, there are two currently approved anti-PD-1 antibodies and many more in clinical testing. Thus, suitable anti-PD-1 antibodies for use in combination therapies as outlined herein include, but are not limited to, the two currently FDA approved antibodies, pembrolizumab and nivolizumab, as well as those in clinical testing currently, including, but not limited to, tislelizumab, Sym021, REGN2810 (developed by Rengeneron), JNJ-63723283 (developed by J and J), SHR-1210, pidilizumab, AMP-224, MEDIo680, PDR001 and CT-001, as well as others outlined in Liu et al., J. Hemat. & Oncol. (2017)10:136, the antibodies therein expressly incorporated by reference. As above, anti-PD-1 antibodies are used in combination when the targeted IL-15/IL-15Rα-Fc fusion proteins of the invention do not have an antigen binding domain that binds PD-1.

2. Anti-PD-L1 Antibodies for Use in Co-Administration Therapies

In some embodiments, anti-PD-L1 antibodies are used in combination. As is known in the art, there are three currently approved anti-PD-L1 antibodies and many more in clinical testing. Thus, suitable anti-PD-L1 antibodies for use in combination therapies as outlined herein include, but are not limited to, the three currently FDA approved antibodies, atezolizumab, avelumab, durvalumab, as well as those in clinical testing currently, including, but not limited to, LY33000054 and CS1001, as well as others outlined in Liu et al., J. Hemat. & Oncol. (2017)10:136, the antibodies therein expressly incorporated by reference. As above, anti-PD-L1 antibodies are used in combination when the targeted IL-15/IL-15Rα-Fc fusion proteins of the invention do not have an antigen binding domain that binds PD-L1.

3. Anti-TIGIT Antibodies for Use in Co-Administration Therapies

In some embodiments, anti-TIGIT antibodies can be used in combination with the targeted IL-15/IL-15Rα-Fc fusion proteins of the invention. There are several TIGIT antibodies in clinical development, BMS-986207, OMP-313M32 and MTIG7192A. As above, anti-TIGIT antibodies are used in combination when the targeted IL-15/IL-15Rα-Fc fusion protein of the invention do not have an antigen binding domain that binds TIGIT.

4. Anti-CTLA-4 Antibodies for Use in Co-Administration Therapies

In some embodiments, anti-CTLA-4 antibodies can be used in combination with the targeted IL-15/IL-15Rα-Fc fusion protein of the invention. Ipilimumab has been approved, and there are several more in development, including CP-675,206 and AGEN-1884. As above, anti-CTLA-4 antibodies are used in combination when the targeted IL-15/IL-15Rα-Fc fusion proteins of the invention do not have an antigen binding domain that binds CTLA-4.

5. Anti-TIM-3 Antibodies for Use in Co-Administration Therapies

In some embodiments, anti-TIM-3 antibodies can be used in combination with the targeted IL-15/IL-15Rα-Fc fusion protein of the invention. There are several TIM-3 antibodies in clinical development including BMS-986016, LAG525 and REGN3767. As above, anti-TIM-3 antibodies are used in combination when the targeted IL-15/IL-15Rα-Fc fusion proteins of the invention do not have an antigen binding domain that binds TIM-3.

C. Administrative Modalities

The targeted IL-15/IL-15Rα-Fc fusion proteins and chemotherapeutic agents of the invention are administered to a subject, in accord with known methods, such as intravenous administration as a bolus or by continuous infusion over a period of time.

D. Treatment Modalities

In the methods of the invention, therapy is used to provide a positive therapeutic response with respect to a disease or condition. By "positive therapeutic response" is intended an improvement in the disease or condition, and/or an improvement in the symptoms associated with the disease or condition. For example, a positive therapeutic response would refer to one or more of the following improvements in the disease: (1) a reduction in the number of neoplastic cells; (2) an increase in neoplastic cell death; (3) inhibition of neoplastic cell survival; (5) inhibition (i.e., slowing to some extent, preferably halting) of tumor growth; (6) an increased patient survival rate; and (7) some relief from one or more symptoms associated with the disease or condition.

Positive therapeutic responses in any given disease or condition can be determined by standardized response criteria specific to that disease or condition. Tumor response can be assessed for changes in tumor morphology (i.e., overall tumor burden, tumor size, and the like) using screening techniques such as magnetic resonance imaging (MRI) scan, x-radiographic imaging, computed tomographic (CT) scan, bone scan imaging, endoscopy, and tumor biopsy sampling including bone marrow aspiration (BMA) and counting of tumor cells in the circulation.

In addition to these positive therapeutic responses, the subject undergoing therapy may experience the beneficial effect of an improvement in the symptoms associated with the disease.

Treatment according to the present invention includes a "therapeutically effective amount" of the medicaments used. A "therapeutically effective amount" refers to an amount effective, at dosages and for periods of time necessary, to achieve a desired therapeutic result.

A therapeutically effective amount may vary according to factors such as the disease state, age, sex, and weight of the individual, and the ability of the medicaments to elicit a desired response in the individual. A therapeutically effective amount is also one in which any toxic or detrimental effects of the antibody or antibody portion are outweighed by the therapeutically beneficial effects.

A "therapeutically effective amount" for tumor therapy may also be measured by its ability to stabilize the progression of disease. The ability of a compound to inhibit cancer may be evaluated in an animal model system predictive of efficacy in human tumors.

Alternatively, this property of a composition may be evaluated by examining the ability of the compound to inhibit cell growth or to induce apoptosis by in vitro assays known to the skilled practitioner. A therapeutically effective amount of a therapeutic compound may decrease tumor size, or otherwise ameliorate symptoms in a subject. One of ordinary skill in the art would be able to determine such amounts based on such factors as the subject's size, the severity of the subject's symptoms, and the particular composition or route of administration selected.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. Parenteral compositions may be formulated in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

The specification for the dosage unit forms of the present invention are dictated by and directly dependent on (a) the unique characteristics of the active compound and the particular therapeutic effect to be achieved, and (b) the limitations inherent in the art of compounding such an active compound for the treatment of sensitivity in individuals.

The efficient dosages and the dosage regimens for the targeted IL-15/IL-15Rα-Fc fusion protein used in the present invention depend on the disease or condition to be treated and may be determined by the persons skilled in the art.

An exemplary, non-limiting range for a therapeutically effective amount of the targeted IL-15/IL-15Rα-Fc fusion protein used in the present invention is about 0.1-100 mg/kg.

All cited references are herein expressly incorporated by reference in their entirety.

Whereas particular embodiments of the invention have been described above for purposes of illustration, it will be appreciated by those skilled in the art that numerous variations of the details may be made without departing from the invention as described in the appended claims.

IX. Examples

Examples are provided below to illustrate the present invention. These examples are not meant to constrain the present invention to any particular application or theory of operation. For all constant region positions discussed in the present invention, numbering is according to the EU index as in Kabat (Kabat et al., 1991, Sequences of Proteins of Immunological Interest, 5th Ed., United States Public Health Service, National Institutes of Health, Bethesda, entirely incorporated by reference). Those skilled in the art of antibodies will appreciate that this convention consists of nonsequential numbering in specific regions of an immunoglobulin sequence, enabling a normalized reference to conserved positions in immunoglobulin families. Accordingly, the positions of any given immunoglobulin as defined by the EU index will not necessarily correspond to its sequential sequence.

General and specific scientific techniques are outlined in US Publications 2015/0307629, 2014/0288275 and WO2014/145806, all of which are expressly incorporated by reference in their entirety and particularly for the techniques outlined therein. Examples 1 and 2 from U.S. Ser. No. 62/416,087, filed on Nov. 1, 2016 are expressly incorporated by reference in their entirety, including the corresponding figures. Additionally, U.S. Ser. Nos. 62/408,655, 62/443, 465, 62/477,926, 15/785,401, 62/416,087 and 15/785,393 are expressly incorporated by reference in their entirety, and specifically for all the sequences, Figures and Legends therein.

A. Example 1: Anti-TIM-3 ABDs

Examples of antigen-binding domains which bind TIM-3 are described in WO2017/218707, herein incorporated by reference, the contents are hereby incorporated in its entirety for all purposes, and in particular for the TIM-3 ABDs in FIG. 13, the data in FIG. 21 and FIG. 22 and SEQ ID NO:s 20765-20884, SEQ ID NO:s 37587-37698 and SEQ ID NO:s 36347-36706 sequences in the sequence listing (which can be formatted either as scFvs or as Fabs as discussed therein and herein). Additional illustrative sequences of anti-TIM-3 Fvs are depicted in FIG. 12 and FIG. 13. Additional non-limiting examples of TIM-3 ABDs which may find use in the TIM-3-targeted IL-15/Rα-Fc fusion proteins of the invention are depicted in FIG. 16 and in the sequence listing.

B. Example 2: TIM-3-Targeted IL-15/Rα-Fc Fusions

Reference is made to WO2018/071919 which describes IL-15/RA-Fc fusions that do not contain ABDs as are generally depicted in FIG. 9 and FIG. 39.

WO2018/071919 is expressly incorporated by reference herein, and specifically for all of the sequences, formats, Figures and Legends therein.

2A: Generation of TIM-3-targeted IL-15/Rα-Fc fusions

Plasmids coding for IL-15, IL-15Rα sushi domain, or the anti-TIM-3 variable regions were constructed by standard gene synthesis, followed by subcloning into a pTT5 expression vector containing Fc fusion partners (e.g., constant regions as depicted in FIG. 13). Cartoon schematics of illustrative TIM-3-targeted IL-15/Rα-Fc fusions are depicted in FIG. 21.

The "scIL-15/RαxscFv" format (FIG. 21A) comprises IL-15Rα(sushi) fused to IL-15 by a variable length linker (termed "scIL-15/Rα") which is then fused to the N-terminus of a heterodimeric Fc-region, with an scFv fused to the other side of the heterodimeric Fc.

The "scFvxncIL-15/Rα" format (FIG. 21B) comprises an scFv fused to the N-terminus of a heterodimeric Fc-region, with IL-15Rα(sushi) fused to the other side of the heterodimeric Fc, while IL-15 is transfected separately so that a non-covalent IL-15/Rα complex is formed.

The "scFvxdsIL-15/Rα" format (FIG. 21C) is the same as the "scFvxncIL-15/Rα" format, but wherein IL-15Rα(sushi) and IL-15 are covalently linked as a result of engineered cysteines.

The "scIL-15/RαxFab" format (FIG. 21D) comprises IL-15Rα(sushi) fused to IL-15 by a variable length linker (termed "scIL-15/Rα") which is then fused to the N-terminus of a heterodimeric Fc-region, with a variable heavy chain (VH) fused to the other side of the heterodimeric Fc, while a corresponding light chain is transfected separately so as to form a Fab with the VH. Sequences for illustrative TIM-3-targeted IL-15/Rα-Fc fusion proteins of this format are depicted in FIG. 61.

The "ncIL-15/RαxFab" format (FIG. 21E) comprises a VH fused to the N-terminus of a heterodimeric Fc-region, with IL-15Rα(sushi) fused to the other side of the heterodimeric Fc, while a corresponding light chain is transfected separately so as to form a Fab with the VH, and while IL-15 is transfected separately so that a non-covalent IL-15/Rα complex is formed.

The "dsIL-15/RαxFab" format (FIG. 21F) is the same as the "ncIL-15/Rα x Fab" format, but wherein IL-15Rα (sushi) and IL-15 are covalently linked as a result of engineered cysteines.

The "mAb-scIL-15/Rα" format (FIG. 21G) comprises VH fused to the N-terminus of a first and a second heterodimeric Fc, with IL-15 is fused to IL-15Rα(sushi) which is then further fused to the C-terminus of one of the heterodimeric Fc-region, while corresponding light chains are transfected separately so as to form a Fabs with the VHs.

The "mAb-ncIL-15/Rα" format (FIG. 21H) comprises VH fused to the N-terminus of a first and a second heterodimeric Fc, with IL-15Rα(sushi) fused to the C-terminus of one of the heterodimeric Fc-region, while corresponding light chains are transfected separately so as to form a Fabs with the VHs, and while and while IL-15 is transfected separately so that a non-covalent IL-15/Rα complex is formed.

The "mAb-dsIL-15/Rα" format (FIG. 21I) is the same as the "mAb-ncIL-15/Rα" format, but wherein IL-15Rα(sushi) and IL-15 are covalently linked as a result of engineered cysteines.

The "central-IL-15/Rα" format (FIG. 21J) comprises a VH recombinantly fused to the N-terminus of IL-15 which is then further fused to one side of a heterodimeric Fc and a VH recombinantly fused to the N-terminus of IL-15Rα (sushi) which is then further fused to the other side of the heterodimeric Fc, while corresponding light chains are transfected separately so as to form a Fabs with the VHs.

The "central-scIL-15/Rα" format (FIG. 21K) comprises a VH fused to the N-terminus of IL-15Rα(sushi) which is fused to IL-15 which is then further fused to one side of a heterodimeric Fc and a VH fused to the other side of the heterodimeric Fc, while corresponding light chains are transfected separately so as to form a Fabs with the VHs.

2B: TIM-3-Targeted IL-15/Rα-Fc Fusions Enhance GVHD, and Combines Synergistically with Anti-PD-1 Antibody Illustrative TIM-3-targeted IL-15/Rα-Fc fusion protein, XENP27974 alone or in combination with (a bivalent anti-PD-1 mAb based on nivolumab with ablated effector function; sequences for which is depicted in FIG. 23), was evaluated in a Graft-versus-Host Disease (GVHD) model conducted in NSG (NOD-SCID-gamma) immunodeficient mice. When the NSG mice are injected with human PBMCs, the human PBMCs develop an autoimmune response against mouse cells. Dosing of NSG mice injected with human PBMCs followed with TIM-3-targeted IL-15/Rα-Fc fusion proteins proliferate the engrafted T cells and enhances engraftment.

10 million human PBMCs were engrafted into NSG mice via IV-OSP on Day −1 followed by dosing with the indicated test articles at the indicated concentrations on Days 0, 7, 14, and 21. Counts of various lymphocyte populations were performed on Days 6 and 10, data for which are depicted in FIG. 24 to FIG. 27. Body weights of mice were measured over time and depicted in FIG. 28 as percentage of initial body weight. The data show that dosing XENP27974 following engraftment with human PBMCs enhanced GVHD as indicated by increased T cell (CD8+ and CD4+), NK cell, and CD45+ cell counts as well as decreased body weight in comparison to engraftment with PBMC alone. Notably, XENP27974 enhanced GVHD to a greater extent than dosing with XENP16432 alone. Additionally, the data show that XENP27974 combined synergistically with XENP16432 in enhancing GVHD as indicated by the death of all mice by Day 19 following dosing with a combination of XENP27974 and XENP16432. This suggests that, in an immuno-oncology setting, treatment with TIM-3-targeted IL-15/Rα-Fc fusion proteins alone or in combination with checkpoint blockade antibodies will proliferate tumor-infiltrating lymphocytes and enhance anti-tumor activity.

2C: In Vitro Characterization of TIM-3-Targeted IL-15/Rα-Fc Fusions

The TIM-3-targeted IL-15/Rα-Fc fusions were further characterized in a cell proliferation assay. Human PBMCs were stimulated for 48 hours with 500 ng/ml plate-bound anti-CD3 (OKT3) and then labeled with CFSE and incubated with the following test articles for 4 days at 37° C.: XENP27974 (TIM-3-targeted IL-15/Rα-Fc fusion based on 2A5B4 and having N4D/N65D IL-15 variant); XENP24306 (control untargeted IL-15(D30N/E64Q/N65D)/Rα-Fc fusion having D30N/E64Q/N65D IL-15 variant); and XENP26007 (control RSV-targeted IL-15/Rα-Fc fusion having N4D/N65D IL-15 variant). Cells were stained with the following antibodies: anti-CD8-PerCP-Cy5.5 (SK1), anti-CD3-PE-Cy7 (OKT3), anti-CD45RO-APC-Fire750 (UCHL1), anti-HLA-DR-Alexa700 (L243), anti-CD16-BV605 (3G6), anti-CD56-BV605 (HCD56), anti-CD25-BV711 (M-A251), anti-CD45RA-BV785 (HI100), anti-CD4-BUV395 (SK3), and Zombie Aqua-BV510 and analyzed by flow for various cell populations.

The proliferation of various T cell populations based on CFSE dilution (Zombie Aqua to exclude dead cells) was investigated, data for which are depicted in FIGS. 30-35. The data show that the TIM-3-targeted IL-15/Rα-Fc fusion is much more potent in inducing proliferation of both CD8+ and CD4+ T cells in comparison to untargeted IL-15(D30N/ E64Q/N65D))/Rα-Fc fusion (as well as control RSV-targeted IL-15/Rα-Fc fusion). Notably, the TIM-3-targeted IL-15/

Rα-Fc fusions preferentially targets memory T cells over naive T cells, suggesting that in a clinical setting, the TIM-3-targeted IL-15/Rα-Fc fusions will be selective for activated tumor-infiltrating lymphocytes in the tumor environment. Additionally, as shown in FIG. 35, TIM-3-targeted IL-15/Rα-Fc fusions are much more potent in inducing proliferation of NK cells.

The activation of various T cell populations based on expression of CD25 (a late stage T cell activation marker) and HLA-DR (another activation marker) was also investigated, data for which are depicted in FIGS. 36-38. The data depicted in FIG. 36 show that TIM-3-targeted IL-15/Rα-Fc fusions appear more potent in inducing activation of CD8 T cell populations in comparison to untargeted IL-15(D30N/E64Q/N65D)/Rα-Fc fusion (as well as control RSV-targeted IL-15/Rα-Fc fusion).

C. Example 3: TIM-3-Targeted IL-15/Rα-Fc Fusions with Tuned IL-15 Potency

3A: IL-15(D30N/N65D) Variant

In a study investigating the pharmacokinetics of IL-15-Fc potency variants with Xtend, cynomolgus monkeys were administered a first single intravenous (i.v.) dose of XENP22853 (WT IL-15/Rα-heteroFc with Xtend; sequences depicted in FIG. 39), XENP24306 (IL-15(D30N/E64Q/N65D)/Rα-heteroFc with Xtend; sequences depicted in FIG. 42), XENP24113 (IL-15(N4D/N65D)/Rα-heteroFc with Xtend; sequences depicted in FIG. 40), and XENP24294 (scIL-15(N4D/N65D)/Rα-Fc with Xtend; sequences depicted in FIG. 41) at varying concentrations.

FIG. 43 depicts the serum concentration of the test articles over time following the first dose. As expected, incorporating potency variants in addition to Xtend substitution (as in XENP24306 and XENP24113) greatly improves the pharmacokinetics of IL-15-Fc fusions (in comparison to XENP22583). Unexpectedly, however, IL-15/Rα-heteroFc fusion XENP24113 and scIL-15/Rα-Fc fusion XENP24294 (which have the same IL-15(N4D/N65D) potency variant) demonstrated reduced pharmacokinetics in comparison to XENP24306. This suggests that the reduced pharmacokinetics was due to the particular IL-15 potency variant rather than the format of the IL-15-Fc fusion. While a decrease in pharmacokinetics for XENP24113 and XENP24294 was expected on the basis of previous findings which demonstrated that the IL-15-Fc fusions having IL-15(N4D/N65D) variant had greater in vitro potency than IL-15-Fc fusions having the IL-15(D30N/E64Q/N65D) variant, the decrease in pharmacokinetics was unexpectedly disproportionate to the increase in potency. Accordingly, identification of alternative IL-15 potency variants for use in the TIM-3-targeted IL-15-Fc fusions of the invention was carried out.

It is noted that IL-15(N4D/N65D) has both its substitutions at the IL-15 interface responsible for binding to CD122, while IL-15(D30N/E64Q/N65D) has two substitutions (E64Q and N65D) at IL-15:CD122 interface; and one substitution (D30N) at the IL-15 interface responsible for binding to CD132. Accordingly, it is believed that the modification at the IL-15:CD132 interface may contribute to the superior pharmacokinetics observed for XENP24306. Notably, it was observed that scIL-15/Rα-Fc fusions comprising IL-15(N4D/N65D) variant and IL-15(D30N/N65D) variant demonstrated very similar potency in vitro, as depicted in FIG. 45. In view of the above, illustrative TIM-3-targeted IL-15-Fc fusion comprising the IL-15(D30N/N65D) variants were conceived, sequences for which are depicted in FIG. 46. A control RSV-targeted IL-15/Rα-Fc fusion protein XENP29481 with IL-15(D30N/N65D) variant was also generated, sequences for which are depicted in FIG. 49.

3B: IL-15(D30N/E64Q/N65D) Variant

Although the TIM-3-targeted IL-15/Rα-Fc fusions were designed with the aim to be targeted to the tumor environment via the TIM-3-targeting arm, the cytokine moiety is still capable of signaling before reaching the tumor site and may contribute to systemic toxicity. Accordingly, further reduce the IL-15 potency TIM-3-targeted IL-15/Rα-Fc fusions with IL-15(D30N/E64Q/N65D) variant were constructed to further reduce the IL-15 potency, which as illustrated in Example 2C, has drastically reduced activity and in FIG. 45. Sequences for illustrative TIM-3-targeted IL-15/Rα-Fc fusions comprising IL-15(D30N/E64Q/N65D) variant are depicted in FIG. 47. Additionally, XENP30432, a RSV-targeted IL-15/Rα-Fc fusion comprising IL-15(D30N/E64Q/N65D) variant (sequences for which are depicted in FIG. 49), was constructed to act as a surrogate for investigating the behavior of TIM-3-targeted IL-15/Rα-Fc fusions comprising IL-15(D30N/E64Q/N65D) variant outside of the tumor environment.

---

What is claimed is:

1. A heterodimeric fusion protein comprising:
   a) a first monomer comprising, from N- to C-terminal:
      i) an IL-15Rα(sushi) domain;
      ii) a first domain linker;
      iii) an IL-15 variant;
      iv) a hinge; and
      v) a first variant Fc domain comprising CH2-CH3; and
   b) a second monomer comprising, from N- to C-terminal, VH-CH1-hinge-CH2-CH3, wherein the CH2-CH3 is a second variant Fc domain; and
   c) a third monomer comprising a VL-CL,
   wherein the VH and VL are a variable heavy domain and a variable light domain, respectively, that form a human T-cell immunoglobulin and mucin-domain containing-3 (TIM-3) antigen binding domain,
   wherein the first variant Fc domain comprises skew variants L368D/K370S and the second variant Fc domain comprises skew variants S364K/E357Q,
   wherein the first and second variant Fc domains each comprise FcKO variants E233P/L234V/L235A/G236del/S267K,
   wherein the first variant Fc domain comprises pI variants Q295E/N384D/Q418E/N421D, and wherein numbering is according to EU numbering, and
   wherein the first variant Fc domain and the second variant Fc domain are each a variant of a human IgG Fc domain.

2. A heterodimeric fusion protein according to claim 1, wherein the hinge of the first monomer comprises amino acid substitution C220S, and wherein numbering is according to EU numbering.

3. A heterodimeric fusion protein according to claim 1, wherein the first and second variant Fc domains each further comprise half-life extension variants M428L/N434S.

4. A heterodimeric fusion protein according to claim 1, wherein the IL-15 variant is a variant human IL-15 comprising amino acid substitution(s) selected from the group consisting of N1D, N4D, D8N, D30N, D61N, E64Q, N65D, Q108E, N4D/N65D, D30N/N65D, and D30N/E64Q/N65D.

5. A heterodimeric fusion protein according to claim 4, wherein the IL-15 variant comprises amino acid substitutions N4D/N65D, D30N/N65D, or D30N/E64Q/N65D.

6. A heterodimeric fusion protein according to claim 1, wherein the variable heavy domain and the variable light domain of the TIM-3 antigen binding domain is selected from the group consisting of SEQ ID NOS:56 and 60, SEQ ID NOS:64 and 68, SEQ ID NOS:72 and 76, SEQ ID NOS:80 and 84, SEQ ID NOS:88 and 92, SEQ ID NOS:96 and 100, SEQ ID NOS:104 and 108, SEQ ID NOS:112 and 116, SEQ ID NOS:120 and 124, SEQ ID NOS:128 and 132, SEQ ID NOS:136 and 140, SEQ ID NOS:144 and 148, SEQ ID NOS:152 and 156, SEQ ID NOS:160 and 164, SEQ ID NOS:168 and 172, SEQ ID NOS:176 and 180, and SEQ ID NOS:184 and 188.

7. A heterodimeric fusion protein according to claim 6, wherein the variable heavy domain and the variable light domain of the TIM-3 antigen binding domain is 3H3_H1_L2.1 (SEQ ID NOS:72 and 76).

8. A heterodimeric fusion protein according to claim 1, wherein the heterodimeric fusion protein is selected from the group consisting of: XENP27974 (SEQ ID NOS:241, 242 and 243), XENP27979 (SEQ ID NOS:246, 247 and 248), XENC1000 (SEQ ID NOS:267, 268 and 269), XENC1001 (SEQ ID NOS:270, 271 and 272), XENC1002 (SEQ ID NOS:273, 274 and 275), and XENC1003 (SEQ ID NOS: 276, 277 and 278).

9. A nucleic acid composition comprising:
a) a first nucleic acid encoding said first monomer of claim 1;
b) a second nucleic acid encoding said second monomer of claim 1; and
c) a third nucleic acid encoding said third monomer of claim 1; respectively.

10. An expression vector composition comprising:
a) a first expression vector comprising said first nucleic acid of claim 9;
b) a second expression vector comprising said second nucleic acid of claim 9;
c) a third expression vector comprising said third nucleic acid of claim 9.

11. A host cell comprising the expression vector composition according to claim 10.

12. A method of making a heterodimeric fusion protein comprising culturing the host cell of claim 11 and recovering the heterodimeric fusion protein from the cell culture.

* * * * *

SEQUENCE LISTING

```
<160> NUMBER OF SEQ ID NOS: 290

<210> SEQ ID NO 1
<211> LENGTH: 162
<212> TYPE: PRT
<213> ORGANISM: Homo sapiens

<400> SEQUENCE: 1

Met Arg Ile Ser Lys Pro His Leu Arg Ser Ile Ser Ile Gln Cys Tyr
1               5                   10                  15

Leu Cys Leu Leu Leu Asn Ser His Phe Leu Thr Glu Ala Gly Ile His
            20                  25                  30

Val Phe Ile Leu Gly Cys Phe Ser Ala Gly Leu Pro Lys Thr Glu Ala
        35                  40                  45

Asn Trp Val Asn Val Ile Ser Asp Leu Lys Lys Ile Glu Asp Leu Ile
    50                  55                  60
```

```
Gln Ser Met His Ile Asp Ala Thr Leu Tyr Thr Glu Ser Asp Val His
 65                  70                  75                  80

Pro Ser Cys Lys Val Thr Ala Met Lys Cys Phe Leu Leu Glu Leu Gln
                 85                  90                  95

Val Ile Ser Leu Glu Ser Gly Asp Ala Ser Ile His Asp Thr Val Glu
            100                 105                 110

Asn Leu Ile Ile Leu Ala Asn Asn Ser Leu Ser Ser Asn Gly Asn Val
        115                 120                 125

Thr Glu Ser Gly Cys Lys Glu Cys Glu Glu Leu Glu Glu Lys Asn Ile
    130                 135                 140

Lys Glu Phe Leu Gln Ser Phe Val His Ile Val Gln Met Phe Ile Asn
145                 150                 155                 160

Thr Ser
```

<210> SEQ ID NO 2
<211> LENGTH: 114
<212> TYPE: PRT
<213> ORGANISM: Homo sapiens

<400> SEQUENCE: 2

```
Asn Trp Val Asn Val Ile Ser Asp Leu Lys Lys Ile Glu Asp Leu Ile
 1               5                  10                  15

Gln Ser Met His Ile Asp Ala Thr Leu Tyr Thr Glu Ser Asp Val His
             20                  25                  30

Pro Ser Cys Lys Val Thr Ala Met Lys Cys Phe Leu Leu Glu Leu Gln
         35                  40                  45

Val Ile Ser Leu Glu Ser Gly Asp Ala Ser Ile His Asp Thr Val Glu
     50                  55                  60

Asn Leu Ile Ile Leu Ala Asn Asn Ser Leu Ser Ser Asn Gly Asn Val
 65                  70                  75                  80

Thr Glu Ser Gly Cys Lys Glu Cys Glu Glu Leu Glu Glu Lys Asn Ile
                 85                  90                  95

Lys Glu Phe Leu Gln Ser Phe Val His Ile Val Gln Met Phe Ile Asn
            100                 105                 110

Thr Ser
```

<210> SEQ ID NO 3
<211> LENGTH: 267
<212> TYPE: PRT
<213> ORGANISM: Homo sapiens

<400> SEQUENCE: 3

```
Met Ala Pro Arg Arg Ala Arg Gly Cys Arg Thr Leu Gly Leu Pro Ala
 1               5                  10                  15

Leu Leu Leu Leu Leu Leu Leu Arg Pro Pro Ala Thr Arg Gly Ile Thr
             20                  25                  30

Cys Pro Pro Pro Met Ser Val Glu His Ala Asp Ile Trp Val Lys Ser
         35                  40                  45

Tyr Ser Leu Tyr Ser Arg Glu Arg Tyr Ile Cys Asn Ser Gly Phe Lys
     50                  55                  60

Arg Lys Ala Gly Thr Ser Ser Leu Thr Glu Cys Val Leu Asn Lys Ala
 65                  70                  75                  80

Thr Asn Val Ala His Trp Thr Thr Pro Ser Leu Lys Cys Ile Arg Asp
                 85                  90                  95

Pro Ala Leu Val His Gln Arg Pro Ala Pro Pro Ser Thr Val Thr Thr
            100                 105                 110
```

```
Ala Gly Val Thr Pro Gln Pro Glu Ser Leu Ser Pro Ser Gly Lys Glu
        115                 120                 125
Pro Ala Ala Ser Ser Pro Ser Ser Asn Asn Thr Ala Ala Thr Thr Ala
130                 135                 140
Ala Ile Val Pro Gly Ser Gln Leu Met Pro Ser Lys Ser Pro Ser Thr
145                 150                 155                 160
Gly Thr Thr Glu Ile Ser Ser His Glu Ser Ser His Gly Thr Pro Ser
                165                 170                 175
Gln Thr Thr Ala Lys Asn Trp Glu Leu Thr Ala Ser Ala Ser His Gln
        180                 185                 190
Pro Pro Gly Val Tyr Pro Gln Gly His Ser Asp Thr Thr Val Ala Ile
                195                 200                 205
Ser Thr Ser Thr Val Leu Leu Cys Gly Leu Ser Ala Val Ser Leu Leu
    210                 215                 220
Ala Cys Tyr Leu Lys Ser Arg Gln Thr Pro Pro Leu Ala Ser Val Glu
225                 230                 235                 240
Met Glu Ala Met Glu Ala Leu Pro Val Thr Trp Gly Thr Ser Ser Arg
                    245                 250                 255
Asp Glu Asp Leu Glu Asn Cys Ser His His Leu
                260                 265

<210> SEQ ID NO 4
<211> LENGTH: 65
<212> TYPE: PRT
<213> ORGANISM: Homo sapiens

<400> SEQUENCE: 4

Ile Thr Cys Pro Pro Pro Met Ser Val Glu His Ala Asp Ile Trp Val
1               5                   10                  15
Lys Ser Tyr Ser Leu Tyr Ser Arg Glu Arg Tyr Ile Cys Asn Ser Gly
            20                  25                  30
Phe Lys Arg Lys Ala Gly Thr Ser Ser Leu Thr Glu Cys Val Leu Asn
        35                  40                  45
Lys Ala Thr Asn Val Ala His Trp Thr Thr Pro Ser Leu Lys Cys Ile
    50                  55                  60
Arg
65

<210> SEQ ID NO 5
<211> LENGTH: 175
<212> TYPE: PRT
<213> ORGANISM: Homo sapiens

<400> SEQUENCE: 5

Ile Thr Cys Pro Pro Pro Met Ser Val Glu His Ala Asp Ile Trp Val
1               5                   10                  15
Lys Ser Tyr Ser Leu Tyr Ser Arg Glu Arg Tyr Ile Cys Asn Ser Gly
            20                  25                  30
Phe Lys Arg Lys Ala Gly Thr Ser Ser Leu Thr Glu Cys Val Leu Asn
        35                  40                  45
Lys Ala Thr Asn Val Ala His Trp Thr Thr Pro Ser Leu Lys Cys Ile
    50                  55                  60
Arg Asp Pro Ala Leu Val His Gln Arg Pro Ala Pro Pro Ser Thr Val
65                  70                  75                  80
Thr Thr Ala Gly Val Thr Pro Gln Pro Glu Ser Leu Ser Pro Ser Gly
                85                  90                  95
```

-continued

Lys Glu Pro Ala Ala Ser Ser Pro Ser Ser Asn Asn Thr Ala Ala Thr
                100                 105                 110

Thr Ala Ala Ile Val Pro Gly Ser Gln Leu Met Pro Ser Lys Ser Pro
            115                 120                 125

Ser Thr Gly Thr Thr Glu Ile Ser Ser His Glu Ser Ser His Gly Thr
    130                 135                 140

Pro Ser Gln Thr Thr Ala Lys Asn Trp Glu Leu Thr Ala Ser Ala Ser
145                 150                 155                 160

His Gln Pro Pro Gly Val Tyr Pro Gln Gly His Ser Asp Thr Thr
                165                 170                 175

<210> SEQ ID NO 6
<211> LENGTH: 551
<212> TYPE: PRT
<213> ORGANISM: Homo sapiens

<400> SEQUENCE: 6

Met Ala Ala Pro Ala Leu Ser Trp Arg Leu Pro Leu Leu Ile Leu Leu
1               5                   10                  15

Leu Pro Leu Ala Thr Ser Trp Ala Ser Ala Ala Val Asn Gly Thr Ser
            20                  25                  30

Gln Phe Thr Cys Phe Tyr Asn Ser Arg Ala Asn Ile Ser Cys Val Trp
        35                  40                  45

Ser Gln Asp Gly Ala Leu Gln Asp Thr Ser Cys Gln Val His Ala Trp
    50                  55                  60

Pro Asp Arg Arg Arg Trp Asn Gln Thr Cys Glu Leu Leu Pro Val Ser
65                  70                  75                  80

Gln Ala Ser Trp Ala Cys Asn Leu Ile Leu Gly Ala Pro Asp Ser Gln
                85                  90                  95

Lys Leu Thr Thr Val Asp Ile Val Thr Leu Arg Val Leu Cys Arg Glu
                100                 105                 110

Gly Val Arg Trp Arg Val Met Ala Ile Gln Asp Phe Lys Pro Phe Glu
            115                 120                 125

Asn Leu Arg Leu Met Ala Pro Ile Ser Leu Gln Val Val His Val Glu
        130                 135                 140

Thr His Arg Cys Asn Ile Ser Trp Glu Ile Ser Gln Ala Ser His Tyr
145                 150                 155                 160

Phe Glu Arg His Leu Glu Phe Glu Ala Arg Thr Leu Ser Pro Gly His
                165                 170                 175

Thr Trp Glu Glu Ala Pro Leu Leu Thr Leu Lys Gln Lys Gln Glu Trp
            180                 185                 190

Ile Cys Leu Glu Thr Leu Thr Pro Asp Thr Gln Tyr Glu Phe Gln Val
        195                 200                 205

Arg Val Lys Pro Leu Gln Gly Glu Phe Thr Thr Trp Ser Pro Trp Ser
    210                 215                 220

Gln Pro Leu Ala Phe Arg Thr Lys Pro Ala Ala Leu Gly Lys Asp Thr
225                 230                 235                 240

Ile Pro Trp Leu Gly His Leu Leu Val Gly Leu Ser Gly Ala Phe Gly
                245                 250                 255

Phe Ile Ile Leu Val Tyr Leu Leu Ile Asn Cys Arg Asn Thr Gly Pro
            260                 265                 270

Trp Leu Lys Lys Val Leu Lys Cys Asn Thr Pro Asp Pro Ser Lys Phe
        275                 280                 285

Phe Ser Gln Leu Ser Ser Glu His Gly Gly Asp Val Gln Lys Trp Leu

```
            290                 295                 300

Ser Ser Pro Phe Pro Ser Ser Phe Ser Pro Gly Gly Leu Ala Pro
305                 310                 315                 320

Glu Ile Ser Pro Leu Glu Val Leu Glu Arg Asp Lys Val Thr Gln Leu
                325                 330                 335

Leu Leu Gln Gln Asp Lys Val Pro Glu Pro Ala Ser Leu Ser Ser Asn
                340                 345                 350

His Ser Leu Thr Ser Cys Phe Thr Asn Gln Gly Tyr Phe Phe Phe His
                355                 360                 365

Leu Pro Asp Ala Leu Glu Ile Glu Ala Cys Gln Val Tyr Phe Thr Tyr
                370                 375                 380

Asp Pro Tyr Ser Glu Glu Asp Pro Asp Glu Gly Val Ala Gly Ala Pro
385                 390                 395                 400

Thr Gly Ser Ser Pro Gln Pro Leu Gln Pro Leu Ser Gly Glu Asp Asp
                405                 410                 415

Ala Tyr Cys Thr Phe Pro Ser Arg Asp Asp Leu Leu Leu Phe Ser Pro
                420                 425                 430

Ser Leu Leu Gly Gly Pro Ser Pro Ser Thr Ala Pro Gly Gly Ser
435                 440                 445

Gly Ala Gly Glu Glu Arg Met Pro Pro Ser Leu Gln Glu Arg Val Pro
                450                 455                 460

Arg Asp Trp Asp Pro Gln Pro Leu Gly Pro Pro Thr Pro Gly Val Pro
465                 470                 475                 480

Asp Leu Val Asp Phe Gln Pro Pro Pro Glu Leu Val Leu Arg Glu Ala
                485                 490                 495

Gly Glu Glu Val Pro Asp Ala Gly Pro Arg Glu Gly Val Ser Phe Pro
                500                 505                 510

Trp Ser Arg Pro Pro Gly Gln Gly Glu Phe Arg Ala Leu Asn Ala Arg
                515                 520                 525

Leu Pro Leu Asn Thr Asp Ala Tyr Leu Ser Leu Gln Glu Leu Gln Gly
                530                 535                 540

Gln Asp Pro Thr His Leu Val
545                 550

<210> SEQ ID NO 7
<211> LENGTH: 214
<212> TYPE: PRT
<213> ORGANISM: Homo sapiens

<400> SEQUENCE: 7

Ala Val Asn Gly Thr Ser Gln Phe Thr Cys Phe Tyr Asn Ser Arg Ala
1               5                   10                  15

Asn Ile Ser Cys Val Trp Ser Gln Asp Gly Ala Leu Gln Asp Thr Ser
                20                  25                  30

Cys Gln Val His Ala Trp Pro Asp Arg Arg Arg Trp Asn Gln Thr Cys
                35                  40                  45

Glu Leu Leu Pro Val Ser Gln Ala Ser Trp Ala Cys Asn Leu Ile Leu
                50                  55                  60

Gly Ala Pro Asp Ser Gln Lys Leu Thr Thr Val Asp Ile Val Thr Leu
65                  70                  75                  80

Arg Val Leu Cys Arg Glu Gly Val Arg Trp Arg Val Met Ala Ile Gln
                85                  90                  95

Asp Phe Lys Pro Phe Glu Asn Leu Arg Leu Met Ala Pro Ile Ser Leu
                100                 105                 110
```

```
Gln Val Val His Val Glu Thr His Arg Cys Asn Ile Ser Trp Glu Ile
            115                 120                 125

Ser Gln Ala Ser His Tyr Phe Glu Arg His Leu Glu Phe Glu Ala Arg
130                 135                 140

Thr Leu Ser Pro Gly His Thr Trp Glu Glu Ala Pro Leu Leu Thr Leu
145                 150                 155                 160

Lys Gln Lys Gln Glu Trp Ile Cys Leu Glu Thr Leu Thr Pro Asp Thr
            165                 170                 175

Gln Tyr Glu Phe Gln Val Arg Val Lys Pro Leu Gln Gly Glu Phe Thr
            180                 185                 190

Thr Trp Ser Pro Trp Ser Gln Pro Leu Ala Phe Arg Thr Lys Pro Ala
            195                 200                 205

Ala Leu Gly Lys Asp Thr
210

<210> SEQ ID NO 8
<211> LENGTH: 369
<212> TYPE: PRT
<213> ORGANISM: Homo sapiens

<400> SEQUENCE: 8

Met Leu Lys Pro Ser Leu Pro Phe Thr Ser Leu Leu Phe Leu Gln Leu
1               5                   10                  15

Pro Leu Leu Gly Val Gly Leu Asn Thr Thr Ile Leu Thr Pro Asn Gly
            20                  25                  30

Asn Glu Asp Thr Thr Ala Asp Phe Phe Leu Thr Thr Met Pro Thr Asp
            35                  40                  45

Ser Leu Ser Val Ser Thr Leu Pro Leu Pro Glu Val Gln Cys Phe Val
50                  55                  60

Phe Asn Val Glu Tyr Met Asn Cys Thr Trp Asn Ser Ser Ser Glu Pro
65                  70                  75                  80

Gln Pro Thr Asn Leu Thr Leu His Tyr Trp Tyr Lys Asn Ser Asp Asn
            85                  90                  95

Asp Lys Val Gln Lys Cys Ser His Tyr Leu Phe Ser Glu Glu Ile Thr
            100                 105                 110

Ser Gly Cys Gln Leu Gln Lys Lys Glu Ile His Leu Tyr Gln Thr Phe
            115                 120                 125

Val Val Gln Leu Gln Asp Pro Arg Glu Pro Arg Arg Gln Ala Thr Gln
            130                 135                 140

Met Leu Lys Leu Gln Asn Leu Val Ile Pro Trp Ala Pro Glu Asn Leu
145                 150                 155                 160

Thr Leu His Lys Leu Ser Glu Ser Gln Leu Glu Leu Asn Trp Asn Asn
            165                 170                 175

Arg Phe Leu Asn His Cys Leu Glu His Leu Val Gln Tyr Arg Thr Asp
            180                 185                 190

Trp Asp His Ser Trp Thr Glu Gln Ser Val Asp Tyr Arg His Lys Phe
            195                 200                 205

Ser Leu Pro Ser Val Asp Gly Gln Lys Arg Tyr Thr Phe Arg Val Arg
            210                 215                 220

Ser Arg Phe Asn Pro Leu Cys Gly Ser Ala Gln His Trp Ser Glu Trp
225                 230                 235                 240

Ser His Pro Ile His Trp Gly Ser Asn Thr Ser Lys Glu Asn Pro Phe
            245                 250                 255

Leu Phe Ala Leu Glu Ala Val Val Ile Ser Val Gly Ser Met Gly Leu
            260                 265                 270
```

```
Ile Ile Ser Leu Leu Cys Val Tyr Phe Trp Leu Glu Arg Thr Met Pro
            275                 280                 285

Arg Ile Pro Thr Leu Lys Asn Leu Glu Asp Leu Val Thr Glu Tyr His
        290                 295                 300

Gly Asn Phe Ser Ala Trp Ser Gly Val Ser Lys Gly Leu Ala Glu Ser
305                 310                 315                 320

Leu Gln Pro Asp Tyr Ser Glu Arg Leu Cys Leu Val Ser Glu Ile Pro
                325                 330                 335

Pro Lys Gly Gly Ala Leu Gly Glu Gly Pro Gly Ala Ser Pro Cys Asn
                340                 345                 350

Gln His Ser Pro Tyr Trp Ala Pro Pro Cys Tyr Thr Leu Lys Pro Glu
            355                 360                 365

Thr

<210> SEQ ID NO 9
<211> LENGTH: 240
<212> TYPE: PRT
<213> ORGANISM: Homo sapiens

<400> SEQUENCE: 9

Leu Asn Thr Thr Ile Leu Thr Pro Asn Gly Asn Glu Asp Thr Thr Ala
1               5                   10                  15

Asp Phe Phe Leu Thr Thr Met Pro Thr Asp Ser Leu Ser Val Ser Thr
            20                  25                  30

Leu Pro Leu Pro Glu Val Gln Cys Phe Val Phe Asn Val Glu Tyr Met
        35                  40                  45

Asn Cys Thr Trp Asn Ser Ser Ser Glu Pro Gln Pro Thr Asn Leu Thr
50                  55                  60

Leu His Tyr Trp Tyr Lys Asn Ser Asp Asn Asp Lys Val Gln Lys Cys
65                  70                  75                  80

Ser His Tyr Leu Phe Ser Glu Glu Ile Thr Ser Gly Cys Gln Leu Gln
                85                  90                  95

Lys Lys Glu Ile His Leu Tyr Gln Thr Phe Val Val Gln Leu Gln Asp
            100                 105                 110

Pro Arg Glu Pro Arg Arg Gln Ala Thr Gln Met Leu Lys Leu Gln Asn
        115                 120                 125

Leu Val Ile Pro Trp Ala Pro Glu Asn Leu Thr Leu His Lys Leu Ser
    130                 135                 140

Glu Ser Gln Leu Glu Leu Asn Trp Asn Asn Arg Phe Leu Asn His Cys
145                 150                 155                 160

Leu Glu His Leu Val Gln Tyr Arg Thr Asp Trp Asp His Ser Trp Thr
                165                 170                 175

Glu Gln Ser Val Asp Tyr Arg His Lys Phe Ser Leu Pro Ser Val Asp
            180                 185                 190

Gly Gln Lys Arg Tyr Thr Phe Arg Val Arg Ser Arg Phe Asn Pro Leu
        195                 200                 205

Cys Gly Ser Ala Gln His Trp Ser Glu Trp Ser His Pro Ile His Trp
    210                 215                 220

Gly Ser Asn Thr Ser Lys Glu Asn Pro Phe Leu Phe Ala Leu Glu Ala
225                 230                 235                 240

<210> SEQ ID NO 10
<211> LENGTH: 300
<212> TYPE: PRT
<213> ORGANISM: Homo sapiens
```

<400> SEQUENCE: 10

```
Met Phe Ser His Leu Pro Phe Asp Cys Val Leu Leu Leu Leu Leu
1               5                   10                  15

Leu Leu Thr Arg Ser Ser Glu Val Glu Tyr Arg Ala Glu Val Gly Gln
            20                  25                  30

Asn Ala Tyr Leu Pro Cys Phe Tyr Thr Pro Ala Ala Pro Gly Asn Leu
            35                  40                  45

Val Pro Val Cys Trp Gly Lys Gly Ala Cys Pro Val Phe Glu Cys Gly
    50                  55                  60

Asn Val Val Leu Arg Thr Asp Glu Arg Asp Val Asn Tyr Trp Thr Ser
65                  70                  75                  80

Arg Tyr Trp Leu Asn Gly Asp Phe Arg Lys Gly Asp Val Ser Leu Thr
                85                  90                  95

Ile Glu Asn Val Thr Leu Ala Asp Ser Gly Ile Tyr Cys Cys Arg Ile
                100                 105                 110

Gln Ile Pro Gly Ile Met Asn Asp Glu Lys Phe Asn Leu Lys Leu Val
            115                 120                 125

Ile Lys Pro Ala Lys Val Thr Pro Ala Pro Thr Arg Gln Arg Asp Phe
130                 135                 140

Thr Ala Ala Phe Pro Arg Met Leu Thr Thr Arg Gly His Gly Pro Ala
145                 150                 155                 160

Glu Thr Gln Thr Leu Gly Ser Leu Pro Asp Ile Asn Leu Thr Gln Ile
                165                 170                 175

Ser Thr Leu Ala Asn Glu Leu Arg Asp Ser Arg Leu Ala Asn Asp Leu
            180                 185                 190

Arg Asp Ser Gly Ala Thr Ile Arg Ile Gly Ile Tyr Ile Gly Ala Gly
            195                 200                 205

Ile Cys Ala Gly Leu Ala Leu Ala Leu Ile Phe Gly Ala Leu Ile Phe
210                 215                 220

Lys Trp Tyr Ser His Ser Lys Glu Lys Ile Gln Asn Leu Ser Leu Ile
225                 230                 235                 240

Ser Leu Ala Asn Leu Pro Pro Ser Gly Leu Ala Asn Ala Val Ala Glu
                245                 250                 255

Gly Ile Arg Ser Glu Glu Asn Ile Tyr Thr Ile Glu Glu Asn Val Tyr
            260                 265                 270

Glu Val Glu Glu Pro Asn Glu Tyr Tyr Cys Tyr Val Ser Ser Arg Gln
            275                 280                 285

Gln Pro Ser Gln Pro Leu Gly Cys Arg Phe Ala Met
290                 295                 300
```

<210> SEQ ID NO 11
<211> LENGTH: 181
<212> TYPE: PRT
<213> ORGANISM: Homo sapiens

<400> SEQUENCE: 11

```
Ser Glu Val Glu Tyr Arg Ala Glu Val Gly Gln Asn Ala Tyr Leu Pro
1               5                   10                  15

Cys Phe Tyr Thr Pro Ala Ala Pro Gly Asn Leu Val Pro Val Cys Trp
            20                  25                  30

Gly Lys Gly Ala Cys Pro Val Phe Glu Cys Gly Asn Val Val Leu Arg
            35                  40                  45

Thr Asp Glu Arg Asp Val Asn Tyr Trp Thr Ser Arg Tyr Trp Leu Asn
50                  55                  60
```

-continued

```
Gly Asp Phe Arg Lys Gly Asp Val Ser Leu Thr Ile Glu Asn Val Thr
 65                  70                  75                  80

Leu Ala Asp Ser Gly Ile Tyr Cys Cys Arg Ile Gln Ile Pro Gly Ile
                 85                  90                  95

Met Asn Asp Glu Lys Phe Asn Leu Lys Leu Val Ile Lys Pro Ala Lys
            100                 105                 110

Val Thr Pro Ala Pro Thr Arg Gln Arg Asp Phe Thr Ala Ala Phe Pro
        115                 120                 125

Arg Met Leu Thr Thr Arg Gly His Gly Pro Ala Glu Thr Gln Thr Leu
130                 135                 140

Gly Ser Leu Pro Asp Ile Asn Leu Thr Gln Ile Ser Thr Leu Ala Asn
145                 150                 155                 160

Glu Leu Arg Asp Ser Arg Leu Ala Asn Asp Leu Arg Asp Ser Gly Ala
                165                 170                 175

Thr Ile Arg Ile Gly
                180

<210> SEQ ID NO 12
<211> LENGTH: 302
<212> TYPE: PRT
<213> ORGANISM: Macaca fascicularis

<400> SEQUENCE: 12

Met Phe Ser His Leu Pro Phe Asp Cys Val Leu Leu Leu Leu Leu Leu
  1               5                  10                  15

Leu Leu Thr Arg Ser Ser Glu Val Glu Tyr Ile Ala Glu Val Gly Gln
             20                  25                  30

Asn Ala Tyr Leu Pro Cys Ser Tyr Thr Pro Ala Pro Pro Gly Asn Leu
         35                  40                  45

Val Pro Val Cys Trp Gly Lys Gly Ala Cys Pro Val Phe Asp Cys Ser
     50                  55                  60

Asn Val Val Leu Arg Thr Asp Asn Arg Asp Val Asn Asp Arg Thr Ser
 65                  70                  75                  80

Gly Arg Tyr Trp Leu Lys Gly Asp Phe His Lys Gly Asp Val Ser Leu
                 85                  90                  95

Thr Ile Glu Asn Val Thr Leu Ala Asp Ser Gly Val Tyr Cys Cys Arg
            100                 105                 110

Ile Gln Ile Pro Gly Ile Met Asn Asp Glu Lys His Asn Val Lys Leu
        115                 120                 125

Val Val Ile Lys Pro Ala Lys Val Thr Pro Ala Pro Thr Leu Gln Arg
    130                 135                 140

Asp Leu Thr Ser Ala Phe Pro Arg Met Leu Thr Thr Gly Glu His Gly
145                 150                 155                 160

Pro Ala Glu Thr Gln Thr Pro Gly Ser Leu Pro Asp Val Asn Leu Thr
                165                 170                 175

Val Ser Asn Phe Phe Cys Glu Leu Gln Ile Phe Thr Leu Thr Asn Glu
            180                 185                 190

Leu Arg Asp Ser Gly Ala Thr Ile Arg Thr Ala Ile Tyr Ile Ala Ala
        195                 200                 205

Gly Ile Ser Ala Gly Leu Ala Leu Ala Leu Ile Phe Gly Ala Leu Ile
    210                 215                 220

Phe Lys Trp Tyr Ser His Ser Lys Glu Lys Thr Gln Asn Leu Ser Leu
225                 230                 235                 240

Ile Ser Leu Ala Asn Ile Pro Pro Ser Gly Leu Ala Asn Ala Val Ala
```

```
            245                 250                 255
Glu Gly Ile Arg Ser Glu Glu Asn Ile Tyr Thr Ile Glu Glu Asp Val
            260                 265                 270

Tyr Glu Val Glu Glu Pro Asn Glu Tyr Tyr Cys Tyr Val Ser Ser Gly
        275                 280                 285

Gln Gln Pro Ser Gln Pro Leu Gly Cys Arg Val Ala Met Pro
    290                 295                 300
```

<210> SEQ ID NO 13
<211> LENGTH: 182
<212> TYPE: PRT
<213> ORGANISM: Macaca fascicularis

<400> SEQUENCE: 13

```
Ser Glu Val Glu Tyr Ile Ala Glu Val Gly Gln Asn Ala Tyr Leu Pro
1               5                   10                  15

Cys Ser Tyr Thr Pro Ala Pro Pro Gly Asn Leu Val Pro Val Cys Trp
            20                  25                  30

Gly Lys Gly Ala Cys Pro Val Phe Asp Cys Ser Asn Val Val Leu Arg
        35                  40                  45

Thr Asp Asn Arg Asp Val Asn Asp Arg Thr Ser Gly Arg Tyr Trp Leu
    50                  55                  60

Lys Gly Asp Phe His Lys Gly Asp Val Ser Leu Thr Ile Glu Asn Val
65                  70                  75                  80

Thr Leu Ala Asp Ser Gly Val Tyr Cys Cys Arg Ile Gln Ile Pro Gly
                85                  90                  95

Ile Met Asn Asp Glu Lys His Asn Val Lys Leu Val Val Ile Lys Pro
            100                 105                 110

Ala Lys Val Thr Pro Ala Pro Thr Leu Gln Arg Asp Leu Thr Ser Ala
        115                 120                 125

Phe Pro Arg Met Leu Thr Thr Gly Glu His Gly Pro Ala Glu Thr Gln
    130                 135                 140

Thr Pro Gly Ser Leu Pro Asp Val Asn Leu Thr Val Ser Asn Phe Phe
145                 150                 155                 160

Cys Glu Leu Gln Ile Phe Thr Leu Thr Asn Glu Leu Arg Asp Ser Gly
                165                 170                 175

Ala Thr Ile Arg Thr Ala
            180
```

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 14

```
Gly Gly Gly Gly Ser
1               5
```

<210> SEQ ID NO 15
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 15

Gly Gly Gly Gly Ser Gly Gly Gly Gly Ser
1               5                   10

<210> SEQ ID NO 16
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Gly Gly Gly Ser Gly Gly Gly Gly Ser Gly Gly Gly Gly Ser
1               5                   10                  15

<210> SEQ ID NO 17
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Gly Gly Gly Ser Gly Gly Gly Gly Ser Gly Gly Gly Gly Ser Gly
1               5                   10                  15

Gly Gly Gly Ser
            20

<210> SEQ ID NO 18
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 19
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 20
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

```
Gly Gly Gly Gly Ser Gly Gly Gly Ser Gly Gly Gly Ser Gly
1               5                   10                  15

Gly Gly Gly Ser Gly Gly Gly Ser Gly Gly Gly Ser Gly Gly
                20                  25                  30

Gly Gly Ser
        35

<210> SEQ ID NO 21
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Asp Pro Ala Leu Val His Gln Arg Pro Ala Pro Gly Gly Gly
1               5                   10                  15

Ser Gly Gly Gly Gly Ser Gly Gly Gly Gly Ser Gly Gly Gly
                20                  25                  30

<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gly Lys Pro Gly Ser
1               5

<210> SEQ ID NO 23
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly Lys Pro Gly Ser Gly Lys Pro Gly Ser Gly Lys Pro Gly Ser Gly
1               5                   10                  15

Lys Pro Gly Ser Gly Lys Pro Gly Ser
                20                  25

<210> SEQ ID NO 24
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Gly Lys Pro Gly Ser Gly Lys Pro Gly Ser Gly Lys Pro Gly Ser Gly
1               5                   10                  15

Lys Pro Gly Ser Gly Lys Pro Gly Ser Gly Lys Pro Gly Ser
                20                  25                  30

<210> SEQ ID NO 25
<211> LENGTH: 5
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 25

Gly Gly Gly Glu Ser
1               5

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Lys Thr His Thr Cys Pro Pro Cys Pro
1               5

<210> SEQ ID NO 27
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Glu Pro Lys Ser Ser Asp Lys Thr His Thr Cys Pro Pro Cys Pro
1               5                   10                  15

<210> SEQ ID NO 28
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gly Gly Gly Gly Ser Gly Gly Gly Ser Lys Thr His Thr Cys Pro
1               5                   10                  15

Pro Cys Pro

<210> SEQ ID NO 29
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gly Lys Pro Gly Ser Gly Lys Pro Gly Ser Lys Thr His Thr Cys Pro
1               5                   10                  15

Pro Cys Pro

<210> SEQ ID NO 30
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 30

Gly Lys Pro Gly Ser Lys Thr His Thr Cys Pro Pro Cys Pro
1               5                   10

<210> SEQ ID NO 31
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gly Ser Thr Ser Gly Ser Gly Lys Pro Gly Ser Gly Glu Gly Ser Thr
1               5                   10                  15

Lys Gly

<210> SEQ ID NO 32
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Ile Arg Pro Arg Ala Ile Gly Gly Ser Lys Pro Arg Val Ala
1               5                   10

<210> SEQ ID NO 33
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gly Lys Gly Gly Ser Gly Lys Gly Gly Ser Gly Lys Gly Gly Ser
1               5                   10                  15

<210> SEQ ID NO 34
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gly Gly Lys Gly Ser Gly Gly Lys Gly Ser Gly Gly Lys Gly Ser
1               5                   10                  15

<210> SEQ ID NO 35
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gly Gly Gly Lys Ser Gly Gly Gly Lys Ser Gly Gly Gly Lys Ser
1               5                   10                  15

<210> SEQ ID NO 36
```

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gly Lys Gly Lys Ser Gly Lys Gly Lys Ser Gly Lys Gly Lys Ser
1               5                   10                  15

<210> SEQ ID NO 37
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gly Gly Gly Lys Ser Gly Gly Lys Gly Ser Gly Lys Gly Gly Ser
1               5                   10                  15

<210> SEQ ID NO 38
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gly Lys Pro Gly Ser Gly Lys Pro Gly Ser Gly Lys Pro Gly Ser
1               5                   10                  15

<210> SEQ ID NO 39
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gly Lys Pro Gly Ser Gly Lys Pro Gly Ser Gly Lys Pro Gly Ser Gly
1               5                   10                  15

Lys Pro Gly Ser
            20

<210> SEQ ID NO 40
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gly Lys Gly Lys Ser Gly Lys Gly Lys Ser Gly Lys Gly Lys Ser Gly
1               5                   10                  15

Lys Gly Lys Ser
            20

<210> SEQ ID NO 41
<211> LENGTH: 14
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 41

Ser Thr Ala Gly Asp Thr His Leu Gly Gly Glu Asp Phe Asp
1               5                   10

<210> SEQ ID NO 42
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Gly Glu Gly Gly Ser Gly Glu Gly Gly Ser Gly Glu Gly Gly Ser
1               5                   10                  15

<210> SEQ ID NO 43
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gly Gly Glu Gly Ser Gly Gly Glu Gly Ser Gly Gly Glu Gly Ser
1               5                   10                  15

<210> SEQ ID NO 44
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gly Gly Gly Glu Ser Gly Gly Gly Glu Ser Gly Gly Gly Glu Ser
1               5                   10                  15

<210> SEQ ID NO 45
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Gly Glu Gly Glu Ser Gly Glu Gly Glu Ser Gly Glu Gly Glu Ser
1               5                   10                  15

<210> SEQ ID NO 46
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gly Gly Gly Glu Ser Gly Gly Glu Gly Ser Gly Glu Gly Gly Ser
1               5                   10                  15
```

```
<210> SEQ ID NO 47
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gly Glu Gly Glu Ser Gly Glu Gly Glu Ser Gly Glu Gly Glu Ser Gly
1               5                   10                  15

Glu Gly Glu Ser
            20

<210> SEQ ID NO 48
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Pro Val Ala Gly Pro Ser Val Phe Leu Phe Pro Pro Lys
        115                 120                 125

Pro Lys Asp Thr Leu Met Ile Ser Arg Thr Pro Glu Val Thr Cys Val
    130                 135                 140

Val Val Asp Val Lys His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Ala Leu Pro Ala Pro Ile Glu Lys Thr Ile Ser Lys Ala Lys Gly Gln
    210                 215                 220

Pro Arg Glu Pro Gln Val Tyr Thr Leu Pro Pro Ser Arg Glu Gln Met
225                 230                 235                 240

Thr Lys Asn Gln Val Lys Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270
```

```
Tyr Lys Thr Thr Pro Pro Val Leu Asp Ser Asp Gly Ser Phe Phe Leu
            275                 280                 285

Tyr Ser Lys Leu Thr Val Asp Lys Ser Arg Trp Gln Gln Gly Asn Val
    290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                325
```

<210> SEQ ID NO 49
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

```
Glu Pro Lys Ser Ser Asp Lys Thr His Thr Cys Pro Pro Cys Pro Ala
1               5                   10                  15

Pro Pro Val Ala Gly Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Lys His Glu Asp Pro Glu Val Lys Phe Asn Trp Tyr Val Asp
    50                  55                  60

Gly Val Glu Val His Asn Ala Lys Thr Lys Pro Arg Glu Glu Glu Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Glu Glu Met Thr Lys
    130                 135                 140

Asn Gln Val Ser Leu Thr Cys Asp Val Ser Gly Phe Tyr Pro Ser Asp
145                 150                 155                 160

Ile Ala Val Glu Trp Glu Ser Asp Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Glu Gln Gly Asp Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys
225                 230
```

<210> SEQ ID NO 50
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asp Thr Lys Val Asp Lys
                85                  90                  95

Lys Val Glu Pro Lys Ser Cys Asp Lys Thr His Thr Cys Pro Pro Cys
            100                 105                 110

Pro Ala Pro Pro Val Ala Gly Pro Ser Val Phe Leu Phe Pro Pro Lys
        115                 120                 125

Pro Lys Asp Thr Leu Met Ile Ser Arg Thr Pro Glu Val Thr Cys Val
    130                 135                 140

Val Val Asp Val Lys His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Glu Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Ala Leu Pro Ala Pro Ile Glu Lys Thr Ile Ser Lys Ala Lys Gly Gln
    210                 215                 220

Pro Arg Glu Pro Gln Val Tyr Thr Leu Pro Pro Ser Arg Glu Glu Met
225                 230                 235                 240

Thr Lys Asn Gln Val Ser Leu Thr Cys Asp Val Ser Gly Phe Tyr Pro
                245                 250                 255

Ser Asp Ile Ala Val Glu Trp Glu Ser Asp Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Lys Leu Thr Val Asp Lys Ser Arg Trp Gln Gln Gly Asp Val
    290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                325

<210> SEQ ID NO 51
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Glu Pro Lys Ser Ser Asp Lys Thr His Thr Cys Pro Pro Cys Pro Ala
1               5                   10                  15

Pro Pro Val Ala Gly Pro Ser Val Phe Leu Phe Pro Pro Lys Pro Lys
            20                  25                  30
```

```
Asp Thr Leu Met Ile Ser Arg Thr Pro Glu Val Thr Cys Val Val Val
        35                  40                  45

Asp Val Lys His Glu Asp Pro Glu Val Lys Phe Asn Trp Tyr Val Asp
 50                  55                  60

Gly Val Glu Val His Asn Ala Lys Thr Lys Pro Arg Glu Glu Gln Tyr
 65                  70                  75                  80

Asn Ser Thr Tyr Arg Val Val Ser Val Leu Thr Val Leu His Gln Asp
                 85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Glu Gln Met Thr Lys
    130                 135                 140

Asn Gln Val Lys Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys
225                 230

<210> SEQ ID NO 52
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asp Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Pro Val Ala Gly Pro Ser Val Phe Leu Phe Pro Pro Lys
        115                 120                 125

Pro Lys Asp Thr Leu Met Ile Ser Arg Thr Pro Glu Val Thr Cys Val
    130                 135                 140

Val Val Asp Val Lys His Glu Asp Pro Glu Val Lys Phe Asn Trp Tyr
```

```
                145                 150                 155                 160
Val Asp Gly Val Glu Val His Asn Ala Lys Thr Lys Pro Arg Glu Glu
                    165                 170                 175

Glu Tyr Asn Ser Thr Tyr Arg Val Val Ser Val Leu Thr Val Leu His
                180                 185                 190

Gln Asp Trp Leu Asn Gly Lys Glu Tyr Lys Cys Lys Val Ser Asn Lys
            195                 200                 205

Ala Leu Pro Ala Pro Ile Glu Lys Thr Ile Ser Lys Ala Lys Gly Gln
        210                 215                 220

Pro Arg Glu Pro Gln Val Tyr Thr Leu Pro Pro Ser Arg Glu Glu Met
225                 230                 235                 240

Thr Lys Asn Gln Val Ser Leu Thr Cys Asp Val Ser Gly Phe Tyr Pro
                245                 250                 255

Ser Asp Ile Ala Val Glu Trp Glu Ser Asp Gly Gln Pro Glu Asn Asn
                260                 265                 270

Tyr Lys Thr Thr Pro Pro Val Leu Asp Ser Asp Gly Ser Phe Phe Leu
            275                 280                 285

Tyr Ser Lys Leu Thr Val Asp Lys Ser Arg Trp Glu Gln Gly Asp Val
        290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                325

<210> SEQ ID NO 53
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asn His Lys Pro Ser Asn Thr Lys Val Asp Lys
                85                  90                  95

Lys Val Glu Arg Lys Ser Cys Asp Lys Thr His Thr Cys Pro Arg Cys
            100                 105                 110

Pro Ala Pro Pro Val Ala Gly Pro Ser Val Phe Leu Phe Pro Pro Lys
        115                 120                 125

Pro Lys Asp Thr Leu Met Ile Ser Arg Thr Pro Glu Val Thr Cys Val
130                 135                 140

Val Val Asp Val Lys His Glu Asp Pro Glu Val Lys Phe Lys Trp Tyr
                145                 150                 155                 160

Val Asp Gly Val Glu Val His Asn Ala Lys Thr Lys Pro Arg Glu Glu
                    165                 170                 175
```

```
Gln Tyr Asn Ser Thr Tyr Arg Val Val Ser Val Leu Thr Val Leu His
                180                 185                 190

Gln Asp Trp Leu Asn Gly Lys Glu Tyr Lys Cys Lys Val Ser Asn Lys
            195                 200                 205

Ala Leu Pro Ala Pro Ile Glu Lys Thr Ile Ser Lys Ala Lys Gly Gln
    210                 215                 220

Pro Arg Glu Pro Gln Val Tyr Thr Leu Pro Pro Ser Arg Glu Gln Met
225                 230                 235                 240

Thr Lys Asn Gln Val Lys Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
    275                 280                 285

Tyr Ser Lys Leu Thr Val Asp Lys Ser Arg Trp Gln Gln Gly Asn Val
290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                325

<210> SEQ ID NO 54
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 55
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30
```

```
Phe Tyr Pro Gly Ala Val Thr Val Ala Trp Lys Ala Asp Ser Ser Pro
            35                  40                  45

Val Lys Ala Gly Val Glu Thr Thr Thr Pro Ser Lys Gln Ser Asn Asn
 50                  55                  60

Lys Tyr Ala Ala Ser Ser Tyr Leu Ser Leu Thr Pro Glu Gln Trp Lys
 65                  70                  75                  80

Ser His Arg Ser Tyr Ser Cys Gln Val Thr His Glu Gly Ser Thr Val
                 85                  90                  95

Glu Lys Thr Val Ala Pro Thr Glu Cys Ser
            100                 105
```

```
<210> SEQ ID NO 56
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 3H3[TIM-3]_H0L0 Variable Heavy

<400> SEQUENCE: 56
```

```
Gln Val Gln Leu Lys Glu Ser Gly Pro Gly Leu Val Ala Pro Ser Gln
 1               5                  10                  15

Ser Leu Ser Ile Thr Cys Thr Val Ser Gly Phe Ser Leu Asn Gly Tyr
             20                  25                  30

Gly Val Asn Trp Val Arg Gln Pro Pro Gly Lys Gly Leu Glu Trp Leu
         35                  40                  45

Gly Met Ile Trp Gly Asp Gly Ser Thr Asp Tyr Asn Ser Ala Leu Lys
 50                  55                  60

Ser Arg Leu Ser Ile Ser Lys Asp Asn Ser Lys Ser Gln Val Phe Leu
 65                  70                  75                  80

Lys Met Asn Ser Leu Gln Thr Asp Asp Thr Ala Arg Tyr Tyr Cys Ala
                 85                  90                  95

Arg Ser Tyr Tyr Thr Ser Asp Glu Asp Tyr Trp Gly Gln Gly Thr Leu
             100                 105                 110

Val Thr Val Ser Ala
        115
```

```
<210> SEQ ID NO 57
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 3H3[TIM-3]_H0L0 Variable Heavy vhCDR1

<400> SEQUENCE: 57
```

```
Gly Tyr Gly Val Asn
 1               5
```

```
<210> SEQ ID NO 58
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 3H3[TIM-3]_H0L0 Variable Heavy vhCDR2
```

```
<400> SEQUENCE: 58

Met Ile Trp Gly Asp Gly Ser Thr Asp Tyr Asn Ser Ala Leu Lys Ser
1               5                   10                  15

<210> SEQ ID NO 59
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 3H3[TIM-3]_H0L0 Variable Heavy vhCDR3

<400> SEQUENCE: 59

Ser Tyr Tyr Thr Ser Asp Glu Asp Tyr
1               5

<210> SEQ ID NO 60
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 3H3[TIM-3]_H0L0 Variable Light

<400> SEQUENCE: 60

Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Leu Ala Glu Asp Leu Ala Val Tyr Tyr Cys Lys Gln
                85                  90                  95

Ser Tyr Ser Leu Arg Thr Phe Gly Gly Gly Thr Lys Leu Glu Ile Lys
            100                 105                 110

<210> SEQ ID NO 61
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 3H3[TIM-3]_H0L0 Variable Light vlCDR1

<400> SEQUENCE: 61

Lys Ser Ser Gln Ser Leu Leu Asn Ser Arg Thr Arg Lys Asn Tyr Leu
1               5                   10                  15

Ala

<210> SEQ ID NO 62
<211> LENGTH: 7
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<223> OTHER INFORMATION: 3H3[TIM-3]_H0L0 Variable Light vlCDR2

<400> SEQUENCE: 62

Trp Ala Ser Thr Arg Glu Ser
1               5

<210> SEQ ID NO 63
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 3H3[TIM-3]_H0L0 Variable Light vlCDR3

<400> SEQUENCE: 63

Lys Gln Ser Tyr Ser Leu Arg Thr
1               5

<210> SEQ ID NO 64
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 3H3[TIM-3]_H1L2 Variable Heavy

<400> SEQUENCE: 64

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Asn Gly Tyr
                20                  25                  30

Gly Val Asn Trp Val Arg Gln Pro Pro Gly Lys Gly Leu Glu Trp Leu
            35                  40                  45

Ala Met Ile Trp Gly Asp Gly Ser Thr Asp Tyr Asn Ser Ala Leu Lys
50                  55                  60

Ser Arg Leu Thr Ile Ser Lys Asp Asn Ser Lys Ser Gln Val Val Leu
65                  70                  75                  80

Thr Met Thr Asn Met Asp Pro Val Asp Thr Ala Thr Tyr Tyr Cys Ala
                85                  90                  95

Arg Ser Tyr Tyr Thr Ser Asp Glu Asp Tyr Trp Gly Gln Gly Thr Leu
            100                 105                 110

Val Thr Val Ser Ser
        115

<210> SEQ ID NO 65
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 3H3[TIM-3]_H1L2 Variable Heavy vhCDR1

<400> SEQUENCE: 65

Gly Tyr Gly Val Asn
1               5
```

<210> SEQ ID NO 66
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 3H3[TIM-3]_H1L2 Variable Heavy vhCDR2

<400> SEQUENCE: 66

Met Ile Trp Gly Asp Gly Ser Thr Asp Tyr Asn Ser Ala Leu Lys Ser
1               5                   10                  15

<210> SEQ ID NO 67
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 3H3[TIM-3]_H1L2 Variable Heavy vhCDR3

<400> SEQUENCE: 67

Ser Tyr Tyr Thr Ser Asp Glu Asp Tyr
1               5

<210> SEQ ID NO 68
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 3H3[TIM-3]_H1L2 Variable Light

<400> SEQUENCE: 68

Asp Ile Val Leu Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Ser Leu Arg Thr Phe Gly Gly Gly Thr Lys Val Glu Ile Lys
            100                 105                 110

<210> SEQ ID NO 69
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 3H3[TIM-3]_H1L2 Variable Light vlCDR1

<400> SEQUENCE: 69

```
Lys Ser Ser Gln Ser Leu Leu Asn Ser Arg Thr Arg Lys Asn Tyr Leu
1               5                   10                  15
Ala

<210> SEQ ID NO 70
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 3H3[TIM-3]_H1L2 Variable Light vlCDR2

<400> SEQUENCE: 70

Trp Ala Ser Thr Arg Glu Ser
1               5

<210> SEQ ID NO 71
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 3H3[TIM-3]_H1L2 Variable Light vlCDR3

<400> SEQUENCE: 71

Lys Gln Ser Tyr Ser Leu Arg Thr
1               5

<210> SEQ ID NO 72
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 3H3[TIM-3]_H1L2.1 Variable Heavy

<400> SEQUENCE: 72

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Asn Gly Tyr
            20                  25                  30

Gly Val Asn Trp Val Arg Gln Pro Pro Gly Lys Gly Leu Glu Trp Leu
        35                  40                  45

Ala Met Ile Trp Gly Asp Gly Ser Thr Asp Tyr Asn Ser Ala Leu Lys
    50                  55                  60

Ser Arg Leu Thr Ile Ser Lys Asp Asn Ser Lys Ser Gln Val Val Leu
65                  70                  75                  80

Thr Met Thr Asn Met Asp Pro Val Asp Thr Ala Thr Tyr Tyr Cys Ala
                85                  90                  95

Arg Ser Tyr Tyr Thr Ser Asp Glu Asp Tyr Trp Gly Gln Gly Thr Leu
            100                 105                 110

Val Thr Val Ser Ser
        115

<210> SEQ ID NO 73
<211> LENGTH: 5
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<223> OTHER INFORMATION: 3H3[TIM-3]_H1L2.1 Variable Heavy vhCDR1

<400> SEQUENCE: 73

Gly Tyr Gly Val Asn
1               5

<210> SEQ ID NO 74
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 3H3[TIM-3]_H1L2.1 Variable Heavy vhCDR2

<400> SEQUENCE: 74

Met Ile Trp Gly Asp Gly Ser Thr Asp Tyr Asn Ser Ala Leu Lys Ser
1               5                   10                  15

<210> SEQ ID NO 75
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 3H3[TIM-3]_H1L2.1 Variable Heavy vhCDR3

<400> SEQUENCE: 75

Ser Tyr Tyr Thr Ser Asp Glu Asp Tyr
1               5

<210> SEQ ID NO 76
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 3H3[TIM-3]_H1L2.1 Variable Light

<400> SEQUENCE: 76

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
                20                  25                  30

Arg Thr Arg Lys Asn Tyr Leu Ala Trp Tyr Gln Gln Lys Pro Gly Gln
            35                  40                  45

Ser Pro Lys Leu Leu Ile Tyr Trp Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Ser Leu Arg Thr Phe Gly Gly Gly Thr Lys Val Glu Ile Lys
            100                 105                 110

<210> SEQ ID NO 77
```

```
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 3H3[TIM-3]_H1L2.1 Variable Light vlCDR1

<400> SEQUENCE: 77

Lys Ser Ser Gln Ser Leu Leu Asn Ser Arg Thr Arg Lys Asn Tyr Leu
1               5                   10                  15

Ala

<210> SEQ ID NO 78
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 3H3[TIM-3]_H1L2.1 Variable Light vlCDR2

<400> SEQUENCE: 78

Trp Ala Ser Thr Arg Glu Ser
1               5

<210> SEQ ID NO 79
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 3H3[TIM-3]_H1L2.1 Variable Light vlCDR3

<400> SEQUENCE: 79

Lys Gln Ser Tyr Ser Leu Arg Thr
1               5

<210> SEQ ID NO 80
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: APE5137[TIM-3] Variable Heavy

<400> SEQUENCE: 80

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser
            20                  25                  30

Tyr Asp Met Ser Trp Val Arg Gln Ala Pro Gly Lys Gly Leu Asp Trp
            35                  40                  45

Val Ser Thr Ile Ser Gly Gly Gly Thr Tyr Thr Tyr Tyr Gln Asp Ser
50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95
```

```
Cys Ala Ser Met Asp Tyr Trp Gly Gln Gly Thr Thr Val Thr Val Ser
            100                 105                 110

Ser Ala

<210> SEQ ID NO 81
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: APE5137[TIM-3] Variable Heavy vhCDR1

<400> SEQUENCE: 81

Ser Ser Tyr Asp Met Ser
1               5

<210> SEQ ID NO 82
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: APE5137[TIM-3] Variable Heavy vhCDR2

<400> SEQUENCE: 82

Thr Ile Ser Gly Gly Gly Thr Tyr Thr Tyr Tyr Gln Asp Ser Val Lys
1               5                   10                  15

Gly

<210> SEQ ID NO 83
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: APE5137[TIM-3] Variable Heavy vhCDR3

<400> SEQUENCE: 83

Met Asp Tyr
1

<210> SEQ ID NO 84
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: APE5137[TIM-3] Variable Light

<400> SEQUENCE: 84

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Arg Arg Tyr
            20                  25                  30

Leu Asn Trp Tyr His Gln Lys Pro Gly Lys Ala Pro Lys Leu Leu Ile
        35                  40                  45

Tyr Gly Ala Ser Thr Leu Gln Ser Gly Val Pro Ser Arg Phe Ser Gly
    50                  55                  60
```

```
Ser Gly Ser Gly Thr Asp Phe Thr Leu Thr Ile Ser Ser Leu Gln Pro
 65                  70                  75                  80

Glu Asp Phe Ala Val Tyr Tyr Cys Gln Gln Ser His Ser Ala Pro Leu
                 85                  90                  95

Thr Phe Gly Gly Gly Thr Lys Val Glu Ile Lys Arg
            100                 105

<210> SEQ ID NO 85
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: APE5137[TIM-3] Variable Light vlCDR1

<400> SEQUENCE: 85

Arg Ala Ser Gln Ser Ile Arg Arg Tyr Leu Asn
1               5                   10

<210> SEQ ID NO 86
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: APE5137[TIM-3] Variable Light vlCDR2

<400> SEQUENCE: 86

Gly Ala Ser Thr Leu Gln Ser
1               5

<210> SEQ ID NO 87
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: APE5137[TIM-3] Variable Light vlCDR3

<400> SEQUENCE: 87

Gln Gln Ser His Ser Ala Pro Leu Thr
1               5

<210> SEQ ID NO 88
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: APE5121[TIM-3] Variable Heavy

<400> SEQUENCE: 88

Glu Val Gln Val Leu Glu Ser Gly Gly Gly Leu Val Gln Pro Gly Gly
1               5                   10                  15

Ser Leu Arg Leu Tyr Cys Val Ala Ser Gly Phe Thr Phe Ser Gly Ser
            20                  25                  30

Tyr Ala Met Ser Trp Val Arg Gln Ala Pro Gly Lys Gly Leu Glu Trp
        35                  40                  45
```

```
Val Ser Ala Ile Ser Gly Ser Gly Gly Ser Thr Tyr Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Lys Lys Tyr Tyr Val Gly Pro Ala Asp Tyr Trp Gly Gln Gly
            100                 105                 110

Thr Leu Val Thr Val Ser Ser Gly
        115                 120

<210> SEQ ID NO 89
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: APE5121[TIM-3] Variable Heavy vhCDR1

<400> SEQUENCE: 89

Gly Ser Tyr Ala Met Ser
1               5

<210> SEQ ID NO 90
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: APE5121[TIM-3] Variable Heavy vhCDR2

<400> SEQUENCE: 90

Ala Ile Ser Gly Ser Gly Gly Ser Thr Tyr Tyr Ala Asp Ser Val Lys
1               5                   10                  15

Gly

<210> SEQ ID NO 91
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: APE5121[TIM-3] Variable Heavy vhCDR3

<400> SEQUENCE: 91

Lys Tyr Tyr Val Gly Pro Ala Asp Tyr
1               5

<210> SEQ ID NO 92
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: APE5121[TIM-3] Variable Light

<400> SEQUENCE: 92
```

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln His Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Ser Pro Leu Thr Phe Gly Gly Gly Thr Lys Ile Glu Val
            100                 105                 110

Lys

<210> SEQ ID NO 93
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: APE5121[TIM-3] Variable Light vlCDR1

<400> SEQUENCE: 93

Lys Ser Ser Gln Ser Val Leu Tyr Ser Ser Asn Asn Lys Asn Tyr Leu
1               5                   10                  15

Ala

<210> SEQ ID NO 94
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: APE5121[TIM-3] Variable Light vlCDR2

<400> SEQUENCE: 94

Trp Ala Ser Thr Arg Glu Ser
1               5

<210> SEQ ID NO 95
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: APE5121[TIM-3] Variable Light vlCDR3

<400> SEQUENCE: 95

Gln Gln Tyr Tyr Ser Ser Pro Leu Thr
1               5

<210> SEQ ID NO 96
<211> LENGTH: 118
<212> TYPE: PRT
<213> ORGANISM: Artificial Sequence
<220> FEATURE:
```

<223> OTHER INFORMATION: Description of Artificial Sequence: Synthetic
    polypeptide
<220> FEATURE:
<223> OTHER INFORMATION: ABTIM3-hum03[TIM-3] Variable Heavy

<400> SEQUENCE: 96

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asn Met His Trp Val Arg Gln Ala Pro Gly Gln Gly Leu Glu Trp Ile
        35                  40                  45

Gly Asp Ile Tyr Pro Gly Gln Gly Asp Thr Ser Tyr Asn Gln Lys Phe
    50                  55                  60

Lys Gly Arg Ala Thr Met Thr Ala Asp Lys Ser Thr Ser Thr Val Tyr
65                  70                  75                  80

Met Glu Leu Ser Ser Leu Arg Ser Glu Asp Thr Ala Val Tyr Tyr Cys
            85                  90                  95

Ala Arg Val Gly Gly Ala Phe Pro Met Asp Tyr Trp Gly Gln Gly Thr
            100                 105                 110

Leu Val Thr Val Ser Ser
        115
```

<210> SEQ ID NO 97
<211> LENGTH: 5
<212> TYPE: PRT
<213> ORGANISM: Artificial Sequence
<220> FEATURE:
<223> OTHER INFORMATION: Description of Artificial Sequence: Synthetic
    peptide
<220> FEATURE:
<223> OTHER INFORMATION: ABTIM3-hum03[TIM-3] Variable Heavy vhCDR1

<400> SEQUENCE: 97

```
Ser Tyr Asn Met His
1               5
```

<210> SEQ ID NO 98
<211> LENGTH: 17
<212> TYPE: PRT
<213> ORGANISM: Artificial Sequence
<220> FEATURE:
<223> OTHER INFORMATION: Description of Artificial Sequence: Synthetic
    peptide
<220> FEATURE:
<223> OTHER INFORMATION: ABTIM3-hum03[TIM-3] Variable Heavy vhCDR2

<400> SEQUENCE: 98

```
Asp Ile Tyr Pro Gly Gln Gly Asp Thr Ser Tyr Asn Gln Lys Phe Lys
1               5                   10                  15

Gly
```

<210> SEQ ID NO 99
<211> LENGTH: 9
<212> TYPE: PRT
<213> ORGANISM: Artificial Sequence
<220> FEATURE:
<223> OTHER INFORMATION: Description of Artificial Sequence: Synthetic
    peptide
<220> FEATURE:
<223> OTHER INFORMATION: ABTIM3-hum03[TIM-3] Variable Heavy vhCDR3

<400> SEQUENCE: 99

Val Gly Gly Ala Phe Pro Met Asp Tyr

<210> SEQ ID NO 100
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: ABTIM3-hum03[TIM-3] Variable Light

<400> SEQUENCE: 100

Asp Ile Val Leu Thr Gln Ser Pro Asp Ser Leu Ala Val Ser Leu Gly
1               5                   10                  15

Glu Arg Ala Thr Ile Asn Cys Arg Ala Ser Glu Ser Val Glu Tyr Tyr
            20                  25                  30

Gly Thr Ser Leu Met Gln Trp Tyr Gln Gln Lys Pro Gly Gln Pro Pro
        35                  40                  45

Lys Leu Leu Ile Tyr Ala Ala Ser Asn Val Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Arg
                85                  90                  95

Lys Asp Pro Ser Thr Phe Gly Gly Gly Thr Lys Val Glu Ile Lys
            100                 105                 110

<210> SEQ ID NO 101
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: ABTIM3-hum03[TIM-3] Variable Light vlCDR1

<400> SEQUENCE: 101

Arg Ala Ser Glu Ser Val Glu Tyr Tyr Gly Thr Ser Leu Met Gln
1               5                   10                  15

<210> SEQ ID NO 102
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: ABTIM3-hum03[TIM-3] Variable Light vlCDR2

<400> SEQUENCE: 102

Ala Ala Ser Asn Val Glu Ser
1               5

<210> SEQ ID NO 103
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: ABTIM3-hum03[TIM-3] Variable Light vlCDR3

```
<400> SEQUENCE: 103

Gln Gln Ser Arg Lys Asp Pro Ser Thr
1               5

<210> SEQ ID NO 104
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: ABTIM3-hum11[TIM-3] Variable Heavy

<400> SEQUENCE: 104

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Asn Met His Trp Val Arg Gln Ala Pro Gly Gln Gly Leu Glu Trp Met
        35                  40                  45

Gly Asp Ile Tyr Pro Gly Asn Gly Asp Thr Ser Tyr Asn Gln Lys Phe
    50                  55                  60

Lys Gly Arg Val Thr Ile Thr Ala Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Val Gly Gly Ala Phe Pro Met Asp Tyr Trp Gly Gln Gly Thr
            100                 105                 110

Thr Val Thr Val Ser Ser
        115

<210> SEQ ID NO 105
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: ABTIM3-hum11[TIM-3] Variable Heavy vhCDR1

<400> SEQUENCE: 105

Ser Tyr Asn Met His
1               5

<210> SEQ ID NO 106
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: ABTIM3-hum11[TIM-3] Variable Heavy vhCDR2

<400> SEQUENCE: 106

Asp Ile Tyr Pro Gly Asn Gly Asp Thr Ser Tyr Asn Gln Lys Phe Lys
1               5                   10                  15

Gly

<210> SEQ ID NO 107
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: ABTIM3-hum11[TIM-3] Variable Heavy vhCDR3

<400> SEQUENCE: 107

Val Gly Gly Ala Phe Pro Met Asp Tyr
1               5

<210> SEQ ID NO 108
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: ABTIM3-hum11[TIM-3] Variable Light

<400> SEQUENCE: 108

Ala Ile Gln Leu Thr Gln Ser Pro Ser Ser Leu Ser Ala Ser Val Gly
1               5                   10                  15

Asp Arg Val Thr Ile Thr Cys Arg Ala Ser Glu Ser Val Glu Tyr Tyr
            20                  25                  30

Gly Thr Ser Leu Met Gln Trp Tyr Gln Gln Lys Pro Gly Lys Ala Pro
        35                  40                  45

Lys Leu Leu Ile Tyr Ala Ala Ser Asn Val Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Phe Cys Gln Gln Ser Arg
                85                  90                  95

Lys Asp Pro Ser Thr Phe Gly Gly Gly Thr Lys Val Glu Ile Lys
            100                 105                 110

<210> SEQ ID NO 109
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: ABTIM3-hum11[TIM-3] Variable Light vlCDR1

<400> SEQUENCE: 109

Arg Ala Ser Glu Ser Val Glu Tyr Tyr Gly Thr Ser Leu Met Gln
1               5                   10                  15

<210> SEQ ID NO 110
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: ABTIM3-hum11[TIM-3] Variable Light vlCDR2

<400> SEQUENCE: 110

Ala Ala Ser Asn Val Glu Ser
1               5
```

<210> SEQ ID NO 111
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: ABTIM3-hum11[TIM-3] Variable Light vlCDR3

<400> SEQUENCE: 111

Gln Gln Ser Arg Lys Asp Pro Ser Thr
1               5

<210> SEQ ID NO 112
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: ABTIM3-hum21[TIM-3] Variable Heavy

<400> SEQUENCE: 112

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Asn Met His Trp Val Arg Gln Ala Pro Gly Gln Gly Leu Glu Trp Ile
            35                  40                  45

Gly Asp Ile Tyr Pro Gly Gln Gly Asp Thr Ser Tyr Asn Gln Lys Phe
        50                  55                  60

Lys Gly Arg Ala Thr Met Thr Ala Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Val Gly Gly Ala Phe Pro Met Asp Tyr Trp Gly Gln Gly Thr
            100                 105                 110

Leu Val Thr Val Ser Ser
        115

<210> SEQ ID NO 113
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: ABTIM3-hum21[TIM-3] Variable Heavy vhCDR1

<400> SEQUENCE: 113

Ser Tyr Asn Met His
1               5

<210> SEQ ID NO 114
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: ABTIM3-hum21[TIM-3] Variable Heavy vhCDR2

<400> SEQUENCE: 114

Asp Ile Tyr Pro Gly Gln Gly Asp Thr Ser Tyr Asn Gln Lys Phe Lys
1               5                   10                  15

Gly

<210> SEQ ID NO 115
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: ABTIM3-hum21[TIM-3] Variable Heavy vhCDR3

<400> SEQUENCE: 115

Val Gly Gly Ala Phe Pro Met Asp Tyr
1               5

<210> SEQ ID NO 116
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: ABTIM3-hum21[TIM-3] Variable Light

<400> SEQUENCE: 116

Asp Ile Val Leu Thr Gln Ser Pro Asp Ser Leu Ala Val Ser Leu Gly
1               5                   10                  15

Glu Arg Ala Thr Ile Asn Cys Arg Ala Ser Glu Ser Val Glu Tyr Tyr
            20                  25                  30

Gly Thr Ser Leu Met Gln Trp Tyr Gln Gln Lys Pro Gly Gln Pro Pro
        35                  40                  45

Lys Leu Leu Ile Tyr Ala Ala Ser Asn Val Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Arg
                85                  90                  95

Lys Asp Pro Ser Thr Phe Gly Gly Gly Thr Lys Val Glu Ile Lys
            100                 105                 110

<210> SEQ ID NO 117
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: ABTIM3-hum21[TIM-3] Variable Light vlCDR1

<400> SEQUENCE: 117

Arg Ala Ser Glu Ser Val Glu Tyr Tyr Gly Thr Ser Leu Met Gln
1               5                   10                  15

<210> SEQ ID NO 118
<211> LENGTH: 7
<212> TYPE: PRT
<213> ORGANISM: Artificial Sequence

```
<220> FEATURE:
<223> OTHER INFORMATION: Description of Artificial Sequence: Synthetic
      peptide
<220> FEATURE:
<223> OTHER INFORMATION: ABTIM3-hum21[TIM-3] Variable Light vlCDR2

<400> SEQUENCE: 118

Ala Ala Ser Asn Val Glu Ser
1               5

<210> SEQ ID NO 119
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: ABTIM3-hum21[TIM-3] Variable Light vlCDR3

<400> SEQUENCE: 119

Gln Gln Ser Arg Lys Asp Pro Ser Thr
1               5

<210> SEQ ID NO 120
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4177[TIM-3] Variable Heavy

<400> SEQUENCE: 120

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Phe His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Gly Glu Tyr Phe Asp Met Leu Thr Gly Phe Asp Tyr Trp Gly
            100                 105                 110

Gln Gly Thr Leu Val Thr Val Ser Ser
        115                 120

<210> SEQ ID NO 121
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 4177[TIM-3] Variable Heavy vhCDR1

<400> SEQUENCE: 121

Ser Tyr Tyr Trp Ser
1               5
```

<210> SEQ ID NO 122
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 4177[TIM-3] Variable Heavy vhCDR2

<400> SEQUENCE: 122

Tyr Ile Phe His Ser Gly Ser Thr Asn Tyr Asn Pro Ser Leu Lys Ser
1               5                   10                  15

<210> SEQ ID NO 123
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 4177[TIM-3] Variable Heavy vhCDR3

<400> SEQUENCE: 123

Asp Gly Glu Tyr Phe Asp Met Leu Thr Gly Phe Asp Tyr
1               5                   10

<210> SEQ ID NO 124
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4177[TIM-3] Variable Light

<400> SEQUENCE: 124

Arg Cys Asp Ile Gln Met Thr Gln Ser Pro Ser Ser Leu Ser Ala Ser
1               5                   10                  15

Val Gly Asp Arg Val Thr Ile Thr Cys Arg Ala Ser Gln Gly Ile Ser
            20                  25                  30

Ser Trp Leu Ala Trp Tyr Gln Gln Lys Pro Glu Lys Ala Pro Lys Ser
        35                  40                  45

Leu Ile Tyr Ala Ala Ser Ser Leu Gln Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gln Tyr Asn Ser Tyr
                85                  90                  95

Pro Arg Thr Phe Gly Gln Gly Thr Lys Val Glu Ile Lys
            100                 105

<210> SEQ ID NO 125
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 4177[TIM-3] Variable Light vlCDR1

<400> SEQUENCE: 125

```
Arg Ala Ser Gln Gly Ile Ser Ser Trp Leu Ala
1               5                   10

<210> SEQ ID NO 126
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 4177[TIM-3] Variable Light vlCDR2

<400> SEQUENCE: 126

Ala Ala Ser Ser Leu Gln Ser
1               5

<210> SEQ ID NO 127
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 4177[TIM-3] Variable Light vlCDR3

<400> SEQUENCE: 127

Gln Gln Tyr Asn Ser Tyr Pro Arg Thr
1               5

<210> SEQ ID NO 128
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4545[TIM-3] Variable Heavy

<400> SEQUENCE: 128

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Phe Ser Arg Gly
            20                  25                  30

Gly Tyr Tyr Trp Asn Trp Ile Arg Gln Pro Pro Gly Lys Gly Leu Glu
        35                  40                  45

Trp Ile Gly Tyr Ile Tyr Tyr Ser Gly Ser Thr Asn Tyr Asn Pro Ser
    50                  55                  60

Leu Lys Ser Arg Val Thr Ile Ser Leu Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp His Tyr Ser Ser Ser Trp Thr Phe Asp Tyr Trp Gly
            100                 105                 110

Gln Gly Thr Leu Val Thr Val Ser Ser
        115                 120

<210> SEQ ID NO 129
<211> LENGTH: 7
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<223> OTHER INFORMATION: 4545[TIM-3] Variable Heavy vhCDR1

<400> SEQUENCE: 129

Arg Gly Gly Tyr Tyr Trp Asn
1               5

<210> SEQ ID NO 130
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 4545[TIM-3] Variable Heavy vhCDR2

<400> SEQUENCE: 130

Tyr Ile Tyr Tyr Ser Gly Ser Thr Asn Tyr Asn Pro Ser Leu Lys Ser
1               5                   10                  15

<210> SEQ ID NO 131
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 4545[TIM-3] Variable Heavy vhCDR3

<400> SEQUENCE: 131

Asp His Tyr Ser Ser Ser Trp Thr Phe Asp Tyr
1               5                   10

<210> SEQ ID NO 132
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4545[TIM-3] Variable Light

<400> SEQUENCE: 132

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Thr Phe Gly Gln Gly Thr Lys Leu Glu Ile Lys
            100                 105

<210> SEQ ID NO 133
<211> LENGTH: 11
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 4545[TIM-3] Variable Light vlCDR1

<400> SEQUENCE: 133

Arg Ala Ser Gln Ser Val Ser Ser Tyr Leu Ala
1               5                   10

<210> SEQ ID NO 134
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 4545[TIM-3] Variable Light vlCDR2

<400> SEQUENCE: 134

Asp Ala Ser Asn Arg Ala Thr
1               5

<210> SEQ ID NO 135
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 4545[TIM-3] Variable Light vlCDR3

<400> SEQUENCE: 135

Gln Gln Arg Ser Asn Trp Pro Pro Thr
1               5

<210> SEQ ID NO 136
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 8213[TIM-3] Variable Heavy

<400> SEQUENCE: 136

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Glu Ile Asn Pro Ser Asn Gly Arg Thr Asn Tyr Asn Glu Lys Phe
    50                  55                  60

Lys Thr Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Tyr Leu Tyr Phe Asp Tyr Trp Gly Gln Gly Thr Leu
            100                 105                 110
```

Val Thr Val Ser Ser
        115

<210> SEQ ID NO 137
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 8213[TIM-3] Variable Heavy vhCDR1

<400> SEQUENCE: 137

Ser Tyr Trp Met His
1               5

<210> SEQ ID NO 138
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 8213[TIM-3] Variable Heavy vhCDR2

<400> SEQUENCE: 138

Glu Ile Asn Pro Ser Asn Gly Arg Thr Asn Tyr Asn Glu Lys Phe Lys
1               5                   10                  15

Thr

<210> SEQ ID NO 139
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 8213[TIM-3] Variable Heavy vhCDR3

<400> SEQUENCE: 139

Gly Tyr Tyr Leu Tyr Phe Asp Tyr
1               5

<210> SEQ ID NO 140
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 8213[TIM-3] Variable Light

<400> SEQUENCE: 140

Asp Ile Gln Met Thr Gln Ser Pro Ser Ser Leu Ser Ala Ser Val Gly
1               5                   10                  15

Asp Arg Val Thr Ile Thr Cys His Ala Ser Gln Gly Ile Arg Ile Asn
            20                  25                  30

Ile Gly Trp Tyr Gln Gln Lys Pro Gly Lys Ala Pro Lys Leu Leu Ile
        35                  40                  45

Tyr His Gly Thr Asn Leu Glu Asp Gly Val Pro Ser Arg Phe Ser Gly
    50                  55                  60

Ser Gly Ser Gly Thr Asp Phe Thr Leu Thr Ile Ser Ser Leu Gln Pro

```
                65                  70                  75                  80
            Glu Asp Phe Ala Thr Tyr Tyr Cys Val Gln Tyr Gly Gln Phe Pro Trp
                            85                  90                  95
            Thr Phe Gly Gln Gly Thr Lys Leu Glu Ile Lys
                        100                 105

<210> SEQ ID NO 141
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 8213[TIM-3] Variable Light vlCDR1

<400> SEQUENCE: 141

His Ala Ser Gln Gly Ile Arg Ile Asn Ile Gly
1               5                   10

<210> SEQ ID NO 142
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 8213[TIM-3] Variable Light vlCDR2

<400> SEQUENCE: 142

His Gly Thr Asn Leu Glu Asp
1               5

<210> SEQ ID NO 143
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 8213[TIM-3] Variable Light vlCDR3

<400> SEQUENCE: 143

Val Gln Tyr Gly Gln Phe Pro Trp Thr
1               5

<210> SEQ ID NO 144
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: mAb15[TIM-3] Variable Heavy

<400> SEQUENCE: 144

Gln Val Gln Leu Lys Glu Ser Gly Pro Gly Leu Val Ala Pro Ser Gln
1               5                   10                  15
Ser Leu Ser Ile Thr Cys Thr Val Ser Gly Phe Ser Leu Thr Gly Tyr
                20                  25                  30
Gly Val Thr Trp Val Arg Gln Pro Pro Gly Lys Gly Leu Glu Trp Leu
            35                  40                  45
Gly Met Ile Trp Gly Asp Gly Asn Thr Asp Tyr Asn Ser Gly Leu Lys
```

```
                50                  55                  60
Ser Arg Leu Asn Ile Ser Lys Asp Asn Ser Lys Ser Gln Val Phe Leu
 65                  70                  75                  80

Lys Met Asn Ser Leu Gln Thr Asp Asp Thr Ala Arg Tyr Tyr Cys Ala
                 85                  90                  95

Arg Ser Tyr Tyr Tyr Gly Pro Pro Asp Tyr Trp Gly Gln Gly Thr Thr
            100                 105                 110

Leu Thr Val Ser Ser
        115
```

```
<210> SEQ ID NO 145
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: mAb15[TIM-3] Variable Heavy vhCDR1

<400> SEQUENCE: 145

Gly Tyr Gly Val Thr
 1               5
```

```
<210> SEQ ID NO 146
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: mAb15[TIM-3] Variable Heavy vhCDR2

<400> SEQUENCE: 146

Met Ile Trp Gly Asp Gly Asn Thr Asp Tyr Asn Ser Gly Leu Lys Ser
 1               5                  10                  15
```

```
<210> SEQ ID NO 147
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: mAb15[TIM-3] Variable Heavy vhCDR3

<400> SEQUENCE: 147

Ser Tyr Tyr Tyr Gly Pro Pro Asp Tyr
 1               5
```

```
<210> SEQ ID NO 148
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: mAb15[TIM-3] Variable Light

<400> SEQUENCE: 148

Asp Ile Val Met Thr Gln Ser Pro Ser Ser Leu Ala Met Ser Val Gly
 1               5                  10                  15

Gln Lys Val Thr Met Ser Cys Lys Ser Ser Gln Ser Leu Leu Asn Ser
```

```
                    20                  25                  30
Arg Ser Gln Lys Asn Tyr Leu Ala Trp Tyr Gln Arg Lys Pro Gly Gln
                35                  40                  45

Ser Pro Lys Leu Leu Leu Tyr Phe Ala Ser Thr Arg Glu Ser Gly Val
            50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Leu Ala Asp Tyr Phe Cys His Gln
                85                  90                  95

His Tyr Asn Thr Pro Tyr Thr Phe Gly Gly Gly Thr Lys Leu Glu Ile
            100                 105                 110

Lys

<210> SEQ ID NO 149
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: mAb15[TIM-3] Variable Light vlCDR1

<400> SEQUENCE: 149

Lys Ser Ser Gln Ser Leu Leu Asn Ser Arg Ser Gln Lys Asn Tyr Leu
1               5                   10                  15

Ala

<210> SEQ ID NO 150
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: mAb15[TIM-3] Variable Light vlCDR2

<400> SEQUENCE: 150

Phe Ala Ser Thr Arg Glu Ser
1               5

<210> SEQ ID NO 151
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: mAb15[TIM-3] Variable Light vlCDR3

<400> SEQUENCE: 151

His Gln His Tyr Asn Thr Pro Tyr Thr
1               5

<210> SEQ ID NO 152
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: mAb58[TIM-3] Variable Heavy
```

<400> SEQUENCE: 152

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Thr Tyr
            20                  25                  30

Gly Met Ser Trp Val Lys Gln Ala Pro Gly Lys Gly Leu Lys Leu Met
        35                  40                  45

Gly Trp Ile Asn Thr Tyr Ser Gly Ala Pro Thr Tyr Ala Asp Asp Phe
    50                  55                  60

Lys Gly Arg Phe Ala Phe Ser Leu Glu Thr Ser Ala Ser Ala Ala Tyr
65                  70                  75                  80

Leu Gln Ile Asn Asn Leu Lys Asn Glu Asp Thr Ala Thr Tyr Phe Cys
                85                  90                  95

Ala Arg Lys Pro Pro His Tyr Tyr Val Asn Ser Phe Asp Tyr Trp Gly
            100                 105                 110

Gln Gly Thr Thr Leu Thr Val Ser Ser
        115                 120

<210> SEQ ID NO 153
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: mAb58[TIM-3] Variable Heavy vhCDR1

<400> SEQUENCE: 153

Thr Tyr Gly Met Ser
1               5

<210> SEQ ID NO 154
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: mAb58[TIM-3] Variable Heavy vhCDR2

<400> SEQUENCE: 154

Trp Ile Asn Thr Tyr Ser Gly Ala Pro Thr Tyr Ala Asp Asp Phe Lys
1               5                   10                  15

Gly

<210> SEQ ID NO 155
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: mAb58[TIM-3] Variable Heavy vhCDR3

<400> SEQUENCE: 155

Lys Pro Pro His Tyr Tyr Val Asn Ser Phe Asp Tyr
1               5                   10

<210> SEQ ID NO 156

```
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: mAb58[TIM-3] Variable Light

<400> SEQUENCE: 156
```

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Pro Tyr
                85                  90                  95

Thr Phe Gly Gly Gly Thr Lys Leu Glu Ile Lys
            100                 105

```
<210> SEQ ID NO 157
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: mAb58[TIM-3] Variable Light vlCDR1

<400> SEQUENCE: 157
```

Arg Ala Ser Gln Ser Ile Ser Asp Tyr Leu His
1               5                   10

```
<210> SEQ ID NO 158
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: mAb58[TIM-3] Variable Light vlCDR2

<400> SEQUENCE: 158
```

Tyr Ala Ser Gln Ser Ile Ser
1               5

```
<210> SEQ ID NO 159
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: mAb58[TIM-3] Variable Light vlCDR3

<400> SEQUENCE: 159
```

Gln Asn Gly His Ser Phe Pro Tyr Thr
1               5

<210> SEQ ID NO 160
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: TIM3-0433[TIM-3] Variable Heavy

<400> SEQUENCE: 160

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Ser Val Gly Trp Ile Arg Gln Pro Pro Gly Lys Gly Leu Glu
        35                  40                  45

Trp Leu Ala His Ile Trp Leu Asn Asp Asp Val Phe Phe Asn Pro Ala
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Val Arg Ala Asn Gly Tyr Leu Tyr Ala Leu Asp Tyr Trp Gly Gln
            100                 105                 110

Gly Thr Leu Val Thr Val Ser Ser
        115                 120

<210> SEQ ID NO 161
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: TIM3-0433[TIM-3] Variable Heavy vhCDR1

<400> SEQUENCE: 161

Thr Ser Gly Met Ser Val Gly
1               5

<210> SEQ ID NO 162
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: TIM3-0433[TIM-3] Variable Heavy vhCDR2

<400> SEQUENCE: 162

His Ile Trp Leu Asn Asp Asp Val Phe Phe Asn Pro Ala Leu Lys Ser
1               5                   10                  15

<210> SEQ ID NO 163
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:

<223> OTHER INFORMATION: TIM3-0433[TIM-3] Variable Heavy vhCDR3

<400> SEQUENCE: 163

Ala Asn Gly Tyr Leu Tyr Ala Leu Asp Tyr
1               5                   10

<210> SEQ ID NO 164
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: TIM3-0433[TIM-3] Variable Light

<400> SEQUENCE: 164

Glu Thr Thr Leu Thr Gln Ser Pro Ala Phe Met Ser Ala Thr Pro Gly
1               5                   10                  15

Asp Lys Val Asn Ile Ala Cys Ser Ala Ser Ser Val Ser Tyr Thr
            20                  25                  30

Gln Trp Tyr Gln Gln Lys Pro Gly Glu Ala Pro Lys Leu Trp Ile Tyr
        35                  40                  45

Asp Ala Phe Lys Leu Ala Pro Gly Ile Pro Pro Arg Phe Ser Gly Ser
    50                  55                  60

Gly Tyr Gly Thr Asp Phe Thr Leu Thr Ile Asn Asn Ile Glu Ser Glu
65                  70                  75                  80

Asp Ala Ala Tyr Tyr Phe Cys His Gln Trp Ser Ser Tyr Pro Trp Thr
                85                  90                  95

Phe Gly Gln Gly Thr Lys Leu Glu Ile Lys
            100                 105

<210> SEQ ID NO 165
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: TIM3-0433[TIM-3] Variable Light vlCDR1

<400> SEQUENCE: 165

Ser Ala Ser Ser Ser Val Ser Tyr Thr Gln
1               5                   10

<210> SEQ ID NO 166
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: TIM3-0433[TIM-3] Variable Light vlCDR2

<400> SEQUENCE: 166

Asp Ala Phe Lys Leu Ala Pro
1               5

<210> SEQ ID NO 167
<211> LENGTH: 9
<212> TYPE: PRT
<213> ORGANISM: Artificial Sequence
<220> FEATURE:

<223> OTHER INFORMATION: Description of Artificial Sequence: Synthetic
      peptide
<220> FEATURE:
<223> OTHER INFORMATION: TIM3-0433[TIM-3] Variable Light vlCDR3

<400> SEQUENCE: 167

His Gln Trp Ser Ser Tyr Pro Trp Thr
1               5

<210> SEQ ID NO 168
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: TIM3-0434[TIM-3] Variable Heavy

<400> SEQUENCE: 168

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Ser Val Gly Trp Ile Arg Gln Pro Pro Gly Lys Gly Leu Glu
        35                  40                  45

Trp Leu Ala His Ile Trp Leu Asn Asp Asp Val Phe Phe Asn Pro Ala
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Val Arg Ala Asn Gly Tyr Leu Tyr Ala Leu Asp Tyr Trp Gly Gln
            100                 105                 110

Gly Thr Leu Val Thr Val Ser Ser
        115                 120

<210> SEQ ID NO 169
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: TIM3-0434[TIM-3] Variable Heavy vhCDR1

<400> SEQUENCE: 169

Thr Ser Gly Met Ser Val Gly
1               5

<210> SEQ ID NO 170
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: TIM3-0434[TIM-3] Variable Heavy vhCDR2

<400> SEQUENCE: 170

His Ile Trp Leu Asn Asp Asp Val Phe Phe Asn Pro Ala Leu Lys Ser
1               5                   10                  15

<210> SEQ ID NO 171
<211> LENGTH: 10
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: TIM3-0434[TIM-3] Variable Heavy vhCDR3

<400> SEQUENCE: 171

Ala Asn Gly Tyr Leu Tyr Ala Leu Asp Tyr
1               5                   10

<210> SEQ ID NO 172
<211> LENGTH: 106
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: TIM3-0434[TIM-3] Variable Light

<400> SEQUENCE: 172

Asp Ile Gln Leu Thr Gln Ser Pro Ser Phe Leu Ser Ala Ser Val Gly
1               5                   10                  15

Asp Arg Val Thr Ile Thr Cys Ser Ala Ser Ser Val Ser Tyr Thr
            20                  25                  30

Gln Trp Tyr Gln Gln Lys Pro Gly Lys Ala Pro Lys Leu Trp Ile Tyr
        35                  40                  45

Asp Ala Phe Lys Leu Ala Pro Gly Val Pro Ser Arg Phe Ser Gly Ser
    50                  55                  60

Gly Ser Gly Thr Glu Phe Thr Leu Thr Ile Ser Leu Gln Pro Glu
65                  70                  75                  80

Asp Phe Ala Thr Tyr Phe Cys His Gln Trp Ser Ser Tyr Pro Trp Thr
                85                  90                  95

Phe Gly Gln Gly Thr Lys Leu Glu Ile Lys
            100                 105

<210> SEQ ID NO 173
<211> LENGTH: 10
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: TIM3-0434[TIM-3] Variable Light vlCDR1

<400> SEQUENCE: 173

Ser Ala Ser Ser Ser Val Ser Tyr Thr Gln
1               5                   10

<210> SEQ ID NO 174
<211> LENGTH: 7
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: TIM3-0434[TIM-3] Variable Light vlCDR2

<400> SEQUENCE: 174

Asp Ala Phe Lys Leu Ala Pro
1               5

<210> SEQ ID NO 175
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: TIM3-0434[TIM-3] Variable Light vlCDR3

<400> SEQUENCE: 175

His Gln Trp Ser Ser Tyr Pro Trp Thr
1               5

<210> SEQ ID NO 176
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: TIM3-0438[TIM-3] Variable Heavy

<400> SEQUENCE: 176

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Thr Thr
            20                  25                  30

Tyr Met His Trp Val Arg Gln Ala Pro Gly Lys Gly Leu Glu Trp Val
        35                  40                  45

Gly Arg Ile Asp Pro Ala Asp Asp Asn Thr Lys Tyr Ala Pro Lys Phe
    50                  55                  60

Gln Gly Lys Ala Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Val Arg Asp Phe Gly Tyr Val Ala Trp Phe Ala Tyr Trp Gly Gln Gly
            100                 105                 110

Thr Leu Val Thr Val Ser Ser
        115

<210> SEQ ID NO 177
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: TIM3-0438[TIM-3] Variable Heavy vhCDR1

<400> SEQUENCE: 177

Thr Thr Tyr Met His
1               5

<210> SEQ ID NO 178
<211> LENGTH: 17
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: TIM3-0438[TIM-3] Variable Heavy vhCDR2

<400> SEQUENCE: 178

Arg Ile Asp Pro Ala Asp Asn Thr Lys Tyr Ala Pro Lys Phe Gln
1               5                   10                  15

Gly

<210> SEQ ID NO 179
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: TIM3-0438[TIM-3] Variable Heavy vhCDR3

<400> SEQUENCE: 179

Asp Phe Gly Tyr Val Ala Trp Phe Ala Tyr
1               5                   10

<210> SEQ ID NO 180
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: TIM3-0438[TIM-3] Variable Light

<400> SEQUENCE: 180

Asp Ile Val Met Thr Gln Ser Pro Leu Ser Leu Pro Val Thr Pro Gly
1               5                   10                  15

Glu Pro Ala Ser Ile Ser Cys Arg Ala Ser Gln Ser Val Asp Asn Tyr
            20                  25                  30

Val Ala Trp Tyr Leu Gln Lys Pro Gly Gln Ser Pro Gln Leu Leu Ile
        35                  40                  45

Tyr Tyr Ala Ser Asn Arg Tyr Ile Gly Val Pro Asp Arg Phe Ser Gly
    50                  55                  60

Ser Gly Ser Gly Thr Asp Phe Thr Leu Lys Ile Ser Arg Val Glu Ala
65                  70                  75                  80

Glu Asp Val Gly Val Tyr Tyr Cys Gln Gln His Tyr Ser Ser Pro Tyr
                85                  90                  95

Thr Phe Gly Gln Gly Thr Lys Val Glu Ile Lys
            100                 105

<210> SEQ ID NO 181
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: TIM3-0438[TIM-3] Variable Light vlCDR1

<400> SEQUENCE: 181

Arg Ala Ser Gln Ser Val Asp Asn Tyr Val Ala
1               5                   10

<210> SEQ ID NO 182

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: TIM3-0438[TIM-3] Variable Light vlCDR2

<400> SEQUENCE: 182

Tyr Ala Ser Asn Arg Tyr Ile
1               5

<210> SEQ ID NO 183
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: TIM3-0438[TIM-3] Variable Light vlCDR3

<400> SEQUENCE: 183

Gln Gln His Tyr Ser Ser Pro Tyr Thr
1               5

<210> SEQ ID NO 184
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: TIM3-0443[TIM-3] Variable Heavy

<400> SEQUENCE: 184

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Thr Thr
            20                  25                  30

Tyr Met His Trp Val Arg Gln Ala Pro Gly Lys Gly Leu Glu Trp Val
        35                  40                  45

Gly Arg Ile Asp Pro Ala Asp Asp Asn Thr Lys Tyr Ala Pro Lys Phe
    50                  55                  60

Gln Gly Lys Ala Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Val Arg Asp Phe Gly Tyr Val Ala Trp Phe Ala Tyr Trp Gly Gln Gly
            100                 105                 110

Thr Leu Val Thr Phe Ser Ser
        115

<210> SEQ ID NO 185
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: TIM3-0443[TIM-3] Variable Heavy vhCDR1

<400> SEQUENCE: 185
```

```
Thr Thr Tyr Met His
1               5

<210> SEQ ID NO 186
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: TIM3-0443[TIM-3] Variable Heavy vhCDR2

<400> SEQUENCE: 186

Arg Ile Asp Pro Ala Asp Asp Asn Thr Lys Tyr Ala Pro Lys Phe Gln
1               5                   10                  15

Gly

<210> SEQ ID NO 187
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: TIM3-0443[TIM-3] Variable Heavy vhCDR3

<400> SEQUENCE: 187

Asp Phe Gly Tyr Val Ala Trp Phe Ala Tyr
1               5                   10

<210> SEQ ID NO 188
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: TIM3-0443[TIM-3] Variable Light

<400> SEQUENCE: 188

Asp Ile Val Met Thr Gln Ser Pro Leu Ser Leu Pro Val Thr Pro Gly
1               5                   10                  15

Glu Pro Ala Ser Ile Ser Cys Arg Ala Ser Gln Ser Val Asp Asn Tyr
            20                  25                  30

Val Ala Trp Tyr Leu Gln Lys Pro Gly Gln Ser Pro Gln Leu Leu Ile
        35                  40                  45

Tyr Tyr Ala Ser Asn Arg Tyr Ile Gly Val Pro Asp Arg Phe Ser Gly
    50                  55                  60

Ser Gly Ser Gly Thr Asp Phe Thr Leu Lys Ile Ser Arg Val Glu Ala
65                  70                  75                  80

Glu Asp Val Gly Val Tyr Tyr Cys Gln Gln His Tyr Ser Ser Pro Tyr
                85                  90                  95

Thr Phe Gly Gln Gly Thr Lys Val Glu Ile Lys
            100                 105

<210> SEQ ID NO 189
<211> LENGTH: 11
<212> TYPE: PRT
<213> ORGANISM: Artificial Sequence
<220> FEATURE:
<223> OTHER INFORMATION: Description of Artificial Sequence: Synthetic
``` peptide
<220> FEATURE:
<223> OTHER INFORMATION: TIM3-0443[TIM-3] Variable Light vlCDR1

<400> SEQUENCE: 189

Arg Ala Ser Gln Ser Val Asp Asn Tyr Val Ala
1               5                   10

<210> SEQ ID NO 190
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: TIM3-0443[TIM-3] Variable Light vlCDR2

<400> SEQUENCE: 190

Tyr Ala Ser Asn Arg Tyr Ile
1               5

<210> SEQ ID NO 191
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: TIM3-0443[TIM-3] Variable Light vlCDR3

<400> SEQUENCE: 191

Gln Gln His Tyr Ser Ser Pro Tyr Thr
1               5

<210> SEQ ID NO 192
<211> LENGTH: 66
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 192

Ile Thr Cys Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Asp
65

<210> SEQ ID NO 193
<211> LENGTH: 67
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 193

Ile Thr Cys Pro Pro Met Ser Val Glu His Ala Asp Ile Trp Val

-continued

```
                1               5                  10                 15
Lys Ser Tyr Ser Leu Tyr Ser Arg Glu Arg Tyr Ile Cys Asn Ser Gly
                20                 25                 30
Phe Lys Arg Lys Ala Gly Thr Ser Ser Leu Thr Glu Cys Val Leu Asn
            35                 40                 45
Lys Ala Thr Asn Val Ala His Trp Thr Thr Pro Ser Leu Lys Cys Ile
        50                 55                 60
Arg Asp Pro
65

<210> SEQ ID NO 194
<211> LENGTH: 68
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 194

Ile Thr Cys Pro Pro Met Ser Val Glu His Ala Asp Ile Trp Val
1               5                  10                 15
Lys Ser Tyr Ser Leu Tyr Ser Arg Glu Arg Tyr Ile Cys Asn Ser Gly
                20                 25                 30
Phe Lys Arg Lys Ala Gly Thr Ser Ser Leu Thr Glu Cys Val Leu Asn
            35                 40                 45
Lys Ala Thr Asn Val Ala His Trp Thr Thr Pro Ser Leu Lys Cys Ile
        50                 55                 60
Arg Asp Pro Ala
65

<210> SEQ ID NO 195
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 195

Asn Trp Val Asn Val Ile Ser Asp Leu Lys Lys Ile Glu Asp Leu Ile
1               5                  10                 15
Gln Ser Met His Ile Asp Ala Thr Leu Tyr Thr Glu Ser Asp Val His
                20                 25                 30
Pro Ser Cys Lys Val Thr Ala Met Lys Cys Phe Leu Leu Glu Leu Gln
            35                 40                 45
Val Ile Ser Leu Glu Ser Gly Asp Ala Ser Ile His Asp Thr Val Glu
        50                 55                 60
Asn Leu Ile Ile Leu Ala Asn Asn Ser Leu Ser Ser Asn Gly Asn Val
65                 70                 75                 80
Thr Glu Ser Gly Cys Lys Cys Cys Glu Glu Leu Glu Glu Lys Asn Ile
                85                 90                 95
Lys Glu Phe Leu Gln Ser Phe Val His Ile Val Gln Met Phe Ile Asn
            100                105                110
Thr Ser

<210> SEQ ID NO 196
<211> LENGTH: 114
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 196

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
                20                  25                  30

Pro Ser Cys Lys Val Thr Ala Met Lys Cys Phe Leu Leu Glu Leu Gln
            35                  40                  45

Cys Ile Ser Leu Glu Ser Gly Asp Ala Ser Ile His Asp Thr Val Glu
50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 197
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 197

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
                20                  25                  30

Pro Ser Cys Lys Val Thr Ala Met Lys Cys Phe Leu Leu Glu Leu Gln
            35                  40                  45

Val Ile Ser Cys Glu Ser Gly Asp Ala Ser Ile His Asp Thr Val Glu
50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 198
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 198

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
                20                  25                  30
```

```
Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
 50                  55                  60

Asn Leu Ile Ile Leu Ala Asn Asn Ser Leu Ser Ser Asn Gly Asn Val
 65                  70                  75                  80

Thr Glu Ser Gly Cys Lys Glu Cys Cys Glu Leu Glu Glu Lys Asn Ile
                 85                  90                  95

Lys Glu Phe Leu Gln Ser Phe Val His Ile Val Gln Met Phe Ile Asn
            100                 105                 110

Thr Ser

<210> SEQ ID NO 199
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 199

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Cys
        35                  40                  45

Val Ile Ser Leu Glu Ser Gly Asp Ala Ser Ile His Asp Thr Val Glu
 50                  55                  60

Asn Leu Ile Ile Leu Ala Asn Asn Ser Leu Ser Ser Asn Gly Asn Val
 65                  70                  75                  80

Thr Glu Ser Gly Cys Lys Glu Cys Cys Glu Leu Glu Glu Lys Asn Ile
                 85                  90                  95

Lys Glu Phe Leu Gln Ser Phe Val His Ile Val Gln Met Phe Ile Asn
            100                 105                 110

Thr Ser

<210> SEQ ID NO 200
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 200

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Cys Ser Gly Asp Ala Ser Ile His Asp Thr Val Glu
 50                  55                  60

Asn Leu Ile Ile Leu Ala Asn Asn Ser Leu Ser Ser Asn Gly Asn Val
 65                  70                  75                  80

Thr Glu Ser Gly Cys Lys Glu Cys Cys Glu Leu Glu Glu Lys Asn Ile
```

85                  90                  95

Lys Glu Phe Leu Gln Ser Phe Val His Ile Val Gln Met Phe Ile Asn
                100                 105                 110

Thr Ser

<210> SEQ ID NO 201
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 201

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
                20                  25                  30

Pro Ser Cys Lys Val Thr Ala Met Lys Ser Phe Leu Leu Glu Leu Gln
                35                  40                  45

Val Ile Ser Leu Glu Ser Gly Asp Ala Ser Ile His Asp Thr Val Glu
        50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
                100                 105                 110

Thr Ser

<210> SEQ ID NO 202
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 202

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
                20                  25                  30

Pro Ser Cys Lys Val Thr Ala Met Lys Cys Phe Leu Cys Glu Leu Gln
                35                  40                  45

Val Ile Ser Leu Glu Ser Gly Asp Ala Ser Ile His Asp Thr Val Glu
        50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
                100                 105                 110

Thr Ser

<210> SEQ ID NO 203
<211> LENGTH: 67
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 203

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
                20                  25                  30

Phe Lys Arg Lys Ala Gly Thr Ser Ser Leu Thr Glu Cys Val Leu Asn
            35                  40                  45

Lys Ala Thr Asn Val Ala His Trp Thr Thr Pro Ser Leu Lys Cys Ile
        50                  55                  60

Arg Asp Cys
65

<210> SEQ ID NO 204
<211> LENGTH: 68
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 204

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
                20                  25                  30

Phe Lys Arg Lys Ala Gly Thr Ser Ser Leu Thr Glu Cys Val Leu Asn
            35                  40                  45

Lys Ala Thr Asn Val Ala His Trp Thr Thr Pro Ser Leu Lys Cys Ile
        50                  55                  60

Arg Asp Pro Cys
65

<210> SEQ ID NO 205
<211> LENGTH: 68
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 205

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
                20                  25                  30

Phe Lys Arg Lys Ala Gly Thr Ser Ser Leu Thr Glu Cys Val Leu Asn
            35                  40                  45

Lys Ala Thr Asn Val Ala His Trp Thr Thr Pro Ser Leu Lys Cys Ile
        50                  55                  60

Arg Asp Cys Ala
65

<210> SEQ ID NO 206
<211> LENGTH: 65
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 206

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Cys Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg
65

<210> SEQ ID NO 207
<211> LENGTH: 65
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 207

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Cys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg
65

<210> SEQ ID NO 208
<211> LENGTH: 65
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 208

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Cys Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg
65

<210> SEQ ID NO 209
<211> LENGTH: 65
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 209

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Cys Thr Glu Cys Val Leu Asn
        35                  40                  45

Lys Ala Thr Asn Val Ala His Trp Thr Thr Pro Ser Leu Lys Cys Ile
    50                  55                  60

Arg
65

<210> SEQ ID NO 210
<211> LENGTH: 65
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 210

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Cys Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg
65

<210> SEQ ID NO 211
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 211

Asp Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 212
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 212

Asn Trp Val Asp Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 213
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 213

Asn Trp Val Asn Val Ile Ser Asn Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 214
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 214

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asn Val His
                20                  25                  30

Pro Ser Cys Lys Val Thr Ala Met Lys Cys Phe Leu Leu Glu Leu Gln
            35                  40                  45

Val Ile Ser Leu Glu Ser Gly Asp Ala Ser Ile His Asp Thr Val Glu
        50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 215
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 215

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
                20                  25                  30

Pro Ser Cys Lys Val Thr Ala Met Lys Cys Phe Leu Leu Glu Leu Gln
            35                  40                  45

Val Ile Ser Leu Glu Ser Gly Asp Ala Ser Ile His Asn Thr Val Glu
        50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 216
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 216

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
                20                  25                  30

Pro Ser Cys Lys Val Thr Ala Met Lys Cys Phe Leu Leu Glu Leu Gln
            35                  40                  45

Val Ile Ser Leu Glu Ser Gly Asp Ala Ser Ile His Asp Thr Val Gln

-continued

```
                50                  55                  60
Asn Leu Ile Ile Leu Ala Asn Asn Ser Leu Ser Ser Asn Gly Asn Val
 65                  70                  75                  80

Thr Glu Ser Gly Cys Lys Glu Cys Glu Glu Leu Glu Glu Lys Asn Ile
                 85                  90                  95

Lys Glu Phe Leu Gln Ser Phe Val His Ile Val Gln Met Phe Ile Asn
                100                 105                 110

Thr Ser

<210> SEQ ID NO 217
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 217

Asn Trp Val Asn Val Ile Ser Asp Leu Lys Lys Ile Glu Asp Leu Ile
  1               5                  10                  15

Gln Ser Met His Ile Asp Ala Thr Leu Tyr Thr Glu Ser Asp Val His
                 20                  25                  30

Pro Ser Cys Lys Val Thr Ala Met Lys Cys Phe Leu Leu Glu Leu Gln
             35                  40                  45

Val Ile Ser Leu Glu Ser Gly Asp Ala Ser Ile His Asp Thr Val Glu
         50                  55                  60

Asp Leu Ile Ile Leu Ala Asn Asn Ser Leu Ser Ser Asn Gly Asn Val
 65                  70                  75                  80

Thr Glu Ser Gly Cys Lys Glu Cys Glu Glu Leu Glu Glu Lys Asn Ile
                 85                  90                  95

Lys Glu Phe Leu Gln Ser Phe Val His Ile Val Gln Met Phe Ile Asn
                100                 105                 110

Thr Ser

<210> SEQ ID NO 218
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 218

Asn Trp Val Asn Val Ile Ser Asp Leu Lys Lys Ile Glu Asp Leu Ile
  1               5                  10                  15

Gln Ser Met His Ile Asp Ala Thr Leu Tyr Thr Glu Ser Asp Val His
                 20                  25                  30

Pro Ser Cys Lys Val Thr Ala Met Lys Cys Phe Leu Leu Glu Leu Gln
             35                  40                  45

Val Ile Ser Leu Glu Ser Gly Asp Ala Ser Ile His Asp Thr Val Glu
         50                  55                  60

Asn Leu Ile Ile Leu Ala Asn Asn Ser Leu Ser Ser Asn Gly Asn Val
 65                  70                  75                  80

Thr Glu Ser Gly Cys Lys Glu Cys Glu Glu Leu Glu Glu Lys Asn Ile
                 85                  90                  95

Lys Glu Phe Leu Gln Ser Phe Val His Ile Val Glu Met Phe Ile Asn
                100                 105                 110
```

Thr Ser

<210> SEQ ID NO 219
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 219

Asp Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asn Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 220
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 220

Asp Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Gln
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 221
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 221

Asn Trp Val Asp Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
                20                  25                  30

Pro Ser Cys Lys Val Thr Ala Met Lys Cys Phe Leu Leu Glu Leu Gln
            35                  40                  45

Val Ile Ser Leu Glu Ser Gly Asp Ala Ser Ile His Asn Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 222
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 222

Asn Trp Val Asp Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
                20                  25                  30

Pro Ser Cys Lys Val Thr Ala Met Lys Cys Phe Leu Leu Glu Leu Gln
            35                  40                  45

Val Ile Ser Leu Glu Ser Gly Asp Ala Ser Ile His Asp Thr Val Gln
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 223
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 223

Asn Trp Val Asn Val Ile Ser Asn Leu Lys Lys Ile Glu Asp Leu Ile
1               5                   10                  15

Gln Ser Met His Ile Asp Ala Thr Leu Tyr Thr Glu Ser Asp Val His
                20                  25                  30

Pro Ser Cys Lys Val Thr Ala Met Lys Cys Phe Leu Leu Glu Leu Gln
            35                  40                  45

```
Val Ile Ser Leu Glu Ser Gly Asp Ala Ser Ile His Asn Thr Val Glu
 50                  55                  60

Asn Leu Ile Ile Leu Ala Asn Asn Ser Leu Ser Ser Asn Gly Asn Val
 65                  70                  75                  80

Thr Glu Ser Gly Cys Lys Glu Cys Glu Leu Glu Glu Lys Asn Ile
                 85                  90                  95

Lys Glu Phe Leu Gln Ser Phe Val His Ile Val Gln Met Phe Ile Asn
                100                 105                 110

Thr Ser

<210> SEQ ID NO 224
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 224

Asn Trp Val Asn Val Ile Ser Asn Leu Lys Lys Ile Glu Asp Leu Ile
 1               5                  10                  15

Gln Ser Met His Ile Asp Ala Thr Leu Tyr Thr Glu Ser Asp Val His
                 20                  25                  30

Pro Ser Cys Lys Val Thr Ala Met Lys Cys Phe Leu Leu Glu Leu Gln
             35                  40                  45

Val Ile Ser Leu Glu Ser Gly Asp Ala Ser Ile His Asp Thr Val Gln
 50                  55                  60

Asn Leu Ile Ile Leu Ala Asn Asn Ser Leu Ser Ser Asn Gly Asn Val
 65                  70                  75                  80

Thr Glu Ser Gly Cys Lys Glu Cys Glu Leu Glu Glu Lys Asn Ile
                 85                  90                  95

Lys Glu Phe Leu Gln Ser Phe Val His Ile Val Gln Met Phe Ile Asn
                100                 105                 110

Thr Ser

<210> SEQ ID NO 225
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 225

Asn Trp Val Asn Val Ile Ser Asp Leu Lys Lys Ile Glu Asp Leu Ile
 1               5                  10                  15

Gln Ser Met His Ile Asp Ala Thr Leu Tyr Thr Glu Ser Asp Val His
                 20                  25                  30

Pro Ser Cys Lys Val Thr Ala Met Lys Cys Phe Leu Leu Glu Leu Gln
             35                  40                  45

Val Ile Ser Leu Glu Ser Gly Asp Ala Ser Ile His Asn Thr Val Gln
 50                  55                  60

Asn Leu Ile Ile Leu Ala Asn Asn Ser Leu Ser Ser Asn Gly Asn Val
 65                  70                  75                  80

Thr Glu Ser Gly Cys Lys Glu Cys Glu Leu Glu Glu Lys Asn Ile
                 85                  90                  95

Lys Glu Phe Leu Gln Ser Phe Val His Ile Val Gln Met Phe Ile Asn
                100                 105                 110
```

Thr Ser

<210> SEQ ID NO 226
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 226

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Gln
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Glu Met Phe Ile Asn
            100                 105                 110

Thr Ser

<210> SEQ ID NO 227
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 227

Asp Trp Val Asp Val Ile Ser Asn Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 228
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 228

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asn Thr Val Gln
50                  55                  60

Asp Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 229
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 229

Asp Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asn Thr Val Gln
50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Glu Met Phe Ile Asn
            100                 105                 110

Thr Ser

<210> SEQ ID NO 230
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 230

Asn Trp Val Asp Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

```
Val Ile Ser Leu Glu Ser Gly Asp Ala Ser Ile His Asn Thr Val Gln
 50                  55                  60

Asn Leu Ile Ile Leu Ala Asn Asn Ser Leu Ser Ser Asn Gly Asn Val
 65                  70                  75                  80

Thr Glu Ser Gly Cys Lys Glu Cys Glu Leu Glu Glu Lys Asn Ile
                 85                  90                  95

Lys Glu Phe Leu Gln Ser Phe Val His Ile Val Glu Met Phe Ile Asn
                100                 105                 110

Thr Ser

<210> SEQ ID NO 231
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 231

Asp Trp Val Asn Val Ile Ser Asp Leu Lys Lys Ile Glu Asp Leu Ile
 1               5                  10                  15

Gln Ser Met His Ile Asp Ala Thr Leu Tyr Thr Glu Ser Asp Val His
                 20                  25                  30

Pro Ser Cys Lys Val Thr Ala Met Lys Cys Phe Leu Leu Glu Leu Gln
                 35                  40                  45

Val Ile Ser Leu Glu Ser Gly Asp Ala Ser Ile His Asp Thr Val Glu
 50                  55                  60

Asp Leu Ile Ile Leu Ala Asn Asn Ser Leu Ser Ser Asn Gly Asn Val
 65                  70                  75                  80

Thr Glu Ser Gly Cys Lys Glu Cys Glu Leu Glu Glu Lys Asn Ile
                 85                  90                  95

Lys Glu Phe Leu Gln Ser Phe Val His Ile Val Gln Met Phe Ile Asn
                100                 105                 110

Thr Ser

<210> SEQ ID NO 232
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 232

Asp Trp Val Asn Val Ile Ser Asp Leu Lys Lys Ile Glu Asp Leu Ile
 1               5                  10                  15

Gln Ser Met His Ile Asp Ala Thr Leu Tyr Thr Glu Ser Asp Val His
                 20                  25                  30

Pro Ser Cys Lys Val Thr Ala Met Lys Cys Phe Leu Leu Glu Leu Gln
                 35                  40                  45

Val Ile Ser Leu Glu Ser Gly Asp Ala Ser Ile His Asp Thr Val Glu
 50                  55                  60

Asn Leu Ile Ile Leu Ala Asn Asn Ser Leu Ser Ser Asn Gly Asn Val
 65                  70                  75                  80

Thr Glu Ser Gly Cys Lys Glu Cys Glu Leu Glu Glu Lys Asn Ile
                 85                  90                  95

Lys Glu Phe Leu Gln Ser Phe Val His Ile Val Glu Met Phe Ile Asn
                100                 105                 110
```

Thr Ser

<210> SEQ ID NO 233
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 233

Asn Trp Val Asp Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asp Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 234
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 234

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asn Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asp Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 235
<211> LENGTH: 114
<212> TYPE: PRT
<213> ORGANISM: Artificial Sequence
<220> FEATURE:
<223> OTHER INFORMATION: Description of Artificial Sequence: Synthetic -continued polypeptide

<400> SEQUENCE: 235

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asn Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Glu Met Phe Ile Asn
            100                 105                 110

Thr Ser

<210> SEQ ID NO 236
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 236

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
50                  55                  60

Asp Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Glu Met Phe Ile Asn
            100                 105                 110

Thr Ser

<210> SEQ ID NO 237
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 237

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln

```
                35                  40                  45

Val Ile Ser Leu Glu Ser Gly Asp Ala Ser Ile His Asp Thr Val Gln
 50                  55                  60

Asp Leu Ile Ile Leu Ala Asn Asn Ser Leu Ser Ser Asn Gly Asn Val
 65                  70                  75                  80

Thr Glu Ser Gly Cys Lys Glu Cys Glu Glu Leu Glu Glu Lys Asn Ile
                 85                  90                  95

Lys Glu Phe Leu Gln Ser Phe Val His Ile Val Gln Met Phe Ile Asn
                100                 105                 110

Thr Ser

<210> SEQ ID NO 238
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 238

Asp Trp Val Asp Val Ile Ser Asp Leu Lys Lys Ile Glu Asp Leu Ile
 1                5                  10                  15

Gln Ser Met His Ile Asp Ala Thr Leu Tyr Thr Glu Ser Asp Val His
                 20                  25                  30

Pro Ser Cys Lys Val Thr Ala Met Lys Cys Phe Leu Leu Glu Leu Gln
                 35                  40                  45

Val Ile Ser Leu Glu Ser Gly Asp Ala Ser Ile His Asp Thr Val Glu
 50                  55                  60

Asp Leu Ile Ile Leu Ala Asn Asn Ser Leu Ser Ser Asn Gly Asn Val
 65                  70                  75                  80

Thr Glu Ser Gly Cys Lys Glu Cys Glu Glu Leu Glu Glu Lys Asn Ile
                 85                  90                  95

Lys Glu Phe Leu Gln Ser Phe Val His Ile Val Gln Met Phe Ile Asn
                100                 105                 110

Thr Ser

<210> SEQ ID NO 239
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 239

Asn Trp Val Asn Val Ile Ser Asp Leu Lys Lys Ile Glu Asp Leu Ile
 1                5                  10                  15

Gln Ser Met His Ile Asp Ala Thr Leu Tyr Thr Glu Ser Asn Val His
                 20                  25                  30

Pro Ser Cys Lys Val Thr Ala Met Lys Cys Phe Leu Leu Glu Leu Gln
                 35                  40                  45

Val Ile Ser Leu Glu Ser Gly Asp Ala Ser Ile His Asp Thr Val Gln
 50                  55                  60

Asp Leu Ile Ile Leu Ala Asn Asn Ser Leu Ser Ser Asn Gly Asn Val
 65                  70                  75                  80

Thr Glu Ser Gly Cys Lys Glu Cys Glu Glu Leu Glu Glu Lys Asn Ile
                 85                  90                  95
```

```
Lys Glu Phe Leu Gln Ser Phe Val His Ile Val Gln Met Phe Ile Asn
                100                 105                 110
Thr Ser

<210> SEQ ID NO 240
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 240

Asn Trp Val Asp Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asn Thr Val Glu
    50                  55                  60

Asp Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
                100                 105                 110

Thr Ser

<210> SEQ ID NO 241
<211> LENGTH: 435
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 241

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Gly Gly Gly Gly Ser Gly Gly Gly Gly Ser Gly Gly Gly Gly Ser
65                  70                  75                  80

Gly Gly Gly Gly Ser Gly Gly Gly Gly Ser Asn Trp Val Asp Val Ile
                85                  90                  95

Ser Asp Leu Lys Lys Ile Glu Asp Leu Ile Gln Ser Met His Ile Asp
                100                 105                 110

Ala Thr Leu Tyr Thr Glu Ser Asp Val His Pro Ser Cys Lys Val Thr
            115                 120                 125

Ala Met Lys Cys Phe Leu Leu Glu Leu Gln Val Ile Ser Leu Glu Ser
        130                 135                 140

Gly Asp Ala Ser Ile His Asp Thr Val Glu Asp Leu Ile Ile Leu Ala
145                 150                 155                 160
```

Asn Asn Ser Leu Ser Ser Asn Gly Asn Val Thr Glu Ser Gly Cys Lys
            165                 170                 175

Glu Cys Glu Glu Leu Glu Glu Lys Asn Ile Lys Glu Phe Leu Gln Ser
            180                 185                 190

Phe Val His Ile Val Gln Met Phe Ile Asn Thr Ser Glu Pro Lys Ser
            195                 200                 205

Ser Asp Lys Thr His Thr Cys Pro Pro Cys Pro Ala Pro Pro Val Ala
        210                 215                 220

Gly Pro Ser Val Phe Leu Phe Pro Pro Lys Pro Lys Asp Thr Leu Met
225                 230                 235                 240

Ile Ser Arg Thr Pro Glu Val Thr Cys Val Val Val Asp Val Lys His
            245                 250                 255

Glu Asp Pro Glu Val Lys Phe Asn Trp Tyr Val Asp Gly Val Glu Val
            260                 265                 270

His Asn Ala Lys Thr Lys Pro Arg Glu Glu Glu Tyr Asn Ser Thr Tyr
            275                 280                 285

Arg Val Val Ser Val Leu Thr Val Leu His Gln Asp Trp Leu Asn Gly
            290                 295                 300

Lys Glu Tyr Lys Cys Lys Val Ser Asn Lys Ala Leu Pro Ala Pro Ile
305                 310                 315                 320

Glu Lys Thr Ile Ser Lys Ala Lys Gly Gln Pro Arg Glu Pro Gln Val
            325                 330                 335

Tyr Thr Leu Pro Pro Ser Arg Glu Glu Met Thr Lys Asn Gln Val Ser
            340                 345                 350

Leu Thr Cys Asp Val Ser Gly Phe Tyr Pro Ser Asp Ile Ala Val Glu
            355                 360                 365

Trp Glu Ser Asp Gly Gln Pro Glu Asn Asn Tyr Lys Thr Thr Pro Pro
            370                 375                 380

Val Leu Asp Ser Asp Gly Ser Phe Phe Leu Tyr Ser Lys Leu Thr Val
385                 390                 395                 400

Asp Lys Ser Arg Trp Glu Gln Gly Asp Val Phe Ser Cys Ser Val Met
            405                 410                 415

His Glu Ala Leu His Asn His Tyr Thr Gln Lys Ser Leu Ser Leu Ser
            420                 425                 430

Pro Gly Lys
        435

<210> SEQ ID NO 242
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 242

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Asn Gly Tyr
            20                  25                  30

Gly Val Asn Trp Val Arg Gln Pro Pro Gly Lys Gly Leu Glu Trp Leu
            35                  40                  45

Ala Met Ile Trp Gly Asp Gly Ser Thr Asp Tyr Asn Ser Ala Leu Lys
        50                  55                  60

Ser Arg Leu Thr Ile Ser Lys Asp Asn Ser Lys Ser Gln Val Val Leu

```
                65                  70                  75                  80
        Thr Met Thr Asn Met Asp Pro Val Asp Thr Ala Thr Tyr Tyr Cys Ala
                        85                  90                  95

Arg Ser Tyr Tyr Thr Ser Asp Glu Asp Tyr Trp Gly Gln Gly Thr Leu
                        100                 105                 110

Val Thr Val Ser Ser Ala Ser Thr Lys Gly Pro Ser Val Phe Pro Leu
                        115                 120                 125

Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
        145                 150                 155                 160

Gly Ala Leu Thr Ser Gly Val His Thr Phe Pro Ala Val Leu Gln Ser
                        165                 170                 175

Ser Gly Leu Tyr Ser Leu Ser Ser Val Val Thr Val Pro Ser Ser Ser
                        180                 185                 190

Leu Gly Thr Gln Thr Tyr Ile Cys Asn Val Asn His Lys Pro Ser Asn
                        195                 200                 205

Thr Lys Val Asp Lys Lys Val Glu Pro Lys Ser Cys Asp Lys Thr His
        210                 215                 220

Thr Cys Pro Pro Cys Pro Ala Pro Pro Val Ala Gly Pro Ser Val Phe
        225                 230                 235                 240

Leu Phe Pro Pro Lys Pro Lys Asp Thr Leu Met Ile Ser Arg Thr Pro
                        245                 250                 255

Glu Val Thr Cys Val Val Val Asp Val Lys His Glu Asp Pro Glu Val
                        260                 265                 270

Lys Phe Asn Trp Tyr Val Asp Gly Val Glu Val His Asn Ala Lys Thr
                        275                 280                 285

Lys Pro Arg Glu Glu Gln Tyr Asn Ser Thr Tyr Arg Val Val Ser Val
                        290                 295                 300

Leu Thr Val Leu His Gln Asp Trp Leu Asn Gly Lys Glu Tyr Lys Cys
        305                 310                 315                 320

Lys Val Ser Asn Lys Ala Leu Pro Ala Pro Ile Glu Lys Thr Ile Ser
                        325                 330                 335

Lys Ala Lys Gly Gln Pro Arg Glu Pro Gln Val Tyr Thr Leu Pro Pro
                        340                 345                 350

Ser Arg Glu Gln Met Thr Lys Asn Gln Val Lys Leu Thr Cys Leu Val
                        355                 360                 365

Lys Gly Phe Tyr Pro Ser Asp Ile Ala Val Glu Trp Glu Ser Asn Gly
                        370                 375                 380

Gln Pro Glu Asn Asn Tyr Lys Thr Thr Pro Pro Val Leu Asp Ser Asp
        385                 390                 395                 400

Gly Ser Phe Phe Leu Tyr Ser Lys Leu Thr Val Asp Lys Ser Arg Trp
                        405                 410                 415

Gln Gln Gly Asn Val Phe Ser Cys Ser Val Met His Glu Ala Leu His
                        420                 425                 430

Asn His Tyr Thr Gln Lys Ser Leu Ser Leu Ser Pro Gly Lys
                        435                 440                 445

<210> SEQ ID NO 243
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 243

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Ser Leu Arg Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 244
<211> LENGTH: 442
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 244

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
            130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Lys Val Glu Pro Lys Ser Cys Asp Lys Thr His Thr Cys Pro Pro
    210                 215                 220

Cys Pro Ala Pro Pro Val Ala Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Lys His Glu Asp Pro Glu Val Lys Phe Asn Trp
            260                 265                 270

Tyr Val Asp Gly Val Glu Val His Asn Ala Lys Thr Lys Pro Arg Glu
        275                 280                 285

Glu Gln Tyr Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Ala Leu Pro Ala Pro Ile Glu Lys Thr Ile Ser Lys Ala Lys Gly
                325                 330                 335

Gln Pro Arg Glu Pro Gln Val Tyr Thr Leu Pro Pro Ser Arg Glu Glu
            340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
            420                 425                 430

Gln Lys Ser Leu Ser Leu Ser Pro Gly Lys
        435                 440

<210> SEQ ID NO 245
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 245

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile

```
            35                  40                  45
Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Ser Ser Asn Trp Pro Arg
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 246
<211> LENGTH: 435
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 246

Ile Thr Cys Pro Pro Met Ser Val Glu His Ala Asp Ile Trp Val
 1               5                  10                  15

Lys Ser Tyr Ser Leu Tyr Ser Arg Glu Arg Tyr Ile Cys Asn Ser Gly
                 20                  25                  30

Phe Lys Arg Lys Ala Gly Thr Ser Ser Leu Thr Glu Cys Val Leu Asn
             35                  40                  45

Lys Ala Thr Asn Val Ala His Trp Thr Thr Pro Ser Leu Lys Cys Ile
 50                  55                  60

Arg Gly Gly Gly Gly Ser Gly Gly Gly Gly Ser Gly Gly Gly Gly Ser
 65                  70                  75                  80

Gly Gly Gly Gly Ser Gly Gly Gly Ser Asn Trp Val Asp Val Ile
                 85                  90                  95

Ser Asp Leu Lys Lys Ile Glu Asp Leu Ile Gln Ser Met His Ile Asp
            100                 105                 110

Ala Thr Leu Tyr Thr Glu Ser Asp Val His Pro Ser Cys Lys Val Thr
            115                 120                 125

Ala Met Lys Cys Phe Leu Leu Glu Leu Gln Val Ile Ser Leu Glu Ser
130                 135                 140

Gly Asp Ala Ser Ile His Asp Thr Val Glu Asp Leu Ile Ile Leu Ala
145                 150                 155                 160

Asn Asn Ser Leu Ser Ser Asn Gly Asn Val Thr Glu Ser Gly Cys Lys
                165                 170                 175
```

-continued

```
Glu Cys Glu Glu Leu Glu Lys Asn Ile Lys Glu Phe Leu Gln Ser
            180                 185                 190

Phe Val His Ile Val Gln Met Phe Ile Asn Thr Ser Glu Pro Lys Ser
        195                 200                 205

Ser Asp Lys Thr His Thr Cys Pro Pro Cys Pro Ala Pro Pro Val Ala
    210                 215                 220

Gly Pro Ser Val Phe Leu Phe Pro Pro Lys Pro Lys Asp Thr Leu Met
225                 230                 235                 240

Ile Ser Arg Thr Pro Glu Val Thr Cys Val Val Val Asp Val Lys His
                245                 250                 255

Glu Asp Pro Glu Val Lys Phe Asn Trp Tyr Val Asp Gly Val Glu Val
            260                 265                 270

His Asn Ala Lys Thr Lys Pro Arg Glu Glu Glu Tyr Asn Ser Thr Tyr
        275                 280                 285

Arg Val Val Ser Val Leu Thr Val Leu His Gln Asp Trp Leu Asn Gly
    290                 295                 300

Lys Glu Tyr Lys Cys Lys Val Ser Asn Lys Ala Leu Pro Ala Pro Ile
305                 310                 315                 320

Glu Lys Thr Ile Ser Lys Ala Lys Gly Gln Pro Arg Glu Pro Gln Val
                325                 330                 335

Tyr Thr Leu Pro Pro Ser Arg Glu Glu Met Thr Lys Asn Gln Val Ser
            340                 345                 350

Leu Thr Cys Asp Val Ser Gly Phe Tyr Pro Ser Asp Ile Ala Val Glu
        355                 360                 365

Trp Glu Ser Asp Gly Gln Pro Glu Asn Asn Tyr Lys Thr Thr Pro Pro
    370                 375                 380

Val Leu Asp Ser Asp Gly Ser Phe Phe Leu Tyr Ser Lys Leu Thr Val
385                 390                 395                 400

Asp Lys Ser Arg Trp Glu Gln Gly Asp Val Phe Ser Cys Ser Val Leu
                405                 410                 415

His Glu Ala Leu His Ser His Tyr Thr Gln Lys Ser Leu Ser Leu Ser
            420                 425                 430

Pro Gly Lys
        435

<210> SEQ ID NO 247
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 247

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Asn Gly Tyr
            20                  25                  30

Gly Val Asn Trp Val Arg Gln Pro Pro Gly Lys Gly Leu Glu Trp Leu
        35                  40                  45

Ala Met Ile Trp Gly Asp Gly Ser Thr Asp Tyr Asn Ser Ala Leu Lys
    50                  55                  60

Ser Arg Leu Thr Ile Ser Lys Asp Asn Ser Lys Ser Gln Val Val Leu
65                  70                  75                  80

Thr Met Thr Asn Met Asp Pro Val Asp Thr Ala Thr Tyr Tyr Cys Ala
                85                  90                  95
```

```
Arg Ser Tyr Tyr Thr Ser Asp Glu Asp Tyr Trp Gly Gln Gly Thr Leu
                100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
210                 215                 220

Thr Cys Pro Pro Cys Pro Ala Pro Pro Val Ala Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Lys His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Gln Met Thr Lys Asn Gln Val Lys Leu Thr Cys Leu Val
        355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Leu His Glu Ala Leu His
            420                 425                 430

Ser His Tyr Thr Gln Lys Ser Leu Ser Leu Ser Pro Gly Lys
        435                 440                 445

<210> SEQ ID NO 248
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 248

Asp Ile Val Met Thr Gln Ser Pro Asp Ser Leu Ala Val Ser Leu Gly
```

-continued

```
 1               5                  10                  15
Glu Arg Ala Thr Ile Asn Cys Lys Ser Ser Gln Ser Leu Leu Asn Ser
            20                  25                  30
Arg Thr Arg Lys Asn Tyr Leu Ala Trp Tyr Gln Gln Lys Pro Gly Gln
            35                  40                  45
Ser Pro Lys Leu Leu Ile Tyr Trp Ala Ser Thr Arg Glu Ser Gly Val
        50                  55                  60
Pro Asp Arg Phe Thr Gly Ser Gly Ser Gly Thr Asp Phe Thr Leu Thr
 65                  70                  75                  80
Ile Ser Ser Leu Gln Ala Glu Asp Val Ala Val Tyr Tyr Cys Lys Gln
                85                  90                  95
Ser Tyr Ser Leu Arg Thr Phe Gly Gly Gly Thr Lys Val Glu Ile Lys
            100                 105                 110
Arg Thr Val Ala Ala Pro Ser Val Phe Ile Phe Pro Pro Ser Asp Glu
            115                 120                 125
Gln Leu Lys Ser Gly Thr Ala Ser Val Val Cys Leu Leu Asn Asn Phe
        130                 135                 140
Tyr Pro Arg Glu Ala Lys Val Gln Trp Lys Val Asp Asn Ala Leu Gln
145                 150                 155                 160
Ser Gly Asn Ser Gln Glu Ser Val Thr Glu Gln Asp Ser Lys Asp Ser
                165                 170                 175
Thr Tyr Ser Leu Ser Ser Thr Leu Thr Leu Ser Lys Ala Asp Tyr Glu
            180                 185                 190
Lys His Lys Val Tyr Ala Cys Glu Val Thr His Gln Gly Leu Ser Ser
            195                 200                 205
Pro Val Thr Lys Ser Phe Asn Arg Gly Glu Cys
        210                 215

<210> SEQ ID NO 249
<211> LENGTH: 350
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 249

Asn Trp Val Asn Val Ile Ser Asp Leu Lys Lys Ile Glu Asp Leu Ile
 1               5                  10                  15
Gln Ser Met His Ile Asp Ala Thr Leu Tyr Thr Glu Ser Asp Val His
            20                  25                  30
Pro Ser Cys Lys Val Thr Ala Met Lys Cys Phe Leu Leu Glu Leu Gln
            35                  40                  45
Val Ile Ser Leu Glu Ser Gly Asp Ala Ser Ile His Asp Thr Val Glu
        50                  55                  60
Asn Leu Ile Ile Leu Ala Asn Asn Ser Leu Ser Ser Asn Gly Asn Val
 65                  70                  75                  80
Thr Glu Ser Gly Cys Lys Glu Cys Glu Glu Leu Glu Glu Lys Asn Ile
                85                  90                  95
Lys Glu Phe Leu Gln Ser Phe Val His Ile Val Gln Met Phe Ile Asn
            100                 105                 110
Thr Ser Gly Gly Gly Ser Glu Pro Lys Ser Ser Asp Lys Thr His
            115                 120                 125
Thr Cys Pro Pro Cys Pro Ala Pro Pro Val Ala Gly Pro Ser Val Phe
        130                 135                 140
```

Leu Phe Pro Pro Lys Pro Lys Asp Thr Leu Met Ile Ser Arg Thr Pro
145                 150                 155                 160

Glu Val Thr Cys Val Val Val Asp Val Lys His Glu Asp Pro Glu Val
                165                 170                 175

Lys Phe Asn Trp Tyr Val Asp Gly Val Glu Val His Asn Ala Lys Thr
            180                 185                 190

Lys Pro Arg Glu Glu Gln Tyr Asn Ser Thr Tyr Arg Val Val Ser Val
        195                 200                 205

Leu Thr Val Leu His Gln Asp Trp Leu Asn Gly Lys Glu Tyr Lys Cys
210                 215                 220

Lys Val Ser Asn Lys Ala Leu Pro Ala Pro Ile Glu Lys Thr Ile Ser
225                 230                 235                 240

Lys Ala Lys Gly Gln Pro Arg Glu Pro Gln Val Tyr Thr Leu Pro Pro
                245                 250                 255

Ser Arg Glu Glu Met Thr Lys Asn Gln Val Ser Leu Thr Cys Asp Val
            260                 265                 270

Ser Gly Phe Tyr Pro Ser Asp Ile Ala Val Glu Trp Glu Ser Asp Gly
        275                 280                 285

Gln Pro Glu Asn Asn Tyr Lys Thr Thr Pro Pro Val Leu Asp Ser Asp
290                 295                 300

Gly Ser Phe Phe Leu Tyr Ser Lys Leu Thr Val Asp Lys Ser Arg Trp
305                 310                 315                 320

Glu Gln Gly Asp Val Phe Ser Cys Ser Val Leu His Glu Ala Leu His
                325                 330                 335

Ser His Tyr Thr Gln Lys Ser Leu Ser Leu Ser Pro Gly Lys
            340                 345                 350

<210> SEQ ID NO 250
<211> LENGTH: 301
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 250

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
50                  55                  60

Arg Gly Gly Gly Gly Ser Glu Pro Lys Ser Ser Asp Lys Thr His Thr
65                  70                  75                  80

Cys Pro Pro Cys Pro Ala Pro Pro Val Ala Gly Pro Ser Val Phe Leu
                85                  90                  95

Phe Pro Pro Lys Pro Lys Asp Thr Leu Met Ile Ser Arg Thr Pro Glu
            100                 105                 110

Val Thr Cys Val Val Val Asp Val Lys His Glu Asp Pro Glu Val Lys
        115                 120                 125

Phe Asn Trp Tyr Val Asp Gly Val Glu Val His Asn Ala Lys Thr Lys
    130                 135                 140

Pro Arg Glu Glu Gln Tyr Asn Ser Thr Tyr Arg Val Val Ser Val Leu
145                 150                 155                 160

```
Thr Val Leu His Gln Asp Trp Leu Asn Gly Lys Glu Tyr Lys Cys Lys
            165                 170                 175

Val Ser Asn Lys Ala Leu Pro Ala Pro Ile Glu Lys Thr Ile Ser Lys
        180                 185                 190

Ala Lys Gly Gln Pro Arg Glu Pro Gln Val Tyr Thr Leu Pro Pro Ser
    195                 200                 205

Arg Glu Gln Met Thr Lys Asn Gln Val Lys Leu Thr Cys Leu Val Lys
210                 215                 220

Gly Phe Tyr Pro Ser Asp Ile Ala Val Glu Trp Glu Ser Asn Gly Gln
225                 230                 235                 240

Pro Glu Asn Asn Tyr Lys Thr Thr Pro Pro Val Leu Asp Ser Asp Gly
                245                 250                 255

Ser Phe Phe Leu Tyr Ser Lys Leu Thr Val Asp Lys Ser Arg Trp Gln
            260                 265                 270

Gln Gly Asn Val Phe Ser Cys Ser Val Leu His Glu Ala Leu His Ser
        275                 280                 285

His Tyr Thr Gln Lys Ser Leu Ser Leu Ser Pro Gly Lys
    290                 295                 300

<210> SEQ ID NO 251
<211> LENGTH: 350
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 251

Asn Trp Val Asp Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asp Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser Gly Gly Gly Ser Glu Pro Lys Ser Ser Asp Lys Thr His
        115                 120                 125

Thr Cys Pro Pro Cys Pro Ala Pro Pro Val Ala Gly Pro Ser Val Phe
130                 135                 140

Leu Phe Pro Pro Lys Pro Lys Asp Thr Leu Met Ile Ser Arg Thr Pro
145                 150                 155                 160

Glu Val Thr Cys Val Val Val Asp Val Lys His Glu Asp Pro Glu Val
                165                 170                 175

Lys Phe Asn Trp Tyr Val Asp Gly Glu Val His Asn Ala Lys Thr
            180                 185                 190

Lys Pro Arg Glu Glu Glu Tyr Asn Ser Thr Tyr Arg Val Val Ser Val
        195                 200                 205

Leu Thr Val Leu His Gln Asp Trp Leu Asn Gly Lys Glu Tyr Lys Cys
```

```
                 210                 215                 220

Lys Val Ser Asn Lys Ala Leu Pro Ala Pro Ile Glu Lys Thr Ile Ser
225                 230                 235                 240

Lys Ala Lys Gly Gln Pro Arg Glu Pro Gln Val Tyr Thr Leu Pro Pro
                245                 250                 255

Ser Arg Glu Glu Met Thr Lys Asn Gln Val Ser Leu Thr Cys Asp Val
                260                 265                 270

Ser Gly Phe Tyr Pro Ser Asp Ile Ala Val Glu Trp Glu Ser Asp Gly
            275                 280                 285

Gln Pro Glu Asn Asn Tyr Lys Thr Thr Pro Pro Val Leu Asp Ser Asp
        290                 295                 300

Gly Ser Phe Phe Leu Tyr Ser Lys Leu Thr Val Asp Lys Ser Arg Trp
305                 310                 315                 320

Glu Gln Gly Asp Val Phe Ser Cys Ser Val Leu His Glu Ala Leu His
                325                 330                 335

Ser His Tyr Thr Gln Lys Ser Leu Ser Leu Ser Pro Gly Lys
            340                 345                 350

<210> SEQ ID NO 252
<211> LENGTH: 301
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 252

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
                20                  25                  30

Phe Lys Arg Lys Ala Gly Thr Ser Ser Leu Thr Glu Cys Val Leu Asn
            35                  40                  45

Lys Ala Thr Asn Val Ala His Trp Thr Thr Pro Ser Leu Lys Cys Ile
        50                  55                  60

Arg Gly Gly Gly Ser Glu Pro Lys Ser Ser Asp Lys Thr His Thr
65                  70                  75                  80

Cys Pro Pro Cys Pro Ala Pro Pro Val Ala Gly Pro Ser Val Phe Leu
                85                  90                  95

Phe Pro Pro Lys Pro Lys Asp Thr Leu Met Ile Ser Arg Thr Pro Glu
            100                 105                 110

Val Thr Cys Val Val Val Asp Val Lys His Glu Asp Pro Glu Val Lys
        115                 120                 125

Phe Asn Trp Tyr Val Asp Gly Val Glu Val His Asn Ala Lys Thr Lys
130                 135                 140

Pro Arg Glu Glu Gln Tyr Asn Ser Thr Tyr Arg Val Val Ser Val Leu
145                 150                 155                 160

Thr Val Leu His Gln Asp Trp Leu Asn Gly Lys Glu Tyr Lys Cys Lys
                165                 170                 175

Val Ser Asn Lys Ala Leu Pro Ala Pro Ile Glu Lys Thr Ile Ser Lys
            180                 185                 190

Ala Lys Gly Gln Pro Arg Glu Pro Gln Val Tyr Thr Leu Pro Pro Ser
        195                 200                 205

Arg Glu Gln Met Thr Lys Asn Gln Val Lys Leu Thr Cys Leu Val Lys
    210                 215                 220
```

```
Gly Phe Tyr Pro Ser Asp Ile Ala Val Glu Trp Glu Ser Asn Gly Gln
225                 230                 235                 240

Pro Glu Asn Asn Tyr Lys Thr Thr Pro Pro Val Leu Asp Ser Asp Gly
                245                 250                 255

Ser Phe Phe Leu Tyr Ser Lys Leu Thr Val Asp Lys Ser Arg Trp Gln
            260                 265                 270

Gln Gly Asn Val Phe Ser Cys Ser Val Leu His Glu Ala Leu His Ser
            275                 280                 285

His Tyr Thr Gln Lys Ser Leu Ser Leu Ser Pro Gly Lys
        290                 295                 300

<210> SEQ ID NO 253
<211> LENGTH: 435
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 253

Ile Thr Cys Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
                20                  25                  30

Phe Lys Arg Lys Ala Gly Thr Ser Ser Leu Thr Glu Cys Val Leu Asn
            35                  40                  45

Lys Ala Thr Asn Val Ala His Trp Thr Thr Pro Ser Leu Lys Cys Ile
        50                  55                  60

Arg Gly Gly Gly Gly Ser Gly Gly Gly Gly Ser Gly Gly Gly Gly Ser
65                  70                  75                  80

Gly Gly Gly Gly Ser Gly Gly Gly Ser Asn Trp Val Asp Val Ile
                85                  90                  95

Ser Asp Leu Lys Lys Ile Glu Asp Leu Ile Gln Ser Met His Ile Asp
                100                 105                 110

Ala Thr Leu Tyr Thr Glu Ser Asp Val His Pro Ser Cys Lys Val Thr
            115                 120                 125

Ala Met Lys Cys Phe Leu Leu Glu Leu Gln Val Ile Ser Leu Glu Ser
130                 135                 140

Gly Asp Ala Ser Ile His Asp Thr Val Glu Asp Leu Ile Ile Leu Ala
145                 150                 155                 160

Asn Asn Ser Leu Ser Ser Asn Gly Asn Val Thr Glu Ser Gly Cys Lys
                165                 170                 175

Glu Cys Glu Glu Leu Glu Glu Lys Asn Ile Lys Glu Phe Leu Gln Ser
            180                 185                 190

Phe Val His Ile Val Gln Met Phe Ile Asn Thr Ser Glu Pro Lys Ser
        195                 200                 205

Ser Asp Lys Thr His Thr Cys Pro Pro Cys Pro Ala Pro Pro Val Ala
    210                 215                 220

Gly Pro Ser Val Phe Leu Phe Pro Pro Lys Pro Lys Asp Thr Leu Met
225                 230                 235                 240

Ile Ser Arg Thr Pro Glu Val Thr Cys Val Val Val Asp Val Lys His
                245                 250                 255

Glu Asp Pro Glu Val Lys Phe Asn Trp Tyr Val Asp Gly Val Glu Val
            260                 265                 270

His Asn Ala Lys Thr Lys Pro Arg Glu Glu Glu Tyr Asn Ser Thr Tyr
        275                 280                 285
```

```
Arg Val Val Ser Val Leu Thr Val Leu His Gln Asp Trp Leu Asn Gly
    290                 295                 300

Lys Glu Tyr Lys Cys Lys Val Ser Asn Lys Ala Leu Pro Ala Pro Ile
305                 310                 315                 320

Glu Lys Thr Ile Ser Lys Ala Lys Gly Gln Pro Arg Glu Pro Gln Val
                325                 330                 335

Tyr Thr Leu Pro Pro Ser Arg Glu Glu Met Thr Lys Asn Gln Val Ser
            340                 345                 350

Leu Thr Cys Asp Val Ser Gly Phe Tyr Pro Ser Asp Ile Ala Val Glu
        355                 360                 365

Trp Glu Ser Asp Gly Gln Pro Glu Asn Asn Tyr Lys Thr Thr Pro Pro
    370                 375                 380

Val Leu Asp Ser Asp Gly Ser Phe Phe Leu Tyr Ser Lys Leu Thr Val
385                 390                 395                 400

Asp Lys Ser Arg Trp Glu Gln Gly Asp Val Phe Ser Cys Ser Val Leu
                405                 410                 415

His Glu Ala Leu His Ser His Tyr Thr Gln Lys Ser Leu Ser Leu Ser
            420                 425                 430

Pro Gly Lys
        435

<210> SEQ ID NO 254
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 254

Glu Pro Lys Ser Ser Asp Lys Thr His Thr Cys Pro Pro Cys Pro Ala
1               5                   10                  15

Pro Pro Val Ala Gly Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Lys His Glu Asp Pro Glu Val Lys Phe Asn Trp Tyr Val Asp
    50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Glu Gln Met Thr Lys
    130                 135                 140

Asn Gln Val Lys Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
```

```
                195                 200                 205
Cys Ser Val Leu His Glu Ala Leu His Ser His Tyr Thr Gln Lys Ser
        210                 215                 220
Leu Ser Leu Ser Pro Gly Lys
225                 230

<210> SEQ ID NO 255
<211> LENGTH: 350
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 255

Asn Trp Val Asn Val Ile Ser Asp Leu Lys Lys Ile Glu Asp Leu Ile
1               5                   10                  15
Gln Ser Met His Ile Asp Ala Thr Leu Tyr Thr Glu Ser Asn Val His
            20                  25                  30
Pro Ser Cys Lys Val Thr Ala Met Lys Cys Phe Leu Leu Glu Leu Gln
        35                  40                  45
Val Ile Ser Leu Glu Ser Gly Asp Ala Ser Ile His Asp Thr Val Gln
50                  55                  60
Asp Leu Ile Ile Leu Ala Asn Asn Ser Leu Ser Ser Asn Gly Asn Val
65                  70                  75                  80
Thr Glu Ser Gly Cys Lys Glu Cys Glu Glu Leu Glu Glu Lys Asn Ile
                85                  90                  95
Lys Glu Phe Leu Gln Ser Phe Val His Ile Val Gln Met Phe Ile Asn
            100                 105                 110
Thr Ser Gly Gly Gly Gly Ser Glu Pro Lys Ser Ser Asp Lys Thr His
        115                 120                 125
Thr Cys Pro Pro Cys Pro Ala Pro Pro Val Ala Gly Pro Ser Val Phe
130                 135                 140
Leu Phe Pro Pro Lys Pro Lys Asp Thr Leu Met Ile Ser Arg Thr Pro
145                 150                 155                 160
Glu Val Thr Cys Val Val Val Asp Val Lys His Glu Asp Pro Glu Val
                165                 170                 175
Lys Phe Asn Trp Tyr Val Asp Gly Val Glu Val His Asn Ala Lys Thr
            180                 185                 190
Lys Pro Arg Glu Glu Glu Tyr Asn Ser Thr Tyr Arg Val Val Ser Val
        195                 200                 205
Leu Thr Val Leu His Gln Asp Trp Leu Asn Gly Lys Glu Tyr Lys Cys
210                 215                 220
Lys Val Ser Asn Lys Ala Leu Pro Ala Pro Ile Glu Lys Thr Ile Ser
225                 230                 235                 240
Lys Ala Lys Gly Gln Pro Arg Glu Pro Gln Val Tyr Thr Leu Pro Pro
                245                 250                 255
Ser Arg Glu Glu Met Thr Lys Asn Gln Val Ser Leu Thr Cys Asp Val
            260                 265                 270
Ser Gly Phe Tyr Pro Ser Asp Ile Ala Val Glu Trp Glu Ser Asp Gly
        275                 280                 285
Gln Pro Glu Asn Asn Tyr Lys Thr Thr Pro Pro Val Leu Asp Ser Asp
290                 295                 300
Gly Ser Phe Phe Leu Tyr Ser Lys Leu Thr Val Asp Lys Ser Arg Trp
305                 310                 315                 320
```

Glu Gln Gly Asp Val Phe Ser Cys Ser Val Leu His Glu Ala Leu His
                325                 330                 335

Ser His Tyr Thr Gln Lys Ser Leu Ser Leu Ser Pro Gly Lys
            340                 345                 350

<210> SEQ ID NO 256
<211> LENGTH: 301
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 256

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
50                  55                  60

Arg Gly Gly Gly Gly Ser Glu Pro Lys Ser Ser Asp Lys Thr His Thr
65                  70                  75                  80

Cys Pro Pro Cys Pro Ala Pro Val Ala Gly Pro Ser Val Phe Leu
                85                  90                  95

Phe Pro Pro Lys Pro Lys Asp Thr Leu Met Ile Ser Arg Thr Pro Glu
            100                 105                 110

Val Thr Cys Val Val Val Asp Val Lys His Glu Asp Pro Glu Val Lys
        115                 120                 125

Phe Asn Trp Tyr Val Asp Gly Val Glu Val His Asn Ala Lys Thr Lys
    130                 135                 140

Pro Arg Glu Glu Gln Tyr Asn Ser Thr Tyr Arg Val Val Ser Val Leu
145                 150                 155                 160

Thr Val Leu His Gln Asp Trp Leu Asn Gly Lys Glu Tyr Lys Cys Lys
                165                 170                 175

Val Ser Asn Lys Ala Leu Pro Ala Pro Ile Glu Lys Thr Ile Ser Lys
            180                 185                 190

Ala Lys Gly Gln Pro Arg Glu Pro Gln Val Tyr Thr Leu Pro Pro Ser
        195                 200                 205

Arg Glu Gln Met Thr Lys Asn Gln Val Lys Leu Thr Cys Leu Val Lys
210                 215                 220

Gly Phe Tyr Pro Ser Asp Ile Ala Val Glu Trp Glu Ser Asn Gly Gln
225                 230                 235                 240

Pro Glu Asn Asn Tyr Lys Thr Thr Pro Pro Val Leu Asp Ser Asp Gly
                245                 250                 255

Ser Phe Phe Leu Tyr Ser Lys Leu Thr Val Asp Lys Ser Arg Trp Gln
            260                 265                 270

Gln Gly Asn Val Phe Ser Cys Ser Val Leu His Glu Ala Leu His Ser
        275                 280                 285

His Tyr Thr Gln Lys Ser Leu Ser Leu Ser Pro Gly Lys
    290                 295                 300

<210> SEQ ID NO 257
<211> LENGTH: 435
<212> TYPE: PRT
<213> ORGANISM: Artificial Sequence -continued

```
<220> FEATURE:
<223> OTHER INFORMATION: Description of Artificial Sequence: Synthetic
      polypeptide

<400> SEQUENCE: 257

Ile Thr Cys Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
50                  55                  60

Arg Gly Gly Gly Ser Gly Gly Gly Ser Gly Gly Gly Ser
65                  70                  75                  80

Gly Gly Gly Gly Ser Gly Gly Gly Ser Asn Trp Val Asn Val Ile
                85                  90                  95

Ser Asp Leu Lys Lys Ile Glu Asp Leu Ile Gln Ser Met His Ile Asp
                100                 105                 110

Ala Thr Leu Tyr Thr Glu Ser Asp Val His Pro Ser Cys Lys Val Thr
            115                 120                 125

Ala Met Lys Cys Phe Leu Leu Glu Leu Gln Val Ile Ser Leu Glu Ser
        130                 135                 140

Gly Asp Ala Ser Ile His Asp Thr Val Glu Asn Leu Ile Ile Leu Ala
145                 150                 155                 160

Asn Asn Ser Leu Ser Ser Asn Gly Asn Val Thr Glu Ser Gly Cys Lys
                165                 170                 175

Glu Cys Glu Glu Leu Glu Glu Lys Asn Ile Lys Glu Phe Leu Gln Ser
            180                 185                 190

Phe Val His Ile Val Gln Met Phe Ile Asn Thr Ser Glu Pro Lys Ser
        195                 200                 205

Ser Asp Lys Thr His Thr Cys Pro Pro Cys Pro Ala Pro Pro Val Ala
    210                 215                 220

Gly Pro Ser Val Phe Leu Phe Pro Pro Lys Pro Lys Asp Thr Leu Met
225                 230                 235                 240

Ile Ser Arg Thr Pro Glu Val Thr Cys Val Val Val Asp Val Lys His
                245                 250                 255

Glu Asp Pro Glu Val Lys Phe Asn Trp Tyr Val Asp Gly Val Glu Val
            260                 265                 270

His Asn Ala Lys Thr Lys Pro Arg Glu Glu Gln Tyr Asn Ser Thr Tyr
        275                 280                 285

Arg Val Val Ser Val Leu Thr Val Leu His Gln Asp Trp Leu Asn Gly
    290                 295                 300

Lys Glu Tyr Lys Cys Lys Val Ser Asn Lys Ala Leu Pro Ala Pro Ile
305                 310                 315                 320

Glu Lys Thr Ile Ser Lys Ala Lys Gly Gln Pro Arg Glu Pro Gln Val
                325                 330                 335

Tyr Thr Leu Pro Pro Ser Arg Glu Glu Met Thr Lys Asn Gln Val Ser
            340                 345                 350

Leu Thr Cys Asp Val Ser Gly Phe Tyr Pro Ser Asp Ile Ala Val Glu
        355                 360                 365

Trp Glu Ser Asp Gly Gln Pro Glu Asn Asn Tyr Lys Thr Thr Pro Pro
    370                 375                 380

Val Leu Asp Ser Asp Gly Ser Phe Phe Leu Tyr Ser Lys Leu Thr Val
```

```
                385               390               395               400
Asp Lys Ser Arg Trp Glu Gln Gly Asp Val Phe Ser Cys Ser Val Met
                    405               410               415

His Glu Ala Leu His Asn His Tyr Thr Gln Lys Ser Leu Ser Leu Ser
                420               425               430

Pro Gly Lys
        435

<210> SEQ ID NO 258
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 258

Glu Pro Lys Ser Ser Asp Lys Thr His Thr Cys Pro Pro Cys Pro Ala
1               5                   10                  15

Pro Pro Val Ala Gly Pro Ser Val Phe Leu Phe Pro Pro Lys Pro Lys
                20                  25                  30

Asp Thr Leu Met Ile Ser Arg Thr Pro Glu Val Thr Cys Val Val Val
                35                  40                  45

Asp Val Lys His Glu Asp Pro Glu Val Lys Phe Asn Trp Tyr Val Asp
        50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Glu Gln Met Thr Lys
    130                 135                 140

Asn Gln Val Lys Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys
225                 230

<210> SEQ ID NO 259
<211> LENGTH: 435
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 259

Ile Thr Cys Pro Pro Pro Met Ser Val Glu His Ala Asp Ile Trp Val
```

-continued

```
1               5                   10                  15
Lys Ser Tyr Ser Leu Tyr Ser Arg Glu Arg Tyr Ile Cys Asn Ser Gly
                20                  25                  30
Phe Lys Arg Lys Ala Gly Thr Ser Leu Thr Glu Cys Val Leu Asn
            35                  40                  45
Lys Ala Thr Asn Val Ala His Trp Thr Thr Pro Ser Leu Lys Cys Ile
        50                  55                  60
Arg Gly Gly Gly Ser Gly Gly Gly Ser Gly Gly Gly Ser
65                  70                  75                  80
Gly Gly Gly Gly Ser Gly Gly Gly Ser Asn Trp Val Asp Val Ile
                85                  90                  95
Ser Asp Leu Lys Lys Ile Glu Asp Leu Ile Gln Ser Met His Ile Asp
            100                 105                 110
Ala Thr Leu Tyr Thr Glu Ser Asp Val His Pro Ser Cys Lys Val Thr
            115                 120                 125
Ala Met Lys Cys Phe Leu Leu Glu Leu Gln Val Ile Ser Leu Glu Ser
            130                 135                 140
Gly Asp Ala Ser Ile His Asp Thr Val Glu Asp Leu Ile Ile Leu Ala
145                 150                 155                 160
Asn Asn Ser Leu Ser Ser Asn Gly Asn Val Thr Glu Ser Gly Cys Lys
                165                 170                 175
Glu Cys Glu Glu Leu Glu Glu Lys Asn Ile Lys Glu Phe Leu Gln Ser
            180                 185                 190
Phe Val His Ile Val Gln Met Phe Ile Asn Thr Ser Glu Pro Lys Ser
            195                 200                 205
Ser Asp Lys Thr His Thr Cys Pro Pro Cys Pro Ala Pro Pro Val Ala
        210                 215                 220
Gly Pro Ser Val Phe Leu Phe Pro Pro Lys Pro Lys Asp Thr Leu Met
225                 230                 235                 240
Ile Ser Arg Thr Pro Glu Val Thr Cys Val Val Val Asp Val Lys His
                245                 250                 255
Glu Asp Pro Glu Val Lys Phe Asn Trp Tyr Val Asp Gly Val Glu Val
            260                 265                 270
His Asn Ala Lys Thr Lys Pro Arg Glu Glu Glu Tyr Asn Ser Thr Tyr
            275                 280                 285
Arg Val Val Ser Val Leu Thr Val Leu His Gln Asp Trp Leu Asn Gly
            290                 295                 300
Lys Glu Tyr Lys Cys Lys Val Ser Asn Lys Ala Leu Pro Ala Pro Ile
305                 310                 315                 320
Glu Lys Thr Ile Ser Lys Ala Lys Gly Gln Pro Arg Glu Pro Gln Val
                325                 330                 335
Tyr Thr Leu Pro Pro Ser Arg Glu Glu Met Thr Lys Asn Gln Val Ser
            340                 345                 350
Leu Thr Cys Asp Val Ser Gly Phe Tyr Pro Ser Asp Ile Ala Val Glu
            355                 360                 365
Trp Glu Ser Asp Gly Gln Pro Glu Asn Asn Tyr Lys Thr Thr Pro Pro
        370                 375                 380
Val Leu Asp Ser Asp Gly Ser Phe Phe Leu Tyr Ser Lys Leu Thr Val
385                 390                 395                 400
Asp Lys Ser Arg Trp Glu Gln Gly Asp Val Phe Ser Cys Ser Val Met
                405                 410                 415
His Glu Ala Leu His Asn His Tyr Thr Gln Lys Ser Leu Ser Leu Ser
            420                 425                 430
```

Pro Gly Lys
        435

<210> SEQ ID NO 260
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 260

Glu Pro Lys Ser Ser Asp Lys Thr His Thr Cys Pro Pro Cys Pro Ala
1               5                   10                  15

Pro Pro Val Ala Gly Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Lys His Glu Asp Pro Glu Val Lys Phe Asn Trp Tyr Val Asp
    50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Glu Gln Met Thr Lys
    130                 135                 140

Asn Gln Val Lys Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys
225                 230

<210> SEQ ID NO 261
<211> LENGTH: 435
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 261

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

```
Lys Ala Thr Asn Val Ala His Trp Thr Thr Pro Ser Leu Lys Cys Ile
 50                  55                  60

Arg Gly Gly Gly Ser Gly Gly Gly Ser Gly Gly Gly Gly Gly Gly Ser
 65                  70                  75                  80

Gly Gly Gly Gly Ser Gly Gly Gly Ser Asn Trp Val Asn Val Ile
                 85                  90                  95

Ser Asp Leu Lys Lys Ile Glu Asp Leu Ile Gln Ser Met His Ile Asp
             100                 105                 110

Ala Thr Leu Tyr Thr Glu Ser Asn Val His Pro Ser Cys Lys Val Thr
             115                 120                 125

Ala Met Lys Cys Phe Leu Leu Glu Leu Gln Val Ile Ser Leu Glu Ser
         130                 135                 140

Gly Asp Ala Ser Ile His Asp Thr Val Glu Asn Leu Ile Ile Leu Ala
145                 150                 155                 160

Asn Asn Ser Leu Ser Ser Asn Gly Asn Val Thr Glu Ser Gly Cys Lys
                 165                 170                 175

Glu Cys Glu Glu Leu Glu Glu Lys Asn Ile Lys Glu Phe Leu Gln Ser
             180                 185                 190

Phe Val His Ile Val Gln Met Phe Ile Asn Thr Ser Glu Pro Lys Ser
             195                 200                 205

Ser Asp Lys Thr His Thr Cys Pro Pro Cys Pro Ala Pro Pro Val Ala
210                 215                 220

Gly Pro Ser Val Phe Leu Phe Pro Pro Lys Pro Lys Asp Thr Leu Met
225                 230                 235                 240

Ile Ser Arg Thr Pro Glu Val Thr Cys Val Val Val Asp Val Lys His
                 245                 250                 255

Glu Asp Pro Glu Val Lys Phe Asn Trp Tyr Val Asp Gly Val Glu Val
             260                 265                 270

His Asn Ala Lys Thr Lys Pro Arg Glu Glu Glu Tyr Asn Ser Thr Tyr
             275                 280                 285

Arg Val Val Ser Val Leu Thr Val Leu His Gln Asp Trp Leu Asn Gly
         290                 295                 300

Lys Glu Tyr Lys Cys Lys Val Ser Asn Lys Ala Leu Pro Ala Pro Ile
305                 310                 315                 320

Glu Lys Thr Ile Ser Lys Ala Lys Gly Gln Pro Arg Glu Pro Gln Val
                 325                 330                 335

Tyr Thr Leu Pro Pro Ser Arg Glu Glu Met Thr Lys Asn Gln Val Ser
             340                 345                 350

Leu Thr Cys Asp Val Ser Gly Phe Tyr Pro Ser Asp Ile Ala Val Glu
         355                 360                 365

Trp Glu Ser Asp Gly Gln Pro Glu Asn Asn Tyr Lys Thr Thr Pro Pro
         370                 375                 380

Val Leu Asp Ser Asp Gly Ser Phe Phe Leu Tyr Ser Lys Leu Thr Val
385                 390                 395                 400

Asp Lys Ser Arg Trp Glu Gln Gly Asp Val Phe Ser Cys Ser Val Met
                 405                 410                 415

His Glu Ala Leu His Asn His Tyr Thr Gln Lys Ser Leu Ser Leu Ser
             420                 425                 430

Pro Gly Lys
         435

<210> SEQ ID NO 262
<211> LENGTH: 231
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 262

Glu Pro Lys Ser Ser Asp Lys Thr His Thr Cys Pro Pro Cys Pro Ala
1               5                   10                  15

Pro Pro Val Ala Gly Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Lys His Glu Asp Pro Glu Val Lys Phe Asn Trp Tyr Val Asp
    50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Glu Gln Met Thr Lys
    130                 135                 140

Asn Gln Val Lys Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys
225                 230

<210> SEQ ID NO 263
<211> LENGTH: 435
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 263

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Gly Gly Gly Gly Ser Gly Gly Gly Ser Gly Gly Gly Gly Ser
65                  70                  75                  80
```

Gly Gly Gly Gly Ser Gly Gly Gly Ser Asn Trp Val Asn Val Ile
            85              90                  95

Ser Asp Leu Lys Lys Ile Glu Asp Leu Ile Gln Ser Met His Ile Asp
        100                 105                 110

Ala Thr Leu Tyr Thr Glu Ser Asn Val His Pro Ser Cys Lys Val Thr
        115                 120                 125

Ala Met Lys Cys Phe Leu Leu Glu Leu Gln Val Ile Ser Leu Glu Ser
130                 135                 140

Gly Asp Ala Ser Ile His Asp Thr Val Glu Asp Leu Ile Ile Leu Ala
145                 150                 155                 160

Asn Asn Ser Leu Ser Ser Asn Gly Asn Val Thr Glu Ser Gly Cys Lys
                165                 170                 175

Glu Cys Glu Glu Leu Glu Glu Lys Asn Ile Lys Glu Phe Leu Gln Ser
            180                 185                 190

Phe Val His Ile Val Gln Met Phe Ile Asn Thr Ser Glu Pro Lys Ser
        195                 200                 205

Ser Asp Lys Thr His Thr Cys Pro Pro Cys Pro Ala Pro Pro Val Ala
        210                 215                 220

Gly Pro Ser Val Phe Leu Phe Pro Pro Lys Pro Lys Asp Thr Leu Met
225                 230                 235                 240

Ile Ser Arg Thr Pro Glu Val Thr Cys Val Val Val Asp Val Lys His
                245                 250                 255

Glu Asp Pro Glu Val Lys Phe Asn Trp Tyr Val Asp Gly Val Glu Val
            260                 265                 270

His Asn Ala Lys Thr Lys Pro Arg Glu Glu Glu Tyr Asn Ser Thr Tyr
        275                 280                 285

Arg Val Val Ser Val Leu Thr Val Leu His Gln Asp Trp Leu Asn Gly
290                 295                 300

Lys Glu Tyr Lys Cys Lys Val Ser Asn Lys Ala Leu Pro Ala Pro Ile
305                 310                 315                 320

Glu Lys Thr Ile Ser Lys Ala Lys Gly Gln Pro Arg Glu Pro Gln Val
                325                 330                 335

Tyr Thr Leu Pro Pro Ser Arg Glu Glu Met Thr Lys Asn Gln Val Ser
            340                 345                 350

Leu Thr Cys Asp Val Ser Gly Phe Tyr Pro Ser Asp Ile Ala Val Glu
        355                 360                 365

Trp Glu Ser Asp Gly Gln Pro Glu Asn Asn Tyr Lys Thr Thr Pro Pro
        370                 375                 380

Val Leu Asp Ser Asp Gly Ser Phe Phe Leu Tyr Ser Lys Leu Thr Val
385                 390                 395                 400

Asp Lys Ser Arg Trp Glu Gln Gly Asp Val Phe Ser Cys Ser Val Met
                405                 410                 415

His Glu Ala Leu His Asn His Tyr Thr Gln Lys Ser Leu Ser Leu Ser
            420                 425                 430

Pro Gly Lys
        435

<210> SEQ ID NO 264
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 264

```
Glu Pro Lys Ser Ser Asp Lys Thr His Thr Cys Pro Pro Cys Pro Ala
1               5                   10                  15

Pro Pro Val Ala Gly Pro Ser Val Phe Leu Phe Pro Pro Lys Pro Lys
            20                  25                  30

Asp Thr Leu Met Ile Ser Arg Thr Pro Glu Val Thr Cys Val Val Val
            35                  40                  45

Asp Val Lys His Glu Asp Pro Glu Val Lys Phe Asn Trp Tyr Val Asp
        50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
                100                 105                 110

Pro Ala Pro Ile Glu Lys Thr Ile Ser Lys Ala Lys Gly Gln Pro Arg
            115                 120                 125

Glu Pro Gln Val Tyr Thr Leu Pro Pro Ser Arg Glu Gln Met Thr Lys
        130                 135                 140

Asn Gln Val Lys Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
                180                 185                 190

Lys Leu Thr Val Asp Lys Ser Arg Trp Gln Gln Gly Asn Val Phe Ser
            195                 200                 205

Cys Ser Val Met His Glu Ala Leu His Asn His Tyr Thr Gln Lys Ser
            210                 215                 220

Leu Ser Leu Ser Pro Gly Lys
225                 230

<210> SEQ ID NO 265
<211> LENGTH: 435
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 265

Ile Thr Cys Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
            35                  40                  45

Lys Ala Thr Asn Val Ala His Trp Thr Thr Pro Ser Leu Lys Cys Ile
        50                  55                  60

Arg Gly Gly Gly Ser Gly Gly Gly Ser Gly Gly Gly Ser
65                  70                  75                  80

Gly Gly Gly Gly Ser Gly Gly Gly Ser Asn Trp Val Asn Val Ile
                85                  90                  95

Ser Asp Leu Lys Lys Ile Glu Asp Leu Ile Gln Ser Met His Ile Asp
                100                 105                 110

Ala Thr Leu Tyr Thr Glu Ser Asn Val His Pro Ser Cys Lys Val Thr
```

115                 120                 125
Ala Met Lys Cys Phe Leu Leu Glu Leu Gln Val Ile Ser Leu Glu Ser
            130                 135                 140

Gly Asp Ala Ser Ile His Asp Thr Val Gln Asp Leu Ile Ile Leu Ala
145                 150                 155                 160

Asn Asn Ser Leu Ser Ser Asn Gly Asn Val Thr Glu Ser Gly Cys Lys
                165                 170                 175

Glu Cys Glu Glu Leu Glu Glu Lys Asn Ile Lys Glu Phe Leu Gln Ser
            180                 185                 190

Phe Val His Ile Val Gln Met Phe Ile Asn Thr Ser Glu Pro Lys Ser
        195                 200                 205

Ser Asp Lys Thr His Thr Cys Pro Pro Cys Pro Ala Pro Pro Val Ala
    210                 215                 220

Gly Pro Ser Val Phe Leu Phe Pro Pro Lys Pro Lys Asp Thr Leu Met
225                 230                 235                 240

Ile Ser Arg Thr Pro Glu Val Thr Cys Val Val Val Asp Val Lys His
                245                 250                 255

Glu Asp Pro Glu Val Lys Phe Asn Trp Tyr Val Asp Gly Val Glu Val
            260                 265                 270

His Asn Ala Lys Thr Lys Pro Arg Glu Glu Glu Tyr Asn Ser Thr Tyr
        275                 280                 285

Arg Val Val Ser Val Leu Thr Val Leu His Gln Asp Trp Leu Asn Gly
    290                 295                 300

Lys Glu Tyr Lys Cys Lys Val Ser Asn Lys Ala Leu Pro Ala Pro Ile
305                 310                 315                 320

Glu Lys Thr Ile Ser Lys Ala Lys Gly Gln Pro Arg Glu Pro Gln Val
                325                 330                 335

Tyr Thr Leu Pro Pro Ser Arg Glu Glu Met Thr Lys Asn Gln Val Ser
            340                 345                 350

Leu Thr Cys Asp Val Ser Gly Phe Tyr Pro Ser Asp Ile Ala Val Glu
        355                 360                 365

Trp Glu Ser Asp Gly Gln Pro Glu Asn Asn Tyr Lys Thr Thr Pro Pro
    370                 375                 380

Val Leu Asp Ser Asp Gly Ser Phe Phe Leu Tyr Ser Lys Leu Thr Val
385                 390                 395                 400

Asp Lys Ser Arg Trp Glu Gln Gly Asp Val Phe Ser Cys Ser Val Met
                405                 410                 415

His Glu Ala Leu His Asn His Tyr Thr Gln Lys Ser Leu Ser Leu Ser
            420                 425                 430

Pro Gly Lys
        435

<210> SEQ ID NO 266
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 266

Glu Pro Lys Ser Ser Asp Lys Thr His Thr Cys Pro Pro Cys Pro Ala
1               5                   10                  15

Pro Pro Val Ala Gly Pro Ser Val Phe Leu Phe Pro Pro Lys Pro Lys
            20                  25                  30

```
Asp Thr Leu Met Ile Ser Arg Thr Pro Glu Val Thr Cys Val Val Val
             35                  40                  45

Asp Val Lys His Glu Asp Pro Glu Val Lys Phe Asn Trp Tyr Val Asp
 50                  55                  60

Gly Val Glu Val His Asn Ala Lys Thr Lys Pro Arg Glu Glu Gln Tyr
 65                  70                  75                  80

Asn Ser Thr Tyr Arg Val Val Ser Val Leu Thr Val Leu His Gln Asp
                 85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Glu Gln Met Thr Lys
130                 135                 140

Asn Gln Val Lys Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
210                 215                 220

Leu Ser Leu Ser Pro Gly Lys
225                 230

<210> SEQ ID NO 267
<211> LENGTH: 435
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 267

Ile Thr Cys Pro Pro Pro Met Ser Val Glu His Ala Asp Ile Trp Val
  1               5                  10                  15

Lys Ser Tyr Ser Leu Tyr Ser Arg Glu Arg Tyr Ile Cys Asn Ser Gly
             20                  25                  30

Phe Lys Arg Lys Ala Gly Thr Ser Ser Leu Thr Glu Cys Val Leu Asn
         35                  40                  45

Lys Ala Thr Asn Val Ala His Trp Thr Thr Pro Ser Leu Lys Cys Ile
 50                  55                  60

Arg Gly Gly Gly Gly Ser Gly Gly Gly Gly Ser Gly Gly Gly Gly Ser
 65                  70                  75                  80

Gly Gly Gly Gly Ser Gly Gly Gly Gly Ser Asn Trp Val Asn Val Ile
             85                  90                  95

Ser Asp Leu Lys Lys Ile Glu Asp Leu Ile Gln Ser Met His Ile Asp
            100                 105                 110

Ala Thr Leu Tyr Thr Glu Ser Asn Val His Pro Ser Cys Lys Val Thr
        115                 120                 125

Ala Met Lys Cys Phe Leu Leu Glu Leu Gln Val Ile Ser Leu Glu Ser
130                 135                 140

Gly Asp Ala Ser Ile His Asp Thr Val Glu Asp Leu Ile Ile Leu Ala
145                 150                 155                 160
```

Asn Asn Ser Leu Ser Ser Asn Gly Asn Val Thr Glu Ser Gly Cys Lys
            165                 170                 175

Glu Cys Glu Glu Leu Glu Glu Lys Asn Ile Lys Glu Phe Leu Gln Ser
            180                 185                 190

Phe Val His Ile Val Gln Met Phe Ile Asn Thr Ser Glu Pro Lys Ser
            195                 200                 205

Ser Asp Lys Thr His Thr Cys Pro Pro Cys Pro Ala Pro Pro Val Ala
        210                 215                 220

Gly Pro Ser Val Phe Leu Phe Pro Pro Lys Pro Lys Asp Thr Leu Met
225                 230                 235                 240

Ile Ser Arg Thr Pro Glu Val Thr Cys Val Val Val Asp Val Lys His
            245                 250                 255

Glu Asp Pro Glu Val Lys Phe Asn Trp Tyr Val Asp Gly Val Glu Val
            260                 265                 270

His Asn Ala Lys Thr Lys Pro Arg Glu Glu Glu Tyr Asn Ser Thr Tyr
        275                 280                 285

Arg Val Val Ser Val Leu Thr Val Leu His Gln Asp Trp Leu Asn Gly
        290                 295                 300

Lys Glu Tyr Lys Cys Lys Val Ser Asn Lys Ala Leu Pro Ala Pro Ile
305                 310                 315                 320

Glu Lys Thr Ile Ser Lys Ala Lys Gly Gln Pro Arg Glu Pro Gln Val
            325                 330                 335

Tyr Thr Leu Pro Pro Ser Arg Glu Glu Met Thr Lys Asn Gln Val Ser
            340                 345                 350

Leu Thr Cys Asp Val Ser Gly Phe Tyr Pro Ser Asp Ile Ala Val Glu
        355                 360                 365

Trp Glu Ser Asp Gly Gln Pro Glu Asn Asn Tyr Lys Thr Thr Pro Pro
370                 375                 380

Val Leu Asp Ser Asp Gly Ser Phe Phe Leu Tyr Ser Lys Leu Thr Val
385                 390                 395                 400

Asp Lys Ser Arg Trp Glu Gln Gly Asp Val Phe Ser Cys Ser Val Met
            405                 410                 415

His Glu Ala Leu His Asn His Tyr Thr Gln Lys Ser Leu Ser Leu Ser
        420                 425                 430

Pro Gly Lys
        435

<210> SEQ ID NO 268
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 268

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Asn Gly Tyr
            20                  25                  30

Gly Val Asn Trp Val Arg Gln Pro Pro Gly Lys Gly Leu Glu Trp Leu
        35                  40                  45

Ala Met Ile Trp Gly Asp Gly Ser Thr Asp Tyr Asn Ser Ala Leu Lys
    50                  55                  60

Ser Arg Leu Thr Ile Ser Lys Asp Asn Ser Lys Ser Gln Val Val Leu

```
                65                  70                  75                  80
Thr Met Thr Asn Met Asp Pro Val Asp Thr Ala Thr Tyr Tyr Cys Ala
                    85                  90                  95
Arg Ser Tyr Tyr Thr Ser Asp Glu Asp Tyr Trp Gly Gln Gly Thr Leu
                    100                 105                 110
Val Thr Val Ser Ser Ala Ser Thr Lys Gly Pro Ser Val Phe Pro Leu
                    115                 120                 125
Ala Pro Ser Ser Lys Ser Thr Ser Gly Gly Thr Ala Ala Leu Gly Cys
                    130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                    165                 170                 175
Ser Gly Leu Tyr Ser Leu Ser Ser Val Val Thr Val Pro Ser Ser Ser
                    180                 185                 190
Leu Gly Thr Gln Thr Tyr Ile Cys Asn Val Asn His Lys Pro Ser Asn
                    195                 200                 205
Thr Lys Val Asp Lys Lys Val Glu Pro Lys Ser Cys Asp Lys Thr His
            210                 215                 220
Thr Cys Pro Pro Cys Pro Ala Pro Pro Val Ala Gly Pro Ser Val Phe
225                 230                 235                 240
Leu Phe Pro Pro Lys Pro Lys Asp Thr Leu Met Ile Ser Arg Thr Pro
                    245                 250                 255
Glu Val Thr Cys Val Val Val Asp Val Lys His Glu Asp Pro Glu Val
                    260                 265                 270
Lys Phe Asn Trp Tyr Val Asp Gly Val Glu Val His Asn Ala Lys Thr
                    275                 280                 285
Lys Pro Arg Glu Glu Gln Tyr Asn Ser Thr Tyr Arg Val Val Ser Val
                    290                 295                 300
Leu Thr Val Leu His Gln Asp Trp Leu Asn Gly Lys Glu Tyr Lys Cys
305                 310                 315                 320
Lys Val Ser Asn Lys Ala Leu Pro Ala Pro Ile Glu Lys Thr Ile Ser
                    325                 330                 335
Lys Ala Lys Gly Gln Pro Arg Glu Pro Gln Val Tyr Thr Leu Pro Pro
                    340                 345                 350
Ser Arg Glu Gln Met Thr Lys Asn Gln Val Lys Leu Thr Cys Leu Val
                    355                 360                 365
Lys Gly Phe Tyr Pro Ser Asp Ile Ala Val Glu Trp Glu Ser Asn Gly
                    370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Lys Leu Thr Val Asp Lys Ser Arg Trp
                    405                 410                 415
Gln Gln Gly Asn Val Phe Ser Cys Ser Val Met His Glu Ala Leu His
                    420                 425                 430
Asn His Tyr Thr Gln Lys Ser Leu Ser Leu Ser Pro Gly Lys
                    435                 440                 445

<210> SEQ ID NO 269
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 269

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Ser Leu Arg Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 270
<211> LENGTH: 435
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 270

Ile Thr Cys Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Gly Gly Gly Gly Ser Gly Gly Gly Ser Gly Gly Gly Gly Ser
65                  70                  75                  80

Gly Gly Gly Gly Ser Gly Gly Gly Gly Ser Asn Trp Val Asn Val Ile
                85                  90                  95

Ser Asp Leu Lys Lys Ile Glu Asp Leu Ile Gln Ser Met His Ile Asp
            100                 105                 110

Ala Thr Leu Tyr Thr Glu Ser Asn Val His Pro Ser Cys Lys Val Thr
        115                 120                 125

Ala Met Lys Cys Phe Leu Leu Glu Leu Gln Val Ile Ser Leu Glu Ser
130                 135                 140

Gly Asp Ala Ser Ile His Asp Thr Val Gln Asp Leu Ile Ile Leu Ala
145                 150                 155                 160

Asn Asn Ser Leu Ser Ser Asn Gly Asn Val Thr Glu Ser Gly Cys Lys
                165                 170                 175

Glu Cys Glu Glu Leu Glu Glu Lys Asn Ile Lys Glu Phe Leu Gln Ser
            180                 185                 190

Phe Val His Ile Val Gln Met Phe Ile Asn Thr Ser Glu Pro Lys Ser
        195                 200                 205

Ser Asp Lys Thr His Thr Cys Pro Pro Cys Pro Ala Pro Pro Val Ala
210                 215                 220

Gly Pro Ser Val Phe Leu Phe Pro Pro Lys Pro Lys Asp Thr Leu Met
225                 230                 235                 240

Ile Ser Arg Thr Pro Glu Val Thr Cys Val Val Val Asp Val Lys His
                245                 250                 255

Glu Asp Pro Glu Val Lys Phe Asn Trp Tyr Val Asp Gly Val Glu Val
            260                 265                 270

His Asn Ala Lys Thr Lys Pro Arg Glu Glu Glu Tyr Asn Ser Thr Tyr
        275                 280                 285

Arg Val Val Ser Val Leu Thr Val Leu His Gln Asp Trp Leu Asn Gly
290                 295                 300

Lys Glu Tyr Lys Cys Lys Val Ser Asn Lys Ala Leu Pro Ala Pro Ile
305                 310                 315                 320

Glu Lys Thr Ile Ser Lys Ala Lys Gly Gln Pro Arg Glu Pro Gln Val
                325                 330                 335

Tyr Thr Leu Pro Pro Ser Arg Glu Glu Met Thr Lys Asn Gln Val Ser
            340                 345                 350

Leu Thr Cys Asp Val Ser Gly Phe Tyr Pro Ser Asp Ile Ala Val Glu
        355                 360                 365

Trp Glu Ser Asp Gly Gln Pro Glu Asn Asn Tyr Lys Thr Thr Pro Pro
370                 375                 380

Val Leu Asp Ser Asp Gly Ser Phe Phe Leu Tyr Ser Lys Leu Thr Val
385                 390                 395                 400

Asp Lys Ser Arg Trp Glu Gln Gly Asp Val Phe Ser Cys Ser Val Met
                405                 410                 415

His Glu Ala Leu His Asn His Tyr Thr Gln Lys Ser Leu Ser Leu Ser
            420                 425                 430

Pro Gly Lys
        435

<210> SEQ ID NO 271
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 271

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Asn Gly Tyr
            20                  25                  30

Gly Val Asn Trp Val Arg Gln Pro Pro Gly Lys Gly Leu Glu Trp Leu

```
              35                  40                  45
Ala Met Ile Trp Gly Asp Gly Ser Thr Asp Tyr Asn Ser Ala Leu Lys
 50                  55                  60

Ser Arg Leu Thr Ile Ser Lys Asp Asn Ser Lys Ser Gln Val Val Leu
 65                  70                  75                  80

Thr Met Thr Asn Met Asp Pro Val Asp Thr Ala Thr Tyr Tyr Cys Ala
                 85                  90                  95

Arg Ser Tyr Tyr Thr Ser Asp Glu Asp Tyr Trp Gly Gln Gly Thr Leu
                100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
210                 215                 220

Thr Cys Pro Pro Cys Pro Ala Pro Pro Val Ala Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Lys His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Gln Met Thr Lys Asn Gln Val Lys Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 272
```

<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 272

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Ser Leu Arg Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 273
<211> LENGTH: 435
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 273

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Gly Gly Gly Gly Ser Gly Gly Gly Gly Ser Gly Gly Gly Gly Ser
65                  70                  75                  80

Gly Gly Gly Gly Ser Gly Gly Gly Gly Ser Asn Trp Val Asn Val Ile
                85                  90                  95

Ser Asp Leu Lys Lys Ile Glu Asp Leu Ile Gln Ser Met His Ile Asp
            100                 105                 110

Ala Thr Leu Tyr Thr Glu Ser Asn Val His Pro Ser Cys Lys Val Thr
        115                 120                 125

Ala Met Lys Cys Phe Leu Leu Glu Leu Gln Val Ile Ser Leu Glu Ser
    130                 135                 140

Gly Asp Ala Ser Ile His Asp Thr Val Glu Asp Leu Ile Ile Leu Ala
145                 150                 155                 160

Asn Asn Ser Leu Ser Ser Asn Gly Asn Val Thr Glu Ser Gly Cys Lys
                165                 170                 175

Glu Cys Glu Glu Leu Glu Glu Lys Asn Ile Lys Glu Phe Leu Gln Ser
            180                 185                 190

Phe Val His Ile Val Gln Met Phe Ile Asn Thr Ser Glu Pro Lys Ser
        195                 200                 205

Ser Asp Lys Thr His Thr Cys Pro Pro Cys Pro Ala Pro Pro Val Ala
    210                 215                 220

Gly Pro Ser Val Phe Leu Phe Pro Pro Lys Pro Lys Asp Thr Leu Met
225                 230                 235                 240

Ile Ser Arg Thr Pro Glu Val Thr Cys Val Val Val Asp Val Lys His
                245                 250                 255

Glu Asp Pro Glu Val Lys Phe Asn Trp Tyr Val Asp Gly Val Glu Val
            260                 265                 270

His Asn Ala Lys Thr Lys Pro Arg Glu Glu Glu Tyr Asn Ser Thr Tyr
        275                 280                 285

Arg Val Val Ser Val Leu Thr Val Leu His Gln Asp Trp Leu Asn Gly
    290                 295                 300

Lys Glu Tyr Lys Cys Lys Val Ser Asn Lys Ala Leu Pro Ala Pro Ile
305                 310                 315                 320

Glu Lys Thr Ile Ser Lys Ala Lys Gly Gln Pro Arg Glu Pro Gln Val
                325                 330                 335

Tyr Thr Leu Pro Pro Ser Arg Glu Glu Met Thr Lys Asn Gln Val Ser
            340                 345                 350

Leu Thr Cys Asp Val Ser Gly Phe Tyr Pro Ser Asp Ile Ala Val Glu
        355                 360                 365

Trp Glu Ser Asp Gly Gln Pro Glu Asn Asn Tyr Lys Thr Thr Pro Pro
    370                 375                 380

Val Leu Asp Ser Asp Gly Ser Phe Phe Leu Tyr Ser Lys Leu Thr Val
385                 390                 395                 400

Asp Lys Ser Arg Trp Glu Gln Gly Asp Val Phe Ser Cys Ser Val Leu
                405                 410                 415

His Glu Ala Leu His Ser His Tyr Thr Gln Lys Ser Leu Ser Leu Ser
            420                 425                 430

Pro Gly Lys
        435

<210> SEQ ID NO 274
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 274

Gln Val Thr Leu Lys Glu Ser Gly Pro Val Leu Val Lys Pro Thr Glu

-continued

```
1               5                   10                  15
Thr Leu Thr Leu Thr Cys Thr Val Ser Gly Phe Ser Leu Asn Gly Tyr
                20                  25                  30

Gly Val Asn Trp Val Arg Gln Pro Gly Lys Gly Leu Glu Trp Leu
                35                  40                  45

Ala Met Ile Trp Gly Asp Gly Ser Thr Asp Tyr Asn Ser Ala Leu Lys
        50                  55                  60

Ser Arg Leu Thr Ile Ser Lys Asp Asn Ser Lys Ser Gln Val Val Leu
65                  70                  75                  80

Thr Met Thr Asn Met Asp Pro Val Asp Thr Ala Thr Tyr Tyr Cys Ala
                85                  90                  95

Arg Ser Tyr Tyr Thr Ser Asp Glu Asp Tyr Trp Gly Gln Gly Thr Leu
                100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
210                 215                 220

Thr Cys Pro Pro Cys Pro Ala Pro Pro Val Ala Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Lys His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Gln Met Thr Lys Asn Gln Val Lys Leu Thr Cys Leu Val
        355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Leu His Glu Ala Leu His
            420                 425                 430
```

Ser His Tyr Thr Gln Lys Ser Leu Ser Leu Ser Pro Gly Lys
        435                 440                 445

<210> SEQ ID NO 275
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 275

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Ser Leu Arg Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 276
<211> LENGTH: 435
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 276

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Gly Gly Gly Ser Gly Gly Gly Ser Gly Gly Gly Ser
65                  70                 75                 80

Gly Gly Gly Gly Ser Gly Gly Gly Ser Asn Trp Val Asn Val Ile
                    85                 90                      95

Ser Asp Leu Lys Lys Ile Glu Asp Leu Ile Gln Ser Met His Ile Asp
                100                 105                110

Ala Thr Leu Tyr Thr Glu Ser Asn Val His Pro Ser Cys Lys Val Thr
            115                 120                 125

Ala Met Lys Cys Phe Leu Leu Glu Leu Gln Val Ile Ser Leu Glu Ser
130                 135                 140

Gly Asp Ala Ser Ile His Asp Thr Val Gln Asp Leu Ile Ile Leu Ala
145                 150                 155                 160

Asn Asn Ser Leu Ser Ser Asn Gly Asn Val Thr Glu Ser Gly Cys Lys
                165                 170                 175

Glu Cys Glu Glu Leu Glu Glu Lys Asn Ile Lys Glu Phe Leu Gln Ser
            180                 185                 190

Phe Val His Ile Val Gln Met Phe Ile Asn Thr Ser Glu Pro Lys Ser
        195                 200                 205

Ser Asp Lys Thr His Thr Cys Pro Pro Cys Pro Ala Pro Pro Val Ala
210                 215                 220

Gly Pro Ser Val Phe Leu Phe Pro Pro Lys Pro Lys Asp Thr Leu Met
225                 230                 235                 240

Ile Ser Arg Thr Pro Glu Val Thr Cys Val Val Asp Val Lys His
                245                 250                 255

Glu Asp Pro Glu Val Lys Phe Asn Trp Tyr Val Asp Gly Val Glu Val
            260                 265                 270

His Asn Ala Lys Thr Lys Pro Arg Glu Glu Tyr Asn Ser Thr Tyr
        275                 280                 285

Arg Val Val Ser Val Leu Thr Val Leu His Gln Asp Trp Leu Asn Gly
    290                 295                 300

Lys Glu Tyr Lys Cys Lys Val Ser Asn Lys Ala Leu Pro Ala Pro Ile
305                 310                 315                 320

Glu Lys Thr Ile Ser Lys Ala Lys Gly Gln Pro Arg Glu Pro Gln Val
                325                 330                 335

Tyr Thr Leu Pro Pro Ser Arg Glu Glu Met Thr Lys Asn Gln Val Ser
            340                 345                 350

Leu Thr Cys Asp Val Ser Gly Phe Tyr Pro Ser Asp Ile Ala Val Glu
        355                 360                 365

Trp Glu Ser Asp Gly Gln Pro Glu Asn Asn Tyr Lys Thr Thr Pro Pro
    370                 375                 380

Val Leu Asp Ser Asp Gly Ser Phe Phe Leu Tyr Ser Lys Leu Thr Val
385                 390                 395                 400

Asp Lys Ser Arg Trp Glu Gln Gly Asp Val Phe Ser Cys Ser Val Leu
                405                 410                 415

His Glu Ala Leu His Ser His Tyr Thr Gln Lys Ser Leu Ser Leu Ser
            420                 425                 430

Pro Gly Lys
        435

<210> SEQ ID NO 277
<211> LENGTH: 446
<212> TYPE: PRT
<213> ORGANISM: Artificial Sequence
<220> FEATURE:

<223> OTHER INFORMATION: Description of Artificial Sequence: Synthetic polypeptide

<400> SEQUENCE: 277

```
Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Asn Gly Tyr
            20                  25                  30

Gly Val Asn Trp Val Arg Gln Pro Pro Gly Lys Gly Leu Glu Trp Leu
        35                  40                  45

Ala Met Ile Trp Gly Asp Gly Ser Thr Asp Tyr Asn Ser Ala Leu Lys
    50                  55                  60

Ser Arg Leu Thr Ile Ser Lys Asp Asn Ser Lys Ser Gln Val Val Leu
65                  70                  75                  80

Thr Met Thr Asn Met Asp Pro Val Asp Thr Ala Thr Tyr Tyr Cys Ala
                85                  90                  95

Arg Ser Tyr Tyr Thr Ser Asp Glu Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Val Ala Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Lys His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Gln Met Thr Lys Asn Gln Val Lys Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400
```

Gly Ser Phe Phe Leu Tyr Ser Lys Leu Thr Val Asp Lys Ser Arg Trp
            405                 410                 415

Gln Gln Gly Asn Val Phe Ser Cys Ser Val Leu His Glu Ala Leu His
        420                 425                 430

Ser His Tyr Thr Gln Lys Ser Leu Ser Leu Ser Pro Gly Lys
        435                 440                 445

<210> SEQ ID NO 278
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 278

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Ser Leu Arg Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 279
<211> LENGTH: 435
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 279

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

-continued

```
Phe Lys Arg Lys Ala Gly Thr Ser Ser Leu Thr Glu Cys Val Leu Asn
         35                  40                  45
Lys Ala Thr Asn Val Ala His Trp Thr Thr Pro Ser Leu Lys Cys Ile
 50                  55                  60
Arg Gly Gly Gly Ser Gly Gly Gly Ser Gly Gly Gly Ser
 65                  70                  75                  80
Gly Gly Gly Gly Ser Gly Gly Gly Ser Asn Trp Val Asp Val Ile
                 85                  90                  95
Ser Asp Leu Lys Lys Ile Glu Asp Leu Ile Gln Ser Met His Ile Asp
             100                 105                 110
Ala Thr Leu Tyr Thr Glu Ser Asp Val His Pro Ser Cys Lys Val Thr
             115                 120                 125
Ala Met Lys Cys Phe Leu Leu Glu Leu Gln Val Ile Ser Leu Glu Ser
         130                 135                 140
Gly Asp Ala Ser Ile His Asp Thr Val Glu Asp Leu Ile Ile Leu Ala
145                 150                 155                 160
Asn Asn Ser Leu Ser Ser Asn Gly Asn Val Thr Glu Ser Gly Cys Lys
                 165                 170                 175
Glu Cys Glu Glu Leu Glu Glu Lys Asn Ile Lys Glu Phe Leu Gln Ser
             180                 185                 190
Phe Val His Ile Val Gln Met Phe Ile Asn Thr Ser Glu Pro Lys Ser
             195                 200                 205
Ser Asp Lys Thr His Thr Cys Pro Pro Cys Pro Ala Pro Pro Val Ala
         210                 215                 220
Gly Pro Ser Val Phe Leu Phe Pro Pro Lys Pro Lys Asp Thr Leu Met
225                 230                 235                 240
Ile Ser Arg Thr Pro Glu Val Thr Cys Val Val Val Asp Val Lys His
                 245                 250                 255
Glu Asp Pro Glu Val Lys Phe Asn Trp Tyr Val Asp Gly Val Glu Val
             260                 265                 270
His Asn Ala Lys Thr Lys Pro Arg Glu Glu Glu Tyr Asn Ser Thr Tyr
         275                 280                 285
Arg Val Val Ser Val Leu Thr Val Leu His Gln Asp Trp Leu Asn Gly
         290                 295                 300
Lys Glu Tyr Lys Cys Lys Val Ser Asn Lys Ala Leu Pro Ala Pro Ile
305                 310                 315                 320
Glu Lys Thr Ile Ser Lys Ala Lys Gly Gln Pro Arg Glu Pro Gln Val
                 325                 330                 335
Tyr Thr Leu Pro Pro Ser Arg Glu Glu Met Thr Lys Asn Gln Val Ser
             340                 345                 350
Leu Thr Cys Asp Val Ser Gly Phe Tyr Pro Ser Asp Ile Ala Val Glu
         355                 360                 365
Trp Glu Ser Asp Gly Gln Pro Glu Asn Asn Tyr Lys Thr Thr Pro Pro
370                 375                 380
Val Leu Asp Ser Asp Gly Ser Phe Phe Leu Tyr Ser Lys Leu Thr Val
385                 390                 395                 400
Asp Lys Ser Arg Trp Glu Gln Gly Asp Val Phe Ser Cys Ser Val Met
                 405                 410                 415
His Glu Ala Leu His Asn His Tyr Thr Gln Lys Ser Leu Ser Leu Ser
             420                 425                 430
Pro Gly Lys
         435
```

<210> SEQ ID NO 280
<211> LENGTH: 449
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 280

```
Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ala
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Lys His Tyr Asn Pro Ser
    50                  55                  60

Leu Lys Asp Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Asp Met Ile Phe Asn Phe Tyr Phe Asp Val Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Pro Val Ala Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Lys His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Gln Met Thr Lys Asn Gln Val Lys Leu Thr
        355                 360                 365
```

```
Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 281
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 281

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Arg Val Gly Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Glu Phe Thr Leu Thr Ile Ser Leu Gln Pro Asp Asp
65                  70                  75                  80

Phe Ala Thr Tyr Tyr Cys Phe Gln Gly Ser Gly Tyr Pro Phe Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 282
<211> LENGTH: 435
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 282

| | | | | | | | | | | | | | | |
|---|---|---|---|---|---|---|---|---|---|---|---|---|---|---|
|Ile|Thr|Cys|Pro|Pro|Met|Ser|Val|Glu|His|Ala|Asp|Ile|Trp|Val|
|1| | | |5| | | |10| | | | |15| |
|Lys|Ser|Tyr|Ser|Leu|Tyr|Ser|Arg|Glu|Arg|Tyr|Ile|Cys|Asn|Ser|Gly|
| | | |20| | | | |25| | | |30| | | |
|Phe|Lys|Arg|Lys|Ala|Gly|Thr|Ser|Ser|Leu|Thr|Glu|Cys|Val|Leu|Asn|
| | |35| | | | |40| | | | |45| | | |
|Lys|Ala|Thr|Asn|Val|Ala|His|Trp|Thr|Thr|Pro|Ser|Leu|Lys|Cys|Ile|
|50| | | | | |55| | | | |60| | | | |
|Arg|Gly|Gly|Gly|Ser|Gly|Gly|Gly|Ser|Gly|Gly|Gly|Ser|
|65| | | |70| | | |75| | | |80|
|Gly|Gly|Gly|Gly|Ser|Gly|Gly|Gly|Ser|Asn|Trp|Val|Asn|Val|Ile|
| | | | |85| | | |90| | | | |95| |
|Ser|Asp|Leu|Lys|Lys|Ile|Glu|Asp|Leu|Ile|Gln|Ser|Met|His|Ile|Asp|
| | | |100| | | |105| | | | |110| | | |
|Ala|Thr|Leu|Tyr|Thr|Glu|Ser|Asn|Val|His|Pro|Ser|Cys|Lys|Val|Thr|
| | |115| | | | |120| | | | |125| | | |
|Ala|Met|Lys|Cys|Phe|Leu|Leu|Glu|Leu|Gln|Val|Ile|Ser|Leu|Glu|Ser|
| |130| | | | |135| | | | |140| | | | |
|Gly|Asp|Ala|Ser|Ile|His|Asp|Thr|Val|Glu|Asp|Leu|Ile|Ile|Leu|Ala|
|145| | | | |150| | | | |155| | | | |160|
|Asn|Asn|Ser|Leu|Ser|Ser|Asn|Gly|Asn|Val|Thr|Glu|Ser|Gly|Cys|Lys|
| | | | |165| | | | |170| | | | |175| |
|Glu|Cys|Glu|Glu|Leu|Glu|Glu|Lys|Asn|Ile|Lys|Glu|Phe|Leu|Gln|Ser|
| | |180| | | | |185| | | | |190| | | |
|Phe|Val|His|Ile|Val|Gln|Met|Phe|Ile|Asn|Thr|Ser|Glu|Pro|Lys|Ser|
| | |195| | | | |200| | | | |205| | | |
|Ser|Asp|Lys|Thr|His|Thr|Cys|Pro|Pro|Cys|Pro|Ala|Pro|Pro|Val|Ala|
| | |210| | | | |215| | | | |220| | | |
|Gly|Pro|Ser|Val|Phe|Leu|Phe|Pro|Pro|Lys|Pro|Lys|Asp|Thr|Leu|Met|
|225| | | | |230| | | | |235| | | | |240|
|Ile|Ser|Arg|Thr|Pro|Glu|Val|Thr|Cys|Val|Val|Val|Asp|Val|Lys|His|
| | | |245| | | | |250| | | | |255| | |
|Glu|Asp|Pro|Glu|Val|Lys|Phe|Asn|Trp|Tyr|Val|Asp|Gly|Val|Glu|Val|
| | |260| | | | |265| | | | |270| | | |
|His|Asn|Ala|Lys|Thr|Lys|Pro|Arg|Glu|Glu|Tyr|Asn|Ser|Thr|Tyr|
| | |275| | | | |280| | | | |285| | |
|Arg|Val|Val|Ser|Val|Leu|Thr|Val|Leu|His|Gln|Asp|Trp|Leu|Asn|Gly|
| |290| | | | |295| | | | |300| | | | |
|Lys|Glu|Tyr|Lys|Cys|Lys|Val|Ser|Asn|Lys|Ala|Leu|Pro|Ala|Pro|Ile|
|305| | | |310| | | | |315| | | | |320|
|Glu|Lys|Thr|Ile|Ser|Lys|Ala|Lys|Gly|Gln|Pro|Arg|Glu|Pro|Gln|Val|
| | | |325| | | | |330| | | | |335| | |
|Tyr|Thr|Leu|Pro|Pro|Ser|Arg|Glu|Glu|Met|Thr|Lys|Asn|Gln|Val|Ser|
| | |340| | | | |345| | | | |350| | | |
|Leu|Thr|Cys|Asp|Val|Ser|Gly|Phe|Tyr|Pro|Ser|Asp|Ile|Ala|Val|Glu|
| | |355| | | | |360| | | | |365| | | |
|Trp|Glu|Ser|Asp|Gly|Gln|Pro|Glu|Asn|Asn|Tyr|Lys|Thr|Thr|Pro|Pro|
| | |370| | | | |375| | | | |380| | | |
|Val|Leu|Asp|Ser|Asp|Gly|Ser|Phe|Phe|Leu|Tyr|Ser|Lys|Leu|Thr|Val|
|385| | | | |390| | | | |395| | | | |400|
|Asp|Lys|Ser|Arg|Trp|Glu|Gln|Gly|Asp|Val|Phe|Ser|Cys|Ser|Val|Met|

```
                    405                 410                 415
His Glu Ala Leu His Asn His Tyr Thr Gln Lys Ser Leu Ser Leu Ser
                420                 425                 430

Pro Gly Lys
        435

<210> SEQ ID NO 283
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 283

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ala
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys His Tyr Asn Pro Ser
    50                  55                  60

Leu Lys Asp Arg Leu Thr Ile Ser Lys Asp Thr Ser Lys Asn Gln Val
65              70                  75                  80

Val Leu Lys Val Thr Asn Met Asp Pro Ala Asp Thr Ala Thr Tyr Tyr
                85                  90                  95

Cys Ala Arg Asp Met Ile Phe Asn Phe Tyr Phe Asp Val Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Pro Val Ala Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Lys His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320
```

```
Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Gln Met Thr Lys Asn Gln Val Lys Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

<210> SEQ ID NO 284
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 284

```
Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Arg Val Gly Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

```
<210> SEQ ID NO 285
<211> LENGTH: 435
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 285
```

| | | | | | | | | | | | | | | | |
|---|---|---|---|---|---|---|---|---|---|---|---|---|---|---|---|
| Ile | Thr | Cys | Pro | Pro | Met | Ser | Val | Glu | His | Ala | Asp | Ile | Trp | Val | |
| 1 | | | | 5 | | | | | 10 | | | | | 15 | |
| Lys | Ser | Tyr | Ser | Leu | Tyr | Ser | Arg | Glu | Arg | Tyr | Ile | Cys | Asn | Ser | Gly |
| | | | 20 | | | | | 25 | | | | | 30 | | |
| Phe | Lys | Arg | Lys | Ala | Gly | Thr | Ser | Ser | Leu | Thr | Glu | Cys | Val | Leu | Asn |
| | | | 35 | | | | | 40 | | | | | 45 | | |
| Lys | Ala | Thr | Asn | Val | Ala | His | Trp | Thr | Thr | Pro | Ser | Leu | Lys | Cys | Ile |
| | 50 | | | | | 55 | | | | | 60 | | | | |
| Arg | Gly | Gly | Gly | Ser | Gly | Gly | Gly | Ser | Gly | Gly | Gly | Ser | | | |
| 65 | | | | | 70 | | | | 75 | | | | 80 | | |
| Gly | Gly | Gly | Gly | Ser | Gly | Gly | Gly | Ser | Asn | Trp | Val | Asn | Val | Ile | |
| | | | | 85 | | | | | 90 | | | | | 95 | |
| Ser | Asp | Leu | Lys | Lys | Ile | Glu | Asp | Leu | Ile | Gln | Ser | Met | His | Ile | Asp |
| | | | | 100 | | | | | 105 | | | | | 110 | |
| Ala | Thr | Leu | Tyr | Thr | Glu | Ser | Asn | Val | His | Pro | Ser | Cys | Lys | Val | Thr |
| | | | 115 | | | | | 120 | | | | | 125 | | |
| Ala | Met | Lys | Cys | Phe | Leu | Leu | Glu | Leu | Gln | Val | Ile | Ser | Leu | Glu | Ser |
| | 130 | | | | | 135 | | | | | 140 | | | | |
| Gly | Asp | Ala | Ser | Ile | His | Asp | Thr | Val | Gln | Asp | Leu | Ile | Ile | Leu | Ala |
| 145 | | | | | 150 | | | | | 155 | | | | | 160 | |
| Asn | Asn | Ser | Leu | Ser | Ser | Asn | Gly | Asn | Val | Thr | Glu | Ser | Gly | Cys | Lys |
| | | | | 165 | | | | | 170 | | | | | 175 | |
| Glu | Cys | Glu | Glu | Leu | Glu | Glu | Lys | Asn | Ile | Lys | Glu | Phe | Leu | Gln | Ser |
| | | | 180 | | | | | 185 | | | | | 190 | | |
| Phe | Val | His | Ile | Val | Gln | Met | Phe | Ile | Asn | Thr | Ser | Glu | Pro | Lys | Ser |
| | | | 195 | | | | | 200 | | | | | 205 | | |
| Ser | Asp | Lys | Thr | His | Thr | Cys | Pro | Pro | Cys | Pro | Ala | Pro | Pro | Val | Ala |
| | 210 | | | | | 215 | | | | | 220 | | | | |
| Gly | Pro | Ser | Val | Phe | Leu | Phe | Pro | Pro | Lys | Pro | Lys | Asp | Thr | Leu | Met |
| 225 | | | | | 230 | | | | | 235 | | | | | 240 | |
| Ile | Ser | Arg | Thr | Pro | Glu | Val | Thr | Cys | Val | Val | Val | Asp | Val | Lys | His |
| | | | | 245 | | | | | 250 | | | | | 255 | |
| Glu | Asp | Pro | Glu | Val | Lys | Phe | Asn | Trp | Tyr | Val | Asp | Gly | Val | Glu | Val |
| | | | 260 | | | | | 265 | | | | | 270 | | |
| His | Asn | Ala | Lys | Thr | Lys | Pro | Arg | Glu | Glu | Tyr | Asn | Ser | Thr | Tyr | |
| | | | 275 | | | | | 280 | | | | | 285 | | |
| Arg | Val | Val | Ser | Val | Leu | Thr | Val | Leu | His | Gln | Asp | Trp | Leu | Asn | Gly |
| | | | | 290 | | | | | 295 | | | | | 300 | |
| Lys | Glu | Tyr | Lys | Cys | Lys | Val | Ser | Asn | Lys | Ala | Leu | Pro | Ala | Pro | Ile |
| 305 | | | | | 310 | | | | | 315 | | | | | 320 | |
| Glu | Lys | Thr | Ile | Ser | Lys | Ala | Lys | Gly | Gln | Pro | Arg | Glu | Pro | Gln | Val |
| | | | | 325 | | | | | 330 | | | | | 335 | |
| Tyr | Thr | Leu | Pro | Pro | Ser | Arg | Glu | Glu | Met | Thr | Lys | Asn | Gln | Val | Ser |
| | | | | 340 | | | | | 345 | | | | | 350 | |
| Leu | Thr | Cys | Asp | Val | Ser | Gly | Phe | Tyr | Pro | Ser | Asp | Ile | Ala | Val | Glu |
| | | | 355 | | | | | 360 | | | | | 365 | | |

```
Trp Glu Ser Asp Gly Gln Pro Glu Asn Asn Tyr Lys Thr Thr Pro Pro
            370                 375                 380

Val Leu Asp Ser Asp Gly Ser Phe Phe Leu Tyr Ser Lys Leu Thr Val
385                 390                 395                 400

Asp Lys Ser Arg Trp Glu Gln Gly Asp Val Phe Ser Cys Ser Val Met
                405                 410                 415

His Glu Ala Leu His Asn His Tyr Thr Gln Lys Ser Leu Ser Leu Ser
            420                 425                 430

Pro Gly Lys
        435

<210> SEQ ID NO 286
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 286

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ala
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Lys His Tyr Asn Pro Ser
    50                  55                  60

Leu Lys Asp Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Asp Met Ile Phe Asn Phe Tyr Asp Val Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Val Ala Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Lys His Glu Asp
            260                 265                 270

Pro Glu Val Lys Phe Asn Trp Tyr Val Asp Gly Val Glu Val His Asn
```

```
                275                 280                 285
Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Gln Met Thr Lys Asn Gln Val Lys Leu Thr
                355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
                435                 440                 445

Lys

<210> SEQ ID NO 287
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 287

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Arg Val Gly Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
```

```
                180             185             190
Cys Glu Val Thr His Gln Gly Leu Ser Ser Pro Val Thr Lys Ser Phe
        195                 200                 205
Asn Arg Gly Glu Cys
    210

<210> SEQ ID NO 288
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 288

Gly Ser Gly Gly Ser
1               5

<210> SEQ ID NO 289
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 289

Gly Gly Gly Gly Ser
1               5

<210> SEQ ID NO 290
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 290

Gly Gly Gly Ser
1
```